US012799390B2

(12) United States Patent
Gianneschi et al.

(10) Patent No.: US 12,799,390 B2
(45) Date of Patent: Nov. 17, 2026

(54) RETROGRADE NEURONAL TRACERS DETECTABLE BY FLUORESCENCE AND OTHER IMAGING METHODS

(71) Applicants: NORTHWESTERN UNIVERSITY, Evanston, IL (US); THE REGENTS OF THE UNIVERSITY OF CALIFORNIA, Oakland, CA (US)

(72) Inventors: Nathan C. Gianneschi, Evanston, IL (US); Nanzhi Zang, Evanston, IL (US); Massimo Scanziani, Oakland, CA (US); Dante S. Bortone, Oakland, CA (US); Treffly B. Ditri, Oakland, CA (US); Anthony M. Rush, Oakland, CA (US)

(73) Assignees: Northwestem University, Evanston, IL (US); The Regents of the University of California, Oakland, CA (US)

(*) Notice: Subject to any disclaimer, the term of this patent is extended or adjusted under 35 U.S.C. 154(b) by 926 days.

(21) Appl. No.: 17/797,181

(22) PCT Filed: Feb. 12, 2021

(86) PCT No.: PCT/US2021/017874
§ 371 (c)(1),
(2) Date: Aug. 3, 2022

(87) PCT Pub. No.: WO2021/163498
PCT Pub. Date: Aug. 19, 2021

(65) Prior Publication Data

US 2023/0203369 A1 Jun. 29, 2023

Related U.S. Application Data

(60) Provisional application No. 62/976,485, filed on Feb. 14, 2020.

(51) Int. Cl.
*C09K 11/06* (2006.01)
*B82Y 5/00* (2011.01)
(Continued)

(52) U.S. Cl.
CPC ................ *C09K 11/06* (2013.01); *B82Y 5/00* (2013.01); *B82Y 30/00* (2013.01); *C09K 11/02* (2013.01);
(Continued)

(58) Field of Classification Search
CPC ... C09K 11/06; C09K 11/02; C09K 2211/145; C09K 2211/1466
See application file for complete search history.

(56) References Cited

U.S. PATENT DOCUMENTS

| | | | |
|---|---|---|---|
| 3,789,832 | A | 2/1974 | Danadian |
| 3,853,987 | A | 12/1974 | Dreyer |

(Continued)

FOREIGN PATENT DOCUMENTS

| | | | |
|---|---|---|---|
| CN | 102516988 | * | 6/2012 |
| CN | 103940798 | * | 7/2014 |

(Continued)

OTHER PUBLICATIONS

Reisch et al, “Fluorescent Polymer Nanoparticles Nasedon yes: Seeking Brighter Tools for Bioimaging”, www. MaterialViews.com, small 2016, vol. 12, No. 15, pp. 1968-1992, Feb. 22, 2016.*

(Continued)

*Primary Examiner* — C Melissa Koslow
(74) *Attorney, Agent, or Firm* — Leydig, Voit & Mayer, Ltd.

(57) ABSTRACT

Disclosed is composition comprising: a first fluorophore moiety, and nanoparticles, wherein the nanoparticles comprise: a first plurality of a first nanoparticle, the first nanoparticle comprising: a first outer surface, a first interior
(Continued)

bulk, and a first polymer, wherein the first polymer is covalently bonded to the first fluorophore moiety within the first interior bulk of the first nanoparticle. Also disclosed is a composition comprising: a chelate moiety, and nanoparticles, wherein the nanoparticles comprise: a plurality of a chelate nanoparticle, the chelate nanoparticle comprising: an outer surface, an interior bulk, and a polymer, wherein the polymer is covalently bonded to the chelate moiety within the interior bulk of the chelate nanoparticle. Also disclosed are methods of making such compositions and using such composition for brain mapping and tracing of axonal projections.

26 Claims, 140 Drawing Sheets

(51) Int. Cl.
*B82Y 30/00* (2011.01)
*C09K 11/02* (2006.01)
(52) U.S. Cl.
CPC .................. *C09K 2211/145* (2013.01); *C09K 2211/1466* (2013.01)

(56) References Cited

U.S. PATENT DOCUMENTS

| | | | |
|---|---|---|---|
| 3,957,741 A | 5/1976 | Rembaum et al. |
| 4,138,383 A | 2/1979 | Rembaum et al. |
| 4,157,323 A | 6/1979 | Yen et al. |
| 8,303,931 B2 | 11/2012 | Pison et al. |
| 9,675,953 B2 | 6/2017 | Oldenburg et al. |
| 10,308,864 B2 | 6/2019 | Rothrock et al. |
| 2017/0003293 A1 | 1/2017 | Chiu et al. |

FOREIGN PATENT DOCUMENTS

| | | |
|---|---|---|
| EP | 1966248 | 7/2007 |
| JP | S5975152 | 4/1984 |

OTHER PUBLICATIONS

Translation for CN 102516988, Jun. 27, 2012.*
Tain et al., “Twisted perylene dyes enable highly fluorescent and photostable nanoparticles”, Chem. Commun., 2009, pp. 18-0182, Nov. 13, 2008.*
Thielbeer et al., “Polymerizable Fluorescein Derivatives: Synthesis of Fluorescent Particles and Their Cellular Uptake”, Biomacromolecules, 200, 12, pp. 4386-4391, Nov. 7, 2011.*
Ajiki et al. (2003) “Long-lasting gene expression by particle-mediated intramuscular transfection modified with bupivacaine: combinatorial gene therapy with IL-12 and IL-18 cDNA against rat sarcoma at a distant site,” Cancer Gene Therapy 10, 318-329.
Al-Dosari et al. (2009) “Nonviral Gene Delivery: Principle, Limitations, and Recent Progress,” The AAPS Journal 11, 671.
Alivisatos et al. (2013) “Nanotools for Neuroscience and Brain Activity Mapping,” ACS Nano, 7 (3), 1850-1866.
Anderson et al. (2003) “Emulsion polymerisation and latex applications,” vol. 14, pp. 3-31.
Anonymous (2011) “15—Waterproof Materials” in Building Decorative Materials, Y. Li, S. Ren, Eds. (Woodhead Publishing, 2011), pp. 342-358.
Anonymous (2012) “18—Cell line development” in Therapeutic Antibody Engineering, W. R. Strohl, L. M. Strohl, Eds. (Woodhead Publishing, 2012), pp. 421-595.
ASUA (2002) “Miniemulsion polymerization,” Progress in Polymer Science 27, 1283-1346.
Baum et al. (2006) “Mutagenesis and oncogenesis by chromosomal insertion of gene transfer vectors,” Human Gene Therapy 17, 253-263.
Blaese et al. (1995) “T Lymphocyte-Directed Gene Therapy for ADA-SCID: Initial Trial Results After 4 Years,” Science 270, 475-480.
Borst (2005) “Ethidium DNA agarose gel electrophoresis: How it started,” IUBMB Life 57, 745-747.
Brandl et al. (1988) “Pseudomonas oleovorans</em> as a Source of Poly(β-Hydroxyalkanoates) for Potential Applications as Biodegradable Polyesters,” Applied and Environmental Microbiology 54, 1977-1982.
Budker et al. (1998) “The efficient expression of intravascularly delivered DNA in rat muscle,” Gene Therapy 5, 272-276.
Campenot (1977) “Local control of neurite development by nerve growth factor,” Proceedings of the National Academy of Sciences 74, 4516-4519.
Cao et al. (2013) “Synthesis of nanostructured materials in inverse miniemulsions and their applications,” Nanoscale 5, 10093-10107.
Cavazzana-Calvo et al. (2000) “Gene Therapy of Human Severe Combined Immunodeficiency (SCID)-X1 Disease,” Science 288, 669-672.
Chen et al. (2013) “Gene therapy for cardiovascular disease mediated by ultrasound and microbubbles,” Cardiovascular Ultrasound 11, 11.
Chevalier-Larsen et al. (2006) “Axonal transport and neurodegenerative disease,” Biochimica et Biophysica Acta (BBA)—Molecular Basis of Disease 1762, 1094-1108.
Chopra et al. (2012) “Molecular Imaging and Contrast Agent Database (MICAD): Evolution and Progress,” Molecular Imaging and Biology 14, 4-13.
Chuang et al. (2011) “An MRI-based atlas and database of the developing mouse brain,” Neuroimage 54, 80-89.
Couturier et al. (2015) “Responsive Inverse Opal Hydrogels for the Sensing of Macromolecules,” Angewandte Chemie International Edition 54, 6641-6644.
Cross et al. (2006) “Gene therapy for cancer treatment: past, present and future,” Clin Med Res 4, 218-227.
Damadian (1971) “Tumor Detection by Nuclear Magnetic Resonance,” Science 171, 1151-1153.
De Haën (2001) “Conception of the First Magnetic Resonance Imaging Contrast Agents: A Brief History,” Topics in Magnetic Resonance Imaging 12, 221-230.
De León-Rodríguez et al. (2006) “Highly regioselective N-trans symmetrical diprotection of cyclen,” Tetrahedron Letters 47, 6937-6940.
Dewitt et al. (2012) “Cytoplasmic Dynein Moves Through Uncoordinated Stepping of the AAA+ Ring Domains,” Science 335, 221-225.
Distler (2001) “Emulsion Polymerization” in Encyclopedia of Materials: Science and Technology, K. H. J. Buschow et al., Eds. pp. 2769-2774.
Engelis et al. (2016) “Sequence-controlled methacrylic multiblock copolymers via sulfur-free RAFT emulsion polymerization,” Nature Chemistry, 9, 171.
Felgner et al. (1987) “Lipofection: a highly efficient, lipid-mediated DNA-transfection procedure,” P Natl Acad Sci USA 84, 7413-7417.
Fickert et al. (2012) “Efficient Encapsulation of Self-Healing Agents in Polymer Nanocontainers Functionalized by Orthogonal Reactions,” Macromolecules 45, 6324-6332.
Forte et al. (2016) “A composite hydrogel for brain tissue phantoms,” Materials & Design 112, 227-238.
Gaitzsch et al. (2018) “Revisiting Monomer Synthesis and Radical Ring Opening Polymerization of Dimethylated MDO Towards Biodegradable Nanoparticles for Enzymes,” European Polymer Journal 101, 113-119.
Gambino et al. (2013) “Multimodal contrast agents for in vivo neuroanatomical analysis of monosynaptic connections,” Biomaterials, vol. 34, Issue 29, pp. 7135-7142.
Gehl (2003) “Electroporation: theory and methods, perspectives for drug delivery, gene therapy and research,” Acta Physiologica Scandinavica 177, 437-447.
Getz et al. (1999) “A Comparison between the Sulfhydryl Reductants Tris(2-carboxyethyl)phosphine and Dithiothreitol for Use in Protein Biochemistry,” Analytical Biochemistry 273, 73-80.

(56) References Cited

OTHER PUBLICATIONS

Glasser et al. (2016) "The Human Connectome Project's neuroimaging approach," Nature Neuroscience, 19, 1175.
Glover et al. (2005) "Towards safe, non-viral therapeutic gene expression in humans," Nature Reviews Genetics 6, 299-310.
Goodling et al. (Feb. 2019) "Colouration by total internal reflection and interfer-ence at microscale concave interfaces," Nature, 566 (7745), 523-527.
Han et al. (2000) "Development of Biomaterials for Gene Therapy," Molecular Therapy 2, 302-317.
Hedreen (1982) "Tracing Neural Connections with Horseradish Peroxidase," edited by M.-Marsel Mesulam, John Wiley & Sons, 1982.£11.00 (xvi + 251 pages) ISBN 0 471 10029 3. Trends in Neurosciences 5, 447.
Herculano-Houzel (2009) "The human brain in Nos. a linearly scaled-up primate brain," Front Hum Neurosci 3, 31.
Huang et al. (2005) "Comparative analysis of the DNA staining efficiencies of different fluorescent dyes in preparative agarose gel electrophoresis," in Clinical Chemistry and Laboratory Medicine (CCLM), p. 841.
Huh et al. (2010) "Gene transfer in the nervous system and implications for transsynaptic neuronal tracing," Expert Opinion on Biological Therapy, 10 (5), 763-772.
Ibraheem et al. (2014) "Gene therapy and DNA delivery systems," International Journal of Pharmaceutics 459, 70-83.
Inam et al. (2018) "Controlling the Size of Two-Dimensional Polymer Platelets for Water-in-Water Emulsifiers," ACS Central Science, 4 (1), 63-70.
International Search Report and Written Opinion, dated Jun. 25, 2021, corresponding to International Application No. PCT/US2021/017874, (from which the present application claims priority,) 11 pp.
Ji et al. (2011) "Synthesis of high oil-absorption resins of poly(methyl methac-rylate-butyl methacrylate) by suspended emulsion polymerization," Polymers for Advanced Technologies, 22 (12), 1898-1904.
Jiang et al. (2015) "The direct synthesis of interface-decorated reactive block copolymer nanoparticles via polymerisation-induced self-assembly," Polymer Chemistry 6, 4955-4965.
Jin et al. (1998) "Synthesis and Characterization of Functionalized Poly(ϵ-caprolactone) Copolymers by Free-Radical Polymerization," Macromolecules 31, 1010-1015.
Johnson et al. (2016) "3D printed nervous system on a chip," Lab on a Chip 16, 1393-1400.
Kaastrup et al. (2016) "Using photo-initiated polymerization reactions to detect molecular recognition," Chemical Society Reviews 45, 532-545.
Kamimura et al. (2011) "Advances in Gene Delivery Systems," Pharmaceut Med 25, 293-306.
Katz (1987) "Local circuitry of identified projection neurons in cat visual cortex brain slices," The Journal of neuroscience, 7 (4), 1223-1249.
Katz et al. (1984) "Fluorescent latex microspheres as a retrograde neuronal marker for in vivo and in vitro studies of visual cortex," Nature, 310 (5977), 498-500.
Katz et al. (1990) "Green fluorescent latex microspheres: a new retrograde tracer," Neuroscience, 34 (2), 511-20.
Keeler et al. (2017) "Gene Therapy 2017: Progress and Future Directions," Clin Transl Sci 10, 242-248.
Klemm et al. (1999) "Ring-opening polymerization of heterocycles bearing substituted and unsubstituted exo-methylene groups—a review," Acta Polymerica 50, 1-19.
Klionsky et al. (2016) "Guidelines for the use and interpretation of assays for monitoring autophagy (3rd edition)," Autophagy 12, 1-222.
Kovačević et al. (2004) "A Three-dimensional MRI Atlas of the Mouse Brain with Estimates of the Average and Variability," Cerebral Cortex 15, 639-645.
Kumar et al. (2016) "Clinical development of gene therapy: results and lessons from recent successes," Mol Ther Methods Clin Dev 3, 16034-16034.
Kumar et al. (2017) "Nanotechnology for Neuroscience: Promising Ap-proaches for Diagnostics, Therapeutics and Brain Activity Mapping," Advanced Functional Materials, 27 (39), 1700489.
Kuramoto et al. (2017) "Individual mediodorsal thalamic neurons pro-ject to multiple areas of the rat prefrontal cortex: A single neuron-tracing study using virus vectors," Journal of Com-parative Neurology, 525 (1), 166-185.
Lai et al. (2017) "Chemical Probes for Visualizing Intact Animal and Human Brain Tissue," Cell Chemical Biology, 24 (6), 659-672.
Levine et al. (2013) "Peptide functionalized nanoparticles for nonviral gene delivery," Soft Matter 9, 985-1004.
Lewis et al. (1992) "Human immunodeficiency virus infection of cells arrested in the cell cycle," The EMBO Journal 11, 3053-3058.
Li et al. (2017) "A distinct entorhinal cortex to hippocampal CA1 direct circuit for olfactory associative learning," Nature Neuroscience, 20, 559.
Lin et al. (2014) "Genome dynamics of the human embryonic kidney 293 lineage in response to cell biology manipulations," Nature communications, 5, 4767.
Loehr et al. (2000) "Gene Gun-Mediated DNA Immunization Primes Development of Mucosal Immunity against Bovine Herpesvirus 1 in Cattle," Journal of Virology 74, 6077-6086.
Maheswaran et al. (2009) "Longitudinal regional brain volume changes quantified in normal aging and Alzheimer's APPxPS1 mice using MRI," Brain Research 1270, 19-32.
Morse et al. (Feb. 2020) "Neuron labeling with rhodamine-conjugated Gd-based MRI contrast agents delivered to the brain via focused ultrasound, " Theranostics; 10(6):2659-2674. doi:10.7150/thno.42665.
Naser et al. (2013) "Advanced Glycation End Products Acutely Impair Ca2+ Signaling in Bovine Aortic Endothelial Cells," Frontiers in Physiology 4.
Neumann et al. (1982) "Gene transfer into mouse lyoma cells by electroporation in high electric fields," The EMBO Journal 1, 841-845.
Niforou et al. (2008) "The Proteome Profile of the Human Osteosarcoma U2OS Cell Line," Cancer Genomics —Proteomics 5, 63-77.
Nishiyama et al. (2006) "Current state, achievements, and future prospects of polymeric micelles as nanocarriers for drug and gene delivery," Pharmacology & Therapeutics 112, 630-648.
Noble-Vranish et al. (2018) "Ultrasound-Mediated Gene Therapy in Swine Livers Using Single-Element, Multi-lensed, High-Intensity Ultrasound Transducers," Molecular Therapy—Methods & Clinical Development 10, 179-188.
Oh et al. (2014) "A mesoscale connectome of the mouse brain," Nature 508, 207-214.
Palivan et al. (2016) "Bioinspired polymer vesicles and membranes for biological and medical applications," Chemical Society Reviews 45, 377-411.
Pan et al. (2018) "Facile Synthesis of Gadolinium Chelate-Conjugated Polymer Nanoparticles for Fluorescence/Magnetic Resonance Dual-Modal Imaging," Anal. Chem. 90, 3, 1992-2000.
Paulke et al. (1992) "Synthesis of nanoparticles for brain cell labelling in vivo," Acta Polymerica 43, 288-291.
Peterson et al. (2018) "Cell and Gene Therapy for HIV Cure" in HIV-1 Latency, G. Silvestri, M. Lichterfeld, Eds. (Springer International Publishing, Cham, 2018), 10.1007/82_2017_71, pp. 211-248.
Pierre et al. (2014) "Contrast agents for MRI: 30+ years and where are we going?," JBIC Journal of Biological Inorganic Chemistry 19, 127-131.
Pozebon et al. (2017) "Recent applications of laser ablation inductively coupled plasma mass spectrometry (LA-ICP-MS) for biological sample analysis: a follow-up review," Journal of Analytical Atomic Spectrometry 32, 890-919.
Proetto et al. (2016) "Cellular Delivery of Nanoparticles Revealed with Combined Optical and Isotopic Nanoscopy," ACS Nano 10, 4046-4054, doi:10.1021/acsnano.5b06477.
Ramamoorth et al. (2015) "Non viral vectors in gene therapy—an overview," J Clin Diagn Res 9, GE01-GE06.
Randolph et al. (2016) "Polymeric Gd-DOTA amphiphiles form spherical and fibril-shaped nanoparticle MRI contrast agents," Chem. Sci., 7, 4230-4236.

(56) References Cited

OTHER PUBLICATIONS

Reisch et al. (2016) "Fluorescent Polymer Nanoparticles Based on Dyes: Seeking Brighter Tools for Bioimaging," small, 12, No. 15, 1968-1992.
Riddle et al. (1995) "NT-4-mediated rescue of lateral geniculate neurons from effects of monocular deprivation," Nature, 378, 189.
Roy et al. (2005) "Axonal transport defects: a common theme in neurodegenerative diseases," Acta Neuropathologica 109, 5-13.
Sabry et al. (1995) "Axonal transport of tubulin in tit pioneer neurons in situ," Neuron 14, 1247-1256.
Sanford et al. (1987) "Delivery of Substances into Cells and Tissues Using a Particle Bombardment Process," Particulate Science and Technology 5, 27-37.
Shao et al. (2006) "On the hand-over-hand mechanism of kinesin," Proceedings of the National Academy of Sciences 103, 8072-8077.
Shaw et al. (2002) "Preferential transformation of human neuronal cells by human adenoviruses and the origin of HEK 293 cells," The FASEB Journal, 16 (8), 869-871.
Shirley et al. (2014) "Chapter 7—Electroporation Gene Therapy" in Gene Therapy of Cancer (Third Edition), E. C. Lattime, S. L. Gerson, Eds. (Academic Press, San Diego, 2014), pp. 93-106.
Suda et al. (2007) "Hydrodynamic Gene Delivery: Its Principles and Applications," Molecular Therapy 15, 2063-2069.
Thomas et al. (2003) "Progress and problems with the use of viral vectors for gene therapy," Nature Reviews Genetics 4, 346.
Tobita et al. (2000) "Microgel formation in emulsion polymerization," Polymer 41, 481-487.
Tong et al. (2013) "Visible Light Mediated Fast Iterative RAFT Synthesis of Amino-Based Reactive Copolymers in Water at 20° C.," Macromolecular Rapid Communications 34, 1827-1832.
Utama et al. (2012) "Synthesis of hollow polymeric nanoparticles for protein delivery via inverse miniemulsion periphery RAFT polymerization," Chemical Communications 48, 11103-11105.
Utama et al. (2013) "Inverse Miniemulsion Periphery RAFT Polymerization: A Convenient Route to Hollow Polymeric Nanoparticles with an Aqueous Core," Macromolecules 46, 2118-2127.
Utech et al. (2016) "A review of hydrogel-based composites for biomedical applications: enhancement of hydrogel properties by addition of rigid inorganic fillers," Journal of Materials Science 51, 271-310.
Wadas et al. (2010) "Coordinating radiometals of copper, gallium, indium, yttrium, and zirconium for PET and SPECT imaging of disease," Chemical reviews 110, 2858-2902.
Wang et al. (2007) "Area map of mouse visual cortex," Journal of Comparative Neurology 502, 339-357.
Wanke et al. (2016) "Effects of POSS vertex group on structure, thermal and mechanical properties of PMMA/POSS hybrid materials," Polymer Testing 54, 214-222.
Waring (1965) "Complex formation between ethidium bromide and nucleic acids," Journal of Molecular Biology 13, 269-282.
Watkins et al. (2005) "Reporter gene expression in dendritic cells after gene gun administration of plasmid DNA," Vaccine 23, 4247-4256.
Wertz et al. (2015) "Single-cell initiated monosynaptic tracing reveals layer-specific cortical network modules," Science, 349 (6243), 70-74.
Wickel et al. (2003) "Homopolymers and Random Copolymers of 5,6-Benzo-2-methylene-1,3-dioxepane and Methyl Methacrylate: Structural Characterization Using 1D and 2D NMR, " Macromolecules 36, 2397-2403.
Witter et al. (1988) "Entorhinal projections to the hippocampal CA1 region in the rat: An underestimated pathway," Neuroscience Letters, 85 (2), 193-198.
Wold et al. (2013) "Adenovirus vectors for gene therapy, vaccination and cancer gene therapy," Curr Gene Ther 13, 421-433.
Worgall et al. (2014) "Chapter 34—Gene Therapy" in Principles of Tissue Engineering (Fourth Edition), R. Lanza, R. Langer, J. Vacanti, Eds. (Academic Press, Boston, 2014), pp. 657-686.
Yin et al. (2014) "Non-viral vectors for gene-based therapy," Nature Reviews Genetics 15, 541-555.
Ylä-Herttuala et al. (2017) "Cardiovascular Gene Therapy: Past, Present, and Future," Molecular Therapy 25, 1095-1106.
Yu et al. (2009) "Investigation of redox initiators for free radical frontal polymerization," Polymer International 58, 851-857.
Zang (Sep. 2020) "Polymeric Nano-tracers as Tools for Neuroanatomy," PhD thesis.
Zang et al. (Feb. 2020) "Multicolor Polymeric Nanoparticle Neuronal Tracers," ACS Cent. Sci.6, 436-445.
Zhang et al. (1999) "High Levels of Foreign Gene Expression in Hepatocytes after Tail Vein Injections of Naked Plasmid DNA," Human Gene Therapy 10, 1735-1737.
Zhang et al. (2001) "In Vivo Transfection of Lamprey Brain Neurons by Gene Gun Delivery of DNA," Experimental Neurology 167, 304-311.
Zhang et al. (2016) "The evolution of gadolinium based contrast agents: from single-modality to multi-modality," Nanoscale, 8, 10491.
Zhang et al. (Mar. 2019) "Increasing Starch Nanoparticle Content in Emulsion Polymer Latexes," Industrial & Engineering Chemistry Research, 58, 46, 20987-20995.
Zuidam et al. (2000) "Effects of Physicochemical Characteristics of Poly(2-(dimethylamino)ethyl methacrylate)-Based Polyplexes on Cellular Association and Internalization," Journal of Drug Targeting 8, 51-66.

* cited by examiner

FIG. 1A
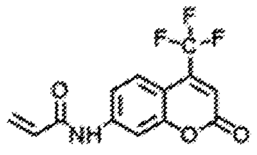
Coumarin Acrylamide
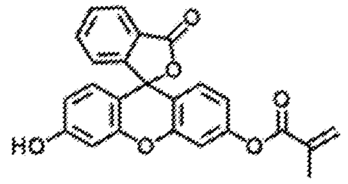
Fluorescein O-methacrylate
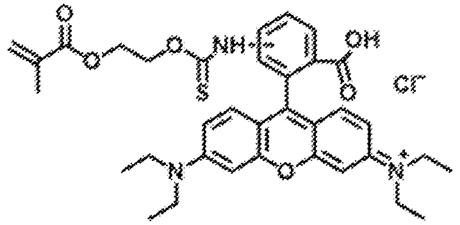
Methacryloxyethyl thiocarbamoyl rhodamine B
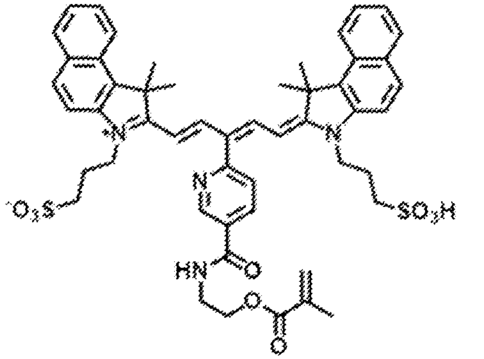
Methacryloxyethyl cyanine 5.5
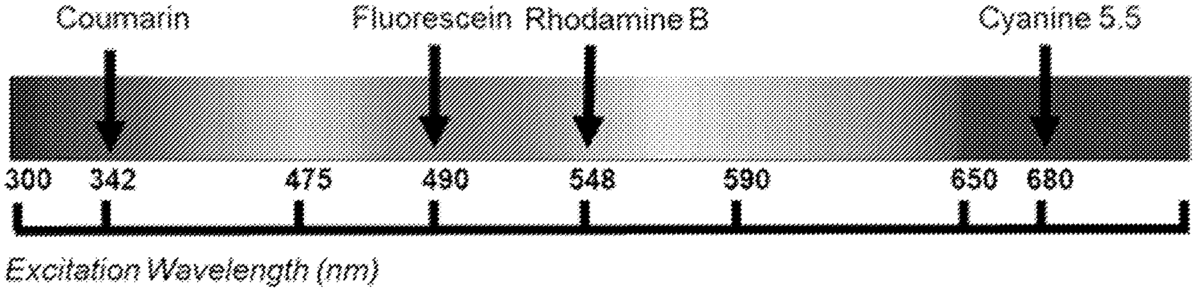
| Dye Monomer | $\lambda_{ex}$ (nm) | $\lambda_{em}$ (nm) |
|---|---|---|
| Coumarin | 342 | 430 |
| Fluorescein | 490 | 520 |
| Rhodamine B | 548 | 570 |
| Cyanine 5.5 | 680 | 700 |
FIG. 1B

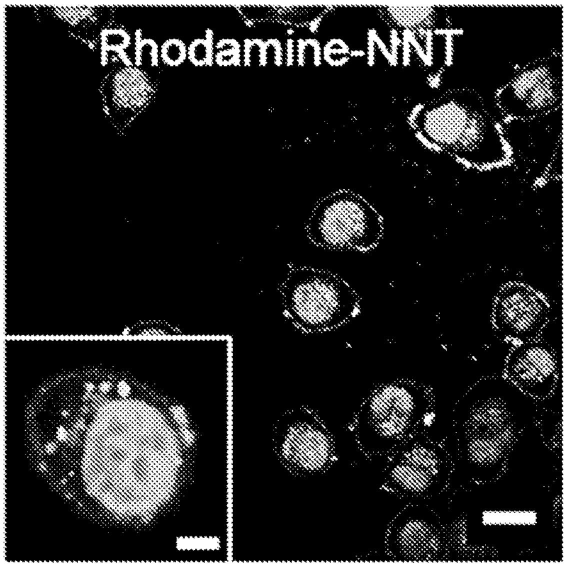
FIG. 2D
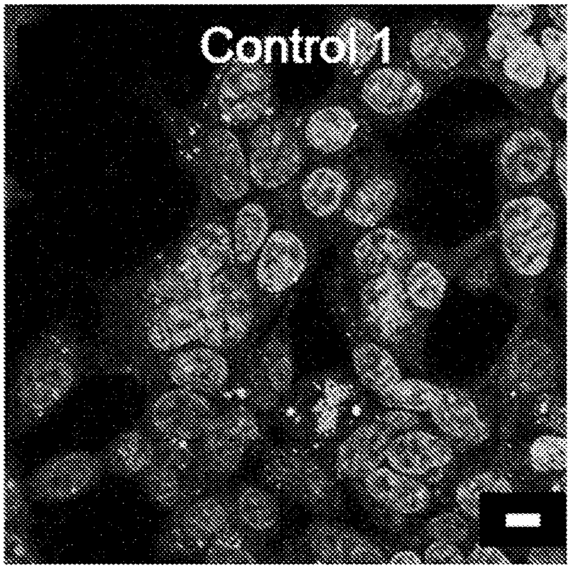
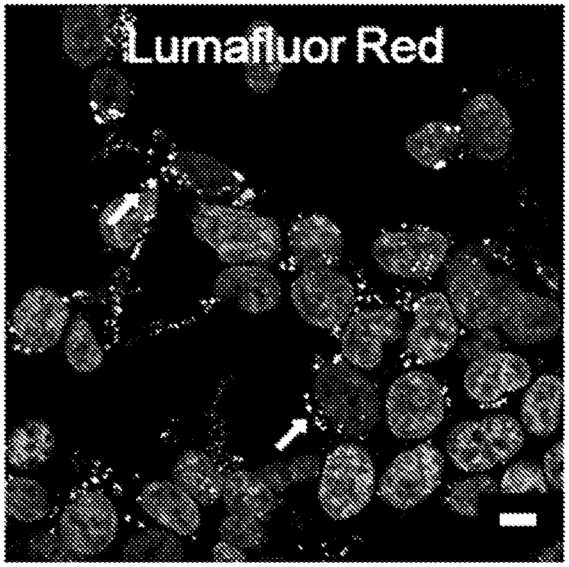
FIG. 3A
FIG. 3B

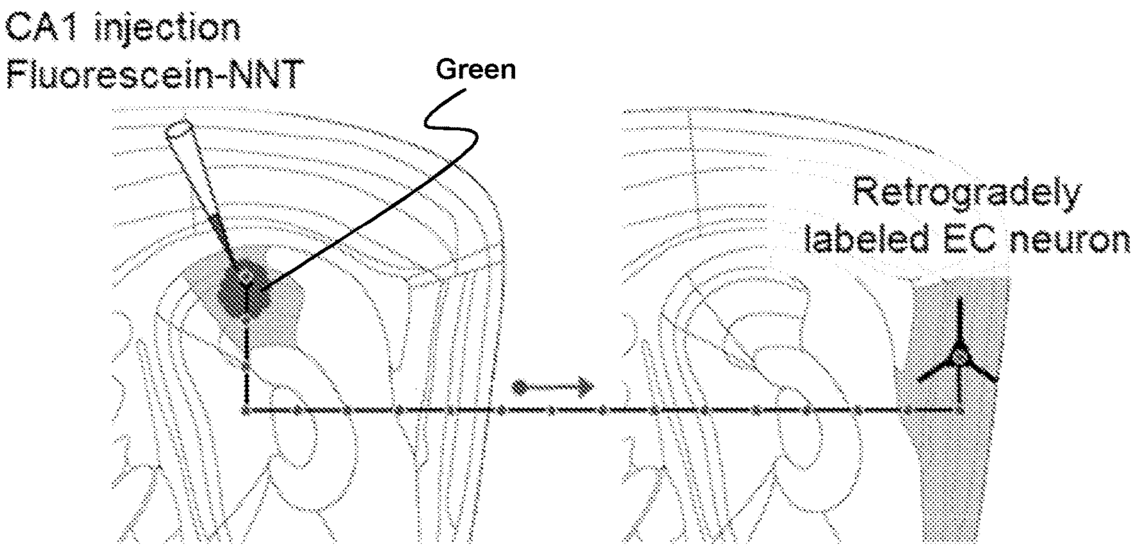
FIG. 5A
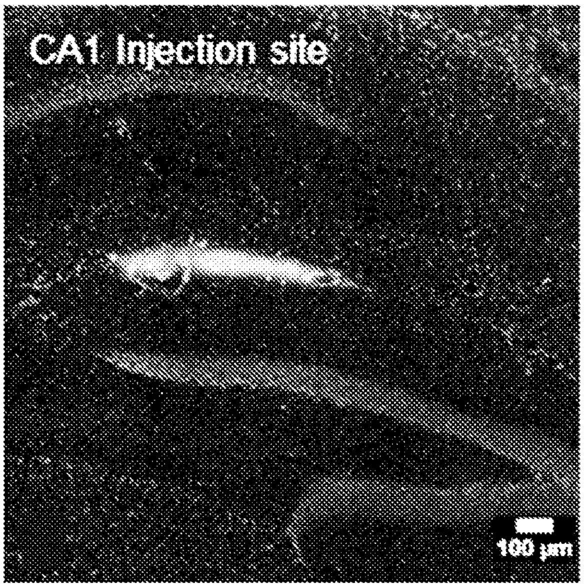
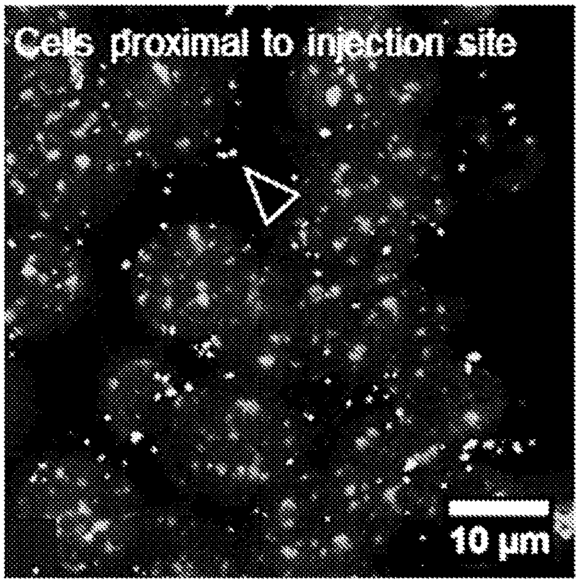
FIG. 5B
FIG. 5C

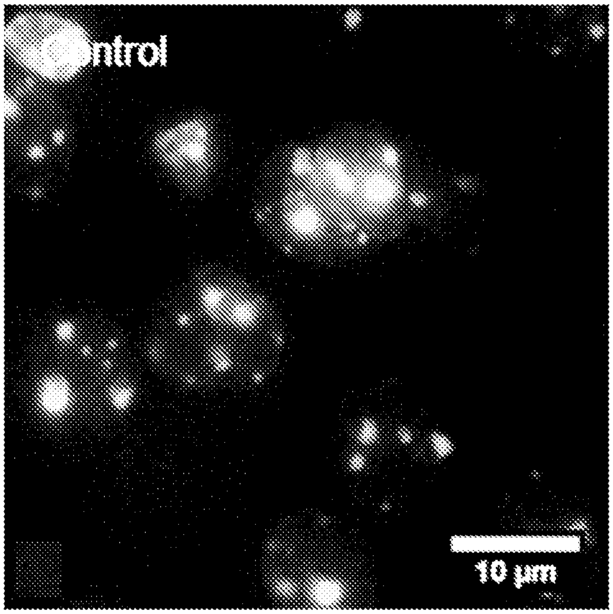
FIG. 5D
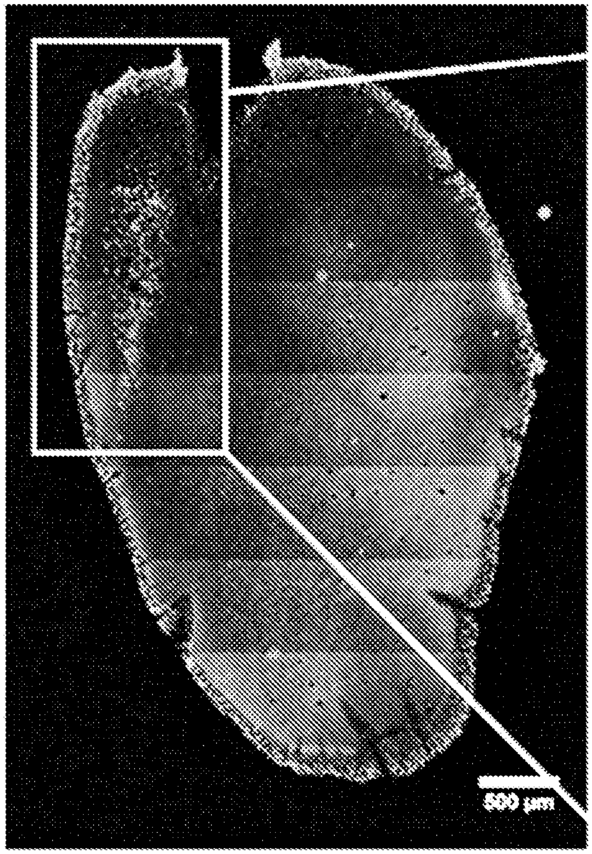
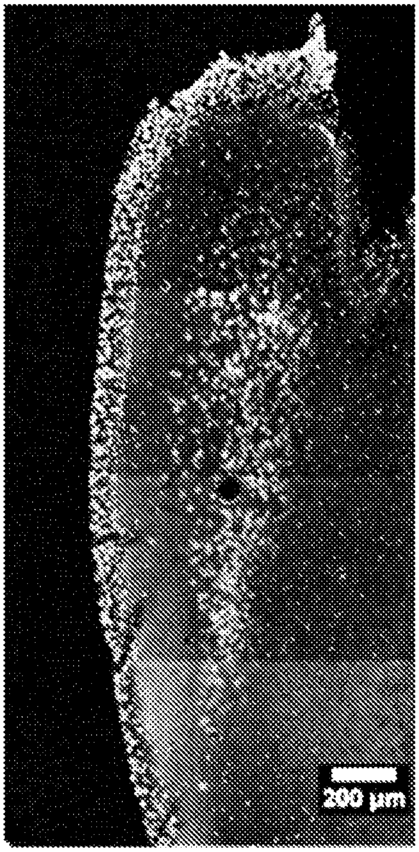
FIG. 5E
FIG. 5F

2

3

1 2 3 4

$$Target\ site\ conc.\,(Gd) = \frac{\boldsymbol{N \cdot k}}{\boldsymbol{M}} \quad \begin{array}{ll} \geq 1 & \text{Yes} \\ < 1 & \text{No} \end{array}$$

$N = How\ much\ nano - tracers\ are\ injected\ (\mu M)$ $k = Transportation\ efficiency (\%)$ $\mathrm{M} = Number\ of\ voxels\ in\ target\ site$

FIG. 55

Mouse: N = 60 $\mu M$

| M \ k | 1% | 10% | 20% | 30% | 40% | 50% | 60% | 70% | 80% | 90% | 100% |
|---|---|---|---|---|---|---|---|---|---|---|---|
| 1 | 0.60 | 6.00 | 12.00 | 18.00 | 24.00 | 30.00 | 36.00 | 42.00 | 48.00 | 54.00 | 60.00 |
| 10 | 0.06 | 0.60 | 1.20 | 1.80 | 2.40 | 3.00 | 3.60 | 4.20 | 4.80 | 5.40 | 6.00 |
| 20 | 0.03 | 0.30 | 0.60 | 0.90 | 1.20 | 1.50 | 1.80 | 2.10 | 2.40 | 2.70 | 3.00 |
| 30 | 0.02 | 0.20 | 0.40 | 0.60 | 0.80 | 1.00 | 1.20 | 1.40 | 1.60 | 1.80 | 2.00 |
| 40 | 0.02 | 0.15 | 0.30 | 0.45 | 0.60 | 0.75 | 0.90 | 1.05 | 1.20 | 1.35 | 1.50 |
| 50 | 0.01 | 0.12 | 0.24 | 0.36 | 0.48 | 0.60 | 0.72 | 0.84 | 0.96 | 1.08 | 1.20 |
| 60 | 0.01 | 0.10 | 0.20 | 0.30 | 0.40 | 0.50 | 0.60 | 0.70 | 0.80 | 0.90 | 1.00 |
| 70 | 0.01 | 0.09 | 0.17 | 0.26 | 0.34 | 0.43 | 0.51 | 0.60 | 0.69 | 0.77 | 0.86 |
| 80 | 0.01 | 0.08 | 0.15 | 0.23 | 0.30 | 0.38 | 0.45 | 0.53 | 0.60 | 0.68 | 0.75 |
| 90 | 0.01 | 0.07 | 0.13 | 0.20 | 0.27 | 0.33 | 0.40 | 0.47 | 0.53 | 0.60 | 0.67 |
| 100 | 0.01 | 0.06 | 0.12 | 0.18 | 0.24 | 0.30 | 0.36 | 0.42 | 0.48 | 0.54 | 0.60 |
| 200 | 0.00 | 0.03 | 0.06 | 0.09 | 0.12 | 0.15 | 0.18 | 0.21 | 0.24 | 0.27 | 0.30 |
| 300 | 0.00 | 0.02 | 0.04 | 0.06 | 0.08 | 0.10 | 0.12 | 0.14 | 0.16 | 0.18 | 0.20 |
| 500 | 0.00 | 0.01 | 0.02 | 0.04 | 0.05 | 0.06 | 0.07 | 0.08 | 0.10 | 0.11 | 0.12 |
| 1000 | 0.00 | 0.01 | 0.01 | 0.02 | 0.02 | 0.03 | 0.04 | 0.04 | 0.05 | 0.05 | 0.06 |
| 2000 | 0.00 | 0.00 | 0.01 | 0.01 | 0.01 | 0.02 | 0.02 | 0.02 | 0.02 | 0.03 | 0.03 |
| 5000 | 0.00 | 0.00 | 0.00 | 0.00 | 0.00 | 0.01 | 0.01 | 0.01 | 0.01 | 0.01 | 0.01 |
| 6500 | 0.00 | 0.00 | 0.00 | 0.00 | 0.00 | 0.00 | 0.01 | 0.01 | 0.01 | 0.01 | 0.01 |

FIG. 56

Monkey: N = 60,000 $\mu M$

| M \ k | 1% | 10% | 20% | 30% | 40% | 50% | 60% | 70% | 80% | 90% | 100% |
|---|---|---|---|---|---|---|---|---|---|---|---|
| 32 | 1.88 | 18.75 | 37.50 | 56.25 | 75.00 | 93.75 | 112.50 | 131.25 | 150.00 | 168.75 | 187.50 |
| 64 | 0.94 | 9.38 | 18.75 | 28.13 | 37.50 | 46.88 | 56.25 | 65.63 | 75.00 | 84.38 | 93.75 |
| 128 | 0.47 | 4.69 | 9.38 | 14.06 | 18.75 | 23.44 | 28.13 | 32.81 | 37.50 | 42.19 | 46.88 |
| 256 | 0.23 | 2.34 | 4.69 | 7.03 | 9.38 | 11.72 | 14.06 | 16.41 | 18.75 | 21.09 | 23.44 |
| 512 | 0.12 | 1.17 | 2.34 | 3.52 | 4.69 | 5.86 | 7.03 | 8.20 | 9.38 | 10.55 | 11.72 |
| 1024 | 0.06 | 0.59 | 1.17 | 1.76 | 2.34 | 2.93 | 3.52 | 4.10 | 4.69 | 5.27 | 5.86 |
| 2048 | 0.03 | 0.29 | 0.59 | 0.88 | 1.17 | 1.46 | 1.76 | 2.05 | 2.34 | 2.64 | 2.93 |
| 4096 | 0.01 | 0.15 | 0.29 | 0.44 | 0.59 | 0.73 | 0.88 | 1.03 | 1.17 | 1.32 | 1.46 |
| 8192 | 0.01 | 0.07 | 0.15 | 0.22 | 0.29 | 0.37 | 0.44 | 0.51 | 0.59 | 0.66 | 0.73 |
| 1E+04 | 0.00 | 0.04 | 0.07 | 0.11 | 0.15 | 0.18 | 0.22 | 0.26 | 0.29 | 0.33 | 0.37 |
| 3E+04 | 0.00 | 0.02 | 0.04 | 0.05 | 0.07 | 0.09 | 0.11 | 0.13 | 0.15 | 0.16 | 0.18 |
| 6E+04 | 0.00 | 0.01 | 0.02 | 0.03 | 0.04 | 0.05 | 0.05 | 0.06 | 0.07 | 0.08 | 0.09 |
| 1E+05 | 0.00 | 0.00 | 0.01 | 0.01 | 0.02 | 0.02 | 0.03 | 0.03 | 0.04 | 0.04 | 0.05 |
| 2E+05 | 0.00 | 0.00 | 0.00 | 0.01 | 0.01 | 0.01 | 0.01 | 0.02 | 0.02 | 0.02 | 0.02 |
| 5E+05 | 0.00 | 0.00 | 0.00 | 0.00 | 0.00 | 0.01 | 0.01 | 0.01 | 0.01 | 0.01 | 0.01 |
| 1E+06 | 0.00 | 0.00 | 0.00 | 0.00 | 0.00 | 0.00 | 0.00 | 0.00 | 0.00 | 0.01 | 0.01 |
| 2E+06 | 0.00 | 0.00 | 0.00 | 0.00 | 0.00 | 0.00 | 0.00 | 0.00 | 0.00 | 0.00 | 0.00 |
| 4E+06 | 0.00 | 0.00 | 0.00 | 0.00 | 0.00 | 0.00 | 0.00 | 0.00 | 0.00 | 0.00 | 0.00 |
| 6E+06 | 0.00 | 0.00 | 0.00 | 0.00 | 0.00 | 0.00 | 0.00 | 0.00 | 0.00 | 0.00 | 0.00 |

FIG. 58

*The product is water, oxygen, and heat sensitive; therefore it was used without further purification.* w+x+y=20

Tween 20

Triton X-100

RETROGRADE NEURONAL TRACERS DETECTABLE BY FLUORESCENCE AND OTHER IMAGING METHODS

CROSS-REFERENCE TO RELATED APPLICATIONS

This application is a U.S. National Stage Application under 35 U.S.C. § 371 of International Application No. PCT/US2021/017874, filed Feb. 12, 2021, which claims the benefit of priority to U.S. Provisional Patent Application No. 62/976,485, filed Feb. 14, 2020, each of which is hereby incorporated by reference in its entirety.

BACKGROUND

Deciphering the targets of axonal projections plays a pivotal role in interpreting neuronal function and pathology. Neuronal tracers are indispensable tools for uncovering the functions and interactions between different subregions of the brain. To visualize and map the anatomical connections in the brain, neuronal tracers (Wertz et al., Science, 349, 70-74 (2015)) typically are injected into a brain region, where they are locally taken up by neurons and transported either in a retrograde fashion (from axon to soma) or in the anterograde direction (from soma to axon). However, the selection of commercially available neuronal tracers is inadequate, currently limited to small molecule dyes, viruses, and a handful of synthetic nanoparticles (Katz et al., Nature, 310, 498-500 (1984); Katz et al., Neuroscience, 34, 511-520 (1990)).

Among these options, non-viral tracers are promising, as they have tunable parameters that bypass inherent pitfalls of viral tracers, but which also have high stability and biosafety (Huh et al., Expert Opinion on Biological Therapy, 10, 763-772 (2010)). Synthetic latex particles are particularly promising with distinct advantages over other neuronal tracers, including exclusive retrograde transportation, low toxicity, high stability, and minimal diffusion from the injection site (Katz, The Journal of Neuroscience, 7, 1223-1249 (1987)). Latex particles containing fluorophores are especially advantageous, affording the ability to observe the particle's path via fluorescence. Although the utility of fluorescent latex particles in identifying a neuron's axonal targets has been demonstrated, neuroscience remains limited to two types of fluorescent synthetic latex particles as retrograde neuronal tracers, each type possessing only one emission wavelength (Katz 1984; Katz 1990). Since a single axon can project to numerous regions, two wavelengths are insufficient to characterize neural anatomy. Additionally, spectral overlap with other fluorescent tools may preclude using one or both of the available excitation and/or emission wavelengths. Moreover, existing fluorescent latex particles are limited to a specific portion of the electromagnetic spectrum, such as from about 490 nm to about 550 nm. Such limitations render some otherwise simple experiments impossible.

Currently available neural tracers are also problematic in other respects. For example, some fluorescent latex particles noncovalently encapsulate fluorophores, which can lead to leakage and imaging imprecision. In addition, other fluorescent latex particles are only functionalized with fluorophores on the outer surface of a particle, which limits the fluorophore amount to the available surface area and could result in insufficient fluorophore to be detectable. Moreover, there is a lack of neuronal tracers that can be imaged or interrogated via methods other than fluorescence, or that can be imaged or interrogated with multiple methods.

As a result, there is a need for neuronal tracers, as well as improved methods of making and using these neuronal tracers. The invention described herein is directed to these, as well as other, important goals.

SUMMARY

Provided herein is a composition comprising:

a first fluorophore moiety, and nanoparticles, wherein the nanoparticles comprise:

a first plurality of a first nanoparticle, the first nanoparticle comprising:

a first outer surface, a first interior bulk, and a first polymer, wherein the first polymer is covalently bonded to the first fluorophore moiety within the first interior bulk of the first nanoparticle.

In some aspects, the nanoparticles are prepared by a process comprising emulsion polymerization of a mixture comprising:

a vinyl-containing first fluorophore, and at least one vinyl-containing monomer, wherein the first fluorophore moiety is derived from the vinyl-containing first fluorophore.

In some aspects, the composition further comprises a second fluorophore moiety having a different emission maximum than the first fluorophore moiety, wherein the nanoparticles further comprise:

a second plurality of a second nanoparticle, the second nanoparticle comprising:

a second outer surface, a second interior bulk, and a second polymer, wherein the second polymer is covalently bonded to the second fluorophore moiety within the second interior bulk of the second nanoparticle.

In some aspects, the first nanoparticle is substantially free of a fluorophore moiety other than the first fluorophore moiety. In some aspects, the second nanoparticle is substantially free of a fluorophore moiety other than the second fluorophore moiety. In some aspects, the first nanoparticle further comprises the second fluorophore moiety. In some aspects, the second nanoparticle further comprises the first fluorophore moiety.

In some aspects, the nanoparticles are prepared by a process comprising emulsion polymerization of a mixture comprising: a vinyl-containing first fluorophore, a vinyl-containing second fluorophore, and at least one vinyl-containing monomer, wherein the first fluorophore moiety is derived from the vinyl-containing first fluorophore and the second fluorophore moiety is derived from the vinyl-containing second fluorophore.

In some aspects, the first plurality of the first nanoparticle is prepared by a process comprising emulsion polymerization of a first mixture comprising:

a vinyl-containing first fluorophore, and at least one vinyl-containing monomer, thereby producing a first composition comprising the first plurality of the first nanoparticle, wherein the first fluorophore moiety is derived from the vinyl-containing first fluorophore, the second plurality of the second nanoparticle is prepared by a process comprising emulsion polymerization of a second mixture comprising:

a vinyl-containing second fluorophore, and at least one vinyl-containing monomer, thereby producing a second composition comprising the second plurality of the second nanoparticle, wherein the second fluorophore moiety is derived from the vinyl-containing second fluorophore, and the composition is prepared by a process comprising combining the first composition and the second composition.

In some aspects, disclosed is a method of brain mapping or tracing an axonal projection, the method comprising: subjecting a first neuron to the composition to form a first infused neuron, and imaging the first infused neuron using at least one of fluorescence spectroscopy, magnetic resonance imaging (MRI), positron emission tomography (PET), single-photon emission computerized tomography (SPECT), or any combination thereof.

In some aspects, disclosed is a composition comprising:

a chelate moiety, and nanoparticles, wherein the nanoparticles comprise:

a plurality of a chelate nanoparticle, the chelate nanoparticle comprising:

an outer surface, an interior bulk, and a polymer, wherein the polymer is covalently bonded to the chelate moiety within the interior bulk of the chelate nanoparticle.

In some aspects, the chelate moiety comprises a magnetic resonance imaging (MRI) contrast agent, a positron emission tomography (PET) contrast agent, a single-photon emission computerized tomography (SPECT) contrast agent, or any combination thereof.

In some aspects, the nanoparticles are prepared by a process comprising emulsion polymerization of a mixture comprising: a vinyl-containing chelate group, and at least one vinyl-containing monomer, wherein the chelate moiety is derived from the vinyl-containing chelate group. In some aspects, the mixture further comprises a fluorophore moiety, wherein the fluorophore moiety is covalently bonded to the polymer within the interior bulk of the chelate nanoparticle.

In some aspects, disclosed is a method of brain mapping or tracing an axonal projection, the method comprising: subjecting a first neuron to the composition (comprising a chelate moiety and optionally a fluorophore moiety) to form a first infused neuron, and imaging the first infused neuron using at least one of fluorescence spectroscopy, magnetic resonance imaging (MRI), positron emission tomography (PET), single-photon emission computerized tomography (SPECT), or any combination thereof.

Also disclosed herein is a method of preparing a composition comprising nanoparticles, the method comprising:

emulsion polymerizing a mixture comprising:

at least one vinyl-containing monomer, and at least one vinyl-containing fluorophore or at least one vinyl-containing chelate group, wherein the nanoparticles comprise:

polymer, at least one fluorophore moiety or at least one chelate moiety, and wherein the at least one fluorophore moiety, if present, is covalently bonded to the polymer, the at least one chelate moiety, if present, is covalently bonded to the polymer.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an aspect of the invention can nonetheless be operative and useful.

BRIEF DESCRIPTION OF THE DRAWINGS

FIGS. 1A-1D: Dye-labeled polymeric nanoparticle neuronal tracers (NNTs). FIG. 1A: Chemical structures of the four fluorescent dye monomers. FIG. 1B: Spectrum overview of the four dye monomers and their excitation and emission maxima. FIG. 1C: Dry-state, uranyl acetate stained transmission electron microscopy (TEM) images, white scale bars=500 nm. FIG. 1D: Cryogenic electron microscopy (cryo-EM) images, black scale bars=100 nm. Black arrows indicate NNTs and white arrows indicate ice.

FIGS. 2A-2D: Cellular uptake of NNTs in HEK 293 cells at 1 h and 24 h as quantified from confocal laser scanning microscopy images and representative images. Mean fluorescence intensity (FIG. 2A) of commercial fluorescent tracers and all 4 NNTs at 1 h and 24 h were quantified from confocal images. Data is presented as mean±SD (n=3). Confocal images show the cells with 24 h treatment with DMEM media only (FIG. 2B), LUMAFLUOR RED (FIG. 2C) and Rhodamine-NNT (FIG. 2D) (see FIGS. 15-16 for other NNTs). Scale bars=20 μm. Inset scale bars=5 μm. In FIGS. 2B-2D, nuclei were stained with DAPI, cell membranes were stained with Wheat Germ Agglutinin, Alexa FLUOR 488 Conjugate. HEK 293 cells were cultured for 24 h, incubated with DMEM media or LUMAFLUOR RED or NNTs for 20 min, washed three times with Dulbecco's Phosphate-Buffered Saline (DPBS), and maintained in fresh media. Significance was determined by an unpaired t-test (*$p<0.05$, $p<0.01$, ns=not significant). At 24 h, all NNTs were not statistically significantly different from one another. For this test, see FIG. 18**.

FIGS. 3A-3H: Colocalization of NNTs with lysosome (FIGS. 3A-3D) and autophagosome (FIGS. 3E-3H) in HEK 293 cells. Representative confocal laser scanning microscopy images after 48 h of cells incubated with media only (FIGS. 3A and 3E), LUMAFLUOR RED (FIGS. 3B and 3F), or Rhodamine-NNT (FIGS. 3C and 3G) (see FIGS. 19-22 and FIGS. 24-27 for other NNTs). Scale bars=10 μm. Percent colocalization with the lysosomes (FIG. 3D) and autophagosomes (FIG. 3H) was quantified from confocal images. Data is presented as mean±SD (n=3). Nuclei of HEK 293 cells were stained with DAPI (blue). In FIGS. 3A-3C, lysosomes were stained with LYSOTRACKER GREEN DND-26 (green). In FIGS. 3E-3G, autophagosomes were immunostained with LC3 antibody with Anti-rabbit IgG (H+L), F(ab')2 Fragment conjugated with ALEXA FLUOR 488. Colocalization is depicted in orange (red and green merge).

FIGS. 5A-5G: Retrograde transport of Fluorescein-NNT in vivo. FIG. 5A: Schematic shows particles injected into the *Cornu Ammonis* (CA1) region in the hippocampus traveling down axons to cell bodies located in the entorhinal cortex (EC). FIG. 5B: Sagittal section of the mouse CA1 region after injection. Green indicates Fluorescein-NNT while blue indicates DAPI stained nuclei. FIG. 5C: Fluorescence image of the area proximal to the injection site. Arrow points to cluster of Fluorescein-NNT. FIG. 5D: No unequivocal labeling in the somatosensory cortex. FIG. 5E: Representative mouse brain sections show EC seen under fluorescence microscopy. FIG. 5F: Zoom of FIG. 5E. FIG. 5G: EC labeled by Fluorescein-NNT. Arrow points to cluster of Fluorescein-NNT proximal to a cell nucleus.

FIG. 6A: Schematic shows particles injected into the visual cortex (V1) travel millimeters down axons to cell bodies located in the primary thalamic nuclei for vision—the lateral geniculate nucleus (LGN). FIG. 6B: First column: Coronal section of mouse visual cortex after NNT injection; Second column: Labeling of the ipsilateral cortical nuclei adjacent to the injection site; Third column: Thalamic labeling by NNTs after injection into mouse visual cortex; Fourth column: No unequivocal labeling of contralateral thalamic area. Each row corresponds to a different fluorescent label on NNTs. In FIG. 6B, scale bars in panels 1A, 2A, 3A, 4A and 5A=100 μm; scale bars in panels 1B-1D, 2B-2D, 3B-3D, 4B-4D and 5B-5D=10 μm.

FIGS. 8A-8B: UV-vis and Fluorescence spectra LUMAFLUOR RED and LUMAFLUOR GREEN. The excitation wavelengths are 520 and 440 nm for LUMAFLUOR RED and LUMAFLUOR GREEN. FIGS. 8C-8D: DLS of LUMAFLUOR RED and LUMAFLUOR GREEN. FIGS. 8E-8F: Dry-state, uranyl acetate stained transmission electron microscopy (TEM) images.

In FIG. 16A, scale bars in panels 1A-1 D and 2A-2D=20 μm; scale bars in panels 3A-3D=10 μm. In FIG. 16B, all scale bars=20 μm. In FIG. 16C, all scale bars=10 μm.

In FIG. 17B, scale bars in panels 4A-4D and 5A-5D=20 μm; scale bars in panels 6A-6D=10 μm.

In FIG. 21C, scale bars in panels 7A-7D and 9A-9D=10 μm; scale bars in panels 8A-8D=15 μm.

In FIG. 22B, the scale bar in panel 4A=10 um; scale bars in panels 4B-4D=15 μm; all scale bars in panels 5A-5D and 6A-6D=10 μm.

FIG. 38A: SEM Image. FIG. 38B: TEM Image. FIG. 38C: Cryo-EM Image. FIG. 38D: Screenshot from the NTA Video. FIG. 38E: Hydrodynamic Diameter Distributions.

FIG. 43A: Optical Microscopy Image of the Interested Brain Slice. FIG. 43B: Brain Atlas Corresponded to the Interested Brain Slice. FIG. 43C: Fluorescence Image of LGN Area that Corresponds to the Area of Green Box. FIG. 43D: Zn Intensity Distribution Map. FIG. 43E: Gd Intensity Distribution Map.

FIG. 44A: Coronal View. FIG. 44B: Sagittal View.

FIG. 47A: SEM Image. FIG. 47B: Hydrodynamic Diameter Distributions.

FIG. 51A: 3D Printer in UCSD Flow Control & Coordinated Robotics Lab. FIG. 51B: Prototypes.

FIG. 53A: Injection Setup. FIG. 53B: Injection Needle filled with Gd-Cy5.5 Nano-tracers.

FIG. 54A: Gd-Cy5.5 Nano-tracer Was Injected to PCR Tubes Filled with Agarose Gel. FIG. 54B: The MRI images of the Phantom Injections.

FIG. 55: Discrete Mass Transport Equation.

FIG. 56: Gd Concentration at the Target Site with Different combinations of M and k Values in Mouse Model.

FIG. 58: Gd Concentration at the Target Site with Different combinations of M and k Values in Monkey Model.

FIG. 61A: Fluorescein Nano-tracer. FIG. 61B: Rhodamine Nano-tracer. FIG. 61C: Cy5.5 Nano-tracer.

FIG. 63A: EC layer 2a: Position 1. FIG. 63B: EC layer 2b: Position 7. FIG. 63C: EC layer 3: Position 3. FIG. 63D: EC layer 3: Position 5.

FIG. 69A: Coronal section of the mouse V1 region after the injection. Red indicates Rhodamine fluorescence from the nano-tracers while blue indicates DAPI, a stain for cell nuclei. FIG. 69B: Ipsilateral area proximal to the injection site. FIG. 69C: Ipsilateral area of LGN in the thalamus.

FIG. 70A: Coronal section of the mouse V1 region after the injection. Red indicates Rhodamine fluorescence from the nano-tracers while blue indicates DAPI, a stain for cell nuclei. FIG. 70B: Ipsilateral area proximal to the injection site.

FIG. 71A: Ipsilateral area proximal to the injection site. FIG. 71B: Ipsilateral area of LGN in thalamus.

FIG. 72A: Coronal section of the mouse V1 region after the injection. Red indicates Rhodamine fluorescence from the nano-tracers while blue indicates DAPI, a stain for cell nuclei. FIG. 72B: Ipsilateral area proximal to the injection site. FIG. 72C: Ipsilateral area of LGN in the thalamus.

FIG. 73A: Coronal section of the mouse V1 region after the injection. Red indicates Rhodamine fluorescence from the nano-tracers while blue indicates DAPI, a stain for cell nuclei. FIG. 73B: Ipsilateral area proximal to the injection site. FIG. 73C: Ipsilateral area of LGN in the thalamus.

FIG. 83A: SEM Image. FIG. 83B: TEM Image.

FIG. 87A: TEM; FIG. 87B: Cryo-EM.

FIG. 93A: TEM; FIG. 93B: Cryo-EM.

FIG. 96A: LUMAFLUOR Red; FIG. 96B: 0.5 mmol in 5% MeOH Rhodamine Nano-tracers; FIG. 96C: 0.5 mmol in 100% MeOH Rhodamine Nano-tracers; and FIG. 96D: 1.0 mmol in 100% MeOH Rhodamine Nano-tracers.

FIG. 101A: LUMAFLUOR Green; FIG. 101B: 1.1 mM Methacryloyloxy O-fluorescein in 100% Water Nano-tracers; FIG. 101C: 1.1 mM Methacryloyloxy O-fluorescein in 100% THF Nano-tracers; and FIG. 101D: 4.5 mM Methacryloyloxy O-fluorescein in 100% THF Nano-tracers.

FIGS. 106A-106C: PEG diacrylate 250; FIGS. 106D-106F: PEG diacrylate 700.

FIGS. 107A-107C: TRITON X-100; FIGS. 107D-107F: TWEEN 20.

FIG. 108A: 365 nm UV light with 10 ml Reaction Scale; FIG. 108B: 405 nm Blue LED light with 50 ml Reaction Scale.

FIG. 110A: TEM Image. FIG. 110B: Distribution of Hydrodynamic Diameter.

FIG. 111A: TEM Image. FIG. 111B: Distribution of Hydrodynamic Diameter.

FIGS. 112A-112B: TEM Images. FIG. 112C: Distribution of Hydrodynamic Diameter. FIG. 112D: Size Distribution from NTA Measurement.

FIG. 113A: TEM Image. FIG. 113B: Distribution of Hydrodynamic Diameter.

FIG. 114A: TEM Image. FIG. 114B: Distribution of Hydrodynamic Diameter.

FIG. 115A: TEM Image. FIG. 115B: Distribution of Hydrodynamic Diameter.

FIG. 116A: TEM Image. FIG. 116B: Distribution of Hydrodynamic Diameter.

FIGS. 117A-1176: Characterization of MMA and EGD Nano-tracers. FIG. 117A: TEM Image.

Figure 118:
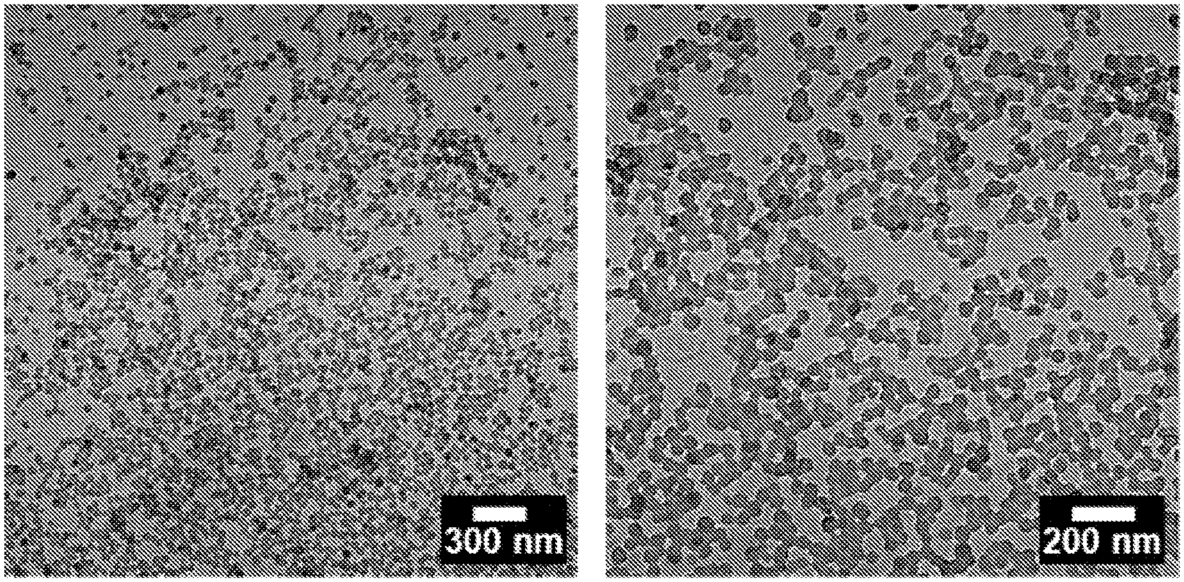

FIG. 118: TEM Images of Nano-tracers with Methacrylamide.

Figure 119:
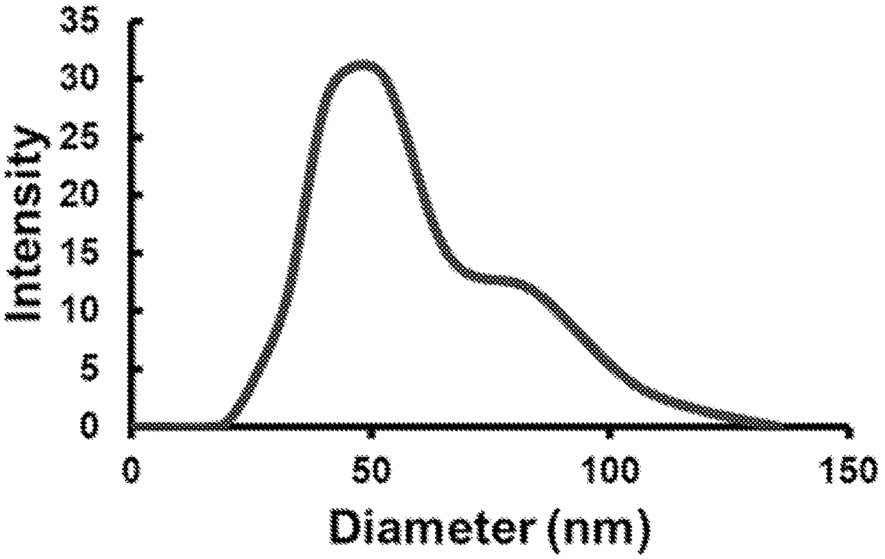

FIG. 119: Distribution of Hydrodynamic Diameter of Nano-tracers with Methacrylamide.

Figure 120:
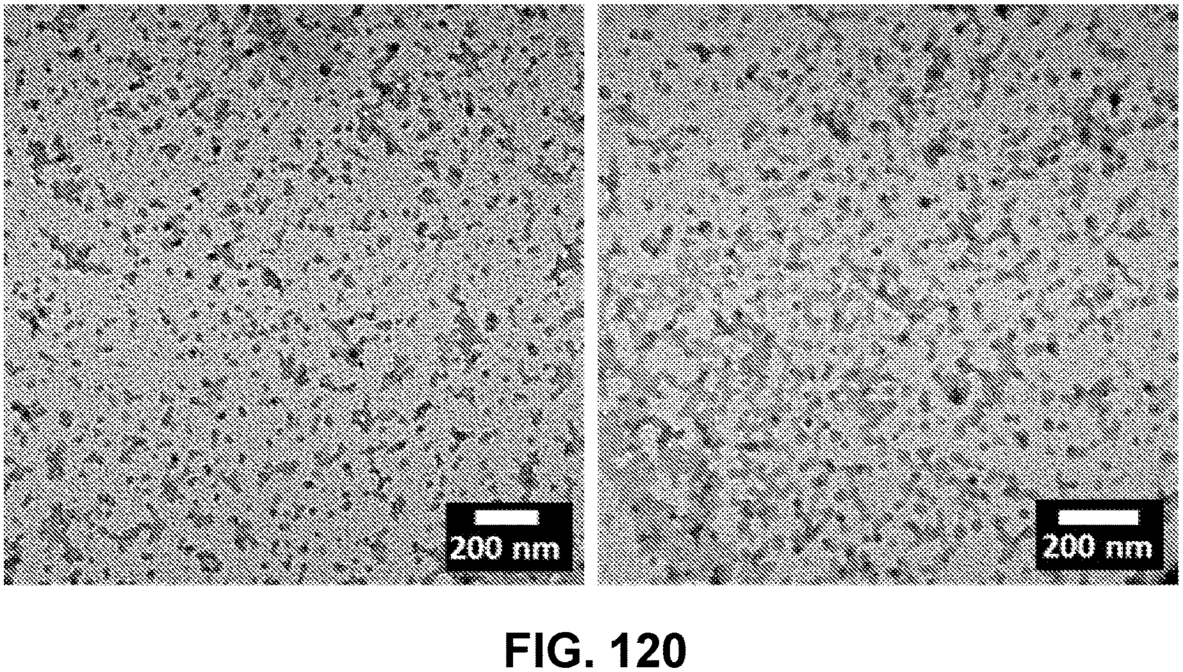

FIG. 120: TEM Images of EPMA Nano-tracers.

Figure 121:
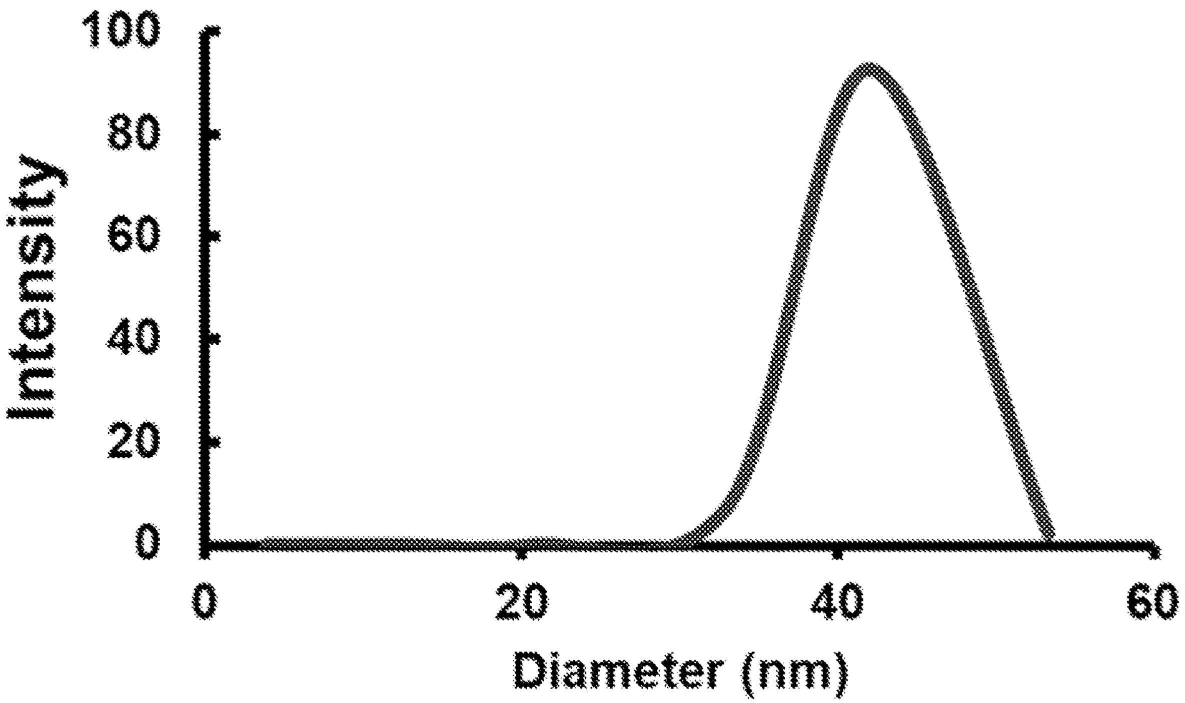

FIG. 121: Distribution of Hydrodynamic Diameter of EPMA Nano-tracers.

STATEMENTS REGARDING CHEMICAL COMPOUNDS AND NOMENCLATURE

In general, the terms and phrases used herein have their art-recognized meaning, which can be found by reference to standard texts, journal references and contexts known to those skilled in the art. The following definitions are provided to clarify their specific use in the context of the invention.

The terms “dye” and “fluorophore” are used interchangeably herein.

The terms “nano-tracer,” “nanotracer,” “nanoparticle,” “microsphere,” “particle,” and the like typically are used interchangeably herein, unless context clearly indicates a more precise definition is intended (e.g., in situations where the term nanoparticle or microsphere is used in a context meant to indicate particle size).

As used herein, the term “retrograde” means transport in a neuron from axon to soma.

As used herein, the term “anterograde” means transport in a neuron from soma to axon.

As used herein, a nanoparticle that is “substantially free of a fluorophore moiety” means that the nanoparticle has an insufficient amount of the fluorophore at issue to observe the fluorescence of that fluorophore under conditions typically used to observe such fluorescence for the relevant application, such as axonal tracing. The same concept is applicable when a nanoparticle is “substantially free of a chelate moiety” concerning detection with a given imaging method (e.g., MRI, PET, or SPECT).

As used herein, the terms “first,” “second,” “third,” and so on are employed to designate and distinguish various terms, but such terms are not intended to imply that a particular number of components is present, unless context clearly indicates otherwise.

In an embodiment, an isolated or purified compound is at least partially isolated or substantially purified as would be understood in the art. In an embodiment, a substantially purified composition, compound or formulation of the invention has a chemical purity of 95%, optionally for some applications 99%, optionally for some applications 99.9%, optionally for some applications 99.99%, and optionally for some applications 99.999% pure.

As used herein, the term “about” means that slight variations from a stated value may be used to achieve substantially the same results as the stated value. In circumstances where this definition cannot be applied or is exceedingly difficult to apply, then the term “about” means a 10% deviation (plus or minus) from the stated value. Also, the disclosure of ranges is intended as a continuous range including every value between the minimum and maximum values recited as well as any ranges that may be formed by such values. Also disclosed herein are any and all ratios (and ranges of any such ratios) that may be formed by dividing a recited numeric value into any other recited numeric value. Accordingly, the skilled person will appreciate that many such ratios, ranges, and ranges of ratios may be unambiguously derived from the numerical values presented herein and in all instances such ratios, ranges, and ranges of ratios represent various embodiments of the present invention.

When disclosing numerical values herein, for example, 1, 2, 3, 4, 5, 6, 7, 8, 9, 10, the following sentence typically follows such numerical values: “Each of the foregoing numbers can be preceded by the term about, ‘at least about,’ or ‘less than about,’ and any of the foregoing numbers can be used singly to describe an open-ended range or in combination to describe a close-ended range.” This sentence means that each of the aforementioned numbers can be used alone (e.g., 4), can be prefaced with the word “about” (e.g., about 8), prefaced with the phrase “at least about” (e.g., at least about 2), prefaced with the phrase “less than about” (e.g., less than about 7), or used in any combination with or without any of the prefatory words or phrases to define a range (e.g., 2 to 9, about 1 to 4, 8 to about 9, about 1 to about 10, and so on). Moreover, when a range is described as “about X or less,” this phrase is the same as a range that is a combination of “about X” and “less than about X” in the alternative. For example, “about 10 or less” is the same as “about 10, or less than about 10.” Such interchangeable range descriptions are contemplated herein. Other range formats may be disclosed herein, but the difference in formats should not be construed to imply that there is a difference in substance.

DETAILED DESCRIPTION

In the following description, numerous specific details of the compounds and methods of the present invention are set forth in order to provide a thorough explanation of the precise nature of the invention. It will be apparent, however, to those of ordinary skill in the art that the invention can be practiced without these specific details.

Synthetic, non-viral neuronal tracers are particularly promising for brain mapping and axonal tracing applications, including latex-based materials. Capitalizing on the tunability of such latex-based materials through alteration of chemical composition broadens the current limited scope of commercially available non-viral neuronal tracer formulations. Of particular interest are those latex nanoparticles that are capable of being imaged by one or more methods, including via fluorescence, magnetic resonance imaging (MRI), positron emission tomography (PET), and single-photon emission computed tomography (SPECT).

Disclosed herein are accessible and scalable retrograde neuronal tracer nanoparticles (e.g., latex) bearing a variety of fluorophores (a so-called “color palette” of neuronal tracers), which nanoparticles are demonstrated to exhibit retrograde transport ability in vivo. In some aspects, this concept is demonstrated by incorporating up to four different fluorophores within the same or different latex neuronal tracers through emulsion polymerization of vinyl modified fluorophores together with, in some aspects, a mixture of methacrylate monomers and, in some aspects, a crosslinker. In some aspects, a single type of fluorophore (e.g., with one emission maximum) is incorporated into a single nanoparticle. In some aspects, multiple types of fluorophores (e.g., with different emission maxim) are incorporated into a single nanoparticle. These various aspects demonstrate the “color palette” available according to the disclosures herein.

Also disclosed herein are nanoparticles (e.g., latex) comprising a chelate moiety that can be used for MRI, PET, and/or SPECT imaging, useful for neuronal tracing and mapping of brain architecture. In some aspects, the nanoparticles comprise a chelate moiety and do not contain a fluorophore moiety. In some aspects, the nanoparticles comprise a fluorophore moiety and do not comprise a chelate moiety. In some aspects, the nanoparticles comprise a chelate moiety and a fluorophore moiety. In some aspects, the nanoparticles comprise one or more fluorophore moieties and a chelate moiety comprising a gadolinium-based MRI contrast agent, allowing for multiple modes of detection. Fluorescently labeled particles foster four different fluorophores that cover a spectral range from about 300 nm to about 800 nm allowing researchers to map the specific areas distinctly, yet in unison. Given these tracers generally do not substantially diffuse in tissue, they can identify cellular resolution pathways that interconnect the brain in vivo. The gadolinium-based MRI contrast agent (Gd-DOTA), an FDA-approved small molecule contrast agent, was modified with a pendant acrylate group allowing for it's easy implementation into fluorescently based tracers, and in turn generating dual-labeled tracers. Further, Gd-DOTA appended with two acrylate functionalities was synthesized as a polymer chain cross-linker to increase the potential Gd concentration in resultant neuronal tracers. These tracers provide the ability to determine neuronal connectivity via MRI, PET, and/or SPECT imaging, optionally in combination with fluorescence imaging, with unprecedented resolution in the whole brain of large animals or even primates in vivo.

In some aspects, disclosed is a composition comprising:

a first fluorophore moiety, and nanoparticles, wherein the nanoparticles comprise:

a first plurality of a first nanoparticle, the first nanoparticle comprising:

a first outer surface, a first interior bulk, and a first polymer, wherein the first polymer is covalently bonded to the first fluorophore moiety within the first interior bulk of the first nanoparticle.

In some aspects, the composition comprises any suitable liquid. In some aspects, the composition comprises water. In some aspects, the composition comprises water, methanol, ethanol, propanol, propylene glycol, glycerol, dimethylformamide (DMF), dimethylsulfoxide (DMSO), or any combination thereof.

In some aspects, the first nanoparticle is made up of a first outer surface, a first interior bulk, and a first polymer. In some aspects, the first nanoparticle is roughly spherical. In some aspects, the first nanoparticle has a first interior bulk makes up the inner portion (e.g., the entire inner portion) of the first nanoparticle that is within the confines of the first outer surface. In some aspects, the first polymer is covalently bonded to the first fluorophore moiety within the first interior bulk of the first nanoparticle. In particular, the first fluorophore moiety is covalently bonded to the first polymer that comprises the first nanoparticle within the interior portion of the first nanoparticle. In some aspects, this covalently bonded nature of the first fluorophore moiety within the first interior bulk of the first nanoparticle results from polymerizing a vinyl-containing first fluorophore along with one or more polymerizable monomers when synthesizing the first nanoparticle, as described elsewhere herein. By preparing a first nanoparticle containing a first fluorophore moiety covalently bonded within its first interior bulk, the first fluorophore moiety is less prone to leakage, or does not leak, from the first nanoparticle, thus resulting in a more stable particle.

In some aspects, the first polymer comprises any suitable polymer. In some aspects, the first polymer is any type of polymer that is biocompatible. For example, a polymer is biocompatible if it can be employed in vivo or ex vivo for its intended purpose (e.g., research, diagnostic, therapeutic, etc.) without substantially hindering the biological processes (e.g., uptake, transport, etc.) necessary to carry out the intended purpose. In some aspects, the first polymer is any type of polymer that can be made by emulsion polymerization. In some aspects, the first polymer is any type of polymer that is biocompatible and can be made by emulsion polymerization. In some aspects, the first polymer comprises a polymer of an unsaturated ester or amide, such as a polyacrylate, a polyacrylic acid, a polymethacrylate, a polymethacrylic acid, a polymethylmethacrylate (PMMA), a polyethylacrylate, a polyethylmethacrylate, a polypropylacrylate, a polypropylmethacrylate, a polybutylacrylate, a polybutyl methacrylate, a poly(hydroxyalkyl)methacrylate (e.g., a poly(2-hydroxyethyl) methacrylate, a poly(3-hydroxypropyl)methacrylate, etc.), a poly(hydroxyalkyl)acrylate (e.g., a poly(2-hydroxyethyl)acrylate, a poly(3-hydroxypropyl)acrylate), a polylaurylacrylate, a polystearylacrylate, a polyglycidylacrylate, a polyglycidyl methacrylate, a polyacrylonitrile, a polyacrylamide, or any combination thereof (i.e., a copolymer of any combination thereof). For example, a copolymer thereof includes PMMA-polymethacrylate, PMMA-polymethacrylate-polyhydroxyethylmethacrylate, polyacrylonitrile-polymethacrylate, and so forth. In some aspects, the first polymer comprises a polymer made of an unsaturated alcohol and/or derivatives thereof, such as a polyvinyl alcohol, a polyvinyl acetate, a polyvinyl butyral, or any combination thereof (i.e., a copolymer thereof). In some aspects, the first polymer can be any combination of polymers disclosed herein, e.g., a copolymer of an unsaturated alcohol, an unsaturated ester, and an unsaturated amide. In some aspects, the first polymer is a copolymer.

In some aspects, the first polymer comprises at least one structure of formula (1) to (6) and (27):

(1)

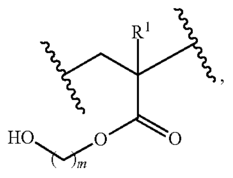

(2)

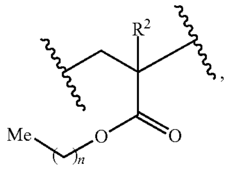

(3)

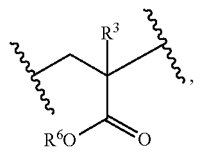

(4)

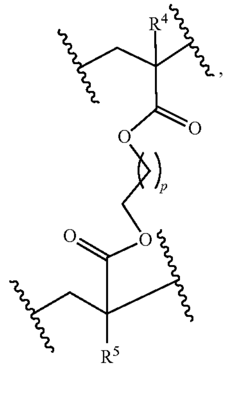

-continued (5)

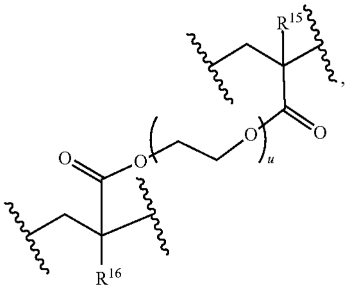

(6)

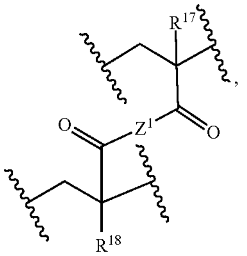

(27)

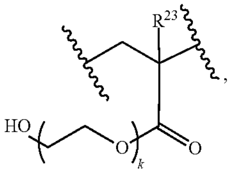

wherein:

m is 2 to 5, n is 0 to 5, k, p, and u independently are 1 to 5, $R^1$, $R^2$, $R^3$, $R^4$, $R^5$, $R^{15}$, $R^{16}$, $R^{17}$, $R^{18}$, and $R^{23}$ independently are H or methyl, $R^6$ is H or a metal ion, and $Z^1$ is a linking group comprising alkyl, aryl, ethylene glycol, oligo(ethylene glycol), poly(ethylene glycol), an amine, an ether, an ester, an amide, an ester when taken together with adjacent atoms, an amide when taken together with adjacent atoms, any substituted version thereof, or any combination thereof.

In some aspects, the first polymer comprises at least one structure of formula (1) to (6) and (27). In these structures, the wavy lines indicate points of covalent attachment within the first polymer. In some aspects, m is 1 to 5, e.g., 1, 2, 3, 4, or 5, or any range made therefrom (e.g., 1 to 4, 2 to 4, 1 to 3, 2 to 5, and so on). In some aspects, n is 0 to 5, e.g., 0, 1, 2, 3, 4, or 5, or any range made therefrom (e.g., 0 to 4, 1 to 4, 1 to 3, 2 to 5, and so on). In some aspects, k, p, and u independently are 1 to 5, e.g., 1, 2, 3, 4, or 5, or any range made therefrom (e.g., 1 to 4, 2 to 4, 1 to 3, 2 to 5, and so on). In some aspects, $R^1$, $R^2$, $R^3$, $R^4$, $R^5$, $R^{15}$, $R^{16}$, $R^{17}$, $R^{18}$, and $R^{23}$ independently are H or methyl. In some aspects, $R^6$ is H or a metal ion. In some aspects, the metal ion comprises an alkali metal, an alkaline earth metal, or a combination thereof. In some aspects, the alkali metal comprises lithium, sodium, potassium, rubidium, cesium, or any combination thereof. In some aspects, the alkaline earth metal comprises beryllium, magnesium, calcium, or any combination thereof. In some aspects, $Z^1$ is any suitable linking group. As used herein, a suitable linking group is one that covalently connects the two carbonyl functionalities on either end of the structure of formula (6). In some aspects, the linking group $Z^1$ comprises alkyl, aryl, ethylene glycol, oligo(ethylene glycol), poly(ethylene glycol) (e.g., polyethyleneglycol 250, or polyethyleneglycol 700), an amine, an ether, an ester, an amide, an ester when taken together with adjacent atoms, an amide when taken together with adjacent atoms, any substituted version thereof, or any combination thereof. For example, in some aspects, the linking group $Z^1$ comprises an alkyl in combination with two amine functionalities, such that $Z^1$ comprises a diamide when taken together with the two adjacent carbonyls shown in the structure of formula (6). In some aspects, a similar linking group is contemplated, but instead of a diamide the linking group is a diester. Other linking groups that can be made using the combination of disclosed options is contemplated herein and generally known.

In some aspects, the first polymer is a copolymer. In some aspects, the copolymer comprises at least two of the structures of formulas (1), (2), (3), (4), (5), (6), and (27). In some aspects, the copolymer comprises the three structures of formulas (1) to (3). In some aspects, the copolymer comprises the four structures of formulas (1) to (4). In some aspects, the copolymer comprises the four structures of formulas (1) to (3) and (5). In some aspects, the copolymer comprises the four structures of formulas (3) to (5) and (27).

In some aspects, with regard to the structures of formulas (1) to (4) and (27), at least one of conditions (a) to (e) is satisfied: (a) m is 2, (b) n is 0, (c) p is 1, (d) $R^1$, $R^2$, $R^3$, $R^4$, and $R^5$ are methyl, or (e) all of conditions (a) to (d) are satisfied. In some aspects, the first polymer comprises the four structures of formulas (1) to (4), and at least one of conditions (a) to (e) is satisfied: (a) m is 2, (b) n is 0, (c) p is 1, (d) $R^1$, $R^2$, $R^3$, $R^4$, and $R^5$ are methyl, or (e) all of conditions (a) to (d) are satisfied. In some aspects, the first polymer comprises the four structures of formulas (1) to (4), and (a) m is 2, (b) n is 0, (c) p is 1, and (d) $R^1$, $R^2$, $R^3$, $R^4$, and $R^5$ are methyl.

In some aspects, the composition is a latex composition. In some aspects, the composition is a synthetic latex composition. In some aspects, the composition is a dispersion of polymer particles in a liquid. In some aspects, the composition is a stable dispersion of polymer particles in a liquid. In some aspects, the liquid comprises water. In some aspects, the composition is an emulsion of polymer particles in a liquid. In some aspects, the composition is a stable emulsion of polymer particles in a liquid. In some aspects, the liquid comprises water. In some aspects, the composition is a colloidal dispersion of polymer particles in a liquid. In some aspects, the liquid comprises water.

In some aspects, the first fluorophore moiety is a moiety that emits light at a given wavelength in response to excitation at a given wavelength of light. In some aspects, the emitted light is in the visible spectrum. In some aspects, the emitted light has a wavelength of about 300 nm to about 800 nm. In some aspects, first fluorophore moiety comprises coumarin, fluorescein, rhodamine, rhodamine B, cyanine, cyanine 5.5, or cyanine 7. In some aspects, the first fluorophore moiety comprises coumarin. In some aspects, the first fluorophore moiety comprises fluorescein. In some aspects, the first fluorophore moiety comprises rhodamine B. In some aspects, the first fluorophore moiety comprises cyanine 5.5. In some aspects, the first fluorophore moiety comprises cyanine 7.

In some aspects, the first fluorophore moiety comprises at least one structure of formula (15) to (18) and (23):

(15)

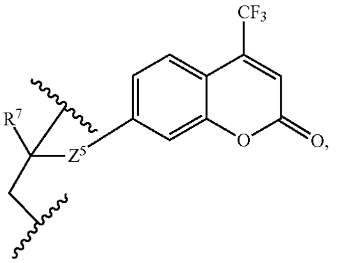

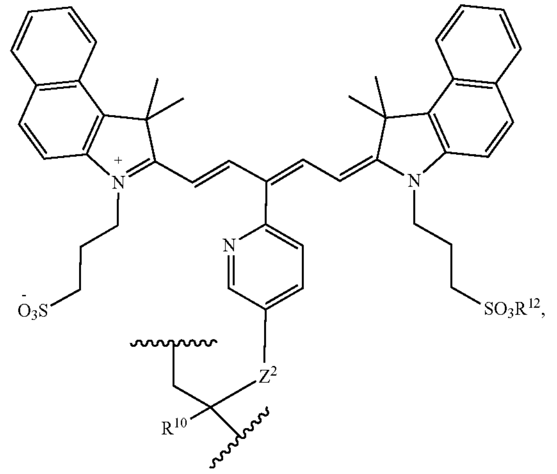

(18)

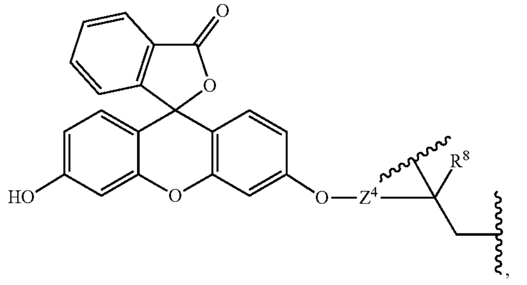

(23)

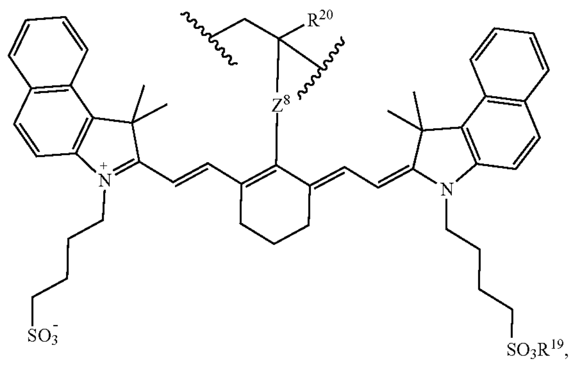

wherein:

$R^7$, $R^8$, $R^9$, $R^{10}$, and $R^{20}$ independently are H or methyl,
$R^{11}$, $R^{12}$, and $R^{19}$ independently are H or a metal ion, and
$Z^2$, $Z^3$, $Z^4$, $Z^5$, and $Z^8$ independently are a linking group comprising alkyl, aryl, ethylene glycol, oligo(ethylene glycol), an amine, an ether, an ester, an amide, a thiocarbamoyl, any substituted version thereof, or any combination thereof.

In some aspects, the first fluorophore moiety comprises at least one structure of formula (15) to (18) and (23). In these structures, the wavy lines indicate points of covalent attachment within the first polymer. In some aspects, $R^7$, $R^8$, $R^9$, $R^{10}$, and $R^{20}$ independently are H or methyl. In some aspects, each of $R^7$, $R^8$, $R^9$, $R^{10}$, and $R^{20}$ independently is H. In some aspects, each of $R^7$, $R^8$, $R^9$, $R^{10}$, and $R^{20}$ independently is methyl. In some aspects, each of $R^8$, $R^9$, $R^{10}$, and $R^{20}$ independently is methyl and $R^7$ independently is H. In some aspects, $R^{11}$, $R^{12}$ and $R^{19}$ independently are H or a metal ion. The disclosures elsewhere herein pertaining to $R^6$ are equally applicable to $R^{11}$, $R^{12}$, and $R^{19}$. In some aspects, each of $R^{11}$, $R^{12}$, and $R^{19}$ independently is H. In some aspects, $Z^2$, $Z^3$, $Z^4$, $Z^5$, and $Z^8$ are any suitable linking group. As used herein, a suitable linking group is one that covalently connects the first fluorophore moiety to the indicated point of attachment within the first polymer. In particular, in some aspects, the linking groups $Z^2$, $Z^3$, $Z^4$, $Z^5$, and $Z^8$ independently comprise alkyl, aryl, ethylene glycol, oligo (ethylene glycol), an amine, an ether, an ester, an amide, any substituted version thereof, or any combination thereof. For example, in some aspects, the linking group $Z^2$, $Z^3$, $Z^4$, $Z^5$, and $Z^8$ independently comprises an ester connected to an ethylene glycol group connected to a thiocarbamoyl group. In some aspects, the linking group $Z^2$, $Z^3$, $Z^4$, $Z^5$, and $Z^8$ independently comprises an amide connected to an ethyl connected to an ester. Various combinations of alkyl, aryl, ethylene glycol, oligo(ethylene glycol), an amine, an ether, an ester, an amide, any substituted version thereof are contemplated as the linking group, independently, of $Z^2$, $Z^3$, $Z^4$, $Z^5$, and $Z^8$. Additional information regarding the linking groups for $Z^2$, $Z^3$, $Z^4$, $Z^5$, and $Z^8$ that is applicable here is disclosed elsewhere herein with respect to the vinyl-containing first fluorophore.

The structure of formula (15) represents one aspect of a coumarin moiety. The structure of formula (16) represents one aspect of a cyanine moiety. The structure of formula (16) represents one aspect of a cyanine 5.5 moiety. The structure of formula (18) represents one aspect of a fluorescein moiety. The structure of formula (23) represents one aspect of a cyanine moiety. The structure of formula (23) represents one aspect of a cyanine 7 moiety.

In some aspects, the nanoparticles comprise any suitable diameter as measured by uranyl acetate stained dry-state transmission electron microscopy, cryogenic electron microscopy, or both. In some aspects, the nanoparticles comprise a diameter (nm) of 30, 35, 40, 45, 50, 55, 60, 65, 70, 75, 80, 85, 90, 95, 100, 105, 110, 115, or 120, as measured by uranyl acetate stained dry-state transmission electron microscopy, cryogenic electron microscopy, or both. Each of the foregoing numbers can be preceded by the word "about," "at least about," or "less than about," and any of the foregoing numbers can be used singly to describe an open-ended range or in combination to describe a close-ended range. For example, in some aspects, the diameter (nm), as measured by uranyl acetate stained dry-state transmission electron microscopy, cryogenic electron microscopy, or both, is about 35 to about 95, about 30 to about 120, less than about 115, or at least about 80. In some aspects, the nanoparticles comprise a diameter of about 30 to about 120 nm, as measured by uranyl acetate stained dry-state transmission electron microscopy, or a diameter of about 30 nm to about 120 nm, as measured by cryogenic electron microscopy. In some aspects, the nanoparticles comprise a diameter of about 30 to about 120 nm, as measured by both uranyl acetate stained dry-state transmission electron microscopy and cryogenic electron microscopy. In some aspects, the nanoparticles comprise a diameter of about 35 to about 95 nm, as measured by uranyl acetate stained dry-state transmission electron microscopy, or a diameter of about 35 nm to about 95 nm, as measured by cryogenic electron microscopy. In some aspects, the nanoparticles comprise a diameter of about 35 to about 95 nm, as measured by both uranyl acetate stained dry-state transmission electron microscopy and cryogenic electron microscopy.

In some aspects, the nanoparticles comprise any suitable hydrodynamic diameter. In some aspects, the nanoparticles comprise a hydrodynamic diameter (nm) of 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200, as measured by dynamic light scattering. Each of the foregoing numbers can be preceded by the word "about," "at least about," or "less than about," and any of the foregoing numbers can be used singly to describe an open-ended range or in combination to describe a close-ended range. For example, in some aspects, the hydrodynamic diameter (nm) is about 50 to about 200, about 90 to about 115, at least about 75, or less than about 150.

In some aspects, the nanoparticles comprise any suitable average zeta potential. In some aspects, the nanoparticles comprise a negative average zeta potential. In some aspects, the nanoparticles comprise an average zeta potential (mV) of −20, −22, −24, −26, −28, −30, −32, −34, −36, −38, −40, −42, −44, −46, −48, −50, −52, −54, −56, −58, or −60. Each of the foregoing numbers can be preceded by the word "about," "at least about," or "less than about," and any of the foregoing numbers can be used singly to describe an open-ended range or in combination to describe a close-ended range. For example, in some aspects, the average zeta potential (mV) is about −20 to about −60, about −30 to about −60, or less than about −24 (i.e., more negative than about −24).

In some aspects, the composition comprises nanoparticles at any suitable concentration, as measured by nanoparticle tracking analysis (NTA). In some aspects, the composition comprises nanoparticles at a concentration of $X \times 10^{11}$ particles per mL where X is 0.1, 0.2, 0.4, 0.6, 0.8, 1, 1.2, 1.4, 1.6, 1.8, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 18, 19, 20, 21, 22, 23, 24, 25, 26, 27, 28, 29, or 30, as measured by NTA. Each of the foregoing numbers can be preceded by the word "about," "at least about," or "less than about," and any of the foregoing numbers can be used singly to describe an open-ended range or in combination to describe a close-ended range. For example, in some aspects, the composition comprises nanoparticles at a concentration of $X \times 10^{11}$ particles per mL, as measured by NTA, where X is about 1.5 to about 25, about 0.1 to about 30, at least about 4, or less than about 25.

In some aspects, composition comprises the first fluorophore moiety at any suitable concentration. In some aspects, the concentration of first fluorophore in the composition is selected at least in part based on the extinction coefficient of the first fluorophore. In some aspects, the composition comprises the first fluorophore moiety at a concentration (μM) of 40, 45, 50, 55, 60, 65, 70, 75, 80, 85, 90, 95, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, or 700, as measured by UV-Visible (UV-Vis) spectroscopy. Each of the foregoing numbers can be preceded by the word "about," "at least about," or "less than about," and any of the foregoing numbers can be used singly to describe an open-ended range or in combination to describe a close-ended range. For example, in some aspects, the composition comprises the first fluorophore moiety at a concentration (μM) of about 40 to about 700, at least about 120, or less than about 620. The concentrations specified in this paragraph can apply to any fluorophore described herein.

In some aspects, the first fluorophore moiety comprises coumarin, and the composition comprises the coumarin at a concentration of about 20 μM to about 120 μM; the first fluorophore moiety comprises fluorescein, and the composition comprises the fluorescein at a concentration of about 500 μM to about 700 μM, the first fluorophore moiety comprises rhodamine B, and the composition comprises the rhodamine B at a concentration of about 380 μM to about 550 μM, or the first fluorophore moiety comprises cyanine 5.5, and the composition comprises the cyanine 5.5 at a concentration of about 70 μM to about 200 μM; as measured by UV-Vis spectroscopy.

In some aspects, the first fluorophore moiety comprises coumarin, and the composition comprises the coumarin at a concentration (μM) of 20, 25, 30, 35, 40, 45, 50, 55, 60, 65, 70, 75, 80, 85, 90, 95, 100, 105, 110, 115, or 120, as measured by UV-Vis spectroscopy. Each of the foregoing numbers can be preceded by the word "about," "at least about," or "less than about," and any of the foregoing numbers can be used singly to describe an open-ended range or in combination to describe a close-ended range. For example, in some aspects, the composition comprises the coumarin at a concentration (μM) of about 40 to about 80, about 20 to about 120, or at least about 60.

In some aspects, the first fluorophore moiety comprises fluorescein, and the composition comprises the fluorescein at a concentration (μM) of 500, 510, 520, 530, 540, 550, 560, 570, 580, 590, 600, 610, 620, 630, 640, 650, 660, 670, 680, 690, or 700, as measured by UV-Vis spectroscopy. Each of the foregoing numbers can be preceded by the word "about," "at least about," or "less than about," and any of the foregoing numbers can be used singly to describe an open-ended range or in combination to describe a close-ended range. For example, in some aspects, the composition comprises the fluorescein at a concentration (μM) of about 590 to about 650, about 500 to about 700, or at least about 600.

In some aspects, the first fluorophore moiety comprises rhodamine B, and the composition comprises the rhodamine B at a concentration (μM) of 380, 390, 400, 410, 420, 430, 440, 450, 460, 470, 480, 490, 500, 510, 520, 530, 540, or 550, as measured by UV-Vis spectroscopy. Each of the foregoing numbers can be preceded by the word "about," "at least about," or "less than about," and any of the foregoing numbers can be used singly to describe an open-ended range or in combination to describe a close-ended range. For example, in some aspects, the composition comprises the rhodamine B at a concentration (μM) of about 380 to about 550, about 430 to about 490, or at least about 400.

In some aspects, the first fluorophore moiety comprises cyanine 5.5, and the composition comprises the cyanine 5.5 at a concentration (μM) of 70, 80, 90, 100, 110, 120, 130, 140, 150, 160, 170, 180, 190, or 200, as measured by UV-Vis spectroscopy. Each of the foregoing numbers can be preceded by the word "about," "at least about," or "less than about," and any of the foregoing numbers can be used singly to describe an open-ended range or in combination to describe a close-ended range. For example, in some aspects, the composition comprises the cyanine 5.5 at a concentration (μM) of about 70 to about 200, about 90 to about 150, or at least about 110.

In some aspects, the composition comprises the first fluorophore moiety at any suitable concentration per nanoparticle. In some aspects, the composition comprises the first fluorophore moiety at a concentration of $X \times 10^{-13}$ μmol per nanoparticle where X is 1.00, 2.00, 3.00, 4.00, 5.00, 6.00, 7.00, 8.00, 9.00, 10.0, 11.0, 12.0, 13.0, 14.0, 15.0, 16.0, 17.0, 18.0, 19.0, 20.0, 21.0, 22.0, 23.0, 24.0, 25.0, 26.0, 27.0, 28.0, 29.0, 30.0, 31.0, or 32.0, as calculated from nanoparticle concentration per mL of the composition and concentration of the first fluorophore moiety in the composition (both of which are described elsewhere herein). Each of the foregoing numbers can be preceded by the word "about," "at least about," or "less than about," and any of the foregoing numbers can be used singly to describe an open-ended range or in combination to describe a close-ended range. For example, in some aspects, the composition comprises the first fluorophore moiety at a concentration of $X \times 10^{-13}$ μmol per nanoparticle where X is about 1.00 to about 32.0, at least about 5.00, or less than about 28, as calculated from nanoparticle concentration per mL of the composition and concentration of the first fluorophore moiety in the composition. The values in this paragraph can apply to any first fluorophore moiety.

In some aspects, the first fluorophore moiety comprises coumarin, and the nanoparticles comprise the coumarin at a concentration of $X \times 10^{-13}$ μmol per nanoparticle where X is 1.00, 1.10, 1.20, 1.30, 1.40, 1.50, 1.60, 1.70, 1.80, 1.90, 2.00, 2.10, 2.20, 2.30, 2.40, 2.50, 2.60, 2.70, 2.80, 2.90, 3.00, 3.20, 3.40, 3.60, 3.80, 4.00, 4.20, 4.40, 4.60, 4.80, or 5.00, as calculated from nanoparticle concentration per mL of the composition and concentration of the coumarin in the composition. Each of the foregoing numbers can be preceded by the word "about," "at least about," or "less than about," and any of the foregoing numbers can be used singly to describe an open-ended range or in combination to describe a close-ended range. For example, in some aspects, the composition comprises the coumarin at a concentration of $X \times 10^{-13}$ μmol per nanoparticle where X is about 1.00 to about 3.00, at least about 2.10, or about 1.00 to about 5.00.

In some aspects, the first fluorophore moiety comprises fluorescein, and the nanoparticles comprise the fluorescein at a concentration of $X \times 10^{-13}$ μmol per nanoparticle where X is 25.0, 25.5, 26.0, 26.5, 27.0, 27.5, 28.0, 28.5, 29.0, 29.5, 30.0, 31.5, 32.0, 32.5, 33.0, 33.5, 34.0, 34.5, or 35.0, as calculated from nanoparticle concentration per mL of the composition and concentration of the fluorescein in the composition. Each of the foregoing numbers can be preceded by the word "about," "at least about," or "less than about," and any of the foregoing numbers can be used singly to describe an open-ended range or in combination to describe a close-ended range. For example, in some aspects, the composition comprises the fluorescein at a concentration of $X \times 10^{-13}$ μmol per nanoparticle where X is about 25.0 to about 35.0, at least about 29.0, or about 27.0 to about 32.0.

In some aspects, the first fluorophore moiety comprises rhodamine B, and the nanoparticles comprise the rhodamine B at a concentration of $X \times 10^{-13}$ μmol per nanoparticle where X is 1.00, 1.10, 1.20, 1.30, 1.40, 1.50, 1.60, 1.70, 1.80, 1.90, 2.00, 2.10, 2.20, 2.30, 2.40, 2.50, 2.60, 2.70, 2.80, 2.90, 3.00, 3.20, 3.40, 3.60, 3.80, 4.00, 4.20, 4.40, 4.60, 4.80, or 5.00, as calculated from nanoparticle concentration per mL of the composition and concentration of the rhodamine B in the composition. Each of the foregoing numbers can be preceded by the word "about," "at least about," or "less than about," and any of the foregoing numbers can be used singly to describe an open-ended range or in combination to describe a close-ended range. For example, in some aspects, the composition comprises the rhodamine B at a concentration of $X \times 10^{-13}$ μmol per nanoparticle where X is about 1.00 to about 3.00, at least about 2.10, or about 1.00 to about 5.00.

In some aspects, the first fluorophore moiety comprises cyanine 5.5, and the nanoparticles comprise the cyanine 5.5 at a concentration of $X \times 10^{-13}$ μmol per nanoparticle where X is 2.00, 2.10, 2.20, 2.30, 2.40, 2.50, 2.60, 2.70, 2.80, 2.90, 3.00, 3.20, 3.40, 3.60, 3.80, 4.00, 4.20, 4.40, 4.60, 4.80, 5.00, 5.20, 5.40, 5.60, 5.80, 6.00, 6.50, 7.00, 7.50, 8.00, 8.50, 9.00, 9.50, or 10.0, as calculated from nanoparticle concentration per mL of the composition and concentration of the cyanine 5.5 in the composition. Each of the foregoing numbers can be preceded by the word "about," "at least about," or "less than about," and any of the foregoing numbers can be used singly to describe an open-ended range or in combination to describe a close-ended range. For example, in some aspects, the composition comprises the cyanine 5.5 at a concentration of $X \times 10^{-13}$ μmol per nanoparticle where X is about 2.00 to about 10.0, at least about 4.20, or about 3.00 to about 6.00.

In some aspects, the first fluorophore moiety comprises cyanine 7, and the nanoparticles comprise the cyanine 7 at a concentration of $X \times 10^{-13}$ μmol per nanoparticle where X is 1.00, 1.10, 1.20, 1.30, 1.40, 1.50, 1.60, 1.70, 1.80, 1.90, 2.00, 2.10, 2.20, 2.30, 2.40, 2.50, 2.60, 2.70, 2.80, 2.90, 3.00, 3.20, 3.40, 3.60, 3.80, 4.00, 4.20, 4.40, 4.60, 4.80, or 5.00, as calculated from nanoparticle concentration per mL of the composition and concentration of the cyanine 7 in the composition. Each of the foregoing numbers can be preceded by the word "about," "at least about," or "less than about," and any of the foregoing numbers can be used singly to describe an open-ended range or in combination to describe a close-ended range. For example, in some aspects, the composition comprises the cyanine 7 at a concentration of $X \times 10^{-13}$ μmol per nanoparticle where X is about 1.00 to about 3.00, at least about 2.10, or about 1.00 to about 5.00.

In some aspects, the composition containing nanoparticles comprises any suitable absorption peak in a UV-Vis spectrum as a result, at least in part, from the inherent structure of the nanoparticles. In some aspects, the composition comprises an absorption peak in a UV-Vis spectrum at a wavelength (nm) of 335, 340, 345, 350, 355, 360, or 365, when measured by NTA at a concentration of about $2.1 \times 10^{11}$ to about $3.2 \times 10^{11}$ particles per mL. Each of the foregoing numbers can be preceded by the word "about," "at least about," or "less than about," and any of the foregoing numbers can be used singly to describe an open-ended range or in combination to describe a close-ended range. For example, in some aspects, when measured by NTA at a concentration of about $2.1 \times 10^{11}$ to about $3.2 \times 10^{11}$ particles per mL, the composition comprises an absorption peak in a UV-Vis spectrum at a wavelength (nm) of about 340 to about 360, about 350 to about 355, or about 350. This measurement typically is performed when the composition comprises water.

In some aspects, the first fluorophore moiety comprises coumarin, and when measured at a concentration of about $3.2 \times 10^{11}$ nanoparticles per mL by NTA, the nanoparticles comprise an excitation maximum of about 340 nm to about 360 nm (e.g., about 345 nm to about 355 nm, or about 350 nm) and an emission maximum of about 402 nm to about 422 nm (e.g., about 407 nm to about 417 nm, or about 412 nm). This measurement typically is performed when the composition comprises water.

In some aspects, the first fluorophore moiety comprises fluorescein, and when measured at a concentration of about $2.1 \times 10^{11}$ nanoparticles per mL by NTA, the nanoparticles comprise an excitation maximum of about 480 nm to about 500 nm (e.g., about 485 nm to about 495 nm, or about 490 nm) and an emission maximum of about 503 nm to about 523 nm (e.g., about 508 nm to about 518 nm, or about 513 nm). This measurement typically is performed when the composition comprises water.

In some aspects, the first fluorophore moiety comprises rhodamine B, and when measured at a concentration of about $23 \times 10^{11}$ nanoparticles per mL by NTA, the nanoparticles comprise an excitation maximum of about 548 nm to about 568 nm (e.g., about 553 nm to about 563 nm, or about 558 nm) and an emission maximum of about 576 nm to about 596 nm (e.g., about 581 nm to about 591 nm, or about 586 nm). This measurement typically is performed when the composition comprises water.

In some aspects, the first fluorophore moiety comprises cyanine 5.5, and when measured at a concentration of about $2.5 \times 10^{11}$ nanoparticles per mL by NTA, the nanoparticles comprise an excitation maximum of about 662 nm to about 682 nm (e.g., about 657 nm to about 667 nm, or about 662 nm) and an emission maximum of about 690 nm to about 710 nm (e.g., about 695 nm to about 705 nm, or about 700 nm). This measurement typically is performed when the composition comprises water.

In some aspects, the first fluorophore moiety comprises cyanine 7, and when measured at a concentration of about $9.4 \times 10^{9}$ nanoparticles per mL by NTA, the nanoparticles comprise an excitation maximum of about 647 nm to about 667 nm (e.g., about 652 nm to about 662 nm, or about 657 nm) and an emission maximum of about 796 nm to about 816 nm (e.g., about 801 nm to about 811 nm, or about 806 nm). This measurement typically is performed when the composition comprises water.

In some aspects, when the composition having a concentration of nanoparticles of about $2.4 \times 10^{10}$ to about $30 \times 10^{10}$ as measured by nanoparticle tracking analysis is subjected to human embryonic kidney 293 (HEK 293) cells, the composition is nontoxic to the HEK 293 cells, as indicated by a cell viability of the HEK 293 cells of at least 20% after incubating the HEK 293 cells with the composition for 48 hours.

In some aspects, when a composition having a concentration of nanoparticles of about $2.4 \times 10^{10}$ to about $30 \times 10^{10}$ as measured by nanoparticle tracking analysis is incubated for 20 minutes with human embryonic kidney 293 (HEK 293) cells, washed with Dulbecco's phosphate-buffered saline, incubated in media for 24 hours, and then fixed with an appropriate stain, the HEK 293 cells subjected to the composition have a higher mean fluorescence intensity than an otherwise identical composition containing otherwise identical nanoparticles as measured by confocal laser scanning microscopy, except that the otherwise identical nanoparticles comprise LUMAFLUOR RED or LUMAFLUOR GREEN.

In some aspects, when human embryonic kidney 293 (HEK 293) cells are subjected to a colocalization assay comprising the composition (which comprises nanoparticles) and LC3 antibody, the nanoparticles are trafficked intracellularly at a faster rate, as measured over a period of 48 hours, than an otherwise identical colocalization assay with an otherwise identical composition with otherwise identical nanoparticles, except that the otherwise identical nanoparticles comprise LUMAFLUOR RED or LUMAFLUOR GREEN.

In some aspects, when the composition comprising nanoparticles is injected into viable neural tissue, the nanoparticles are transported in axons in a retrograde fashion. As used herein, "viable neural tissue" is neural tissue that exhibits sufficient cellular function to transport objects, such as nanoparticles, to a similar extent as if the neural tissue was present in the brain of a living organism (in some aspects, the viable neural tissue is actually present in the brain of a living organism). In some aspects, when the composition is injected into viable neural tissue (e.g., brain) of a mammal (e.g., a living mammal), the nanoparticles are transported in a retrograde fashion. In some aspects, when the composition is injected into viable neural tissue (e.g., brain) of a mammal (e.g., primate or human), the nanoparticles are transported in axons in a retrograde fashion along an entorhinal cortex (EC) to first hippocampal region (CA1) pathway. In some aspects, when the composition is injected into viable neural tissue (e.g., brain) of a mammal (e.g., primate or human), the nanoparticles are transported in axons in a retrograde fashion along a lateral geniculate nucleus (LGN) to primary visual cortex (V1) pathway. In some aspects, when the composition is injected into viable neural tissue (e.g., brain) of a mouse (e.g., living mouse), the nanoparticles are transported in axons in a retrograde fashion along an entorhinal cortex (EC) to first hippocampal region (CA1) pathway. In some aspects, when the composition is injected into viable neural tissue (e.g., brain) of a mouse (e.g., living mouse), the nanoparticles are transported in axons in a retrograde fashion along a lateral geniculate nucleus (LGN) to primary visual cortex (V1) pathway.

In some aspects, the nanoparticles are prepared by a process comprising emulsion polymerization of a mixture comprising: a vinyl-containing first fluorophore, and at least one vinyl-containing monomer, wherein the first fluorophore moiety is derived from the vinyl-containing first fluorophore. As used herein, when the first fluorophore moiety is derived from the vinyl-containing first fluorophore, it means that upon polymerization the vinyl-containing first fluorophore effectively becomes the first fluorophore moiety within the polymeric structure of the nanoparticles.

In some aspects, the vinyl-containing first fluorophore comprises coumarin, fluorescein, rhodamine, rhodamine B, cyanine, cyanine 5.5, or cyanine 7. In some aspects, the vinyl-containing first fluorophore comprises coumarin. In some aspects, the vinyl-containing first fluorophore comprises fluorescein. In some aspects, the vinyl-containing first fluorophore comprises rhodamine B. In some aspects, the vinyl-containing first fluorophore comprises cyanine 5.5. In some aspects, the vinyl-containing first fluorophore comprises cyanine 7.

In some aspects, the vinyl-containing first fluorophore comprises a structure of formula (7) to (14) and (24) to (26):

(7)

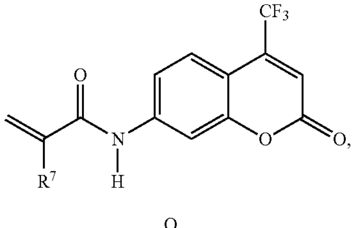

(8)

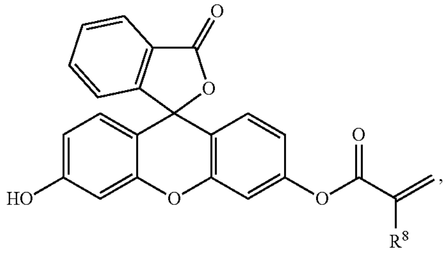

-continued (10)

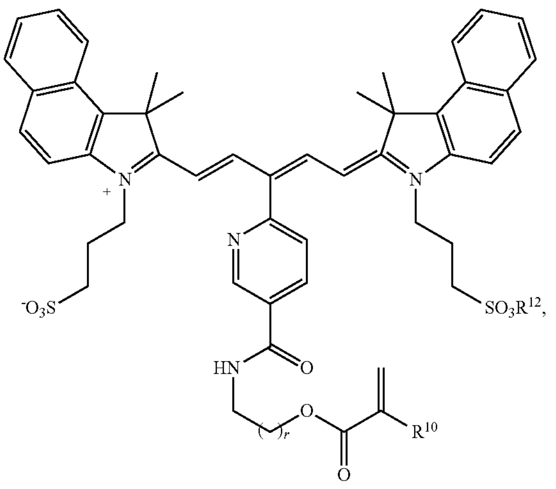

(11)

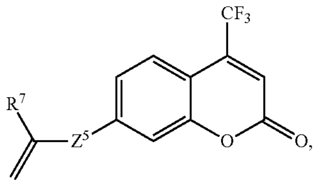

(12)

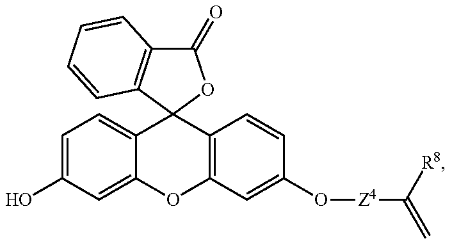

(14)

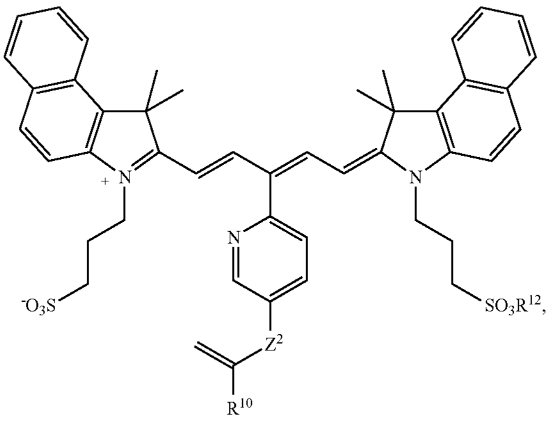

-continued (24)

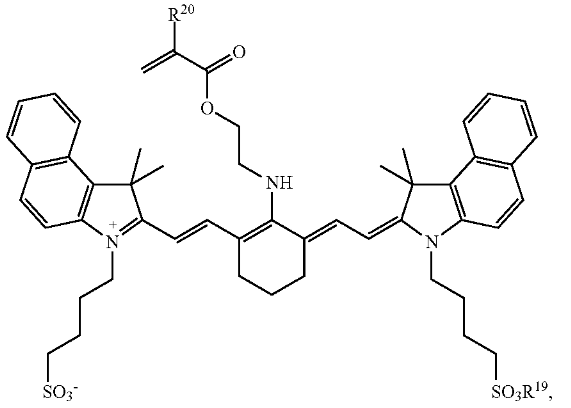

(25)

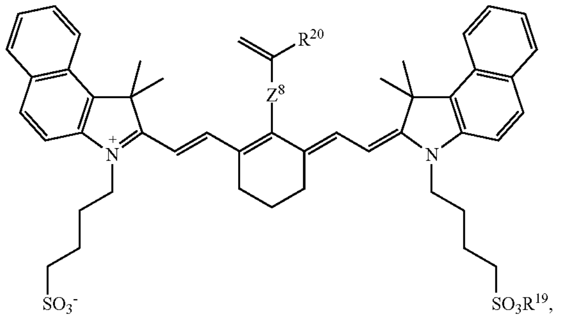

(26)

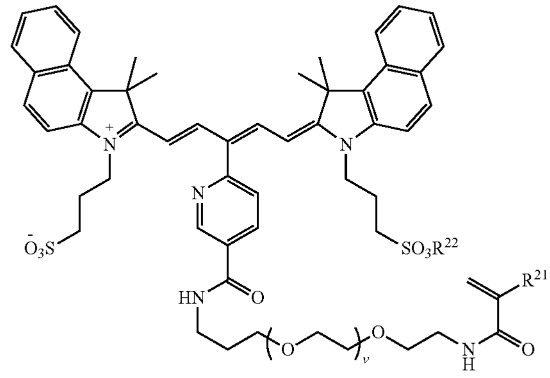

wherein:

$R^7$, $R^8$, $R^9$, $R^{10}$, $R^{20}$, and $R^{21}$ independently are H or methyl, q and r independently are 1 to 5, v is 0 to 5, $R^{11}$, $R^{12}$, $R^{19}$, and $R^{22}$ independently are H or a metal ion, and $Z^2$, $Z^3$, $Z^4$, $Z^5$, and $Z^8$ independently are a linking group comprising alkyl, aryl, ethylene glycol, oligo(ethylene glycol), an amine, an ether, an ester, an amide, a thiocarbamoyl, any substituted version thereof, or any combination thereof.

In some aspects, the vinyl-containing first fluorophore comprises a structure of formula (7) to (14) and (24) to (26). In some aspects, $R^7$, $R^8$, $R^9$, $R^{10}$, $R^{20}$, and $R^{21}$ independently are H or methyl. In some aspects, each of $R^7$, $R^8$, $R^9$, $R^{10}$, $R^{20}$, and $R^{21}$ independently is H. In some aspects, each of $R^7$, $R^8$, $R^9$, $R^{10}$, $R^{20}$, and $R^{21}$ independently is methyl. In some aspects, q and r independently are 1 to 5. In some aspects, q independently is 1 to 5, e.g., 1, 2, 3, 4, or 5, or any range made therefrom (e.g., 1 to 4, 1 to 2, 1 to 3, 2 to 5, 3 to 5, and so on). In some aspects, r independently is 1 to 5, e.g., 1, 2, 3, 4, or 5, or any range made therefrom (e.g., 1 to 4, 1 to 2, 1 to 3, 2 to 5, 3 to 5, 4 to 5, and so on). In some aspects, v is 0 to 5, e.g., 0, 1, 2, 3, 4, or 5, or any range made therefrom (e.g., 0 to 4, 1 to 4, 2 to 5, 1 to 3, and so on). In some aspects, $R^{11}$, $R^{12}$, $R^{19}$, and $R^{22}$ independently are H or a metal ion. In some aspects, each of $R^{11}$, $R^{12}$, $R^{19}$, and $R^{22}$ independently is H. In some aspects, each of $R^{11}$, $R^{12}$, $R^{19}$, and $R^{22}$ independently is a metal ion. The disclosures elsewhere herein pertaining to $R^6$ are equally applicable to $R^{11}$, $R^{12}$, $R^{19}$, and $R^{22}$. In some aspects, $Z^2$, $Z^3$, $Z^4$, $Z^5$, and $Z^8$ independently are any suitable linking group. As used herein, a suitable linking group is one that covalently connects the vinyl-containing first fluorophore to the vinyl group (e.g., polymerizable vinyl group). For example, in some aspects, the linking group comprises alkyl, aryl, ethylene glycol, oligo(ethylene glycol), an amine, an ether, an ester, an amide, a thiocarbamoyl, any substituted version thereof, or any combination thereof. For example, in some aspects, the linking group $Z^2$, $Z^3$, $Z^4$, $Z^5$, and $Z^8$ independently comprises an amide connected to an ethylene glycol connected to another amide. In some aspects, the linking group $Z^2$, $Z^3$, $Z^4$, $Z^5$, and $Z^8$ independently comprises an amide connected to an ethyl connected to an ester. Additional suitable linking groups would be known to those of ordinary skill in the art simply by comparing various generic structures with the more specific structures disclosed herein (e.g., compare structure (7) with (11), structure (8) with (12), structure (10) or (26) with (14), and structure (24) with (25)). It is contemplated that such linking groups are interchangeable among the various vinyl-containing first fluorophores, and other variations can be contemplated in view of the structures of these linking groups.

In some aspects, the emulsion polymerization comprises at least one vinyl-containing monomer comprises an acrylate, a methacrylate, methyl methacrylate, methacrylic acid, acrylic acid, 2-hydroxyethyl methacrylate, 2-hydroxyethyl acrylate, 2-hydroxyethyl methacrylate, 3-hydroxypropyl acrylate, 3-hydroxyethyl methacrylate, ethylacrylate, ethylmethacrylate, propylacrylate, propylmethacrylate, butylacrylate, butylmethacrylate, laurylacrylate, laurylmethacrylate, stearylacrylate, stearylmethacrylate, glycidylacrylate, glycidylmethacrylate, acrylonitrile, acrylamide, vinylalcohol, vinylacetate, vinylbutyral, vinylpyrrolidone, styrene, or any combination thereof. In some aspects, the at least one vinyl-containing monomer comprises 2-hydroxyethyl methacrylate, methyl methacrylate, and methacrylic acid (optionally in combination with a crosslinker, such as ethylene glycol dimethacrylate). In some aspects, the emulsion polymerization comprises one or more monomers that result in one or more of a polyacrylate, a polyacrylic acid, a polymethacrylate, a polymethacrylic acid, a polymethylmethacrylate (PMMA), a polyethylacrylate, a polyethyl methacrylate, a polypropylacrylate, a polypropyl methacrylate, a polybutylacrylate, a polybutylmethacrylate, a polyhydroxyalkyl methacrylate, a poly(2-hydroxyethyl)methacrylate, a poly(3-hydroxypropyl)methacrylate, a poly(hydroxyalkyl)acrylate, a poly(2-hydroxyethyl)acrylate, a poly(3-hydroxypropyl)acrylate, a polylaurylacrylate, a polystearylacrylate, a polyglycidylacrylate, a polyglycidyl methacrylate, a polyacrylonitrile, a polyacrylamide, a polyvinyl alcohol, a polyvinyl acetate, a polyvinyl butyral, a polyvinylpyrrolidone, a polystyrene, or any combination thereof.

In some aspects, the emulsion polymerization comprises at least one crosslinker. In some aspects, the at least one crosslinker comprises any divinyl compound. In some aspects, the at least one crosslinker comprises ethylene glycol dimethacrylate, ethylene glycol diacrylate, oligo(ethylene glycol) diacrylate, oligo(ethylene glycol) dimethacrylate, poly(ethylene glycol) diacrylate, poly(ethylene glycol) dimethacrylate, divinyl benzene, or a combination thereof. In some aspects, the crosslinker comprises ethylene glycol dimethacrylate. In some aspects, the poly(ethylene glycol) diacrylate comprises poly(ethylene glycol) 250 diacrylate (i.e., PEG 250 diacrylate). In some aspects, the poly(ethylene glycol) diacrylate comprises poly(ethylene glycol) 700 diacrylate (i.e., PEG 700 diacrylate).

In some aspects, the first nanoparticle further comprises a chelate moiety covalently bonded to the first polymer within the first interior bulk of the first nanoparticle. In some aspects, the chelate moiety comprises tetraazacyclododecane comprising at least one acetate group, at least one acetic acid group, or a combination thereof. In some aspects, the chelate moiety comprises a magnetic resonance imaging (MRI) contrast agent, a positron emission tomography (PET) contrast agent, a single-photon emission computerized tomography (SPECT) contrast agent, or any combination thereof. In some aspects, the chelate moiety comprises an MRI contrast agent. In some aspects, the chelate moiety comprises a PET contrast agent. In some aspects, the chelate moiety comprises a SPECT contrast agent. In some aspects, the chelate moiety comprises gadolinium, copper, indium, yttrium, yttrium(54), or any combination thereof. In some aspects, the chelate moiety comprises an MRI contrast agent comprising gadolinium. In some aspects, the chelate moiety comprises a PET or SPECT contrast agent comprising copper, indium, yttrium, yttrium(54), or any combination thereof.

In some aspects, disclosed is a composition comprising:
- a first fluorophore moiety, and
- nanoparticles, wherein the nanoparticles comprise:
- a first plurality of a first nanoparticle, the first nanoparticle comprising:
- a first outer surface, a first interior bulk, and a first polymer,
- wherein the first polymer is covalently bonded to the first fluorophore moiety within the first interior bulk of the first nanoparticle.

In some aspects, the composition further comprises a second fluorophore moiety having a different emission maximum than the first fluorophore moiety, wherein the nanoparticles further comprise:
- a second plurality of a second nanoparticle, the second nanoparticle comprising:
  - a second outer surface, a second interior bulk, and a second polymer,
- wherein the second polymer is covalently bonded to the second fluorophore moiety within the second interior bulk of the second nanoparticle.

In some aspects, the second nanoparticle is made up of a second outer surface, a second interior bulk, and a second polymer. In some aspects, the second nanoparticle is roughly spherical. In some aspects, the second nanoparticle has a second interior bulk makes up the inner portion (e.g., the entire inner portion) of the second nanoparticle that is within the confines of the second outer surface. In some aspects, the second polymer is covalently bonded to the second fluorophore moiety within the second interior bulk of the second nanoparticle. In particular, the second fluorophore moiety is covalently bonded to the second polymer that comprises the second nanoparticle within the interior portion of the second nanoparticle. In some aspects, this covalently bonded nature of the second fluorophore moiety within the second interior bulk of the second nanoparticle results from polymerizing a vinyl-containing second fluorophore along with one or more polymerizable monomers when synthesizing the second nanoparticle, as described elsewhere herein. By preparing a second nanoparticle containing a second fluorophore moiety covalently bonded within its second interior bulk, the second fluorophore moiety is less prone to leakage, or does not leak, from the second nanoparticle, thus resulting in a more stable particle.

In some aspects, the disclosures set forth elsewhere herein relating to the first nanoparticle are equally applicable to the second nanoparticle. For example, the disclosures relating to the first fluorophore moiety and first polymer are equally applicable to the second fluorophore moiety and the second polymer, respectively. In this regard, for example, the second fluorophore moiety can have any of the structures or characteristics of the first fluorophore moiety, provided that any specified conditions are met (e.g., that when the first and second fluorophore moieties are in the same composition, the emission maximum of the second fluorophore moiety is different from the emission maximum of the first fluorophore moiety). In addition, for example, any of the disclosures relating to the first polymer are equally applicable to the second polymer. In this regard, the second polymer can comprise any of the structures, or be derived from the monomers, disclosed for the first polymer.

In some aspects, the first nanoparticle is substantially free of a fluorophore moiety other than the first fluorophore moiety. In some aspects, the second nanoparticle is substantially free of a fluorophore moiety other than the second fluorophore moiety. In some aspects, the first nanoparticle is substantially free of a fluorophore moiety other than the first fluorophore moiety, and the second nanoparticle is substantially free of a fluorophore moiety other than the second fluorophore moiety.

In some aspects, the first nanoparticle further comprises the second fluorophore moiety. In some aspects, the first polymer is covalently bonded to the second fluorophore moiety within the first interior bulk of the first nanoparticle. In some aspects, the second nanoparticle further comprises the first fluorophore moiety. In some aspects, the second polymer is covalently bonded to the first fluorophore moiety within the second interior bulk of the second nanoparticle. In some aspects, the first nanoparticle further comprises the second fluorophore moiety and the second nanoparticle further comprises the first fluorophore moiety.

In some aspects, the composition further comprises a third plurality of a third nanoparticle comprising a third fluorophore moiety and a third polymer,

- wherein the third polymer is covalently bonded to the third fluorophore moiety and
- wherein the third fluorophore has a different emission maximum than each of the first fluorophore and the second fluorophore.

In some aspects, the composition further comprises a fourth plurality of a fourth nanoparticle comprising a fourth fluorophore moiety and a fourth polymer, wherein the fourth polymer is covalently bonded to the fourth fluorophore moiety and wherein the fourth fluorophore has a different emission maximum than each of the first fluorophore, the second fluorophore, and the third fluorophore.

In some aspects, the disclosures elsewhere herein regarding the first nanoparticle are equally and independently applicable to the third nanoparticle and the fourth nanoparticle (in the same manner that the disclosures for the first nanoparticle are equally applicable to the second nanoparticle, as discussed elsewhere herein). In some aspects, the third nanoparticle is substantially free of a fluorophore moiety other than the third fluorophore moiety. In some aspects, the fourth nanoparticle is substantially free of a fluorophore moiety other than the fourth fluorophore moiety. In some aspects, the third nanoparticle further comprises the first fluorophore moiety and the second fluorophore moiety. In some aspects, the third nanoparticle further comprises the first fluorophore moiety, the second fluorophore moiety, and the fourth fluorophore moiety. In some aspects, the fourth nanoparticle further comprises the first fluorophore moiety, the second fluorophore moiety, and the third fluorophore moiety. In some aspects, the third fluorophore moiety is covalently bonded to the polymer of the interior bulk of the nanoparticle that it is associated with. In some aspects, the fourth fluorophore moiety is covalently bonded to the polymer of the interior bulk of the nanoparticle that it is associated with.

In some aspects, the nanoparticles are prepared by a process comprising emulsion polymerization of a mixture comprising:

- a vinyl-containing first fluorophore,
- a vinyl-containing second fluorophore, and
- at least one vinyl-containing monomer,
- wherein the first fluorophore moiety is derived from the vinyl-containing first fluorophore and the second fluorophore moiety is derived from the vinyl-containing second fluorophore. In some aspects, the vinyl-containing first fluorophore has a different emission maximum than the vinyl-containing second fluorophore.

In some aspects, the disclosures elsewhere herein relating to the vinyl-containing first fluorophore are equally and independently applicable to the vinyl-containing second fluorophore. In this regard, for example, the vinyl-containing second fluorophore can have any of the structures or characteristics of the vinyl-containing first fluorophore, provided that any conditions are met (e.g., different emission maxima). In addition, in some aspects, the at least one vinyl-containing monomer can have any of the structures or characteristics of the at least one vinyl-containing monomer described elsewhere herein.

In some aspects, the mixture for emulsion polymerization, in addition to the vinyl-containing first fluorophore, the vinyl-containing second fluorophore, and the at least one vinyl-containing monomer can additionally comprise a vinyl-containing third fluorophore. In some aspects, the mixture for emulsion polymerization, in addition to the vinyl-containing first fluorophore, the vinyl-containing second fluorophore, the vinyl-containing third fluorophore, and the at least one vinyl-containing monomer can additionally comprise a vinyl-containing fourth fluorophore. The disclosures elsewhere herein for the vinyl-containing first fluorophore are equally and independently applicable to the vinyl-containing third fluorophore and vinyl-containing fourth fluorophore. In some aspects, the vinyl-containing first fluorophore gives rise to the first fluorophore moiety, the vinyl-containing second fluorophore gives rise to the second fluorophore moiety, the vinyl-containing third fluorophore gives rise to the third fluorophore moiety, and/or the vinyl-containing fourth fluorophore gives rise to the fourth fluorophore moiety.

In some aspects, the first plurality of the first nanoparticle is prepared by a process comprising:

emulsion polymerization of a first mixture comprising:

a vinyl-containing first fluorophore, and at least one vinyl-containing monomer, thereby producing a first composition comprising the first plurality of the first nanoparticle, wherein the first fluorophore moiety is derived from the vinyl-containing first fluorophore, the second plurality of the second nanoparticle is prepared by a process comprising emulsion polymerization of a second mixture comprising:

a vinyl-containing second fluorophore, and at least one vinyl-containing monomer, thereby producing a second composition comprising the second plurality of the second nanoparticle, wherein the second fluorophore moiety is derived from the vinyl-containing second fluorophore, and the composition is prepared by a process comprising combining the first composition and the second composition.

In some aspects where the composition contains a third plurality of a third nanoparticle, the process to make the composition further comprises emulsion polymerizing a third mixture comprising a vinyl-containing third fluorophore and at least one vinyl-containing monomer, thereby producing a third composition comprising the third plurality of the third nanoparticle comprising a third fluorophore moiety, wherein third fluorophore moiety is derived from the vinyl-containing third fluorophore, and combining the third composition with the first and second compositions.

In some aspects where the composition contains a fourth plurality of a fourth nanoparticle, the process to make the composition further comprises emulsion polymerizing a fourth mixture comprising a vinyl-containing fourth fluorophore and at least one vinyl-containing monomer, thereby producing a fourth composition comprising the fourth plurality of the fourth nanoparticle comprising a fourth fluorophore moiety, wherein fourth fluorophore moiety is derived from the vinyl-containing fourth fluorophore, and combining the fourth composition with the first, second, and third compositions.

In some aspects, the second fluorophore moiety, third fluorophore moiety, or the fourth fluorophore moiety independently comprise coumarin, fluorescein, rhodamine, rhodamine B, cyanine, cyanine 5.5, or cyanine 7, or any of the other structures or characteristics disclosed elsewhere herein for the first fluorophore moiety.

In some aspects, the composition is employed in a method of brain mapping or tracing an axonal projection. In some aspects, the method comprises subjecting a first neuron to the composition to form a first infused neuron, and imaging the first infused neuron using at least one of fluorescence spectroscopy, magnetic resonance imaging (MRI), positron emission tomography (PET), single-photon emission computerized tomography (SPECT), or any combination thereof. In some aspects, the method further comprises subjecting a second neuron to the composition to form a second infused neuron, and imaging the second infused neuron using at least one of fluorescence spectroscopy, magnetic resonance imaging (MRI), positron emission tomography (PET), single-photon emission computerized tomography (SPECT), or any combination thereof. In some aspects, the method further comprises subjecting a third neuron to the composition to form a third infused neuron, and imaging the third infused neuron using at least one of fluorescence spectroscopy, magnetic resonance imaging (MRI), positron emission tomography (PET), single-photon emission computerized tomography (SPECT), or any combination thereof. In some aspects, the method further comprises subjecting a fourth neuron (or fifth, sixth, seventh, and so on) to the composition to form a fourth infused neuron (or fifth, sixth, seventh, and so on), and imaging the fourth infused neuron (or fifth, sixth, seventh, and so on) using at least one of fluorescence spectroscopy, magnetic resonance imaging (MRI), positron emission tomography (PET), single-photon emission computerized tomography (SPECT), or any combination thereof. In some aspects, the method comprises fluorescence spectroscopy. In some aspects, the method comprises fluorescence spectroscopy and MRI. In some aspects, the method comprises, MRI. In some aspects, the method comprises PET. In some aspects, the method comprises SPECT.

In some aspects, at least one of the first neuron, the second neuron, the third neuron, the fourth neuron, and so on, are different neurons present in different locations from one another. In some aspects, at least one of the first neuron, the second neuron, the third neuron, the fourth neuron, and so on, are the same neuron. In some aspects, at least one of the first neuron, the second neuron, the third neuron, the fourth neuron, and so on, are the same neuron but infused in different locations as part of the method.

In some aspects, disclosed is a method of brain mapping or tracing an axonal projection, the method comprising injecting a brain in a first location with a first composition and in a second location with a second composition, and performing at least one of imaging the brain using fluorescence spectroscopy, magnetic resonance imaging (MRI), positron emission tomography (PET), single-photon emission computerized tomography (SPECT), or any combination thereof. In some aspects, the first composition and the second composition can be the same or different. In some aspects, the method comprises fluorescence spectroscopy. In some aspects, the method comprises fluorescence spectroscopy and MRI. In some aspects, the method comprises, MRI. In some aspects, the method comprises PET. In some aspects, the method comprises SPECT. In some aspects, the method further comprises injecting the brain in a third location with a third composition that can be the same or different from the first and second compositions, and imaging using fluorescence spectroscopy, MRI, PET, or SPECT. In some aspects, the method further comprises injecting the brain in a fourth location (or fifth, sixth, seventh, and so on) with a fourth composition (or fifth, sixth, seventh, and so on) that can be the same or different from the first, second, and third compositions (or fifth, sixth, seventh, and so on), and imaging using fluorescence spectroscopy, MRI, PET, or SPECT. In some aspects, the first and second locations (or third, fourth, fifth, sixth, seventh, and so on) are in the hippocampus. In some aspects, the first and second locations (or third, fourth, fifth, sixth, seventh, and so on) are in the cerebral cortex, cerebrum, cerebellum, brainstem, amygdala, cingulate gyrus, prefrontal cortex, dentate gyrus, entorhinal cortex, or any combination thereof.

In some aspects, disclosed is a composition comprising:

a chelate moiety, and nanoparticles, wherein the nanoparticles comprise:

a plurality of a chelate nanoparticle, the chelate nanoparticle comprising:

an outer surface, an interior bulk, and a polymer, wherein the polymer is covalently bonded to the chelate moiety within the interior bulk of the chelate nanoparticle.

In some aspects, the composition comprises any suitable liquid. In some aspects, the composition comprises water. In some aspects, the composition comprises water, methanol, ethanol, propanol, propylene glycol, glycerol, dimethylformamide (DMF), dimethylsulfoxide (DMSO), or any combination thereof.

In some aspects, the chelate nanoparticle is made up of an outer surface, an interior bulk, and a polymer. In some aspects, the chelate nanoparticle is roughly spherical. In some aspects, the chelate nanoparticle has an interior bulk makes up the inner portion (e.g., the entire inner portion) of the chelate nanoparticle that is within the confines of the outer surface. In some aspects, the polymer is covalently bonded to the chelate moiety within the interior bulk of the chelate nanoparticle. In particular, the chelate moiety is covalently bonded to the polymer that comprises the chelate nanoparticle within the interior portion of the chelate nanoparticle. In some aspects, this covalently bonded nature of the chelate moiety within the interior bulk of the nanoparticle results from polymerizing a vinyl-containing chelate group along with one or more polymerizable monomers when synthesizing the chelate nanoparticle, as described elsewhere herein.

In some aspects, the disclosures elsewhere herein relating to the first nanoparticle are equally applicable to the chelate nanoparticle. In this regard, for example, the disclosures relating to the first polymer are equally applicable to the polymer. For example, in some aspects, the polymer comprises any suitable polymer. In some aspects, the polymer is any type of polymer that is biocompatible. For example, a polymer is biocompatible if it can be employed in vivo or ex vivo for its intended purpose (e.g., research, diagnostic, therapeutic, etc.) without substantially hindering the biological processes (e.g., uptake, transport, etc.) necessary to carry out the intended purpose. In some aspects, the polymer is any type of polymer that can be made by emulsion polymerization. In some aspects, the polymer is any type of polymer that is biocompatible and can be made by emulsion polymerization. In some aspects, the polymer comprises a polymer of an unsaturated ester or amide, such as a polyacrylate, a polyacrylic acid, a polymethacrylate, a polymethacrylic acid, a polymethylmethacrylate (PMMA), a polyethylacrylate, a polyethylmethacrylate, a polypropylacrylate, a polypropylmethacrylate, a polybutylacrylate, a polybutylmethacrylate, a poly(hydroxyalkyl) methacrylate (e.g., a poly(2-hydroxyethyl) methacrylate, a poly(3-hydroxypropyl)methacrylate, etc.), a poly(hydroxyalkyl)acrylate (e.g., a poly(2-hydroxyethyl)acrylate, a poly (3-hydroxypropyl)acrylate), a polylaurylacrylate, a polystearylacrylate, a polyglycidylacrylate, a polyglycidylmethacrylate, a polyacrylonitrile, a polyacrylamide, or any combination thereof (i.e., a copolymer of any combination thereof). For example, a copolymer thereof includes PMMA-polymethacrylate, PMMA-polymethacrylate-polyhydroxyethylmethacrylate, polyacrylonitrile-polymethacrylate, and so forth. In some aspects, the polymer comprises a polymer made of an unsaturated alcohol and/or derivatives thereof, such as a polyvinyl alcohol, a polyvinyl acetate, a polyvinyl butyral, or any combination thereof (i.e., a copolymer thereof). In some aspects, the polymer can be any combination of polymers disclosed herein, e.g., a copolymer of an unsaturated alcohol, an unsaturated ester, and an unsaturated amide. In some aspects, the polymer is a copolymer.

In some aspects, the polymer comprises at least one structure of formula (1) to (6) and (27):

(1)

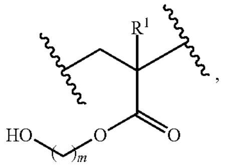

(2)

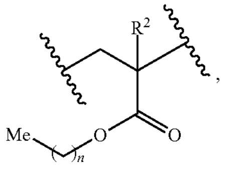

(3)

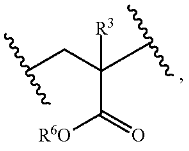

(4)

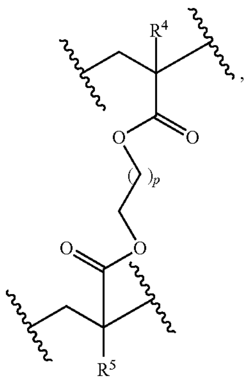

(5)

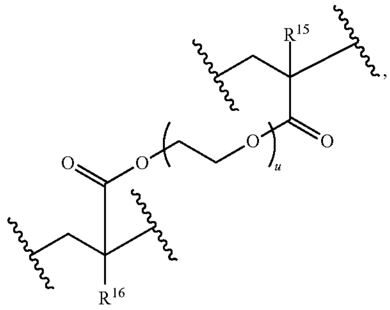

(6)

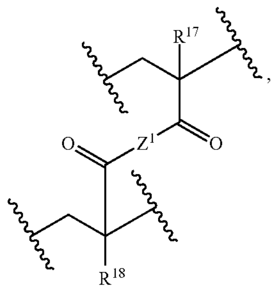

-continued (27)

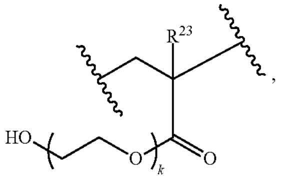

wherein m is 2 to 5, n is 0 to 5, k, p, and u independently are 1 to 5, $R^1$, $R^2$, $R^3$, $R^4$, $R^5$, $R^{15}$, $R^{16}$, $R^{17}$, $R^{18}$, and $R^{23}$ independently are H or methyl, $R^6$ is H or a metal ion, and $Z^1$ is a linking group comprising alkyl, aryl, ethylene glycol, oligo(ethylene glycol), poly(ethylene glycol), an amine, an ether, an ester, an amide, an ester when taken together with adjacent atoms, an amide when taken together with adjacent atoms, any substituted version thereof, or any combination thereof.

In some aspects, the polymer comprises at least one structure of formula (1) to (6) and (27). In these structures, the wavy lines indicate points of covalent attachment within the polymer. In some aspects, m is 1 to 5, e.g., 1, 2, 3, 4, or 5, or any range made therefrom (e.g., 1 to 4, 2 to 4, 1 to 3, 2 to 5, and so on). In some aspects, n is 0 to 5, e.g., 0, 1, 2, 3, 4, or 5, or any range made therefrom (e.g., 0 to 4, 1 to 4, 1 to 3, 2 to 5, and so on). In some aspects, k, p, and u independently are 1 to 5, e.g., 1, 2, 3, 4, or 5, or any range made therefrom (e.g., 1 to 4, 2 to 4, 1 to 3, 2 to 5, and so on). In some aspects, $R^1$, $R^2$, $R^3$, $R^4$, $R^5$, $R^{15}$, $R^{16}$, $R^{17}$, $R^{18}$, and $R^{23}$ independently are H or methyl. In some aspects, $R^6$ is H or a metal ion. In some aspects, the metal ion comprises an alkali metal, an alkaline earth metal, or a combination thereof. In some aspects, the alkali metal comprises lithium, sodium, potassium, rubidium, cesium, or any combination thereof. In some aspects, the alkaline earth metal comprises beryllium, magnesium, calcium, or any combination thereof. In some aspects, $Z^1$ is any suitable linking group. As used herein, a suitable linking group is one that covalently connects the two carbonyl functionalities on either end of the structure of formula (6). In some aspects, the linking group $Z^1$ comprises alkyl, aryl, ethylene glycol, oligo(ethylene glycol), poly(ethylene glycol) (e.g., polyethyleneglycol 250, or polyethyleneglycol 700), an amine, an ether, an ester, an amide, an ester when taken together with adjacent atoms, an amide when taken together with adjacent atoms, any substituted version thereof, or any combination thereof. For example, in some aspects, the linking group 1' comprises an alkyl in combination with two amine functionalities, such that $Z^1$ comprises a diamide when taken together with the two adjacent carbonyls shown in the structure of formula (6). In some aspects, a similar linking group is contemplated, but instead of a diamide the linking group is a diester. Other linking groups that can be made using the combination of disclosed options is contemplated herein and generally known.

In some aspects, the polymer is a copolymer. In some aspects, the copolymer comprises at least two of the structures of formulas (1), (2), (3), (4), (5), (6), and (27). In some aspects, the copolymer comprises the three structures of formulas (1) to (3). In some aspects, the copolymer comprises the four structures of formulas (1) to (4). In some aspects, the copolymer comprises the four structures of formulas (1) to (3) and (5). In some aspects, the copolymer comprises the four structures of formulas (3) to (5) and (27).

In some aspects, with regard to the structures of formulas (1) to (4) and (27), at least one of conditions (a) to (e) is satisfied: (a) m is 2, (b) n is 0, (c) p is 1, (d) $R^1$, $R^2$, $R^3$, $R^4$, and $R^5$ are methyl, or (e) all of conditions (a) to (d) are satisfied. In some aspects, the polymer comprises the four structures of formulas (1) to (4), and at least one of conditions (a) to (e) is satisfied: (a) m is 2, (b) n is 0, (c) p is 1, (d) $R^1$, $R^2$, $R^3$, $R^4$, and $R^5$ are methyl, or (e) all of conditions (a) to (d) are satisfied. In some aspects, the polymer comprises the four structures of formulas (1) to (4), and (a) m is 2, (b) n is 0, (c) p is 1, and (d) $R^1$, $R^2$, $R^3$, $R^4$, and $R^5$ are methyl.

In some aspects, the composition is a latex composition. In some aspects, the composition is a synthetic latex composition. In some aspects, the composition is a dispersion of polymer particles in a liquid. In some aspects, the composition is a stable dispersion of polymer particles in a liquid. In some aspects, the liquid comprises water. In some aspects, the composition is an emulsion of polymer particles in a liquid. In some aspects, the composition is a stable emulsion of polymer particles in a liquid. In some aspects, the liquid comprises water. In some aspects, the composition is a colloidal dispersion of polymer particles in a liquid. In some aspects, the liquid comprises water.

In some aspects, the chelate moiety comprises a magnetic resonance imaging (MRI) contrast agent, a positron emission tomography (PET) contrast agent, a single-photon emission computerized tomography (SPECT) contrast agent, or any combination thereof. In some aspects, the chelate moiety comprises tetraazacyclododecane comprising at least one acetate group, at least one acetic acid group, or a combination thereof. In some aspects, the chelate moiety comprises an MRI contrast agent. In some aspects, the chelate moiety comprises a PET contrast agent. In some aspects, the chelate moiety comprises a SPECT contrast agent. In some aspects, the chelate moiety comprises gadolinium, copper, indium, yttrium, yttrium(54), or any combination thereof. In some aspects, the chelate moiety comprises an MRI contrast agent comprising gadolinium. In some aspects, the chelate moiety comprises a PET or SPECT contrast agent comprising copper, indium, yttrium, yttrium (54), or any combination thereof.

In some aspects, the chelate moiety comprises at least one structure of formula (19) or formula (20):

(19)

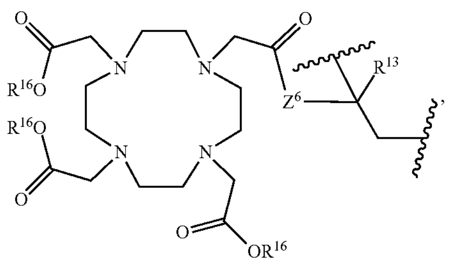

-continued (20)

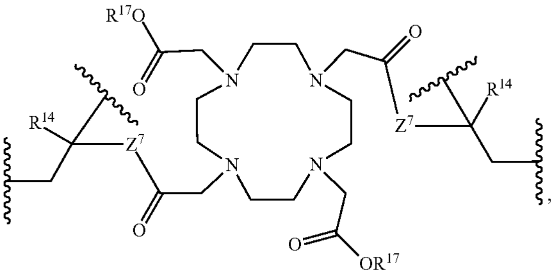

wherein:

$R^{13}$ and $R^{14}$ independently are H or methyl, $R^{16}$ and $R^{17}$ independently are H, a metal ion, a combination thereof, or taken together represent a metal ion that is chelated by the O atoms to which $R^{16}$ or $R^{17}$ are bound, and $Z^6$ and $Z^7$ independently are a linking group comprising alkyl, aryl, ethylene glycol, oligo(ethylene glycol), an amine, an ether, an ester, an amide, an ester when taken together with adjacent atoms, an amide when taken together with adjacent atoms, any substituted version thereof, or any combination thereof.

In some aspects, the chelate moiety comprises at least one structure of formula (19) or formula (20). In these structures, the wavy lines indicate points of covalent attachment within the polymer (e.g., within the interior bulk of the chelate nanoparticle). In some aspects, the chelate moiety comprises the structure of formula (19). In some aspects, the chelate moiety comprises the structure of formula (20). In some aspects, the chelate moiety comprises the structures of both formula (19) and formula (20). In some aspects, the presence of the crosslinking structure of formula (20) increases the concentration of this structure in the chelate nanoparticle (e.g., thereby increasing the concentration of MRI, PET, or SPECT contrast agent in the chelate nanoparticle). In some aspects, $R^{13}$ and $R^{14}$ independently are H or methyl. In some aspects, $R^{13}$ and $R^{14}$ independently are methyl. In some aspects, $R^{13}$ and $R^{14}$ independently are H. In some aspects, $R^{16}$ and $R^{17}$ independently are H, a metal ion, a combination thereof, or taken together represent a metal ion that is chelated by the O atoms to which $R^{16}$ or $R^{17}$ are bound. In some aspects, the metal ion comprises an alkali metal, an alkaline earth metal, or a combination thereof. In some aspects, the alkali metal comprises lithium, sodium, potassium, rubidium, cesium, or any combination thereof. In some aspects, the alkaline earth metal comprises beryllium, magnesium, calcium, or any combination thereof. In some aspects, $R^{16}$ and $R^{17}$ independently taken together represent a metal ion that is chelated by the O atoms to which $R^{16}$ or $R^{17}$ are bound, and such metal ion comprises gadolinium, copper, indium, yttrium, yttrium(54), or any combination thereof. In some aspects, $R^{16}$ and $R^{17}$ independently are H, a metal ion, a combination thereof, and $R^{16}$ and $R^{17}$ independently taken together are not chelated to a metal ion (e.g., such as gadolinium, copper, indium, yttrium, or yttrium (54)).

In some aspects, $Z^6$ and $Z^7$ independently are any suitable linking group. As used herein, a suitable linking group is one that covalently connects the chelate moiety of formula (19) or (20) to the polymer. In some aspects, $Z^6$ and $Z^7$ independently are a linking group comprising alkyl, aryl, ethylene glycol, oligo(ethylene glycol), an amine, an ether, an ester, an amide, an ester when taken together with adjacent atoms, an amide when taken together with adjacent atoms, any substituted version thereof, or any combination thereof. For example, in some aspects the linking groups $Z^6$ and $Z^7$ independently comprise an amide (on the chelate moiety side) connected to an ethyl group connected to an ester connected to a vinyl group. In some aspects, examples of suitable linking groups can be comprising the structures of formula (9) and (10) with (19) and (20). Other examples of linking groups are disclosed elsewhere herein in relation to $Z^1$, $Z^2$, $Z^3$, $Z^4$, $Z^5$, and $Z^8$, and such disclosures are equally applicable here. Any other suitable linking group can be independently employed for $Z^6$ and $Z^7$.

In some aspects, the nanoparticles comprising a plurality of a chelate nanoparticle are prepared by a process comprising emulsion polymerization of a mixture comprising a vinyl-containing chelate group, and at least one vinyl-containing monomer, wherein the chelate moiety is derived from the vinyl-containing chelate group. In some aspects, the emulsion polymerization described elsewhere herein for preparing a composition comprising a first fluorophore moiety is equally applicable here (except the vinyl-containing first fluorophore is replaced with a vinyl-containing chelate group). In some aspects, the vinyl-containing chelate group comprises tetraazacyclododecane comprising at least one acetate group or acetic acid group. In some aspects, the vinyl-containing chelate group comprises gadolinium, copper, indium, yttrium, yttrium(54), or any combination thereof during the emulsion polymerization. In some aspects, the vinyl-containing chelate group does not comprise gadolinium, copper, indium, yttrium, yttrium(54), or any combination thereof during the emulsion polymerization. In some aspects, the vinyl-containing chelate group does not comprise gadolinium, copper, indium, yttrium, yttrium(54), or any combination thereof during the emulsion polymerization, and the process further comprises, after the emulsion polymerization, subjecting the nanoparticles comprising a plurality of a chelate nanoparticle to gadolinium, copper, indium, yttrium, yttrium(54), or any combination thereof. In some aspects, the vinyl-containing chelate group comprises tetraazacyclododecane comprising at least one acetate group or acetic acid group and further comprises gadolinium, copper, indium, yttrium, yttrium(54), or any combination thereof during the emulsion polymerization.

In some aspects, the vinyl-containing chelate group contains one vinyl groups In some aspects, the vinyl-containing chelate group comprises at least two vinyl groups. In some aspects, the vinyl-containing chelate group comprises at least one structure of formulas (9), (10), (21), and (22):

(9)

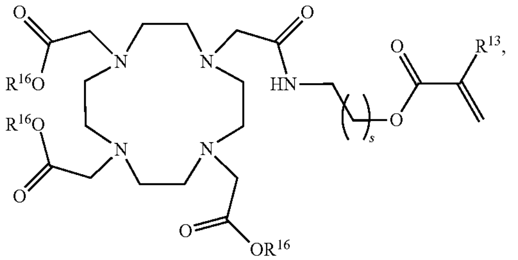

-continued (10)

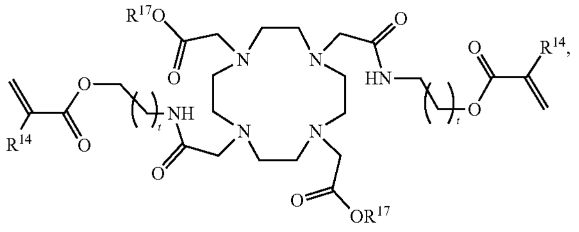

(21)

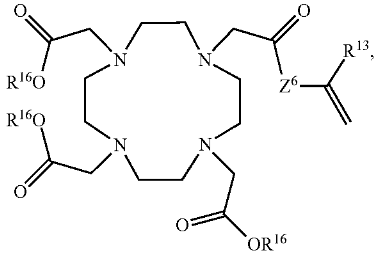

(22)

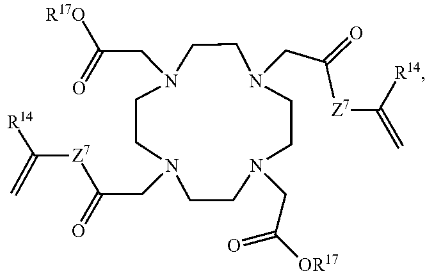

wherein:

$R^{13}$ and $R^{14}$ independently are H or methyl, s and t independently are 1 to 5, $R^{16}$ and $R^{17}$ independently are H, a metal ion, a combination thereof, or taken together represent a metal ion that is chelated by the O atoms to which $R^{16}$ or $R^{17}$ are bound, and $Z^6$ and $Z^7$ independently are a linking group comprising alkyl, aryl, ethylene glycol, oligo(ethylene glycol), an amine, an ether, an ester, an amide, an ester when taken together with adjacent atoms, an amide when taken together with adjacent atoms, any substituted version thereof, or any combination thereof.

In some aspects, $R^{13}$ and $R^{14}$ independently are H or methyl. In some aspects, $R^{13}$ and $R^{14}$ independently are H. In some aspects, $R^{13}$ and $R^{14}$ independently are methyl. In some aspects, s and t independently are 1 to 5, e.g., 1, 2, 3, 4, 5, or any range made therefrom (e.g., 1 to 3, 2 to 4, 2 to 5, 1 to 4, and so on). In some aspects, $R^{16}$ and $R^{17}$ independently are H, a metal ion, a combination thereof, or taken together represent a metal ion that is chelated by the O atoms to which $R^{16}$ or $R^{17}$ are bound. In some aspects, $Z^6$ and $Z^7$ independently are a linking group comprising alkyl, aryl, ethylene glycol, oligo(ethylene glycol), an amine, an ether, an ester, an amide, an ester when taken together with adjacent atoms, an amide when taken together with adjacent atoms, any substituted version thereof, or any combination thereof. $R^{16}$, $R^{17}$, $Z^6$, and $Z^7$ are discussed elsewhere herein with regard to structures of formulas (19) and (20), and such disclosures are equally applicable here with respect to the structures of formulas (9), (10), (21), and (22).

In some aspects, the at least one vinyl-containing monomer comprises an acrylate, a methacrylate, methyl methacrylate, methacrylic acid, acrylic acid, 2-hydroxyethyl methacrylate, 2-hydroxyethyl acrylate, 2-hydroxyethyl methacrylate, 3-hydroxypropyl acrylate, 3-hydroxyethyl methacrylate, ethylacrylate, ethylmethacrylate, propylacrylate, propylmethacrylate, butylacrylate, butylmethacrylate, laurylacrylate, laurylmethacrylate, stearylacrylate, stearylmethacrylate, glycidylacrylate, glycidylmethacrylate, acrylonitrile, acrylamide, vinylalcohol, vinylacetate, vinylbutyral, vinylpyrrolidone, styrene, or any combination thereof. In some aspects, the at least one vinyl-containing monomer comprises 2-hydroxyethyl methacrylate, methyl methacrylate, and methacrylic acid (optionally in combination with a crosslinker, such as ethylene glycol dimethacrylate). In some aspects, the emulsion polymerization comprises one or more monomers that result in one or more of a polyacrylate, a polyacrylic acid, a polymethacrylate, a polymethacrylic acid, a polymethylmethacrylate (PMMA), a polyethylacrylate, a polyethylmethacrylate, a polypropylacrylate, a polypropylmethacrylate, a polybutylacrylate, a polybutylmethacrylate, a polyhydroxyalkyl methacrylate, a poly(2-hydroxyethyl)methacrylate, a poly(3-hydroxypropyl) methacrylate, a poly(hydroxyalkyl)acrylate, a poly(2-hydroxyethyl)acrylate, a poly(3-hydroxypropyl)acrylate, a polylaurylacrylate, a polystearylacrylate, a polyglycidylacrylate, a polyglycidylmethacrylate, a polyacrylonitrile, a polyacrylamide, a polyvinyl alcohol, a polyvinyl acetate, a polyvinyl butyral, a polyvinylpyrrolidone, a polystyrene, or any combination thereof.

In some aspects, the emulsion polymerization comprises at least one crosslinker. In some aspects, the at least one crosslinker comprises any divinyl compound. In some aspects, the at least one crosslinker comprises ethylene glycol dimethacrylate, ethylene glycol diacrylate, oligo(ethylene glycol) diacrylate, oligo(ethylene glycol) dimethacrylate, poly(ethylene glycol) diacrylate, poly(ethylene glycol) dimethacrylate, divinyl benzene, or a combination thereof. In some aspects, the crosslinker comprises ethylene glycol dimethacrylate. In some aspects, the poly(ethylene glycol) diacrylate comprises poly(ethylene glycol) 250 diacrylate (i.e., PEG 250 diacrylate). In some aspects, the poly(ethylene glycol) diacrylate comprises poly(ethylene glycol) 700 diacrylate (i.e., PEG 700 diacrylate).

In some aspects, disclosed is a composition comprising:

a chelate moiety, and nanoparticles, wherein the nanoparticles comprise:

a plurality of a chelate nanoparticle, the chelate nanoparticle comprising:

an outer surface, an interior bulk, and a polymer, wherein the polymer is covalently bonded to the chelate moiety within the interior bulk of the chelate nanoparticle.

In some aspects, the composition is substantially free of a fluorophore moiety. In some aspects, the composition further comprises a fluorophore moiety, wherein the fluorophore moiety is covalently bonded to the polymer within the interior bulk of the chelate nanoparticle. In some aspects, the disclosures elsewhere herein pertaining to the first fluorophore moiety are equally applicable to the fluorophore moiety here. For example, in some aspects, the fluorophore moiety comprises coumarin, fluorescein, rhodamine, rhodamine B, cyanine, cyanine 5.5, or cyanine 7. In some aspects, the fluorophore moiety comprises at least one structure of formula (15) to (18) and (23):

(15)

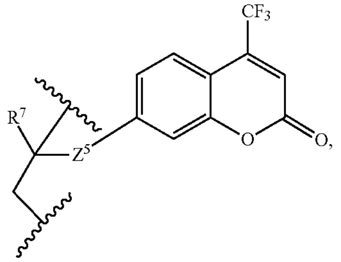

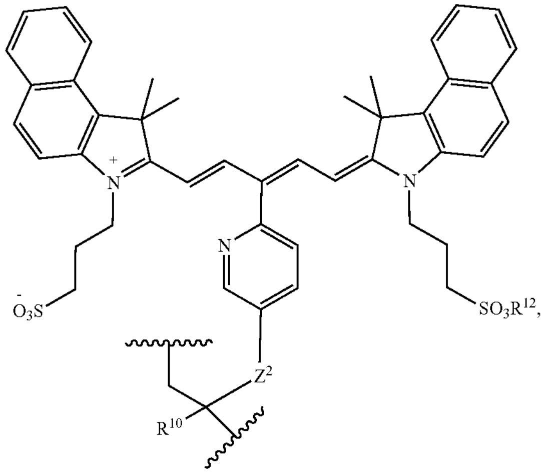

(18)

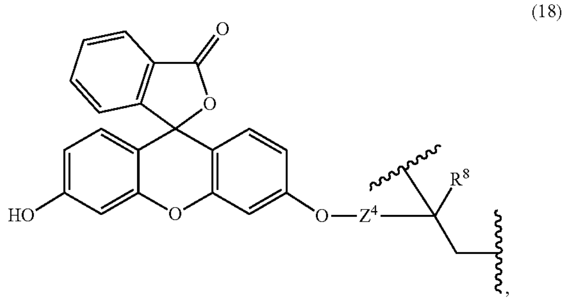

(23)

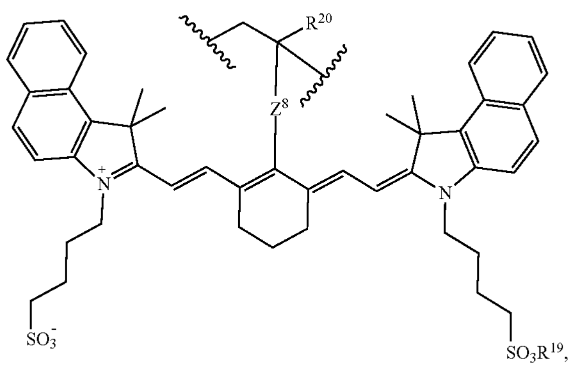

wherein:

$R^7$, $R^8$, $R^9$, $R^{10}$, and $R^{20}$ independently are H or methyl, $R^{11}$, $R^{12}$, and $R^{19}$ independently are H or a metal ion, and $Z^2$, $Z^3$, $Z^4$, $Z^5$, and $Z^8$ independently are a linking group comprising alkyl, aryl, ethylene glycol, oligo(ethylene glycol), an amine, an ether, an ester, an amide, a thiocarbamoyl, any substituted version thereof, or any combination thereof.

The disclosures elsewhere herein defining the R and Z groups (e.g., $R^7$, $R^8$, $R^9$, $R^{10}$, $R^{11}$, $R^{12}$, $R^{19}$, $R^{20}$, $Z^2$, $Z^3$, $Z^4$, $Z^5$, and $Z^8$) with respect to the first fluorophore moiety are equally applicable here to the fluorophore moiety in the context of a plurality of a chelate nanoparticle.

In some aspects, the disclosures elsewhere herein relating to compositions comprising a first fluorophore moiety and nanoparticles, in which the nanoparticles comprise a first plurality of a first nanoparticle, are equally applicable here with respect to the characteristics of the particles.

In some aspects, the nanoparticles (comprising a plurality of a chelate nanoparticle) comprise any suitable hydrodynamic diameter. In some aspects, the nanoparticles comprise a hydrodynamic diameter (nm) of 90, 95, 100, 105, 110, 115, 120, 125, 130, 135, 140, 145, 150, 155, 160, 165, 170, 175, 180, 185, 190, 195, or 200, as measured by dynamic light scattering. Each of the foregoing numbers can be preceded by the word “about,” “at least about,” or “less than about,” and any of the foregoing numbers can be used singly to describe an open-ended range or in combination to describe a close-ended range. For example, in some aspects, the hydrodynamic diameter (nm) is about 90 to about 200, about 95 to about 145, at least about 105, or less than about 130.

In some aspects, the nanoparticles comprise any suitable average zeta potential. In some aspects, the nanoparticles comprise a negative average zeta potential. In some aspects, the nanoparticles comprise an average zeta potential (mV) of −10, −12, −14, −16, −18, −20, −22, −24, −26, −28, −30, −32, −34, −36, −38, −40, −42, −44, −46, −48, −50, −52, −54, −56, −58, or −60. Each of the foregoing numbers can be preceded by the word “about,” “at least about,” or “less than about,” and any of the foregoing numbers can be used singly to describe an open-ended range or in combination to describe a close-ended range. For example, in some aspects, the average zeta potential (mV) is about −10 to about −50, about −30 to about −60, or less than about −38 (i.e., more negative than about −38).

In some aspects, the chelate moiety comprises gadolinium. In some aspects, the chelate moiety comprises gadolinium, and after removal of any free gadolinium by dialysis, the composition comprises the gadolinium at a concentration (μM) of 50, 60, 70, 80, 90, 100, 110, 120, 130, 140, 150, 160, 170, 180, 190, 200, 220, 240, 260, 280, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or 3000, as measured by inductively coupled plasma mass spectrometry (ICP-MS). Each of the foregoing numbers can be preceded by the word “about,” “at least about,” or “less than about,” and any of the foregoing numbers can be used singly to describe an open-ended range or in combination to describe a close-ended range. For example, in some aspects, the after removal of any free gadolinium by dialysis, the composition comprises the gadolinium at a concentration (μM) of about 50 to about 2500, about 50 to about 70, at least about 800, or about 2000 to about 2500.

In some aspects, the chelate moiety comprises gadolinium. In some aspects, the chelate moiety comprises gadolinium, and prior to removal of any free gadolinium by dialysis, the composition comprises the gadolinium at a concentration (μM) of 50, 60, 70, 80, 90, 100, 110, 120, 130, 140, 150, 160, 170, 180, 190, 200, 220, 240, 260, 280, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or 3000, as measured by inductively coupled plasma mass spectrometry (ICP-MS). Each of the foregoing numbers can be preceded by the word “about,” “at least about," or "less than about," and any of the foregoing numbers can be used singly to describe an open-ended range or in combination to describe a close-ended range. For example, in some aspects, the prior to removal of any free gadolinium by dialysis, the composition comprises the gadolinium at a concentration (μM) of about 50 to about 2500, about 50 to about 70, at least about 800, or about 2000 to about 2500, as measured by ICP-MS.

In some aspects, the disclosures elsewhere herein relating to compositions comprising a first fluorophore moiety and nanoparticles, in which the nanoparticles comprise a first plurality of a first nanoparticle, are equally applicable here with respect to the characteristics of the particles. For example, the disclosures relating to the types of fluorophores present, and the associated excitation and emission maxima, are similarly applicable here.

In some aspects, the fluorophore moiety comprises cyanine 5.5. In some aspects, the fluorophore moiety comprises cyanine 5.5, and when excited at a wavelength of 650 nm, the nanoparticles comprise an emission maximum of about 696 nm to about 716 nm (e.g., about 701 nm to about 711 nm, or about 706 nm). The measurement typically is performed in a composition comprising water at the particle concentrations disclosed elsewhere herein.

In some aspects, the nanoparticles comprise chelate moiety at a concentration of $X\times10^{-14}$ μM per chelate nanoparticle where X is 7.0, 7.5, 8.0, 8.5, 9.0, 9.5, 10, 11, 12, 13, 14, 15, 16, 17, 18, 19, 20, 22, 24, 26, 28, 30, 32, 34, 36, 38, 40, 42, 44, 46, 48, or 50, as calculated using the mass of chelate nanoparticle per mL and the concentration of chelated metal (e.g., gadolinium) as measured by ICP-MS. Each of the foregoing numbers can be preceded by the word "about," "at least about," or "less than about," and any of the foregoing numbers can be used singly to describe an open-ended range or in combination to describe a close-ended range. For example, in some aspects, the nanoparticles comprise chelate moiety at a concentration of $X\times10^{-14}$ μM per chelate nanoparticle where X is about 7.0 to 50, at least about 10, or less than about 38. In some aspects, the chelate moiety comprises gadolinium. In some aspects, the chelate moiety comprises gadolinium, copper, indium, yttrium, yttrium(54), or any combination thereof.

In some aspects, the composition comprises the nanoparticles (comprising a plurality of a chelate nanoparticle) in an amount (mg/mL) of 15, 20, 25, 30, 35, 40, 45, 50, 55, 60, 65, 70, 75, 80, 85, 90, 95, or 100. Each of the foregoing numbers can be preceded by the word "about," "at least about," or "less than about," and any of the foregoing numbers can be used singly to describe an open-ended range or in combination to describe a close-ended range. For example, in some aspects, the composition comprises the nanoparticles in an amount (mg/mL) of about 20 to about 100, at least about 35, or about 40 to 60.

In some aspects, the chelate moiety comprises gadolinium, and the nanoparticles comprise a longitudinal relaxation rate ($r_1$) ($mM^{-1}s^{-1}$) of 3, 4, 5, 6, 7, 8, 9, 10, 12, 14, 16, 18, 20, 22, 24, 26, 28, or 30. Each of the foregoing numbers can be preceded by the word "about," "at least about," or "less than about," and any of the foregoing numbers can be used singly to describe an open-ended range or in combination to describe a close-ended range. For example, in some aspects, $r_1$ ($mM^{-1}s^{-1}$) is about 6, about 3 to about 10, about 23, or about 20 to about 28.

In some aspects, the chelate moiety comprises gadolinium, and the nanoparticles comprise a transverse relaxation rate ($r_2$) ($mM^{-1}s^{-1}$) of 70, 75, 80, 85, 87, 89, 90, 92, 94, 95, 100, 105, 110, 115, 120, 125, 130, 135, 140, 145, or 150. Each of the foregoing numbers can be preceded by the word "about," "at least about," or "less than about," and any of the foregoing numbers can be used singly to describe an open-ended range or in combination to describe a close-ended range. For example, in some aspects, $r_2$ ($mM^{-1}s^{-1}$) is about 89, about 85 to about 100, about 130, or about 120 to about 140. In some aspects, adding In some aspects, the composition (containing nanoparticles comprising a plurality of a chelate nanoparticle) further comprises a fluorophore moiety, and the nanoparticles are prepared by a process comprising emulsion polymerization of a mixture comprising a vinyl-containing chelate group, a vinyl-containing fluorophore, and at least one vinyl-containing monomer, wherein the chelate moiety is derived from the vinyl-containing chelate group and the fluorophore moiety is derived from the vinyl-containing fluorophore. The emulsion polymerization described elsewhere herein for preparing nanoparticles comprising a plurality of a chelate nanoparticle is equally applicable here, except here the mixture additionally comprises a vinyl-containing fluorophore. In addition, the at least one vinyl-containing monomer is described elsewhere herein and such disclosures are equally applicable here. Moreover, the vinyl-containing chelate group is described elsewhere herein and such disclosures are equally applicable here. Furthermore, the disclosures elsewhere herein pertaining to the vinyl-containing first fluorophore are equally applicable here to the vinyl-containing fluorophore (e.g., the vinyl-containing fluorophore here can be the vinyl-containing first fluorophore described elsewhere herein). Additionally, the emulsion polymerization of the mixture comprising a vinyl-containing chelate group, a vinyl-containing fluorophore, and at least one vinyl-containing monomer can further comprise at least one crosslinker, which crosslinker is described elsewhere herein and applicable here.

In some aspects, when the composition (comprising nanoparticles comprising a plurality of a chelate nanoparticle optionally comprising a fluorophore moiety) is injected into viable neural tissue, the nanoparticles are transported in axons in a retrograde fashion. As used herein, "viable neural tissue" is neural tissue that exhibits sufficient cellular function to transport objects, such as nanoparticles, to a similar extent as if the neural tissue was present in the brain of a living organism (in some aspects, the viable neural tissue is actually present in the brain of a living organism). In some aspects, when the composition is injected into viable neural tissue (e.g., brain) of a mammal (e.g., a living mammal), the nanoparticles are transported in a retrograde fashion. In some aspects, when the composition is injected into viable neural tissue (e.g., brain) of a mammal (e.g., primate or human), the nanoparticles are transported in axons in a retrograde fashion along an entorhinal cortex (EC) to first hippocampal region (CA1) pathway. In some aspects, when the composition is injected into viable neural tissue (e.g., brain) of a mammal (e.g., primate or human), the nanoparticles are transported in axons in a retrograde fashion along a lateral geniculate nucleus (LGN) to primary visual cortex (V1) pathway. In some aspects, when the composition is injected into viable neural tissue (e.g., brain) of a mouse (e.g., living mouse), the nanoparticles are transported in axons in a retrograde fashion along an entorhinal cortex (EC) to first hippocampal region (CA1) pathway. In some aspects, when the composition is injected into viable neural tissue (e.g., brain) of a mouse (e.g., living mouse), the nanoparticles are transported in axons in a retrograde fashion along a lateral geniculate nucleus (LGN) to primary visual cortex (V1) pathway.

In some aspects, the composition (comprising nanoparticles comprising a plurality of a chelate nanoparticle optionally comprising a fluorophore moiety) is employed in a method of brain mapping or tracing an axonal projection. In some aspects, the method comprises subjecting a first neuron to the composition to form a first infused neuron, and imaging the first infused neuron using at least one of fluorescence spectroscopy, magnetic resonance imaging (MRI), positron emission tomography (PET), single-photon emission computerized tomography (SPECT), or any combination thereof. In some aspects, the method further comprises subjecting a second neuron to the composition to form a second infused neuron, and imaging the second infused neuron using at least one of fluorescence spectroscopy, magnetic resonance imaging (MRI), positron emission tomography (PET), single-photon emission computerized tomography (SPECT), or any combination thereof. In some aspects, the method further comprises subjecting a third neuron to the composition to form a third infused neuron, and imaging the third infused neuron using at least one of fluorescence spectroscopy, magnetic resonance imaging (MRI), positron emission tomography (PET), single-photon emission computerized tomography (SPECT), or any combination thereof. In some aspects, the method further comprises subjecting a fourth neuron (or fifth, sixth, seventh, and so on) to the composition to form a fourth infused neuron (or fifth, sixth, seventh, and so on), and imaging the fourth infused neuron (or fifth, sixth, seventh, and so on) using at least one of fluorescence spectroscopy, magnetic resonance imaging (MRI), positron emission tomography (PET), single-photon emission computerized tomography (SPECT), or any combination thereof. In some aspects, the method comprises fluorescence spectroscopy. In some aspects, the method comprises fluorescence spectroscopy and MRI. In some aspects, the method comprises, MRI. In some aspects, the method comprises PET. In some aspects, the method comprises SPECT.

In some aspects, at least one of the first neuron, the second neuron, the third neuron, the fourth neuron, and so on, are different neurons present in different locations from one another. In some aspects, at least one of the first neuron, the second neuron, the third neuron, the fourth neuron, and so on, are the same neuron. In some aspects, at least one of the first neuron, the second neuron, the third neuron, the fourth neuron, and so on, are the same neuron but infused in different locations as part of the method.

In some aspects, disclosed is a method of brain mapping or tracing an axonal projection, the method comprising injecting a brain in a first location with a first composition and in a second location with a second composition, and performing at least one of imaging the brain using fluorescence spectroscopy, magnetic resonance imaging (MRI), positron emission tomography (PET), single-photon emission computerized tomography (SPECT), or any combination thereof. In some aspects, the first composition and the second composition can be the same or different. In some aspects, the method comprises fluorescence spectroscopy. In some aspects, the method comprises fluorescence spectroscopy and MRI. In some aspects, the method comprises MRI. In some aspects, the method comprises PET. In some aspects, the method comprises SPECT. In some aspects, the method further comprises injecting the brain in a third location with a third composition that can be the same or different from the first and second compositions, and imaging using fluorescence spectroscopy, MRI, PET, or SPECT. In some aspects, the method further comprises injecting the brain in a fourth location (or fifth, sixth, seventh, and so on) with a fourth composition (or fifth, sixth, seventh, and so on) that can be the same or different from the first, second, and third compositions (or fifth, sixth, seventh, and so on), and imaging using fluorescence spectroscopy, MRI, PET, or SPECT. In some aspects, the first and second locations (or third, fourth, fifth, sixth, seventh, and so on) are in the hippocampus. In some aspects, the first and second locations (or third, fourth, fifth, sixth, seventh, and so on) are in the cerebral cortex, cerebrum, cerebellum, brainstem, amygdala, cingulate gyrus, prefrontal cortex, dentate gyrus, entorhinal cortex, or any combination thereof.

In some aspects, the method of brain mapping comprises the use of a composition comprising nanoparticles with a chelate moiety (but substantially free of a fluorophore moiety) in addition to a separate composition comprising nanoparticles with a fluorophore moiety (but substantially free of a chelate group). Such two (or more) compositions can be injected or subjected to neurons in different locations to brain map or trace an axonal projection.

In some aspects, disclosed is a method of preparing a composition comprising nanoparticles, the method comprising:

- emulsion polymerizing a mixture comprising:
  - at least one vinyl-containing monomer, and
  - at least one vinyl-containing fluorophore or at least one vinyl-containing chelate group,
- wherein the nanoparticles comprise:
  - polymer,
  - at least one fluorophore moiety or at least one chelate moiety, and
- wherein the at least one fluorophore moiety, if present, is covalently bonded to the polymer, the at least one chelate moiety, if present, is covalently bonded to the polymer.

In some aspects, this method of preparing a composition comprising nanoparticles is similar to the processes disclosed elsewhere herein for making the compositions comprising nanoparticles also disclosed elsewhere herein. As a result, such disclosures set forth elsewhere herein are equally applicable here.

In some aspects, the at least one vinyl-containing fluorophore is present and comprises a vinyl-containing first fluorophore. In some aspects, the at least one vinyl-containing fluorophore is present and comprises a vinyl-containing first fluorophore and a vinyl-containing second fluorophore. In some aspects, the at least one vinyl-containing fluorophore is present and comprises a vinyl-containing first fluorophore, a vinyl-containing second fluorophore, and a vinyl-containing third fluorophore. In some aspects, the at least one vinyl-containing fluorophore is present and comprises a vinyl-containing first fluorophore, a vinyl-containing second fluorophore, a vinyl-containing third fluorophore, and a vinyl-containing fourth fluorophore. The disclosures elsewhere herein pertaining to the vinyl-containing first fluorophore, the vinyl-containing second fluorophore, the vinyl-containing third fluorophore, and the vinyl-containing fourth fluorophore are equally applicable here.

In some aspects, if present, the vinyl-containing first fluorophore, the vinyl-containing second fluorophore, the vinyl-containing third fluorophore, the vinyl-containing fourth fluorophore, or all such vinyl-containing fluorophores independently comprises coumarin, fluorescein, rhodamine, rhodamine B, cyanine, cyanine 5.5, or cyanine 7. In some aspects, the vinyl-containing first fluorophore comprises rhodamine and the vinyl-containing second fluorophore comprises fluorescein. In some aspects, the vinyl-containing first fluorophore comprises cyanine 5.5 and the vinyl-containing second fluorophore comprises coumarin. In some aspects, the vinyl-containing first fluorophore comprises coumarin, the vinyl-containing second fluorophore comprises fluorescein, the vinyl-containing third fluorophore comprises cyanine 5.5, and the vinyl-containing fourth fluorophore comprises rhodamine B. All other combinations are contemplated herein.

In some aspects, each of the vinyl-containing fluorophores, if present, independently comprise a structure of formula (7) to (14) and (24) to (26). For example, in some aspects, the vinyl-containing first fluorophore, the vinyl-containing second fluorophore, or both the vinyl-containing first fluorophore and the vinyl-containing second fluorophore independently comprises a structure of formula (7) to (14) and (24) to (26):

(7)

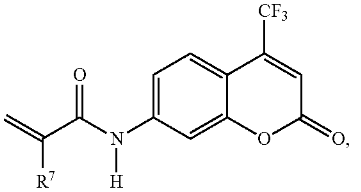

(8)

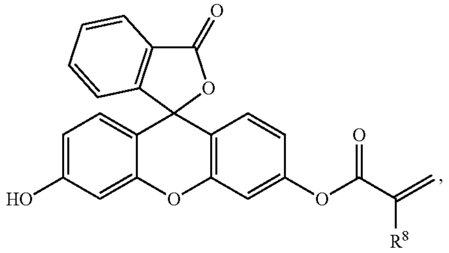

(10)

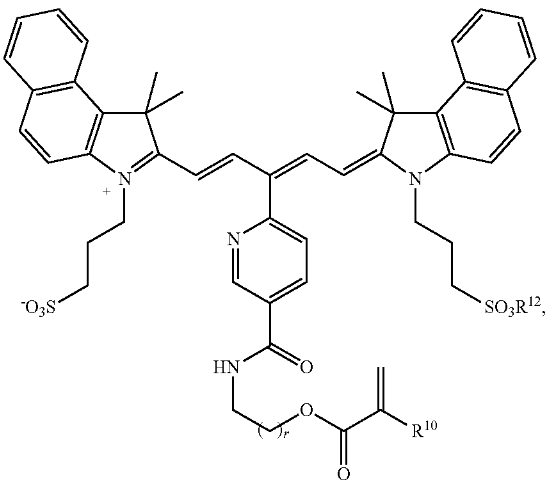

(11)

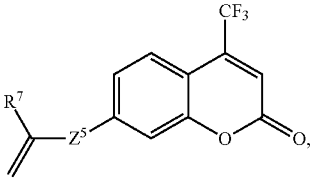

-continued (12)

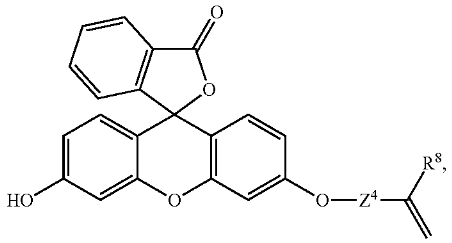

(14)

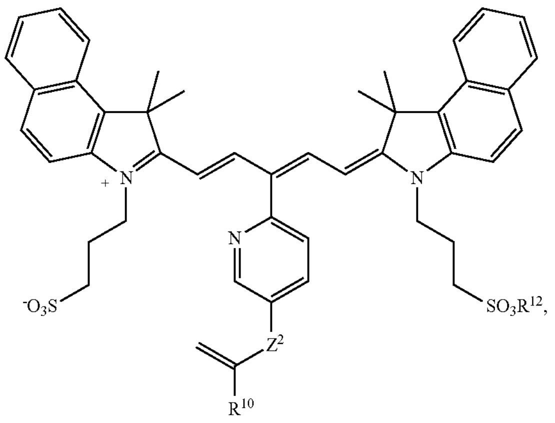

(24)

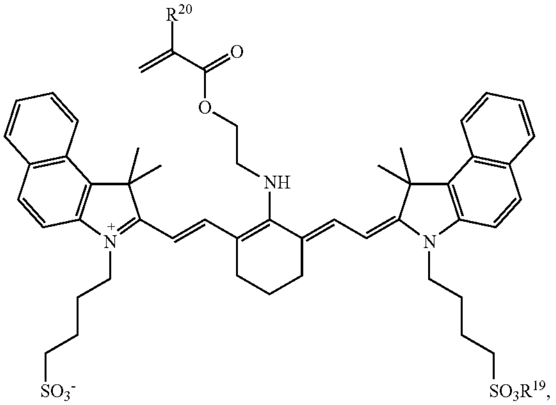

(25)

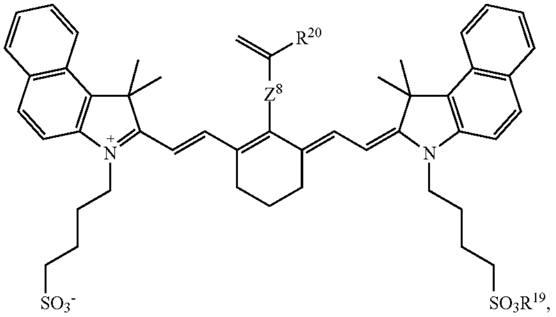

-continued (26)

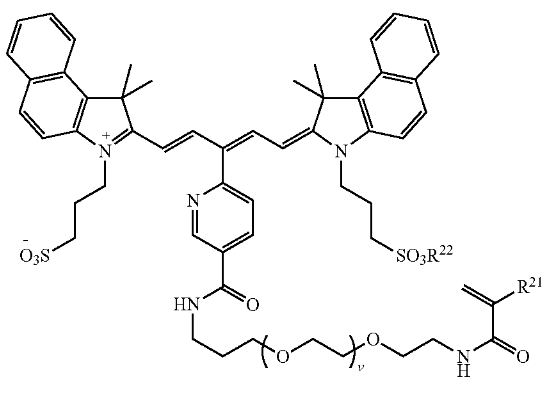

wherein:

$R^7$, $R^8$, $R^9$, $R^{10}$, $R^{20}$, and $R^{21}$ independently are H or methyl, q and r independently are 1 to 5, v is 0 to 5, $R^{11}$, $R^{12}$, $R^{19}$, and $R^{22}$ independently are H or a metal ion, and $Z^2$, $Z^3$, $Z^4$, $Z^5$, and $Z^8$ independently are a linking group comprising alkyl, aryl, ethylene glycol, oligo(ethylene glycol), an amine, an ether, an ester, an amide, a thiocarbamoyl, any substituted version thereof, or any combination thereof.

In some aspects, the disclosures elsewhere herein pertaining to the vinyl-containing first fluorophore are equally applicable here. For example, in some aspects, the vinyl-containing fluorophore (e.g., which can comprise a vinyl-containing first fluorophore, a vinyl-containing second fluorophore, and so on) comprises a structure of formula (7) to (14) and (24) to (26). In some aspects, $R^7$, $R^8$, $R^9$, $R^{10}$, $R^{20}$, and $R^{21}$ independently are H or methyl. In some aspects, each of $R^7$, $R^8$, $R^9$, $R^{10}$, $R^{20}$, and $R^{21}$ independently is H. In some aspects, each of $R^7$, $R^8$, $R^9$, $R^{10}$, $R^{20}$, and $R^{21}$ independently is methyl. In some aspects, q and r independently are 1 to 5. In some aspects, q independently is 1 to 5, e.g., 1, 2, 3, 4, or 5, or any range made therefrom (e.g., 1 to 4, 1 to 2, 1 to 3, 2 to 5, 3 to 5, and so on). In some aspects, r independently is 1 to 5, e.g., 1, 2, 3, 4, or 5, or any range made therefrom (e.g., 1 to 4, 1 to 2, 1 to 3, 2 to 5, 3 to 5, 4 to 5, and so on). In some aspects, v is 0 to 5, e.g., 0, 1, 2, 3, 4, or 5, or any range made therefrom (e.g., 0 to 4, 1 to 4, 2 to 5, 1 to 3, and so on). In some aspects, $R^{11}$, $R^{12}$, $R^{19}$, and $R^{22}$ independently are H or a metal ion. In some aspects, each of $R^{11}$, $R^{12}$, $R^{19}$, and $R^{22}$ independently is H. In some aspects, each of $R^{11}$, $R^{12}$, $R^{19}$, and $R^{22}$ independently is a metal ion. The disclosures elsewhere herein pertaining to $R^6$ are equally applicable to $R^{11}$, $R^{12}$, $R^{19}$, and $R^{22}$. In some aspects, $Z^2$, $Z^3$, $Z^4$, $Z^5$, and $Z^8$ independently are any suitable linking group. As used herein, a suitable linking group is one that covalently connects the vinyl-containing first fluorophore to the vinyl group (e.g., polymerizable vinyl group). For example, in some aspects, the linking group comprises alkyl, aryl, ethylene glycol, oligo(ethylene glycol), an amine, an ether, an ester, an amide, a thiocarbamoyl, any substituted version thereof, or any combination thereof. For example, in some aspects, the linking group $Z^2$, $Z^3$, $Z^4$, $Z^5$, and $Z^8$ independently comprises an amide connected to an ethylene glycol connected to another amide. In some aspects, the linking group $Z^2$, $Z^3$, $Z^4$, $Z^5$, and $Z^8$ independently comprises an amide connected to an ethyl connected to an ester. Additional suitable linking groups would be known to those of ordinary skill in the art simply by comparing various generic structures with the more specific structures disclosed herein (e.g., compare structure (7) with (11), structure (8) with (12), structure (10) or (26) with (14), and structure (24) with (25)). It is contemplated that such linking groups are interchangeable among the various vinyl-containing first fluorophores, and other variations can be contemplated in view of the structures of these linking groups.

In some aspects, the disclosures elsewhere herein relating to the at least one vinyl-containing monomer are equally applicable here. For example, in some aspects, the at least one vinyl-containing monomer comprises an acrylate, a methacrylate, methyl methacrylate, methacrylic acid, acrylic acid, 2-hydroxyethyl methacrylate, 2-hydroxyethyl acrylate, 2-hydroxyethyl methacrylate, 3-hydroxypropyl acrylate, 3-hydroxyethyl methacrylate, ethylacrylate, ethylmethacrylate, propylacrylate, propylmethacrylate, butylacrylate, butylmethacrylate, laurylacrylate, laurylmethacrylate, stearylacrylate, stearylmethacrylate, glycidylacrylate, glycidylmethacrylate, acrylonitrile, acrylamide, vinylalcohol, vinylacetate, vinylbutyral, vinylpyrrolidone, styrene, or any combination thereof. In some aspects, the at least one vinyl-containing monomer comprises 2-hydroxyethyl methacrylate, methyl methacrylate, and methacrylic acid (optionally in combination with a crosslinker, such as ethylene glycol dimethacrylate). In some aspects, the emulsion polymerization comprises one or more monomers that result in one or more of a polyacrylate, a polyacrylic acid, a polymethacrylate, a polymethacrylic acid, a polymethylmethacrylate (PMMA), a polyethylacrylate, a polyethylmethacrylate, a polypropylacrylate, a polypropylmethacrylate, a polybutylacrylate, a polybutylmethacrylate, a polyhydroxyalkyl methacrylate, a poly(2-hydroxyethyl) methacrylate, a poly(3-hydroxypropyl)methacrylate, a poly (hydroxyalkyl)acrylate, a poly(2-hydroxyethyl)acrylate, a poly(3-hydroxypropyl)acrylate, a polylaurylacrylate, a polystearylacrylate, a polyglycidylacrylate, a polyglycidylmethacrylate, a polyacrylonitrile, a polyacrylamide, a polyvinyl alcohol, a polyvinyl acetate, a polyvinyl butyral, a polyvinylpyrrolidone, a polystyrene, or any combination thereof.

In some aspects, in the method, the mixture in the emulsion polymerizing further comprises a crosslinker. The disclosures elsewhere herein pertaining to the crosslinker are equally applicable here. For example, in some aspects, the at least one crosslinker comprises any divinyl compound. In some aspects, the at least one crosslinker comprises ethylene glycol dimethacrylate, ethylene glycol diacrylate, oligo(ethylene glycol) diacrylate, oligo(ethylene glycol) dimethacrylate, poly(ethylene glycol) diacrylate, poly(ethylene glycol) dimethacrylate, divinyl benzene, or a combination thereof. In some aspects, the crosslinker comprises ethylene glycol dimethacrylate. In some aspects, the poly(ethylene glycol) diacrylate comprises poly(ethylene glycol) 250 diacrylate (i.e., PEG 250 diacrylate). In some aspects, the poly(ethylene glycol) diacrylate comprises poly(ethylene glycol) 700 diacrylate (i.e., PEG 700 diacrylate).

In some aspects, the at least one a vinyl-containing chelate group is present during the emulsion polymerization. The vinyl-containing chelate group is disclosed elsewhere herein and such disclosures are equally applicable here. For example, in some aspects, the at least one vinyl-containing chelate group comprises tetraazacyclododecane comprising at least one acetate group or acetic acid group. In some aspects, the vinyl-containing chelate group comprises a magnetic resonance imaging (MRI) contrast agent, a positron emission tomography (PET) contrast agent, a single-photon emission computerized tomography (SPECT) contrast agent, or any combination thereof. In some aspects, the vinyl-containing chelate group comprises an MRI contrast agent. In some aspects, the vinyl-containing chelate group comprises a PET contrast agent. In some aspects, the vinyl-containing chelate group comprises a SPECT contrast agent. In some aspects, the vinyl-containing chelate group comprises gadolinium, copper, indium, yttrium, yttrium(54), or any combination thereof. In some aspects, the chelate moiety comprises an MRI contrast agent comprising gadolinium. In some aspects, the vinyl-containing chelate group comprises a PET or SPECT contrast agent comprising copper, indium, yttrium, yttrium(54), or any combination thereof.

In some aspects, the vinyl-containing chelate group contains one vinyl group. In some aspects, the vinyl-containing chelate group comprises at least two vinyl groups. In some aspects, the vinyl-containing chelate group comprises at least one structure of formulas (9), (10), (21), and (22):

(9)

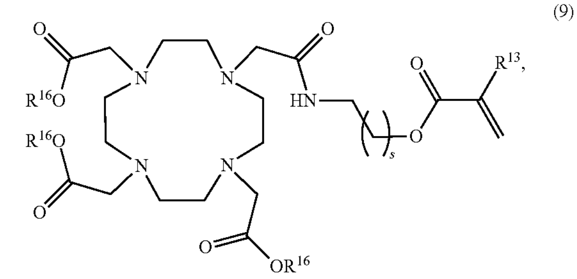

(10)

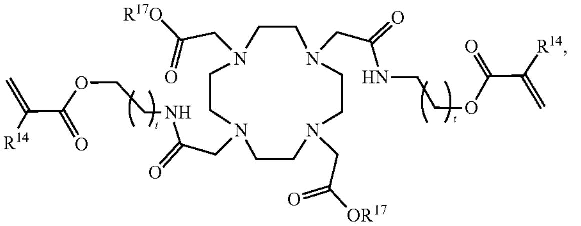

(21)

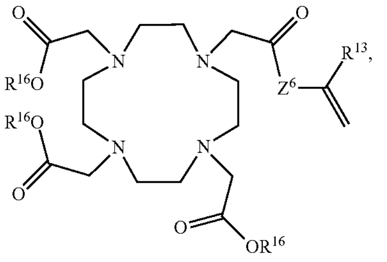

(22)

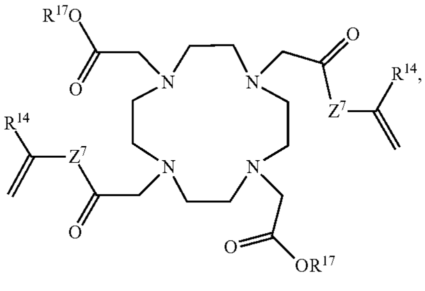

wherein, $R^{13}$ and $R^{14}$ independently are H or methyl, s and t independently are 1 to 5, $R^{16}$ and $R^{17}$ independently are H, a metal ion, a combination thereof, or taken together represent a metal ion that is chelated by the O atoms to which $R^{16}$ or $R^{17}$ are bound, and $Z^6$ and $Z^7$ independently are a linking group comprising alkyl, aryl, ethylene glycol, oligo(ethylene glycol), an amine, an ether, an ester, an amide, an ester when taken together with adjacent atoms, an amide when taken together with adjacent atoms, any substituted version thereof, or any combination thereof.

In some aspects, $R^{13}$ and $R^{14}$ independently are H or methyl. In some aspects, $R^{13}$ and $R^{14}$ independently are H. In some aspects, $R^{13}$ and $R^{14}$ independently are methyl. In some aspects, s and t independently are 1 to 5, e.g., 1, 2, 3, 4, 5, or any range made therefrom (e.g., 1 to 3, 2 to 4, 2 to 5, 1 to 4, and so on). In some aspects, $R^{16}$ and $R^{17}$ independently are H, a metal ion, a combination thereof, or taken together represent a metal ion that is chelated by the O atoms to which $R^{16}$ or $R^{17}$ are bound. In some aspects, $Z^6$ and $Z^7$ independently are a linking group comprising alkyl, aryl, ethylene glycol, oligo(ethylene glycol), an amine, an ether, an ester, an amide, an ester when taken together with adjacent atoms, an amide when taken together with adjacent atoms, any substituted version thereof, or any combination thereof. $R^{16}$, $R^{17}$, $Z^6$ and $Z^7$ are discussed elsewhere herein with regard to structures of formulas (19) and (20), and such disclosures are equally applicable here with respect to the structures of formulas (9), (10), (21), and (22). For example, in some aspects, in some aspects, the metal ion comprises an alkali metal, an alkaline earth metal, or a combination thereof. In some aspects, the alkali metal comprises lithium, sodium, potassium, rubidium, cesium, or any combination thereof. In some aspects, the alkaline earth metal comprises beryllium, magnesium, calcium, or any combination thereof. In some aspects, $R^{16}$ and $R^{17}$ independently taken together represent a metal ion that is chelated by the O atoms to which $R^{16}$ or $R^{17}$ are bound. In some aspects, such chelated metal ion comprises gadolinium, copper, indium, yttrium, yttrium(54), or any combination thereof. In some aspects, $R^{16}$ and $R^{17}$ independently are H, a metal ion, a combination thereof, and $R^{16}$ and $R^{17}$ independently taken together are not chelated to a metal ion (e.g., such as gadolinium, copper, indium, yttrium, or yttrium(54)).

In some aspects, $Z^6$ and $Z^7$ independently are any suitable linking group. As used herein, a suitable linking group is one that covalently connects the macrocycle of formulas (9), (10), (21), and/or (22) to the vinyl group. In some aspects, $Z^6$ and $Z^7$ independently are a linking group comprising alkyl, aryl, ethylene glycol, oligo(ethylene glycol), an amine, an ether, an ester, an amide, an ester when taken together with adjacent atoms, an amide when taken together with adjacent atoms, any substituted version thereof, or any combination thereof. For example, in some aspects the linking groups $Z^6$ and $Z^7$ independently comprise an amide (on the chelate moiety side) connected to an ethyl group connected to an ester connected to a vinyl group. In some aspects, examples of suitable linking groups can be comprising the structures of formula (9) and (10) with (21) and (22). Other examples of linking groups are disclosed elsewhere herein in relation to $Z^1$, $Z^2$, $Z^3$, $Z^4$, $Z^5$, and $Z^8$, and such disclosures are equally applicable here. Any other suitable linking group can be independently employed for $Z^6$ and $Z^7$.

In some aspects, in the method, the mixture further comprises any suitable surfactant to facilitate the emulsion polymerization. For example, in some aspects, the mixture further comprises at least one surfactant present during the emulsion polymerization, wherein the at least one surfactant comprises an ionic surfactant, an anionic surfactant, a cationic surfactant, a nonionic surfactant, sodium dodecyl sulfate (SDS), sodium undecylsulfate, sodium decylsulfate, TRITON X-100, TWEEN 20, polysorbate 20, polysorbate 80, or any combination thereof. In some aspects, the surfactant comprises SDS.

In some aspects, in the method, the mixture further comprises any suitable radical initiator. In some aspects, at least one radical initiator is present during the emulsion polymerization, which radical initiator comprises a persulfate salt, ammonium persulfate, an azo compound (e.g., azobisisobutyronitrile), t-butyl peroctoate, benzoyl peroxide in combination with dimethylaniline, a photoinitiator, eosin Y in combination with triethylamine, sodium phenyl-2,4,6-trimethylbenzoylphosphinate (SPTP), or any combination thereof. In some aspects, the radical initiator comprises ammonium persulfate.

In some aspects, in the emulsion polymerization of a mixture, the mixture comprises any suitable liquid. In some aspects, the liquid comprises water, methanol, tetrahydrofuran, or any combination thereof.

In some aspects, in emulsion polymerization of a mixture, the sum total (wt. %) of all polymerizable monomer (which does not include crosslinker, vinyl-containing fluorophore, or vinyl-containing chelate group) present at the start of the emulsion polymerization, is 20, 21, 22, 23, 24, 25, 26, 27, 28, 29, 30, 31, 32, 33, 34, 35, 36, 37, 38, 39, or 40, based on the total weight of the mixture. Each of the foregoing numbers can be preceded by the word "about," "at least about," or "less than about," and any of the foregoing numbers can be used singly to describe an open-ended range or in combination to describe a close-ended range. For example, in some aspects, the sum total (wt. %) of all polymerizable monomer present at the start of the emulsion polymerization is about 25 to about 30, at least about 19, or less than about 35, based on the total weight of the mixture (which comprises, e.g., surfactant, water, initiator, and so on).

In some aspects, in emulsion polymerization of a mixture, a given monomer or monomers (which does not include crosslinker, vinyl-containing fluorophore, or vinyl-containing chelate group) is present in the mixture at the beginning of emulsion polymerization in an amount (wt. %) of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, based on the total weight of the mixture. Each of the foregoing numbers can be preceded by the word "about," "at least about," or "less than about," and any of the foregoing numbers can be used singly to describe an open-ended range or in combination to describe a close-ended range. For example, in some aspects, a given monomer is present in the mixture at the beginning of emulsion polymerization in an amount (wt. %) of about 5 to about 10, at least about 19, or less than about 35, based on the total weight of the mixture (which comprises, e.g., surfactant, water, initiator, and so on). The foregoing amounts can apply to a single monomer, to any combination of monomers, or to the total amount of all monomers present.

In some aspects, at least one monomer (i.e., vinyl-containing monomer), at least one crosslinker, or both can be employed in any suitable amount during the emulsion polymerization. For example, in some aspects, the mixture for emulsion polymerization comprises about 1 molar equivalent ("eq.") MAA. The amount (eq.) of MAA can vary, however, such that the emulsion polymerization mixture comprises MAA in an amount of 0.8, 0.85, 0.9, 0.95, 1, 1.05, 1.1, 1.15, or 1.2. Each of the foregoing numbers can be preceded by the word "about," "at least about," or "less than about," and any of the foregoing numbers can be used singly to describe an open-ended range or in combination to describe a close-ended range. For example, the mixture can comprise about 0.9 to about 1 eq. MAA, or at least about 0.95 eq. In some aspects, the emulsion polymerization mixture comprises HEMA in an amount (eq.) of 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3. Each of the foregoing numbers can be preceded by the word "about," "at least about," or "less than about," and any of the foregoing numbers can be used singly to describe an open-ended range or in combination to describe a close-ended range. For example, the mixture can comprise about 1.8 to about 2.4 eq. of HEMA, in some aspects in addition to about 1 eq. of MAA (or any other amount disclosed herein). In some aspects, the emulsion polymerization mixture comprises MMA in an amount (eq.) of 3, 3.2, 3.4, 3.6, 3.8, 4, 4.2, 4.4, 4.6, 4.8, 5, 5.2, 5.4, or 5.6. Each of the foregoing numbers can be preceded by the word "about," "at least about," or "less than about," and any of the foregoing numbers can be used singly to describe an open-ended range or in combination to describe a close-ended range. For example, the mixture can comprise about 4 to about 5.2 eq. of MMA, in some aspects in addition to about 1 eq. MAA (or any other amount disclosed herein). In some aspects, the emulsion polymerization mixture comprises a crosslinker (e.g., EGD) in an amount (eq.) of 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, or 1. Each of the foregoing numbers can be preceded by the word "about," "at least about," or "less than about," and any of the foregoing numbers can be used singly to describe an open-ended range or in combination to describe a close-ended range. For example, the mixture can comprise about 0.2 to about 0.4 eq. of a crosslinker (e.g., EGD), in some aspects in addition to about 1 eq. of MAA (or any other amount disclosed herein). In some aspects, MAA is not present in the emulsion polymerization mixture. In some aspects, a monomer that is present is selected to be the about 1 eq. reference point and the equivalents of other components recalculated accordingly. In some aspects, the emulsion polymerization mixture comprises any combination of two or more of any monomer disclosed herein (e.g., MAA, MMA, HEMA), and in some aspects a crosslinker (e.g., EGD) in any suitable amount disclosed herein. For example, in some aspects, the emulsion polymerization mixture comprises MAA in an amount of about 1.05 eq., HEMA in an amount of about 1.8 to about 2 eq., and MMA in an amount of about 4.2 to about 5 eq. In some aspects, HEMA and EGD are employed in any disclosed amount. In some aspects, HEMA, EGD, and MMA are employed in any disclosed amount. In some aspects, HEMA, MMA, and MAA are employed in any disclosed amount. Other combinations are contemplated herein, using any other monomer or crosslinker disclosed herein, and in any suitable amount.

In some aspects, any monomer, crosslinker, or both can be employed in any suitable amount. Any monomer and/or crosslinker disclosed herein can be employed in the amounts disclosed herein. For example, in some aspects, such compound(s) can be employed in the emulsion polymerization in an amount (eq.) of 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.05, 1.1, 1.15, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.2, 4.4, 4.6, 4.8, 5, 5.2, 5.4, 5.6, 5.8, 6, 6.2, 6.4, 6.6, 6.8, 7, 7.5, 8, 8.5, 9, 9.5, or 10. Each of the foregoing numbers can be preceded by the word "about," "at least about," or "less than about," and any of the foregoing numbers can be used singly to describe an open-ended range or in combination to describe a close-ended range. For example, in some aspects, butylmethacrylate is employed in an amount (eq.) of about 1.8 to about 2.4, vinylalcohol is employed in an amount of about 3.6 to about 4.8, methacrylic acid is employed in an amount of about 0.95 to about 1.2, and divinylbenzene is employed in an amount of about 0.2 to about 0.5. Any monomer and/or crosslinker disclosed can be employed in any amount disclosed herein.

In some aspects, in emulsion polymerization of a mixture, crosslinker (which does not include any amount of a divinyl-containing chelate group if present) is present in the mixture at the beginning of emulsion polymerization in an amount (wt. %) of 1, 2, 3, 4, 5, 6, 7, 8, 9, 10, 11, 12, 13, 14, 15, 16, 17, 18, 19, 20, 21, 22, 23, 24, or 25, based on the total weight of the mixture. Each of the foregoing numbers can be preceded by the word "about," "at least about," or "less than about," and any of the foregoing numbers can be used singly to describe an open-ended range or in combination to describe a close-ended range. For example, in some aspects, the crosslinker is present in the mixture at the beginning of emulsion polymerization in an amount (wt. %) of about 5 to about 20 wt. %, at least about 3 wt. % or less than about 18 wt. %.

In some aspects, in emulsion polymerization of a mixture, a radical initiator is present in any suitable amount. For example, in some aspects, the radical initiator is present in the mixture at the beginning of emulsion polymerization in a catalytic amount. In some aspects, the radical initiator is present in the mixture at the beginning of emulsion polymerization in an amount (wt. %) of 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, or 0.2, based on the total weight of all polymerizable monomers present (which does not include crosslinker, vinyl-containing fluorophore, or vinyl-containing chelate group). Each of the foregoing numbers can be preceded by the word "about," "at least about," or "less than about," and any of the foregoing numbers can be used singly to describe an open-ended range or in combination to describe a close-ended range. For example, in some aspects, the radical initiator is present in the mixture at the beginning of emulsion polymerization in an amount (wt. %) of about 0.02 to about 0.1, about 0.08, or less than about 0.9, based on the total weight of all polymerizable monomers present (which does not include crosslinker, vinyl-containing fluorophore, or vinyl-containing chelate group).

In some aspects, in emulsion polymerization of a mixture, surfactant is present in any suitable amount. In some aspects, the total amount (wt. %) of all surfactant present in the mixture at the beginning of emulsion polymerization is 0.008, 0.009, 0.01, 0.012, 0.013, 0.014, 0.015, 0.02, 0.025, 0.03, 0.035, 0.04, 0.045, 0.05, 0.055, 0.060, 0.07, 0.08, 0.09, 0.1, 0.15, 0.2, 0.25, 0.3, 0.35, 0.4, 0.45, 0.5, 0.55, 0.6, 0.65, 0.7, 0.75, or 0.8, based on the total weight of the mixture. Each of the foregoing numbers can be preceded by the word "about," "at least about," or "less than about," and any of the foregoing numbers can be used singly to describe an open-ended range or in combination to describe a close-ended range. For example, in some aspects, the total amount (wt. %) of all surfactant present in the mixture at the beginning of emulsion polymerization is about 0.03 to about 0.5, 0.025 to about 0.1, or at least about 0.08, based on the total weight of the mixture.

In some aspects, in emulsion polymerization of a mixture, a vinyl-containing fluorophore is present in any suitable amount. In some aspects, the amount of vinyl-containing fluorophore is present in a sufficient amount, such that once the polymerization is complete, the resulting fluorophore moiety is visible by the desired imaging method (e.g., fluorescence spectroscopy). In some aspects, the amount of vinyl-containing fluorophore is at least partially related to the extinction coefficient of the particle fluorophore. In some aspects, the vinyl-containing fluorophore is present in the mixture in an amount (molar equivalents) of 0.00001, 0.00002, 0.00003, 0.00004, 0.00005, 0.00006, 0.00007, 0.00008, 0.00009, 0.0001, 0.0002, 0.0003, 0.0004, 0.0005, 0.0006, 0.0007, 0.0008, 0.0009, 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, or 0.05, based on the number of moles of all polymerizable monomer (vinyl-containing monomer) (which amount does not include, if present, crosslinker or vinyl-containing chelate group) present in the mixture at the beginning of emulsion polymerization. Each of the foregoing numbers can be preceded by the word "about," "at least about," or "less than about," and any of the foregoing numbers can be used singly to describe an open-ended range or in combination to describe a close-ended range. For example, in some aspects, the vinyl-containing fluorophore is present in the mixture in an amount (molar equivalents) of about 0.001 to about 0.0035, about 0.00001 to about 0.0001, or at least about 0.0015. Examples 1 and 5 are particularly instructive regarding the amount of vinyl-containing fluorophore. For example, when the vinyl-containing fluorophore comprises cyanine 5.5, the amount (molar equivalents) of such vinyl-containing fluorophore is about 0.001 to about 0.002, based on the number of moles of all polymerizable monomer (which does not include, if present, crosslinker or vinyl-containing chelate group) present in the mixture at the beginning of emulsion polymerization. For example, when the vinyl-containing fluorophore comprises cyanine 7, the amount (molar equivalents) of such vinyl-containing fluorophore is about 0.00001 to about 0.0001, based on the number of moles of all polymerizable monomer (which does not include, if present, crosslinker or vinyl-containing chelate group) present in the mixture at the beginning of emulsion polymerization. For example, when the vinyl-containing fluorophore comprises rhodamine B, the amount (molar equivalents) of such vinyl-containing fluorophore is about 0.0008 to about 0.0015, based on the number of moles of all polymerizable monomer (which does not include, if present, crosslinker or vinyl-containing chelate group) present in the mixture at the beginning of emulsion polymerization. For example, when the vinyl-containing fluorophore comprises fluorescein, the amount (molar equivalents) of such vinyl-containing fluorophore is about 0.0025 to about 0.004, based on the number of moles of all polymerizable monomer (which does not include, if present, crosslinker or vinyl-containing chelate group) present in the mixture at the beginning of emulsion polymerization. For example, when the vinyl-containing fluorophore comprises coumarin, the amount (molar equivalents) of such vinyl-containing fluorophore is about 0.0005 to about 0.002, based on the number of moles of all polymerizable monomer (which does not include, if present, crosslinker or vinyl-containing chelate group) present in the mixture at the beginning of emulsion polymerization. However, such amounts can be increased (e.g., to enable observation of a strong single) or decreased (e.g., to prevent another signal from being obscured) for a desired purpose.

In some aspects, in emulsion polymerization of a mixture, a vinyl-containing chelate group is present in any suitable amount. In some aspects, the amount of vinyl-containing chelate group is present in a sufficient amount, such that once the polymerization is complete, the resulting chelate moiety is observable by the desired imaging method (e.g., at least one of MRI, PET, and SPECT). For example, in some aspects, MRI contrast agents are observable in the nanomolar concentration range, whereas PET and SPECT contrast agents are observable in the picomolar concentration range. As such, if MRI is the desired imaging method, the vinyl-containing chelate group should be present in a relatively higher concentration as compared to if PET or SPECT in the desired imaging method. In some aspects, the vinyl-containing chelate group is present in the mixture in an amount (molar equivalents) of 0.000005, 0.00001, 0.000015, 0.00002, 0.00003, 0.00004, 0.00005, 0.00006, 0.00007, 0.00008, 0.00009, 0.0001, 0.0002, 0.0003, 0.0004, 0.0005, 0.0006, 0.0007, 0.0008, 0.0009, 0.001, 0.002, 0.003, 0.004, 0.005, 0.006, 0.007, 0.008, 0.009, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.3, 0.35, 0.4, 0.45, 0.5, 0.55, 0.6, 0.65, 0.7, 0.75, or 0.8, based on the number of moles of all polymerizable monomer (vinyl-containing monomer) (which does not include, if present, crosslinker, vinyl-containing fluorophore, vinyl-containing chelate group, or chelated metal such as gadolinium) present in the mixture at the beginning of emulsion polymerization. Each of the foregoing numbers can be preceded by the word "about," "at least about," or "less than about," and any of the foregoing numbers can be used singly to describe an open-ended range or in combination to describe a close-ended range. For example, in some aspects, the vinyl-containing chelate group is present in an amount (molar equivalents) of about 0.01 to about 0.03, less than about 0.04, or at least about 0.0003. For clarity, such molar amounts herein with respect to the vinyl-containing chelate group are based on the molar mass of the vinyl-containing chelate group without accounting for the molar mass of any chelated metal that might be present (for example, even if one or more metals are chelated, the molar equivalents are calculated as if the metal(s) are not present, and such calculations are made as if protons are present to the extent the chemical structure would otherwise be incomplete, e.g., if acetate groups are present and are actually chelated to a metal: such metal would be replaced by a proton for calculation purposes). The breadth of possible ranges for the vinyl-containing chelate group is necessitated by the large variation in detection limits amount the various detection methods (e.g., MRI, PET, SPECT, fluorescence).

In some aspects, the mixture comprises at least one vinyl-containing monomer in an amount of about 20 wt. % to about 40 wt. %; crosslinker in an amount of about 1 wt. % to about 25 wt. %; and surfactant in an amount of about 0.008 wt. % to about 0.8 wt. %, wherein all amounts are based on the total weight of the mixture. Any other combination of components and amounts disclosed herein is contemplated herein. In some aspects, the mixture comprises (or further comprises) at least one of vinyl-containing fluorophore in an amount of about 0.001 molar equivalents to about 0.004 molar equivalents; and vinyl-containing chelate group in an amount of about 0.01 molar equivalents to about 0.1 molar equivalents; wherein all amounts are based on number of moles of all vinyl-containing monomer.

Other conditions for emulsion polymerization are those typically employed for such a reaction, such as employing an elevated temperature to facilitate emulsion polymerization. For example, the temperature (° C.) is 70, 75, 80, 85, 90, 95, 100, 105, or 110. Each of the foregoing numbers can be preceded by the word "about," "at least about," or "less than about," and any of the foregoing numbers can be used singly to describe an open-ended range or in combination to describe a close-ended range. For example, in some aspects, the temperature (° C.) is about 90, at least about 85, or about 85 to about 105. In addition, the emulsion polymerization is carried out at a specified temperature for any suitable time until the reaction is completed, e.g., the time (min) is 20, 25, 30, 35, 40, 45, 50, 55, 60, 65, 70, 75, 80, 85, or 90. Each of the foregoing numbers can be preceded by the word "about," "at least about," or "less than about," and any of the foregoing numbers can be used singly to describe an open-ended range or in combination to describe a close-ended range. For example, in some aspects, the time (min) is about 60, about 45 to about 75, or less than about 65.

In some aspects of the emulsion polymerization, the monomers are distilled in vacuo before use. In some aspects nanopure water is added to a flask, followed by addition of the monomers to the nanopure water while under argon. In some aspects, the monomers are added in a particular order: e.g., HEMA (about 2 equivalents), then MMA (about 4.6 eq.), then MAA (about 1 eq.), then EGD (about 0.31 eq.). In some aspects the mixture at this point is stirred at about 300 rpm. In some aspects, a surfactant (e.g., SDS) (about 0.047 eq.) and a radical initiator (e.g., ammonium persulfate) (e.g., about 0.0064 eq.) are then added to the flask. In some aspects, then at least one vinyl-containing fluorophore, at least one vinyl-containing chelate group, or both, are then added to the flask. In some aspects, this addition is done by first dissolving the vinyl-containing fluorophore and/or vinyl-containing chelate group in a suitable solvent, e.g., tetrahydrofuran, methanol, water, or any combination thereof, and then adding to the flask containing the monomer(s) and water. In some aspects, this mixture is then stirred for a short time, e.g., about 5 min, before immersing the flask in an oil bath for about 90° C. for about 1 hour. In some aspects, the reaction mixture is then removed from the oil bath, allowed to rest at room temperature, and then the resulting nanoparticles purified, e.g., by dialysis into MILLI-Q water. In some aspects, further incubation is performed with an AG 501-X8(D) mixed bed resin overnight to remove excess surfactant prior to use (e.g., in vitro and/or in vivo use).

In some aspects, the method is employed to make any of the compositions disclosed elsewhere herein (e.g., the composition comprising nanoparticles comprising a first plurality of a first nanoparticle, the composition comprising nanoparticles comprising a plurality of a chelate nanoparticle, and so on).

Various aspects are contemplated herein, several of which are set forth in the paragraphs below. It is explicitly contemplated that any aspect or portion thereof can be combined.

Aspect 1: A composition comprising:

a first fluorophore moiety, and nanoparticles, wherein the nanoparticles comprise:

a first plurality of a first nanoparticle, the first nanoparticle comprising:

a first outer surface, a first interior bulk, and a first polymer, wherein the first polymer is covalently bonded to the first fluorophore moiety within the first interior bulk of the first nanoparticle.

Aspect 2: The composition of aspect 1, wherein the first polymer comprises a polyacrylate, a polyacrylic acid, a polymethacrylate, a polymethacrylic acid, a polymethylmethacrylate (PMMA), a polyethylacrylate, a polyethylmethacrylate, a polypropylacrylate, a polypropylmethacrylate, a polybutylacrylate, a polybutylmethacrylate, a polyhydroxyalkyl methacrylate, a poly(2-hydroxyethyl) methacrylate, a poly(3-hydroxypropyl)methacrylate, a poly(hydroxyalkyl)acrylate, a poly(2-hydroxyethyl)acrylate, a poly(3-hydroxypropyl)acrylate, a polylaurylacrylate, a polystearylacrylate, a polyglycidylacrylate, a polyglycidylmethacrylate, a polyacrylonitrile, a polyacrylamide, a polyvinyl alcohol, a polyvinyl acetate, a polyvinyl butyral, a polyvinylpyrrolidone, a polystyrene, or any combination thereof.

Aspect 3: The composition of any preceding aspect, wherein the first polymer comprises at least one structure of formula (1) to (6) and (27):

(1)

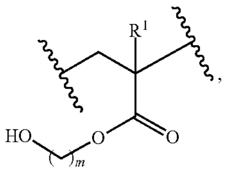

(2)

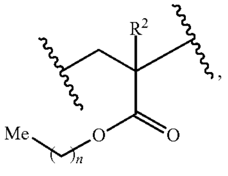

(3)

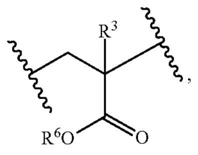

(4)

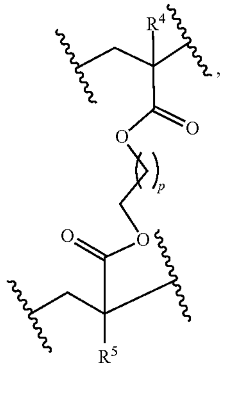

-continued (5)

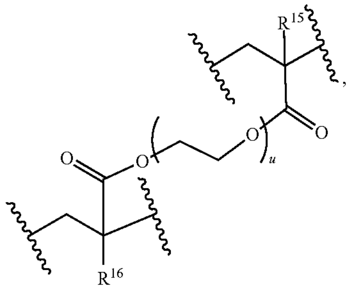

(6)

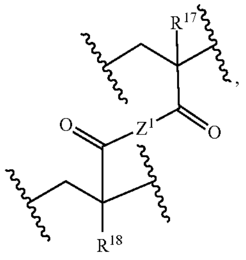

(27)

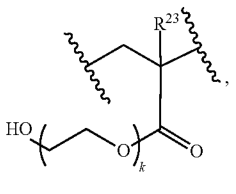

wherein:

m is 2 to 5, n is 0 to 5, k, p, and u independently are 1 to 5, $R^1$, $R^2$, $R^3$, $R^4$, $R^5$, $R^{15}$, $R^{16}$, $R^{17}$, $R^{18}$, and $R^{23}$ independently are H or methyl, $R^6$ is H or a metal ion, and $Z^1$ is a linking group comprising alkyl, aryl, ethylene glycol, oligo(ethylene glycol), poly(ethylene glycol), an amine, an ether, an ester, an amide, an ester when taken together with adjacent atoms, an amide when taken together with adjacent atoms, any substituted version thereof, or any combination thereof.

Aspect 4: The composition of any preceding aspect, wherein the first polymer is a copolymer.

Aspect 5: The composition of aspect 4, wherein the copolymer comprises the structures of formulas (1) to (4).

Aspect 6: The composition of any one of aspects 3-5, wherein at least one of conditions (a) to (e) is satisfied:

(a) m is 2, (b) n is 0, (c) p is 1, (d) $R^1$, $R^2$, $R^3$, $R^4$, and $R^5$ are methyl, or (e) all of conditions (a) to (d) are satisfied.

Aspect 7: The composition of any preceding aspect, wherein the composition is a latex composition.

Aspect 8: The composition of any preceding aspect, wherein the first fluorophore moiety comprises coumarin, fluorescein, rhodamine, rhodamine B, cyanine, cyanine 5.5, or cyanine 7.

Aspect 9: The composition of aspect 8, wherein the first fluorophore moiety comprises at least one structure of formula (15) to (18) and (23):

(15)

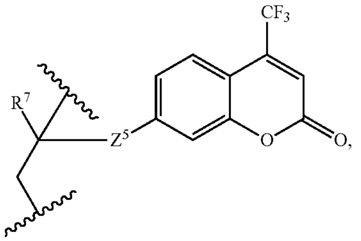

(16)

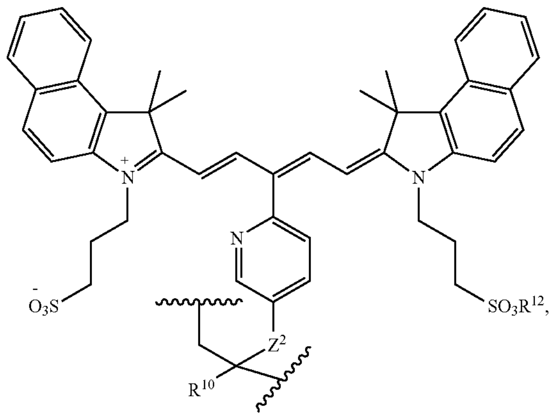

(18)

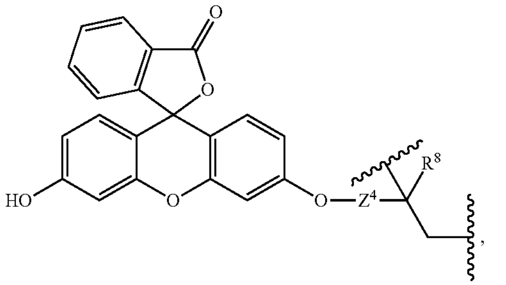

(23)

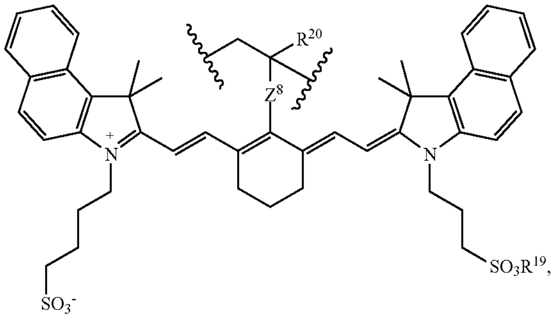

wherein:

$R^7$, $R^8$, $R^9$, $R^{10}$, and $R^{20}$ independently are H or methyl, $R^{11}$, $R^{12}$, and $R^{19}$ independently are H or a metal ion, and $Z^2$, $Z^3$, $Z^4$, $Z^5$, and $Z^8$ independently are a linking group comprising alkyl, aryl, ethylene glycol, oligo(ethylene glycol), an amine, an ether, an ester, an amide, a thiocarbamoyl, any substituted version thereof, or any combination thereof.

Aspect 10: The composition of any preceding aspect, wherein the nanoparticles comprise:

a diameter of about 30 to about 120 nm, as measured by uranyl acetate stained dry-state transmission electron microscopy, or a diameter of about 30 nm to about 120 nm, as measured by cryogenic electron microscopy.

Aspect 11: The composition of any preceding aspect, wherein the nanoparticles comprise:

a hydrodynamic diameter of about 50 nm to 200 nm, as measured by dynamic light scattering.

Aspect 12: The composition of any preceding aspect, wherein the nanoparticles comprise:

an average zeta potential of about −20 mV to about −60 mV.

Aspect 13: The composition of any preceding aspect, wherein the composition comprises nanoparticles at a concentration of about $0.1\times10^{11}$ to about $30\times10^{11}$ particles per mL, as measured by nanoparticle tracking analysis.

Aspect 14: The composition of any preceding aspect, wherein the composition comprises the first fluorophore moiety at a concentration of about 40 μM to about 700 μM, as measured by UV-Vis spectroscopy.

Aspect 15: The composition of any preceding aspect, wherein, as measured by UV-Vis spectroscopy:

the first fluorophore moiety comprises coumarin, and the composition comprises the coumarin at a concentration of about 20 μM to about 120 μM, the first fluorophore moiety comprises fluorescein, and the composition comprises the fluorescein at a concentration of about 500 μM to about 700 μM, the first fluorophore moiety comprises rhodamine B, and the composition comprises the rhodamine B at a concentration of about 380 μM to about 550 μM, or the first fluorophore moiety comprises cyanine 5.5, and the composition comprises the cyanine 5.5 at a concentration of about 70 μM to about 200 μM.

Aspect 16: The composition of any preceding aspect, wherein:

the composition comprises the first fluorophore moiety at a concentration of about $1.00\times10^{-13}$ μmol/nanoparticle to about $32.0\times10^{-13}$ μmol/nanoparticle, as calculated from nanoparticle concentration per mL of the composition and concentration of the first fluorophore moiety in the composition.

Aspect 17: The composition of any preceding aspect, wherein, as calculated from nanoparticle concentration per mL and first fluorophore moiety:

the first fluorophore moiety comprises coumarin, and the nanoparticles comprise the coumarin at a concentration of about $1.00\times10^{-13}$ μmol/nanoparticle to about $5.00\times10^{-13}$ μmol/nanoparticle, the fluorophore moiety comprises fluorescein, and the nanoparticles comprise the fluorescein at a concentration of about $25.0\times10^{-13}$ μmol/nanoparticle to about $35.0\times10^{13}$ μmol/nanoparticle, the fluorophore moiety comprises rhodamine B, and the nanoparticles comprise the rhodamine B at a concentration of about $1.00\times10^{-13}$ μmol/nanoparticle to about $5.00\times10^{-13}$ μmol/nanoparticle, the fluorophore moiety comprises cyanine 5.5, and the nanoparticles comprise the cyanine 5.5 at a concentration of about $2.00\times10^{-13}$ μmol/nanoparticle to about $10.0\times10^{-13}$ μmol/nanoparticle, or the first fluorophore moiety comprises cyanine 7, and the nanoparticles comprise the cyanine 7 at a concentration of about $1.00\times10^{-13}$ μmol/nanoparticle to about $5.00\times10^{-13}$ μmol/nanoparticle.

Aspect 18: The composition of any preceding aspect, wherein, when measured at a concentration of about 2.1×

$10^{11}$ to about $3.2\times10^{11}$ particles per mL, the composition comprises an absorption peak in a UV-Vis spectrum of about 340 nm to about 360 nm.

Aspect 19: The composition of any preceding aspect, wherein:

- the first fluorophore moiety comprises coumarin, and when measured at a concentration of about $3.2\times10^{11}$ nanoparticles per mL, the nanoparticles comprise an excitation maximum of about 340 nm to about 360 nm and an emission maximum of about 402 nm to about 422 nm,
- the first fluorophore moiety comprises fluorescein, and when measured at a concentration of about $2.1\times10^{11}$ nanoparticles per mL, the nanoparticles comprise an excitation maximum of about 480 nm to about 500 nm and an emission maximum of about 503 nm to about 523 nm,
- the first fluorophore moiety comprises rhodamine B, and when measured at a concentration of about $23\times10^{11}$ nanoparticles per mL, the nanoparticles comprise an excitation maximum of about 548 nm to about 568 nm and an emission maximum of about 576 nm to about 596 nm,
- the first fluorophore moiety comprises cyanine 5.5, and when measured at a concentration of about $2.5\times10^{11}$ nanoparticles per mL, the nanoparticles comprise an excitation maximum of about 662 nm to about 682 nm and an emission maximum of about 690 nm to about 710 nm, or
- the first fluorophore moiety comprises cyanine 7, and when measured at a concentration of about $9.4\times10^{9}$ nanoparticles per mL, the nanoparticles comprise an excitation maximum of about 647 nm to about 667 nm and an emission maximum of about 796 nm to about 816 nm.

Aspect 20: The composition of any preceding aspect, wherein, when the composition having a concentration of nanoparticles of about $2.4\times10^{10}$ to about $30\times10^{10}$ as measured by nanoparticle tracking analysis is subjected to human embryonic kidney 293 (HEK 293) cells, the composition is nontoxic to the HEK 293 cells, as indicated by a cell viability of the HEK 293 cells of at least 20% after incubating the HEK 293 cells with the composition for 48 hours.

Aspect 21: The composition of any preceding aspect, wherein, when a composition having a concentration of nanoparticles of about $2.4\times10^{10}$ to about $30\times10^{10}$ as measured by nanoparticle tracking analysis is incubated for 20 minutes with human embryonic kidney 293 (HEK 293) cells, washed with Dulbecco's phosphate-buffered saline, incubated in media for 24 hours, and then fixed with an appropriate stain, the HEK 293 cells subjected to the composition have a higher mean fluorescence intensity than an otherwise identical composition containing otherwise identical nanoparticles as measured by confocal laser scanning microscopy, except that the otherwise identical nanoparticles comprise LUMAFLUOR RED or LUMAFLUOR GREEN.

Aspect 22: The composition of any preceding aspect, wherein, when human embryonic kidney 293 (HEK 293) cells are subjected to a colocalization assay comprising the composition and LC3 antibody, the nanoparticles are trafficked intracellularly at a faster rate, as measured over a period of 48 hours, than an otherwise identical colocalization assay with an otherwise identical composition with otherwise identical nanoparticles, except that the otherwise identical nanoparticles comprise LUMAFLUOR RED or LUMAFLUOR GREEN.

Aspect 23: The composition of any preceding aspect, wherein, when the composition is injected into viable neural tissue of a mouse, the nanoparticles are transported in axons in a retrograde fashion along an entorhinal cortex (EC) to first hippocampal region (CA1) pathway.

Aspect 24: The composition of any preceding aspect, wherein, when the composition is injected into viable neural tissue of a mouse, the nanoparticles are transported in axons in a retrograde fashion along a lateral geniculate nucleus (LGN) to primary visual cortex (V1) pathway.

Aspect 25: The composition of any preceding aspect, wherein the nanoparticles are prepared by a process comprising emulsion polymerization of a mixture comprising:

a vinyl-containing first fluorophore, and at least one vinyl-containing monomer, wherein the first fluorophore moiety is derived from the vinyl-containing first fluorophore.

Aspect 26: The composition of aspect 25, wherein the vinyl-containing first fluorophore comprises coumarin, fluorescein, rhodamine, rhodamine B, cyanine, cyanine 5.5, or cyanine 7.

Aspect 27: The composition of aspect 25 or aspect 26, wherein the vinyl-containing first fluorophore comprises a structure of formula (7) to (14) and (24) to (26):

(7)

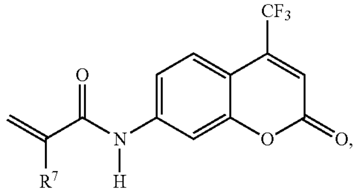

(8)

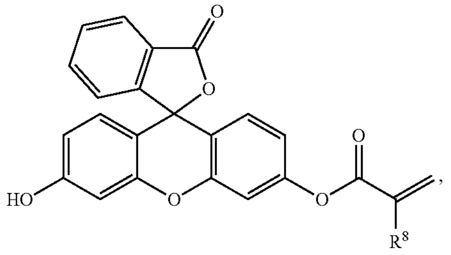

(10)

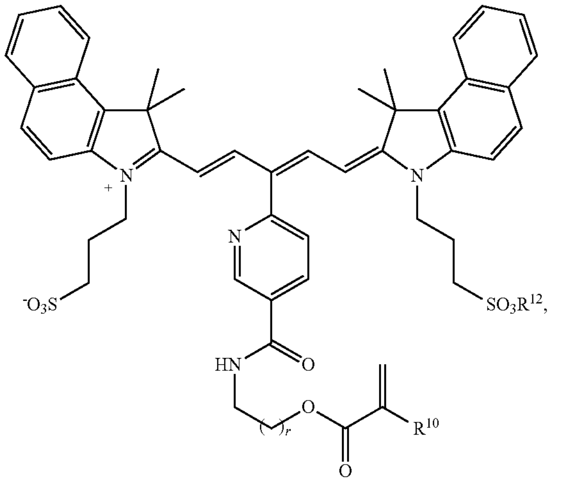

-continued (11)

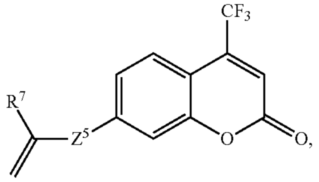

(12)

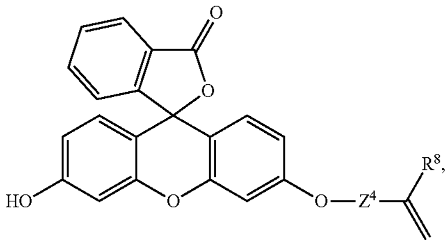

(14)

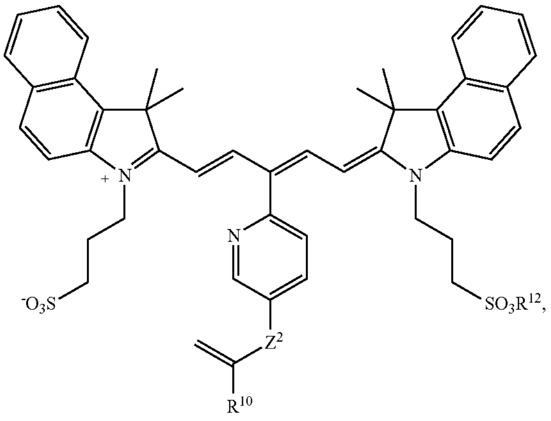

(24)

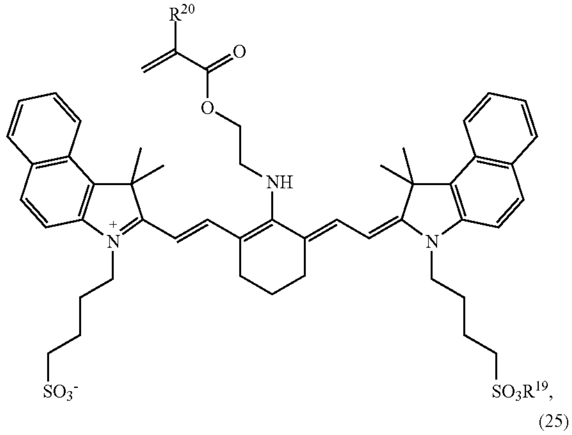

(25)

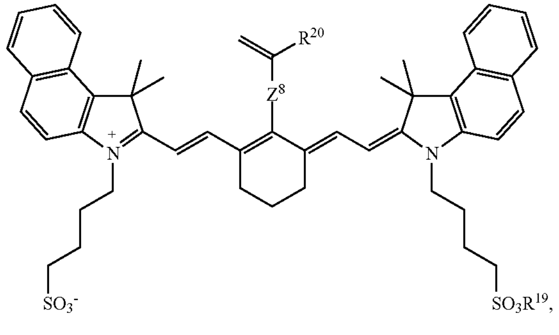

-continued (26)

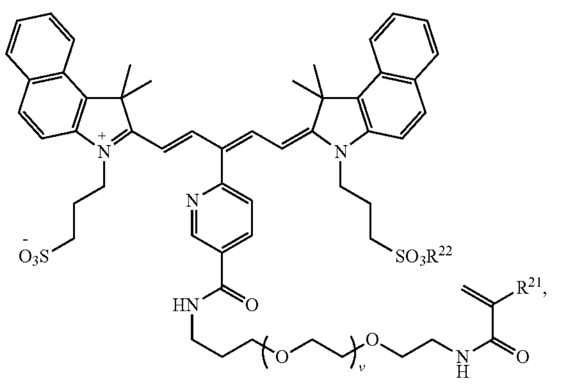

wherein $R^7$, $R^8$, $R^9$, $R^{10}$, $R^{20}$, and $R^{21}$ independently are H or methyl, q and r independently are 1 to 5, v is 0 to 5, $R^{11}$, $R^{12}$, $R^{19}$, and $R^{22}$ independently are H or a metal ion, and $Z^2$, $Z^3$, $Z^4$, $Z^5$, and $Z^8$ independently are a linking group comprising alkyl, aryl, ethylene glycol, oligo(ethylene glycol), an amine, an ether, an ester, an amide, a thiocarbamoyl, any substituted version thereof, or any combination thereof.

Aspect 28: The composition of any one of aspects 25-27, wherein the at least one vinyl-containing monomer comprises an acrylate, a methacrylate, methyl methacrylate, methacrylic acid, acrylic acid, 2-hydroxyethyl methacrylate, 2-hydroxyethyl acrylate, 2-hydroxyethyl methacrylate, 3-hydroxypropyl acrylate, 3-hydroxyethyl methacrylate, ethylacrylate, ethylmethacrylate, propylacrylate, propylmethacrylate, butylacrylate, butylmethacrylate, laurylacrylate, laurylmethacrylate, stearylacrylate, stearylmethacrylate, glycidylacrylate, glycidylmethacrylate, acrylonitrile, acrylamide, vinylalcohol, vinylacetate, vinylbutyral, vinylpyrrolidone, styrene, or any combination thereof.

Aspect 29: The composition of any one of aspects 25-28, further comprising at least one crosslinker.

Aspect 30: The composition of aspect 29, wherein the at least one crosslinker comprises ethylene glycol dimethacrylate, ethylene glycol diacrylate, oligo(ethylene glycol) diacrylate, oligo(ethylene glycol) dimethacrylate, poly(ethylene glycol) diacrylate, poly(ethylene glycol) dimethacrylate, divinyl benzene, or a combination thereof.

Aspect 31: The composition of any preceding aspect, wherein the first nanoparticle further comprises a chelate moiety covalently bonded to the first polymer within the first interior bulk of the first nanoparticle.

Aspect 32: The composition of aspect 31, wherein the chelate moiety comprises a magnetic resonance imaging (MRI) contrast agent, a positron emission tomography (PET) contrast agent, a single-photon emission computerized tomography (SPECT) contrast agent, or any combination thereof.

Aspect 33: The composition of aspect 31 or aspect 32, wherein the chelate moiety comprises tetraazacyclododecane comprising at least one acetate group, at least one acetic acid group, or a combination thereof.

Aspect 34: The composition of any one of aspects 31-33, wherein the chelate moiety comprises gadolinium, copper, indium, yttrium, yttrium(54), or any combination thereof.

Aspect 35: The composition of any preceding aspect, further comprising a second fluorophore moiety having a different emission maximum than the first fluorophore moiety, wherein the nanoparticles further comprise:

a second plurality of a second nanoparticle, the second nanoparticle comprising:

a second outer surface, a second interior bulk, and a second polymer, wherein the second polymer is covalently bonded to the second fluorophore moiety within the second interior bulk of the second nanoparticle.

Aspect 36: The composition of aspect 35, wherein the first nanoparticle is substantially free of a fluorophore moiety other than the first fluorophore moiety.

Aspect 37: The composition of aspect 36, wherein the second nanoparticle is substantially free of a fluorophore moiety other than the second fluorophore moiety.

Aspect 38: The composition of aspect 35, wherein the first nanoparticle further comprises the second fluorophore moiety.

Aspect 39: The composition of aspect 38, wherein the second nanoparticle further comprises the first fluorophore moiety.

Aspect 40: The composition of any preceding aspect, further comprising:

a third plurality of a third nanoparticle comprising a third fluorophore moiety and a third polymer, wherein the third polymer is covalently bonded to the third fluorophore moiety and wherein the third fluorophore has a different emission maximum than each of the first fluorophore and the second fluorophore.

Aspect 41: The composition of aspect 40, further comprising:

a fourth plurality of a fourth nanoparticle comprising a fourth fluorophore moiety and a fourth polymer, wherein the fourth polymer is covalently bonded to the fourth fluorophore moiety and wherein the fourth fluorophore has a different emission maximum than each of the first fluorophore, the second fluorophore, and the third fluorophore.

Aspect 42: The composition of any one of aspects 35-41, wherein the nanoparticles are prepared by a process comprising emulsion polymerization of a mixture comprising:

a vinyl-containing first fluorophore, a vinyl-containing second fluorophore, and at least one vinyl-containing monomer, wherein the first fluorophore moiety is derived from the vinyl-containing first fluorophore and the second fluorophore moiety is derived from the vinyl-containing second fluorophore.

Aspect 43: The composition of any one of aspects 35-41, wherein:

the first plurality of the first nanoparticle is prepared by a process comprising emulsion polymerization of a first mixture comprising:

a vinyl-containing first fluorophore, and at least one vinyl-containing monomer, thereby producing a first composition comprising the first plurality of the first nanoparticle, wherein the first fluorophore moiety is derived from the vinyl-containing first fluorophore, the second plurality of the second nanoparticle is prepared by a process comprising emulsion polymerization of a second mixture comprising:

a vinyl-containing second fluorophore, and at least one vinyl-containing monomer, thereby producing a second composition comprising the second plurality of the second nanoparticle, wherein the second fluorophore moiety is derived from the vinyl-containing second fluorophore, and the composition is prepared by a process comprising combining the first composition and the second composition.

Aspect 44: The composition of any one of aspects 35-43, wherein the second fluorophore moiety, third fluorophore moiety, or the fourth fluorophore moiety independently comprise coumarin, fluorescein, rhodamine, rhodamine B, cyanine, cyanine 5.5, or cyanine 7.

Aspect 45: A method of brain mapping or tracing an axonal projection, the method comprising:

subjecting a first neuron to the composition of any preceding aspect to form a first infused neuron, and imaging the first infused neuron using at least one of fluorescence spectroscopy, magnetic resonance imaging (MRI), positron emission tomography (PET), single-photon emission computerized tomography (SPECT), or any combination thereof.

Aspect 46: The method of aspect 45, further comprising:

subjecting a second neuron to the composition of any one of aspects 1-44 to form a second infused neuron, and imaging the second infused neuron using at least one of fluorescence spectroscopy, magnetic resonance imaging (MRI), positron emission tomography (PET), single-photon emission computerized tomography (SPECT), or any combination thereof.

Aspect 47: The method of aspect 46, further comprising:

subjecting a third neuron to the composition of any one of aspects 1-44 to form a third infused neuron, and at least one of (1) imaging the third infused neuron using fluorescence spectroscopy, and (2) analyzing the third infused neuron using magnetic resonance imaging (MRI), positron emission tomography (PET), single-photon emission computerized tomography (SPECT), or any combination thereof.

Aspect 48: The method of any one of aspects 45-47, wherein the first neuron, the second neuron, and the third neuron are present in different locations from one another.

Aspect 49: A method of brain mapping or tracing an axonal projection, the method comprising:

injecting a brain in a first location with a first composition and in a second location with a second composition, and performing at least one of (1) imaging the brain using fluorescence spectroscopy, and (2) analyzing the brain using magnetic resonance imaging (MRI), positron emission tomography (PET), single-photon emission computerized tomography (SPECT), or any combination thereof, wherein the first composition and the second composition can be the same or different and are the composition of any one of aspects 1-44.

Aspect 50: The method of aspect 49, further comprising injecting the brain in a third location with a third composition that can be the same or different from the first and second compositions.

Aspect 51: The method of aspect 49 or aspect 50, wherein the first and second locations are in a hippocampus.

Aspect 52: A composition comprising:

a chelate moiety, and nanoparticles, wherein the nanoparticles comprise:

a plurality of a chelate nanoparticle, the chelate nanoparticle comprising:

an outer surface, an interior bulk, and a polymer, wherein the polymer is covalently bonded to the chelate moiety within the interior bulk of the chelate nanoparticle.

Aspect 53: The composition of aspect 52, wherein the polymer comprises a polyacrylate, a polyacrylic acid, a polymethacrylate, a polymethacrylic acid, a polymethylmethacrylate (PMMA), a polyethylacrylate, a polyethylmethacrylate, a polypropylacrylate, a polypropylmethacrylate, a polybutylacrylate, a polybutyl methacrylate, a polyhydroxyalkyl methacrylate, a poly(2-hydroxyethyl) methacrylate, a poly(3-hydroxypropyl)methacrylate, a poly (hydroxyalkyl)acrylate, a poly(2-hydroxyethyl)acrylate, a poly(3-hydroxypropyl)acrylate, a polylaurylacrylate, a polystearylacrylate, a polyglycidylacrylate, a polyglycidylmethacrylate, a polyacrylonitrile, a polyacrylamide, a polyvinyl alcohol, a polyvinyl acetate, a polyvinyl butyral, a polyvinylpyrrolidone, a polystyrene, or any combination thereof.

Aspect 54: The composition of aspect 52 or aspect 53, wherein the polymer comprises at least one structure of formula (1) to (6) and (27):

(1)

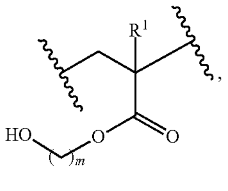

(2)

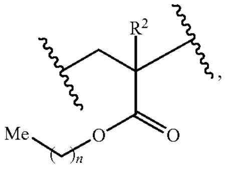

(3)

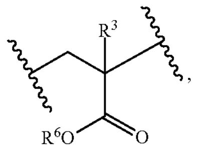

(4)

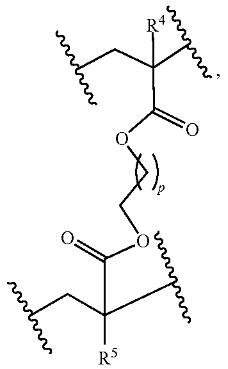

-continued (5)

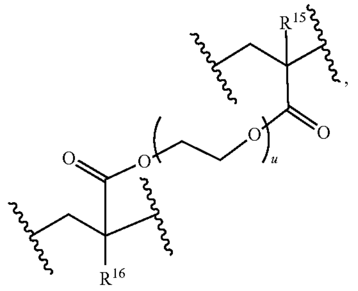

(6)

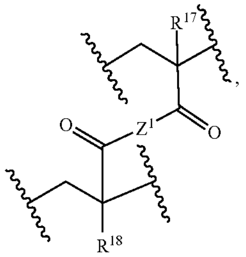

(27)

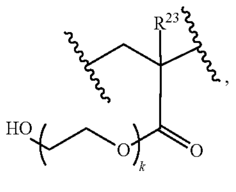

wherein:

m is 2 to 5, n is 0 to 5, k, p and u independently are 1 to 5, $R^1$, $R^2$, $R^3$, $R^4$, $R^5$, $R^{15}$, $R^{16}$, $R^{17}$, $R^{18}$, and $R^{23}$ independently are H or methyl, $R^6$ is H or a metal ion, and $Z^1$ is a linking group comprising alkyl, aryl, ethylene glycol, oligo(ethylene glycol), poly(ethylene glycol), an amine, an ether, an ester, an amide, an ester when taken together with adjacent atoms, an amide when taken together with adjacent atoms, any substituted version thereof, or any combination thereof.

Aspect 55: The composition of any one of aspects 52-54, wherein the polymer is a copolymer.

Aspect 56: The composition of aspect 55, wherein the copolymer comprises the structures of formulas (1) to (4).

Aspect 57: The composition of any one of aspects 52-56, wherein at least one of conditions (a) to (e) is satisfied:

(a) m is 2, (b) n is 0, (c) p is 1, (d) $R^1$, $R^2$, $R^3$, $R^4$, and $R^5$ are methyl, or (e) all of conditions (a) to (d) are satisfied.

Aspect 58: The composition of any one of aspects 52-57, wherein the composition is a latex composition.

Aspect 59: The composition of any one of aspects 52-58, wherein the chelate moiety comprises a magnetic resonance imaging (MRI) contrast agent, a positron emission tomography (PET) contrast agent, a single-photon emission computerized tomography (SPECT) contrast agent, or any combination thereof.

Aspect 60: The composition of any one of aspects 52-59, wherein the chelate moiety comprises tetraazacyclododecane comprising at least one acetate group, at least one acetic acid group, or a combination thereof.

Aspect 61: The composition of any one of aspects 52-60, wherein the chelate moiety comprises gadolinium, copper, indium, yttrium, yttrium(54), or any combination thereof.

Aspect 62: The composition of any one of aspects 52-61, wherein the chelate moiety comprises at least one structure of formula (19) or formula (20):

(19)

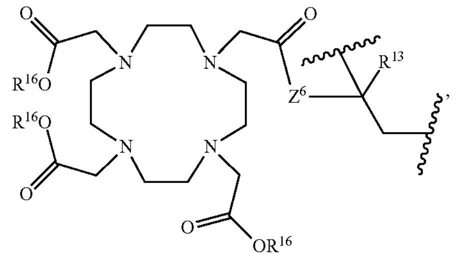

(20)

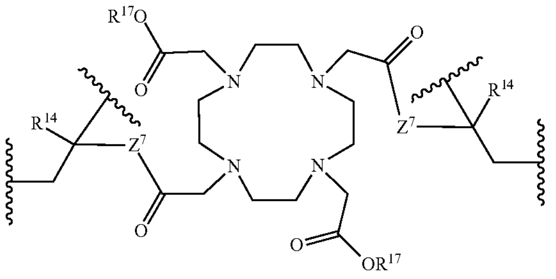

wherein:

$R^{13}$ and $R^{14}$ independently are H or methyl, $R^{16}$ and $R^{17}$ independently are H, a metal ion, a combination thereof, or taken together represent a metal ion that is chelated by the O atoms to which $R^{16}$ or $R^{17}$ are bound, and $Z^6$ and $Z^7$ independently are a linking group comprising alkyl, aryl, ethylene glycol, oligo(ethylene glycol), an amine, an ether, an ester, an amide, an ester when taken together with adjacent atoms, an amide when taken together with adjacent atoms, any substituted version thereof, or any combination thereof.

Aspect 63: The composition of any one of aspects 52-62, wherein the nanoparticles are prepared by a process comprising emulsion polymerization of a mixture comprising:

a vinyl-containing chelate group, and at least one vinyl-containing monomer, wherein the chelate moiety is derived from the vinyl-containing chelate group.

Aspect 64: The composition of aspect 63, wherein the vinyl-containing chelate group comprises tetraazacyclododecane comprising at least one acetate group or acetic acid group.

Aspect 65: The composition of aspect 63 or aspect 64, wherein the vinyl-containing chelate group comprises gadolinium, copper, indium, yttrium, yttrium(54), or any combination thereof.

Aspect 66: The composition of any one of aspects 63-65, wherein the vinyl-containing chelate group comprises at least two vinyl groups.

Aspect 67: The composition of any one of aspects 63-66, wherein the vinyl-containing chelate group comprises at least one structure of formulas (9), (10), (21), and (22):

(9)

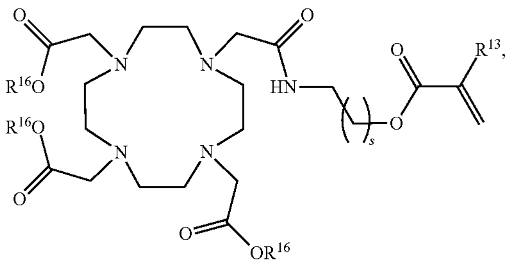

(10)

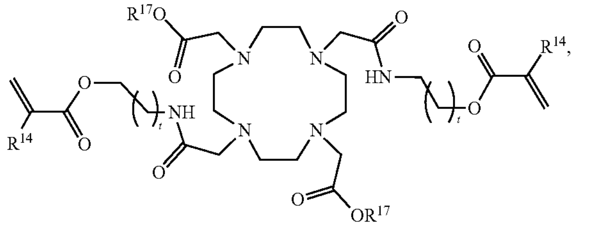

(21)

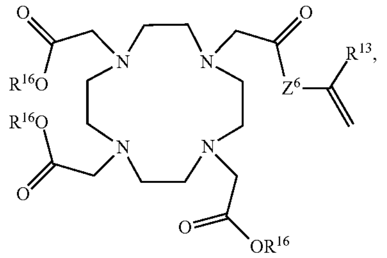

(22)

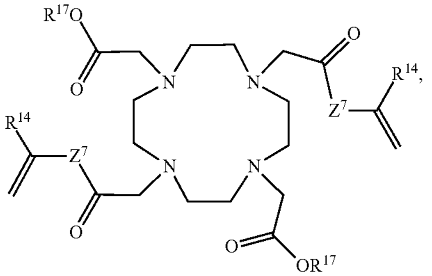

wherein:

$R^{13}$ and $R^{14}$ independently are H or methyl, s and t independently are 1 to 5, $R^{16}$ and $R^{17}$ independently are H, a metal ion, a combination thereof, or taken together represent a metal ion that is chelated by the O atoms to which $R^{16}$ or $R^{17}$ are bound, and $Z^6$ and $Z^7$ independently are a linking group comprising alkyl, aryl, ethylene glycol, oligo(ethylene glycol), an amine, an ether, an ester, an amide, an ester when taken together with adjacent atoms, an amide when taken together with adjacent atoms, any substituted version thereof, or any combination thereof.

Aspect 68: The composition of any one of aspects 63-67, wherein the at least one vinyl-containing monomer comprises an acrylate, a methacrylate, methyl methacrylate, methacrylic acid, acrylic acid, 2-hydroxyethyl methacrylate, 2-hydroxyethyl acrylate, 2-hydroxyethyl methacrylate, 3-hydroxypropyl acrylate, 3-hydroxyethyl methacrylate, ethylacrylate, ethylmethacrylate, propylacrylate, propylmethacrylate, butylacrylate, butylmethacrylate, laurylacrylate, laurylmethacrylate, stearylacrylate, stearylmethacrylate, glycidylacrylate, glycidylmethacrylate, acrylonitrile, acrylamide, vinylalcohol, vinylacetate, vinylbutyral, vinylpyrrolidone, styrene, or any combination thereof.

Aspect 69: The composition of any one of aspects 63-68, further comprising at least one crosslinker.

Aspect 70: The composition of any one of aspects 52-68, further comprising:

a fluorophore moiety, wherein the fluorophore moiety is covalently bonded to the polymer within the interior bulk of the chelate nanoparticle.

Aspect 71: The composition of aspect 70, wherein the fluorophore moiety comprises coumarin, fluorescein, rhodamine, rhodamine B, cyanine, cyanine 5.5, or cyanine 7.

Aspect 72: The composition of aspect 70 or aspect 71, wherein the fluorophore moiety comprises at least one structure of formula (15) to (18) and (23):

(15)

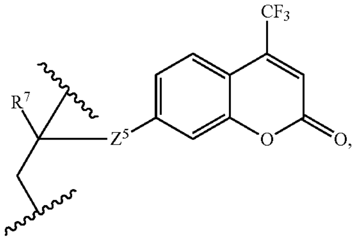

(16)

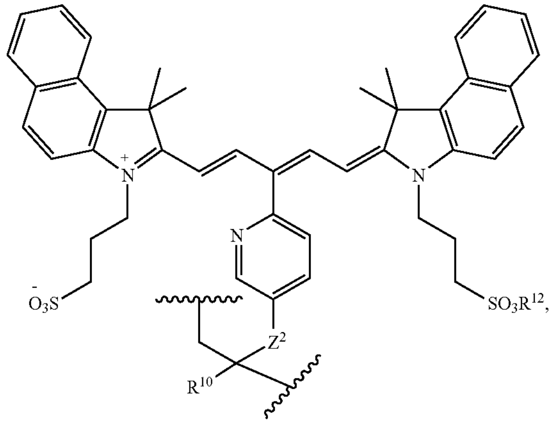

(18)

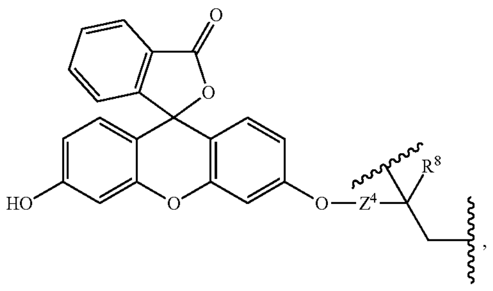

-continued (23)

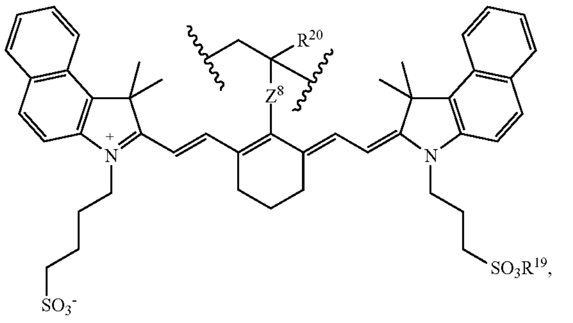

wherein:

$R^7$, $R^8$, $R^9$, $R^{10}$, and $R^{20}$ independently are H or methyl, $R^{11}$, $R^{12}$, and $R^{19}$ independently are H or a metal ion, and $Z^2$, $Z^3$, $Z^4$, $Z^5$, and $Z^8$ independently are a linking group comprising alkyl, aryl, ethylene glycol, oligo(ethylene glycol), an amine, an ether, an ester, an amide, a thiocarbamoyl, any substituted version thereof, or any combination thereof.

Aspect 73: The composition of any one of aspects 52-71, wherein the nanoparticles comprise:

a hydrodynamic diameter of about 90 nm to 200 nm, as measured by dynamic light scattering.

Aspect 74: The composition of any one of aspects 52-73, wherein the nanoparticles comprise an average zeta potential of about −10 mV to about −50 mV.

Aspect 75: The composition of any one of aspects 52-74, wherein the chelate moiety comprises gadolinium, and after removal of any free gadolinium by dialysis, the composition comprises the gadolinium at a concentration of about 50 μM to about 2500 μM, as measured by inductively coupled plasma mass spectrometry (ICP-MS).

Aspect 76: The composition of any one of aspects 70-75, wherein the fluorophore moiety comprises cyanine 5.5, and when excited at a wavelength of 650 nm, the nanoparticles comprise an emission maximum of about 696 nm to about 716 nm.

Aspect 77: The composition of any one of aspects 52-76, wherein the nanoparticles comprise chelate moiety at a concentration of about $7.0\times10^{-14}$ μM/chelate nanoparticle to about $50\times10^{-14}$ μM/chelate nanoparticle.

Aspect 78: The composition of aspect 77, wherein the chelate moiety comprises gadolinium.

Aspect 79: The composition of any one of aspects 52-78, wherein the composition comprises the nanoparticles in an amount of about 20 mg/mL to about 100 mg/mL Aspect 80: The composition of any one of aspects 52-79, wherein the chelate moiety comprises gadolinium, and the nanoparticles comprise:

a longitudinal relaxation rate ($r_1$) of about 5 $mM^{-1}s^{-1}$ to about 30 $mM^{-1}s^{-1}$, a transverse relaxation rate ($r_2$) of about 70 $mM^{-1}s^{-1}$ to about 150 $mM^{-1}s^{-1}$, a ratio of $r_1/r_2$ of about 2 to about 20, or any combination thereof.

Aspect 81: The composition of any one of aspects 70-80, wherein the nanoparticles are prepared by a process comprising emulsion polymerization of a mixture comprising:

a vinyl-containing chelate group, a vinyl-containing fluorophore, and at least one vinyl-containing monomer, wherein the chelate moiety is derived from the vinyl-containing chelate group and the fluorophore moiety is derived from the vinyl-containing fluorophore.

Aspect 82: The composition of aspect 81, wherein the vinyl-containing chelate group comprises tetraazacyclododecane comprising at least one acetate group or acetic acid group.

Aspect 83: The composition of aspect 81 or aspect 82, wherein the vinyl-containing chelate group comprises gadolinium, copper, indium, yttrium, yttrium(54), or any combination thereof.

Aspect 84: The composition of any one of aspects 81-83, wherein the vinyl-containing chelate group comprises at least two vinyl groups.

Aspect 85: The composition of any one of aspects 81-84, wherein the vinyl-containing chelate group comprises at least one structure of formulas (9), (10), (21), and (22):

(9)

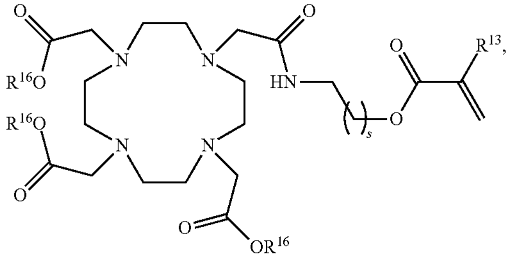

(10)

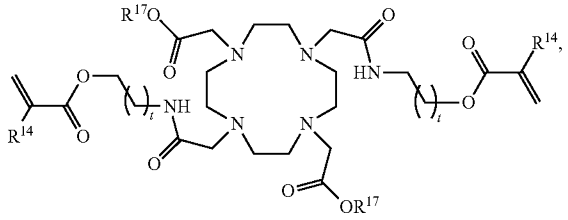

(21)

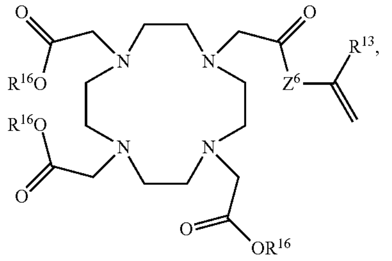

(22)

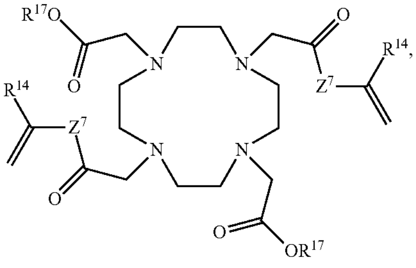

wherein:

$R^{13}$ and $R^{14}$ independently are H or methyl, s and t independently are 1 to 5, $R^{16}$ and $R^{17}$ independently are H, a metal ion, a combination thereof, or taken together represent a metal ion that is chelated by the O atoms to which $R^{16}$ or $R^{17}$ are bound, and $Z^6$ and $Z^7$ independently are a linking group comprising alkyl, aryl, ethylene glycol, oligo(ethylene glycol), an amine, an ether, an ester, an amide, an ester when taken together with adjacent atoms, an amide when taken together with adjacent atoms, any substituted version thereof, or any combination thereof.

Aspect 86: The composition of any one of aspects 81-85, wherein the at least one vinyl-containing monomer comprises an acrylate, a methacrylate, methyl methacrylate, methacrylic acid, acrylic acid, 2-hydroxyethyl methacrylate, 2-hydroxyethyl acrylate, 2-hydroxyethyl methacrylate, 3-hydroxypropyl acrylate, 3-hydroxyethyl methacrylate, ethylacrylate, ethylmethacrylate, propylacrylate, propylmethacrylate, butylacrylate, butylmethacrylate, laurylacrylate, laurylmethacrylate, stearylacrylate, stearylmethacrylate, glycidylacrylate, glycidylmethacrylate, acrylonitrile, acrylamide, vinylalcohol, vinylacetate, vinylbutyral, vinylpyrrolidone, styrene, or any combination thereof.

Aspect 87: The composition of any one of aspects 81-86, wherein the vinyl-containing fluorophore comprises coumarin, fluorescein, rhodamine, rhodamine B, cyanine, cyanine 5.5, or any combination thereof.

Aspect 88: The composition of any one of aspects 81-87, wherein the vinyl-containing fluorophore comprises a structure of formula (7) to (14) and (24) to (26):

(7)

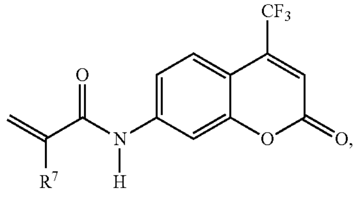

(8)

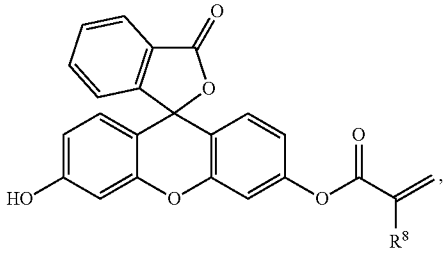

-continued (10)

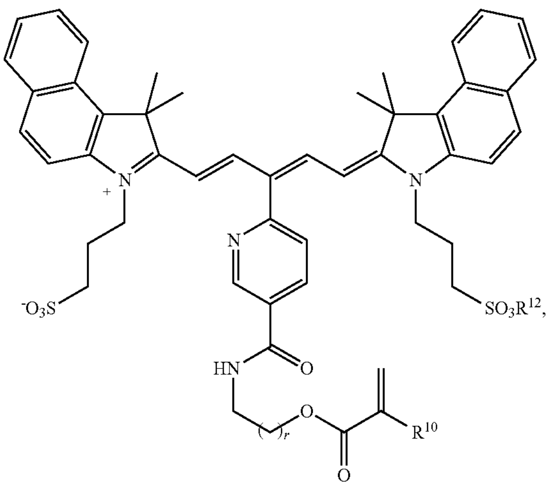

(11)

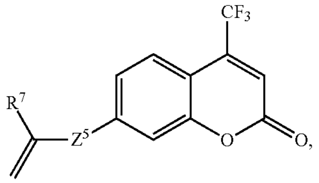

(12)

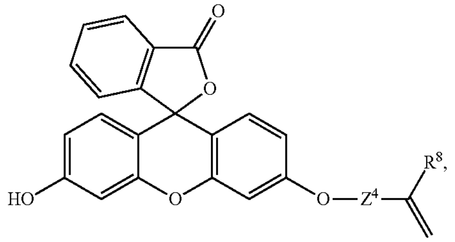

(14)

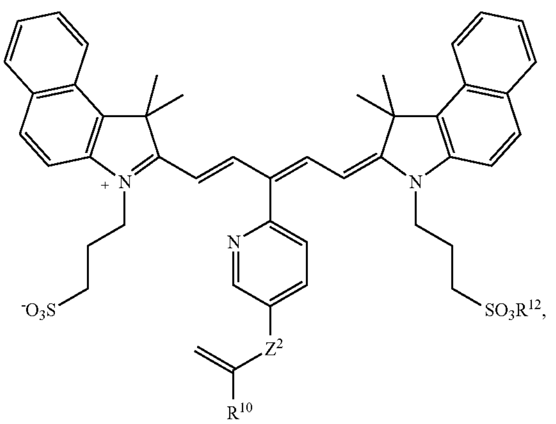

-continued (24)

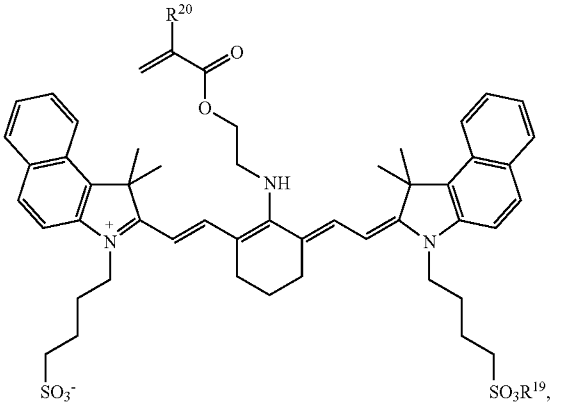

(25)

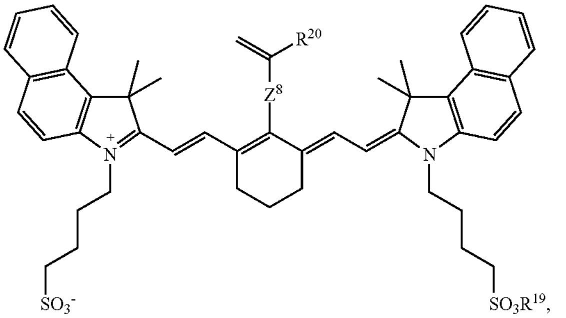

(26)

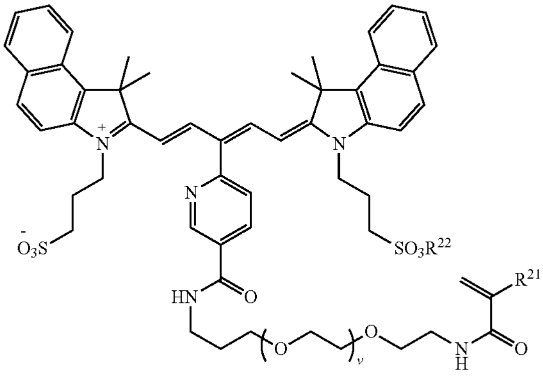

wherein:

$R^7$, $R^8$, $R^9$, $R^{10}$, $R^{20}$, and $R^{21}$ independently are H or methyl, q and r independently are 1 to 5, v is 0 to 5, $R^{11}$, $R^{12}$, $R^{19}$, and $R^{22}$ independently are H or a metal ion, and $Z^2$, $Z^3$, $Z^4$, $Z^5$, and $Z^8$ independently are a linking group comprising alkyl, aryl, ethylene glycol, oligo(ethylene glycol), an amine, an ether, an ester, an amide, a thiocarbamoyl, any substituted version thereof, or any combination thereof.

Aspect 89: The composition of any one of aspects 81-88, wherein the at least one vinyl-containing monomer comprises an acrylate, a methacrylate, methyl methacrylate, methacrylic acid, acrylic acid, 2-hydroxyethyl methacrylate, 2-hydroxyethyl acrylate, 2-hydroxyethyl methacrylate, 3-hydroxypropyl acrylate, 3-hydroxyethyl methacrylate, ethylacrylate, ethylmethacrylate, propylacrylate, propylmethacrylate, butylacrylate, butylmethacrylate, laurylacrylate, laurylmethacrylate, stearylacrylate, stearylmethacrylate, glycidylacrylate, glycidylmethacrylate, acrylonitrile, acrylamide, vinylalcohol, vinylacetate, vinylbutyral, vinylpyrrolidone, styrene, or any combination thereof.

Aspect 90: The composition of any one of aspects 81-89, further comprising at least one crosslinker.

Aspect 91: The composition of aspect 90, wherein the at least one crosslinker comprises ethylene glycol dimethacrylate, ethylene glycol diacrylate, oligo(ethylene glycol) diacrylate, oligo(ethylene glycol) dimethacrylate, poly(ethylene glycol) diacrylate, poly(ethylene glycol) dimethacrylate, divinyl benzene, or a combination thereof.

Aspect 92: The composition of one of aspects 52-91, wherein, when the composition is injected into the brain of a living mouse, the nanoparticles are transported in axons in a retrograde fashion.

Aspect 93: The composition of one of aspects 52-92, wherein the nanoparticles are transported in axons in a retrograde fashion along a lateral geniculate nucleus (LGN) to primary visual cortex (V1) pathway.

Aspect 94: A method of brain mapping or tracing an axonal projection, the method comprising:

subjecting a first neuron to the composition of any one of aspects 52-93 to form a first infused neuron, and at least one of (1) imaging the first infused neuron using fluorescence spectroscopy, and (2) analyzing the first infused neuron using magnetic resonance imaging (MRI), positron emission tomography (PET), single-photon emission computerized tomography (SPECT), or any combination thereof.

Aspect 95: The method of aspect 94, further comprising:

subjecting a second neuron to the composition of any one of aspects 52-93 to form a second infused neuron, and at least one of (1) imaging the second infused neuron using fluorescence spectroscopy, and (2) analyzing the second infused neuron using magnetic resonance imaging (MRI), positron emission tomography (PET), single-photon emission computerized tomography (SPECT), or any combination thereof.

Aspect 96: The method of aspect 95, further comprising:

subjecting a third neuron to the composition of any one of aspects 52-93 to form a third infused neuron, and at least one of (1) imaging the third infused neuron using fluorescence spectroscopy, and (2) analyzing the third infused neuron using magnetic resonance imaging (MRI), positron emission tomography (PET), single-photon emission computerized tomography (SPECT), or any combination thereof.

Aspect 97: The method of any one of aspects 94-96, wherein the first neuron, the second neuron, and the third neuron are present in different locations from one another.

Aspect 98: A method of brain mapping or tracing an axonal projection, the method comprising:

injecting a brain in a first location with a first composition and in a second location with a second composition, and performing at least one of (1) imaging the brain using fluorescence spectroscopy, and (2) analyzing the brain using magnetic resonance imaging (MRI), positron emission tomography (PET), single-photon emission computerized tomography (SPECT), or any combination thereof, wherein the first composition and the second composition can be the same or different and are the composition of any one of aspects 52-93.

Aspect 99: The method of aspect 98, further comprising injecting the brain in a third location with a third composition that can be the same or different from the first and second compositions.

Aspect 100: The method of aspect 98 or aspect 99, wherein the first and second locations are in a hippocampus.

Aspect 101: A method of preparing a composition comprising nanoparticles, the method comprising:

emulsion polymerizing a mixture comprising:

at least one vinyl-containing monomer, and at least one vinyl-containing fluorophore or at least one vinyl-containing chelate group, wherein the nanoparticles comprise:

polymer, at least one fluorophore moiety or at least one chelate moiety, and wherein the at least one fluorophore moiety, if present, is covalently bonded to the polymer, the at least one chelate moiety, if present, is covalently bonded to the polymer.

Aspect 102: The method of aspect 101, wherein the at least one vinyl-containing fluorophore is present and comprises a vinyl-containing first fluorophore.

Aspect 103: The method of aspect 101 or aspect 102, wherein the at least one vinyl-containing fluorophore is present and comprises:

a vinyl-containing first fluorophore, and a vinyl-containing second fluorophore.

Aspect 104: The method of any one of aspects 101-103, wherein the vinyl-containing first fluorophore, the vinyl-containing second fluorophore, or both the vinyl-containing first fluorophore and the vinyl-containing second fluorophore independently comprises coumarin, fluorescein, rhodamine, rhodamine B, cyanine, cyanine 5.5, or cyanine 7.

Aspect 105: The method of any one of aspects 101-104, wherein the vinyl-containing first fluorophore, the vinyl-containing second fluorophore, or both the vinyl-containing first fluorophore and the vinyl-containing second fluorophore independently comprises a structure of formula (7) to (14) and (24) to (26):

(7)

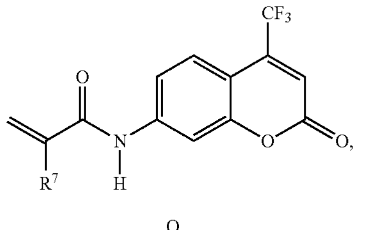

(8)

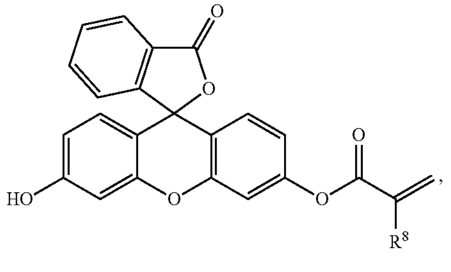

-continued (10)

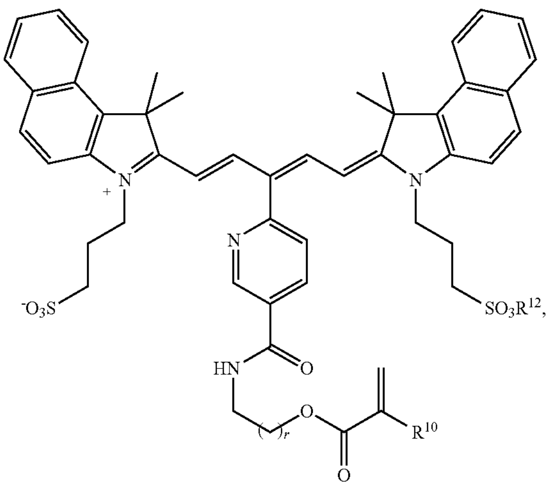

(11)

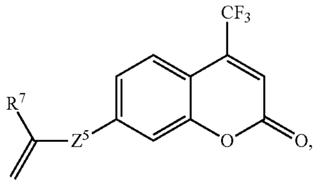

(12)

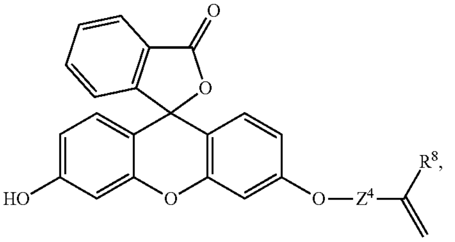

(14)

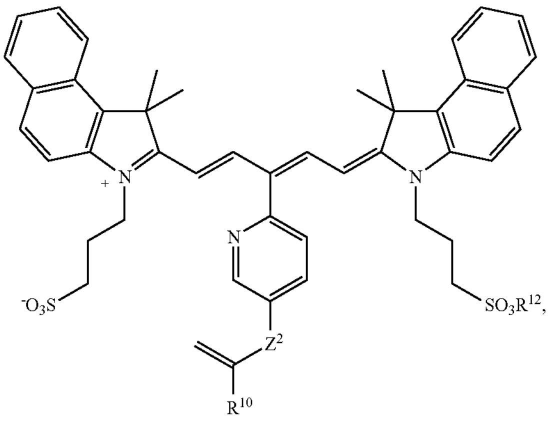

-continued (24)

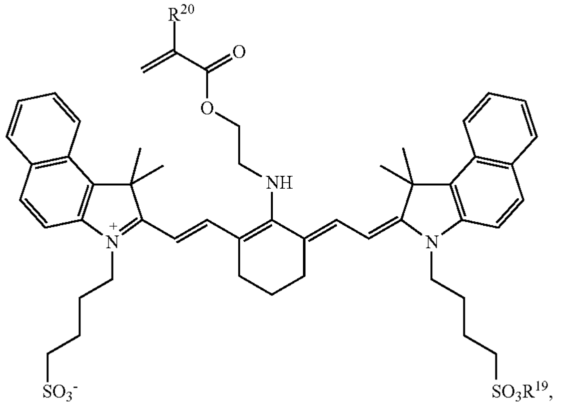

(25)

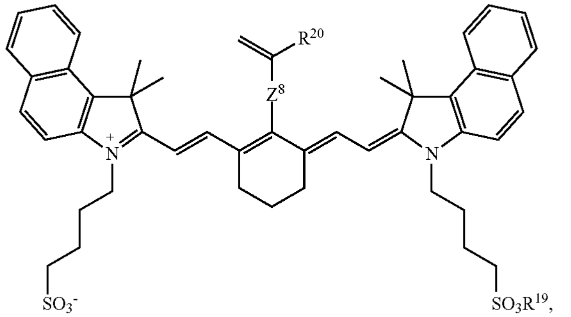

(26)

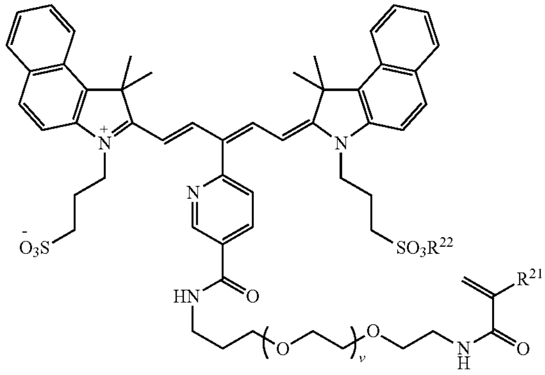

wherein:

$R^7$, $R^8$, $R^9$, $R^{10}$, $R^{20}$, and $R^{21}$ independently are H or methyl, q and r independently are 1 to 5, v is 0 to 5, $R^{11}$, $R^{12}$, $R^{19}$, and $R^{22}$ independently are H or a metal ion, and $Z^2$, $Z^3$, $Z^4$, $Z^5$, and $Z^8$ independently are a linking group comprising alkyl, aryl, ethylene glycol, oligo(ethylene glycol), an amine, an ether, an ester, an amide, a thiocarbamoyl, any substituted version thereof, or any combination thereof.

Aspect 106: The method of any one of aspects 101-105, wherein the at least one vinyl-containing monomer comprises an acrylate, a methacrylate, methyl methacrylate, methacrylic acid, acrylic acid, 2-hydroxyethyl methacrylate, 2-hydroxyethyl acrylate, 2-hydroxyethyl methacrylate, 3-hydroxypropyl acrylate, 3-hydroxyethyl methacrylate, ethylacrylate, ethylmethacrylate, propylacrylate, propylmethacrylate, butylacrylate, butylmethacrylate, laurylacrylate, laurylmethacrylate, stearylacrylate, stearylmethacrylate, glycidylacrylate, glycidylmethacrylate, acrylonitrile, acrylamide, vinylalcohol, vinylacetate, vinylbutyral, vinylpyrrolidone, styrene, or any combination thereof.

Aspect 107: The method of any one of aspects 101-106, further comprising at least one crosslinker presenting during the emulsion polymerization, wherein the at least one crosslinker comprises ethylene glycol dimethacrylate, ethylene glycol diacrylate, oligo(ethylene glycol) diacrylate, oligo (ethylene glycol) dimethacrylate, poly(ethylene glycol) diacrylate, poly(ethylene glycol) dimethacrylate, divinyl benzene, or a combination thereof.

Aspect 108: The method of any one of aspects 101-107, wherein the at least one a vinyl-containing chelate group is present during the emulsion polymerization.

Aspect 109: The method of aspect 108, wherein the at least one vinyl-containing chelate group comprises tetraazacyclododecane comprising at least one acetate group or acetic acid group.

Aspect 110: The method of aspect 108 or aspect 109, wherein the at least one a vinyl-containing chelate group comprises an MRI contrast agent, PET contrast agent, or SPECT contrast agent.

Aspect 111: The method of any one of aspects 108-110, wherein the vinyl-containing chelate group comprises gadolinium, copper, indium, yttrium, yttrium(54), or any combination thereof.

Aspect 112: The method of any one of aspects 108-111, wherein the vinyl-containing chelate group comprises at least two vinyl groups.

Aspect 113: The method of any one of aspects 108-112, wherein the vinyl-containing chelate group comprises at least one structure of formulas (9), (10), (21), and (22):

(9)

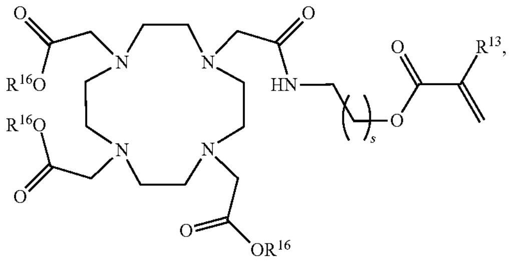

(10)

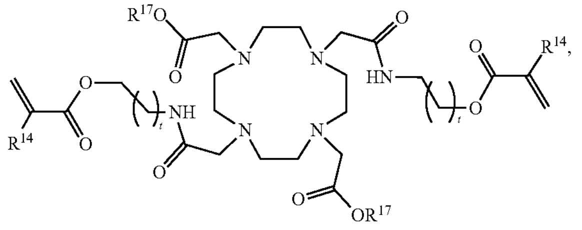

-continued (21)

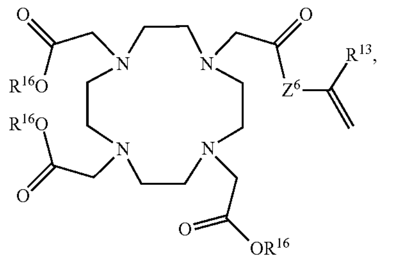

(22)

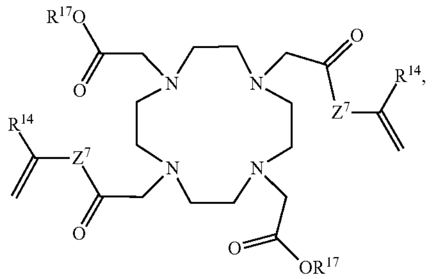

wherein:

$R^{13}$ and $R^{14}$ independently are H or methyl, s and t independently are 1 to 5, $R^{16}$ and $R^{17}$ independently are H, a metal ion, a combination thereof, or taken together represent a metal ion that is chelated by the O atoms to which $R^{16}$ or $R^{17}$ are bound, and $Z^6$ and $Z^7$ independently are a linking group comprising alkyl, aryl, ethylene glycol, oligo(ethylene glycol), an amine, an ether, an ester, an amide, an ester when taken together with adjacent atoms, an amide when taken together with adjacent atoms, any substituted version thereof, or any combination thereof.

Aspect 114: The method of any one of aspects 101-113, further comprising at least one surfactant present during the emulsion polymerization, wherein the at least one surfactant comprises a nonionic surfactant, sodium dodecyl sulfate, TRITON X-100, TWEEN 20, polysorbate 20, or any combination thereof.

Aspect 115: The method of any one of aspects 101-114, further comprising at least one radical initiator present during the emulsion polymerization, which radical initiator comprises a persulfate salt, ammonium persulfate, azobisisobutyronitrile, benzoyl peroxide in combination with dimethylaniline, a photoinitiator, eosin Y in combination with triethylamine, sodium phenyl-2,4,6-trimethylbenzoylphosphinate (SPTP), or any combination thereof.

Aspect 116: The method of any one of aspects 101-115, comprising:

at least one vinyl-containing monomer in an amount of about 20 wt. % to about 40 wt. %;

crosslinker in an amount of about 1 wt. % to about 25 wt. %; and surfactant in an amount of about 0.008 wt. % to about 0.8 wt. %, wherein all amounts are based on the total weight of the mixture.

Aspect 117: The method of aspect 116, further comprising at least one of:

vinyl-containing fluorophore in an amount of about 0.001 molar equivalents to about 0.004 molar equivalents;

vinyl-containing chelate group in an amount of about 0.01 molar equivalents to about 0.1 molar equivalents, wherein all amounts are based on number of moles of all vinyl-containing monomer.

Aspect 118: The method of any one of aspects 101-117, wherein the at least one vinyl-containing monomer comprises:

methacrylic acid in an amount of about 0.8 to about 1.2 molar equivalents, 2-hydroxyethylmethacrylate in an amount of about 1 to about 3 molar equivalents, methylmethacrylate in an amount of about 3 to about 5.6 molar equivalents, and ethylene glycol dimethacrylate in an amount of about 0.05 to about 1 molar equivalents.

Aspect 119: The method of any one of aspects 101-118, wherein the composition or nanoparticles resulting from the method have a property of any one of aspects 1-100.

EXAMPLES

The invention can be further understood by the following non-limiting examples.

Example 1: Multi-Color Polymeric Nanoparticle Neuronal Tracers

This example demonstrates the preparation, characterization, and testing of a series of polymer-based nanoparticles capable of retrograde transport along neurons in vivo, including in mice. These polymeric nanoparticle neuronal tracers (NNTs) were prepared with a palette of fluorescent labels (i.e., dyes or fluorophores). The morphologies, charges and optical properties of NNTs were characterized by analytical methods including fluorescence microscopy, electron microscopy, and dynamic light scattering. Cytotoxicity and cellular uptake were investigated to analyze cellular interactions in vitro. Regardless of the type of fluorophore used in labeling, each tracer was of similar morphology, size, and charge, and all were competent for retrograde transport in vivo. This example demonstrates a convenient, scalable synthetic approach for non-viral tracers labeled with a range of fluorophores for in vivo neuronal projection mapping.

Figures 1C, 1D:
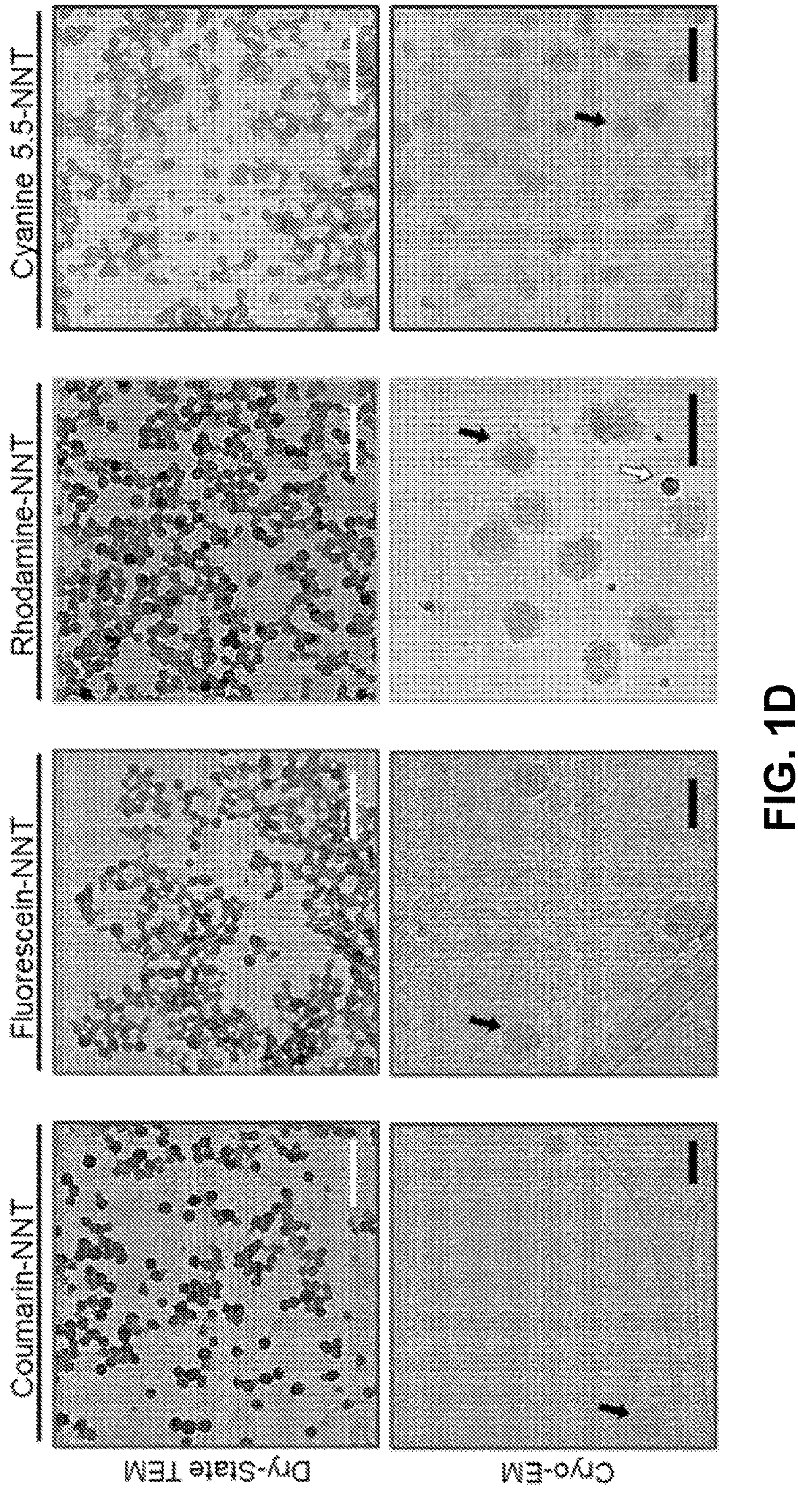
Figure 7:
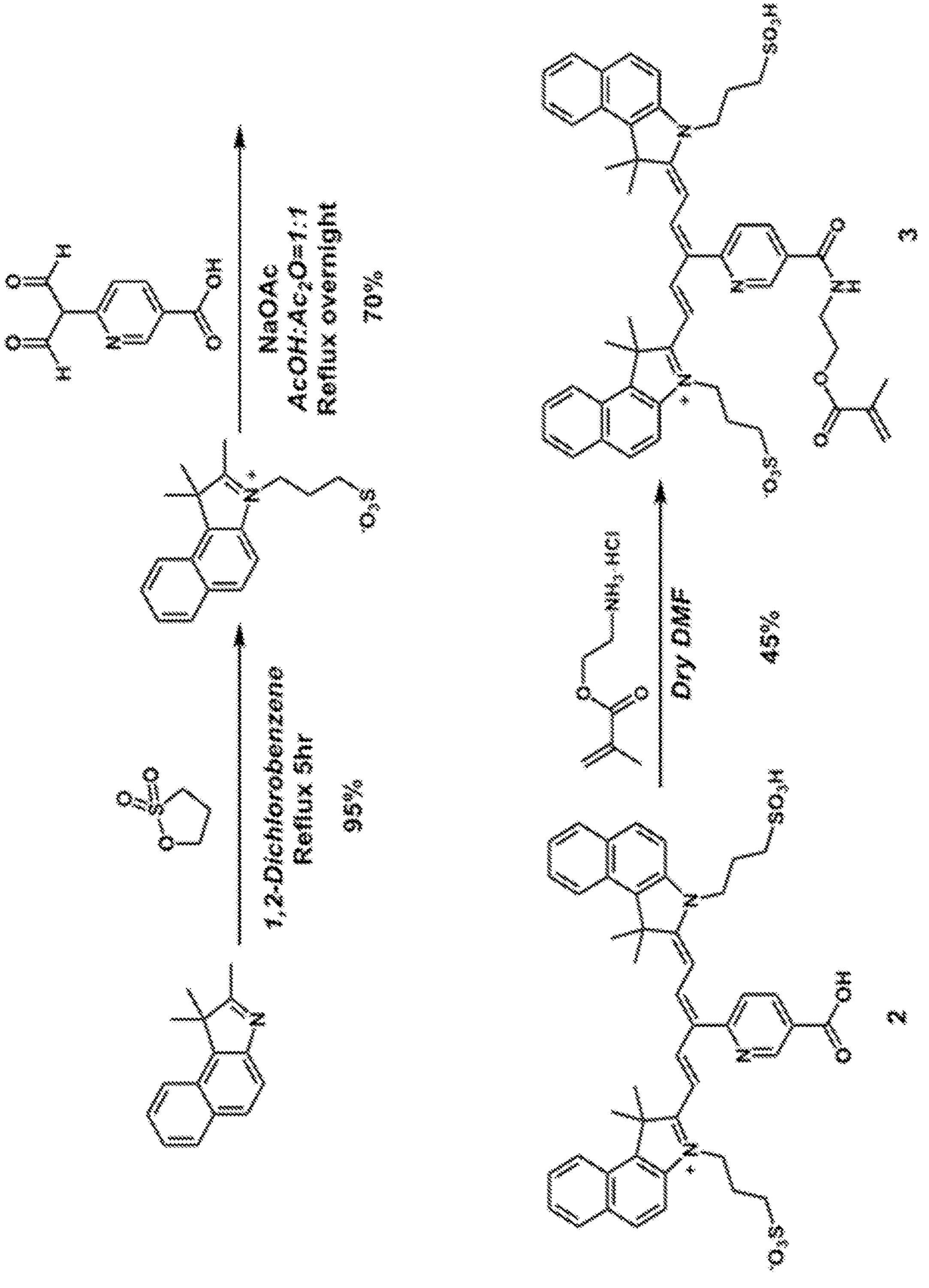
FIG. 7: Synthetic scheme for Cy5.5 monomer.
Figure 8A:
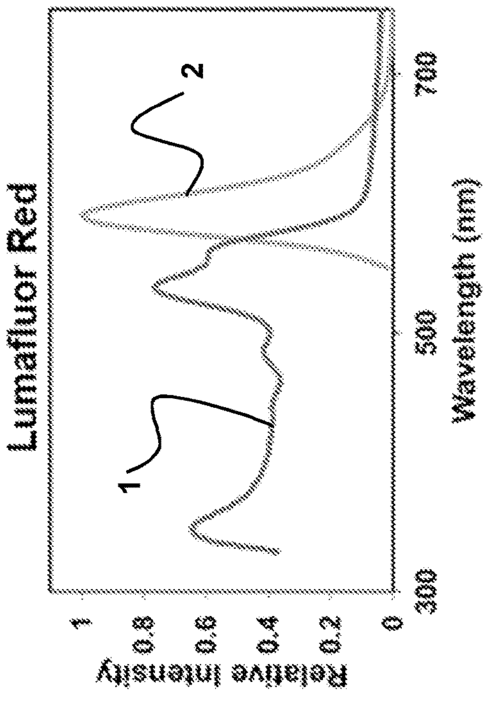
FIGS. 8A-8F: Characterization of the commercial latex neuronal tracers LUMAFLUOR RED and LUMAFLUOR GREEN.
Figure 8B:
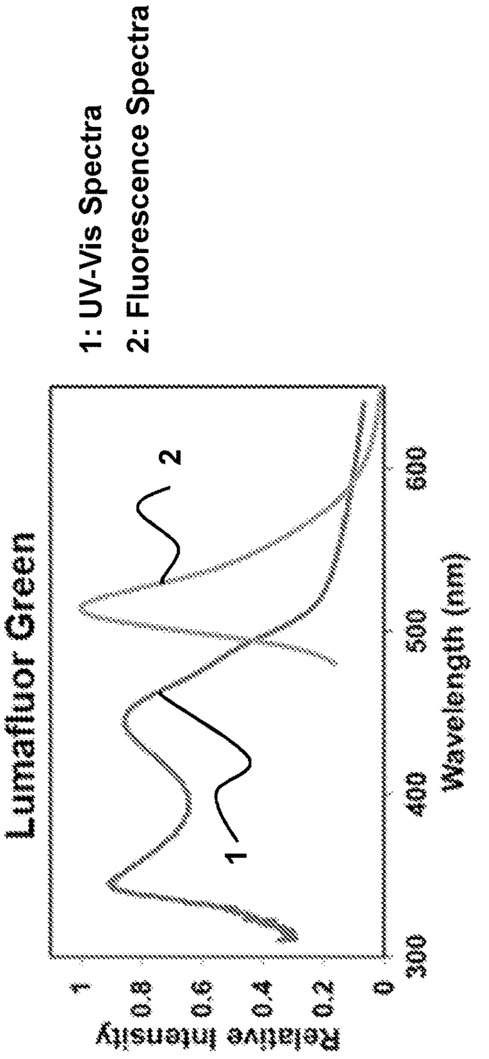
Figure 8C:
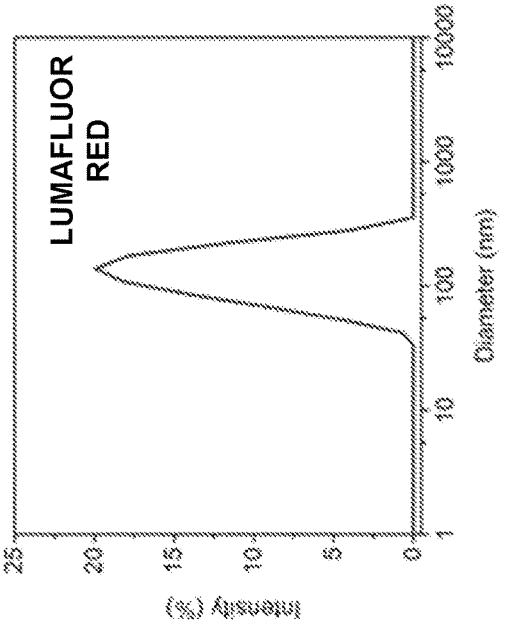
Figure 8D:
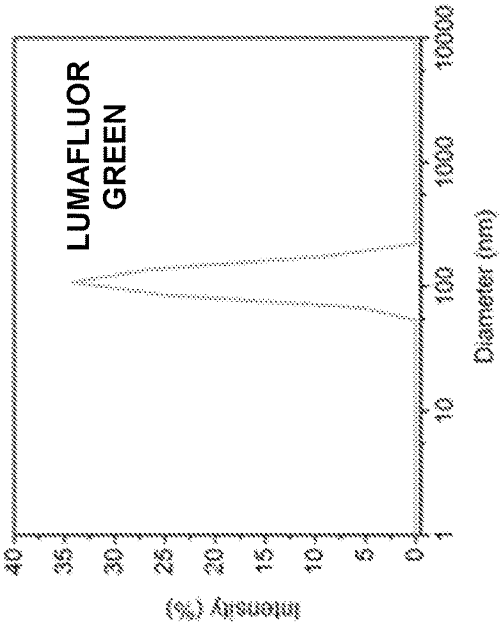
Figure 8F:
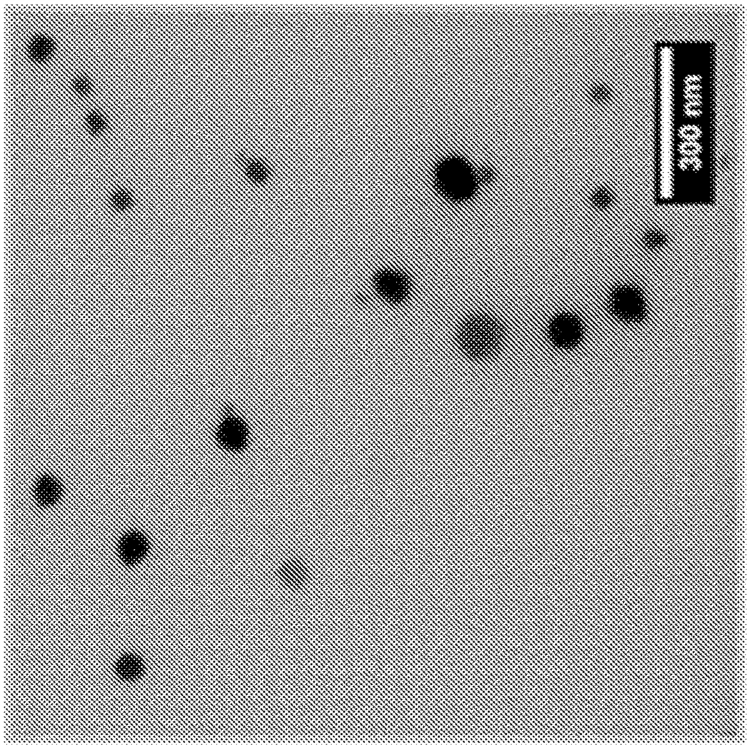
Figure 8E:
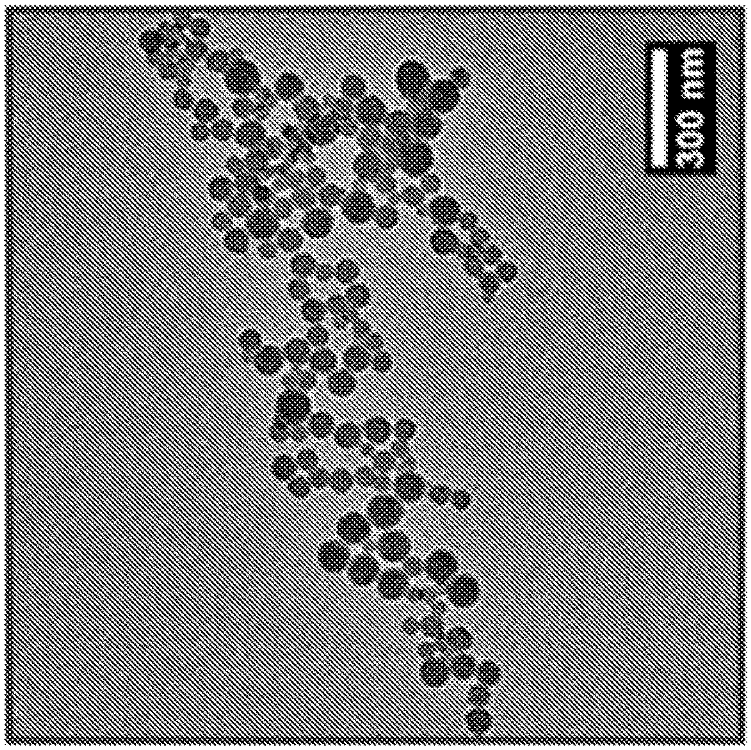

Synthesis and Characterization. Four fluorescent dyes were selected and prepared as either acrylamide or methacrylate monomers with colors covering a range of the spectrum (FIGS. 1A-1D), distinguishable from each other without crosstalk (FIG. 1A). Specifically, coumarin acrylamide ($\lambda_{ex}$=342 nm, $\lambda_{em}$=430 nm), methacryloyloxy O-fluorescein ($\lambda_{ex}$=490 nm, $\lambda_{em}$=520 nm), and methacryloxyethyl thiocarbamoyl rhodamine B ($\lambda_{ex}$=548 nm, $\lambda_{em}$=570 nm) were chosen, each of which have emission wavelengths commonly employed in ex vivo biological studies (FIG. 1B). Novel monomer methacryloyloxy cyanine 5.5 (Cy5.5) ($\lambda_{ex}$=680 nm, $\lambda_{em}$=700 nm) was prepared, based on near-infrared dyes. Briefly, carboxyl-Cy5.5 (Proetto et al., ACS Nano, 10, 4046-4054 (2016)) was modified with 2-aminoethyl methacrylate hydrochloride (AEMA) to incorporate a methacrylate group for subsequent incorporation into polymeric nanoparticles (FIG. 7). All dye-labeled monomers were purified and characterized by high-performance liquid chromatography (HPLC), $^1$H NMR, and mass spectrometry.

Specifically, novel monomer methacryloyloxy cyanine 5.5 (Cy5.5) (FIG. 7, compound 3), i.e., 3-(2-((1E,3Z,5E)-5-(1, 1-dimethyl-3-(3-sulfopropyl)-1,3-dihydro-2H-benzo[e]indol-2-ylidene)-3-(5-((2-(methacryloyloxy)ethyl)carbamoyl)pyridin-2-yl)penta-1, 3-dien-1-yl)-1, 1-dimethyl-1H-benzo[e]indol-3-ium-3-yl)propane-1-sulfonate, was synthesized as follows. 3-(2 ((1E,3Z,5E)-3-(5-carboxypyridin-2-yl)-5-(1, 1-di methyl-3-(3-sulfopropyl)-1, 3-dihydro-2H-benzo[e]indol-2-ylidene)penta-1,3-dien-1-yl)-1, 1-dimethyl-1H-benzo[e]indol-3-ium-3-yl)propane-1-sulfonate has been reported previously[1] (FIG. 7, compound 2). Carboxyl-Cy 5.5 (FIG. 7, compound 2) (72 mg, 0.085 mmol), AEMA (28 mg, 0.171 mmol), DMAP (12 mg, 0.0937 mmol) was dissolved in 30 mL of anhydrous DMF under argon. After 10 min, DIPEA (60 μL, 0.342 mmol) was added into the reaction following by adding EDC (15 mg, 0.0936 mmol) with a cold bath surrounding the reaction flask. The reaction was left to stir for 5 hours and cold diethyl ether was added to the reaction and the precipitate was collected and dried under vacuum. The dry dark blue powder was dissolved in buffer A (water with 0.1% TFA) and purified on reverse phase HPLC (gradient 30-60% buffer B, ACN with 0.1% TFA). The pure fractions were collected and lyophilized, to yield novel monomer methacryloyloxy cyanine 5.5 (Cy5.5) (FIG. 7, compound 3). Yield: 36 mg, 45%. 1H NMR (500 MHz, CDCl3): δ=9.53 (s, 1H), 9.04 (s, 1H), 8.82 (d, 1H), 8.52 (b, 2H), 7.96 (s, 2H), 7.85 (m, 2H), 7.79 (m, 3H), 7.51 (m, 2H), 7.41 (m, 2H), 7.29 (m, 3H), 6.12 (s, 1H), 5.89 (br, 2H), 5.49 (s, 1H), 4.34 (m, 9H), 3.72 (t, 2H), 2.91 (m, 4H), 2.07 (m, 4H), 2.04 (s, 3H), 1.87 (s, 12H). HR-MS (ESI-TOF): m/z (%) [M+H]+ calcd for C51H54N4O9S2: 931.33, found: 931.40.

2-hydroxyethyl methacrylate (HEMA), methyl methacrylate (MMA), methacrylic acid (MAA), and the crosslinker, ethylene glycol dimethacrylate (EGD) were used in emulsion polymerizations together with the dye monomers to generate all four, individually dye-labeled, polymeric nanoparticle neuronal tracers (NNTs: Coumarin-NNT, Fluorescein-NNT, Rhodamine-NNT, Cy5.5-NNT). NNT preparation involved the addition of HEMA, MMA, MAA, and EGD sequentially into water under argon, followed by addition of the free radical initiator and surfactant. Each dye was then added at different ratios depending on quantum yield of the fluorophore, and the reaction vessel was heated to about 90° C. for about 1 h. Resulting NNTs were purified via dialysis into MILLI-Q water and further incubated with a mixed-bed ion exchange resin overnight to remove excess surfactant prior to in vitro and in vivo use. Synthetic conditions and monomer compositions were arrived at through empirical optimization for the generation of stable, spherical polymeric nanoparticles with dimensions similar to commercial latex neuronal tracer particles (Katz 1984; Katz 1990; Katz 1987; Rembaum et al., U.S. Pat. No. 4,138,383).

Commercial latex neuronal tracers LUMAFLUOR GREEN and RED were characterized (Table 1 and FIGS. 8A-8F). The in-house measurement of excitation and emission maxima are on par with those reported by the commercial source. The solvated diameter of LUMAFLUOR GREEN and RED as measured by dynamic light scattering (DLS) was determined to be about 115 nm and about 125 nm, respectively. Dry-state transmission electron microscopy (TEM) with uranyl acetate staining showed a diameter range from about 35 nm to about 80 nm for both particles. The surface of both LUMAFLUOR GREEN and RED were negatively charged, as measured by zeta potential analysis, with values of −9.8 and −43.7 mV, respectively. Nanoparticle concentrations were in the range of $10^{12}$ particles per milliliter, as determined by nanoparticle tracking analysis (NTA).

TABLE 1

Excitation and Emission Maxima, Hydrodynamic Diameter Measured by TEM, Zeta Potential and Particles Concentration of LUMAFLUOR GREEN and LUMAFLUOR RED

| Commercial Fluorescent Tracers | $\lambda_{ex}$ (nm) Website Reported | $\lambda_{ex}$ (nm) Measured in House | $\lambda_{em}$ (nm) Website Reported | $\lambda_{em}$ (nm) Measured in House | $D_h$ (nm) | D (nm) (dry-state TEM) | Average mV | Particle concentration (particles/mL) |
|---|---|---|---|---|---|---|---|---|
| Lumafluor Green | 460 | 443 | 505 | 516 | 115 | 55 ± 19 | −9.8 | $9.5 \times 10^{11}$ |
| Lumafluor Red | 530 | 536 | 590 | 591 | 125 | 66 ± 16 | −43.7 | $1.2 \times 10^{12}$ |

Figure 9:
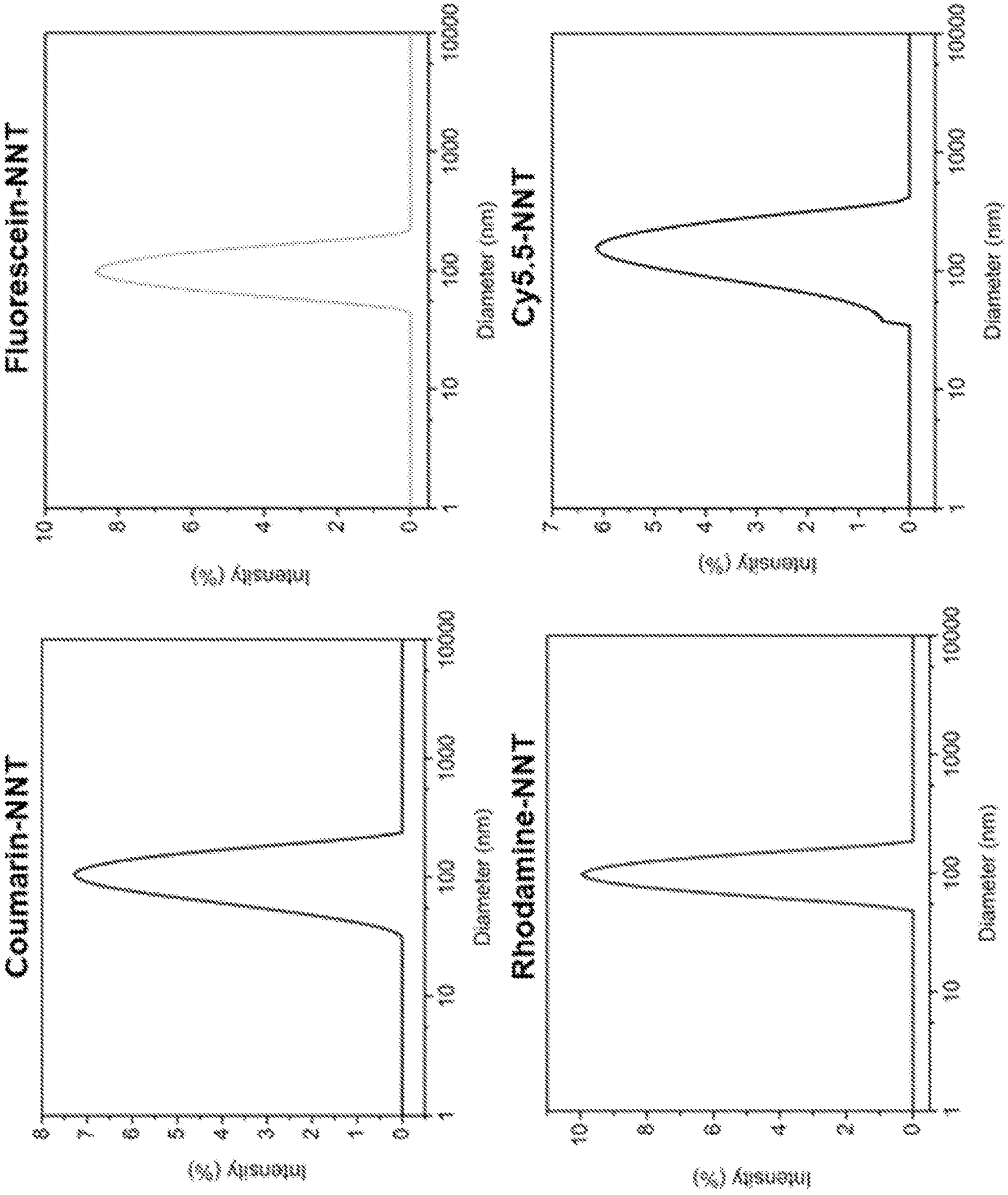
FIG. 9: DLS of Coumarin-NNT, Fluorescein-NNT, Rhodamine-NNT, Cy5.5-NNT.

The particle sizes of the dye-labeled NNTs were measured, all of which were in the diameter range of about 37 to about 95 nm (Table 2), as characterized by uranyl acetate stained dry-state TEM and cryogenic electron microscopy (cryo-EM) (FIGS. 1C-1D). By DLS, the NNTs exhibited hydrodynamic diameters ($D_h$) from about 100 to about 106 nm (Table 2 and FIG. 9). These discrepancies may be explained by sample preparation of the particles for TEM, coupled with the inherent nature of the DLS measurement showing diameters of swollen particles with some dispersity. These discrepancies are also present in the commercial LUMAFLUOR tracers (FIGS. 8A-8F).

TABLE 2

Excitation and Emission Maxima, Hydrodynamic Diameter, Diameter Measured by TEM, Zeta Potential and Particles Concentration of 4 Different NNTs

| Dye-labeled NNTs | $\lambda_{ex}$ (nm) | $\lambda_{em}$ (nm) | $D_h$ (nm) | D (nm) (dry-state TEM) | D (nm) (cryo-EM) | Average mV | Particle concentration (particles/mL) |
|---|---|---|---|---|---|---|---|
| Coumarin-NNT | 351 | 412 | 106 | 57 ± 12 | 46 ± 19 | −34.3 | $3.2 \times 10^{11}$ |
| Fluorescein-NNT | 490 | 513 | 104 | 67 ± 12 | 78 ± 17 | −33.2 | $2.1 \times 10^{11}$ |
| Rhodamine-NNT | 558 | 586 | 100 | 58 ± 4 | 62 ± 3 | −35.2 | $2.3 \times 10^{12}$ |
| Cy5.5-NNT | 672 | 700 | 102 | 45 ± 8 | 47 ± 10 | −46.1 | $2.5 \times 10^{13}$ |

Furthermore, zeta potential analysis was employed to characterize the bulk NN solutions. All NNTs had a similar negative zeta potential (Table 2), except for Cy5.5-NNT, which had a slightly more negatively charged surface than the other NNTs, possible owing to the presence of two sulfate groups on the Cy5.5 monomer. To discern the concentrations of NNTs, we employed NTA and determined that all NNTs except Rhodamine-NNT had concentrations between about $2.1\times10^{11}$ to about $3.2\times10^{11}$ particles per milliliter.

The dye content of each NNT was determined to be about 60.0 μM, about 617 μM, about 460.5 μM, and about 123.6 μM for Coumarin-NNT, Fluorescein-NNT, Rhodamine-NNT and Cy5.5-NNT, respectively, using UV-visible (UV-Vis) spectroscopy. The dye concentration per particle was then calculated, using the particle concentrations as determined by NTA, to be about $1.88\times10^{-13}$ μmol/particle, about $2.92\times10^{-12}$ μmol/particle, about $2.00\times10^{-13}$ μmol/particle, and about $4.94\times10^{-13}$ μmol/particle for Coumarin-NNT, Fluorescein-NNT, Rhodamine-NNT and Cy5.5-NNT, respectively.

Figure 10:
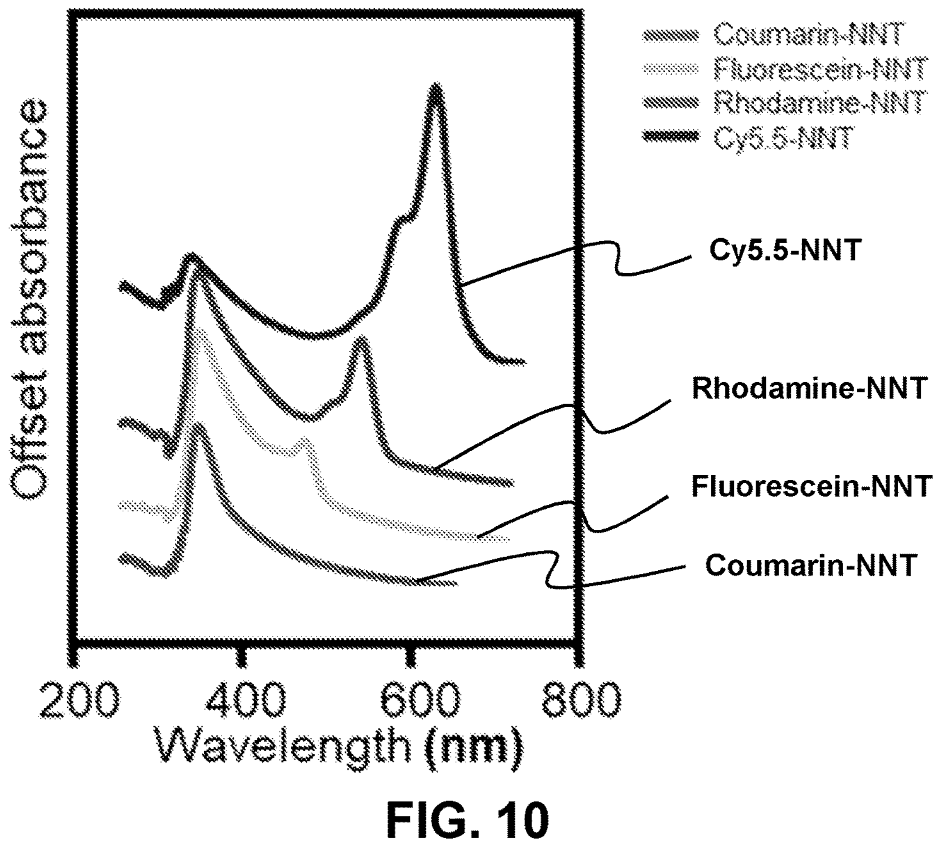
FIG. 10: UV-vis spectra of Coumarin-NNT, Fluorescein-NNT, Rhodamine-NNT and Cy5.5-NNT.
Figure 11:
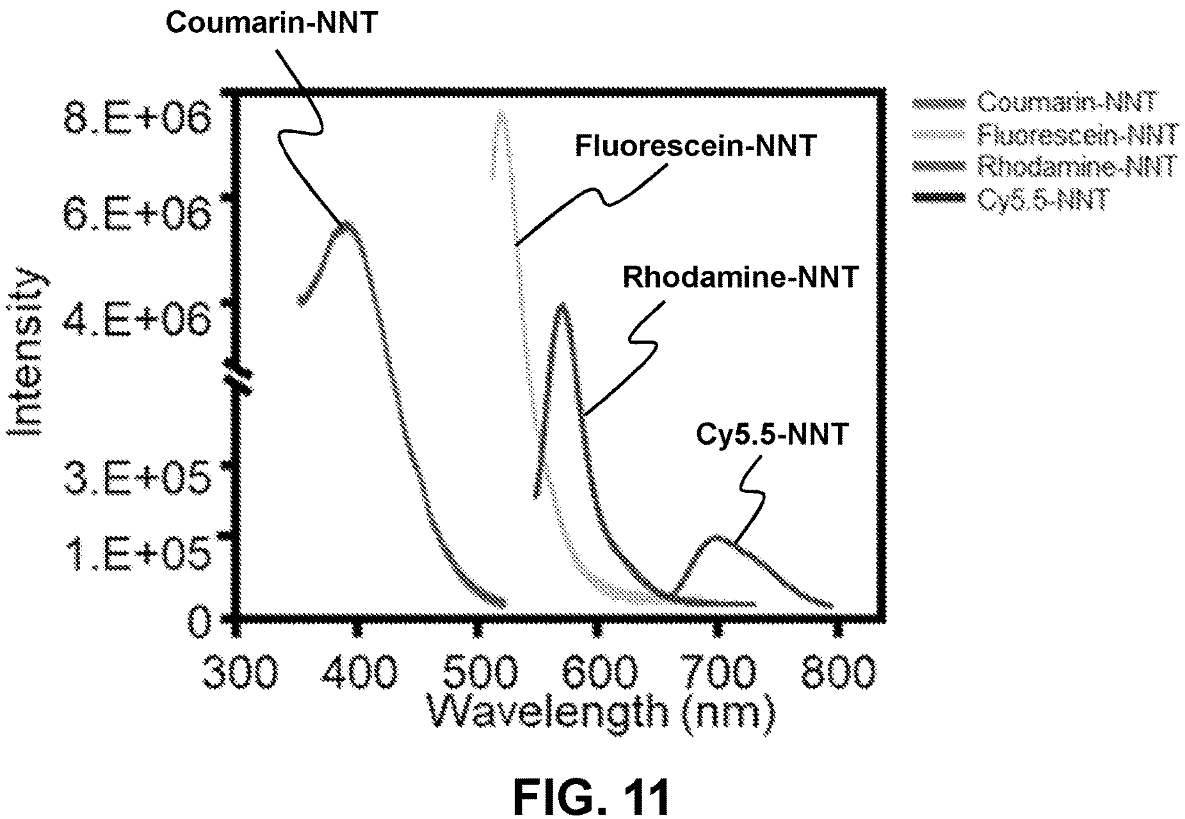
FIG. 11: Fluorescence spectra of Coumarin-NNT, Fluorescein-NNT, Rhodamine-NNT and Cy5.5-NNT. The excitation wavelengths are 350, 490, 540, and 650 nm for Coumarin-NNT, Fluorescein-NNT, Rhodamine-NNT and Cy5.5-NNT, respectively.
Figure 12:
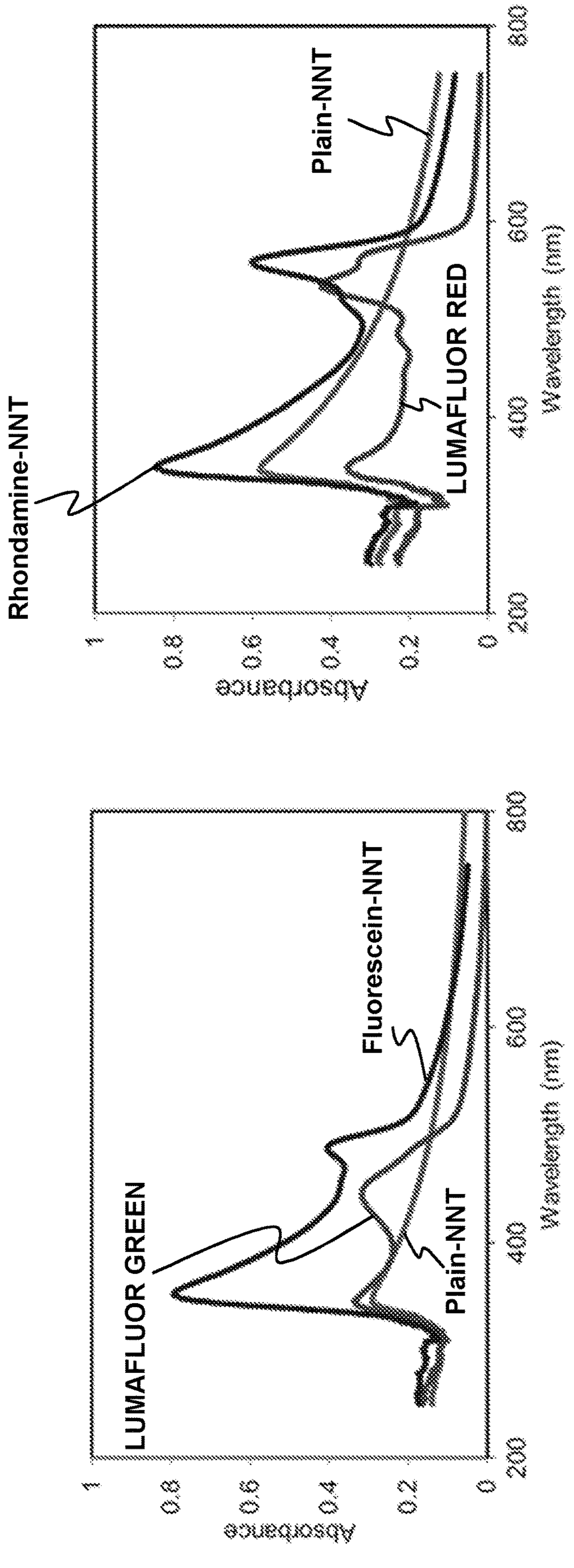
FIG. 12: Fluorescence spectra of Coumarin-NNT, Fluorescein-NNT, Rhodamine-NNT and Cy5.5-NNT. The excitation wavelengths are 350, 490, 540, and 650 nm for Coumarin-NNT, Fluorescein-NNT, Rhodamine-NNT and Cy5.5-NNT, respectively.
Figure 13:
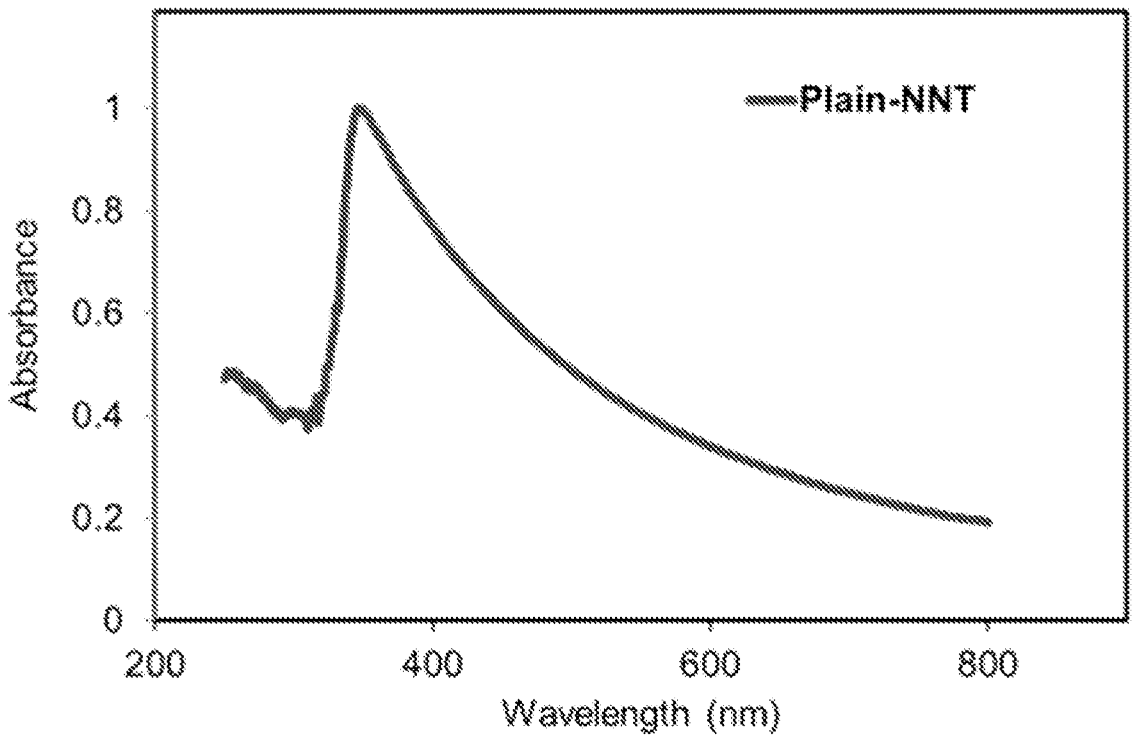
FIG. 13: UV-vis spectroscopy of the NNT without dye (Plain-NNT).
Figure 14:
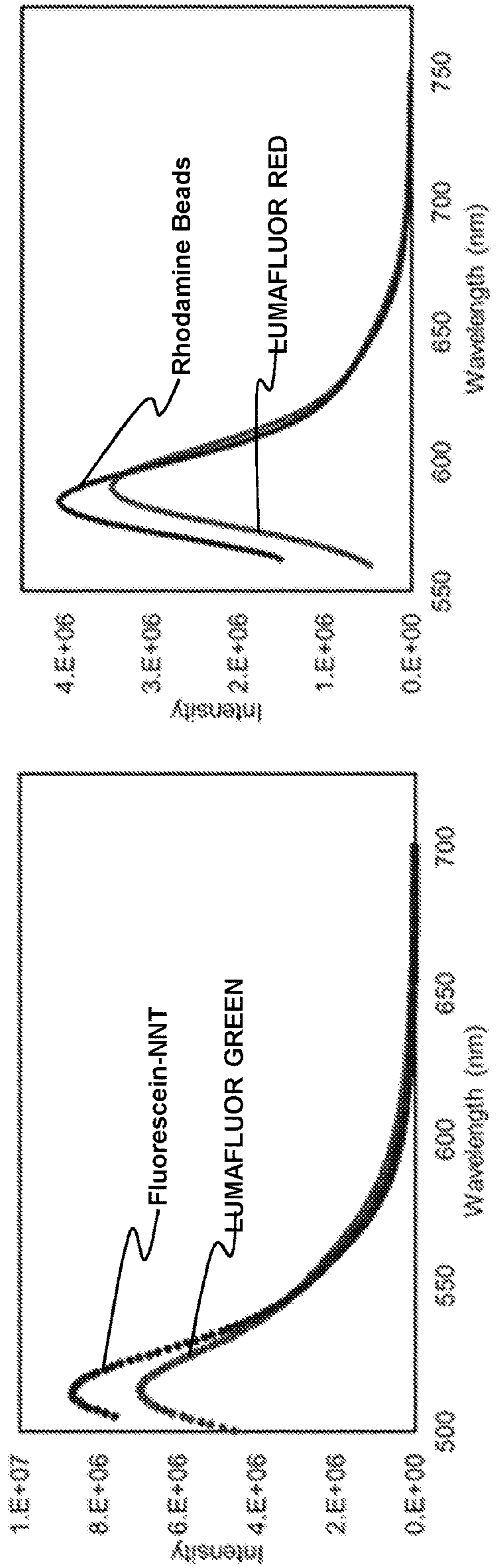
FIG. 14: Comparison of fluorescence spectra for LUMAFLUOR GREEN and Fluorescein-NNT; LUMAFLUOR RED and Rhodamine-NNT. The excitation wavelengths are 490 nm for LUMAFLUOR GREEN and Fluorescein-NNT, 540 nm for LUMAFLUOR RED and Rhodamine-NNT.
Figure 15:
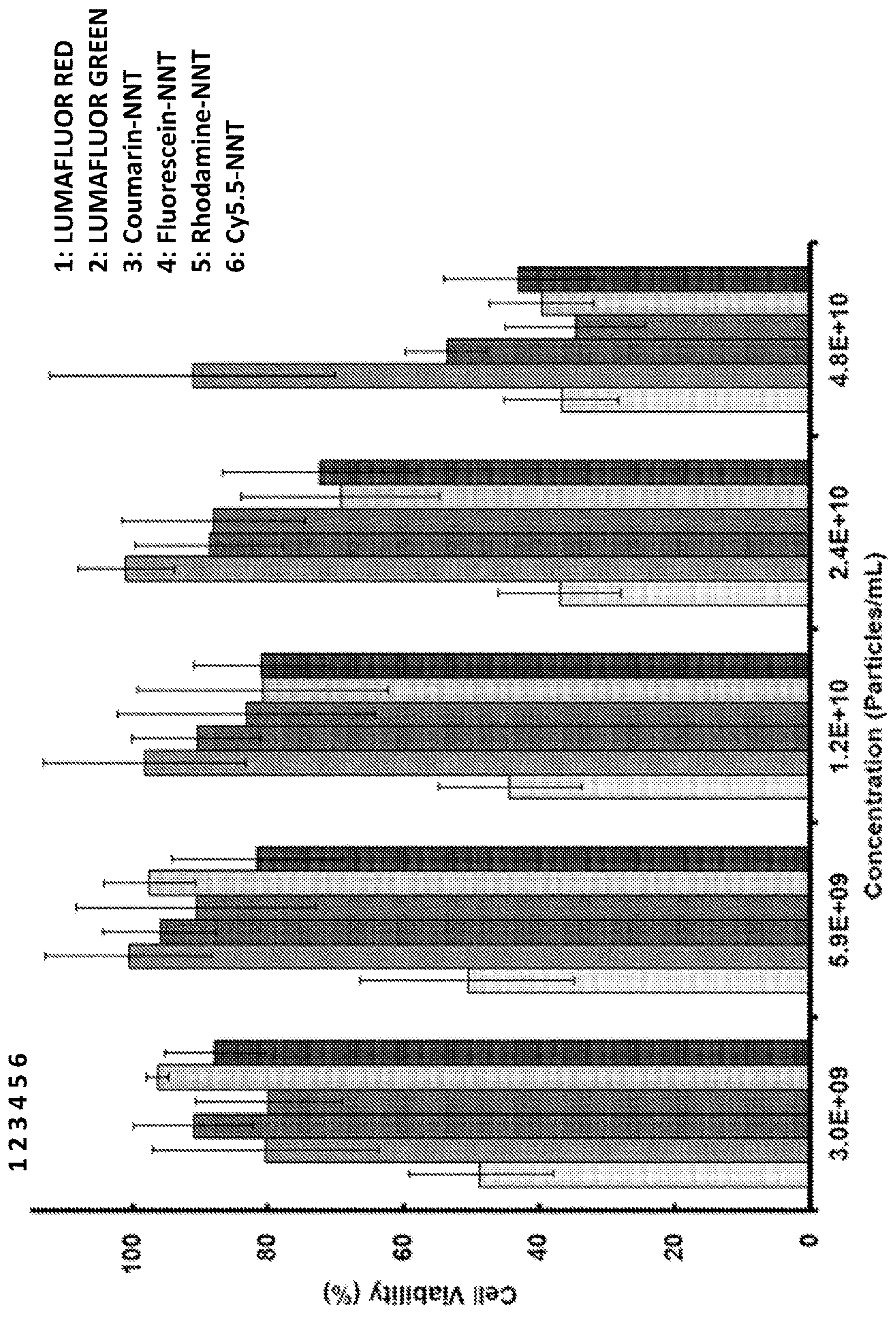
FIG. 15: Comparison of fluorescence spectra for LUMAFLUOR GREEN and Fluorescein-NNT; LUMAFLUOR RED and Rhodamine-NNT. The excitation wavelengths are 490 nm for LUMAFLUOR GREEN and Fluorescein-NNT, 540 nm for LUMAFLUOR RED and Rhodamine-NNT.

To elucidate the optical properties of NNTs, excitation and emission spectra of NNTs were acquired by UV-Vis and fluorescence spectroscopy (FIGS. 10 and 11), and the maxima are summarized in Table 2. The UV-Vis and fluorescence spectra for each NNT were measured at the particle concentrations set forth in Table 2, as measured by NTA. The different fluorescence intensities of each NNT reflects the difference in extinction coefficient between each dye used in the NNT syntheses. As the commercial fluorescent tracers have two colors available (LUMAFLUOR GREEN $\lambda_{ex}$=460 nm, $\lambda_{em}$=505 nm and LUMAFLUOR RED $\lambda_{ex}$=530 nm, $\lambda_{em}$=590 nm), UV-Vis and fluorescence spectra of LUMAFLUOR GREEN and LUMAFLUOR RED can be compared to Fluorescein-NNT and Rhodamine-NNT, respectively. Indeed, the UV-Vis absorptions of LUMAFLUOR GREEN and Fluorescein-NNT share a similar pattern and similar maximum of absorptions (FIG. 12). Similar results were observed in the case of LUMAFLUOR RED and Rhodamine-NNT. According to the UV-Vis absorption of an NNT prepared without a dye, the absorbance peak at about 350 nm on the UV-Vis spectroscopy was attributed to the inherent structure of NNTs (FIG. 13). Moreover, the fluorescence intensity between LUMAFLUOR GREEN and Fluorescein-NNT, LUMAFLUOR RED and Rhodamine-NNT were in the same order of magnitude, suggesting that the optical behavior of NNTs in vitro or in vivo may be similar to these two commercial tracers (FIG. 14).

Cytotoxicity and Cellular Uptake. Prior to in vivo experiments, the cytotoxicity of all four dye-labeled NNTs was investigated. Towards this end, the viability of human embryonic kidney 293 (HEK 293) cells was evaluated following 48 h incubation with nanoparticles, as this cell line expresses several neuron-specific genes and is considered a standard proxy for early stage analysis of materials (Shaw et al., The FASEB Journal, 16, 869-871 (2002)). The nanoparticle concentrations of all NNTs and the commercial fluorescent tracers (LUMAFLUOR GREEN and RED) were determined by NTA and particles were evaluated for cytotoxicity at a range of concentrations between $3.0\times10^{9}$ to $4.8\times10^{10}$ particles per milliliter. Coumarin-NNT and Fluorescein-NNT were all nontoxic at concentrations up to $2.4\times10^{10}$ particles per milliliter (toxicity defined as cell viability<80%). Rhodamine-NNT and Cy5.5-NNT were nontoxic up to $1.2\times10^{10}$ particles per milliliter. Interestingly, the commercial fluorescent tracer LUMAFLUOR RED was toxic at all tested concentrations, while LUMAFLUOR GREEN showed no toxicity at any concentration tested, and the NNTs all exhibited dose-dependent toxicity.

Figure 2A:
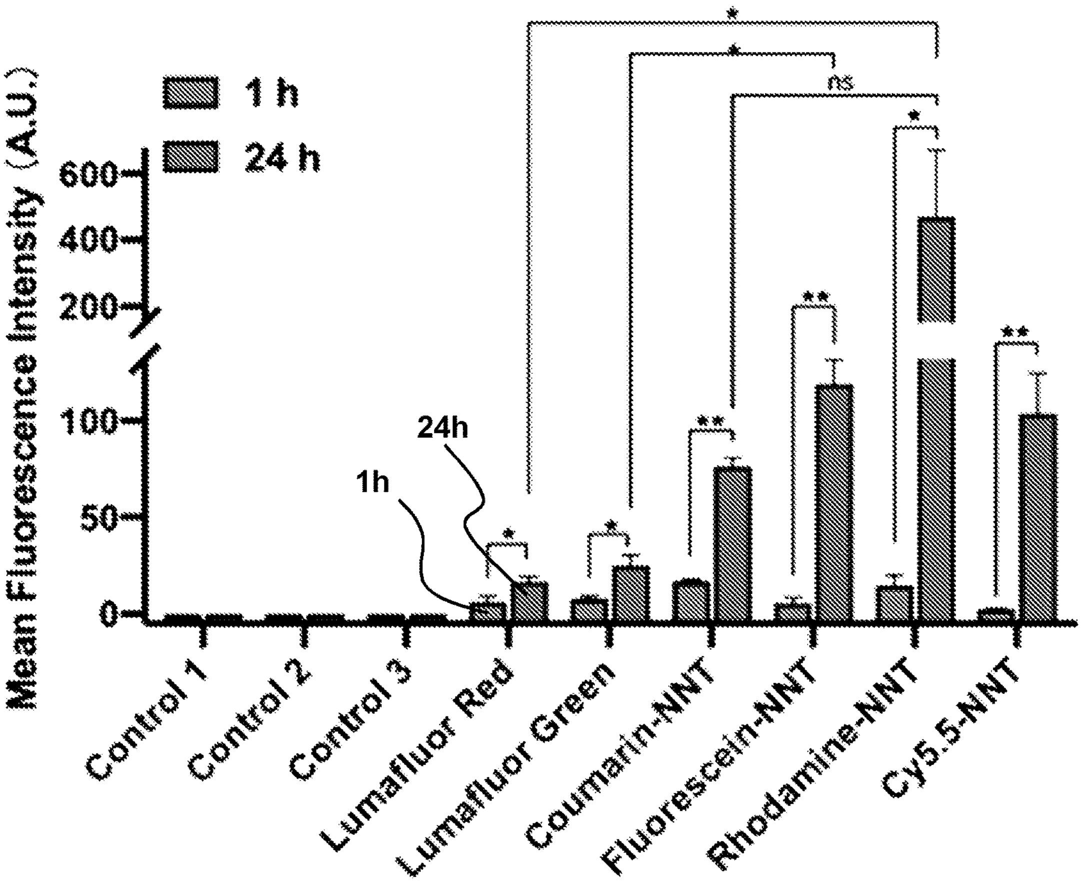
Figure 2B:
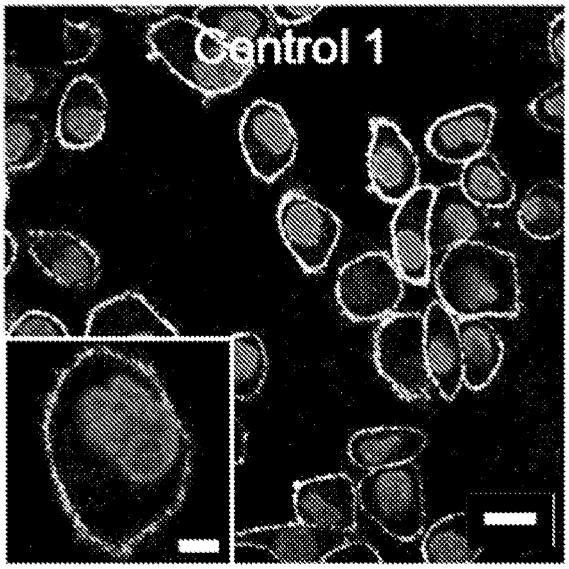
Figure 2C:
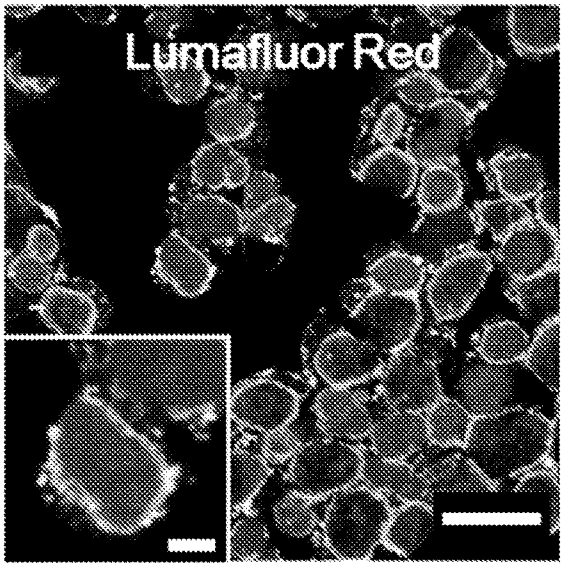
Figure 16A:
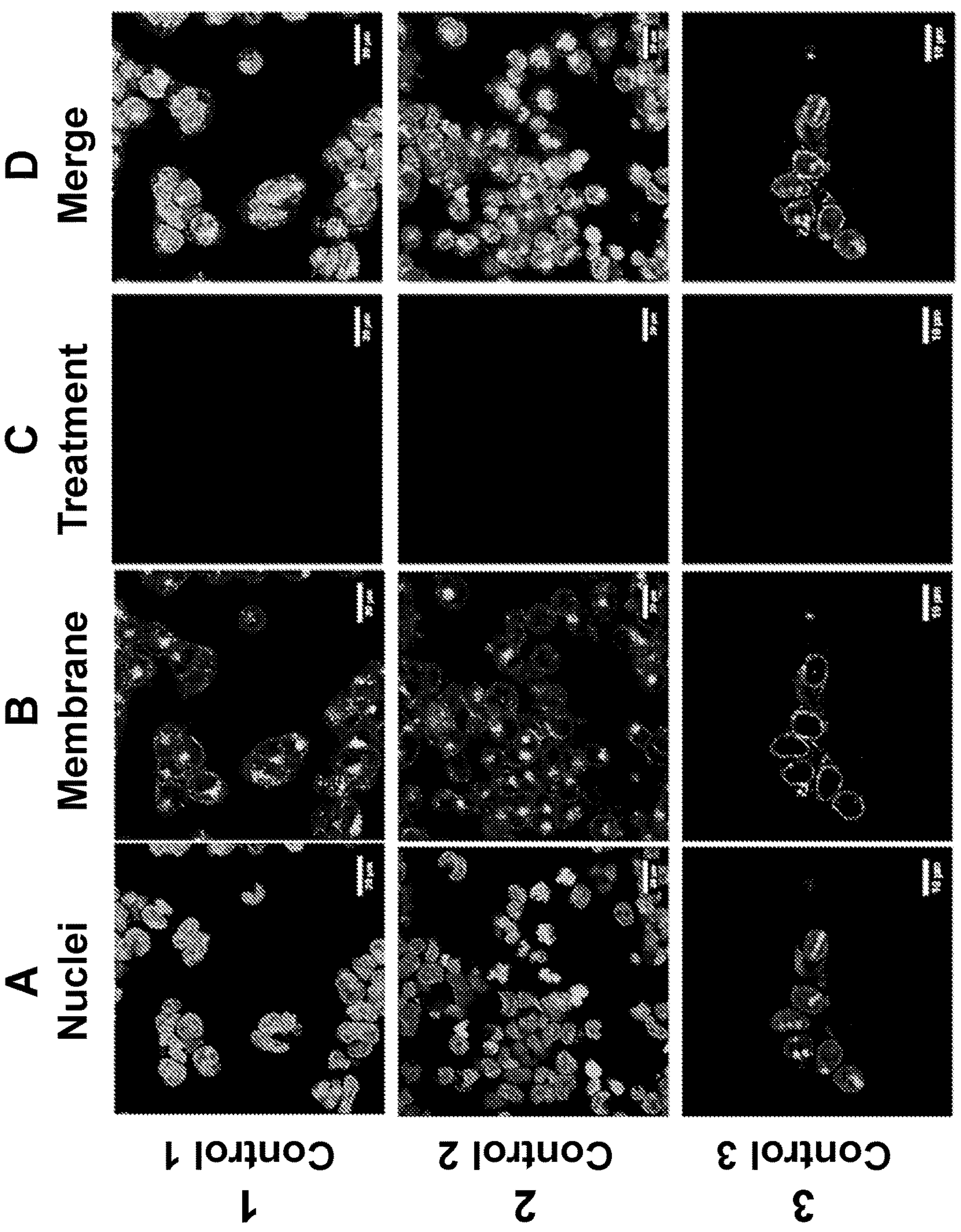
FIGS. 16A-16C: Cellular uptake confocal images of HEK 293 cells after 1 h incubation with commercial fluorescent tracers (LUMAFLUOR RED and GREEN), Coumarin-NNT, Fluorescein-NNT, Rhodamine-NNT and Cy5.5-NNT. In control 1, control 2, LUMAFLUOR RED, Fluorescein-NNT, Rhodamine-NNT, Cy5.5-NNT, cell nuclei were stained with DAPI. For Coumarin-NNT, cell nuclei were stained with propidium iodide. All cells in the control 1, control 3, LUMAFLUOR RED, Coumarin-NNT, Rhodamine-NNT and Cy5.5-NNT were stained with Wheat Germ Agglutinin with ALEXA FLUOR 488 Conjugate. Cells in the control 2, LUMAFLUOR GREEN and Fluorescein-NNT were stained with Wheat Germ Agglutinin with ALEXA FLUOR 633 Conjugate. HEK 293 cells were cultured for 24 h and then incubated with cell media as control, commercial fluorescent tracers or NNTs for 20 min following with washing with Dulbecco's phosphate-buffered saline (DPBS) for three times.
Figure 16B:
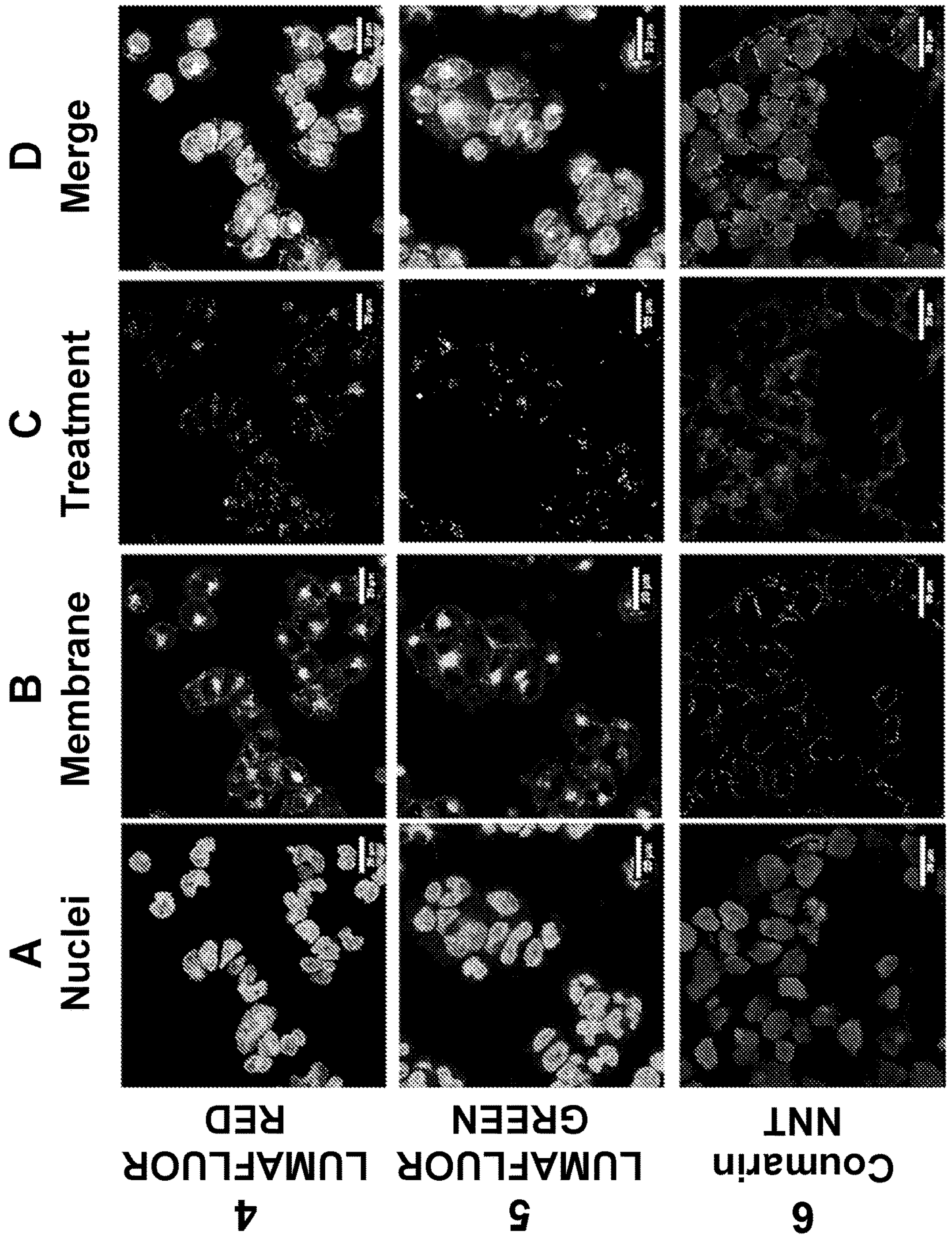
Figure 16C:
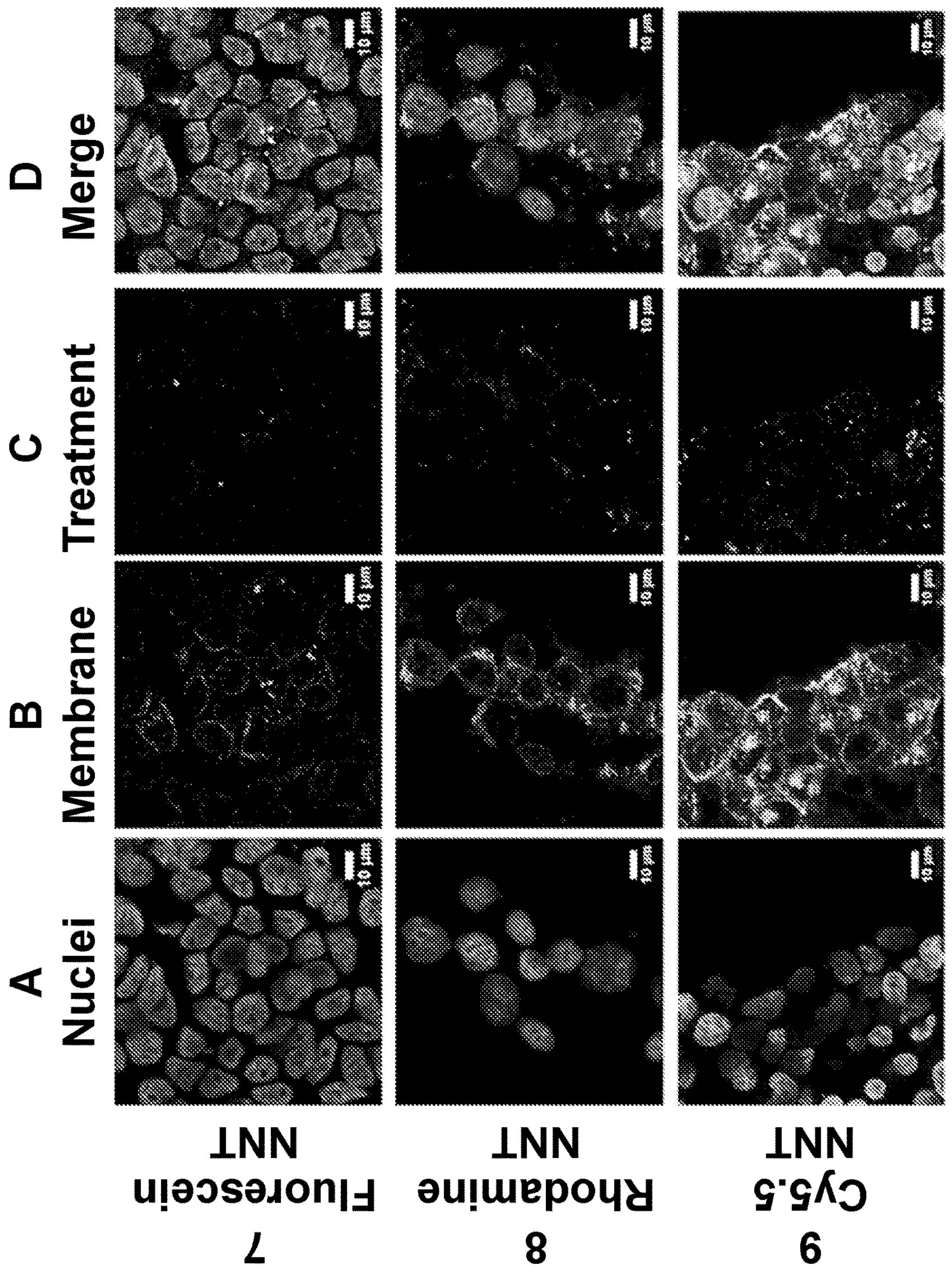
Figure 17A:
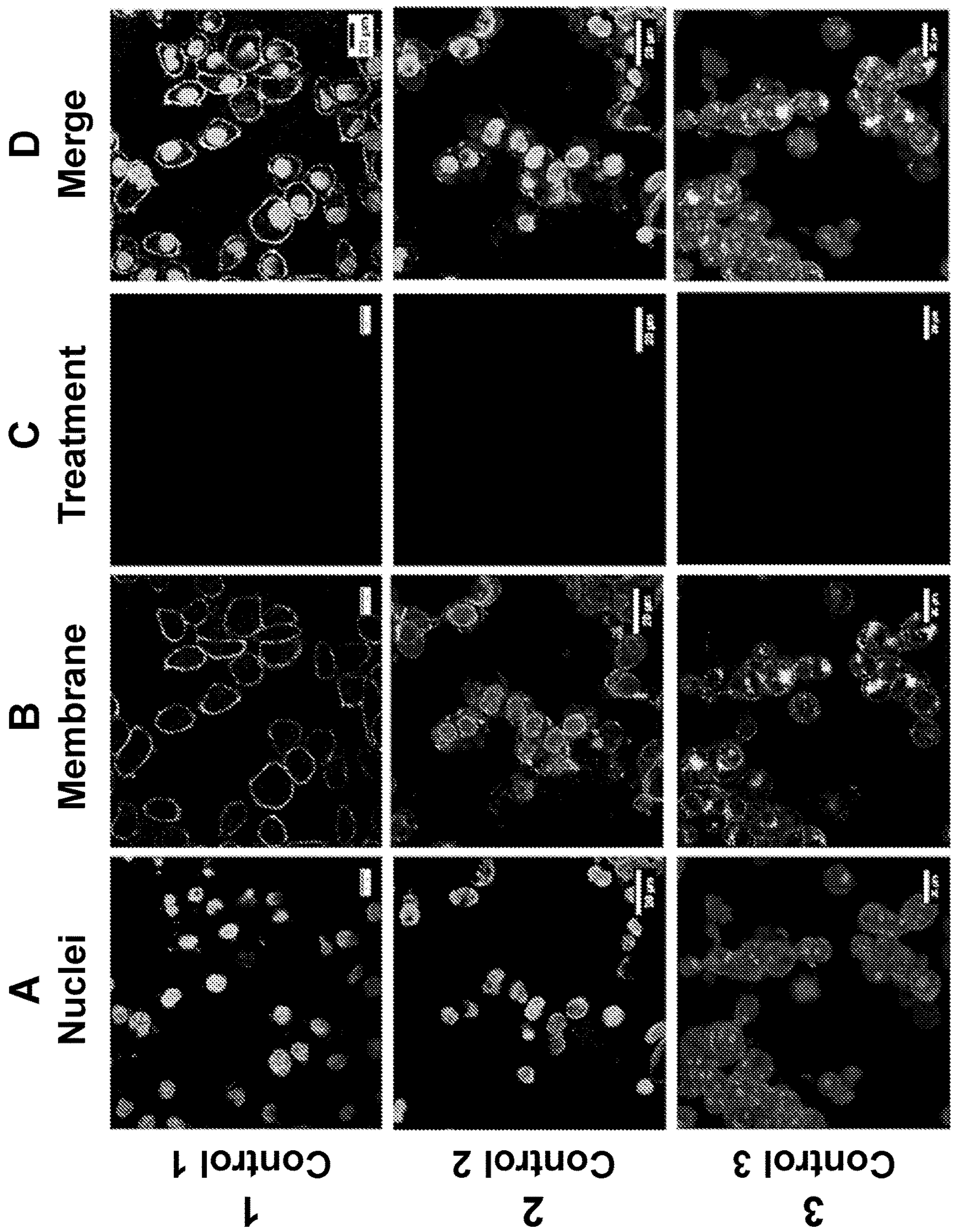
FIGS. 17A-17C: Cellular uptake confocal images of HEK 293 cells after 24 h incubation with commercial fluorescent tracers (LUMAFLUOR RED and GREEN), Coumarin-NNT, Fluorescein-NNT, Rhodamine-NNT and Cy5.5-NNT. In control 1, control 2, LUMAFLUOR RED, Fluorescein-NNT, Rhodamine-NNT, Cy5.5-NNT, cell nuclei were stained with DAPI. For Coumarin-NNT, cell nuclei were stained with propidium iodide. All cells in the control 1, control 3, LUMAFLUOR RED, Coumarin-NNT, Rhodamine-NNT and Cy5.5-NNT were stained with Wheat Germ Agglutinin with ALEXA FLUOR 488 Conjugate. Cells in the control 2, LUMAFLUOR GREEN and Fluorescein-NNT were stained with Wheat Germ Agglutinin with ALEXA FLUOR 633 Conjugate. HEK 293 cells were cultured for 24 h and then incubated with cell media as control, commercial fluorescent tracers or NNTs for 20 min following with washing with Dulbecco's phosphate-buffered saline (DPBS) three times. All scale bars in FIGS. 17A and 17C=20 μm.
Figure 17B:
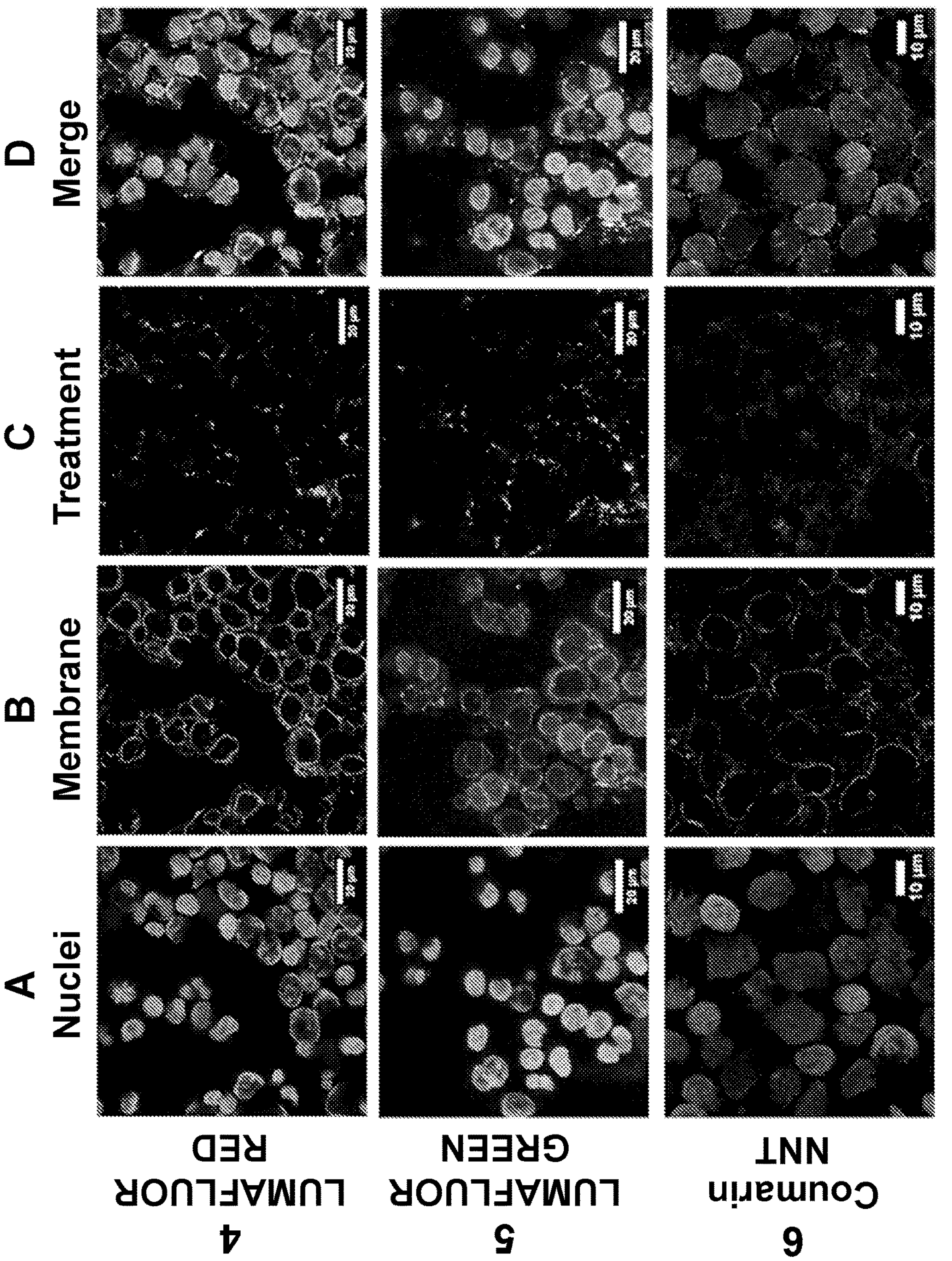
Figure 17C:
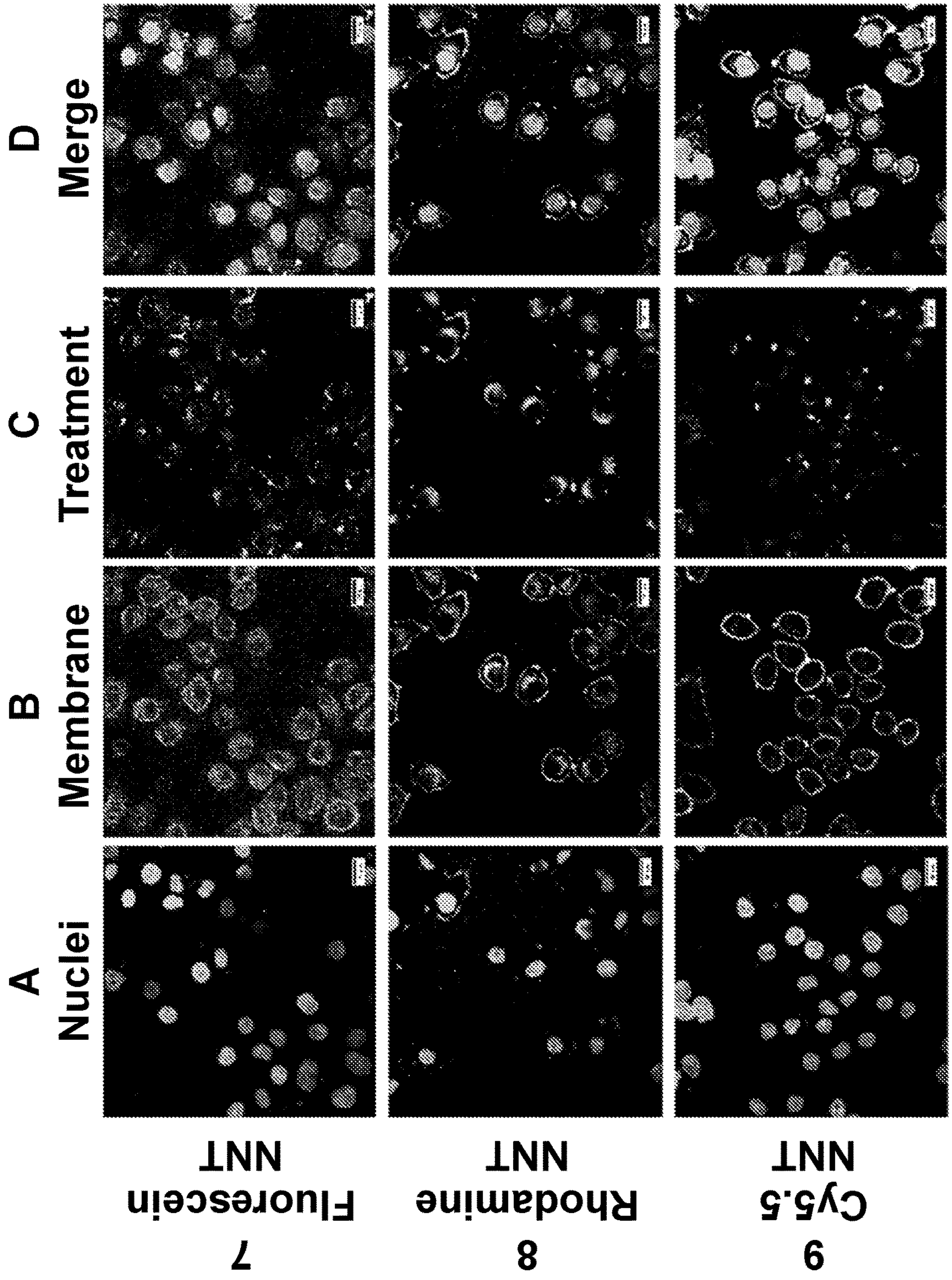
Figure 18:
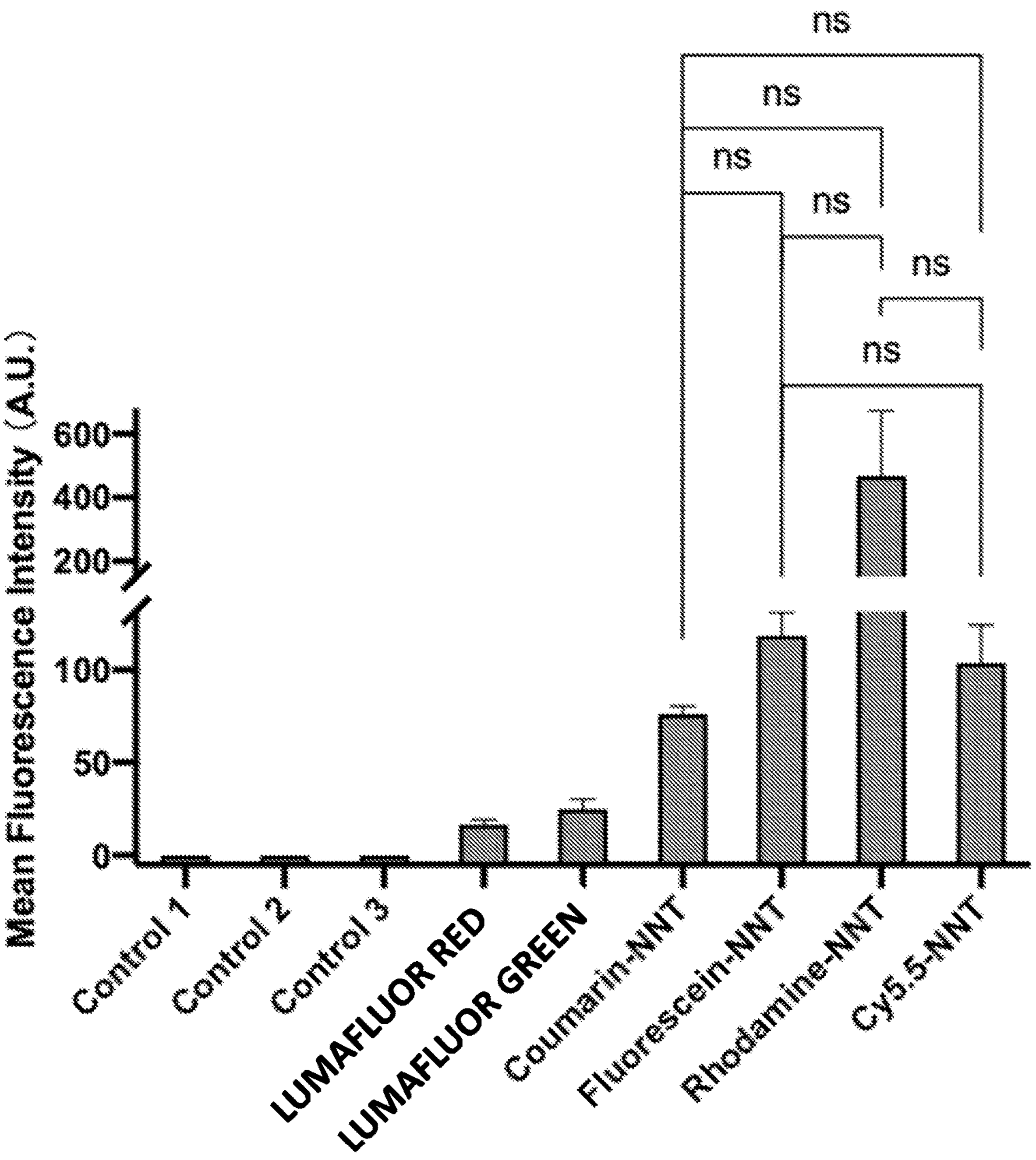
FIG. 18: Quantified cellular uptake of commercial fluorescent tracers (LUMAFLUOR RED and GREEN), and 4 NNTs (Coumarin-NNT, Fluorescein-NNT, Rhodamine-NNT and Cy5.5-NNT) in HEK 293 cells. Mean fluorescence intensity were quantified from confocal images. Significance was determined by an unpaired t-test (*$p<0.05$, **$p<0.01$, ns=not significant).
Figure 19A:
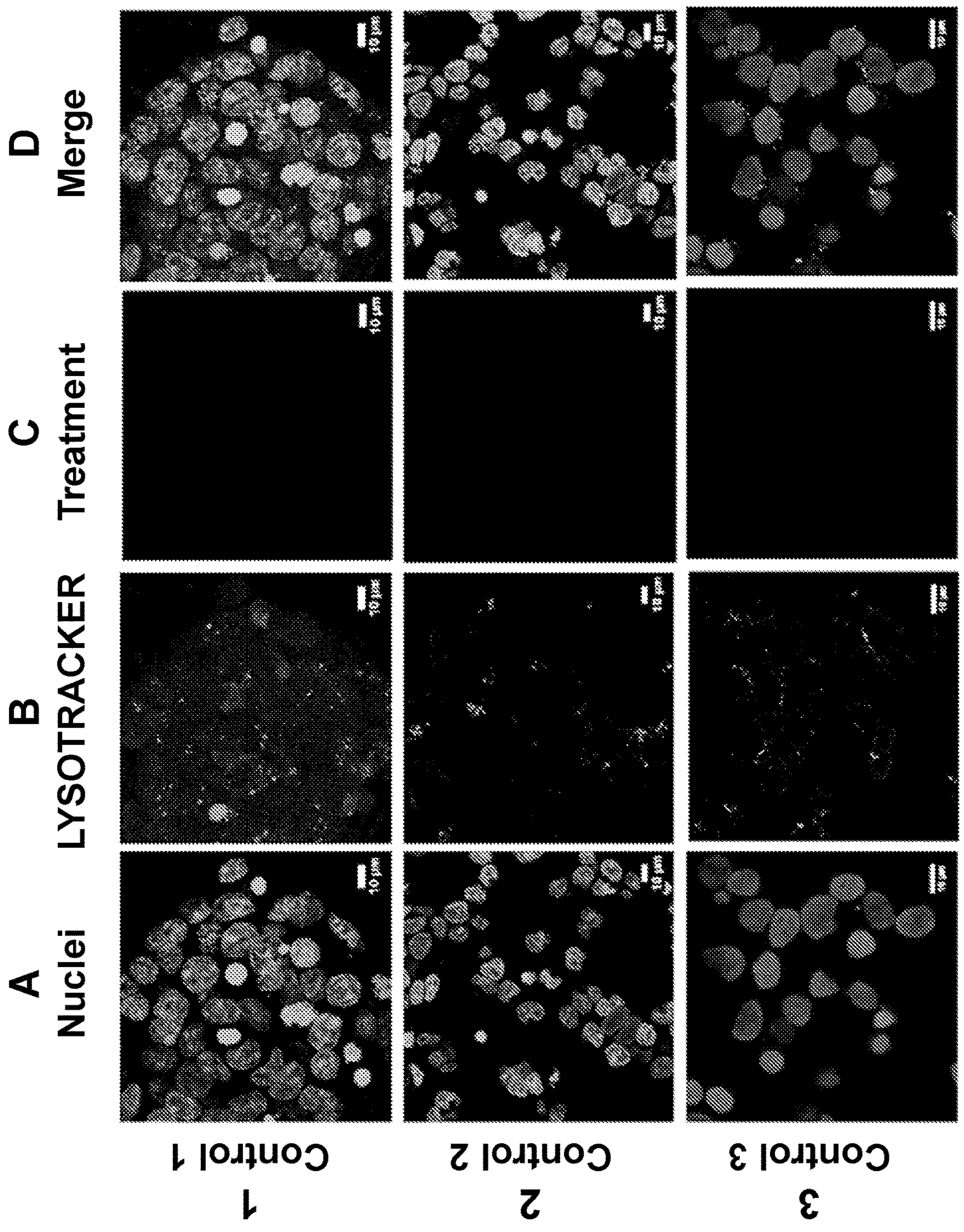
FIGS. 19A-19C: Confocal laser scanning microscopy images for colocalization with lysosomes in HEK 293 cells 1 h after the treatment. Treatments are commercial fluorescent tracers (LUMAFLUOR RED and GREEN), Coumarin-NNT, Fluorescein-NNT, Rhodamine-NNT and Cy5.5-NNT. The nuclei of HEK 293 cells were stained by DAPI (blue) for control 1, control 2, LUMAFLUOR RED and GREEN, Fluorescein-NNT, Rhodamine-NNT and Cy5.5-NNT; propidium iodide for control 3 and Coumarin-NNT. Lysosomes were stained by LYSOTRACKER GREEN DND-26 for control 1, control 3, LUMAFLUOR RED, Coumarin-NNT, Rhodamine-NNT and Cy5.5-NNT; by LYSOTRACKER RED DND-99 for control 2, LUMAFLUOR GREEN, and Fluorescein-NNT. Colocalization is shown in orange (RED and GREEN) or white (magenta and green). HEK 293 cells were cultured for 24 h and then incubated with commercial fluorescent tracer or NNTs for 20 min. All scale bars in FIGS. 19A-19C=10 μm.
Figure 19B:
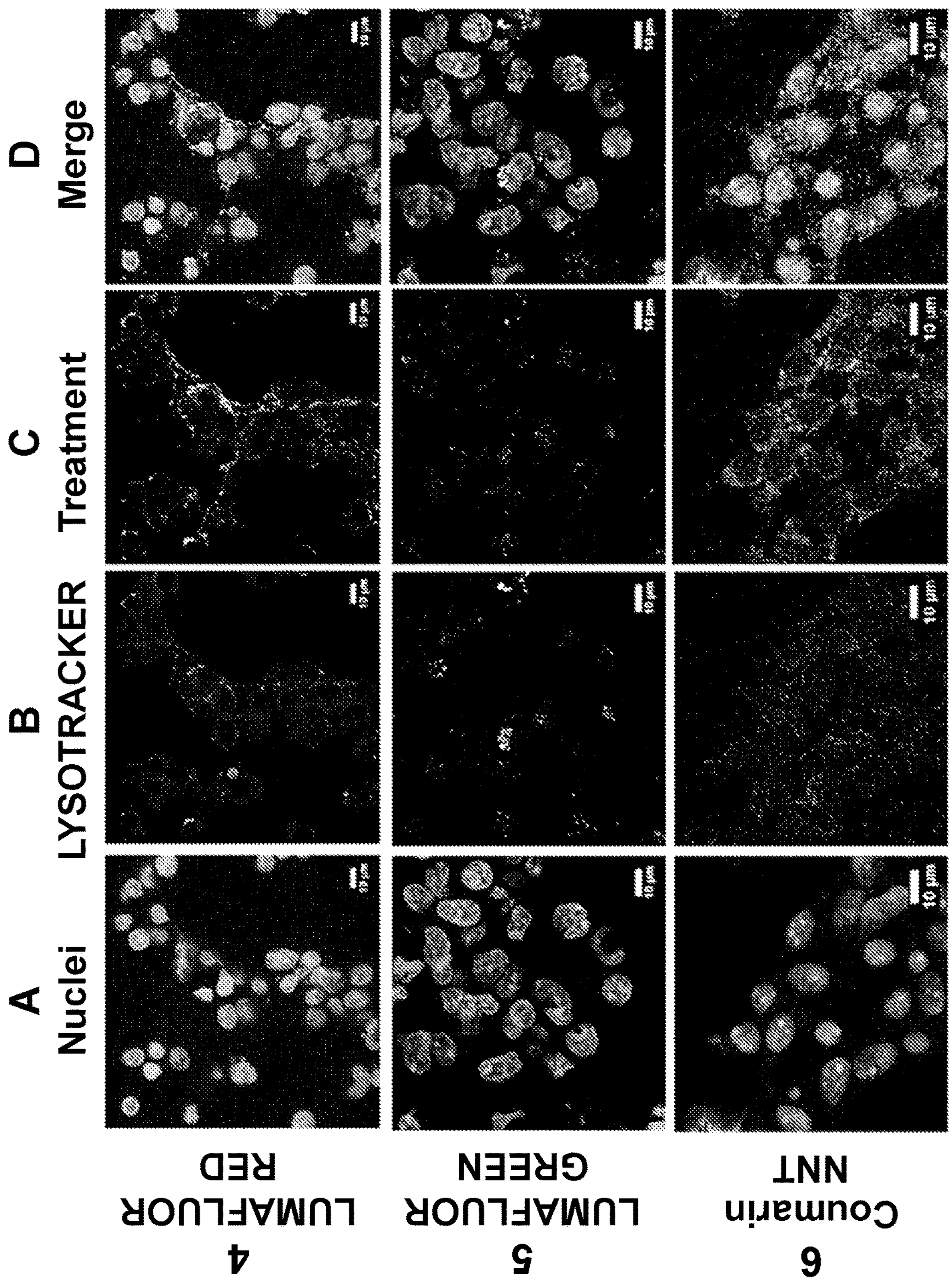
Figure 19C:
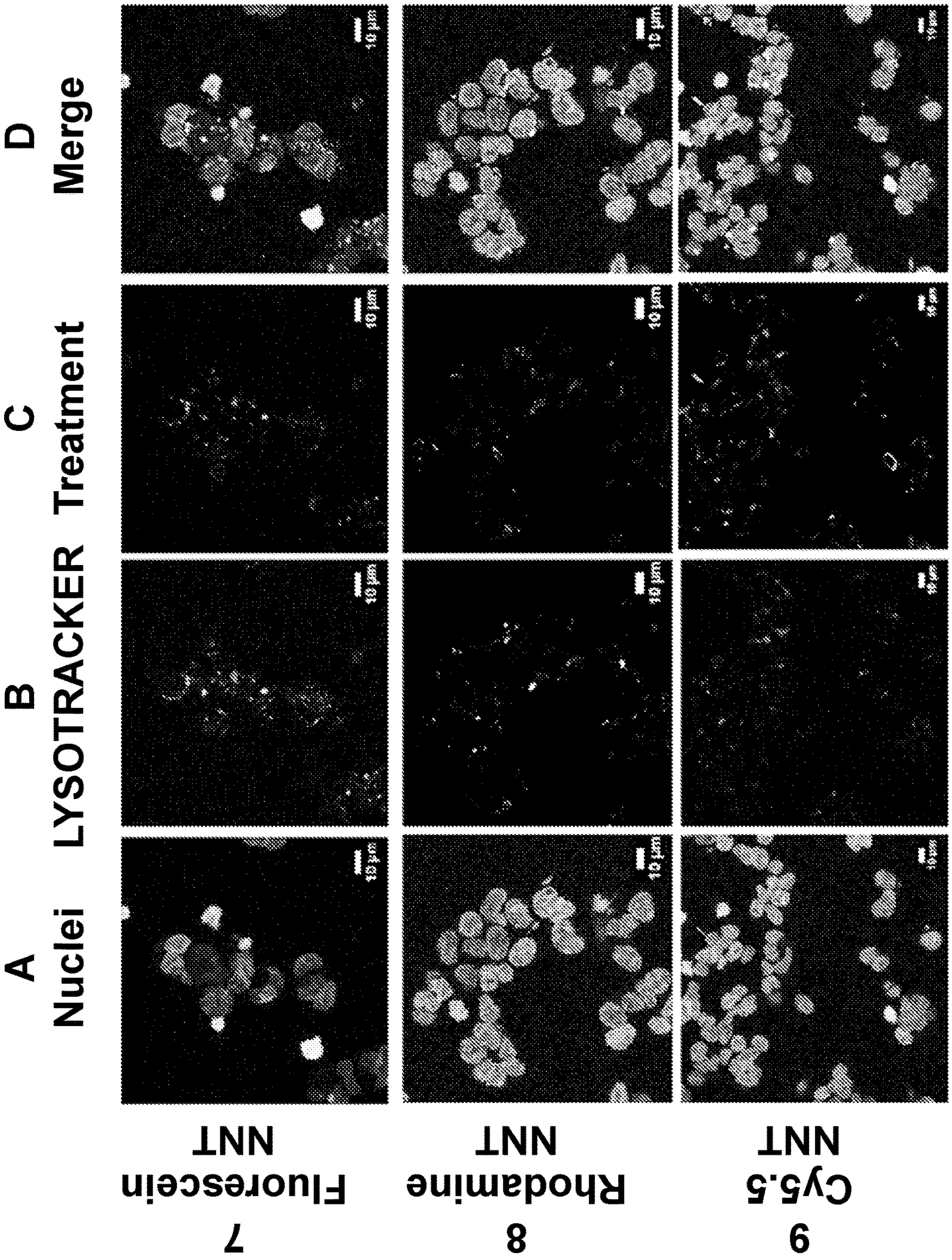
Figure 20A:
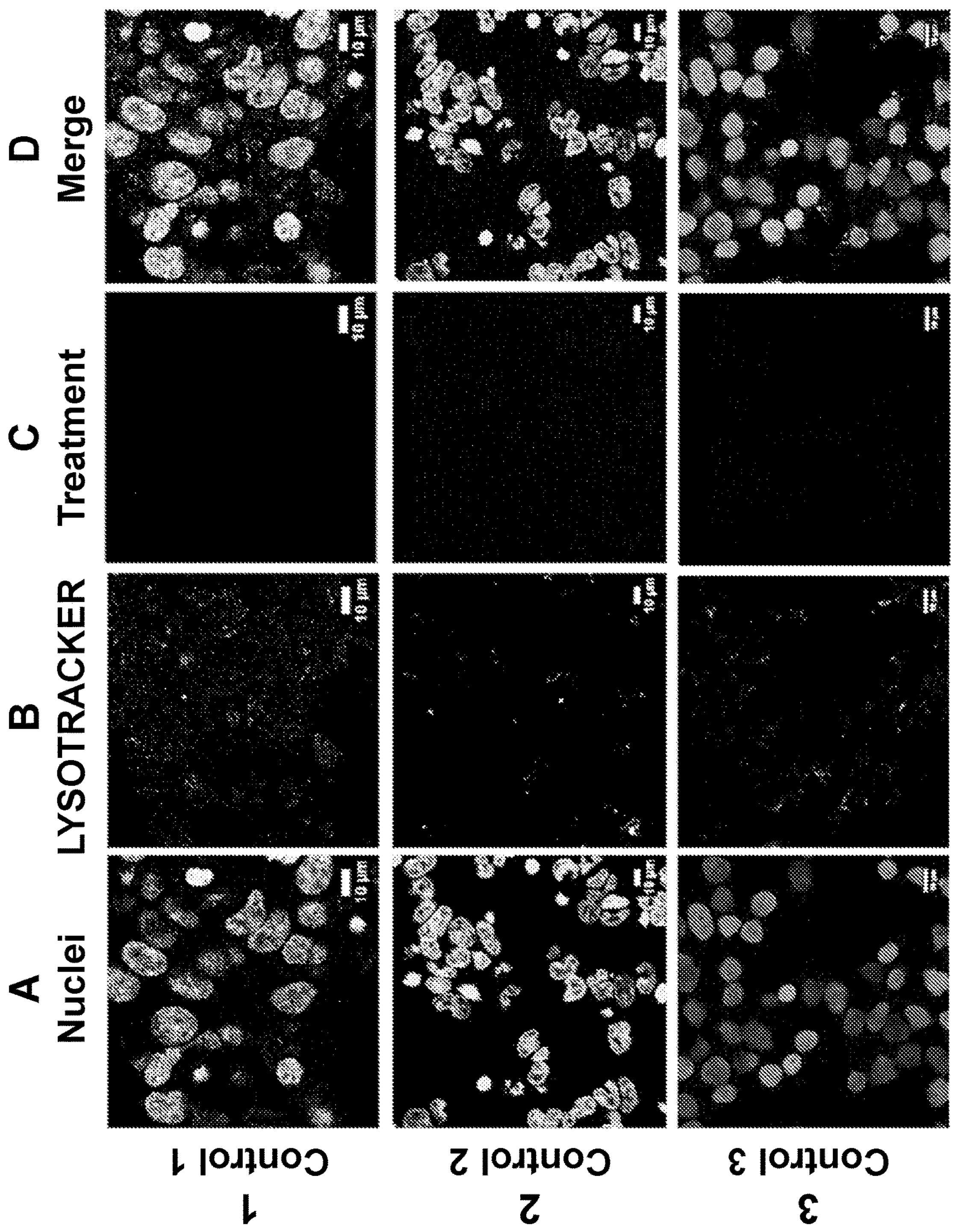
FIGS. 20A-20C: Confocal laser scanning microscopy images for colocalization with lysosomes in HEK 293 cells 4 h after treatment. Treatments are commercial fluorescent tracers (LUMAFLUOR RED and GREEN), Coumarin-NNT, Fluorescein-NNT, Rhodamine-NNT and Cy5.5-NNT. The nuclei of HEK 293 cells were stained by DAPI (blue) for control 1, control 2, LUMAFLUOR RED and GREEN, Fluorescein-NNT, Rhodamine-NNT and Cy5.5-NNT; propidium iodide for control 3 and Coumarin-NNT. Lysosomes were stained by LYSOTRACKER GREEN DND-26 for control 1, control 3, LUMAFLUOR RED, Coumarin-NNT, Rhodamine-NNT and Cy5.5-NNT; by LYSOTRACKER RED DND-99 for control 2, LUMAFLUOR GREEN, and Fluorescein-NNT. Colocalization is shown in orange (RED and GREEN) or white (magenta and green). HEK 293 cells were cultured for 24 h and then incubated with commercial fluorescent tracer or NNTs for 20 min. All scale bars in FIGS. 20A-20C=10 μm.
Figure 20B:
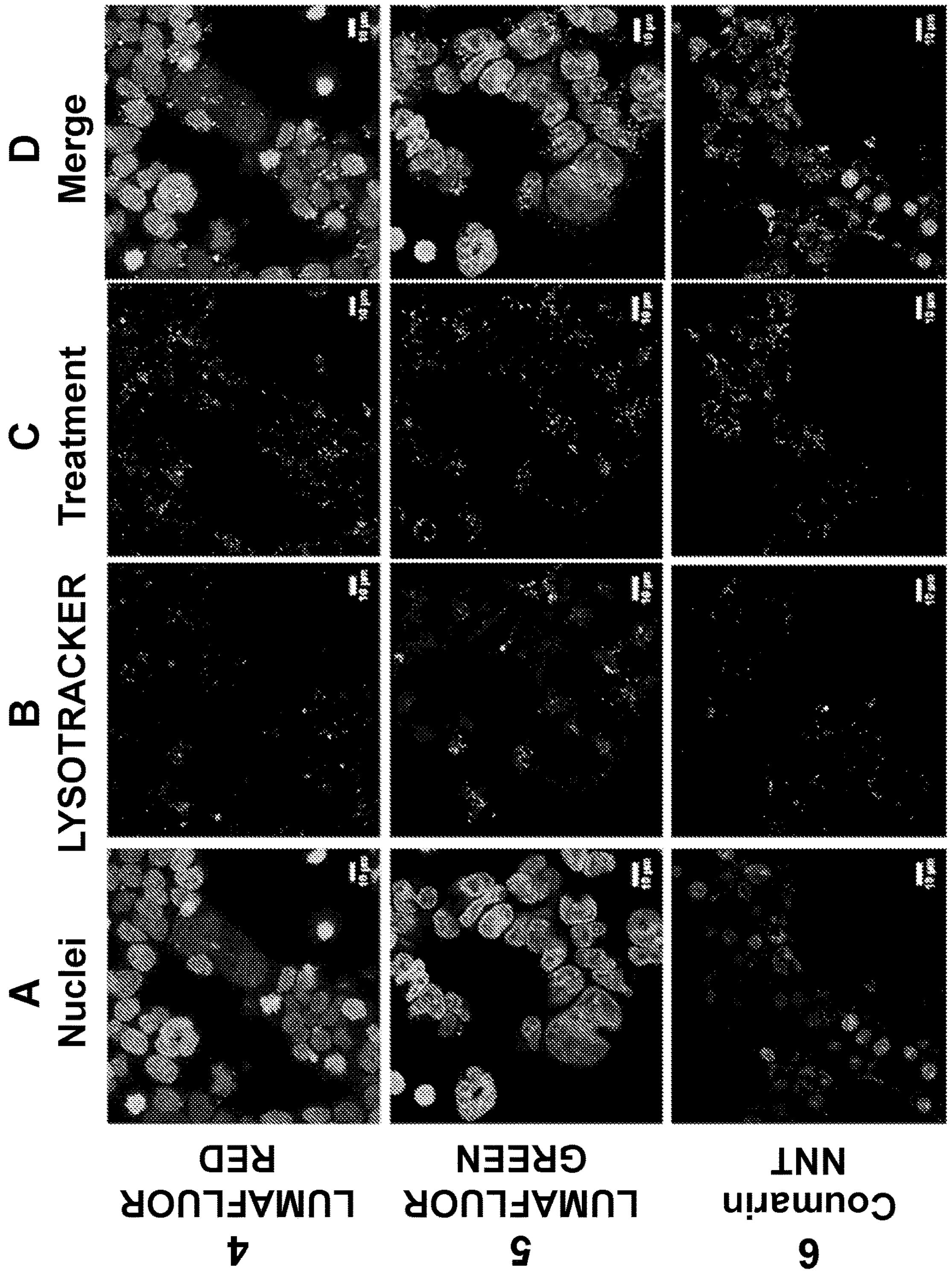
Figure 20C:
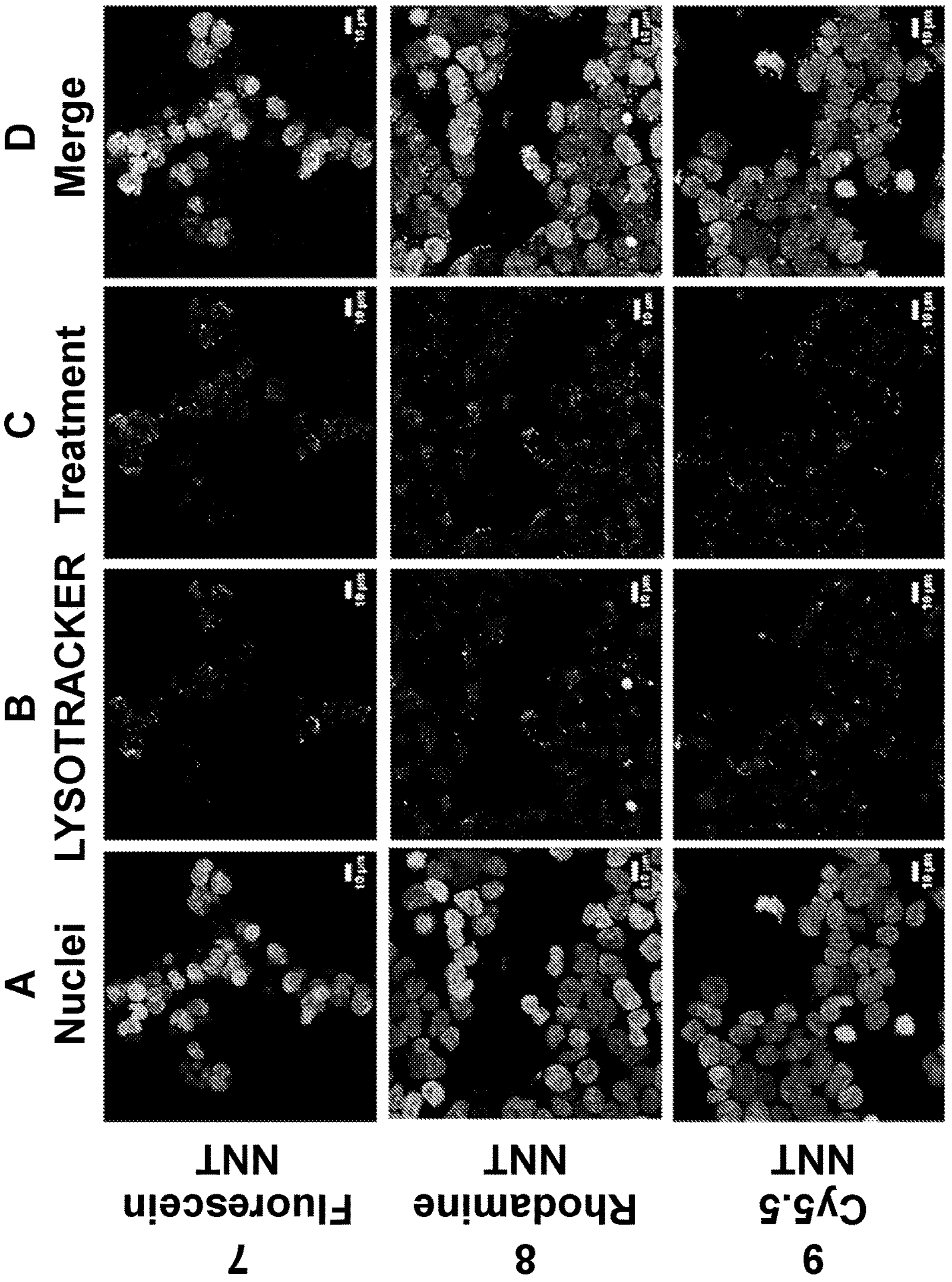
Figure 21A:
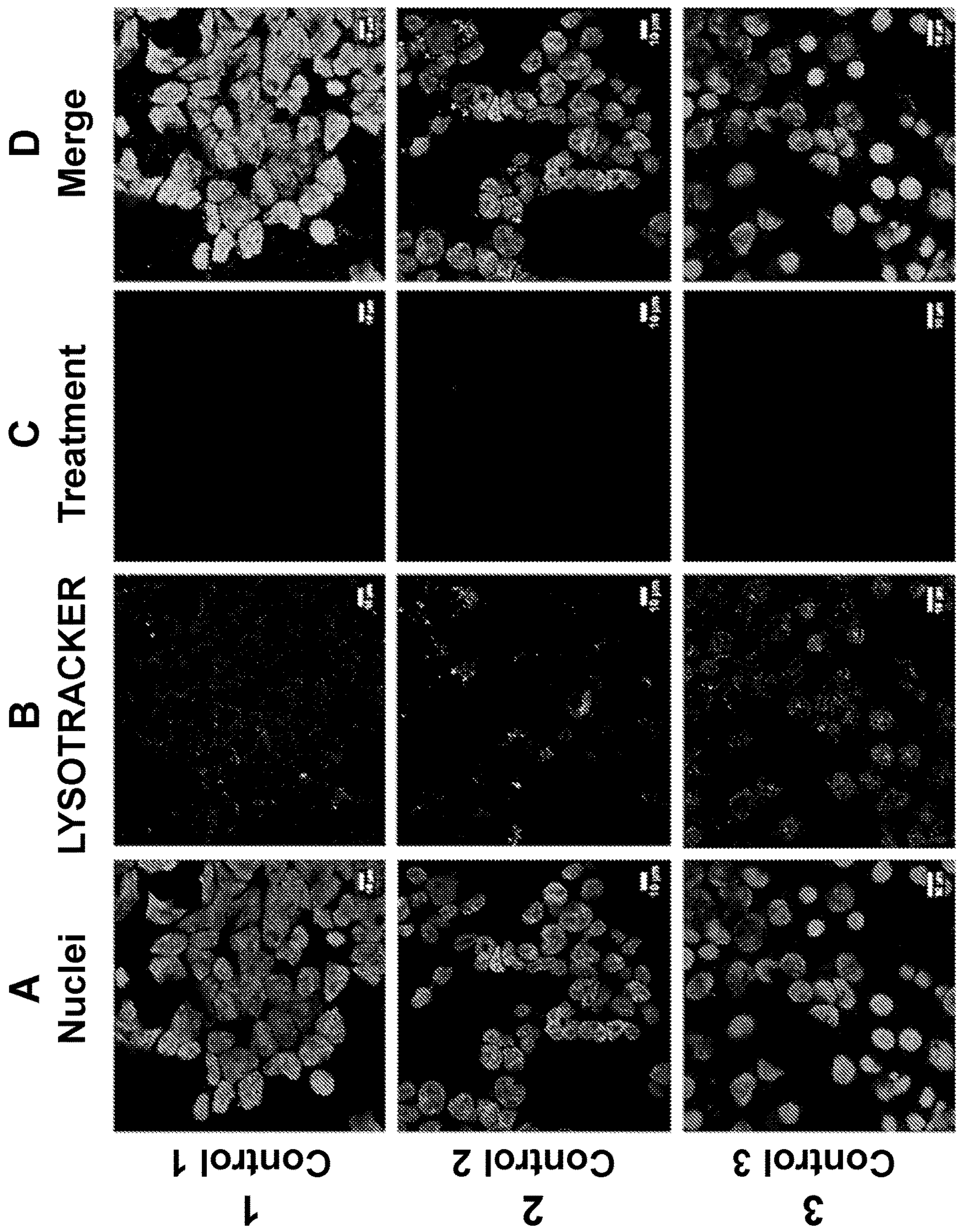
FIGS. 21A-21C: Confocal laser scanning microscopy images for colocalization with lysosomes in HEK 293 cells 24 h after treatment. Treatments are commercial fluorescent tracers (LUMAFLUOR RED and GREEN), Coumarin-NNT, Fluorescein-NNT, Rhodamine-NNT and Cy5.5-NNT. The nuclei of HEK 293 cells were stained by DAPI (blue) for control 1, control 2, LUMAFLUOR RED and GREEN, Fluorescein-NNT, Rhodamine-NNT and Cy5.5-NNT; propidium iodide for control 3 and Coumarin-NNT. Lysosomes were stained by LYSOTRACKER GREEN DND-26 for control 1, control 3, LUMAFLUOR RED, Coumarin-NNT, Rhodamine-NNT and Cy5.5-NNT; by LYSOTRACKER RED DND-99 for control 2, LUMAFLUOR GREEN, and Fluorescein-NNT. Colocalization is shown in orange (RED and GREEN) or white (magenta and green). HEK 293 cells were cultured for 24 h and then incubated with commercial fluorescent tracer or NNTs for 20 min. All scale bars in FIGS. 21A and 21B=10 μm.
Figure 21B:
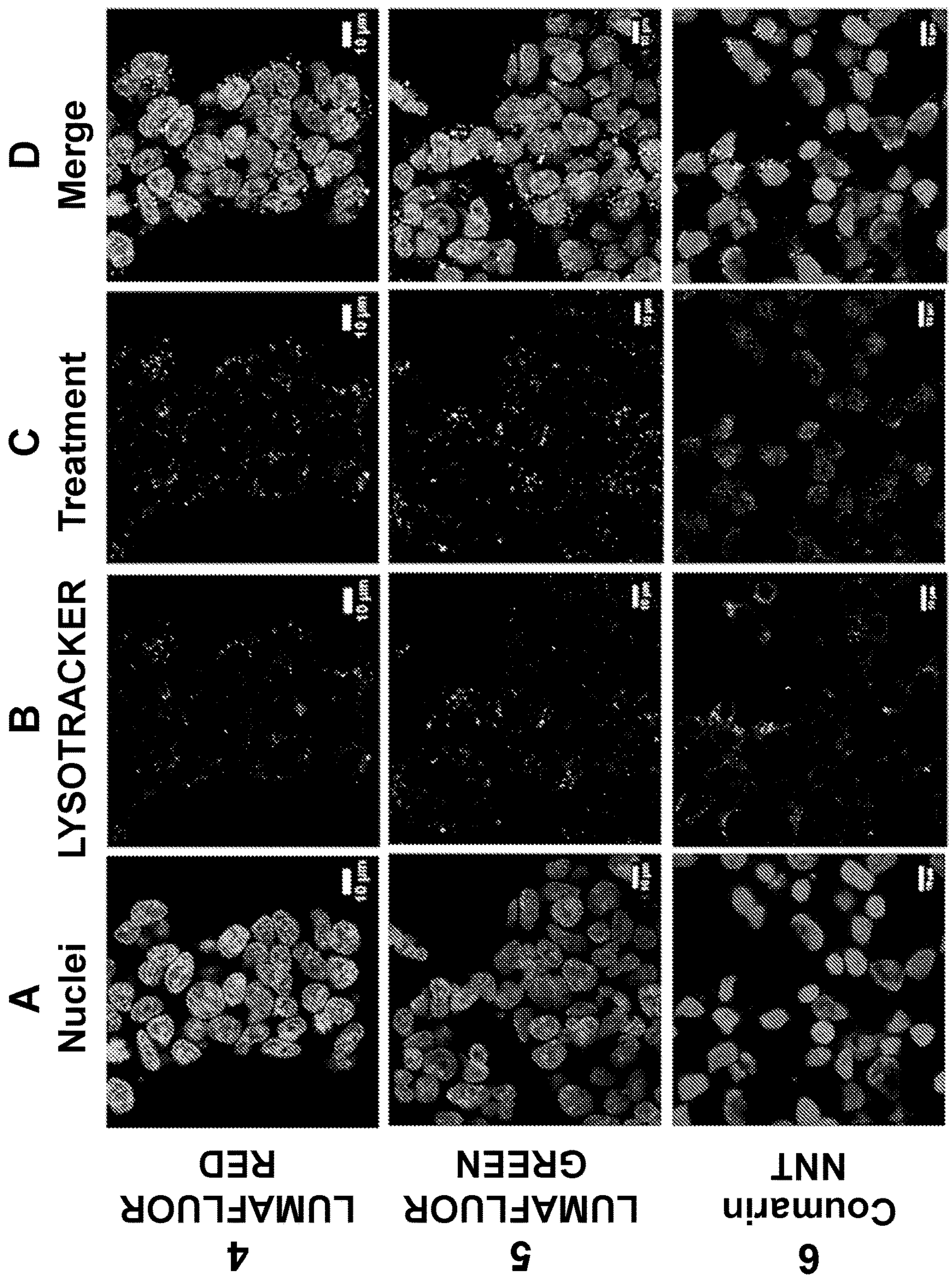
Figure 21C:
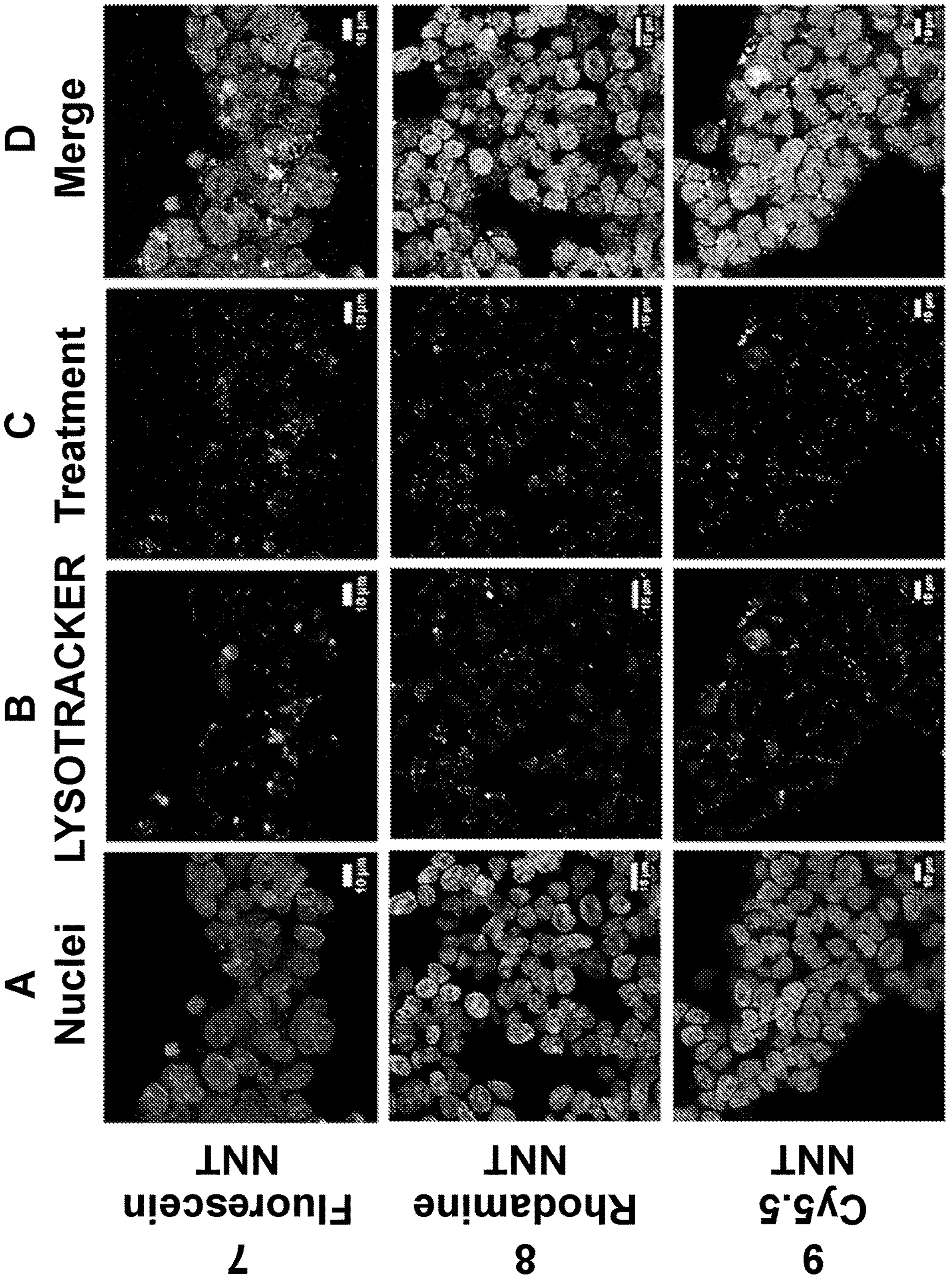
Figure 22A:
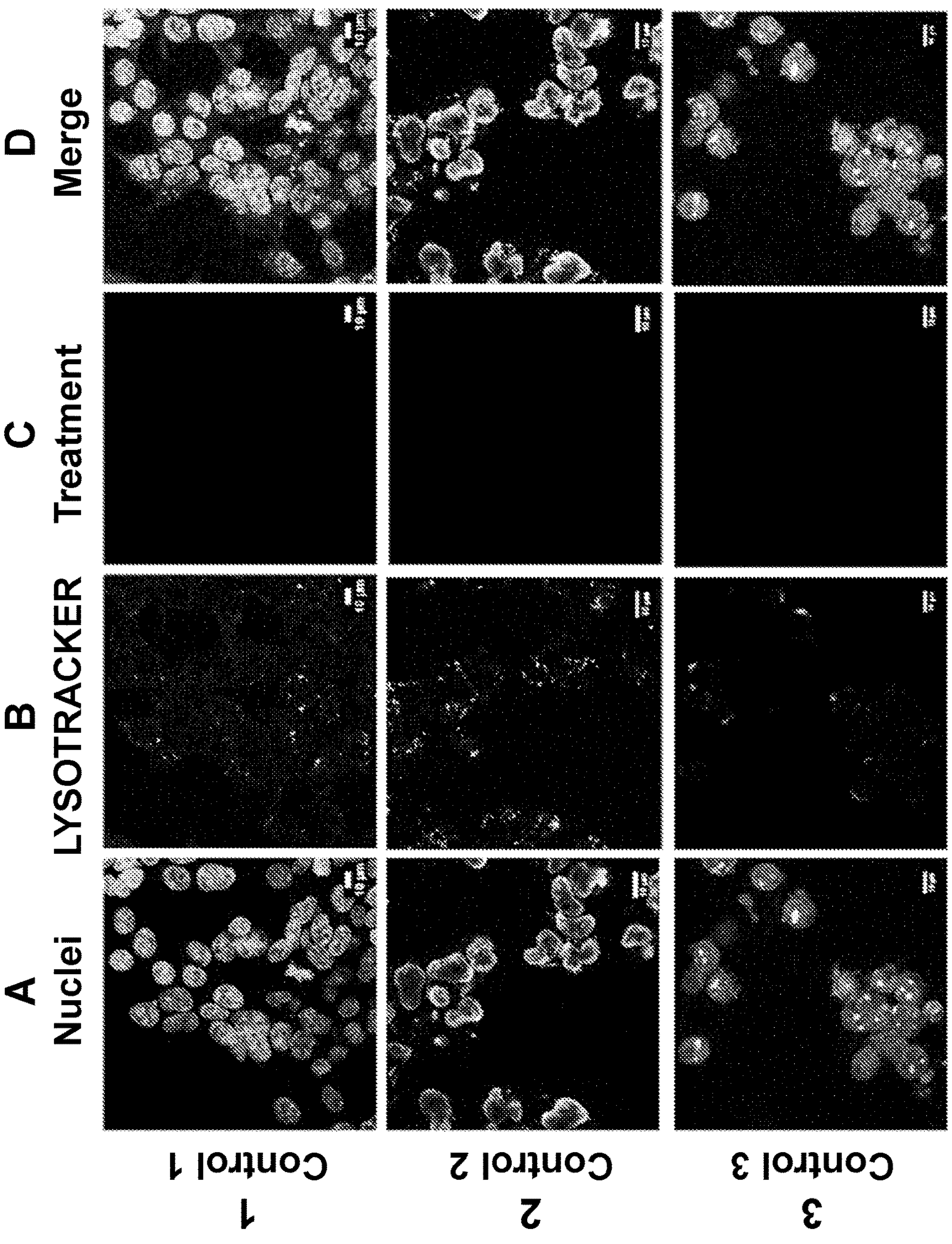
FIGS. 22A-22C: Confocal laser scanning microscopy images for colocalization with lysosomes in HEK 293 cells 48 h after treatment. Treatments are commercial fluorescent tracers (LUMAFLUOR RED and GREEN), Coumarin-NNT, Fluorescein-NNT, Rhodamine-NNT and Cy5.5-NNT. The nuclei of HEK 293 cells were stained by DAPI (blue) for control 1, control 2, LUMAFLUOR RED and GREEN, Fluorescein-NNT, Rhodamine-NNT and Cy5.5-NNT; propidium iodide for control 3 and Coumarin-NNT. Lysosomes were stained by LYSOTRACKER GREEN DND-26 for control 1, control 3, LUMAFLUOR RED, Coumarin-NNT, Rhodamine-NNT and Cy5.5-NNT; by LYSOTRACKER RED DND-99 for control 2, LUMAFLUOR GREEN, and Fluorescein-NNT. Colocalization is shown in orange (RED and GREEN) or white (magenta and green). HEK 293 cells were cultured for 24 h and then incubated with commercial fluorescent tracer or NNTs for 20 min. All scale bars in FIGS. 22A and 22C=10 μm.
Figure 22B:
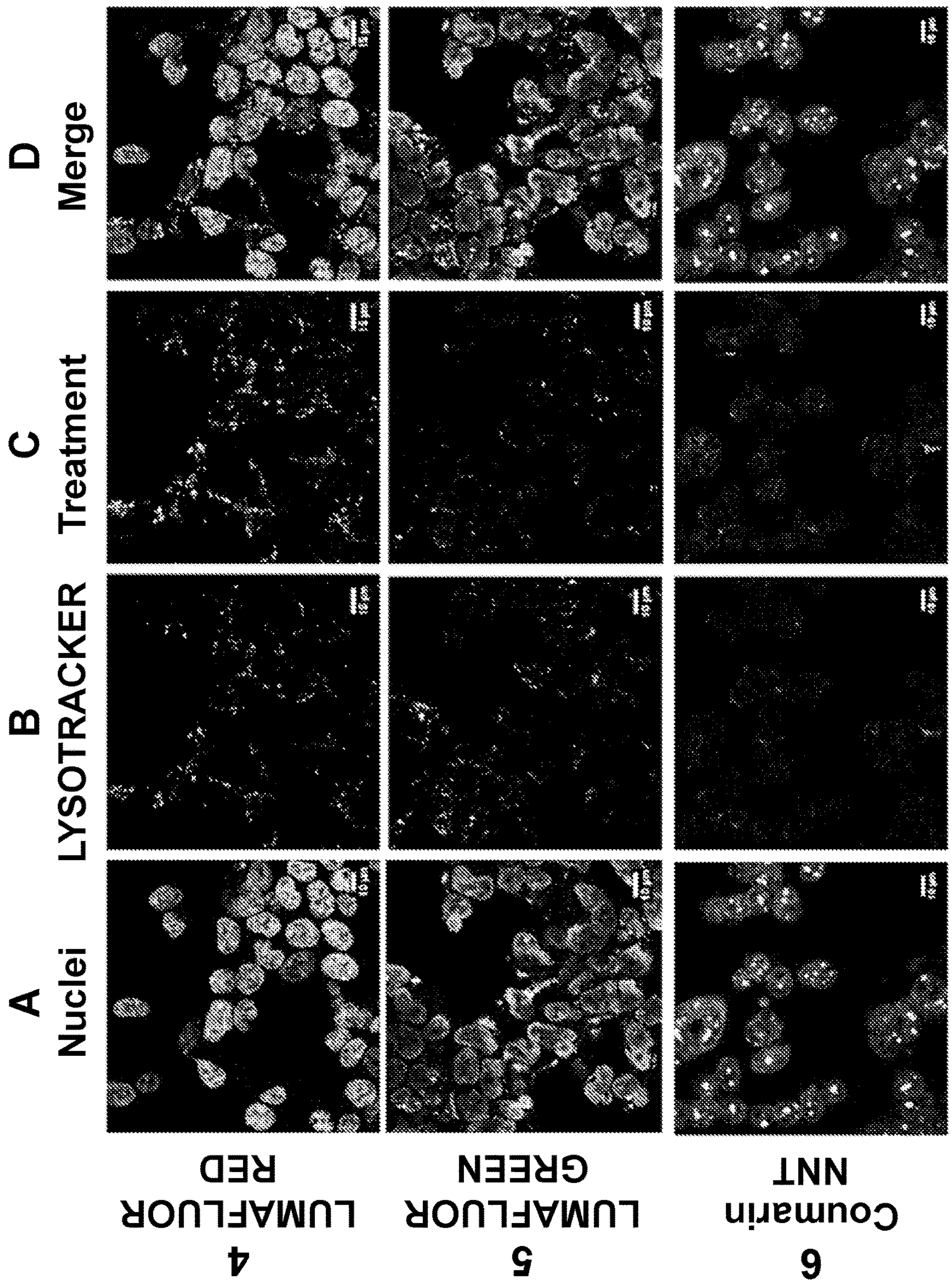
Figure 22C:
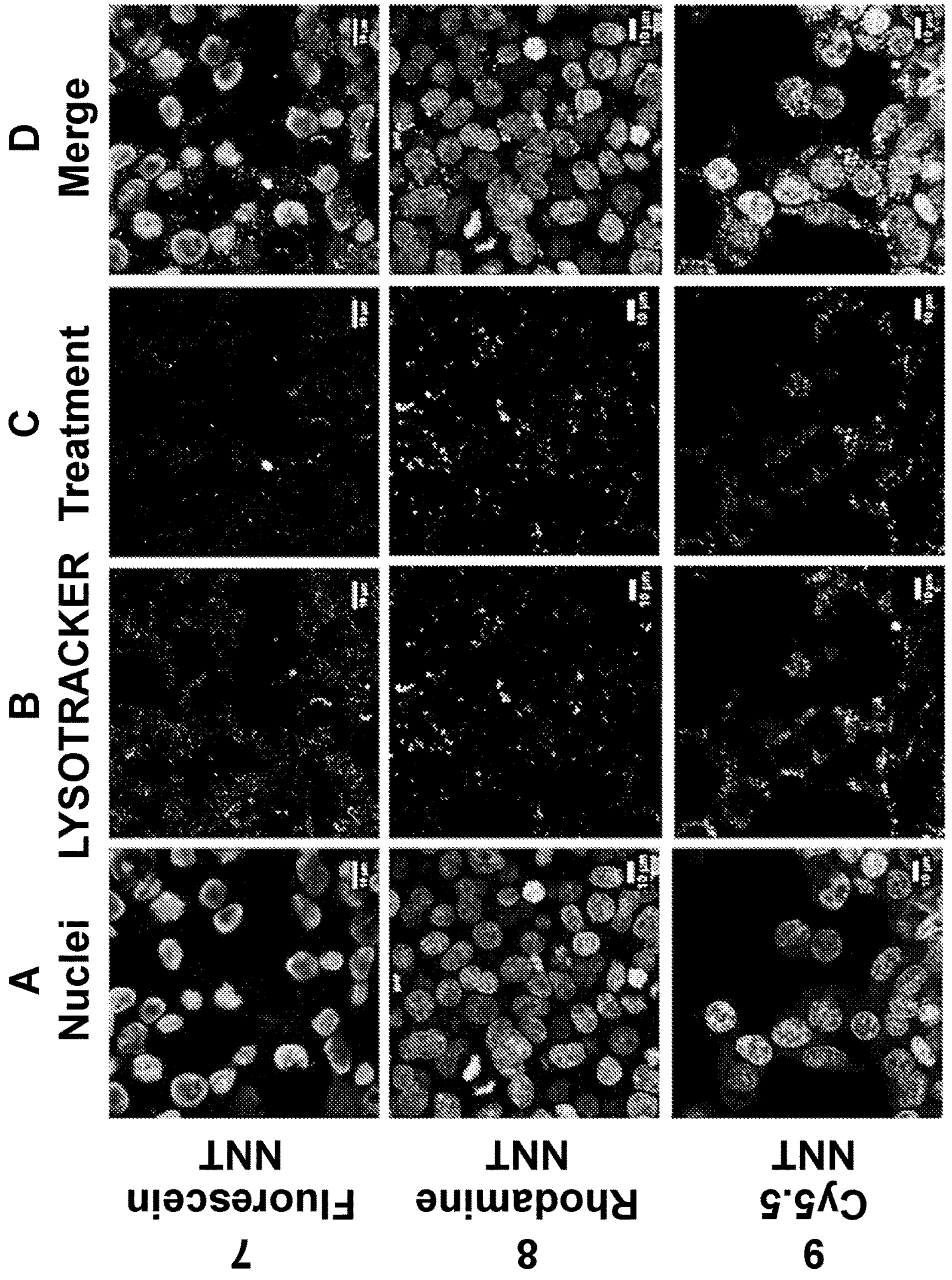

In addition, the cellular uptake of all NNTs and both commercial fluorescent tracers were assessed. Cells were incubated with nanoparticles for 20 minutes, washed with DPBS, and then incubated in media for 1 h (FIG. 16) or 24 h (FIGS. 2A-2D and FIG. 17) prior to fixation and confocal imaging. The mean fluorescence intensity (MFI) of all materials increased as a function of time, and at 24 h, the MFI of the Rhodamine-NNT and the Fluorescein-NNT was significantly greater than that of the LUMAFLUOR RED and LUMAFLUOR GREEN, respectively (FIG. 2A). Representative confocal microscopy images are shown in FIGS. 2B-2D. Unpaired t-test shows that there is no significant different in uptake between each NNT from one another (FIG. 18).

Figure 3C:
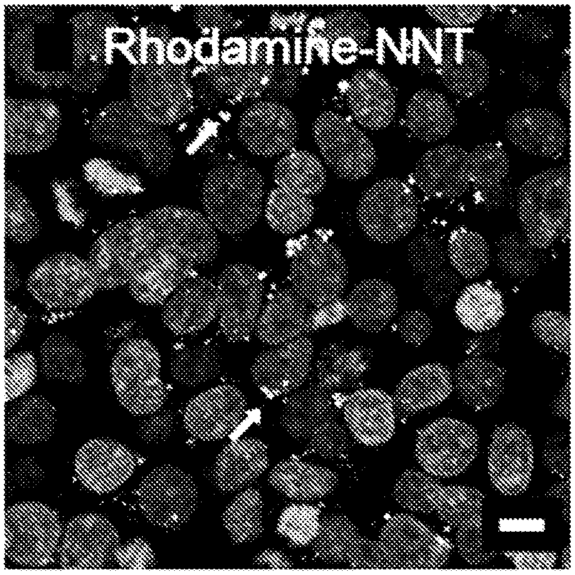
Figure 3D:
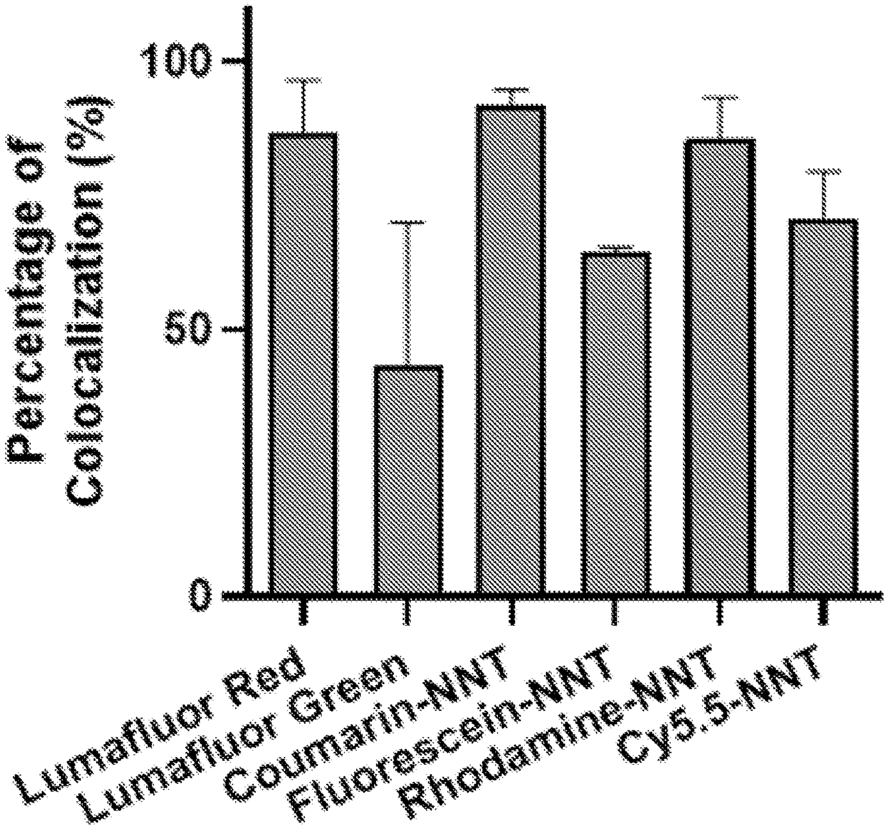
Figure 3E:
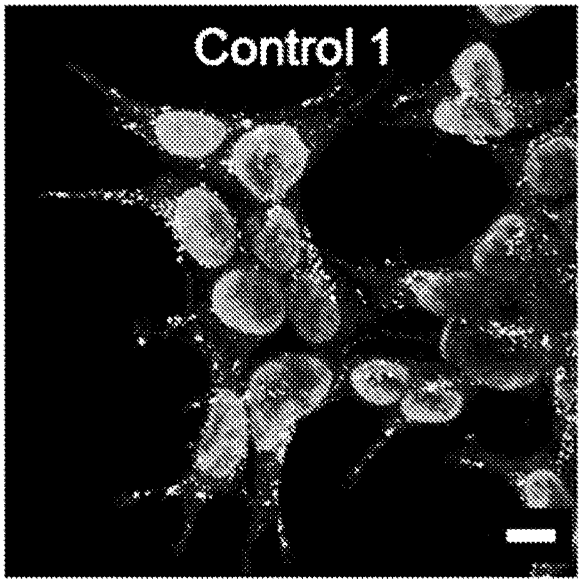
Figure 3F:
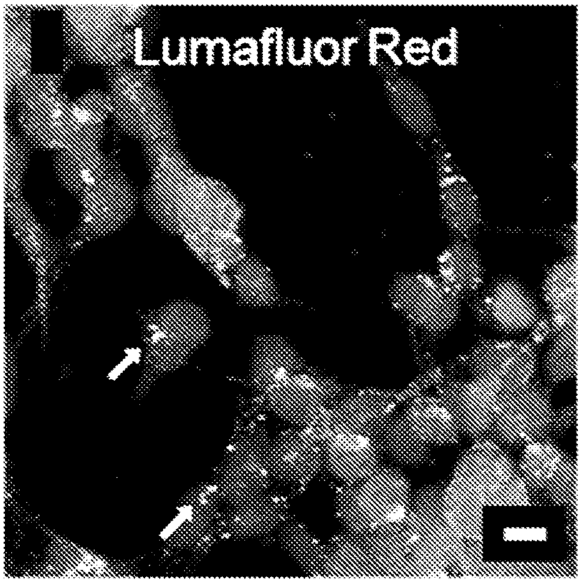
Figure 3G:
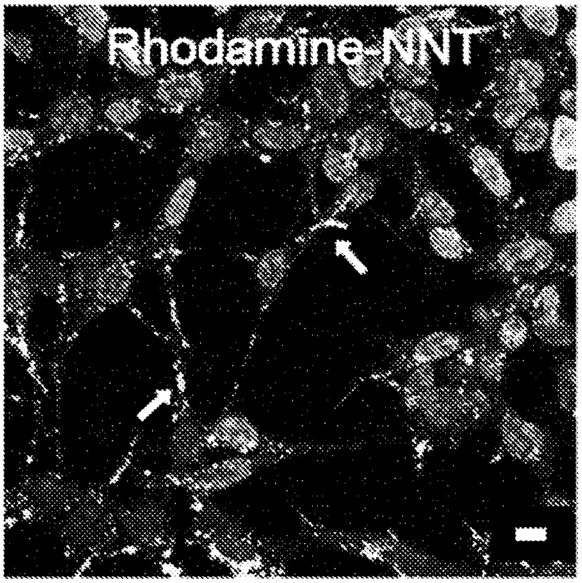
Figure 29:
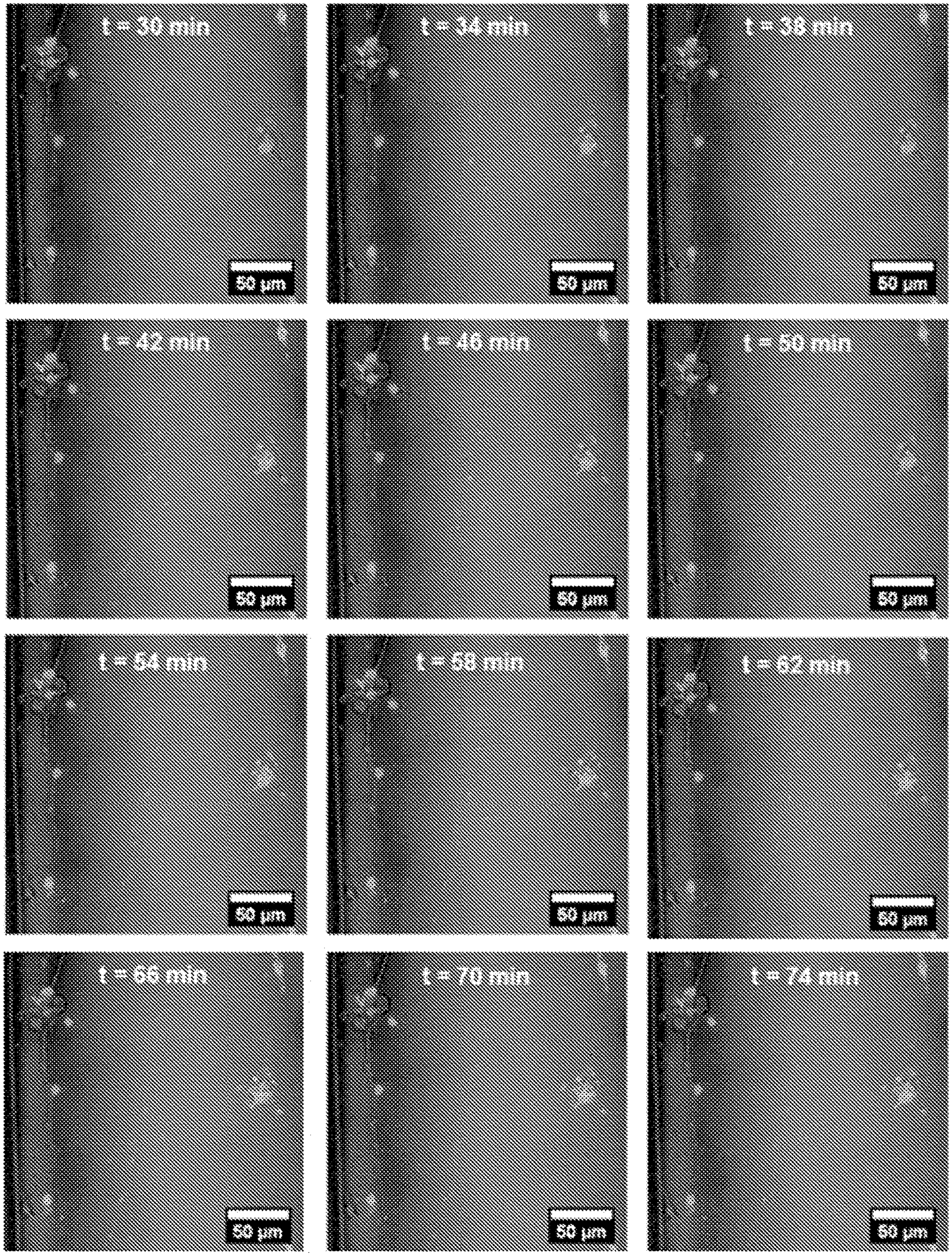
FIG. 29: Time-lapse series of live cell confocal microscopy images of Fluorescein-NNT from 30 min to 74 min after the treatment in primary rat cortex neurons. The nuclei of primary rat cortex neurons were stained by Hoechst. Lysosomes were stained by LYSOTRACKER RED DND-99. Colocalization is shown in orange (RED and GREEN). Primary rat cortex neurons were cultured for 30 days and then incubated with Fluorescein-NNT for 20 min. Z-stack images were taken every 4 min. All scale bars=50 μm.
Figure 30:
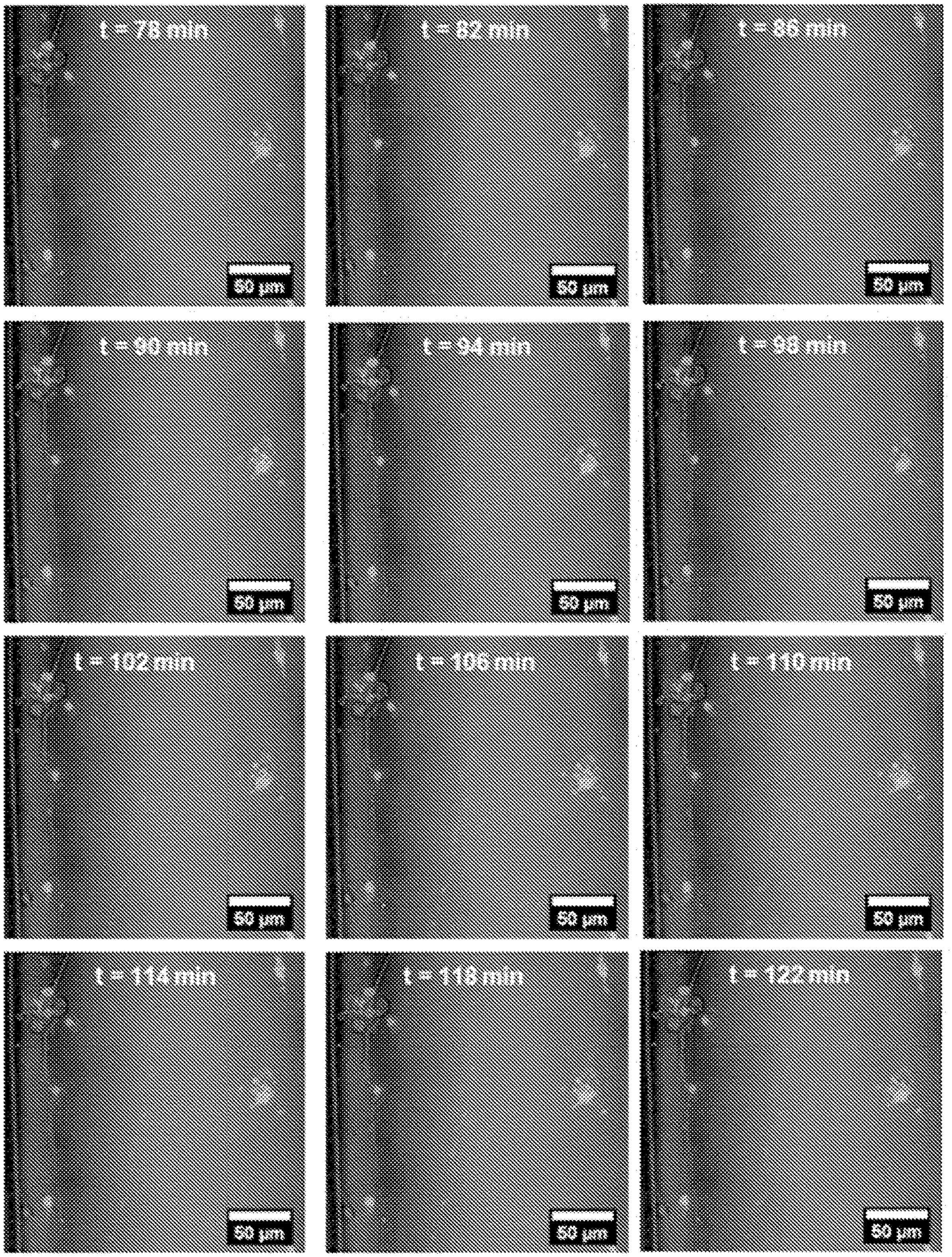
FIG. 30: Time-lapse series of live cell confocal microscopy images of Fluorescein-NNT from 78 min to 122 min after the treatment in primary rat cortex neurons. The nuclei of primary rat cortex neurons were stained by Hoechst. Lysosomes were stained by LYSOTRACKER RED DND-99. Colocalization is shown in orange (RED and GREEN). Primary rat cortex neurons were cultured for 30 days and then incubated with Fluorescein-NNT for 20 min. Z-stack images were taken every 4 min. All scale bars=50 μm.
Figure 31:
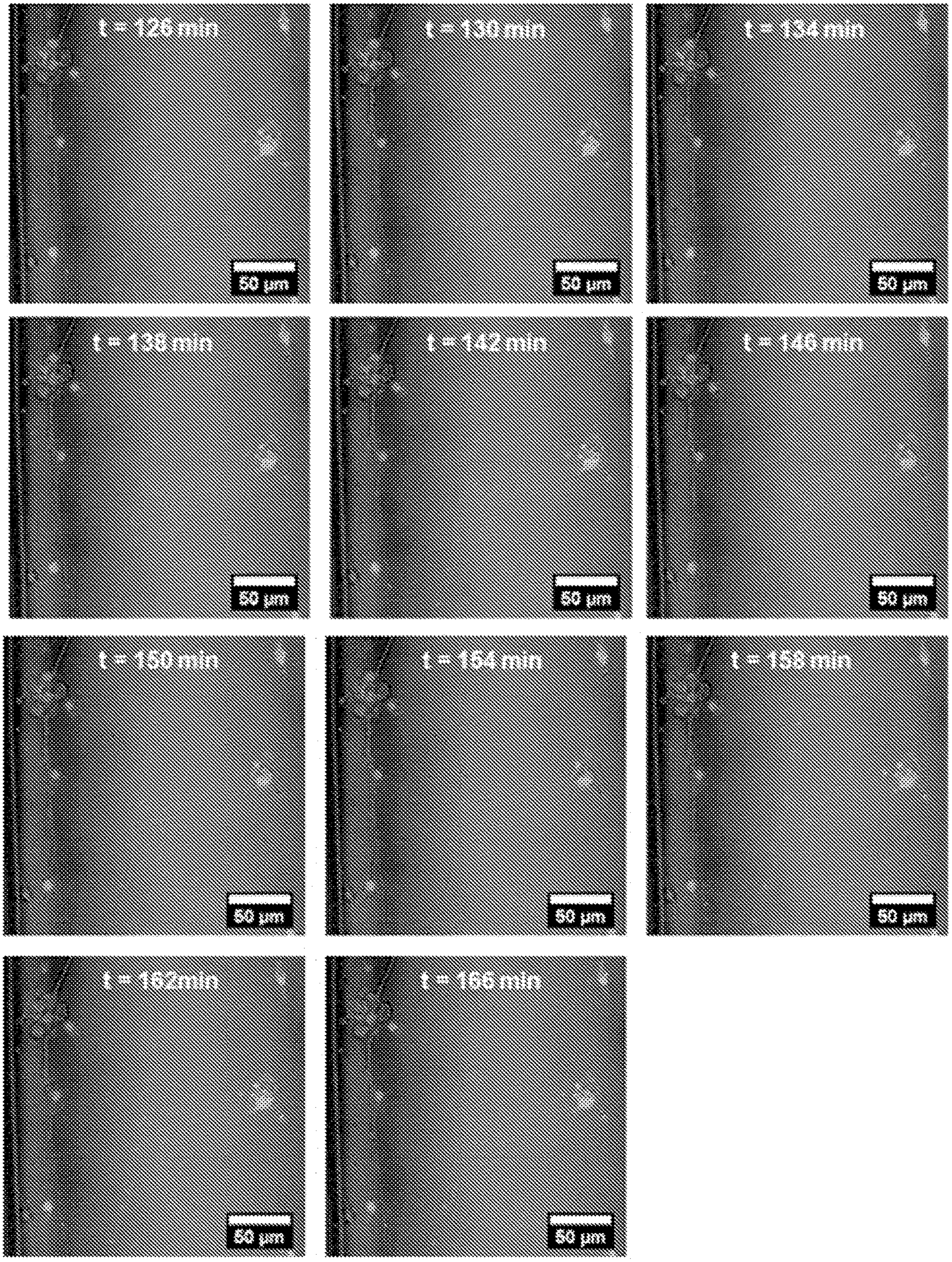
FIG. 31: Time-lapse series of live cell confocal microscopy images of Fluorescein-NNT from 126 min to 166 min after the treatment in primary rat cortex neurons. The nuclei of primary rat cortex neurons were stained by Hoechst. Lysosomes were stained by LYSOTRACKER RED DND-99. Colocalization is shown in orange (RED and GREEN). Primary rat cortex neurons were cultured for 30 days and then incubated with Fluorescein-NNT for 20 min. Z-stack images were taken every 4 min. All scale bars=50 μm.
Figure 32:
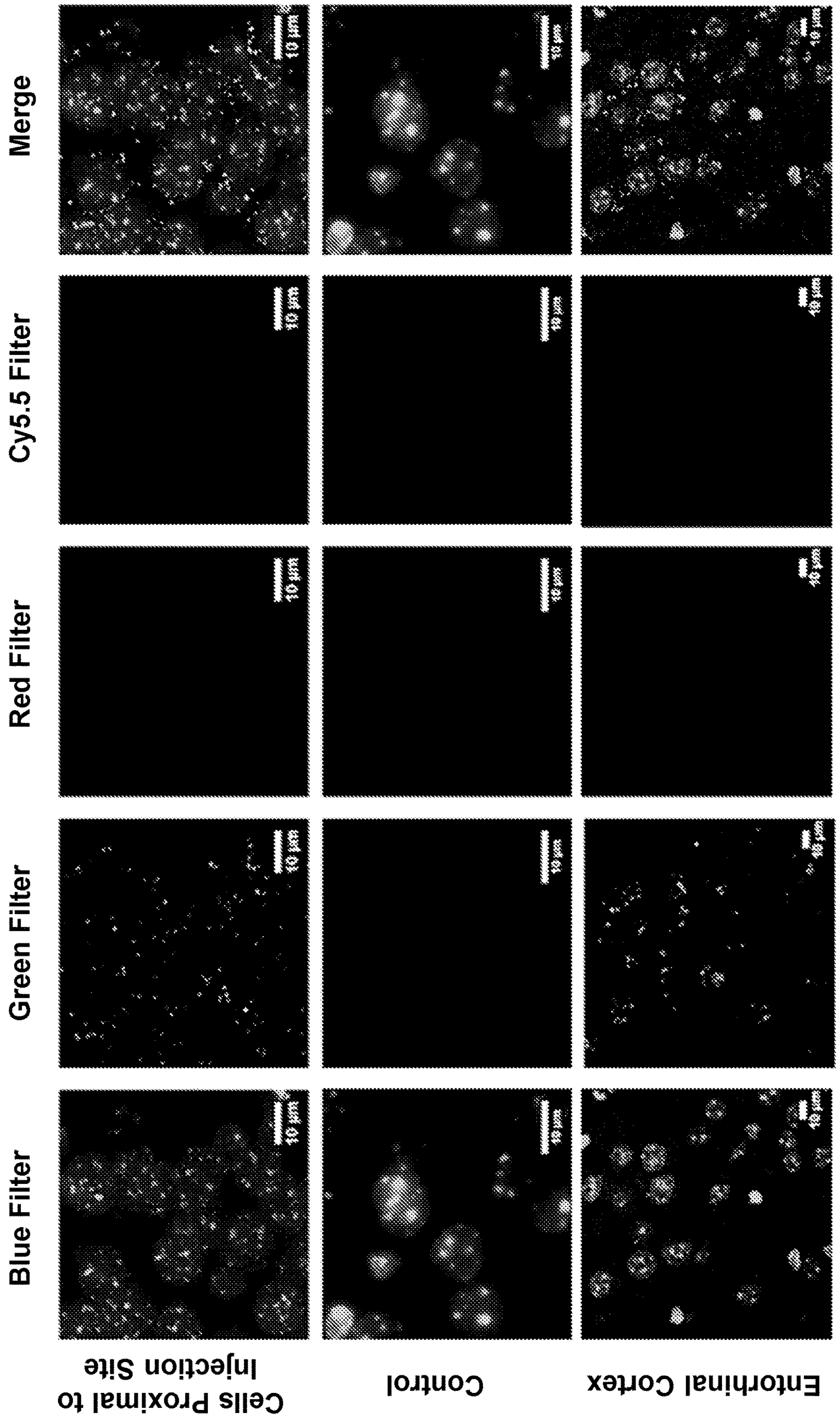
FIG. 32: All channels, corresponding to FIGS. 5C, 5D and 5G. All scale bars=10 μm.

The uptake mechanism and clearance pathways were then explored by evaluating colocalization of nanoparticles with lysosome and autophagosome (FIGS. 3A-3H and FIGS. 19-28) markers (LYSOTRACKER and microtubule-associated proteins 1A/1B light chain 3B (LC3) antibody, respectively) at 1, 4, 24, and 48 h following a 20 min incubation of nanoparticles with cells. Representative confocal microscopy images are shown in FIGS. 3A-3C and FIGS. 3E-3G. All NNTs colocalize with the lysosome marker (FIG. 3D), suggesting endocytosis as an entrance mechanism. Interestingly, Coumarin-NNT exhibits greater colocalization with autophagosomes compared to other NNTs (FIG. 3H), suggesting that the Coumarin-NNTs are being trafficked faster intracellularly. In addition, the neuronal uptake of Fluorescein-NNT was confirmed using confocal microscopy following incubation with primary rat neurons in vitro, observed in a time dependent manner (FIG. 4). In these experiments the neurons were treated with particles, washed, and then observed over 136 min, with imaging every 4 min (for full time-lapse series see FIGS. 29-31).

Figure 5G:
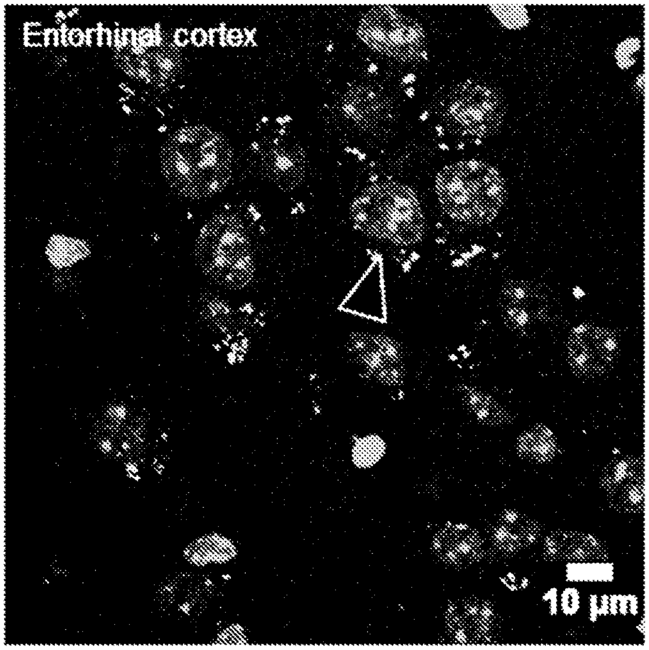

Fluorescein-NNT for Tracing: Entorhinal Cortex (EC) to CA1 Pathway. The major cortical input to the hippocampus is from the projection of entorhinal cortex (EC) (Li et al., Nature Neuroscience, 20, 559 (2017)). The temporoammonic path to CA1 (pp-CA1) synapse refers that the EC neurons directly connect to the CA1 area (Witter et al., Neuroscience Letters, 85, 193-198 (1988)). Therefore, the EC to CA1 pathway was chosen for an in vivo study for testing NNTs (FIG. 11). If NNTs transport in a retrograde fashion, it is expected to observe them at the EC region after injection at CA1 in the hippocampus. Fluorescein-NNT was injected into CA1 in the hippocampus of C57BL/6J mice (FIG. 5A). After 2 days, the brain was fixed to investigate the labeling pattern. Fluorescence images of the sagittal sections of the brain confirm fluorescein fluorescence at the CA1 injection site (FIG. 5B) and in the neurons or neuropil proximal to the injection site (FIG. 5C). Further, we imaged two areas distant from CA1 to look for retrograde transport of Fluorescein-NNT. As a control, the somatosensory cortex was first imaged, a region known to lack strong projections to CA1. Indeed, we observed a lack of Fluorescein-NNT labeling in this region (FIG. 5D). However, in the EC, strong fluorescence was observed, indicating retrograde transport of Fluorescein-NNT along the EC to CA1 pathway, confirming the ability of Fluorescein-NNT to traverse along a known anatomical pathway (FIGS. 5E-5G and FIG. 32).

Figure 6A:
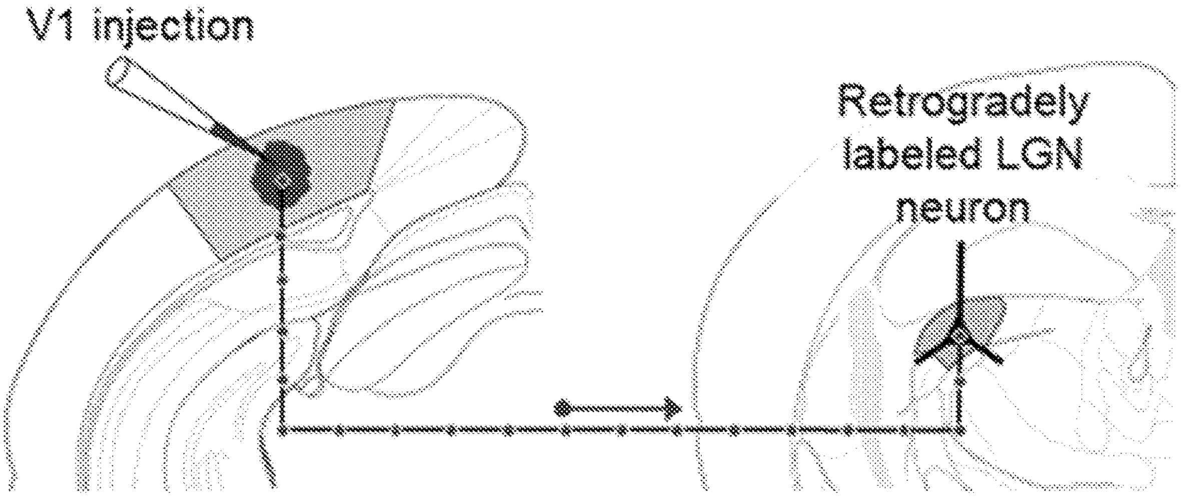
FIGS. 6A-6B: Retrograde transport of multi-color NNTs at 48 h post-injection.
Figure 6B:
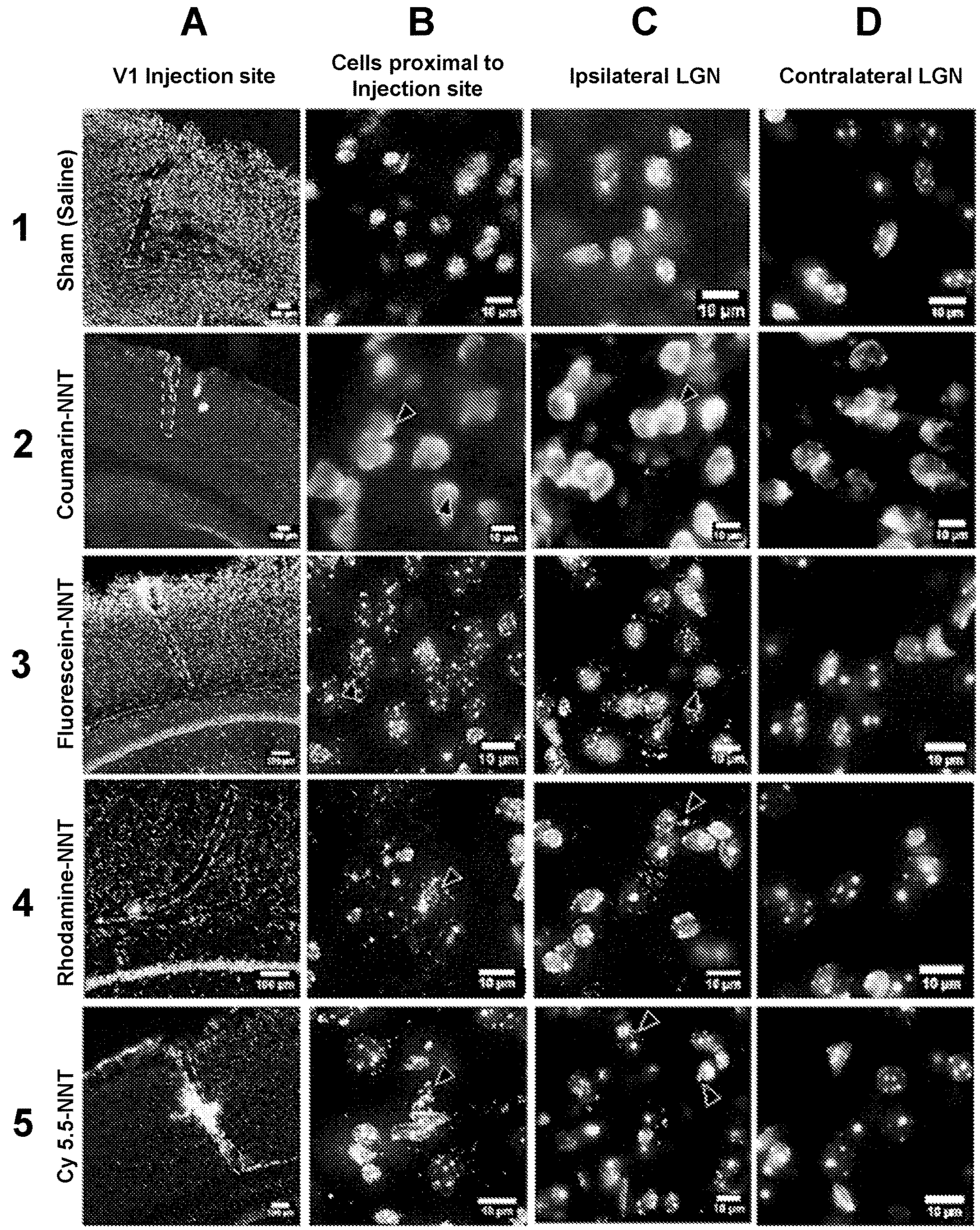
Figure 33:
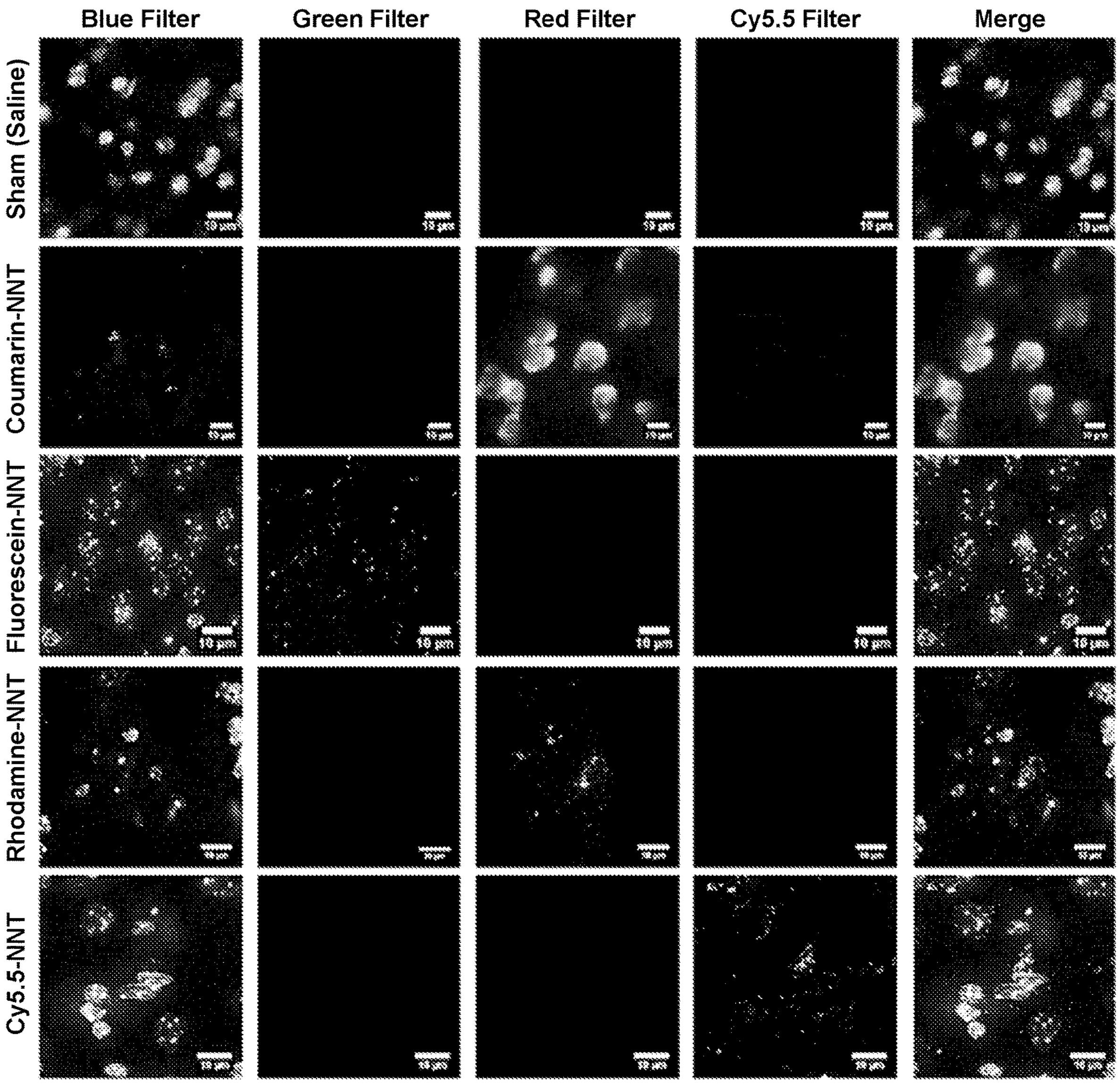
FIG. 33: All channels, corresponding to FIG. 6B, column B (Cell proximal to injection site). All scale bars=10 μm.
Figure 34:
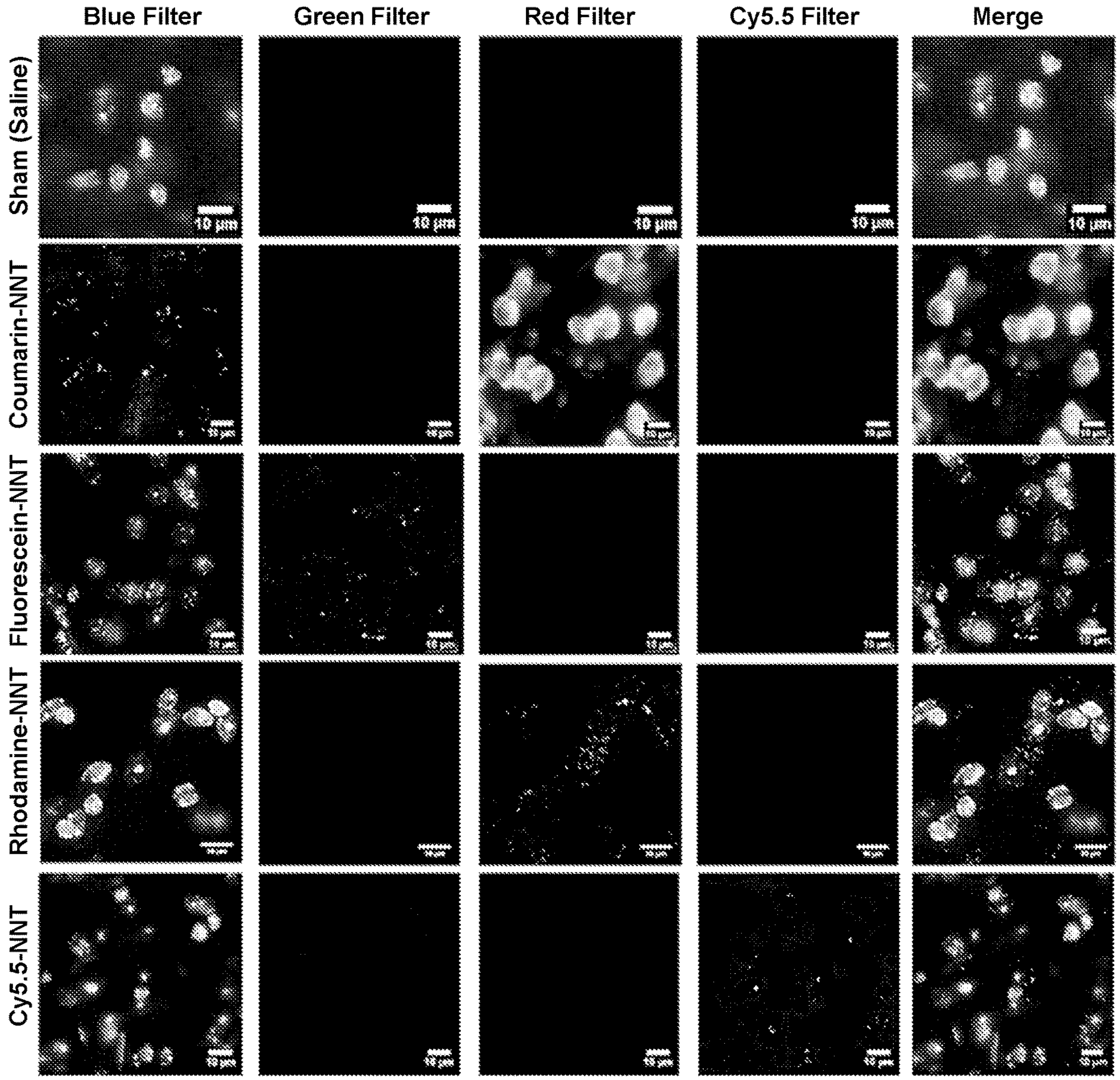
FIG. 34: All channels, corresponding to FIG. 6B, column C (Ipsilateral LGN). All scale bars=10 μm.
Figure 35:
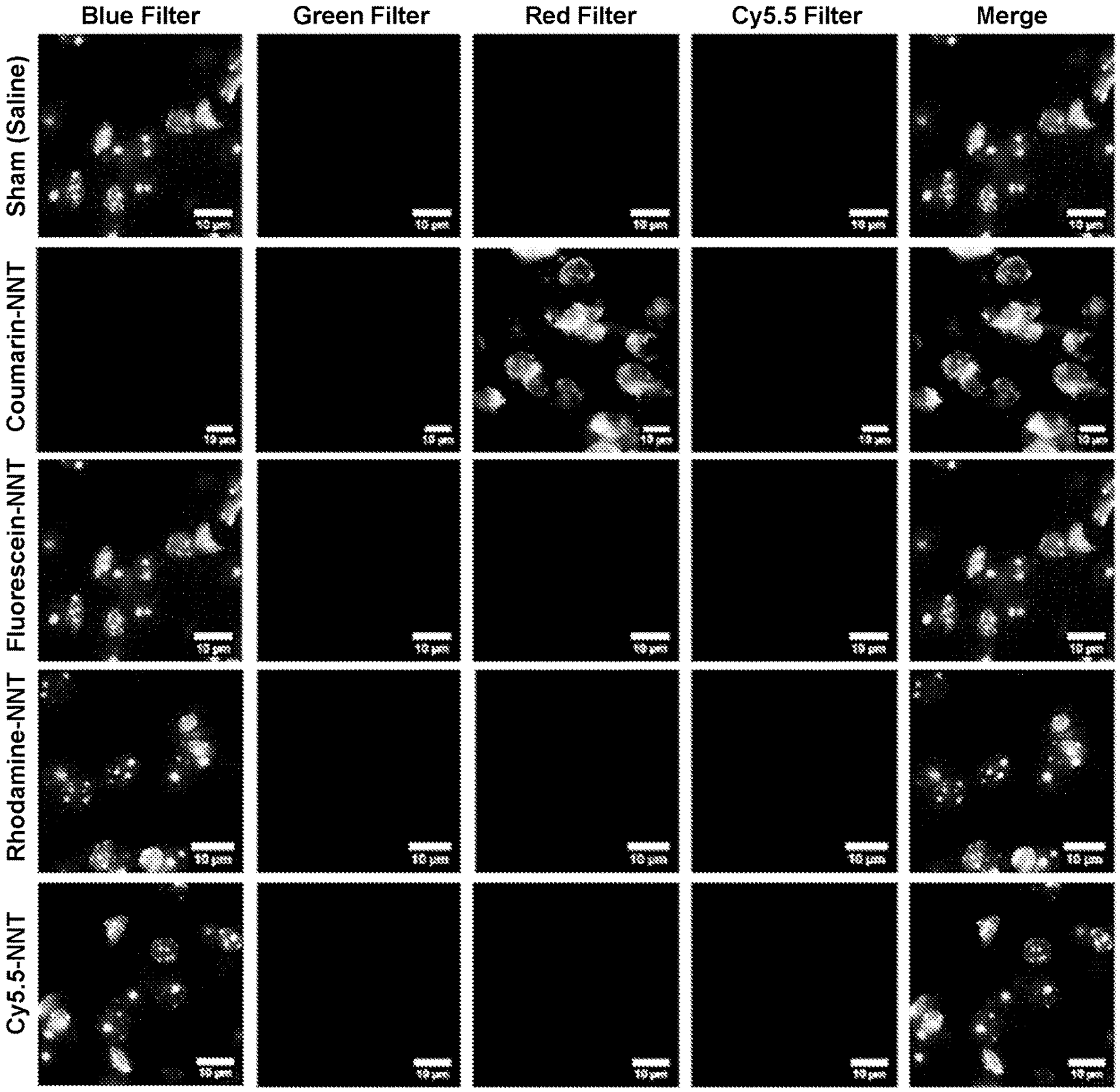
FIG. 35: All channels, corresponding to FIG. 6B, column D (Contralateral LGN). All scale bars=10 μm.
Figure 36:
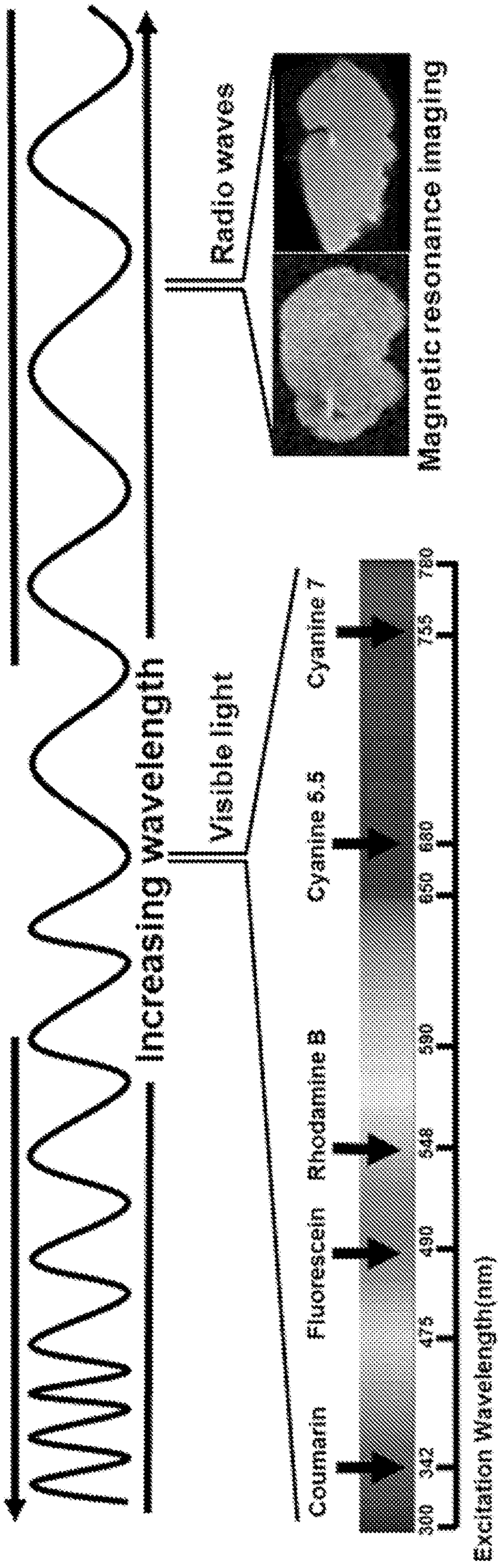
FIG. 36: Extended Multi-color Nano-tracers Spectrum to Radio Waves: Gd-based MRI Contrast Agents.

NNTs for tracing: lateral geniculate nucleus (LGN) to primary visual cortex (V1) pathway. The dorsolateral geniculate nucleus (LGN) projects to the primary visual cortex (V1) (Riddle et al., Nature, 378, 189 (1995)). The hypothesis is that if NNTs are transported in a retrograde fashion, fluorescence from NNTs will be observed at LGN after V1 injection. Each color of the NNTs was directly injected into a mouse V1 (FIGS. 6A-6B). Saline injection was used as a negative control. 48 h after injection the mouse brains were perfused, dissected, and sliced in the coronal plane. The results were analyzed by ex vivo fluorescence microscopy confirming (FIG. 6A) that NNTs were injected into the V1 region (FIG. 6B). In addition, the cells or neuropil proximal to the injection site were labeled by NNTs, indicating an active uptake process, rather than passive diffusion through the disruption of cell membranes by the injection needle (FIG. 6B, left two columns). Further, irrespective of the type of NNT, the particles underwent retrograde transport to the LGN area (FIG. 6B, third column). No labeling of the contralateral LGN area was observed (FIG. 6B, fourth column), consistent with weaker projections of LGN to contralateral V1. Importantly, no crosstalk between the channels for NNTs was observed (FIGS. 33-35). For the saline control, we observed no fluorescence labeling in any part of the brain (FIG. 6B, top row). These results confirm the multi-color NNTs transport in a retrograde fashion.

DISCUSSION

Four novel dye-labeled NNTs were developed, which expand the current color palette of fluorescent neuronal tracers while remaining functionally similar to each other. The physical and chemical properties of these NNTs were evaluated by electron microscopy and additional analytical methods (FIGS. 1A-1D). Since the commercial fluorescent tracers (LUMAFLUOR GREEN and RED) have fluorescence spectra similar to Fluorescein-NNT and Rhodamine-NNT, each set of novel NNT and commercial analogue were directly compared. Fluorescence intensity is a crucial property in subsequent biological studies; thus, the polymerization conditions of each NNT were optimized and matched to one another.

With a lack of data available in the literature, a detailed cytotoxicity and cellular uptake study of the commercial fluorescent tracers, LUMAFLUOR GREEN and RED was conducted. The initial studies focused on revealing those properties and comparing them with the novel NNTs. Cell viability was assessed, as a guideline for further in vivo analyses. The tested concentration range was chosen based on the hypothetical dilution of the nanoparticles by the brain extracellular matrix following intracranial injection. Due to the inaccessibility and required quantity of primary neurons, HEK 293 was employed as the model cell line for in vitro evaluation, as it originates from the same precursor cell line as neurons (Lin et al., Nature Communications, 5, 4767 (2014)).

Figure 23:
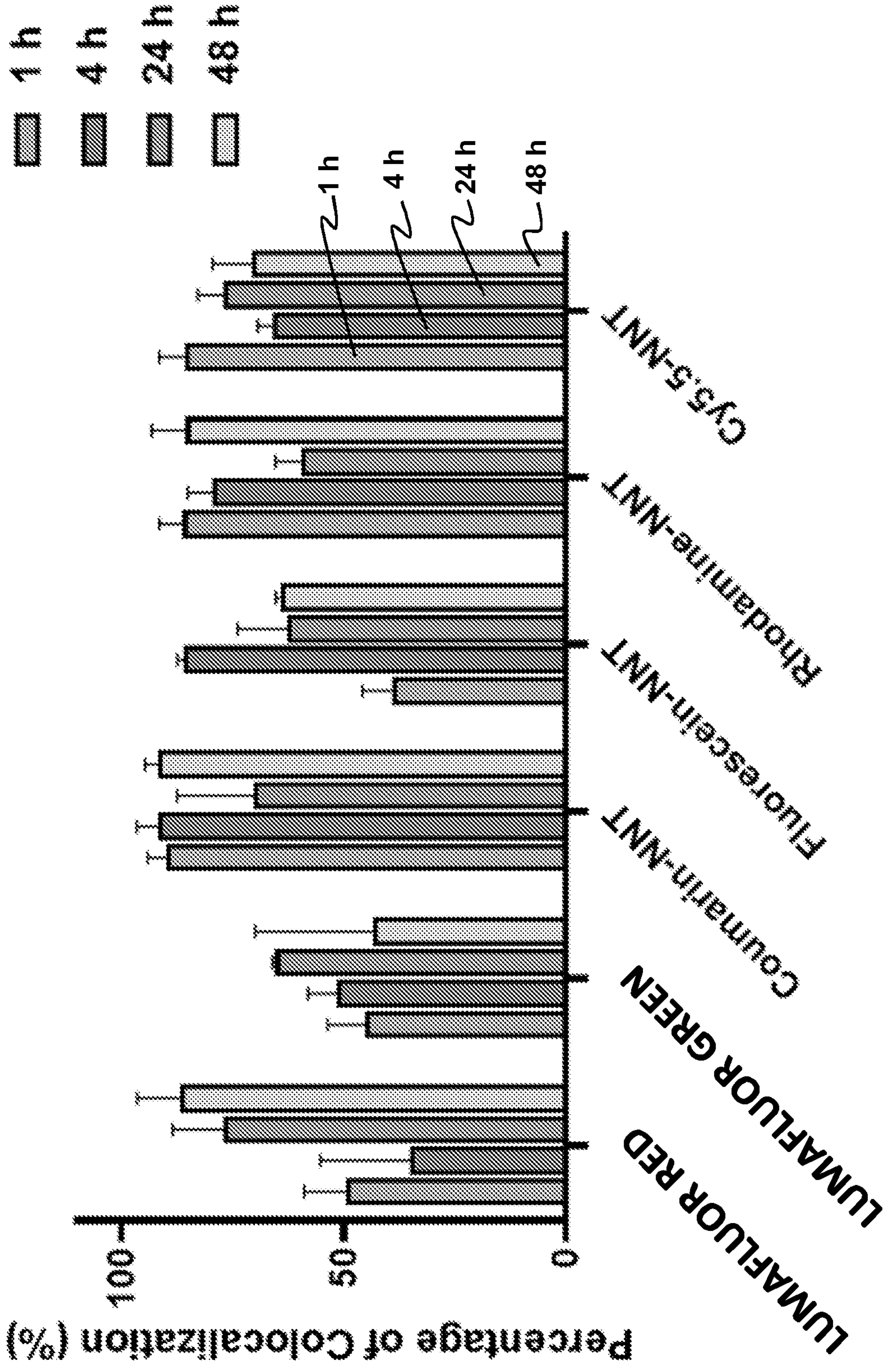
FIG. 23: Percentage of lysosomes colocalization of commercial fluorescent tracers and 4 NNTs at 1 h, 4 h, 24 h and 48 h quantified by confocal laser scanning microscopy images. Data is presented as mean±SD (n=3).
Figure 24A:
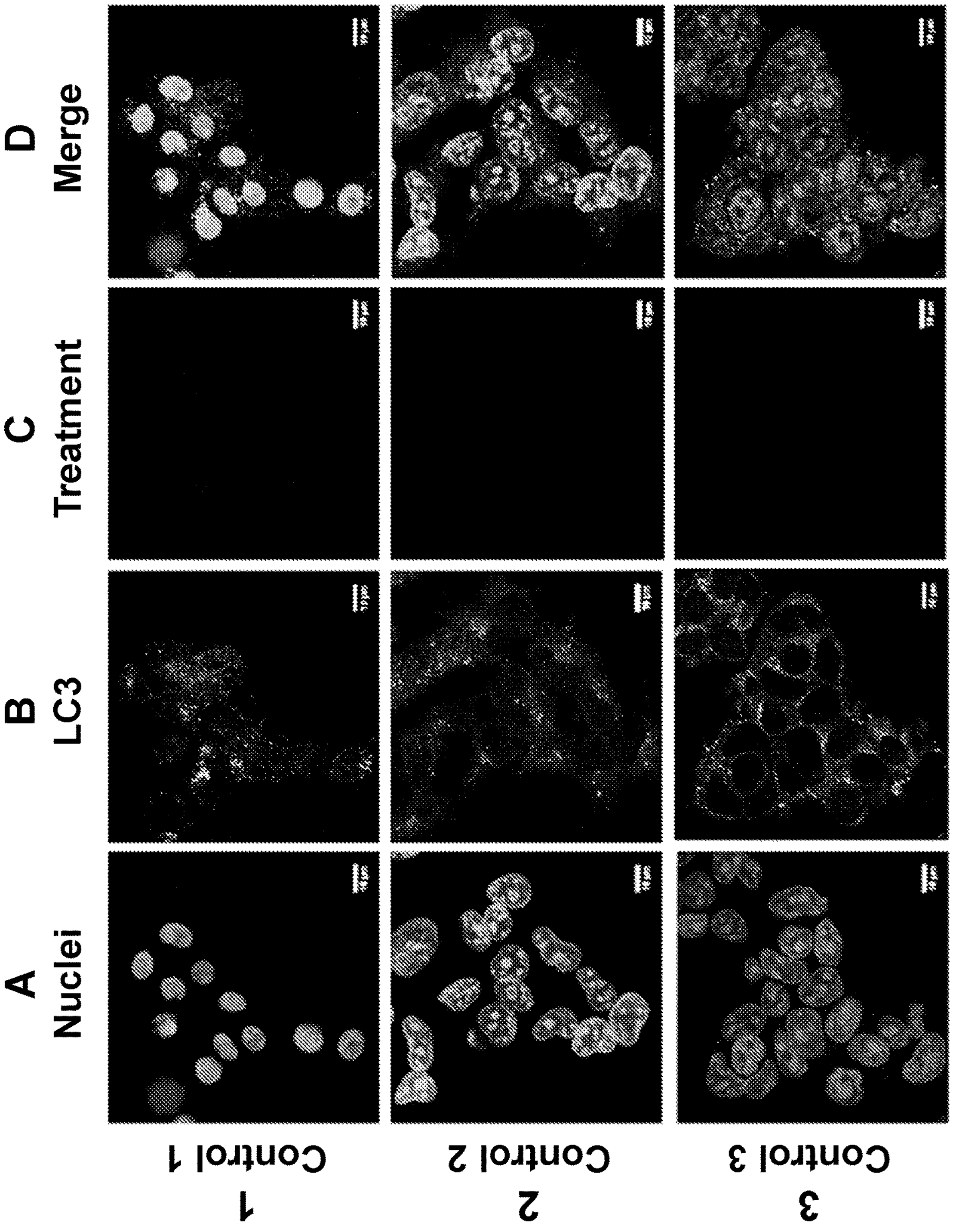
FIGS. 24A-24C: The colocalization assay of autophagosomes for 1 h treatment by confocal laser scanning microscopy in HEK 293 cells. Treatments are DMEM media for control 1, 2 and 3, commercial fluorescent tracers (LUMAFLUOR RED and GREEN), Coumarin-NNT, Fluorescein-NNT, Rhodamine-NNT and Cy5.5-NNT. The nuclei of HEK 293 cells were stained by DAPI (blue) for control 1, control 2, LUMAFLUOR RED and GREEN, Fluorescein-NNT, Rhodamine-NNT and Cy5.5-NNT; propidium iodide for control 3 and Coumarin-NNT. Autophagosomes were immunostained by LC3 antibody, with Anti-rabbit IgG (H+L), F(ab')2 Fragment conjugated with ALEXA FLUOR 488 for control 1, control 3, LUMAFLUOR RED, Coumarin-NNT, Rhodamine-NNT and Cy5.5-NNT, or ALEXA FLUOR 555 for control 2, LUMAFLUOR GREEN, and Fluorescein-NNT; Colocalization is shown in orange or white. HEK 293 cells were cultured for 24 h and then incubated with LUMAFLUOR RED or Rhodamine-NNT for 20 min. The images were taken 1 h after treatment. All scale bars in FIGS. 24A-24C=10 μm.
Figure 24B:
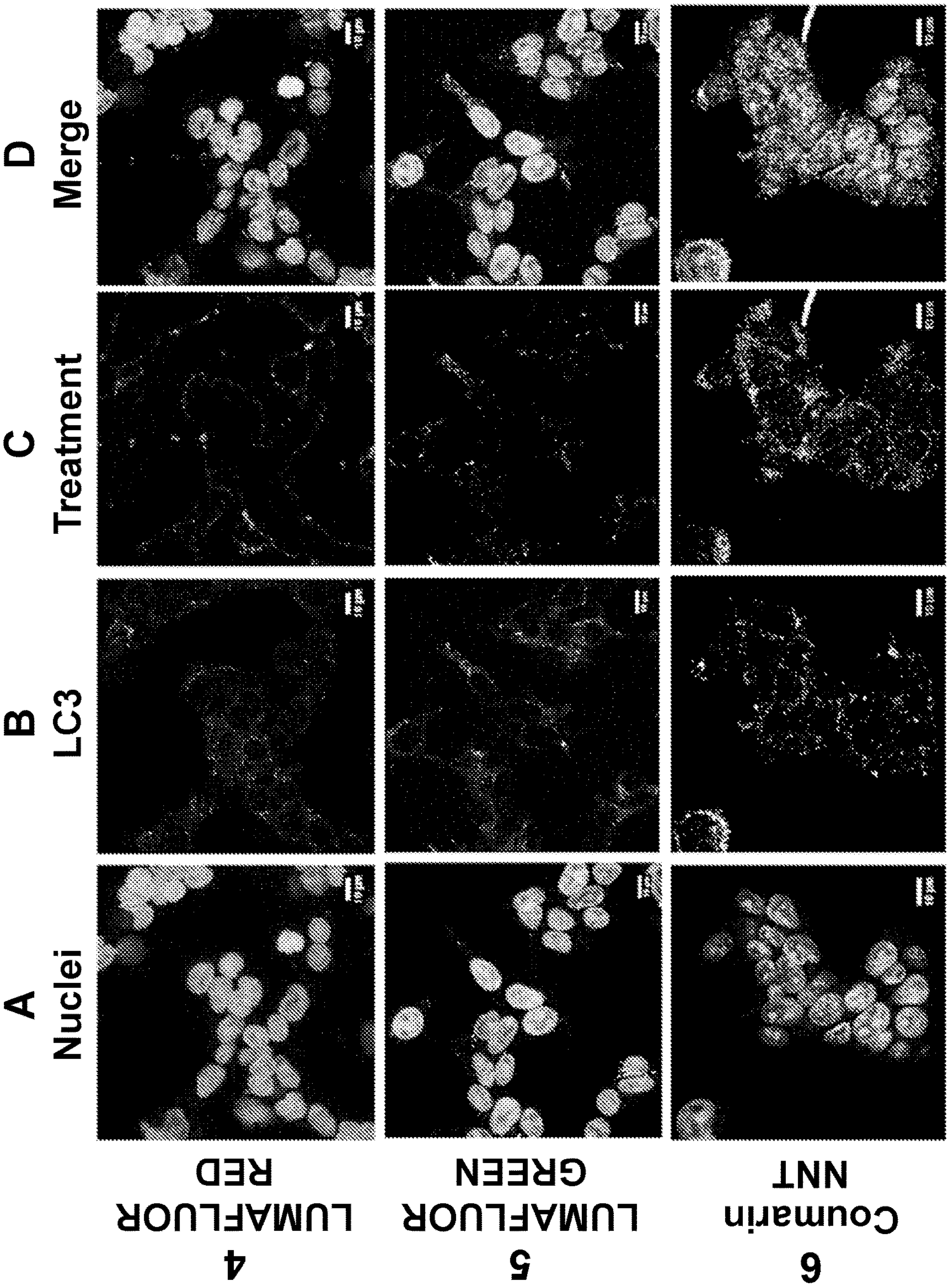
Figure 24C:
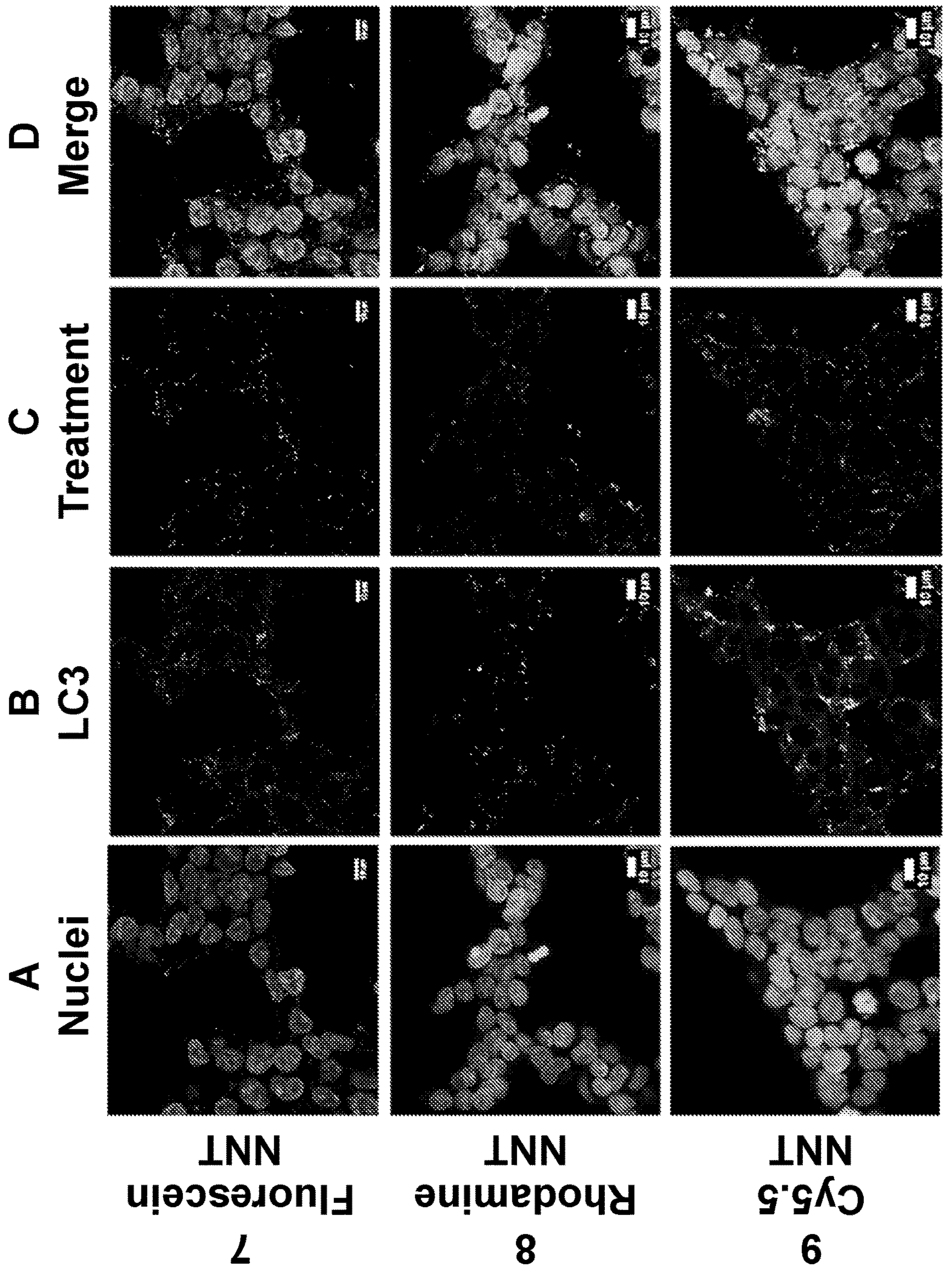
Figure 25A:
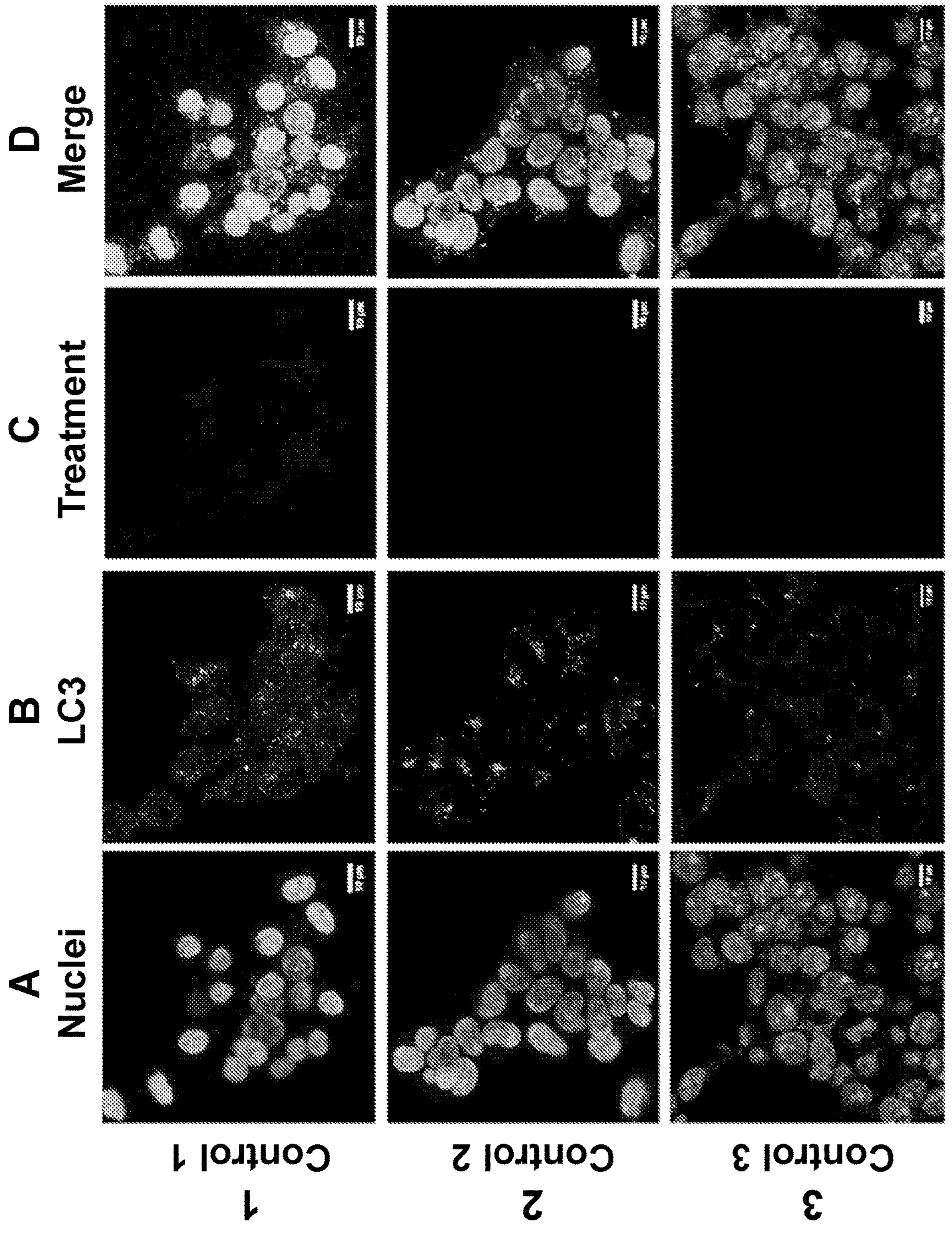
FIGS. 25A-25C: The colocalization assay of autophagosomes for 4 h treatment by confocal laser scanning microscopy in HEK 293 cells. Treatments are DMEM media for control 1, 2 and 3, commercial fluorescent tracers (LUMAFLUOR RED and GREEN), Coumarin-NNT, Fluorescein-NNT, Rhodamine-NNT and Cy5.5-NNT. The nuclei of HEK 293 cells were stained by DAPI (blue) for control 1, control 2, LUMAFLUOR RED and GREEN, Fluorescein-NNT, Rhodamine-NNT and Cy5.5-NNT; propidium iodide for control 3 and Coumarin-NNT. Autophagosomes were immunostained by LC3 antibody, with Anti-rabbit IgG (H+L), F(ab')2 Fragment conjugated with ALEXA FLUOR 488 for control 1, control 3, LUMAFLUOR RED, Coumarin-NNT, Rhodamine-NNT and Cy5.5-NNT, or ALEXA FLUOR 555 for control 2, LUMAFLUOR GREEN, and Fluorescein-NNT; Colocalization is shown in orange or white. HEK 293 cells were cultured for 24 h and then incubated with LUMAFLUOR RED or Rhodamine-NNT for 20 min. The images were taken 4 h after treatment. All scale bars in FIGS. 25A-25C=10 μm.
Figure 25B:
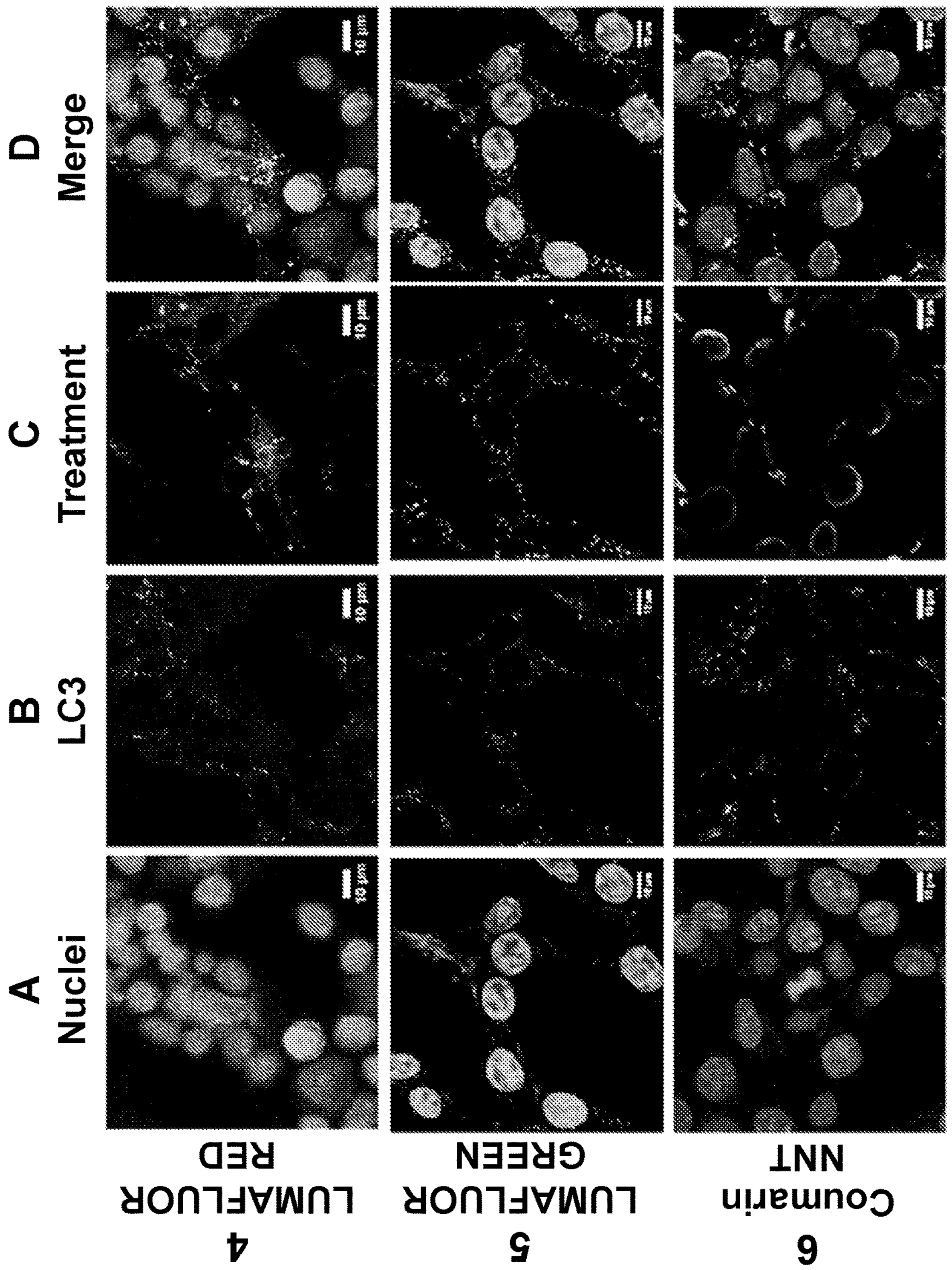
Figure 25C:
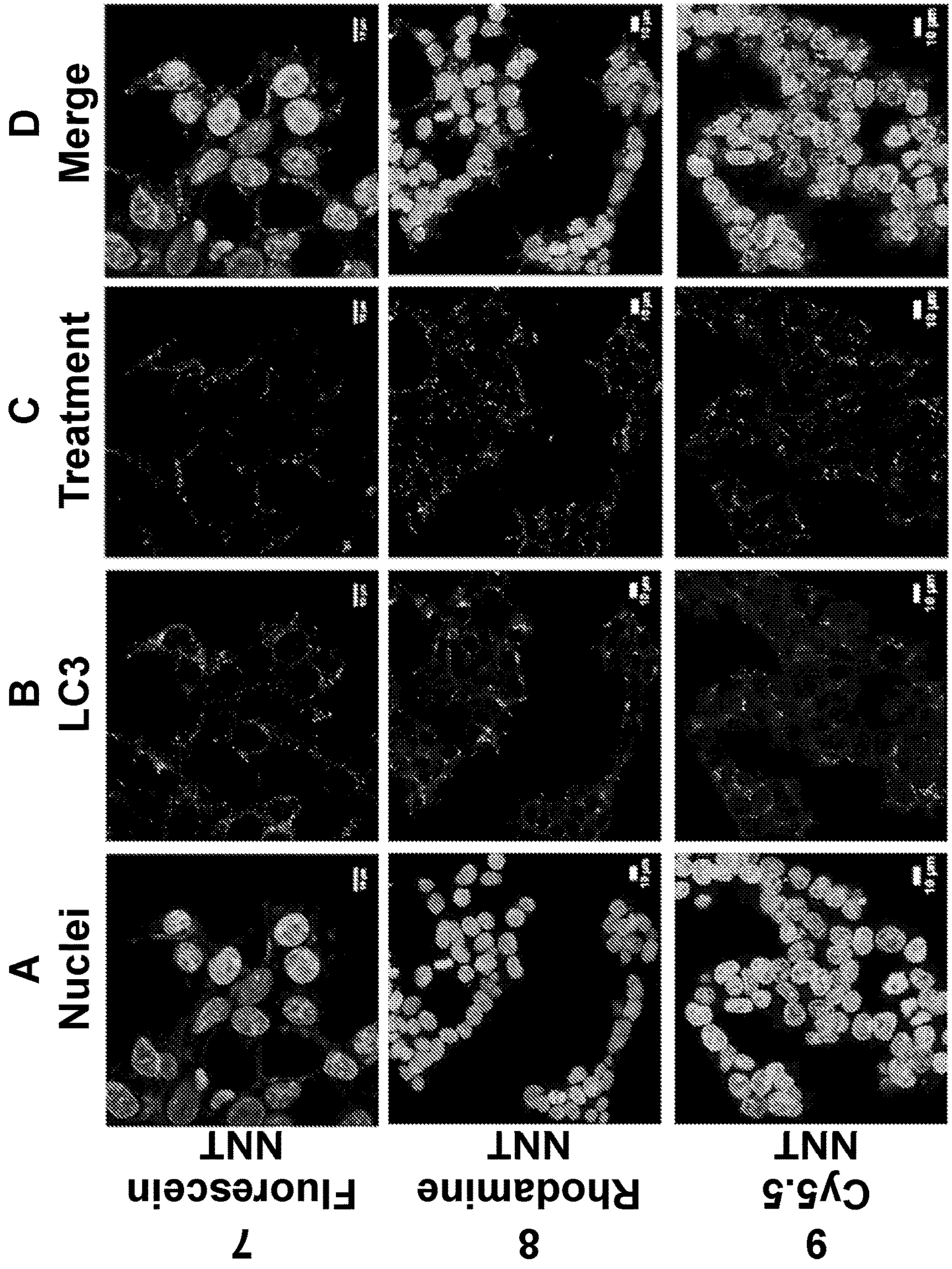
Figure 26A:
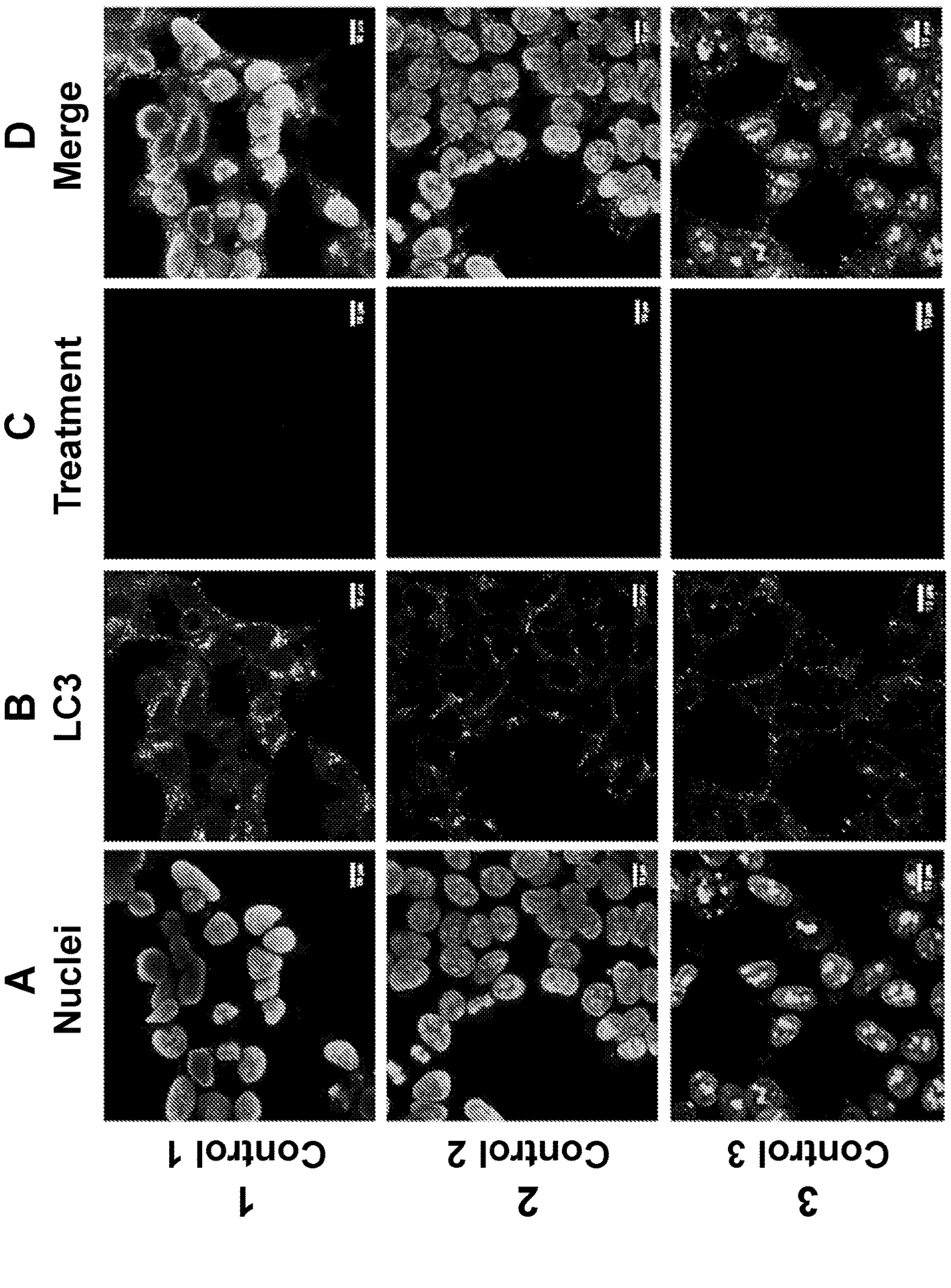
FIGS. 26A-26C: The colocalization assay of autophagosomes for 24 h treatment by confocal laser scanning microscopy in HEK 293 cells. Treatments are DMEM media for control 1, 2 and 3, commercial fluorescent tracers (LUMAFLUOR RED and GREEN), Coumarin-NNT, Fluorescein-NNT, Rhodamine-NNT and Cy5.5-NNT. The nuclei of HEK 293 cells were stained by DAPI (blue) for control 1, control 2, LUMAFLUOR RED and GREEN, Fluorescein-NNT, Rhodamine-NNT and Cy5.5-NNT; propidium iodide for control 3 and Coumarin-NNT. Autophagosomes were immunostained by LC3 antibody, with Anti-rabbit IgG (H+L), F(ab')2 Fragment conjugated with ALEXA FLUOR 488 for control 1, control 3, LUMAFLUOR RED, Coumarin-NNT, Rhodamine-NNT and Cy5.5-NNT, or ALEXA FLUOR 555 for control 2, LUMAFLUOR GREEN, and Fluorescein-NNT; Colocalization is shown in orange or white. HEK 293 cells were cultured for 24 h and then incubated with LUMAFLUOR RED or Rhodamine-NNT for 20 min. The images were taken 24 h after treatment. All scale bars in FIGS. 26A-26C=10 μm.
Figure 26B:
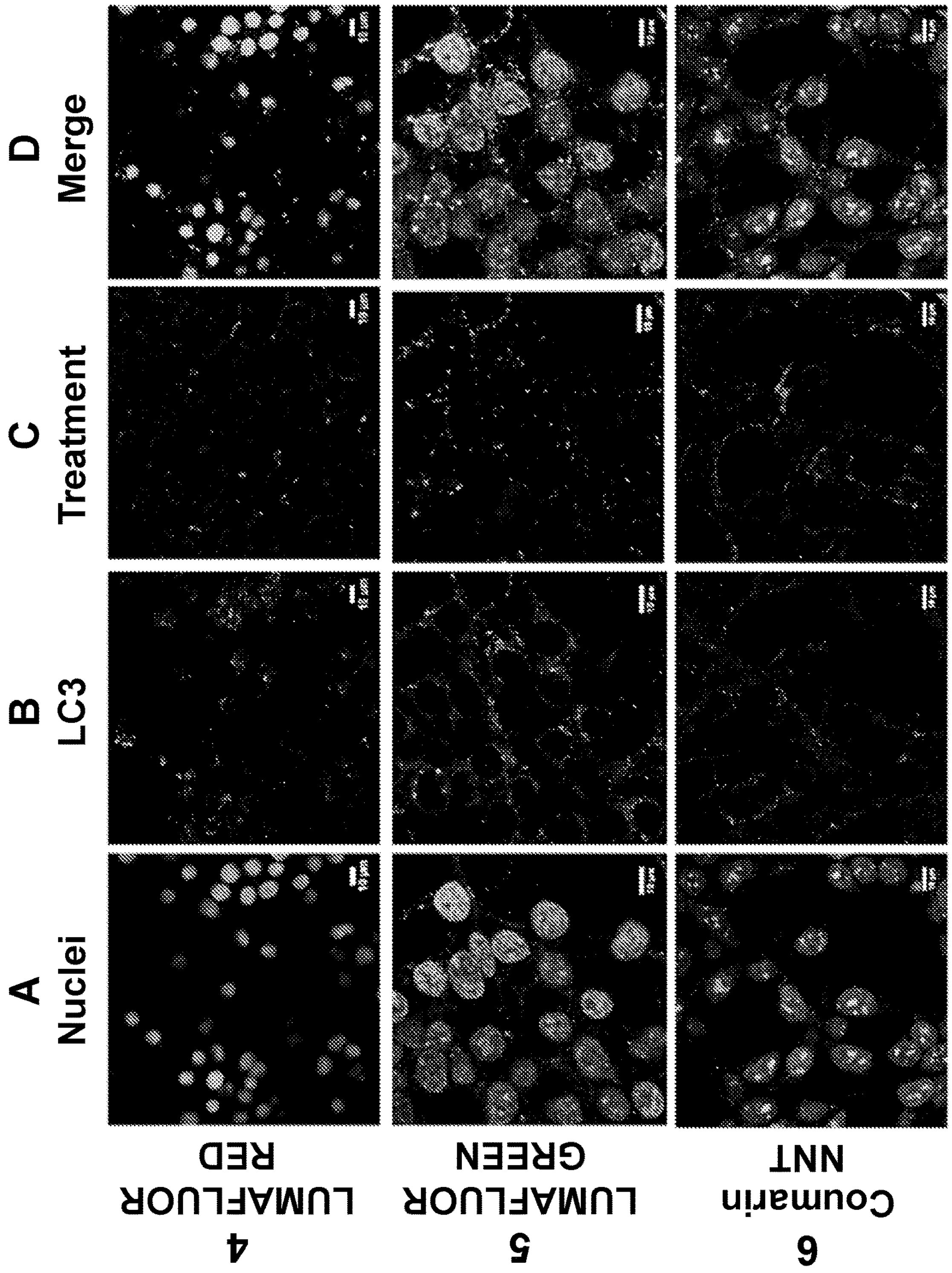
Figure 26C:
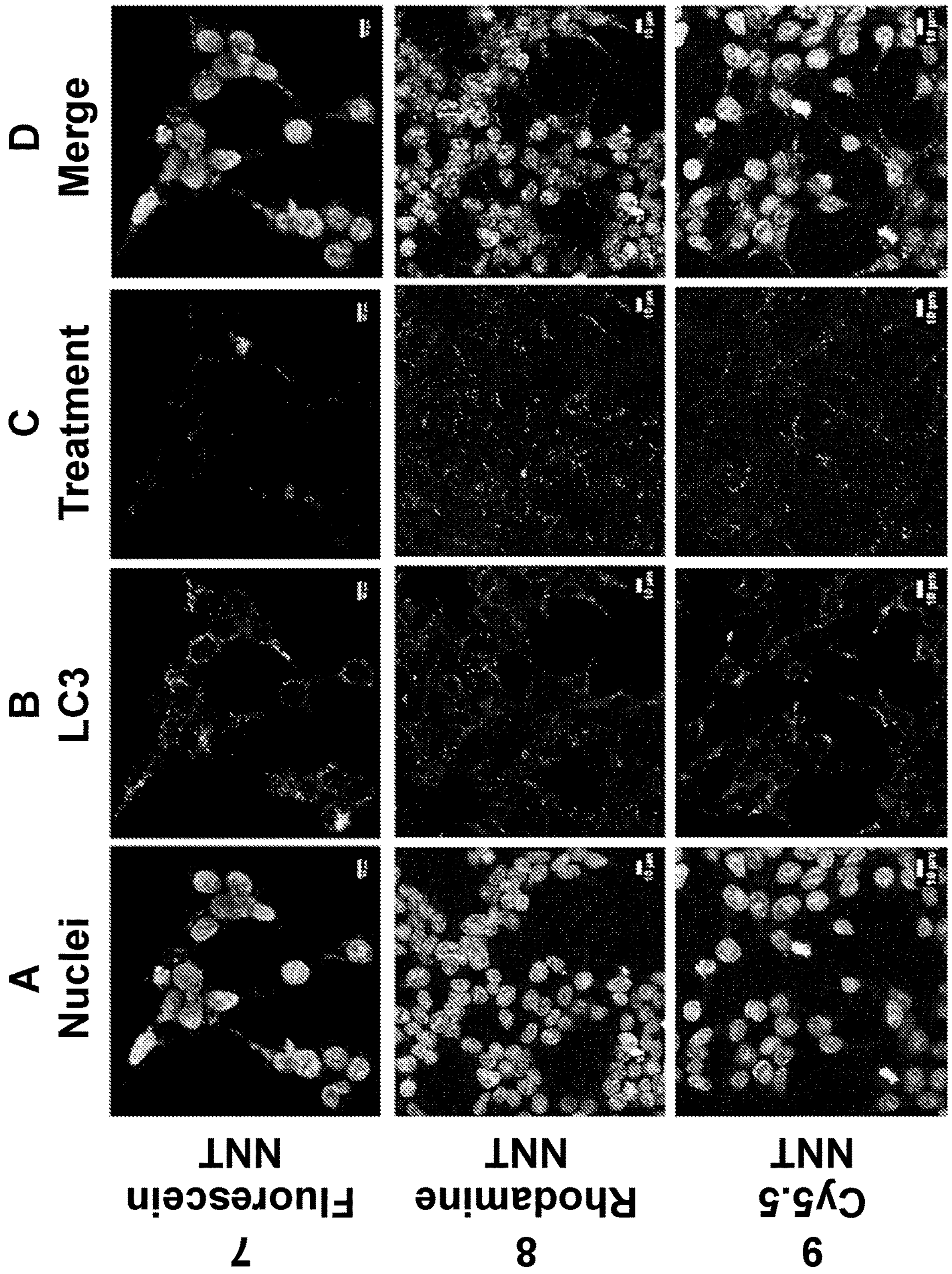
Figures 27, 27A:
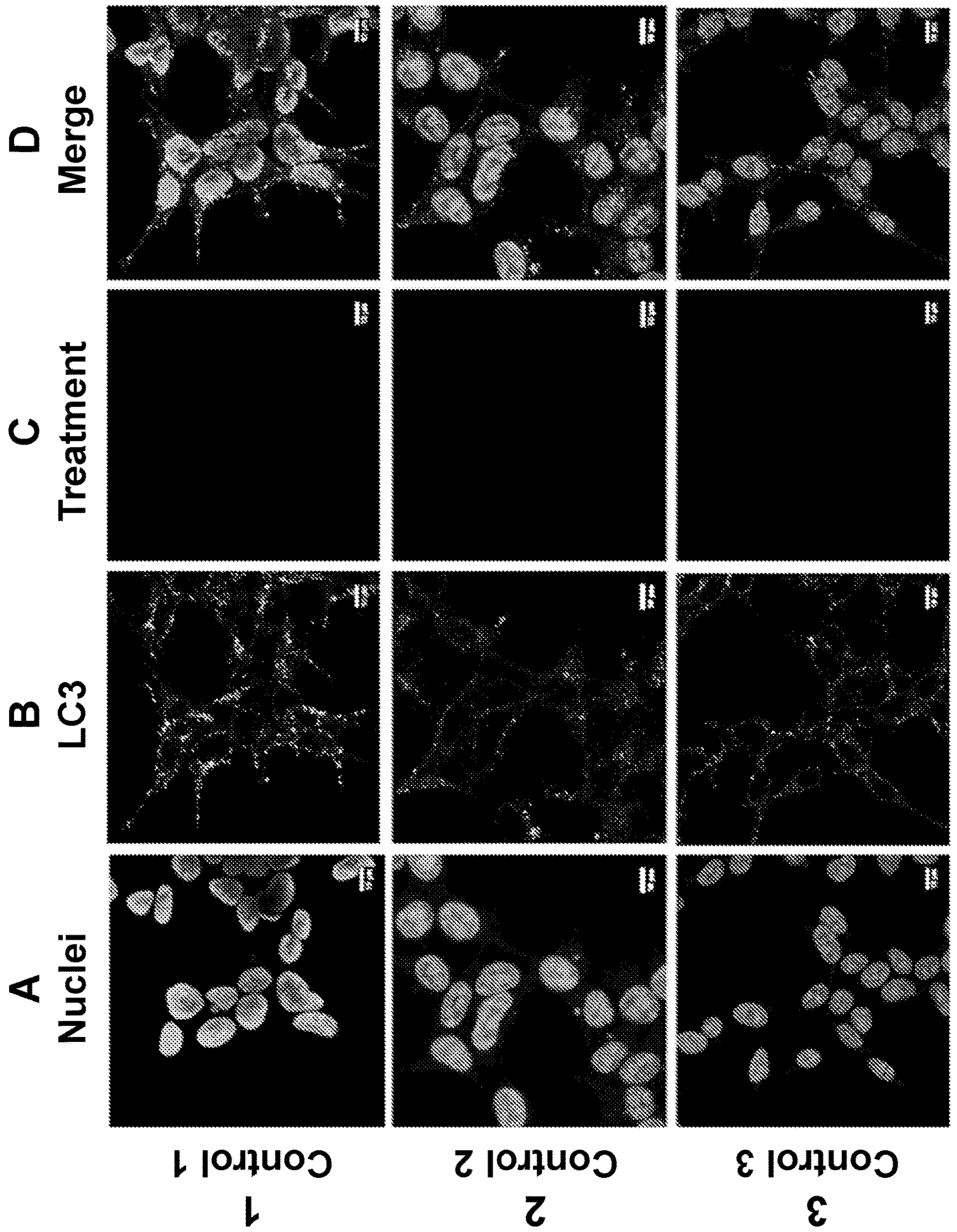
FIGS. 27A-27C: The colocalization assay of autophagosomes for 48 h treatment by confocal laser scanning microscopy in HEK 293 cells. Treatments are DMEM media for control 1, 2 and 3, commercial fluorescent tracers (LUMAFLUOR RED and GREEN), Coumarin-NNT, Fluorescein-NNT, Rhodamine-NNT and Cy5.5-NNT. The nuclei of HEK 293 cells were stained by DAPI (blue) for control 1, control 2, LUMAFLUOR RED and GREEN, Fluorescein-NNT, Rhodamine-NNT and Cy5.5-NNT; propidium iodide for control 3 and Coumarin-NNT. Autophagosomes were immunostained by LC3 antibody, with Anti-rabbit IgG (H+L), F(ab')2 Fragment conjugated with ALEXA FLUOR 488 for control 1, control 3, LUMAFLUOR RED, Coumarin-NNT, Rhodamine-NNT and Cy5.5-NNT, or ALEXA FLUOR 555 for control 2, LUMAFLUOR GREEN, and Fluorescein-NNT; Colocalization is shown in orange or white. HEK 293 cells were cultured for 24 h and then incubated with LUMAFLUOR RED or Cy5.5-NNT for 20 min. The images were taken 48 h after treatment. All scale bars in FIGS. 27A-27C=10 μm.
Figure 27B:
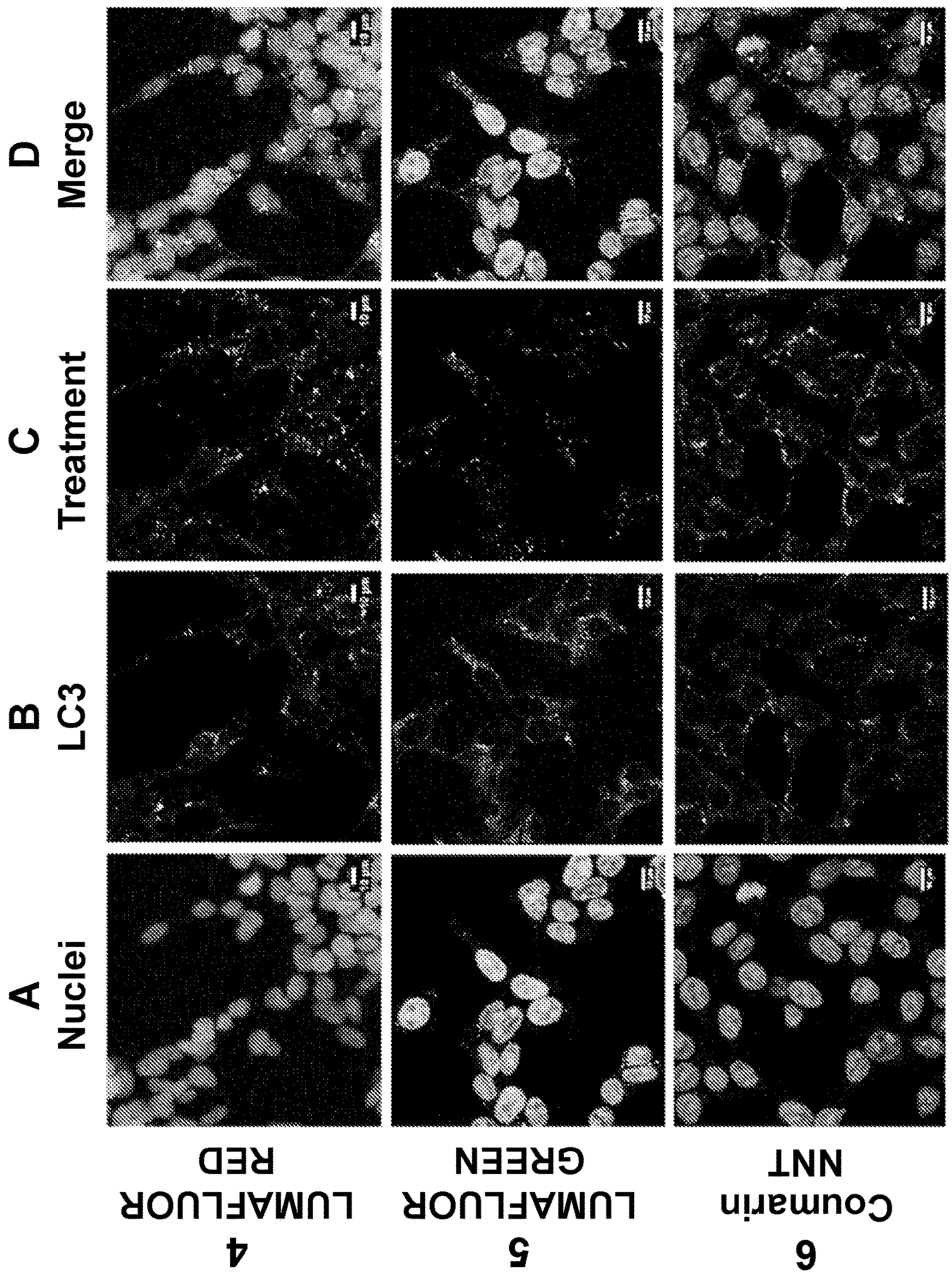
Figure 27C:
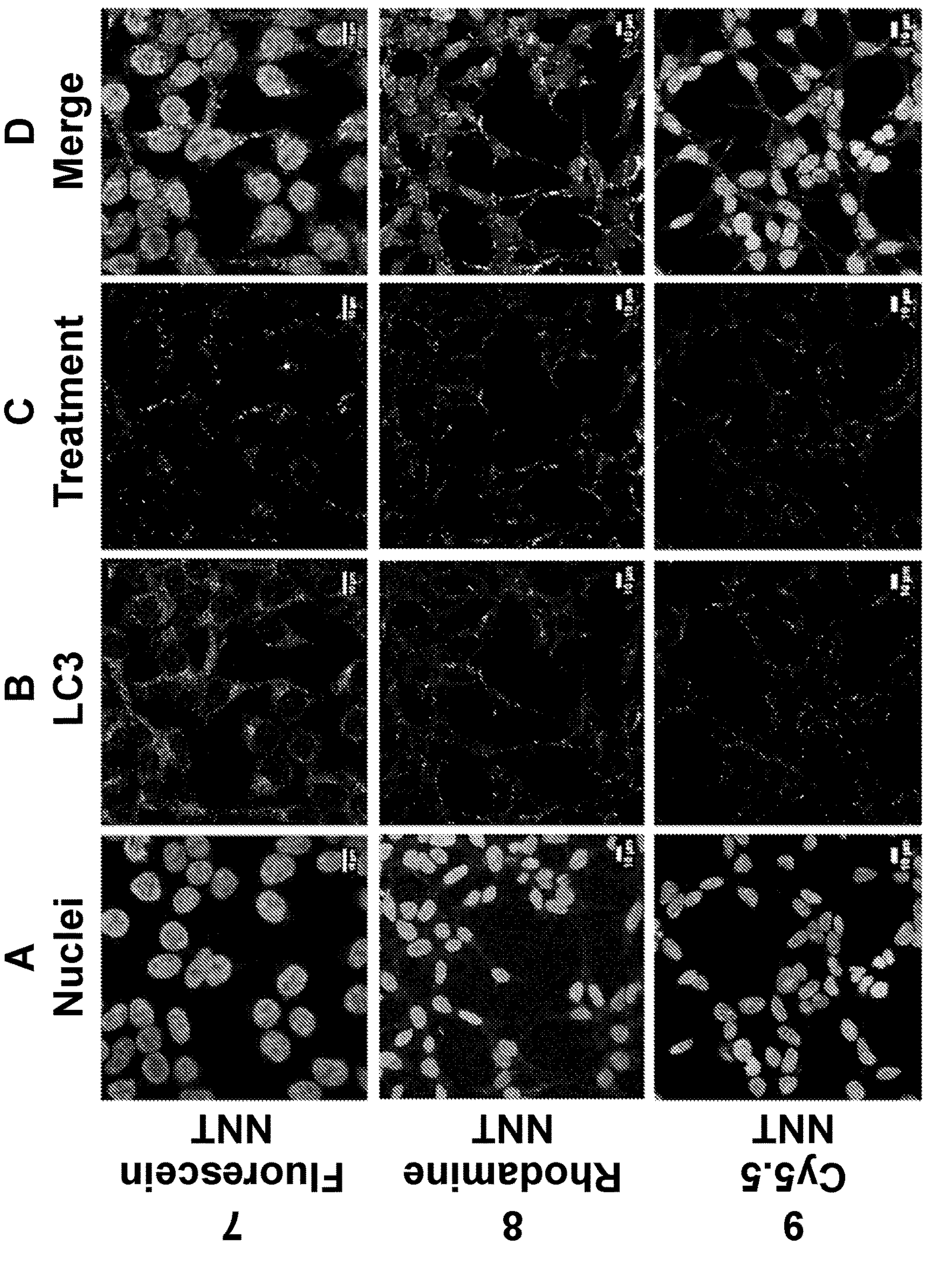

Time dependent uptake (FIGS. 2A-2D) shows NNTs have higher mean fluorescence intensity (MFI) compared to LUMAFLUOR RED and GREEN. As the fluorescent intensity per particle is matched between samples, this suggests that NNTs more efficiently enter cells than their commercial counterparts. Furthermore, at both timepoints assessed, the difference in uptake between each NNT was not significantly different from one another, suggesting that these materials are being taken by cells in a similar manner (FIG. 18). To elucidate the downstream cellular processing mechanisms, the colocalization with the lysosome, starting at 1 h post-treatment, was monitored as a function of time. All NNTs and commercial tracers remain at least 40% colocalized with the lysosomes throughout the course of the study, indicating that these materials are being processed by cells in the same manner (FIG. 3D and FIG. 23).

Figure 3H:
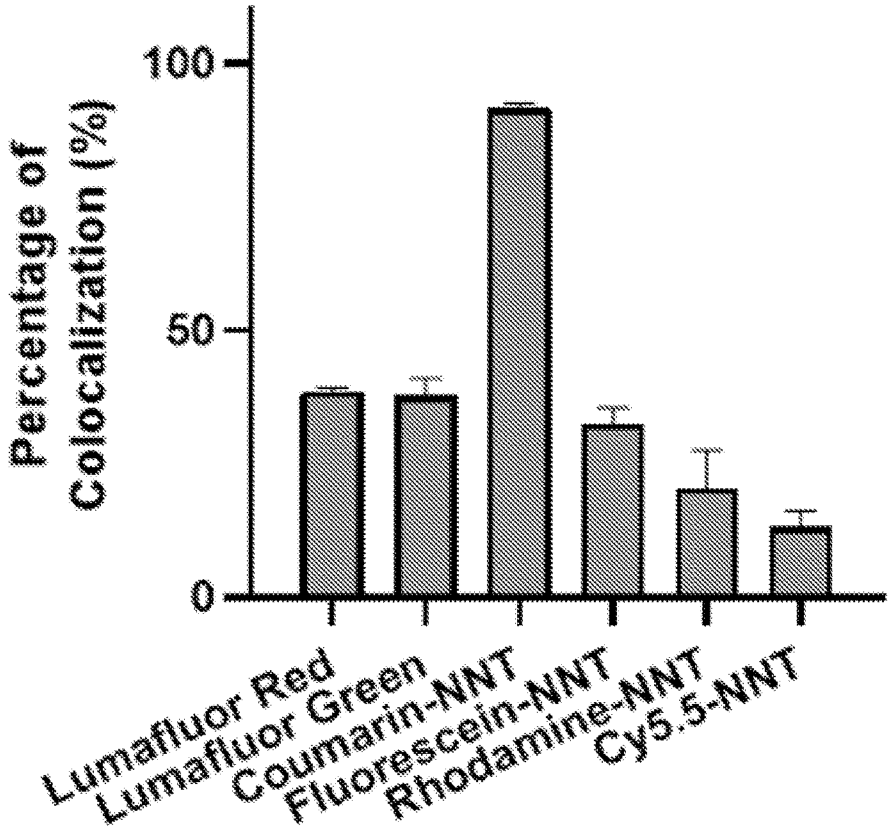
Figure 4:
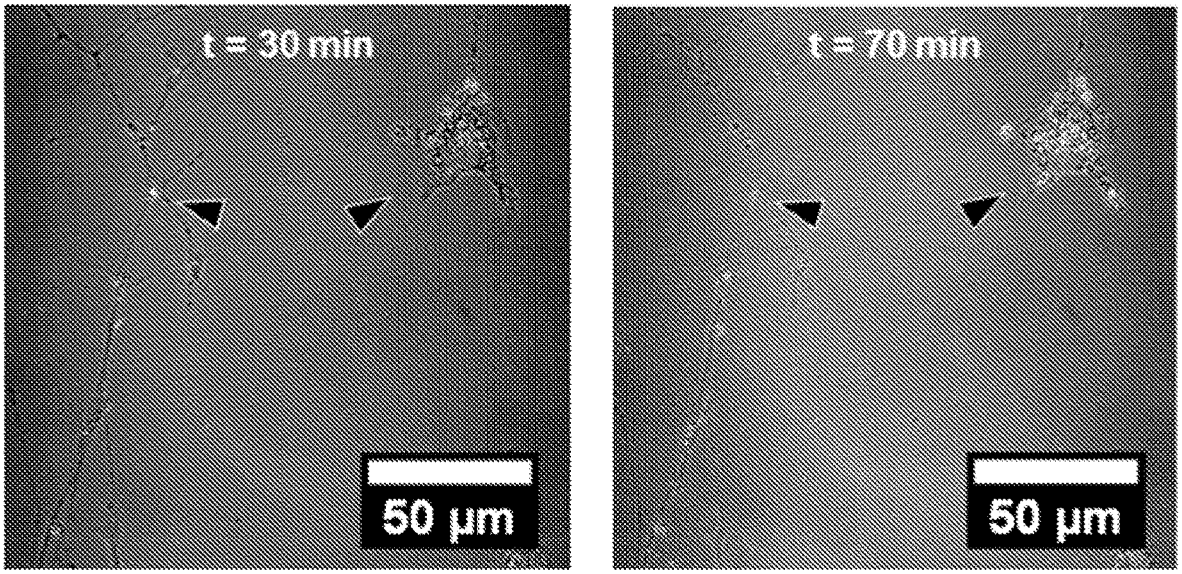
FIG. 4: Zoomed confocal microscopy images of lysosomes colocalization of Fluorescein-NNT at 30 min and 70 min after the treatment in primary rat cortex neurons. The nuclei of primary rat cortex neurons were stained by Hoechst. Lysosomes were stained by LYSOTRACKER RED DND-99. Colocalization is shown in orange (RED and GREEN). Primary rat cortex neurons were cultured for 30 days and then incubated with Fluorescein-NNT for 20 min.
Figure 28:
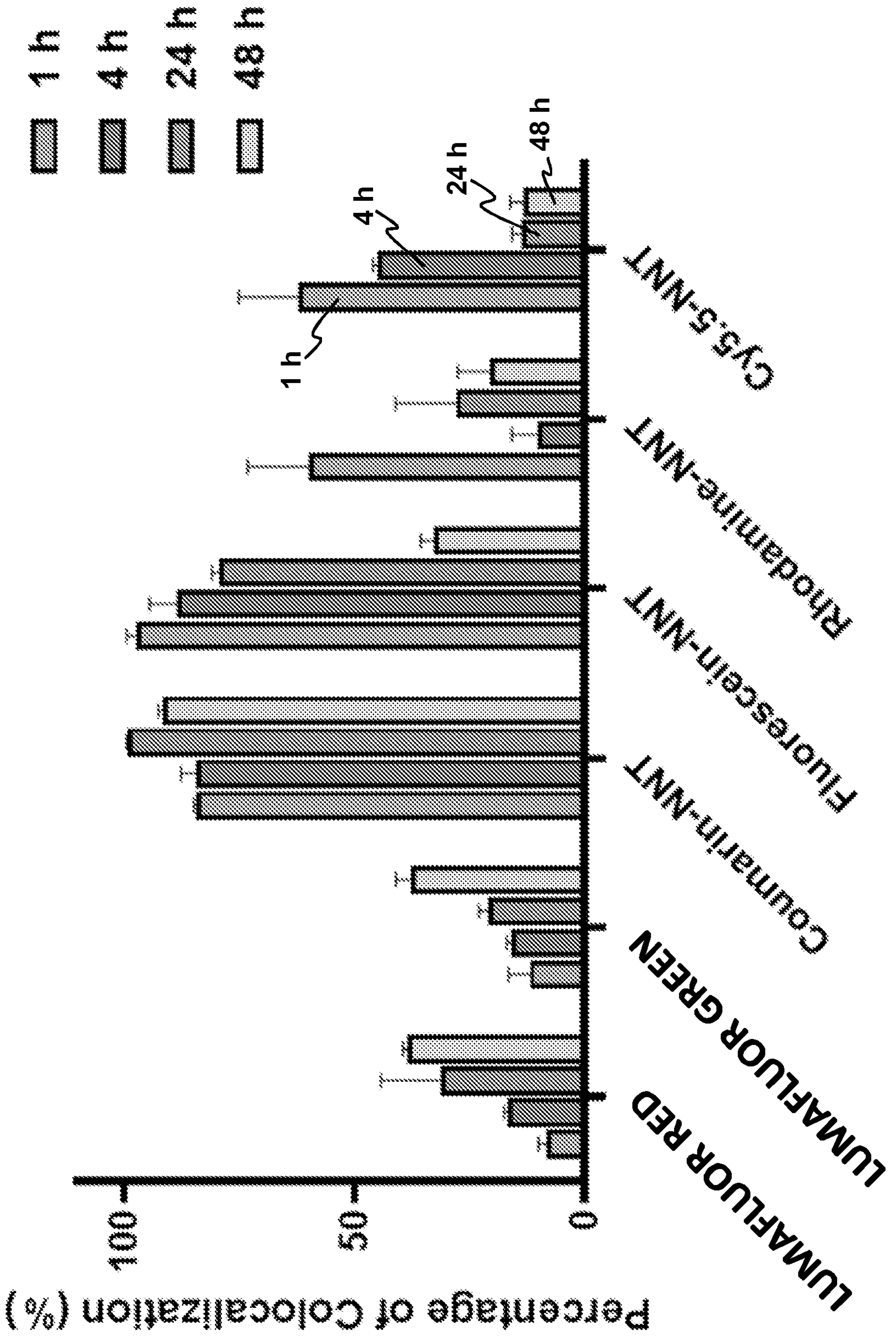
FIG. 28: Percentage of autophagosomes colocalization of commercial fluorescent tracers and 4 NNTs at 1 h, 4 h, 24 h and 48 h quantified by confocal laser scanning microscopy images. Data is presented as mean±SD (n=3).

The clearance pathway of all NNTs and both commercial fluorescent tracers was assessed by colocalization with LC3, a core protein in the autophagy pathway (FIG. 3H and FIG. 28). The highest colocalization of LUMAFLUOR RED, LUMAFLUOR GREEN and Coumarin-NNT during experiment period is at 48 h, while for the Fluorescein-NNT, Rhodamine-NNT and Cy5.5-NNT is at 1 h. This indicates that the commercial fluorescent tracers are trafficked intracellularly at different rates from the NNTs. Conversely, all NNTs are taken up by cells and are generally processed in the same manner, albeit at slightly different rates. These results show that the interactions of NNTs with cells are distinct from those of the commercially available tracers. In addition, primary neurons take up NNTs, showing increasing colocalization with lysosomes in the cell body as a function of time as measured by live cell confocal microscopy.

Retrograde tracing of NNTs was validated in two neuronal pathways in mice models, EC to CA1 (FIG. 5A-5G) and LGN to V1 (FIGS. 6A-6B). First tested was Fluorescein-NNT in the hippocampus, since the primary direct projections from principal neurons in EC is to hippocampal field CA1 (i.e., to the first hippocampal region). Fluorescein signal was observed at EC by confocal microscopy indicating that Fluorescein-NNT was transported in a retrograde fashion. Furthermore, all four NNT were tested in another well-studied neuronal projection system: LGN to V1, as the outputs of the LGN majorly terminate in V1. Regardless of the type of labeling utilized, the NNTs were all capable of retrograde transport in vivo, with all four NNTs observed in the target area. These results provide a demonstration of the utility of NNTs as tools in neurobiological studies.

In summary, in this example a set of multi-color NNTs was provided that expand the scope of fluorescent neuronal tracers. In total, four different colors of NNTs have been synthesized through emulsion polymerization and evaluated for their chemical properties and their retrograde transport performance in vivo. Each NNT has distinct excitation and emission wavelengths, which imparts the capability of using multiple NNTs in a single analysis of retrograde transport. The commonly used retrograde tracers in the field, such as Cholera toxin subunit B (CTB) and Fluoro-gold (FG) are taken from natural systems and not subsequently optimized. The promise of NNTs as neuronal tracers lies where modification and optimization are inherently possible

Materials and Methods

The materials and methods in Example 1 are also applicable to the other examples and disclosures herein, unless contradictory information is set forth in those examples or disclosures.

All reagents were purchased from VWR, Alfa Aesar, Acros, Sigma-Aldrich or Polysciences, Inc. and used as received, unless otherwise noted.

General method of synthesizing NNTs. 2-Hydroxyethyl methacrylate (HEMA), methyl methacrylate (MMA), methacrylic acid (MAA) and ethylene glycol dimethacrylate (EGD) were distilled in vacuo. 50 mL nanopure $H_2O$ and a stir bar were placed in a Schlenk flask. Monomers were added to water, under the argon in the following order while stirring at 300 rpm: HEMA (0.981 mL, 8.10 mmol), MMA (1.973 mL, 18.58 mmol), MAA (0.345 mL, 4.06 mmol) and EGD (0.233 mL, 1.24 mmol). Sodium dodecyl sulfate (55 mg, 0.19 mmol) and ammonium persulfate (6 mg, 0.026 mmol) were then added to the flask. Finally, dye monomers were added. Coumarin acrylamide (15 mg, 0.05 mmol) was dissolved in 600 μL tetrahydrofuran (THF); methacryloxyethyl thiocarbamoyl rhodamine B (20.47 mg, 0.03 mmol) was dissolved in 500 μL methanol; methacryloyloxy O-fluorescein (40 mg, 0.10 mM) was dissolved in 500 μL THF; methacryloyloxy cyanine 5.5 (36 mg, 0.04 mmol) was dissolved in 1 mL of a mixture of the starting solution and 1 mL of MILLI-Q water. The monomers and dye mixture were stirred for 5 min at which point the flask was placed in an oil bath at 90° C. for 1 h. Over 1 h, the solution turned opaque/opalescent. At that time the solution was removed from the oil bath and allowed to rest at room temperature. Resulting NNTs were purified via dialysis into MILLI-Q water and further incubated with AG® 501-X8(D) mixed bed resin (analytical grade, with indicator dye, Bio-Rad) overnight to remove excess surfactant prior to in vitro and in vivo use. AG® 501-X8(D) is a mixed bed resin irreversibly bound indicator dye that turns from blue to gold when exchange capacity is exhausted. Blue resin still can be observed after mixing with NNTs overnight suggesting that all the excess surfactants are removed.

Dynamic light scattering. Particle diameters were determined via DLS using a DynaPro NanoStar (Wyatt Technology). The autocorrelation functions were averaged over 10 measurements consisting of 10 s acquisitions each. Particle diameters were determined from a regularization analysis.

UV-vis spectroscopy. Absorption of monomer (nano-tracers) were determined via UV-vis spectroscopy on a Cary 100 instrument (Agilent Technologies) in a quartz cuvette with a path length, d=1 cm. Aliquots of the stock solutions were diluted with water. Measurements of the extinction coefficient at the excitation maxima yielded concentrations using the Lambert-Beer-Law ($E=\varepsilon\lambda\cdot c\cdot d$) with known molar extinction coefficients.

Fluorometer. Fluorescent measurements were obtained using a Photon Technology International fluorescence detector, Horiba fluorolog-3 fluorimeter system.

Dry-state transmission electron microscopy. 5 μL of sample was applied to 400 mesh carbon grids (Ted Pella, Inc., Redding, CA, USA). Grids were glow discharged using an Emitech K350 glow discharge unit and plasma-cleaned for 90 s in an E. A. Fischione 1020 unit. 5 μL of a 1% (w/v) uranyl acetate solution was applied to each grid for 20 seconds, then the grids were washed with deionized water and allow to dry. TEM imaging was performed on a FEI Sphera microscope operated at 200 keV. Micrographs were recorded on a 2 k×2 k Gatan CCD camera.

Cryogenic transmission electron microscopy (cryo-TEM). Cryo-TEM samples were prepared by freshly glow discharging 400 mesh holey carbon TEM grids (Quantifoil R2/2, 400 mesh Cu support) or lacey carbon TEM grids (Electron Microscopy Sciences, Hatfield, PA) using an Emitech K350 glow discharge unit and plasma-cleaned for 90 s in an E. A. Fischione 1020 unit. 4 μL of sample was applied to each grid, gently blotted to form a thin film, then rapidly plunged into liquid ethane. The grids were transferred to liquid nitrogen then imaged on a FEI Tecnai G2 Sphera microscope operating at 200 keV. The samples were kept <175° C. during imaging. Micrographs were recorded on a 2 k×2 k Gatan CCD camera.

$^1H$ Nuclear magnetic resonance. $^1H$ Nuclear magnetic resonance (NMR) spectra were recorded on a Varian Mercury Plus spectrometer (400 MHz) Varian VX 500 spectrometer (500 MHz) in different deuterated solvents. Chemical shifts are given in ppm downfield from tetramethylsilane (TMS).

Mass spectrometry. Mass spectra were obtained at the UCSD Chemistry and Biochemistry Molecular Mass Spectrometry Facility by using Agilent 6230 Accurate-Mass TOFMS.

Zeta potential. Zeta potential was measured using a Zetasizer (3000 HS, Malvern Instruments Ltd, Worcestershire, UK).

High performance liquid chromatography. HPLC analysis was performed on a Jupiter Proteo90 Å phenomenex column (150×4.60 mm) using a Hitachi-Elite LaChrom L-2130 pump equipped with a UV-vis detector (Hitachi-Elite LaChrome L-2420). Purification was done using a Jupiter Proteo90 Å Phenomenex column (2050×25.0 mm) on a Waters DeltaPrep 300 system.

Nanoparticle tracking analysis. Particle concentration of each nano-tracer was obtained by MANTA Instruments (San Diego, CA, USA) using a ViewSizer® 3000.

Determine dye concentration of each NNT. Stock solutions of coumarin acrylamide, methacryloyloxy O-fluorescein, methacryloxyethyl thiocarbamoyl rhodamine B, and methacryloyloxy cyanine 5.5 were first prepared in methanol. Then, a series of concentrations of each dye monomer solution was prepared via serial dilution and their absorbances were determined using UV-Vis. A calibration curve was then plotted. To determine the dye content of each NNT, the NNT solutions were first dialyzed against methanol and then absorbance measured. The absorbance values were converted to concentrations using their respective calibration curves.

HEK 293 cell viability with NNTs or LUMAFLUOR (Red or Green) particles. A 96-well plate was treated with poly-L-lysine (10 μg/$cm^2$) for 1 h and rinsed with DPBS 3 times. HEK 293 cells were plated and kept in a 5% $CO_2$ atmosphere at 37° C. using DMEM medium overnight. A concentration range of NNTs or LUMAFLUOR (Red or Green) from $3.0\times10^9$ to $4.8\times10^{10}$ particles per milliliter was tested with a 48 h incubation. Cells were washed with DPBS three times and 100 μL of DMEM medium without phenol red was added back to each well. Then 20 μL of CellTiter-Blue® reagent was added directly to each well. The plate was incubated at 37° C. for 2 h to allow cells to convert resazurin to resorufin. The fluorescence signal was measured at excitation=560 nm, emission=590 nm on a PerkinElmer EnSpire 2300 multi-plate reader.

Time-dependent uptake of NNTs or LUMAFLUOR (Red or Green) in HEK 293 cells. 4-chamber 35 mm round glass-bottom dishes were treated with poly-L-lysine (10 μg/$cm^2$) for 1 h. Dishes were rinsed with DPBS 3 times. HEK 293 cells were plated in the 4-chamber 35 mm round glass-bottom dishes in a 5% $CO_2$ atmosphere at 37° C. using DMEM medium overnight. $1.2\times10^{10}$ particles per milliliter of NNTs or LUMAFLUOR (Red or Green) were suspended in phenol red free DMEM medium, then incubated with cells for either 1 h or 24 h. After washing with DPBS buffer for 3 times, the cells were stained with 5 μg/mL Wheat Germ Agglutinin with ALEXA FLUOR 488 Conjugate or Wheat Germ Agglutinin with ALEXA FLUOR 633 Conjugate at 37° C. for 10 min. 300 nM of DAPI or 500 nM propidium iodide was used to counterstain.

Colocalization of NNTs or LUMAFLUOR (RED or GREEN) and LYSOTRACKER. 4-chamber 35 mm round glass-bottom dishes were treated with poly-L-lysine (10 μg/$cm^2$) for 1 h. Dishes were rinsed with DPBS 3 times. HEK 293 cells were plated in the 4-chamber 35 mm round glass-bottom dishes in a 5% $CO_2$ atmosphere at 37° C. using DMEM medium overnight. $1.2\times10^{10}$ particles per milliliter of NNTs or LUMAFLUOR (RED or GREEN) were suspended in phenol red free DMEM medium and incubated with cells for 20 min. The cells were then washed to remove free NNTs or LUMAFLUOR (RED or GREEN). After 1 h, 4 h, 24 h and 48 h of treatment, the cells were incubated with 75 nM LYSOTRACKER RED DND-99 or LYSOTRACKER GREEN DND-26 (Life Technologies) for 30 min at 37° C. The cells were fixed with 4% PFA for 10 min. 300 nM of DAPI or 500 nM propidium iodide was used to counterstain.

Data analysis of quantifying confocal laser scanning microscopy images (cellular uptake). The area within the cell was selected by thresholding the cell membrane (WGA) channel. The resulting area was applied to the treatment (DMEM media, or LUMAFLUOR RED/GREEN, or NNT) channel. Then mean fluorescence intensity were measured by Image J.

Data analysis of quantifying confocal lasering scanning microscopy images (colocalization). The percentage colocalization between the lysosome or autophagosome and treatment was determined by Image J. The threshold was set to the same level as noise in the image.

Colocalization of Fluorescein-NNT and LYSOTRACKER in primary rat cortex neurons. Primary rat cortex neurons were plated on CORNING BIOCOAT Collagen IV 100 mm TC-treated Culture Dishes in a 5% $CO_2$ atmosphere at 37° C., using GIBCO B-27™ Plus Neuronal Culture System as medium for 30 days to allow the axons fully grow. $2.1\times10^9$ particles per milliliter of NNTs were suspended in medium and incubated with cells for 20 min. The cells were then washed to remove free NNTs with DPBS. The neurons were incubated with 75 nM LYSOTRACKER RED DND-99 (Life Technologies) for 30 min at 37° C. and washed 3 times with DPBS. The neurons were then incubated with 0.5 mL INVITROGEN NUCBLUE LIVE READYPROBES Reagent (Hoescht) for 30 min at 37° C. and washed 3 times with DPBS.

Time-lapse confocal laser scanning microscopy. Imaging was accomplished using a LEICA SP5 confocal with a 63× oil immersion objective at 1.5× optical zoom. All the images are presented as Z-stack. Images were taken every 4 min for a total of 140 min. The section thickness was 2.0 μm with a scan size of 512×512 pixels and a scan speed of 600 Hz. Each z-stack contained 6 steps and the line average was 4. The cell nuclei (stained with Hoescht) was imaged using a 405 nm laser at 8% laser power. Lysosomes were imaged using a 488 nm laser at 12% laser power (for LYSOTRACKER GREEN DND-26). Cell imaging for Fluorescein-NNT was performed using a 488 nm laser at 8% laser power.

Immunostaining. 4-chamber 35 mm round glass-bottom dishes were pretreated with poly-L-lysine (10 μg/$cm^2$) for 1 h. Dishes were rinsed with DPBS 3 times. HEK 293 cells were plated in the 4-chamber 35 mm round glass-bottom dishes in a 5% $CO_2$ atmosphere at 37° C. using DMEM medium overnight. $1.2\times10^{10}$ particles per milliliter of NNTs or LUMAFLUOR (RED or GREEN) were suspended in phenol red free DMEM medium and incubated with the cells for 20 min. Cells were washed to remove free NNTs or LUMAFLUOR (RED or GREEN). After 1 h, 4 h, 24 h and 48 h of treatment, the cells were fixed with 100% ice-cold methanol at −20° C. for 15 min and rinsed three times in 1×DPBS for 5 min each. The cells were then treated with blocking buffer containing 1×DPBS, 5% normal serum and 0.3% TRITON X-100 for 60 min. Cells were incubated overnight with antibodies against LC3B in antibody dilution buffer (1×DPBS, 1% BSA and 0.3% TRITON X-100)

(1:200; Cell Signaling Technology) at 4° C. After washing, cells were incubated in fluorochrome-conjugated anti-rabbit secondary antibodies (Anti-Rabbit IgG (H+L), F(ab')2 Fragment (ALEXA FLUOR 488 Conjugate) or Anti-Rabbit IgG (H+L), F(ab')2 Fragment (ALEXA FLUOR 555 Conjugate)) diluted in antibody dilution buffer (1:500; Cell Signaling Technology) for 2 h at room temperature in the dark. 300 nM of DAPI or 500 nM propidium iodide was used to counterstain.

Injection of NNT and fixation (Surgical procedures). Experiments were approved by the Northwestern University Animal Care and Use Committee. Injections were performed in adult C57BL/6J mice under inhaled anesthesia (1-2% isoflurane in 0.5 L/min $O_2$). After a midline skin incision and alignment of the skull, a small (0.5 to 1.0 mm) craniotomy was performed and a glass micropipette containing the nano-tracers lowered into the brain to reach the desired stereotaxic location of the injection site (CA1: 1.8 mm lateral, 2.3 mm caudal of bregma, 1.4 mm deep from dura; V1: 2.5 mm lateral, 3.3 mm caudal of bregma, and 0.5 mm deep from dura). A calibrated volume (typically 30 nL) of solution was injected by applying positive pressure (typically 1-2 psi). After withdrawing the micropipette, the craniotomy was filled with Kwik-Sil (WPI) and the incision site closed with 5-0 silk suture. After 48-72 hours, mice were deeply anesthetized and perfused with 4% paraformaldehyde (PFA). Brains were set in PFA overnight and then transferred to 30% sucrose in PBS for ~3 days before 50 μm thick sagittal (for CA1 injections) or coronal (for V1 injections) sections were cut with a microtome. Slices were mounted on glass slides using VECTASHIELD (Vector Laboratories) with DAPI, except for Coumarin injections, in which case slices were instead placed in propidium iodide in PBS for 3-5 minutes before mounting with VECTASHIELD, without DAPI Fluorescence microscopy. Fluorescence images were acquired using a LEICA DM6B fluorescence microscope with a DFC7000T camera (40 fps at full resolution, pixel size: 4.54 μm). 10× (Numerical aperture (NA):0.4) dry, 40× (NA: 0.85), and 63× (NA: 1.32) oil-immersion objectives were used for imaging. The following filters were used: Blue filter (DAP) excitation 350/50 nm, dichroic 400, emission 460/50; Green filter (L5) excitation 480/40, dichroic 505, emission 527/30; Red filter (RHO) excitation 546/10 nm, dichroic 560, emission 585/40; Cy5.5 filter (Y5) excitation 620/60, dichroic 660, emission 700/75. All images were further processed using the Leica Application Suite X (LAS X).

Confocal laser scanning microscopy. Imaging was accomplished using LEICA SP5 confocal with a 63× oil immersion objective at 1.5× optical zoom. All the images are presented as Z-stack. Slice thickness was 0.26 μm with a scan size of 1024×1024 pixels and a scan speed of 400 Hz. The cell nuclei (stained with DAPI) was imaged using a 405 nm laser at 15% laser power. The cell nuclei (stained with propidium iodide, for coumarin treated cells) was imaged using a 561 nm laser at 10% laser power. The cell membrane (stained with Wheat Germ Agglutinin, ALEXA FLUOR 488 Conjugate) was imaged using a 488 nm laser at 12% laser power. The cell membrane (stained with Wheat Germ Agglutinin, ALEXA FLUOR 633 Conjugate) was imaged using a 633 nm laser at 18% laser power. Lysosomes were imaged using a 488 nm laser at 20% laser power (for LYSOTRACKER GREEN DND-26) or a 555 nm laser at 14% laser power (for LYSOTRACKER RED DND-99). Autophagosome was imaged using a 488 nm laser at 10% laser power (for LC3 antibody with ALEXA FLUOR 488 Conjugate) or a 555 nm laser at 12% laser power (for LC3 antibody with ALEXA FLUOR 555 Conjugate). Cell imaging for Coumarin-NNT was performed using a 405 nm laser with an 28% laser power. Cell imaging for Fluorescein-NNT and LUMAFLUOR GREEN was performed using a 488 nm laser at 12% laser power. Cell imaging for Rhodamine-NNT and LUMAFLUOR RED was performed using a 561 nm laser at 15% laser power. Cell imaging for Cy5.5-NNT was performed using a 633 nm laser at 8% laser power.

Although this example described the preparation of nanoparticles containing a single type of fluorophore moiety, it is contemplated that a nanoparticle containing two or more types of fluorophore moieties (with different emission maxima) could be readily prepared using the techniques described herein, for example, by adding one or more additional types of vinyl-containing fluorophores (with different emission maxima) in the currently described synthetic conditions.

It is also contemplated that compositions synthesized according to Example 1 (each composition containing nanoparticles with a single type of fluorophore moiety) can be combined with one another to produce a combined composition containing nanoparticles, in which some nanoparticles contain one type of fluorophore and other nanoparticles contain a different type of fluorophore (with a different emission maximum), yet each nanoparticle contains only one type of fluorophore (i.e., nanoparticles do not contain two or more types of fluorophores in certain aspects).

Example 2: Contrast Agents and Retrograde Neural Tracers

The example demonstrates the synthesis and the in vivo retrograde transport of nanoparticles comprising a chelate moiety (chelating gadolinium) and a fluorophore.

The concept of MRI was first published in the 1970s. MRI is a medical diagnostic technique used to produce images of bones and soft tissues using magnetic fields and radiofrequency energy. For some conditions and needs (for example, visualization of inflammation or tumors), intravenous (IV) drugs are used as MRI contrast agents to improve the accuracy of MRI image interpretation.

There are thousands of molecular contrast agents and imaging probes documented in the Molecular Imaging and Contrast Agent Database. As of 2018, over one hundred contrast agents are approved by U.S. Food and Drug Administration (FDA) on the market for positron emission tomography (PET), single-photon emission computed tomography (SPECT), computed tomography (CT) and ultrasound, MR imaging modalities.

Gadolinium-based contrast agents (GBCAs) are the most commonly used MRI contrast agents in the clinic. Of the few FDA-approved GBCAs, Gd-DOTA was selected as the contrast agent for the Nano-tracer systems, as DOTA is a macrocylic chelator that binds Gd more tightly than other GBCAs, which means it is less likely to release free Gd ions (which can be toxic to the body) in vivo. The DOTA chemical structure is depicted below, though in some aspects the carboxylate protons can be replaced by one or more metals (e.g., metal ions) as disclosed and depicted elsewhere herein:

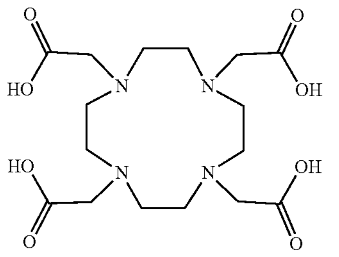

DOTA

Fluorescent retrograde nano-tracers capable of retrograde transportation within neurons are powerful tools in brain mapping and axonal tracing applications. However, visible light is only a small collection of wavelengths in the electromagnetic spectrum. Extending this spectrum to include radio waves enables the use of nano-tracers with a broader spectrum of identifiable wavelengths. One potential advantage of these Gd nano-tracers is that they can be viewed in live subjects.

These retrograde nano-tracers cover the full visible light spectrum and are sensitive to radio wave frequencies, enabling them to emit a detectable signal. They can be utilized for fluorescence imaging or MRI, and we propose enhancing the functionality of these materials by modifying their morphology in order to learn more about brain connectivity and as well as improve therapeutic applications.

1st Generation Gd-DOTA Nano-Tracers: Gd-DOTA Cy5.5 Dual Labeled Nano-Tracers

Figure 37:
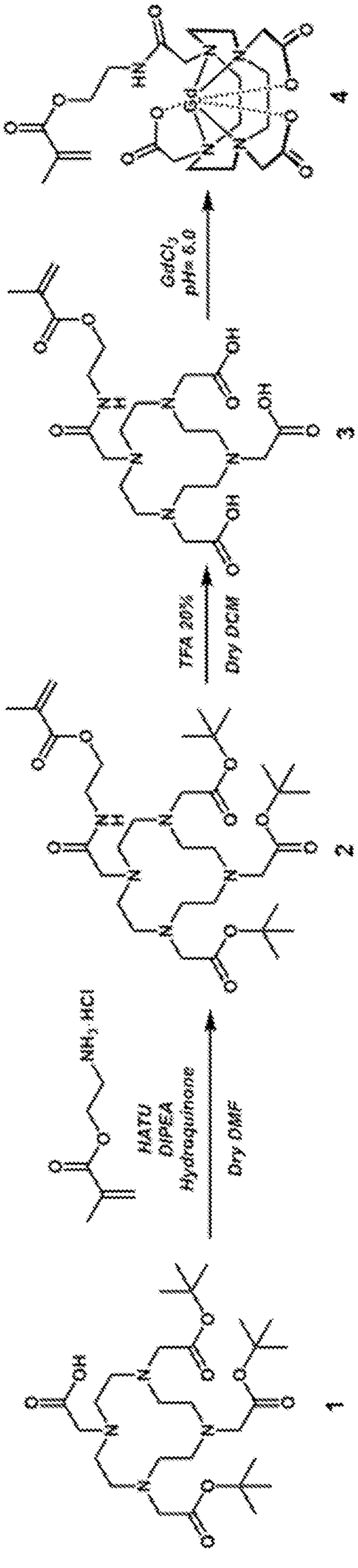
FIG. 37: Synthetic Route of Gadolinium-Tetraazacyclododecane-1,4,7,10-tetraacetic Acid (Gd-DOTA) Appended to an Acrylate.
Figure 38A:
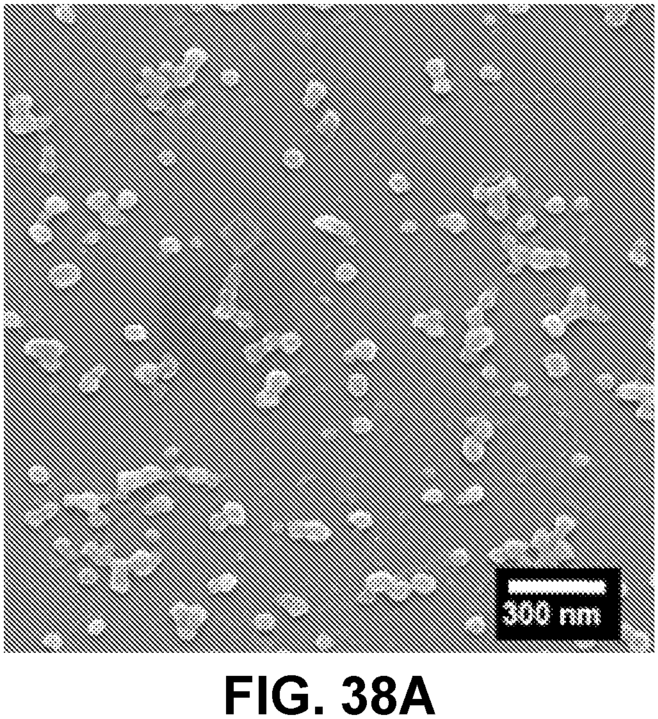
FIGS. 38A-38E: Characterization of the Gd-Cy5.5 Nano-tracer.
Figure 38B:
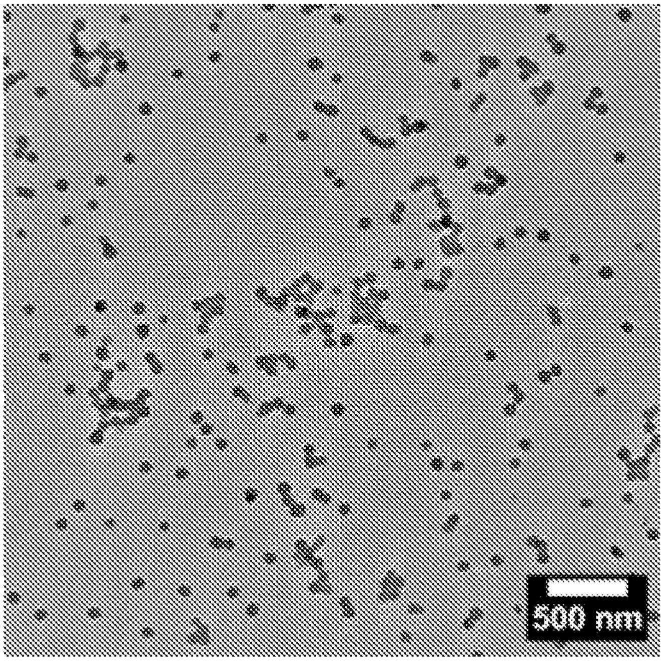
Figure 38C:
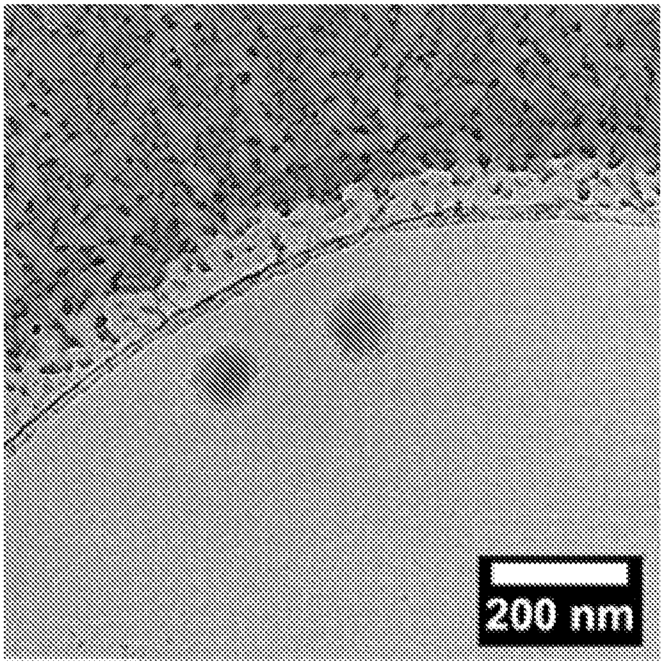
Figure 38D:
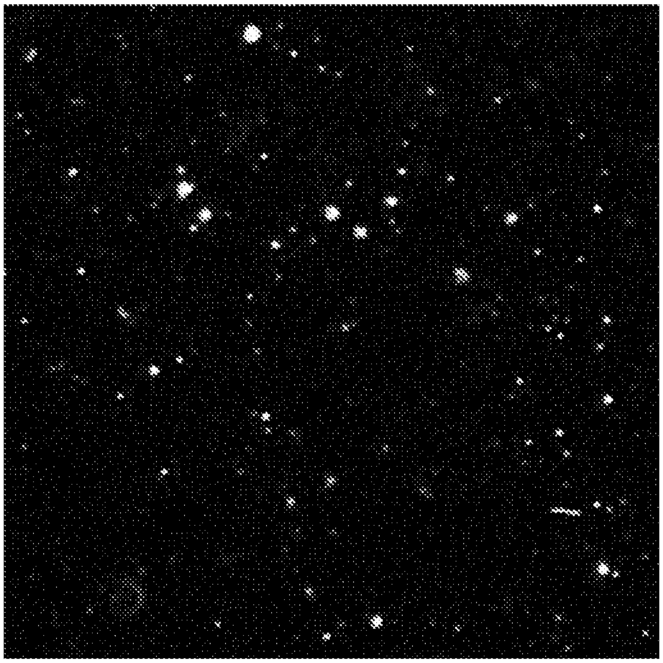
Figure 38E:
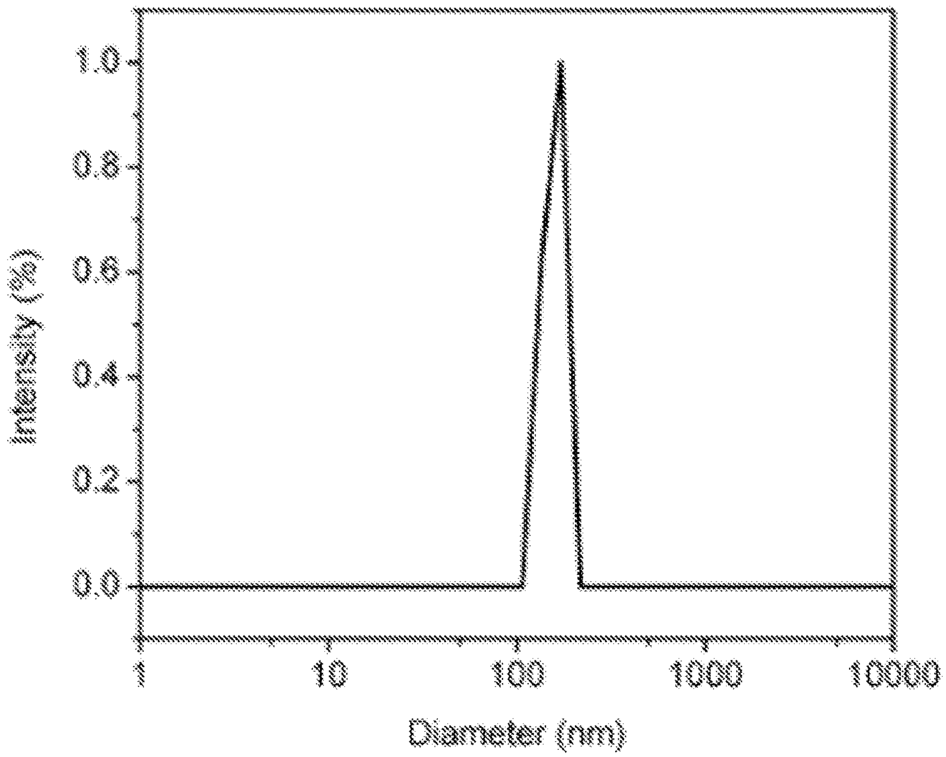

Synthesis and Characterization of Gadolinium-Tetraazacyclododecane-1,4,7,10 Tetraacetic Acid (Gd-DOTA) Appended to an Acrylate FIG. 37 shows the synthetic route of the first generation Gd-DOTA monomer (Gd-DOTA AEMA), which was modified with a pendant acrylate group. This route allows for its easy implementation into fluorescently based tracers, and in turn generates dual-labeled tracers. DOTA-tris (tert-butyl ester) was reacted with AEMA through an amide coupling reaction. It was then treated with 20% TFA to deprotect the 3 tert-butyl groups, which in turn allows the sites to become available to chelate gadolinium. Gd was chelated to DOTA by mixing gadolinium chloride at pH=6.

Synthesis of tri-tert-butyl 2,2',2"-(10-(2-((2-(methacryloyloxy)ethyl)amino)-2-oxoethyl)-1,4,7,10-tetraazacyclododecane-1,4,7-triyl)triacetate. DOTA-tris(tert-butyl ester) 1 (1 g, 1.746 mmol), AEMA (0.274 g, 1.659 mmol) and hydroquinone (5 mg, 0.0454 mmol) was dissolved by anhydrous DMF under argon flow. 1-[Bis(dimethylamino)methylene]-1H-1,2,3-triazolo[4,5-b]pyridinium 3-oxide hexafluorophosphate (HATU) (0.730 g, 1.92 mmol) and DIPEA (668 μL, 3.841 mmol) was added into the reaction flask after 10 min. The reaction was left to stir over night with a foil covered. The reaction was concentrated to dryness to give brown oil that was purified by flash chromatography (100% Ethyl Acetate (EtOAc)). Then the product was washed by brine (×3) and water (×3), was dried over $MgSO_4$, and filtered and concentrated to dryness to give a white oil under the vacuum. Yield: 310 mg, 32%. $^1H$ NMR ($CDCl_3$): δ=6.16 (s, 1H), 5.60 (s, 1H), 4.24 (t, 2H), 3.91 (s, 2H), 3.62 (s, 2H), 3.57 (q, 2H), 3.41-2.53 (bm, 20H), 1.93 (s, 3H), 1.46 (s, 27H). HR-MS (ESI-TOF): m/z (%) $[M+H]^+$ calcd for $C_{34}H_{61}N_5O_9$: 684.45, found: 684.32. Although AEMA was employed in this example to append a vinyl group to the chelate group, any other suitable compound may be employed to link the chelate moiety to a vinyl group.

Deprotection of tri-tert-butyl 2,2',2"-(10-(2-((2-(methacryloyloxy)ethyl)amino)-2-oxoethyl)-1,4,7,10-tetraazacyclododecane-1,4,7-triyl)triacetate. Protected monomer 2 (310 mg, 0.453 mmol) were deprotected by 20% TFA in anhydrous dichloromethane (DCM) under argon. The reaction was left to stir after 8 hours and cold diethyl ether was added to the reaction and the precipitate was collected and dried under vacuum. Yield: 200 mg, 85.7%. $^1H$ NMR ($D_2O$): δ=6.12 (s, 1H), 5.72 (s, 1H), 4.25 (q, 2H), 3.53 (m, 8H), 2.94 (t, 2H), 2.2 (s, 3H), 1.45 (s, 16H). HR-MS (ESI-TOF): m/z (%) $[M+H]^+$ calcd for $C_{22}H_{37}N_5O_9$: 516.26, found: 516.32.

Chelation of 2,2',2"-(10-(2-((2-(methacryloyloxy)ethyl)amino)-2-oxoethyl)-1,4,7,10-tetraazacyclododecane-1,4,7-triyl)triacetic acid: Deprotected monomer 3 (104 mg, 0.202 mmol) and gadolinium chloride (106 mg, 0.406 mmol) was added in to degassed water under argon. 0.1 mol/L sodium hydroxide (NaOH) was added to the reaction to adjust the pH to 6.0. The reaction was monitoring and maintained at a pH of 7. The reaction was heated to 60° C. for one day. The precipitate was filtered and purified on reverse phase HPLC (gradient 0-20% buffer B, ACN with 0.1% TFA). The pure fractions were collected and lyophilized. Yield: 60 mg, 45%. HR-MS (ESI-TOF): m/z (%) $[M-H]^-$ calcd for $C_{22}H_{34}GdN_5O_9$: 669.16, found: 669.31.

Synthesis and Characterization of 1st Generation Gd-DOTA Nano-Tracers: Gd-DOTA Cy5.5 Dual Labeled Nano-Tracers Gd-DOTA Cy5.5 dual labeled nano-tracer is (Gd-Cy5.5 nano-tracer) designed to incorporate not only with Gd-DOTA as an MRI contrast agent but also Cy5.5 as a fluorescent nanoparticle. The polymerization condition of the Gd-Cy5.5 nano-tracer was identical to the section "Optimization of Polymerization Condition of Plain Nano-tracers" in Example 5. 30 mg Cy5.5-AEMA was dissolved into 2 mL of MILLI-Q water. Gd-DOTA AEMA was dissolved in 1.5 mL of MILLI-Q water. Then both the Cy5.5-AEMA and Gd-DOTA AEMA solutions were added into the reaction. The polymerization was kept at 100° C. for 1 h.

Figure 39:
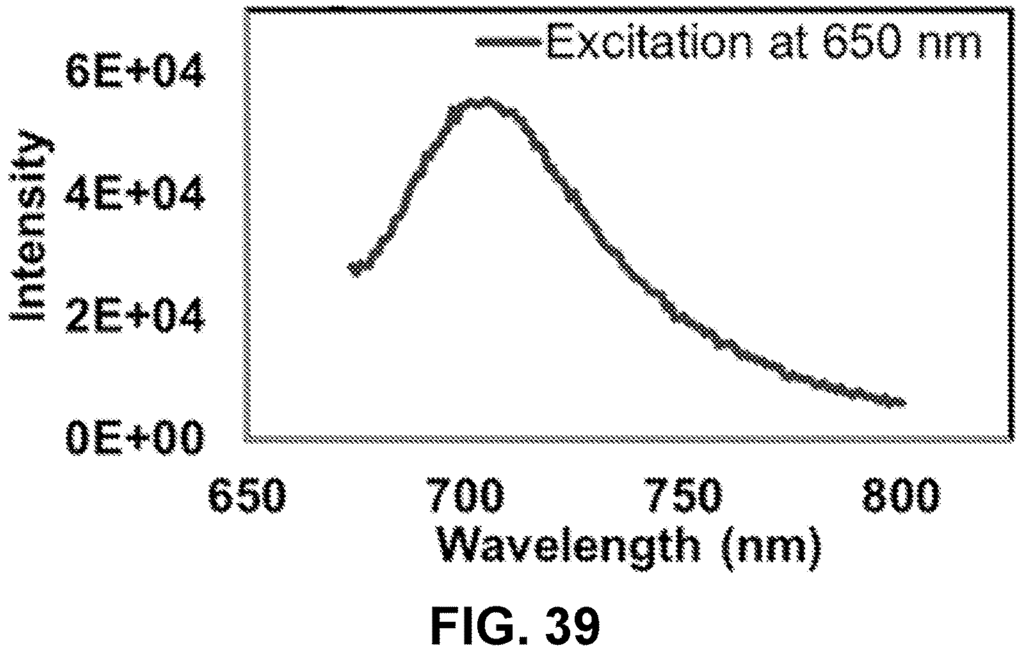
FIG. 39: Fluorescence Spectra of 1st Generation Gd-DOTA Nano-tracers Excited at 650 nm.
Figure 40:
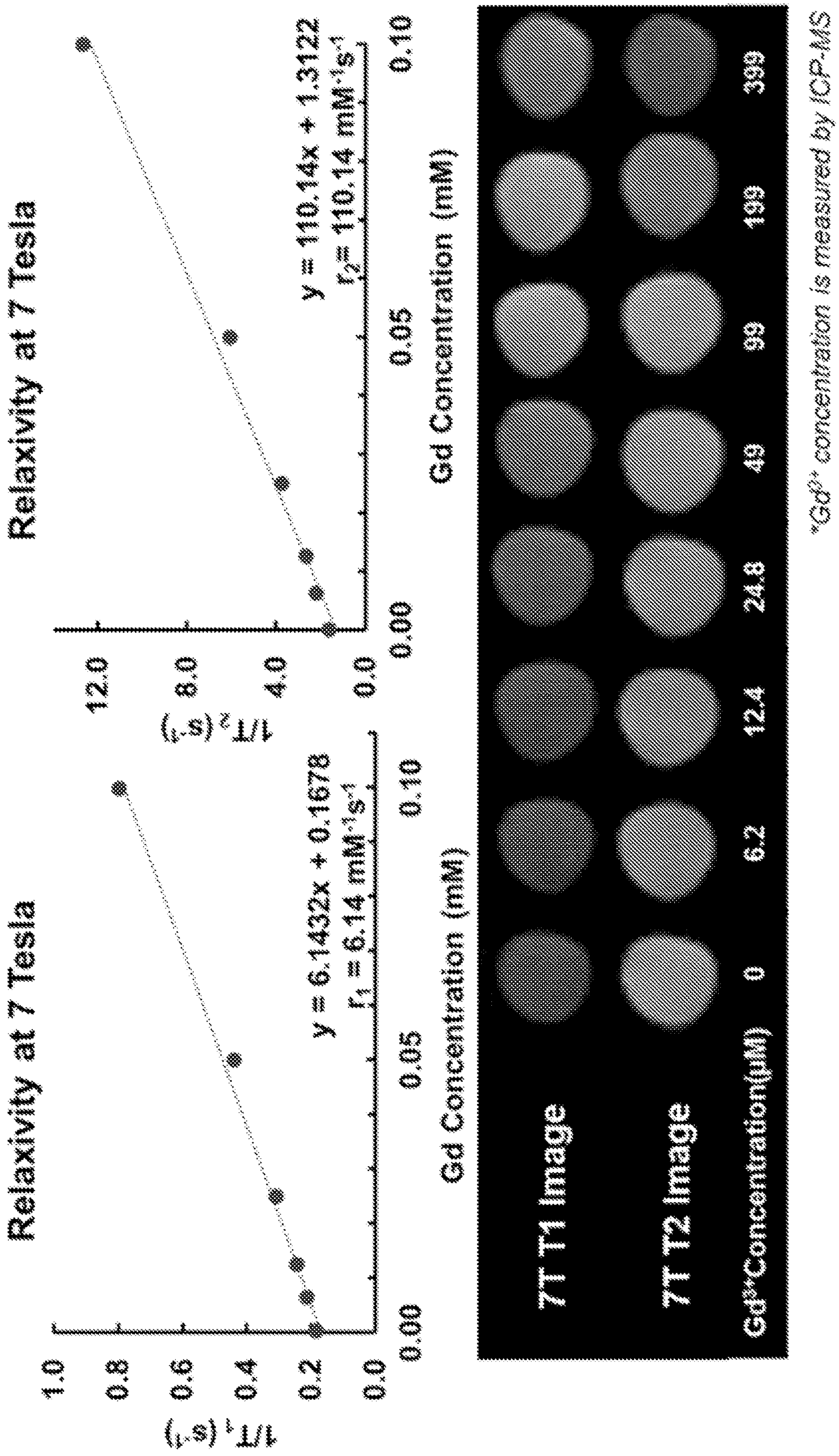
FIG. 40: $r_1$ and $r_2$ Relaxivities and $T_1$, $T_2$-weighted Images of Gd-Cy5.5 Nano-tracer.

The morphologies of Gd-Cy5.5 nano-tracer was characterized by SEM, uranyl acetate stained dry-state TEM, and cyro-EM (FIGS. 38A-38E). Particle concentration is 4.24×$10^{12}$, which was determined by NTA. FIGS. 38A-38E show a screenshot from the NTA video. By DLS, the hydrodynamic diameter of the Gd-Cy5.5 nano-tracer is 158 nm. Since the nano-tracer is incorporated with Cy5.5, the emission profile was examined and shown in FIG. 39. The emission maxima ($\lambda_{em}$) is 706 nm and the fluorescence profile matches Cy5.5-AEMA Nano-tracers. Zeta potential was determined to be −19.2 mV.

Moreover, the mass concentration of the Gd-Cy5.5 nano-tracer was determined to be 47.67 mg/mL. Gd concentration was measured by Inductively coupled plasma mass spectrometry (ICP-MS), which was 369.8 μM. Thus, the Gd concentration per particle is 8.72×$10^{-14}$ μM/particle.

Additionally, the longitudinal and transverse relaxation time ($T_1$ and $T_2$) of the Gd-Cy5.5 nano-tracer were measured by MRI phantom scans using a Bruker 7.0 T magnet with Avance II hardware equipped with a 72 mm quadrature transmit/receive coil. $T_1$ and $T_2$ contrast was determined by selecting regions of interest (ROI) using Software ParaVision Version 5.1. The parameters for 7T MRI are repetition time (TR)=1250.0 ms, echo time (TE)=12.6 ms, echo=1/1, Field-of-view (FOV)=7.31/3.12 cm, slice thickness=1 mm, nex=1 mm, matrix=256*116. The $r_1$ value of Gd-Cy5.5 nano-tracer is 6.14 $mM^{-1}s^{-1}$, $r_2$ value is 110.14 $mM^{-1}s^{-1}$, and the $r_2/r_1$ value is 14.17.

Incorporating an MRI contrast agent in the nano-tracers will allow in vivo imaging and enable whole-brain scans in larger animals, eventually even in primates. The dual-labeled nano-tracers enable the examination of the same animal through multiple imaging techniques following a single in vivo procedure.

In Vivo Studies of Gd-Cy5.5 Nano-Tracer

Figure 41:
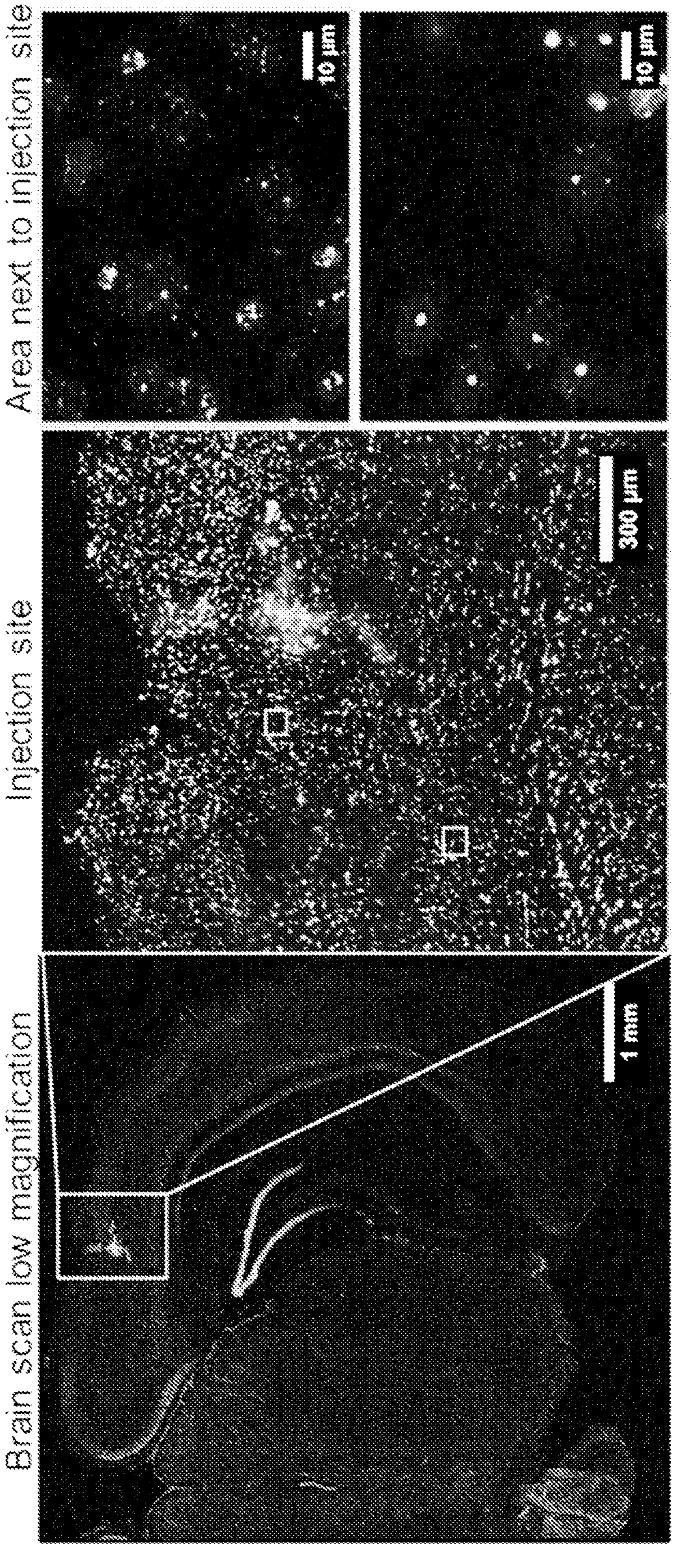
FIG. 41: Fluorescence Images of the Gd-Cy5.5 Nano-tracer Retrograde Ability Test at the Injection Site.

The retrograde ability test of the Gd-Cy5.5 nano-tracer was conducted in the V1 to LGN neuronal projection system. The surgical procedure is the same as described elsewhere herein, particularly as described in Example 1. The results from confocal images confirmed (FIG. 41) that nano-tracers were injected into the V1 region. Two different areas proximal to the injection site were examined, and Gd-Cy5.5 nano-tracers were observed in neurons located in the two areas.

Figure 42:
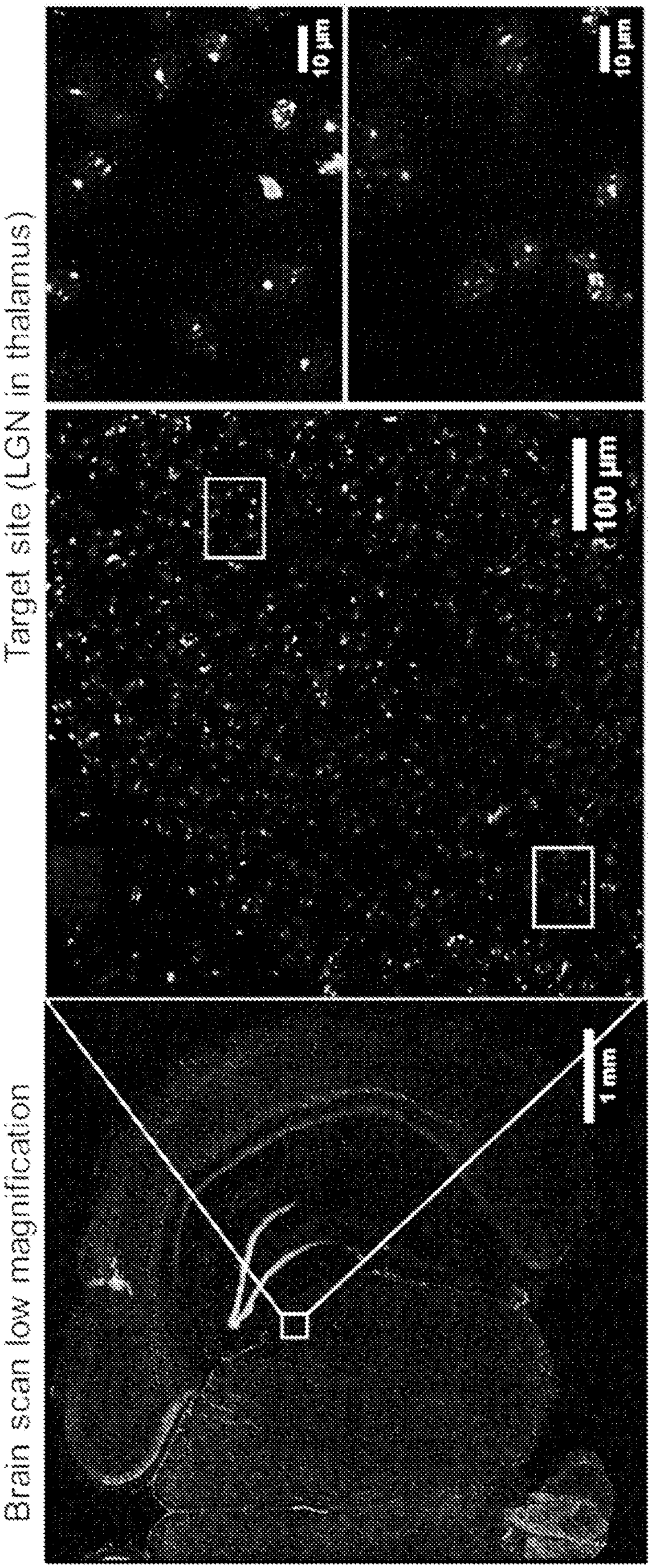
FIG. 42: Fluorescence Images of the Gd-Cy5.5 Nano-tracer Retrograde Ability Test at the Target Site.

Further, two areas in LGN were imaged. FIG. 42 shows that both of the areas were labeled by Gd-Cy5.5 nano-tracers, which suggests that the nano-tracers underwent retrograde transport to the LGN area. The result confirmed that adding the Gd-AEMA monomer into a nano-tracer does not affect its retrograde transportation ability.

Figure 43B:
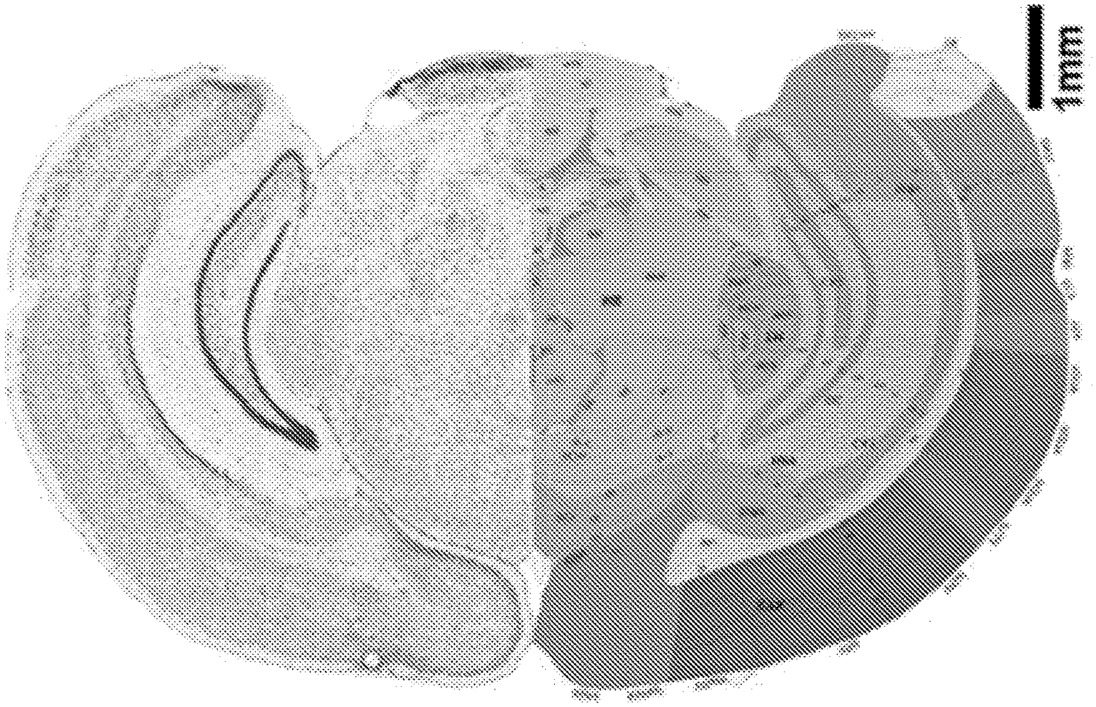
FIGS. 43A-43E: ICP-Laser Ablation Mapping Analysis and Fluorescence Analysis.
Figure 43A:
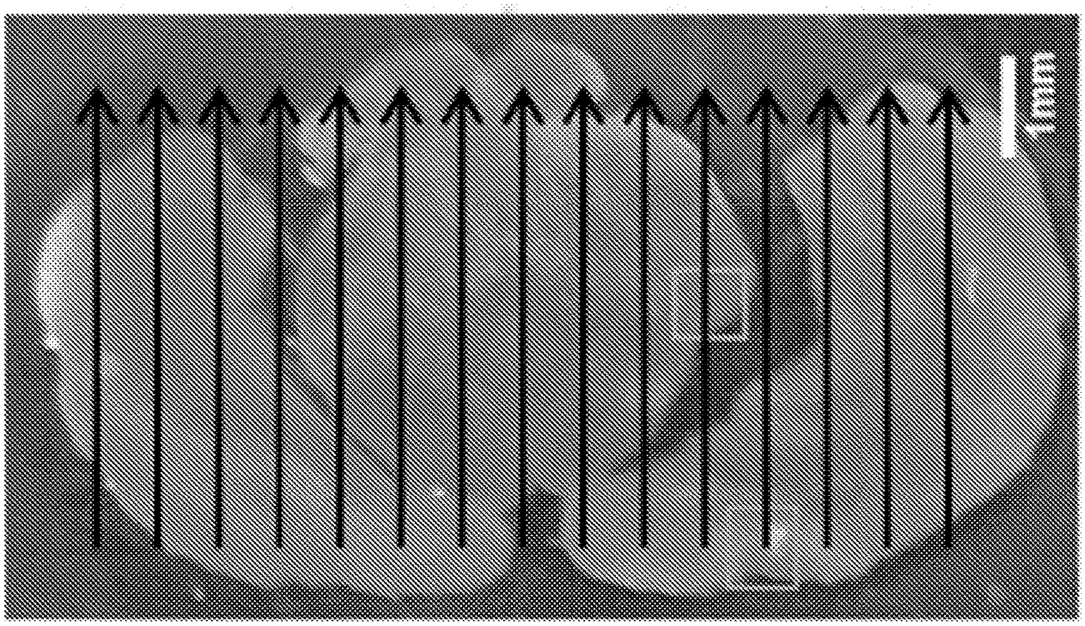
Figure 43C:
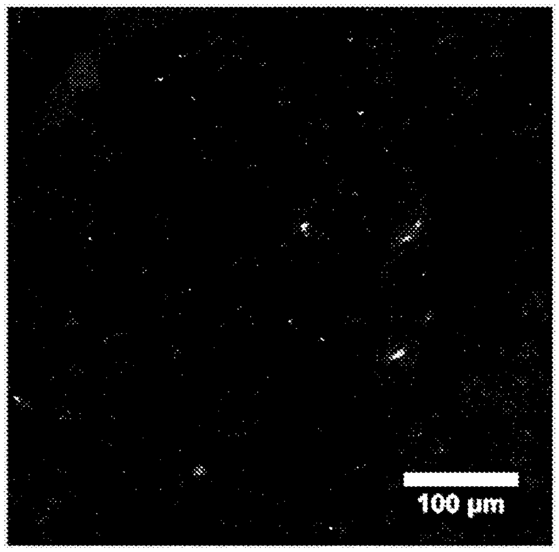
Figure 43D:
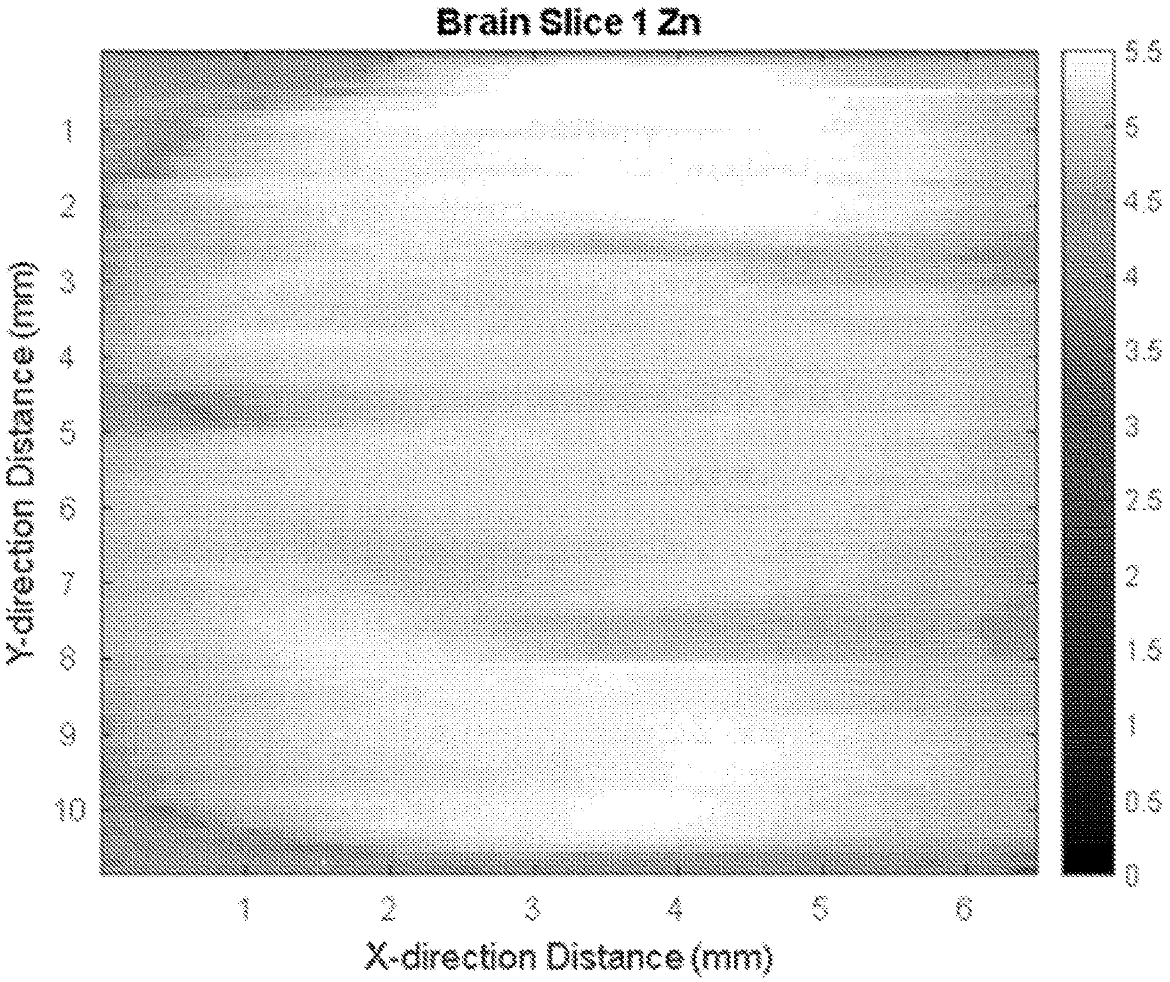
Figure 43E:
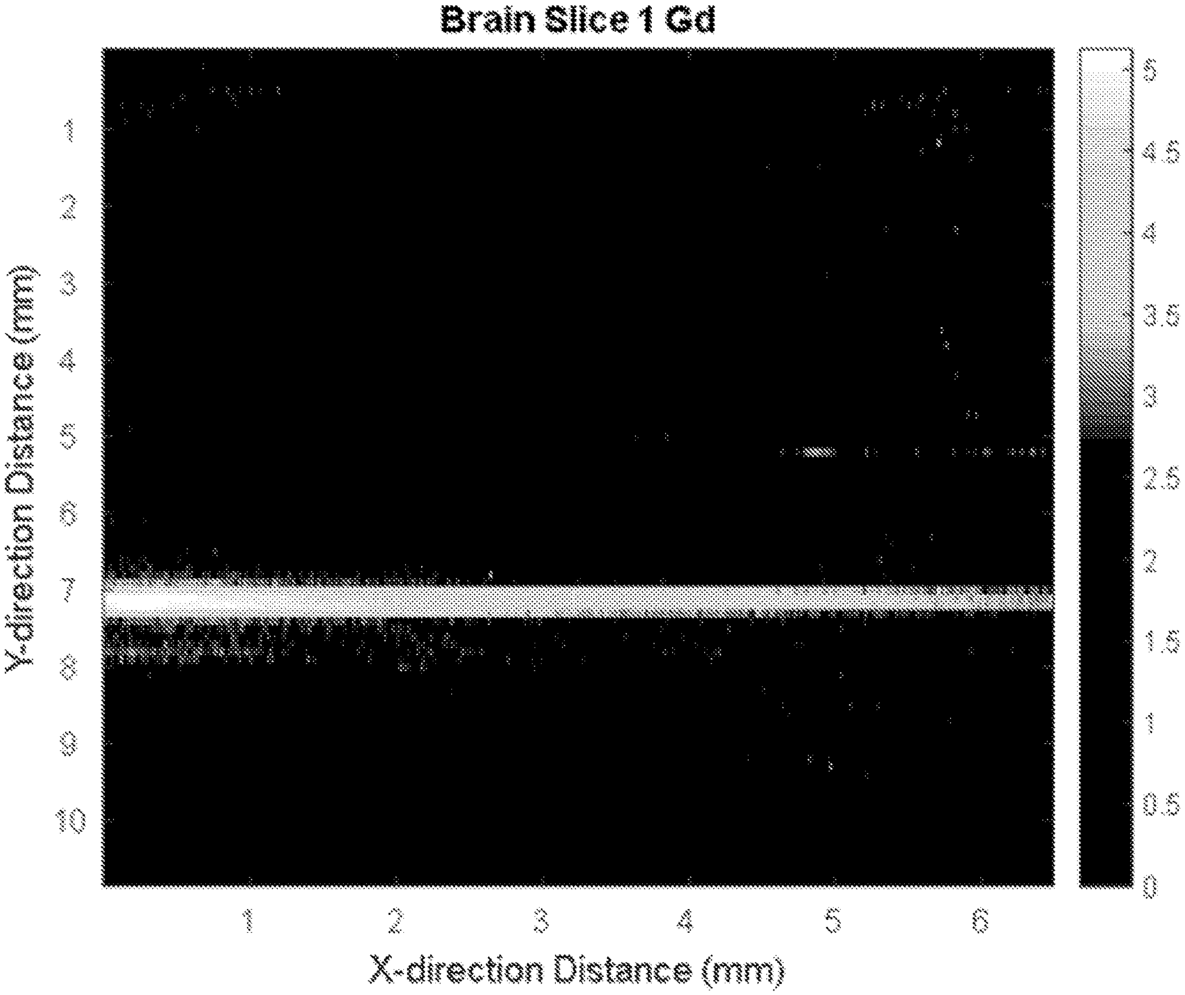

To validate the retrograde transportation from the elemental perspective, laser-ablation ICP-MS (LA-ICP-MS) was used for the analysis. LA-ICP-MS was performed by ablating a circular spot into the brain slice of interest. It provides the spatially resolved mapping of elements of the brain slice(48). Ablation was performed at 20 Hz laser frequency with a 100 μm×100 μm laser aperture. The scan speed was 200 μm/s. There were a total of 109 lines scanned in the brain slice region of interest. However, LA-ICP-MS analysis is destructive. So, the optical image and fluorescence images of the brain slice were taken prior to LC-ICP-MS analysis. FIG. 43A shows the optical image of the brain slice containing both the V1 injection site (orange box) and the LGN target site (green box). The arrows show the moving direction of the laser that occurs when scanning. FIG. 43B shows how the corresponding brain atlas assisted in finding the area of the interest anatomically. FIG. 43C illustrates the fluorescence image of the LGN area that corresponds to the area of the green box, which confirms that the Gd-Cy5.5 nano-tracers are transported to the target site. FIGS. 43D-43E present the LA-ICP-MS element maps of Zn and Gd. In the Gd element map, at the 7 mm from Y direction, a strong signal was observed at the V1 area. We can observe that the scanning direction of the X axis has a lot of saturation. The signal from previous values of X affect the signals detected in larger values of X, and the signal intensity tends to decrease as X increases. At the position X=4.7 mm, Y=5 mm, the bright spot of the signal indicates the existence of Gd-Cy5.5 nano-tracers at the LGN target site.

In addition, an in vivo injection and an ex vivo MRI scan was conducted in P0 mice. The surgical procedure is the same as described elsewhere herein (e.g., Example 1). The animal model was changed from the adult mouse to the P0 mouse, because the MRI scanning time exponentially increases with the size of the brain. The size of an adult mouse is 500 $mm^3$ (49), while the P0 mouse brain size is 100 $mm^3$ (50, 51).

Gd-Cy5.5 nano-tracers were injected into the visual cortex area of the the right hemisphere in the P0 mouse. Unlike previous in vivo injections that only inject at one depth at the injection site, three depths of 600 μm, 400 μm, and 200 μm from the brain pial surface were carried out for the ex vivo MRI scan experiment. Approximately 160 nL of Gd-Cy5.5 nano-tracers was injected at each depth. The mouse was sacrificed 2 hours after the injection, and the brain was perfused afterward. The whole perfused brain was scanned by a 7 T MRI, using the optimized scanning condition developed by Dr. Robert Russel from the Center for Functional MRI in the department of radiology at UCSD.

Since the 7 T MRI cylinder is designed for scanning a live mouse, a special holder needs to be designed specifically for this ex vivo scan. The apparatus that holds the mouse brain is made of a plastic test tube with a rubber septum. Galden HT200 is filled in the tube, which is a high boiling point dielectric perfluorinated polyethers. A desired amount of cotton is surrounded by the mouse brain to minimize vibration during the scan. Since air bubbles create artifacts during the scan, a needle syringe is usually used to remove air bubbles after assembling the holder.

Figure 44A:
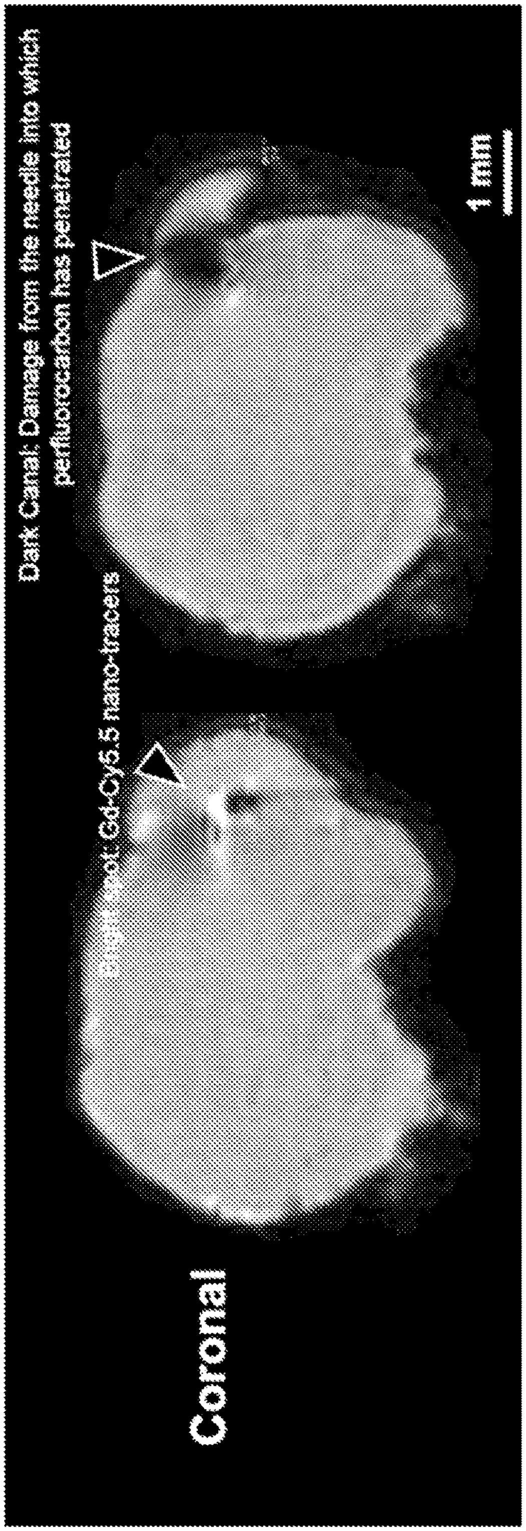
FIGS. 44A-44B: Ex vivo MRI 7T Scan of P0 Mouse Brain.
Figure 44B:
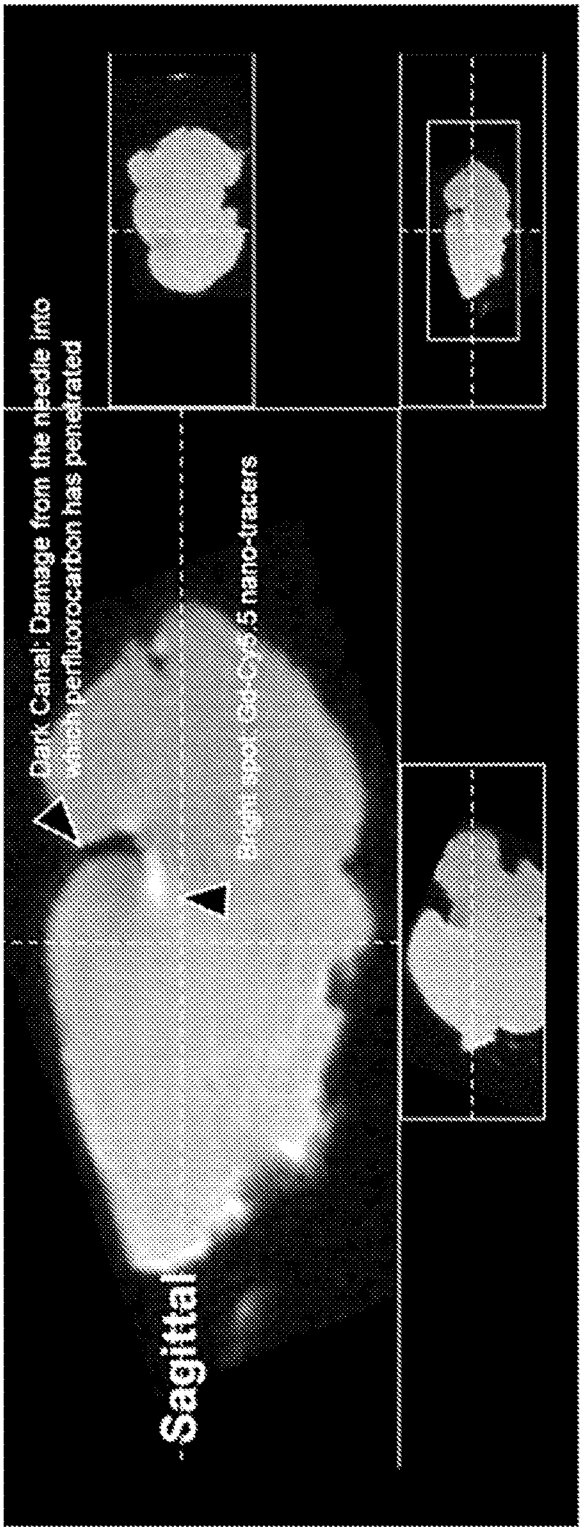

FIGS. 44A-44B show the ex vivo MRI scan result of the P0 mouse brain injected with Gd-Cy5.5 nano-tracers. FIG. 44A is the coronal view of the selected plans of the brain. The white spot indicates the existence of Gd-Cy5.5 nano-tracers, and the position of the white spot is within the V1 area from an anatomical perspective. The dark canal observed indicates that there is tissue damage from the injection needle where the perfluorocarbon penetrates into the damaged part of brain. However, after carefully searching the imaging result, we are not be able to see the target site lit up in the MRI image.

Figure 45A:
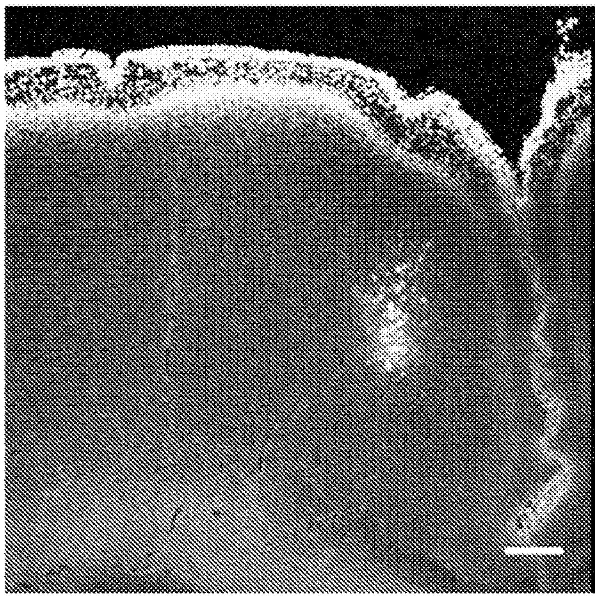
FIGS. 45A-45B: Confocal Images of the Gd-Cy5.5 Nano-tracer Retrograde Ability Test (FIG. 45A) at the Injection Site and (FIG. 45B) at the Target Site. Scale Bar is 100 μm.
Figure 45B:
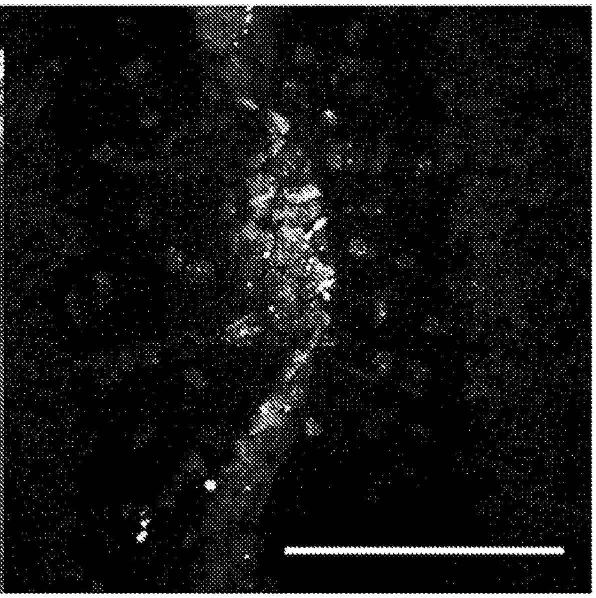

After the MRI scan, the brain was taken out of the scanning device, washed with MILLI-Q water three times, and sliced in the coronal plane. The brain slices were imaged under confocal microscopy where Gd-Cy5.5 nano-tracers were observed both at the V1 injection site and the LGN target site by confocal microscopy. See FIGS. 45A-45B.

Figure 46:
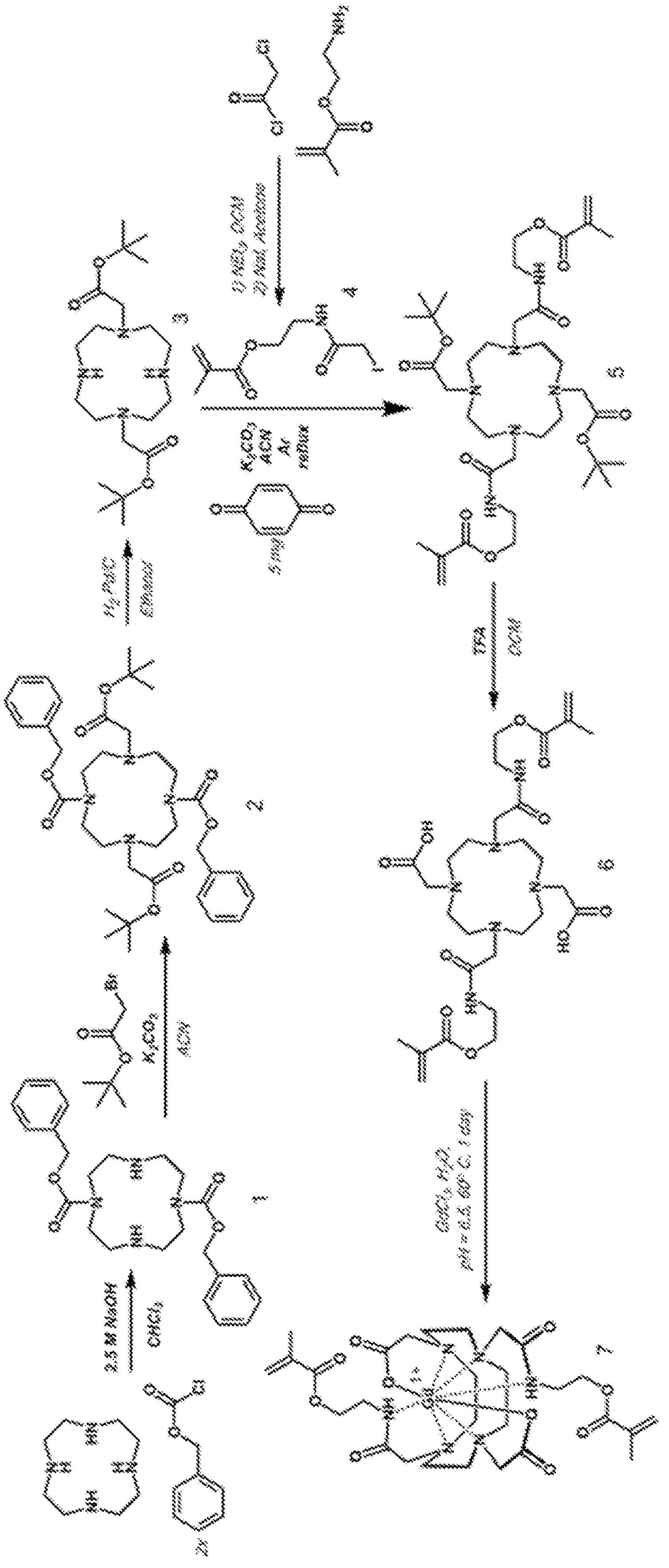
FIG. 46: Synthetic Route of Diacrylate Cross-linker Bridged by Gd-DOTA.

$2^{nd}$ Generation Gd-DOTA Nano-Tracers: Gd-DOTA Cross-linker-Rhodamine Nano-Tracers Synthesis and Characterization of the Diacrylate Cross-Linker Bridged by Gd-DOTA the 2-Arms Gd-DOTA Cross-linker Because mice have brain volumes that are small, only a limited amount of nano-tracers can be injected without damaging the brain, since the nano-tracers take up physical space within the very small brain area. In larger vertebrates, this limitation does not exist, as the volume of the nano-tracers relative to the total brain volume is much smaller. Thus, it is recognized that the studies involving mice, though necessary to progress the development of nano-tracers, have their own unique considerations that do not necessarily apply to larger animals or other organisms. Therefore, the Gd concentration within each Nano-tracer was increased, so that fewer nano-tracers need to be injected to observe the same signal level intensity of MRI scans as would be seen in larger vertebrates. Because of the two acrylate arms on Gd-DOTA, its vibration and free rotation will be constrained, resulting in a lower rotational correlation time and a higher relaxivity. Towards this end, Gd-DOTA appended with two acrylate functionalities was designed and synthesized from 1,4,7,10-tetraazacyclododecane (cyclen) as a polymer chain crosslinker (FIG. 46).

The two amines on trans positions of cyclen were protected by slowly adding benzyl chloroformate at 0° C. overnight. Then trans-substituted cyclen was reacted with tert-butyl bromoacetate at 90° C. at reflux overnight, followed by catalytic hydrogenation to remove the benzyl groups on the 4 and 10 positions.(52) AEMA was reacted with chloroacetyl chloride followed by refluxing with sodium iodide in acetone. 2-(2-iodoacetamido) ethyl methacrylate was then reacted with the di-tert-butyl 2,2'-(1,4,7,10-tetraazacyclododecane-1,7-diyl) diacetate in the presence of hydroquinone and potassium carbonate. This afforded the protected version of the DOTA chelator, with two methacrylate arms on the 4 and 10 positions (Compound 4). TFA was used to deprotect the 2 tert-butyl groups (Compound 5). To chelate Gd to the deprotected DOTA, gadolinium chloride was mixed in the DOTA solution at pH=6.5. This resulted in the final product: Gd-DOTA modified with 2 pendant acrylate groups in positions 4 and 10 (Compound 6).

Synthesis of dibenzyl 1,4,7,10-tetraazacyclododecane-1,7-dicarboxylate. Cyclen (10 g, 58 mmol) was dissolved in anhydrous chloroform and the reaction system was cooled down to 0° C. by ice bath under argon. Benzyl carbonochloridate (19.8 g, 116 mmol) was added to the reaction dropwise with vigorous stirring. The reaction was concentrated to dryness and washed by diethyl ether (×3), 3M of NaOH. The aqueous suspension was extracted by DCM (×4) and the organic layer was dried over Na2SO4, filtered, and concentrated to dryness to give a white powder under the vacuum. Yield: 21.70 g, 85%. $^1$H NMR ($CDCl_3$): δ=7.28 (m, 10H), 5.15 (s, 4H), 3.47 (br, 8H), 2.83 (br, 8H). HR-MS (ESI-TOF): m/z (%) $[M+H]^+$ calcd for C24H32N4O4: 440.24, found: 441.27.

Synthesis of dibenzyl 4,10-bis(2-(tert-butoxy)-2-oxoethyl)-1,4,7,10-tetraazacyclododecane-1,7-dicarboxylate. 1 (21.7 g, 49.3 mmol) and potassium carbonate (17.01 g, 123.9 mmol) was added into anhydrous ACN under argon. Then tert-butyl 2-bromoacetate (14.54 mL, 98.6 mmol) was added at room temperature. The reaction was heated to 90° C. overnight. The reaction was filtered and concentrated to dryness and purified by flash chromatography (EtOAc and hexane, 60:40). Yield: 25 g, 76%. HR-MS (ESI-TOF): m/z (%) $[M+H]^+$ calcd for $C_{35}H_{52}N_4O_8$: 669.38, found: 669.67.

Synthesis of di-tert-butyl 2,2'-(1,4,7,10-tetraazacyclododecane-1,7-diyl)diacetate. A mixture of 3 (25 g, 37.4 mmol) and 10% Pd/C in methanol was stirred under hydrogen atmosphere at 100 psi at room temperature for 48 hours. The mixture was filtered through Celite (Sigma-Aldrich) and washed with methanol (×3), EtOAc (×2), water concentrated to dryness. The semi-oil product was re-dissolved to DCM, extracted by hexane and concentrated to dryness under vacuum. Yield: 13.25 g, 88.5%. HR-MS (ESI-TOF): m/z (%) $[M+H]^+$ calcd for $C_{20}H_{40}N_4O_4$: 401.30, found: 401.88.

Synthesis of 2-(2-iodoacetamido)ethyl methacrylate. AEMA (10 g, 60.37 mmol) and chloroacetyl chloride (6.819 g, 60.37 mmol) was dissolved in anhydrous DCM under argon. Triethylamine was added into the reaction dropwise at 0° C. After 8 hours, the reaction turned bright orange. The solution was washed by 0.1 M hydrogen chloride (HCl) (×3), saturated sodium bicarbonate, water and concentrated to dryness. Black oil was obtained. Yield: 11.36 g, 91.5%. Then the product (11.36 g 55.2 mmol), NaI (41.5 g, 276 mmol), and hydroquinone were dissolved in anhydrous acetone and heated to 40° C. for 48 hours. The reaction was filtered, and the resulting solvent was evaporated and re-dissolved in DCM. Then the solution was passed through celite, then filtered and further purified by flash chromatography (100% EtOAc). Yield: 11.43 g, 70%. $^1$H NMR ($CDCl_3$): δ=6.42 (br, 1H), 6.15 (s, 1H), 5.62 (s, 1H), 4.27 (t, 2H), 3.71 (s, 2H), 3.60 (q, 2H), 1.96 (s, 3H). HR-MS (ESI-TOF): m/z (%) $[M+H]^+$ calcd for $C_3H_{12}IN_3$: 297.99, found: 298.02. Although AEMA was employed in this example to append two vinyl groups to the chelate group, any other suitable compound may be employed to link the chelate moiety to two vinyl groups.

Synthesis of ((2,2'-(4,10-bis(2-(tert-butoxy)-2-oxoethyl)-1,4,7,10-tetraazacyclododecane-1,7-diyl)bis(acetyl))bis(azanediyl))bis(ethane-2,1-diyl) bis(2-methylacrylate). 3 (7.55 g, 18.9 mmol), 4 (11.5 g, 38.7 mmol) and potassium carbonate was added to anhydrous ACN. The reaction was heated to 60° C. reflux for 2 hours. Then the mixture was filtered, concentrated, and re-dissolved to EtOAc. The solid was filtered again and washed with ACN and hexane. The solvent was evaporated, and the product was dried under the vacuum. Yield: 10 g, 75%. $^1$H NMR ($CDCl_3$): δ=7.20 (t, 2H), 6.15 (s, 2H), 5.55 (s, 2H), 4.20 (t, 4H), 3.51 (t, 4H), 3.30-2.19 (m, 24H), 1.92 (s, 6H), 1.41 (s, 18H). HR-MS (ESI-TOF): m/z (%) [M+H]+ calcd for C36H62N6O10: 739.45, found: 739.37.

Deprotection of ((2,2'-(4,10-bis(2-(tert-butoxy)-2-oxoethyl)-1,4,7,10-tetraazacyclododecane-1,7-diyl)bis(acetyl))bis(azanediyl))bis(ethane-2,1-diyl) bis(2-methylacrylate). 5 (10 g, 13.5 mmol) were deprotected by 20% TFA in anhydrous DCM in the presence of hydroquinone under an argon atmosphere. The reaction completed after 12 hours and was concentrated to dryness. The yellow solid was re-dissolved in water and extracted with DCM followed by ×3 DCM wash. The solution was lyophilized to get monomer 6. Yield: 8.48 g, 84.8%. $^1$H NMR (DMSO-$d_6$): δ=6.1 (s, 2H), 5.70 (s, 2H), 4.27 (t, 4H), 4.02 (s, 4H), 3.70 (br, 4H), 3.53 (q, 4H), 3.38-3.21 (m, 16H), 1.87 (s, 6H). HR-MS (ESI-TOF): m/z (%) $[M+Na]^+$ calcd for $C_{28}H_{46}N_6O_{10}$: 649.33, found: 649.46.

Chelation of 2,2'-(4,10-bis(2-((2-(methactyloyloxy)ethyl)amino)-2-oxoethyl)-1,4,7,10-tetraazacyclododecane-1,7-diyl)diacetic acid. 6 (8.48 g, 13.53 mmol) and gadolinium chloride (10.06 g, 27.06 mmol) was added into degassed water in the presence of hydroquinone under argon. 1 mol/L degassed NaOH was added to the reaction to adjust the pH=6.0. The reaction was monitored and maintained at a pH of 7. The reaction was heated to 60° C. for one day. The precipitate was filtered and lyophilized. Then the powder was re-dissolved in degassed acetone and filtered. The solution was dried over $Na_2SO_4$, and filtered and concentrated to dryness to give a white powder under vacuum. Yield: 4.1 g, 39.5%. HR-MS (ESI-TOF): m/z (%)$[M-2H]^-$ calcd for $C_{27}H_{42}GdN_6O_{10}$: 780.24, found: 780.57.

Synthesis and Characterization of 2$^{nd}$ Generation Gd-DOTA Nano-Tracers: Gd-DOTA Crosslinker-Rhodamine Nano-Tracers The Gd-DOTA crosslinker-rhodamine dual labeled nano-tracer is (Gd-Crosslinker-Rhodamine nano-tracer) designed to improve the R1 value of the nano-tracer in order to inject less volume of the nano-tracer's solution during an in vivo experiment. The polymerization condition of the Gd-DOTA crosslinker-rhodamine nano-tracer was identical to Section 2.9.1. 20.98 mg methacryloxyethyl thiocarbamoyl rhodamine B was first dissolved into 0.2 mL of methanol and 0.6 mL of MILLI-Q water was then added into the dye solution. 507 mg Gd-DOTA crosslinker was dissolved in 3.6 mL of MILLI-Q water. Then both the dye solution and Gd-DOTA crosslinker solutions were added into the reaction. The polymerization was kept at 75° C. for 1 h.

Figure 47A:
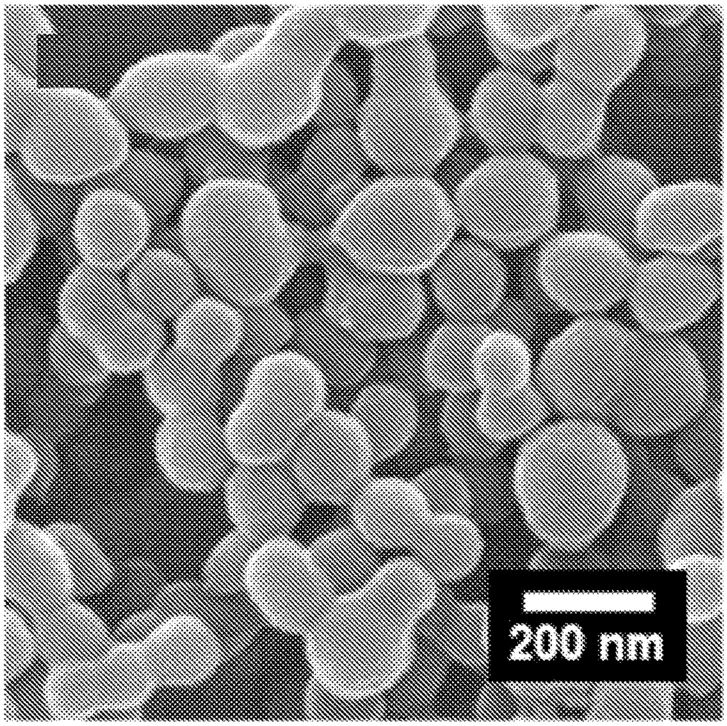
FIGS. 47A-47B: Characterization of the Gd-Crosslinker-Rhodamine Nano-tracer.
Figure 47B:
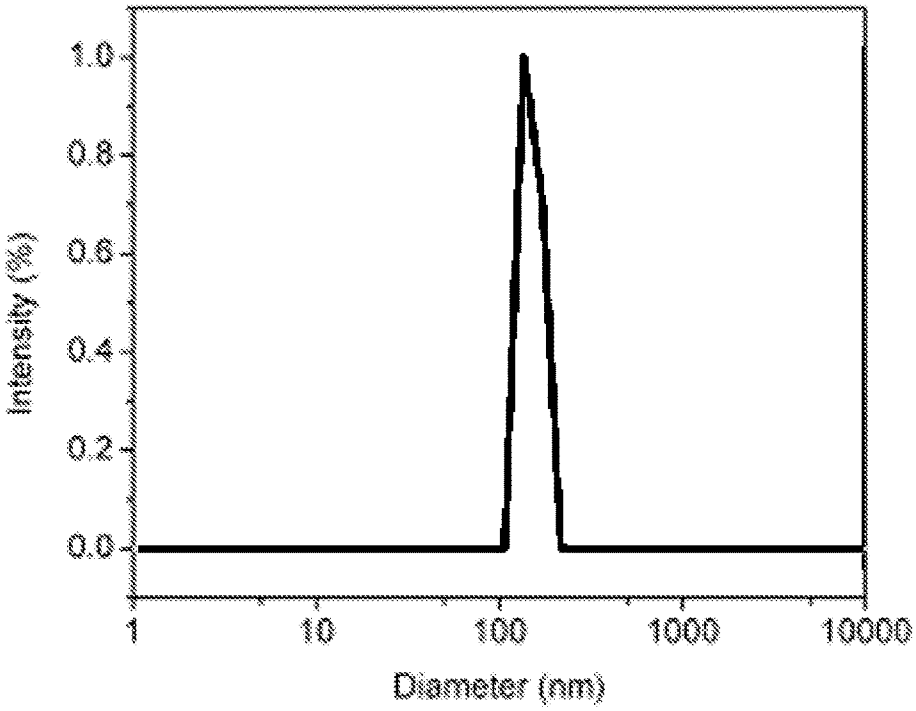
Figure 48A:
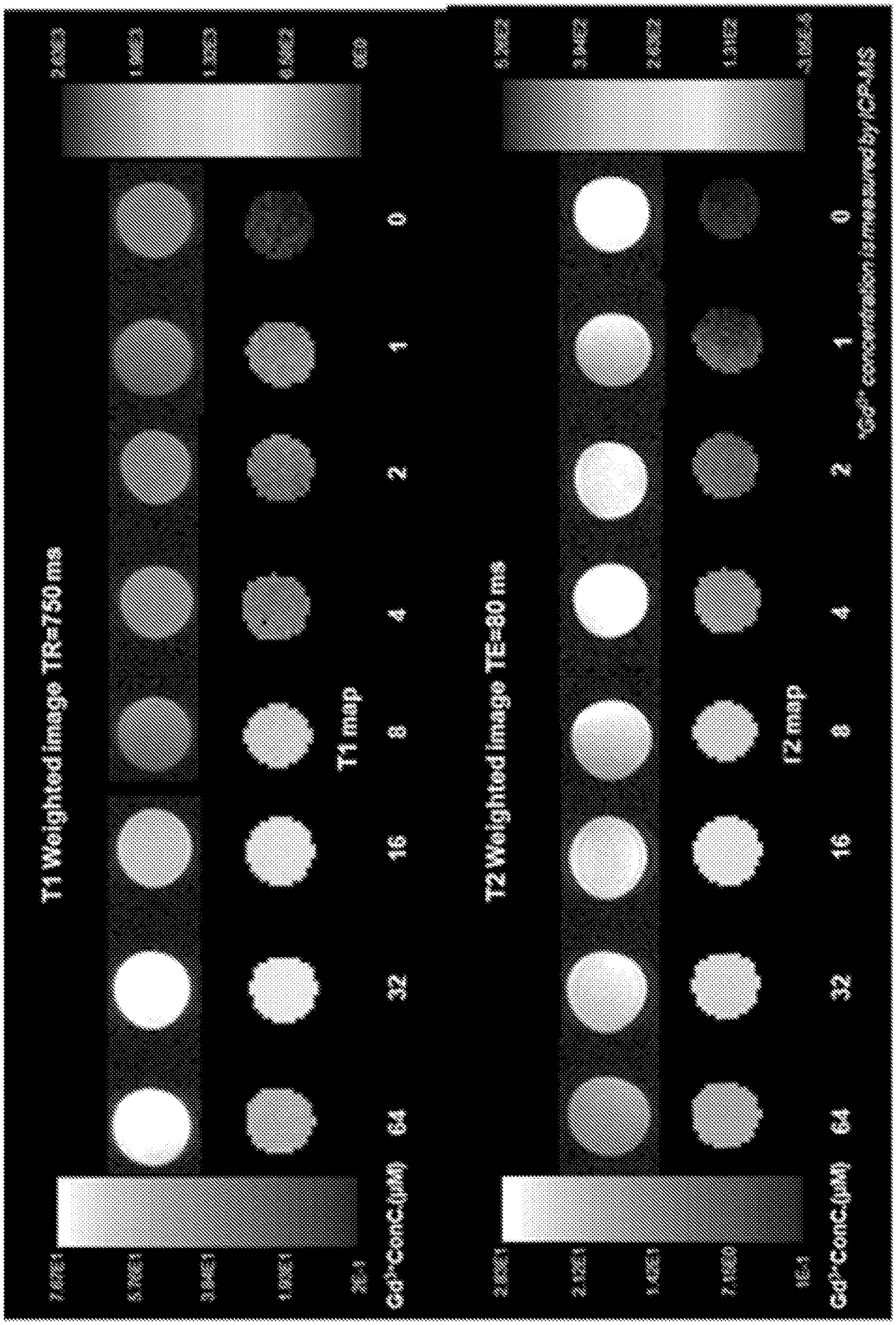
FIG. 48A: $T_1$, $T_2$-weighted Images and (FIG. 48B) $r_1$ and $r_2$ Relaxivities of Gd-Crosslinker-Rhodamine Nano-tracer.
Figure 48B:
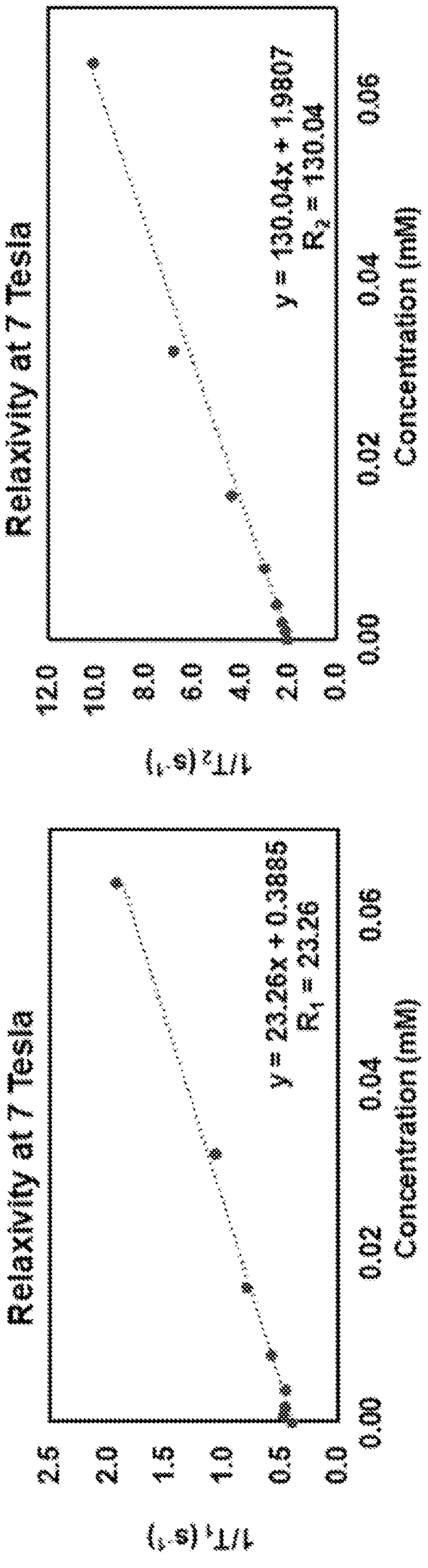
Figure 49:
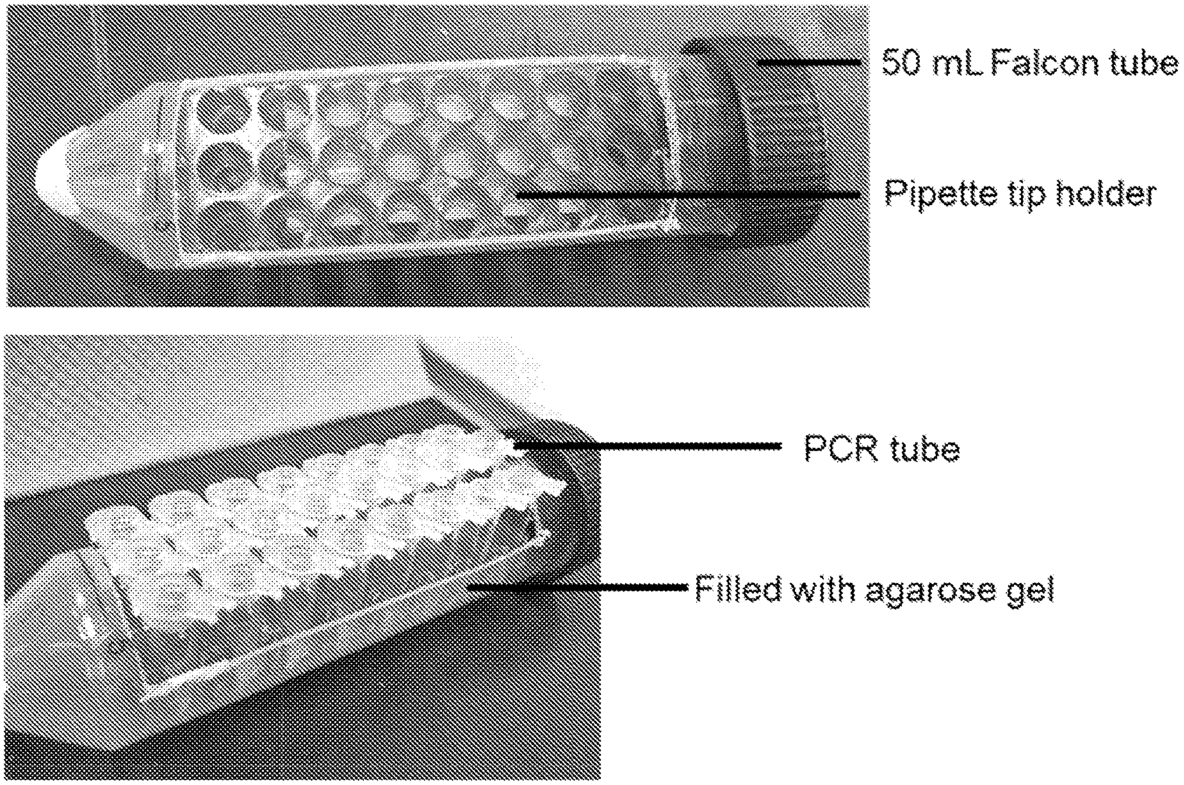
FIG. 49: The MRI Phantom Scan Sample Holder Designed by Gianneschi Lab.

The morphology of the Gd-Crosslinker-Rhodamine nano-tracer was characterized by SEM (FIGS. 47A-47B). By DLS, the hydrodynamic diameter of the Gd-Crosslinker-Rhodamine nano-tracer is 150.7 nm. The Zeta potential was determined to be −21.2 mV. The Gd concentration was measured by ICP-MS, which is 1946 μM. The theoretical Gd concentration is 2400 μM. About 81% of Gd-Crosslinker was incorporated into the nano-tracers. However, the Gd-Crosslinker leaked out from the nano-tracer after 4 months. The free Gd-crosslinker was removed by dialysis and the Gd concentration was remeasured by ICP-MS. The Gd-Cross-linker-Rhodamine nano-tracers contain 64 μM of Gd. It is reasonable to assume that employing the synthesized nano-tracer in a brain mapping or axonal tracing application more quickly than 4 months would enable suitable imaging. Alternatively, alternate polymerization conditions, including other conditions disclosed herein, may be employed to achieve a more stable Gd-containing nano-tracer.

Moreover, the longitudinal and transverse relaxation time ($T_1$ and $T_2$) of the Gd-Crosslinker-Rhodamine nano-tracer were measured by a Bruker 7.0 T magnet with Avance II hardware equipped with a 72 mm quadrature transmit/receive coil. $T_1$ and $T_2$ contrast was determined by selecting regions of interest (ROI) using Software ParaVision Version 5.1. The parameters for 7T MRI are: TR=1250.0 ms, TE=12.6 ms, echo=1/1, FOV=7.31/3.12 cm, slice thickness=1 mm, nex=1 mm, matrix=256*116. The $r_1$ value of Gd-Crosslinker-Rhodamine nano-tracer nano-tracer is 23.26 $mM^{-1}s^{-1}$, the $r_2$ value is 130.04 $mM^{-1}s^{-1}$, and the $r_2/r_1$ value is 5.59. We summarized the relaxivity of gadolinium-based nano-tracers in Table 3.

TABLE 3

Relaxivity of Gadolinium-based Nano-tracers

| Nano-tracers | $R_1$ | $R_2$ | $R_2/R_1$ |
|---|---|---|---|
| Gd-Cyanine 5.5 | 6.14 | 88.87 | 14.17 |
| Gd-Crosslinker-Rhodamine | 23.26 | 130.04 | 5.59 |

Development of Sample Holder for MRI Phantom Test

The MRI phantom scans in sections 0 and [0494] used the Bruker 7.0 T magnet with Avance II hardware equipped with a 72 mm quadrature transmit/receive radiofrequency coil (RF coil). This coil has a cylindrical shape and was originally designed for scanning live animals, not for phantom scanning. Since researchers rarely do phantom scans, the Center for Functional MRI at UCSD does not own a coil that could be used for phantom scans. Thus, a sample holder that can fit inside the RF coil was developed. In order to make the sample holder, first cut a rectangular cross-section out of the 50 mL Falcon tube; Second, insert a 3×8 matrix of the pipette tip holder inside of the Falcon tube; Third, fill the test sample into polymerase chain reaction (PCR) tubes; Fourth, fill the space in the Falcon tube with warmed agarose gel and wait until the agarose gel solidifies. However, there are some practical issues to consider when using this sample holder. First of all, the sample holder design is based on a Falcon tube that has a cap on one side of the holder. This asymmetrical shape makes the holder hard to level in the RF coil when scanning. Secondly, the PRC tubes do not fit perfectly in the holder, so not all of the PRC tubes are in an even level height. Thirdly, agarose gel is required in every scan to minimize the vibration of the tubes during the scan, but it takes a long time to solidify the agarose gel.

Figure 50A:
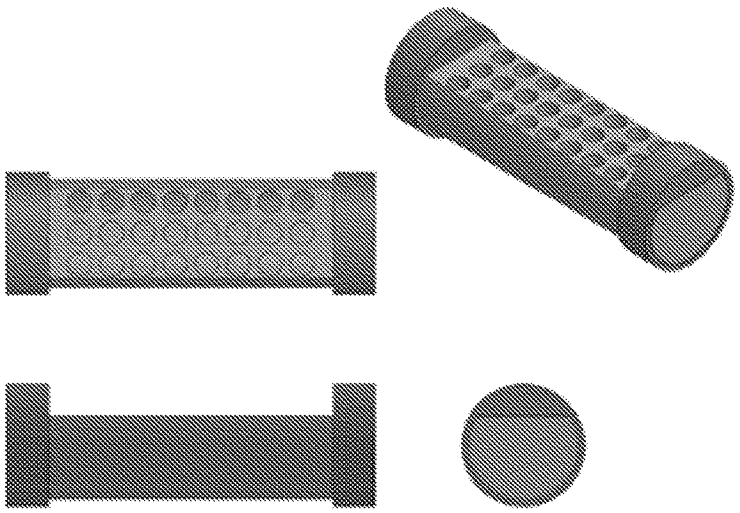
FIGS. 50A-50B: 3D Structure of the New Sample Holder.
Figure 50B:
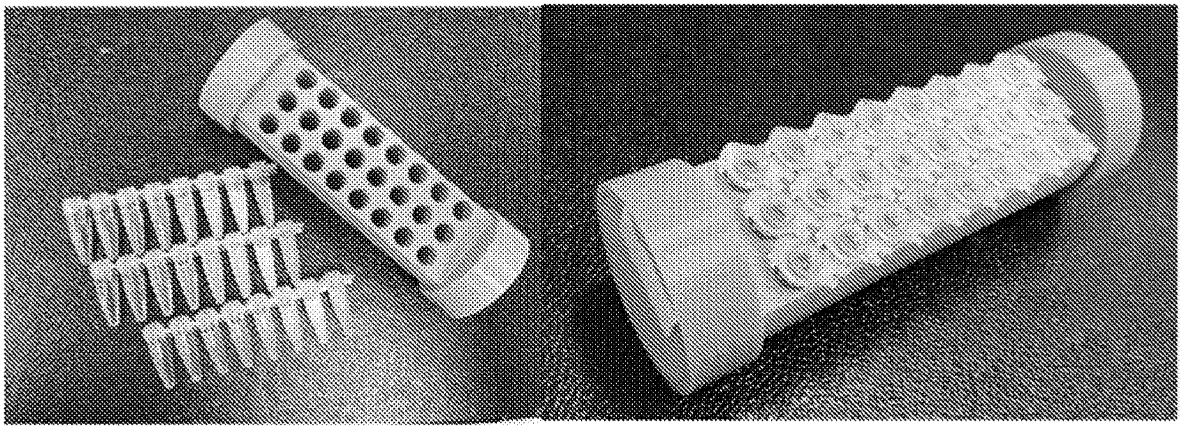
Figure 51A:
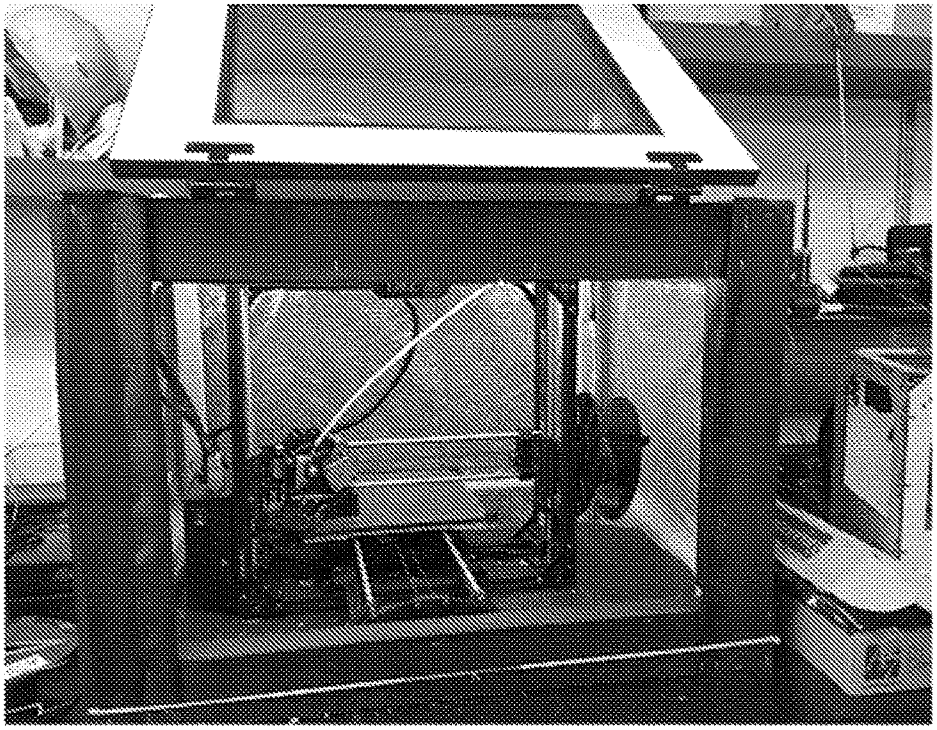
FIGS. 51A-51B: New Sample Holder by 3D printing.
Figure 51B:
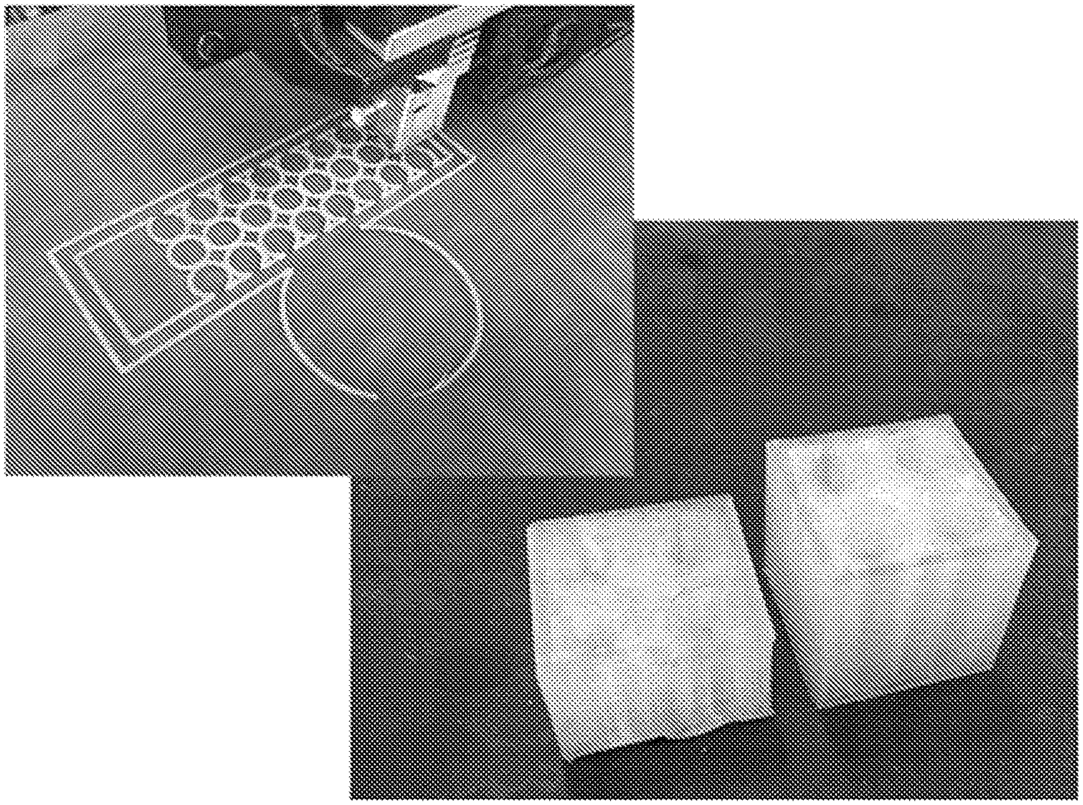

Thus, a new 3D printed sample holder that could fit in the RF coil was designed in Solidworks (FIGS. 50A-50B). The new sample holder is printed in UCSD Flow Control & Coordinated Robotics Lab in the Department of Mechanical and Aerospace Engineering (FIGS. 51A-51B).

Figure 52A:
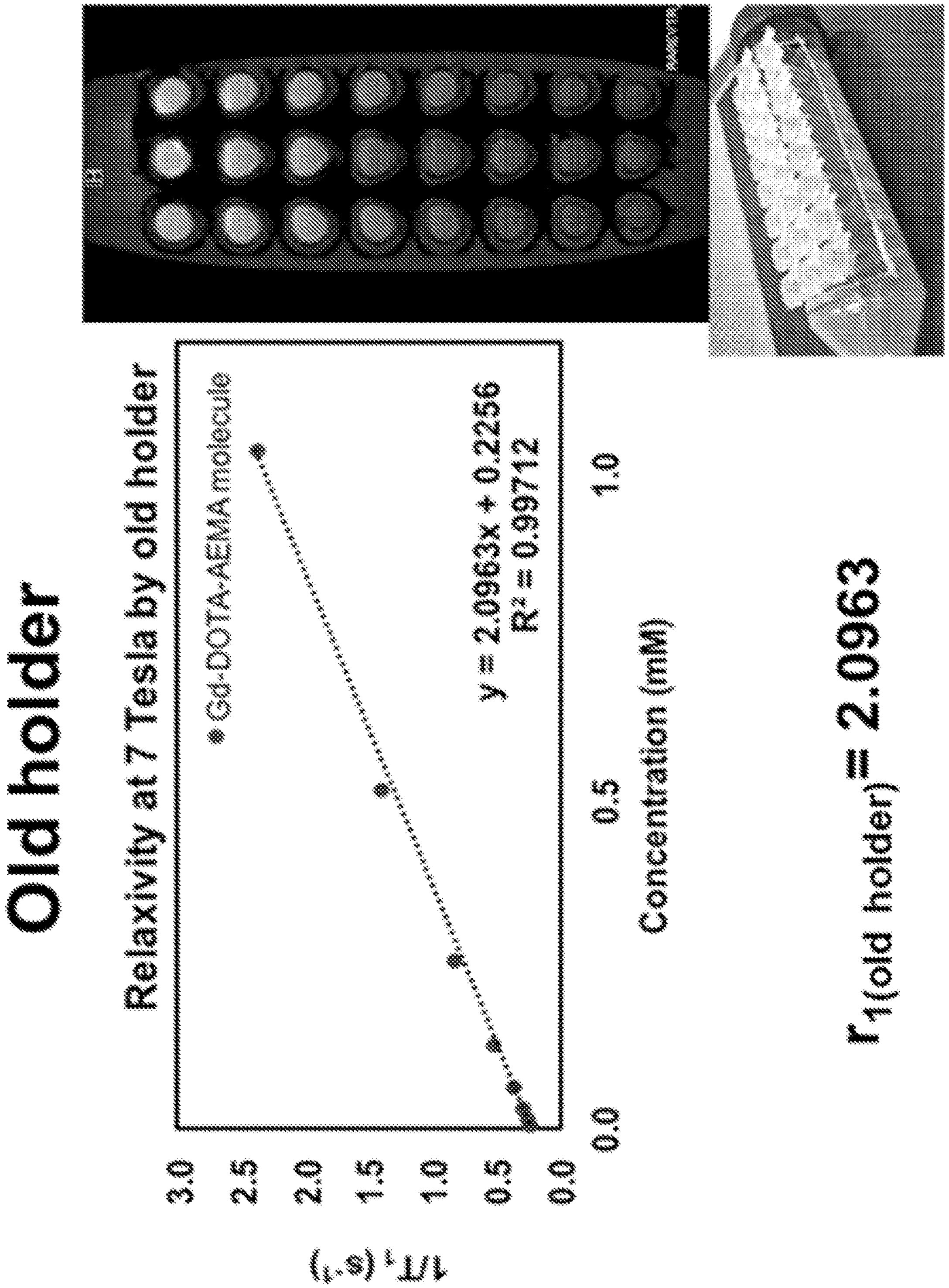
FIGS. 52A-52B: $r_1$ Relaxivity and $T_1$-weighted Image of Gd-DOTA-AEMA by (FIG. 52A) Old and (FIG. 52B) New Sample Holder.
Figure 52B:
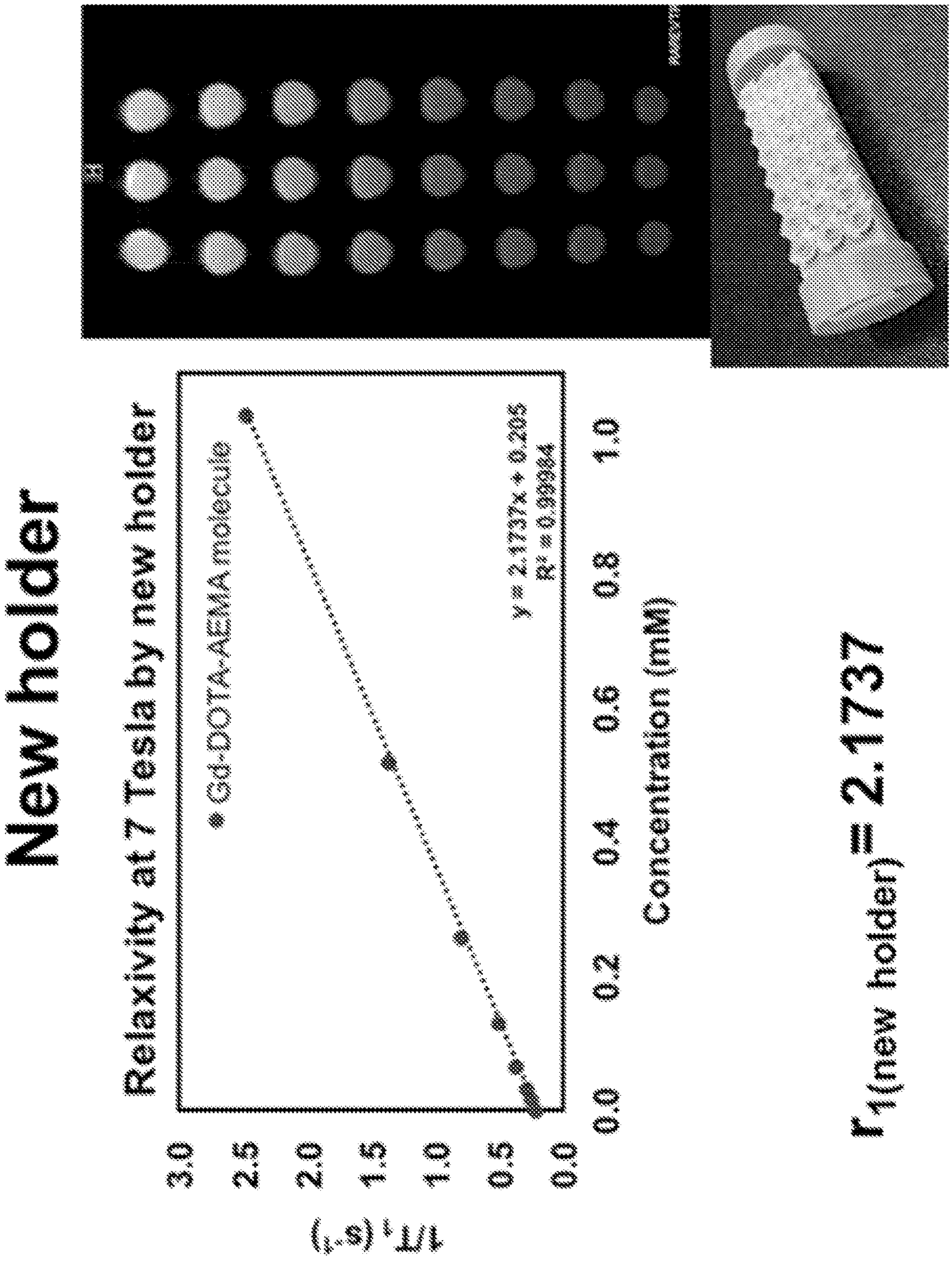

To test the reliability of the new 3D printed sample holder, different concentrations of the Gd-DOTA-AEMA monomer were added to the PCR tubes and scanned by MRI. The $T_1$ weighted images were captured and the $r_1$ value was calculated by the old holder and new holder separately (FIGS. 52A-52B). The $r_1$ of the old holder design of Gd-DOTA-AEMA equals 2.096 and the $r_1$ of the new holder equals 2.1737. The system error is 3.67%. This result indicates that the 3D printed new holder does not affect the test result of the MRI scan.

Discussion and Future Direction

Figure 53A:
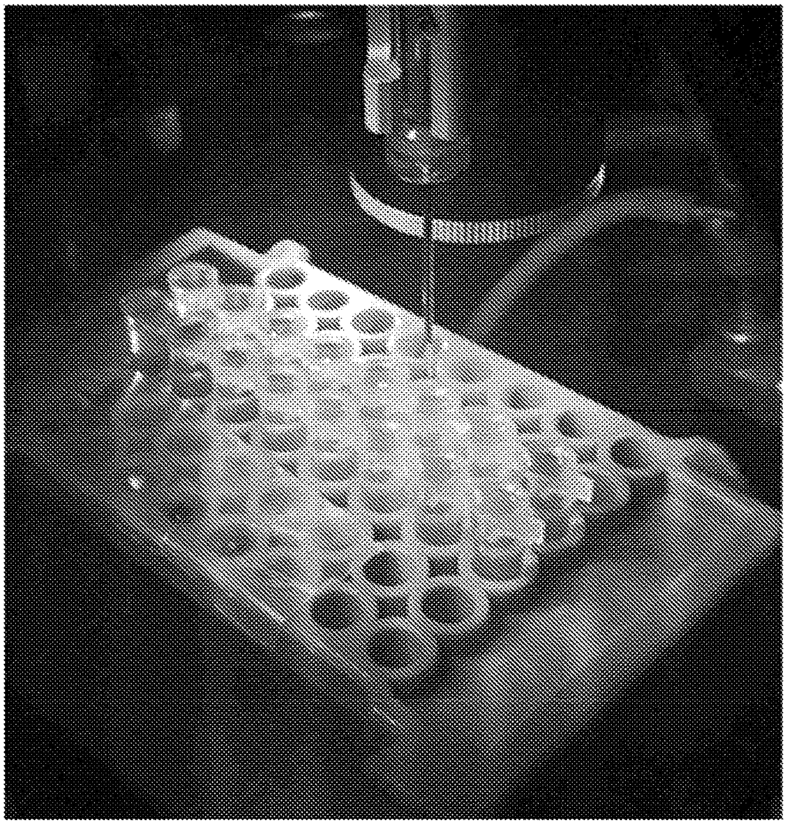
FIGS. 53A-53B: Gd-Cy5.5 Nano-tracer Phantom Injections by Stereotaxic Station.
Figure 53B:
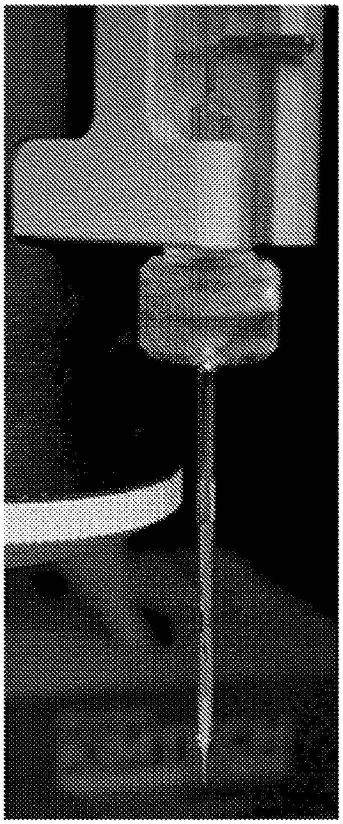

Based on the ex vivo MRI scan result where the target site was unable to be seen with an MRI scan, there are two questions to consider in in relation to higher relaxivity contrast agents: (1) In the current mouse model, will nano-tracers in the target site be observable by MRI by improving the relaxivity? (2) Will nano-tracers be seen in the target site in bigger animals (e.g., primates) by MRI? To answer these questions, the minimum amount of Gd-Cy5.5 nano-tracer that can be detected by 7T MRI under the optimized condition needs to be determined. The Gd-Cy5.5 nano-tracer injections to an agarose gel, which is a material that is commonly used for brain phantoms(53), were conducted (FIGS. 53A-53B). Various amounts of the Gd-Cy5.5 nano-tracer (from 0 nL to 700 nL) were injected into the PCR tubes which were filled with 200 µL of 0.6% agarose in Tris-borate-EDTA (TBE) to mimic healthy mice brain tissue. The injection rate was 100 nL/min. After the injection, the agarose gel was heated by a microwave oven for 10 s. This heating process was conducted to mimic the healing process of the brain tissue.

Figure 54A:
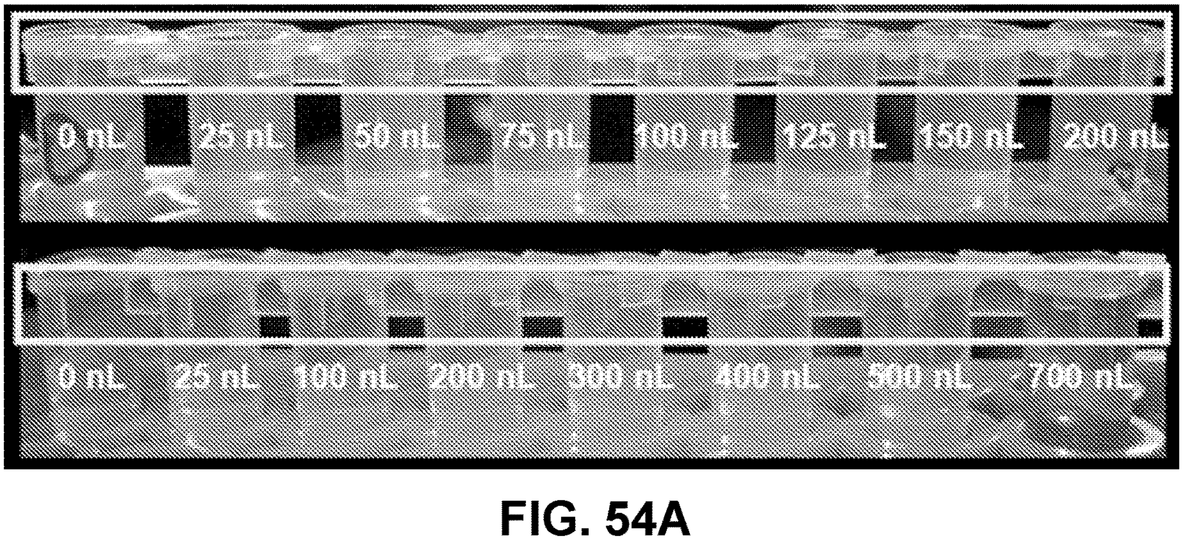
FIGS. 54A-54B: Gd-Cy5.5 Nano-tracer Phantom Injections and Result.
Figure 54B:
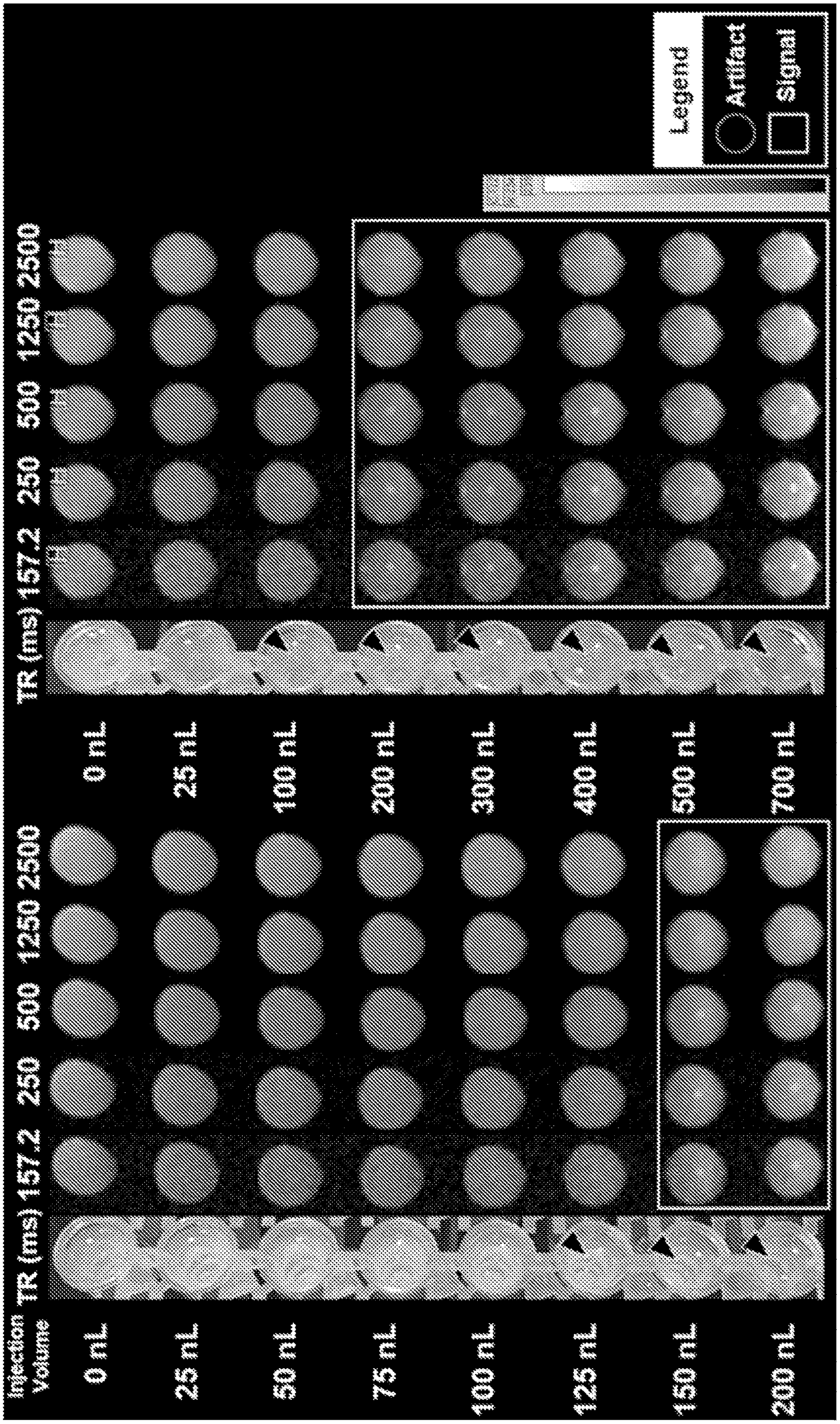

The Gd-Cy5.5 nano-tracer phantom injections were scanned using different TR settings (TR=157.2, 250, 500, 1250, and 2500 ms). The parameters for 7T MRI are TE=12.6 ms, echo=1/1, FOV=6.91/3.12 cm, slice thickness=2 mm, nex=3 mm, matrix=256*116. As the MRI scan images show in FIGS. 54A-54B, we can see 100 nL injections by setting TR=157.2 ms, 125 nL injections by setting TR up to 1250 ms, and 150 nL volume and above under all the settings. A conservative estimate for the minimum volume of Gd-Cy5.5 nano-tracer that can be detected by MRI is 150 nL.

To answer the first question of whether or not nano-tracers can be observed at the target site in the mouse model, we can simplify and fit to the discrete mass transport equation (FIG. 55). The relationship is best described as the Gd concentration at the target site (µM) equals the amount of nano-tracers injected (µM) times the transportation efficiency (%) divided by the number of voxels in the target site.

Based on the optimized MRI scanning condition, the voxel size is 400 µm isotropic. The detection limit of MRI in vivo scans is conc. (Gd) per voxel, and the theoretical detection limit of MRI is 1 µM per voxel. Thus, if the output of the equation is larger than one, it means that theoretically we will be able to see the nano-tracers at the target site, and vice versa.

Figure 57:
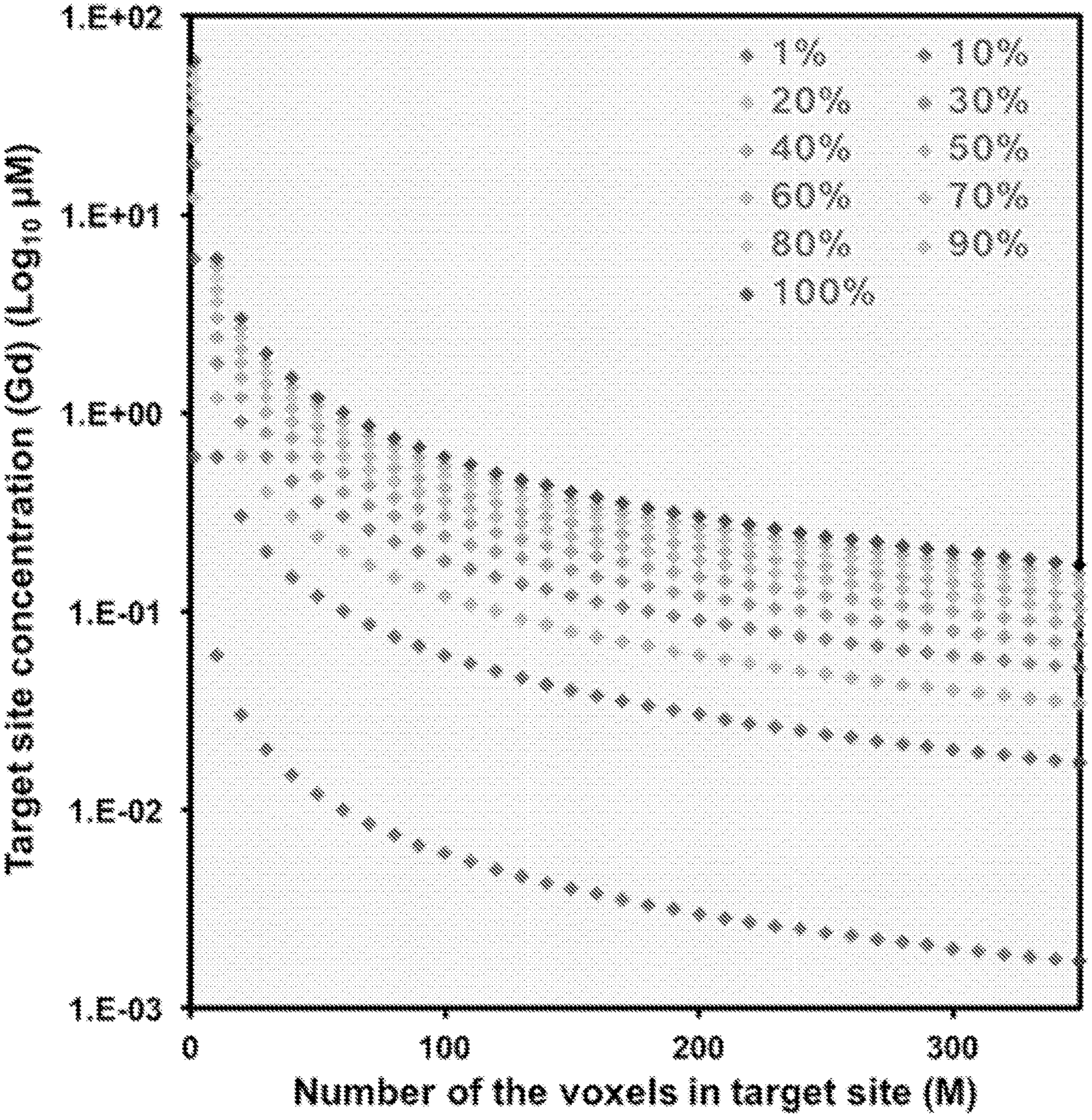
FIG. 57: Logarithmic Scale of Gd Concentration at the Target Site with Different combinations of M and k Values in Mouse Model.
Figure 59:
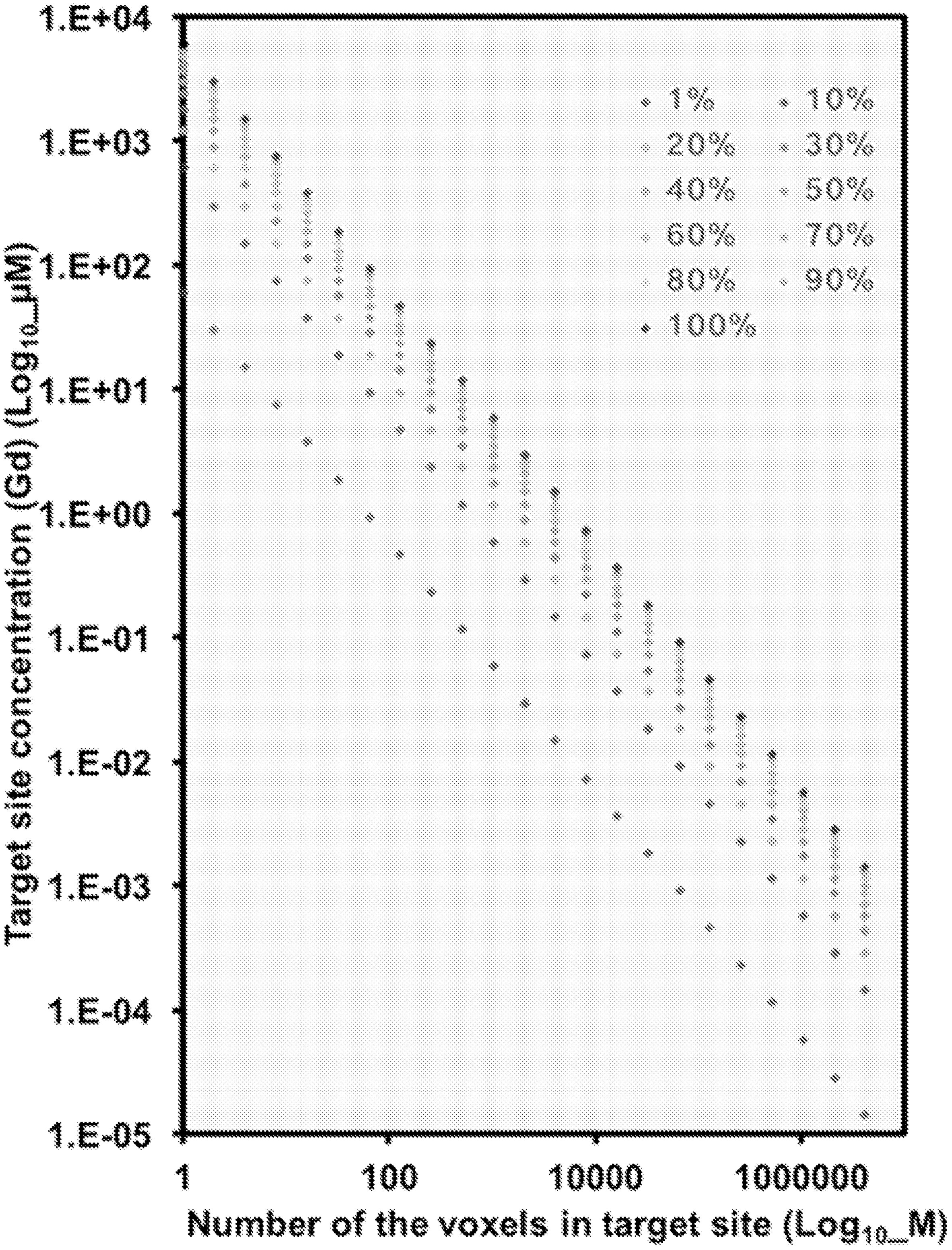
FIG. 59: Logarithmic Scale of Gd Concentration at the Target Site with Different combinations of M and k Values in Monkey Model.

With a Gd concentration of Gd-Cy5.5 nano-tracer of 400 µM and a minimum volume that can be detected by MRI of 150 nL, the N in the discrete mass transport equation equals 60 µM. An average mouse's brain volume is 420 $mm^3$. A voxel in the 7 T MRI volume is 0.063 $mm^3$. Thus, the total number of voxels in a mouse brain is 6563. FIGS. 56 and 57 show the different combinations of the transportation efficiency ($0<k<100\%$) and the number of voxels in the target site ($0<M<6563$). The area shown in lighter shading indicates Gd concentration at the target site larger than 1 µM, while the area shown in darker shading shows Gd concentrations at the target site lower than 1 µM which cannot be seen by MRI.

Next, we move to the larger animal model, the monkey model, whose average brain volume is 400 $cm^3$. Thus, the maximum nano-tracer injection volume is 187.5 µL, assuming it is proportional to the mouse brain size. The whole monkey brain contains in total 6.25E+6 voxels. FIGS. 58 and 59 show the different combinations of the transportation efficiency (0<k<100%) and the number of voxels in the target site (0<M<6.0E+6). The result shows more promise compared to the mouse model as the brain size is bigger.

Based on the theoretical calculation, it is not impossible to observe retrograde transportation of Gd-based nano-tracers in live animals. However, to more fully understand the mechanisms involved, more studies could be done, such as testing the transportation efficiency of nano-tracers in different pathways by using ICP-MS.

One possibility for employing the chelate nanoparticles for imaging purposes is to change the imaging methodology from MRI to PET or SPECT. The detection limit of the contrast agent in PET and SPECT scans is much lower compared to MRI, from nanomolar to picomolar. Thus, even with a little amount of the nano-tracers transported to the target site in the brain, nano-tracers would still be able to be detected. Since all the contrast agents developed in this example are DOTA based, and it is known that DOTA can also chelate with Copper, Indium, Yttrium, the DOTA-based chelate nanoparticles could be easily translated to a PET and SPECT contrast agents with an expectation of success.

Although this example described the preparation of nanoparticles containing both a fluorophore moiety and a chelate moiety, it is contemplated that nanoparticles containing only a chelate moiety, and no fluorophore moiety, could be readily prepared using the techniques described herein, for example, by omitting from the synthesis the vinyl-containing fluorophore. Similarly, it is contemplated that multiple fluorophores (with different emission maxima) could be synthesized into a nanoparticle that also contains a chelate moiety, by adding one or more additional types of vinyl-containing fluorophores (with different emission maxima) in the currently described synthetic conditions.

Example 3: Multiple-Fluorophore Brain Mapping and Axonal Tracing

This example demonstrates the injection of multiple compositions of nanoparticles into a brain, in which each composition has nanoparticles comprising a different type of fluorophore (e.g., different emission maxima). This protocol holds promise as a method for more complex neuronal tracing involving nanoparticles with different fluorophores (e.g., different fluorophores in different injected compositions, or multiple different fluorophores in the same nanoparticle).

Hippocampus Multi-Color Injection

Figure 60:
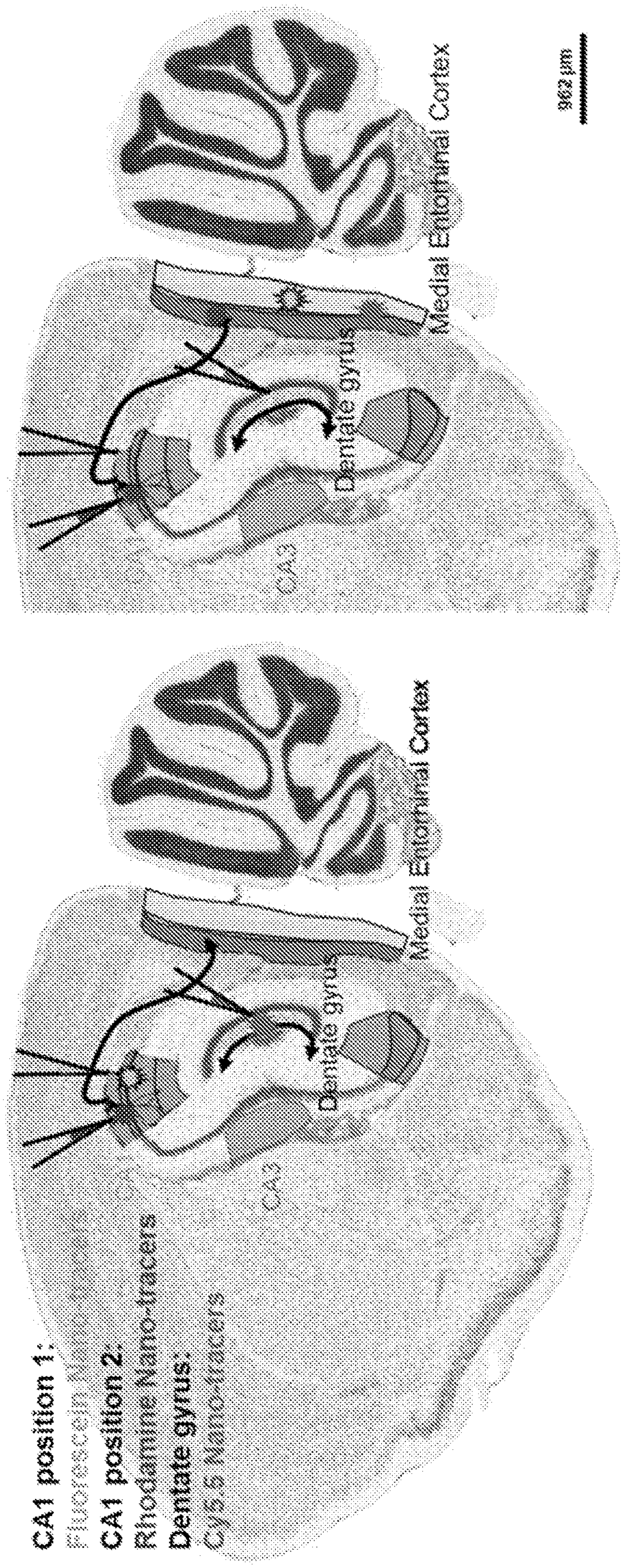
FIG. 60: Hippocampus Multi-color Injection with Fluorescein, Rhodamine, and Cy5.5 Nano-tracers.

To further demonstrate the potential of the multi-color nano-tracers, a multi-color injection was performed in vivo. The surgery detailed was described elsewhere (e.g., Example 1). Dentate gyrus (DG) has strong projections to EC layer 2 and CA1 projections to EC, but it is not clear to which specific layer. Based on the current understanding of anatomy, two different locations in CA1 were injected with fluorescein nano-tracers and rhodamine nano-tracers, and DG was injected with Cy5.5 nano-tracers (FIG. 60). It is expected to observe the fluorescein and rhodamine and Cy5.5 labeling in EC and Cy5.5 labeling specifically in EC layer 2.

Figure 61A:
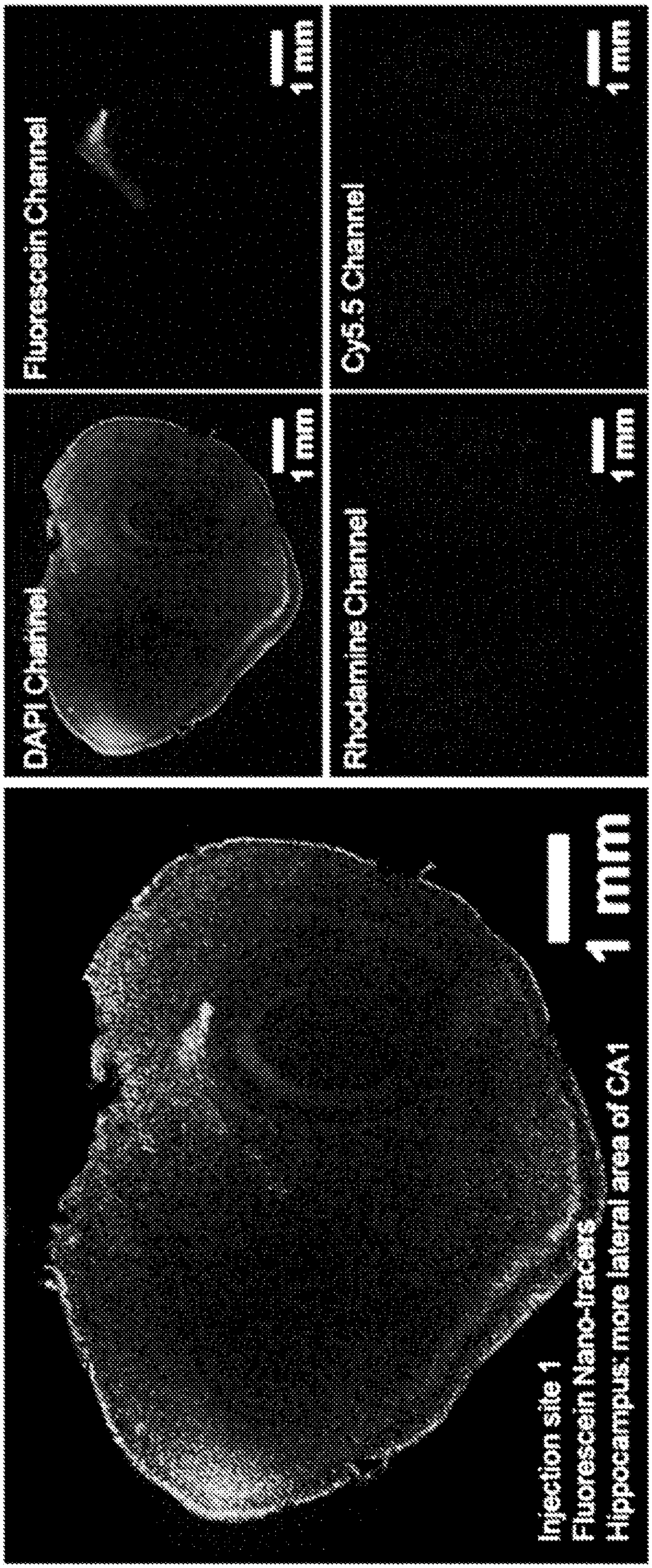
FIGS. 61A-61C: Fluorescence Images of Multi-color Injection in Hippocampus.
Figure 61B:
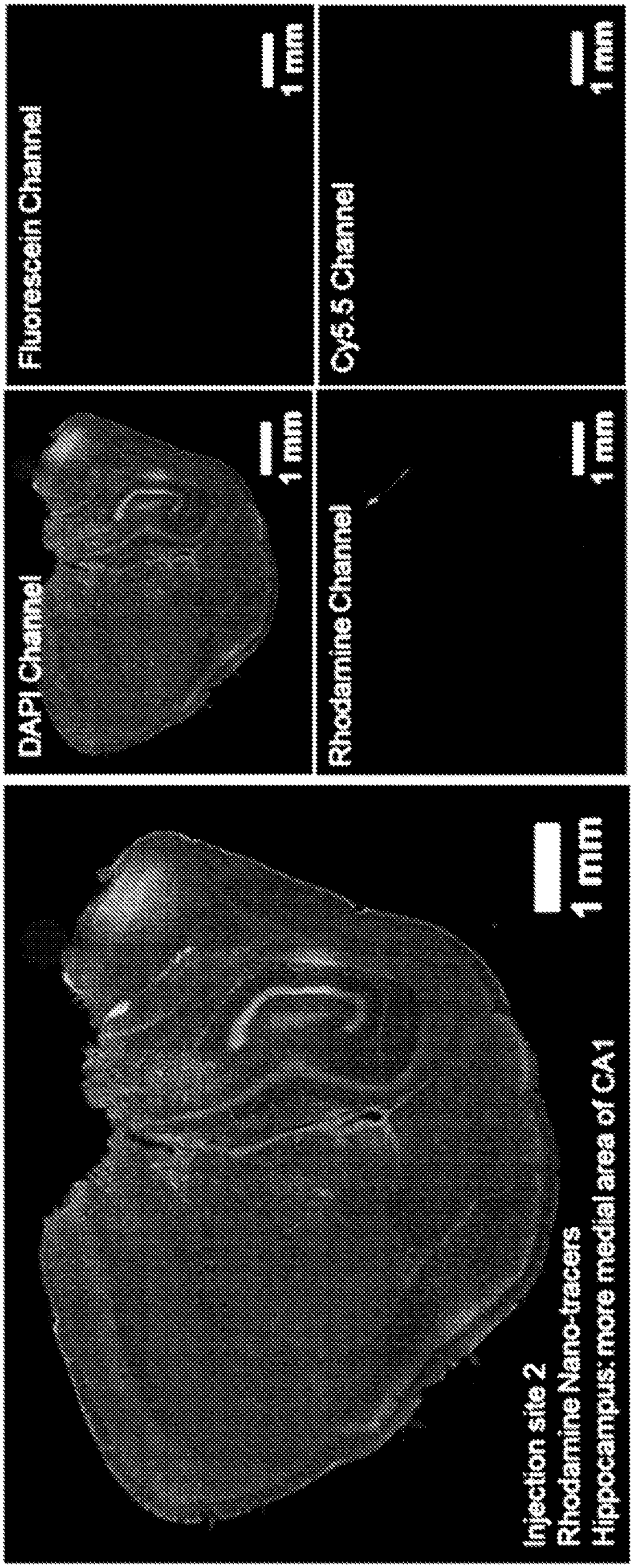
Figure 61C:
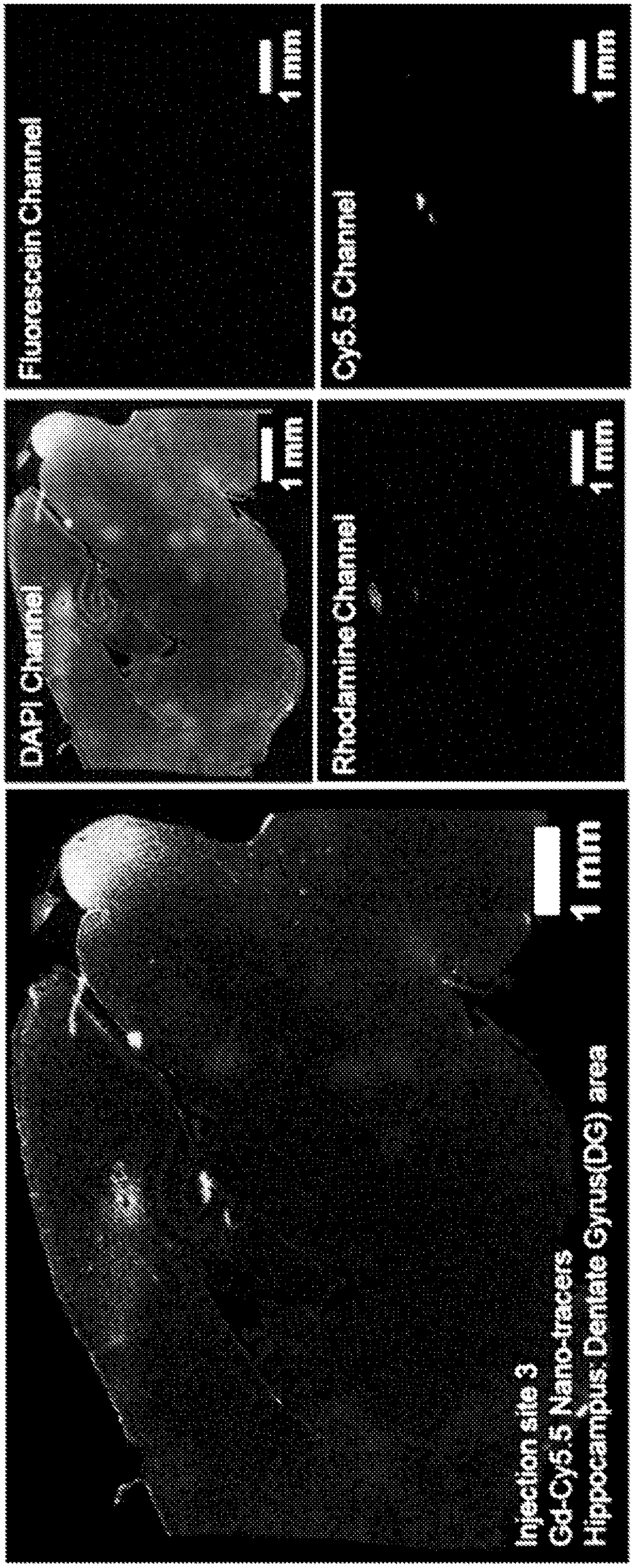
Figure 62:
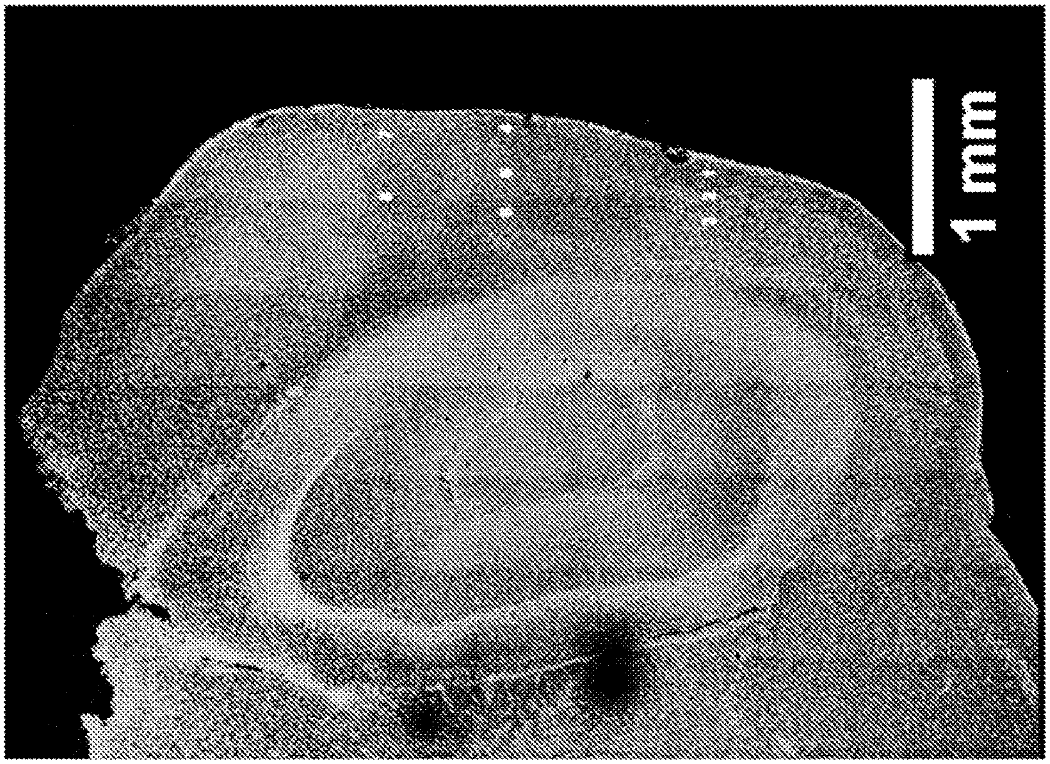
FIG. 62: Location of EC Layer 1, 2a, 2b, 3, 5/6.

After 48 h of post-injection, the mouse brain was fixed and sliced in the sagittal section. Cell nuclei blue was stained by DAPI, shown in blue in FIGS. 61A-61C. FIG. 61A depicts injection site 1, which is a more lateral area of CA1 in the hippocampus with fluorescein labeling. FIG. 61B shows injection site 2, which is a more medial area of CA1 in hippocampus labeled with rhodamine nano-tracers. FIG. 61C presents injection site 3, which is DG in hippocampus labeled with rhodamine nano-tracers. The other channels in all three injection sites show that is no crosstalk between nano-tracers of different colors. FIG. 62 shows the fluorescein image of the brain slice, which can be compared to the Brain Atlas map available from the Allen Institute. 8 areas of interest were specified in the fluorescein image. The EC layer of each location was then determined using the brain atlas from the Allen Institute. These 8 locations were further imaged by Leica TCS SP8 Confocal Microscope.

Figure 63A:
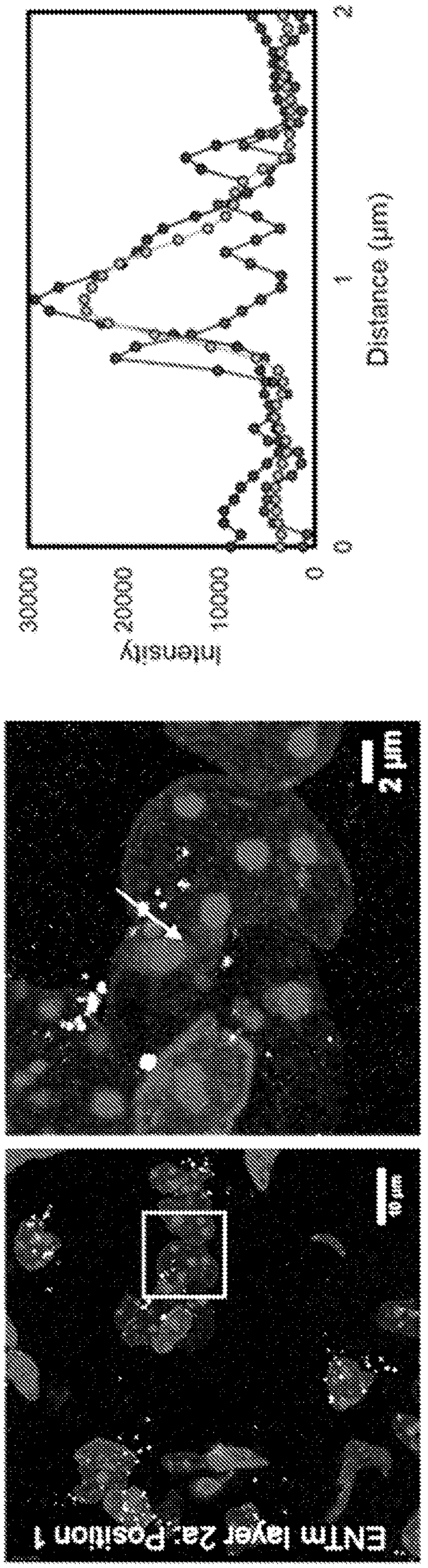
FIGS. 63A-63D: Ultra-high resolution deconvoluted confocal image of Target Site.
Figure 63B:
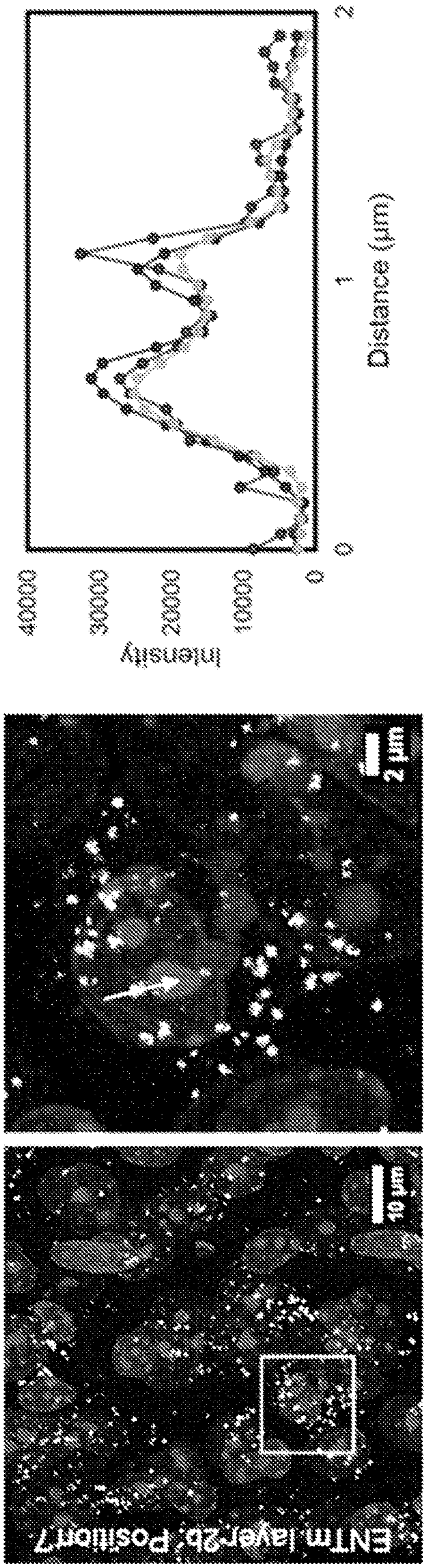
Figure 63C:
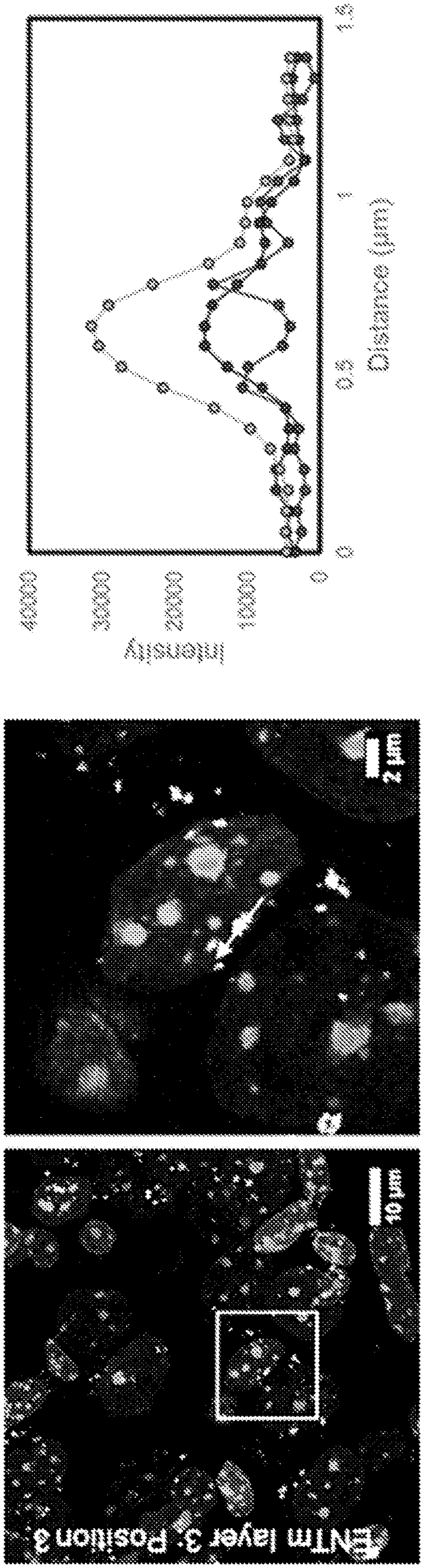
Figure 63D:
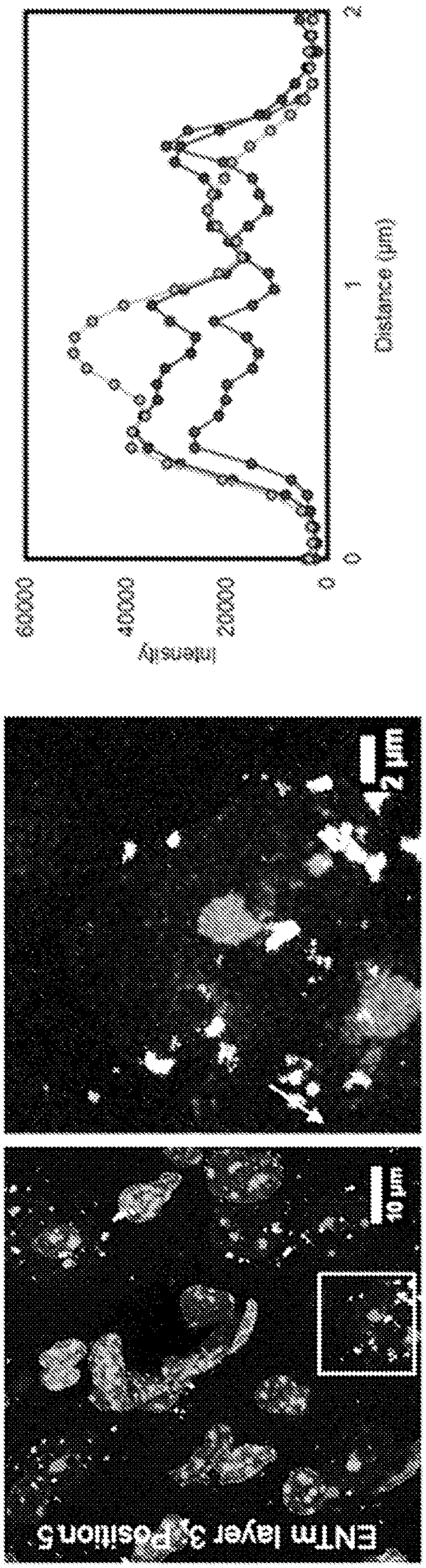

Ultra-high resolution deconvoluted confocal images were shown in FIGS. 63A-63D. Confocal images and the line intensities from fluorescein, rhodamine and Cy5,5 channel analysis of EC layer 2a, position 1 are shown in FIG. 63A; EC layer 2b, position 7 is shown in FIG. 63B; EC layer 3, position 3 is shown FIG. 63C; EC layer 3, position 5 is shown in FIG. 63D. The line intensity analyses show most of the puncta has the fluorescent signal from all DAPI, fluorescein and rhodamine channel, with the intensity of one channel occasionally higher than the other two. The result that signal intensities from all the channels from all the locations examined almost completely overlap is abnormal. The conclusion that the three colors of nano-tracers were transported to all the areas that were examined in EC cannot be drawn.

Figure 64:
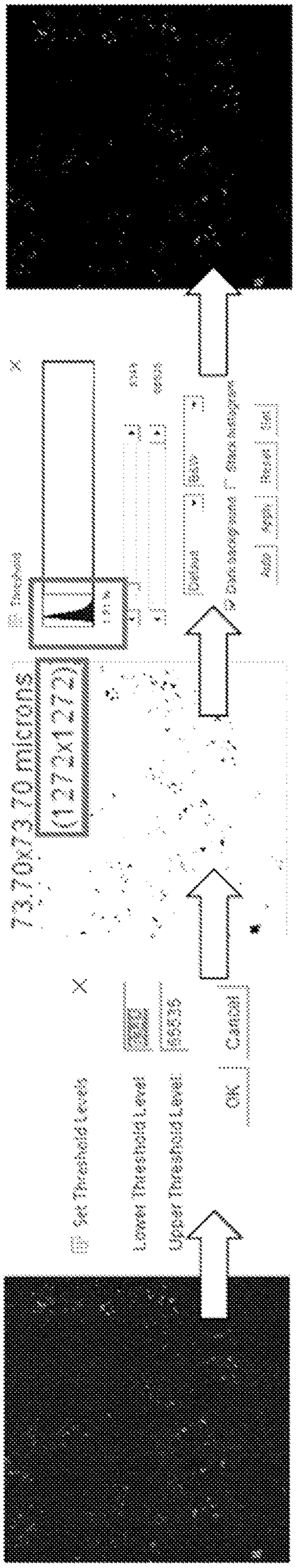
FIG. 64: Data Analysis Flow of Signal Intensity Quantification.
Figure 65:
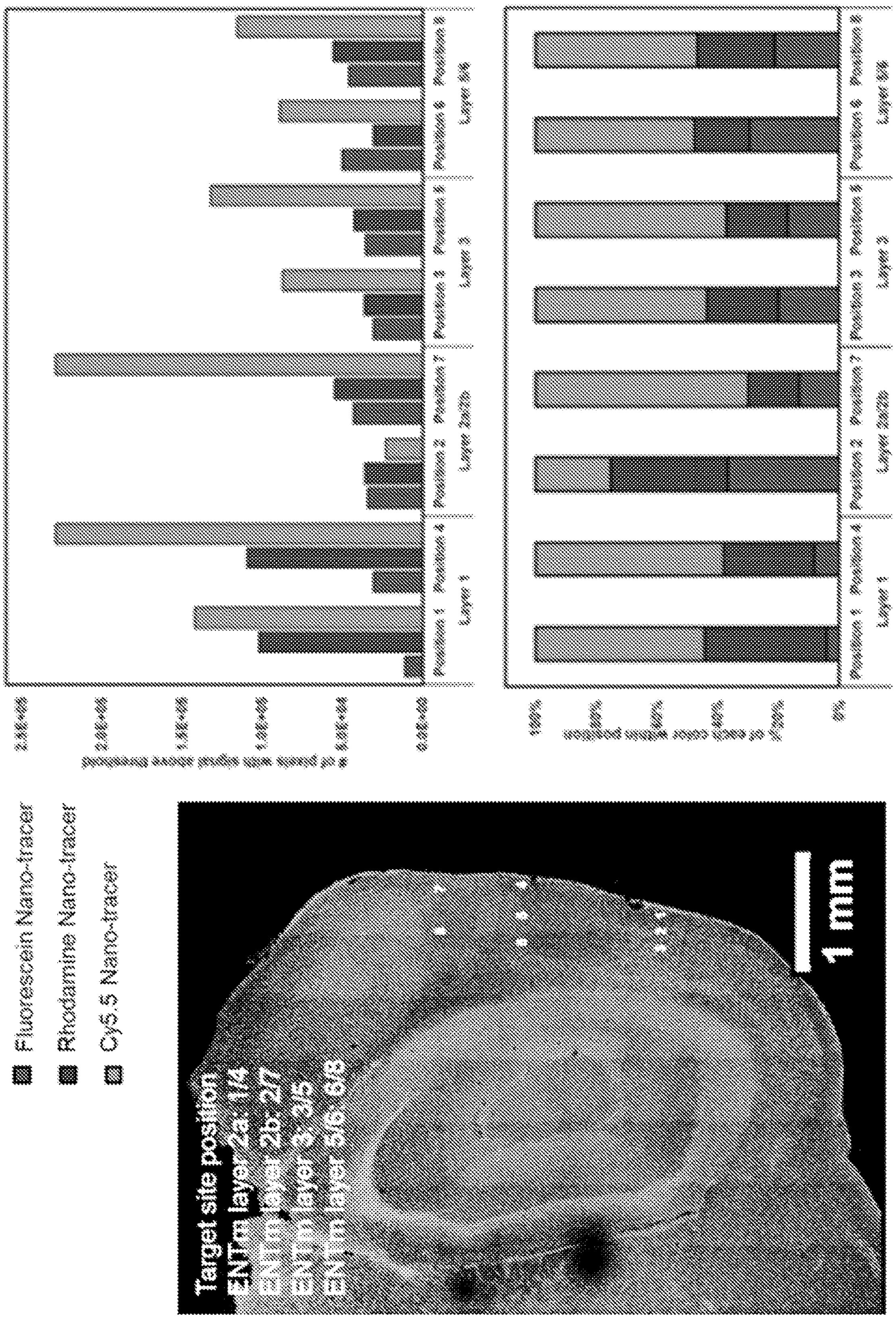
FIG. 65: Signal Intensity Analysis of Target Site of Multi-injection in Hippocampus.

To have a better understanding of the imaging result, the signal intensities were quantified by using Image J (FIG. 64). To quantify the signal count from each channel, the data analysis methodology of signal intensity is described as follows: First, apply maximum projection function to the z stack of the image of interest. Second, set the lower signal cut off. The lower signal threshold of each channel can be determined by imaging a plain brain sample under the same laser setting. Third, pull out the percentage of pixels that are above the lower signal threshold. Fourth, calculate the absolute number of pixel count for each channel, e.g., 1272×1272×1.91%. Lastly, repeat 1-4 for all the images. The result is shown in FIG. 65. All the positions except position 2 has higher Cy5.5 intensities. In the EC layer 2a/2b at position 1 and 4, there is a higher rhodamine signal than in the other positions. However, we cannot conclude any new findings on neuronal projections between the injection location (CA1) and EC.

Figure 66:
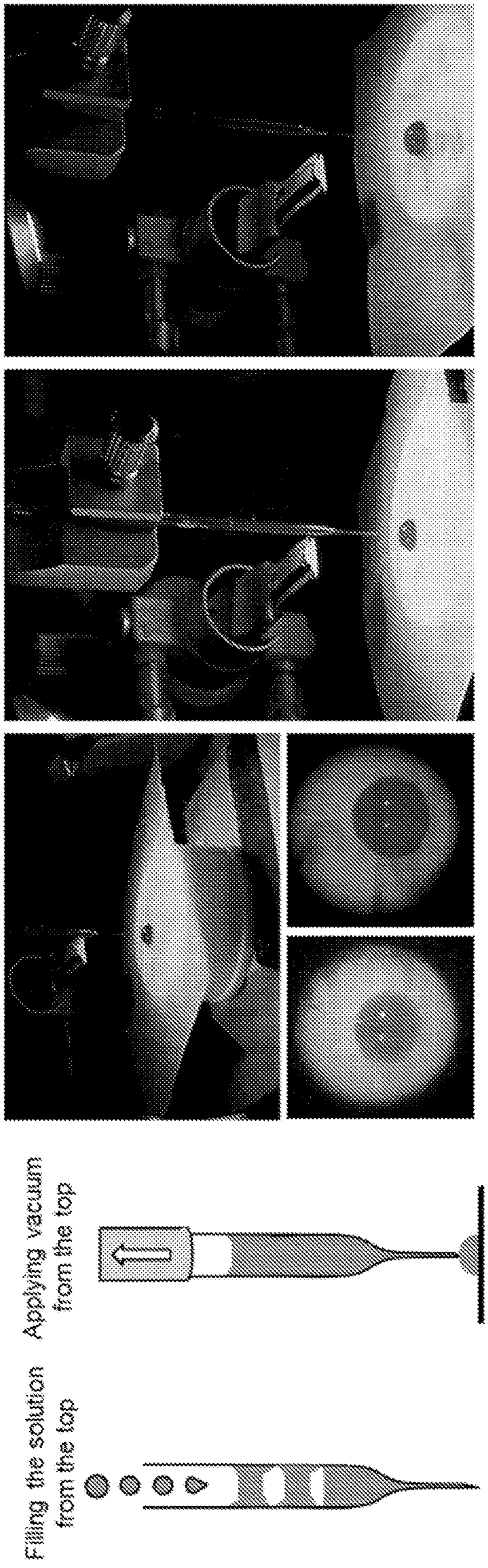
FIG. 66: Pre-load the Nano-tracer Solution into the Needle.
Figure 67:
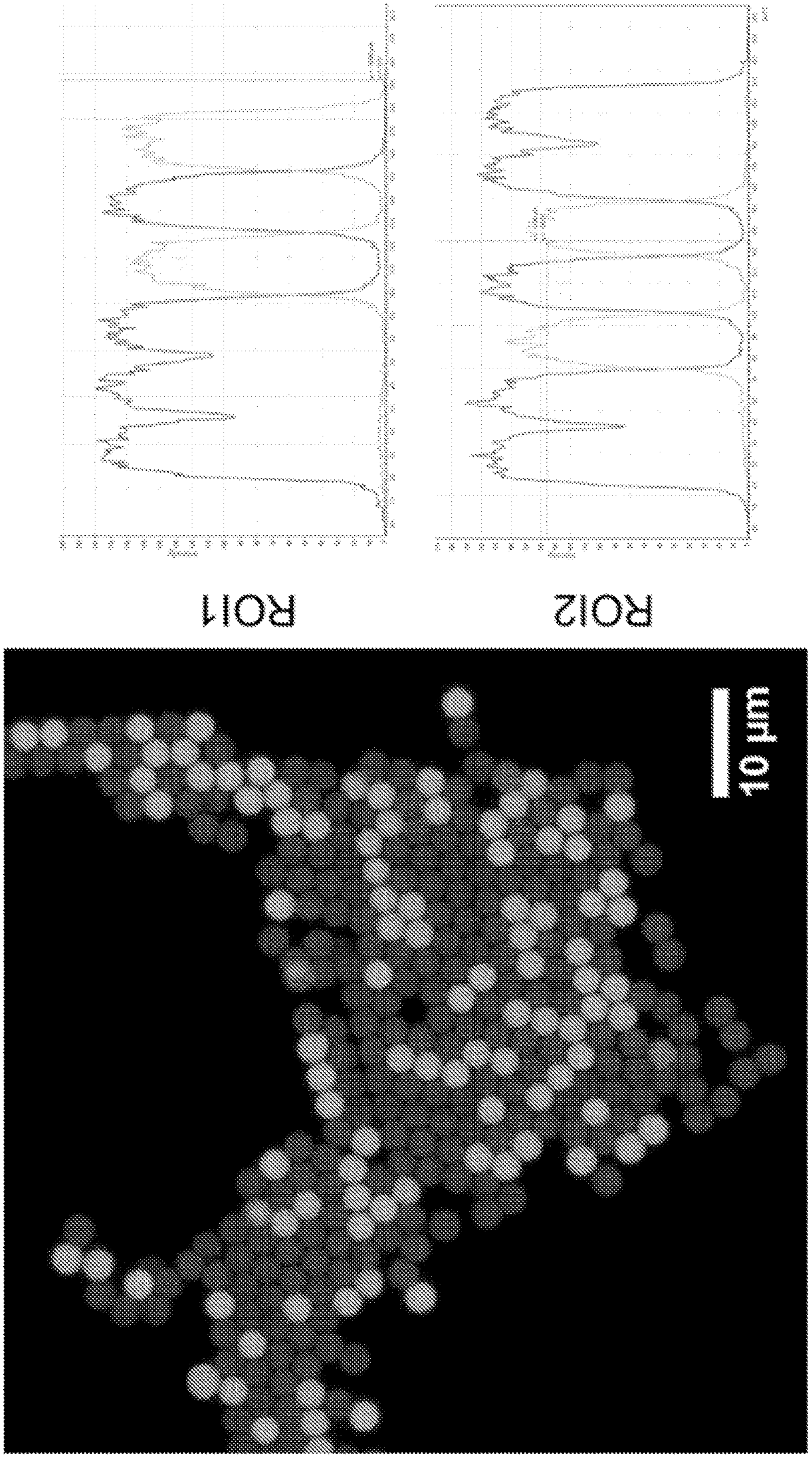
FIG. 67: Test the Separation of the Signal of Confocal Microscopy.

The pixel size of the image is 58 nm×58 nm×65 nm. However, the theoretical optical limit of the objective from the Leica TCS SP8 Confocal Microscope is used, in other word, the diffraction limit is 136 nm. Based on the size analysis of the nano-tracers described elsewhere herein (e.g., Examples 1 and 5), the range of particles size is 100-150 nm. Therefore, the resolution limit is about the same as individual particle size. To eliminate instrument error, the ability of the microscope to distinguish between the different signal intensities was tested. Commercial fluorescein resin beads and commercial rhodamine resin beads were mixed together and dropped on a microscope slide for imaging. The size of the fluorescein and rhodamine resin beads are 2.5 μm. The laser settings were unchanged in order to be consistent with previous imaging condition. The test result is shown in FIG. 66 and indicates that the microscopy can distinguish between the fluorescein and rhodamine signal with no overlap at the edges between two beads.

Figure 68:
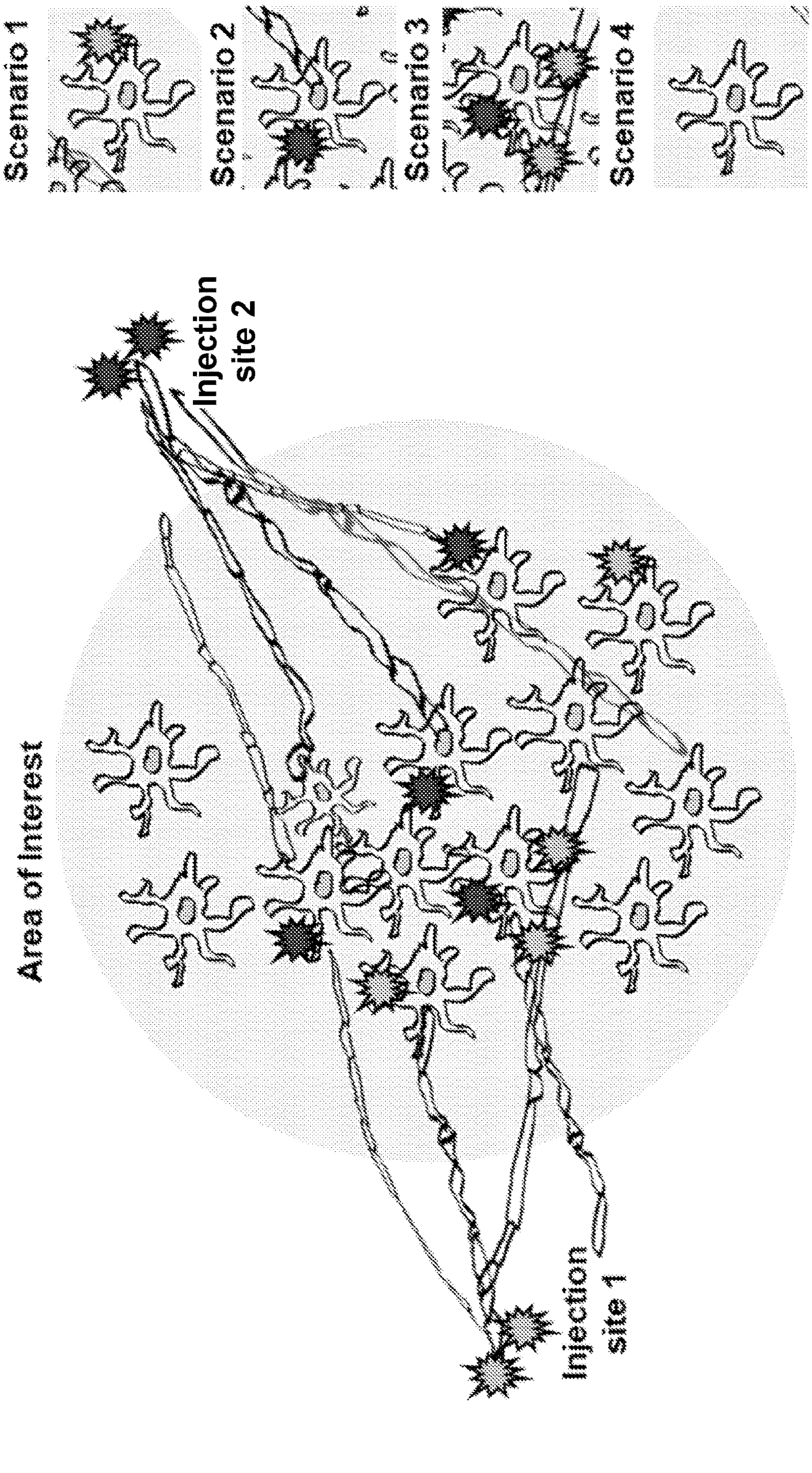
FIG. 68: Expected Result of Multi-injection in Hippocampus.

FIG. 68 shows the expected result in the target site when 2 different colors of nano-tracers are injected into two injection sites that have the same neuronal projection. 4 total scenarios are anticipated. Scenario 1 and 2 represent areas where exactly one of the two colors of nano-tracers are present. Scenario 3 represents areas where both colors of the nano-tracers are present. Scenario 4 represents areas where no nano-tracers are present. It is abnormal to see more than 95% puncta that have overlaps in all three channels. However, we observed that almost 100% of the puncta have overlaps in all three channels.

There are some possibilities to explain what those puncta are. The first explanation is that the puncta are artifacts from the fixation of the brain. The second possibility is inflammation, or an unknown age-related factor in the mouse brain, especially 2 months after birth. Another explanation could be that the puncta are due to the microscope objective lens artifacts. The last possibility is that the experiment time is too long, so that nano-tracers are transported to the target site, move around, and eventually cluster. To eliminate the possibilities mentioned above, we can use the same laser setting to revisit the single-color injection's brain slides (experiments in Example 1). Conducting the experiment in a shorter amount of time (less than 48 h) is an alternative way to validate the assumption. Another attempt is to move to a simple projection system, e.g. Basal ganglion. All of those attempts require more in-depth in vivo experiments. However, due to the collaborator's limited availability, we were not be able to finish those studies.

Example 4: Additional Vinyl-Containing Fluorophores

This example demonstrates the synthesis and characterization of additional vinyl-containing fluorophores. This example also summarizes the excitation and emission maxima of various vinyl-containing fluorophores.

Synthetic Route of Cy5.5-Methacrylamide Linker

Figure 74:
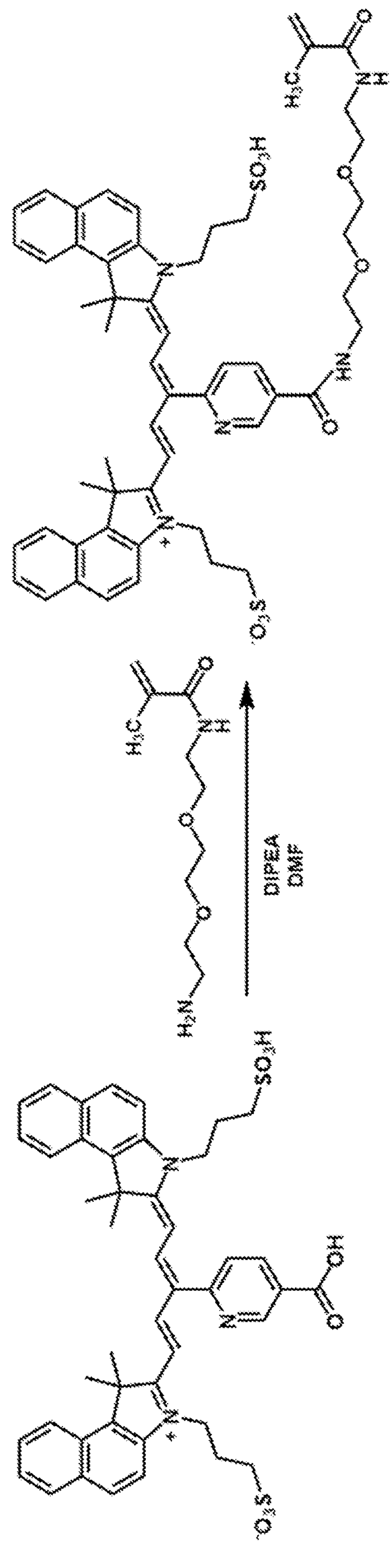
FIG. 74: Synthetic Route of Cy5.5—Methacrylamide Linker.
Figure 75:
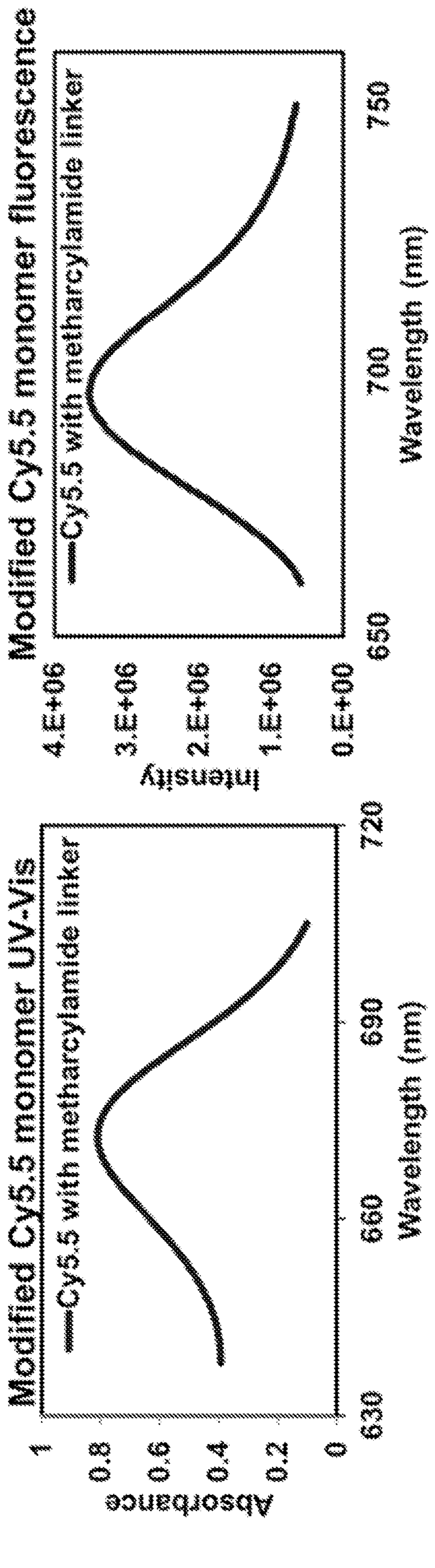
FIG. 75: UV-Vis and Fluorescence Spectra of Cy5.5-Methacrylamide Monomer.

FIG. 74 illustrates the synthetic route to the Cy5.5-Methacrylamide monomer. Excitation and emission spectra of Cy5.5-Methacrylamide were acquired by UV-Vis and fluorescence spectroscopy and shown in FIG. 75. The excitation maxima was determined to be $\lambda_{ex}$=672 nm, while the emission maxima was found to be $\lambda_{em}$=700 nm.

Synthetic Route, Purification and Characterization of Cyanine 7 (Cy7)-AEMA

Figure 76:
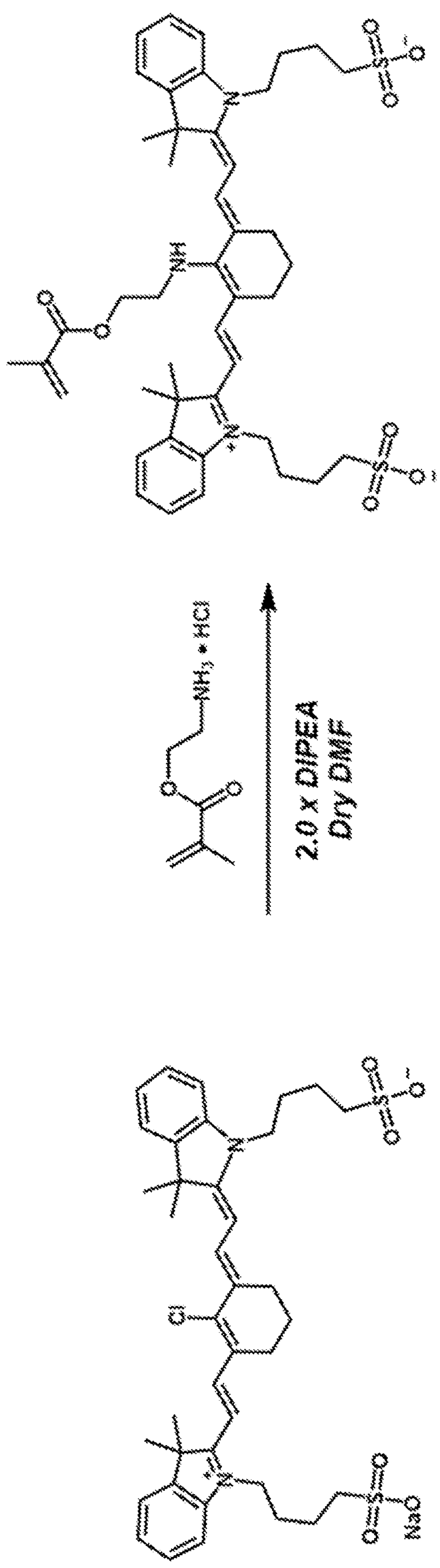
FIG. 76: Synthetic Scheme for Cy7-AEMA.

The synthetic scheme for 4-((E)-2-((E)-2-(3-((E)-2-(3,3-dimethyl-1-(4-sulfonatobutyl)-3H-indol-1-ium-2-yl)vinyl)-2-((2-(methacryloyloxy)ethyl)amino)cyclohex-2-en-1-ylidene)ethylidene)-3,3-dimethylindolin-1-yl)butane-1-sulfonate is shown in FIG. 76.

Figure 77:
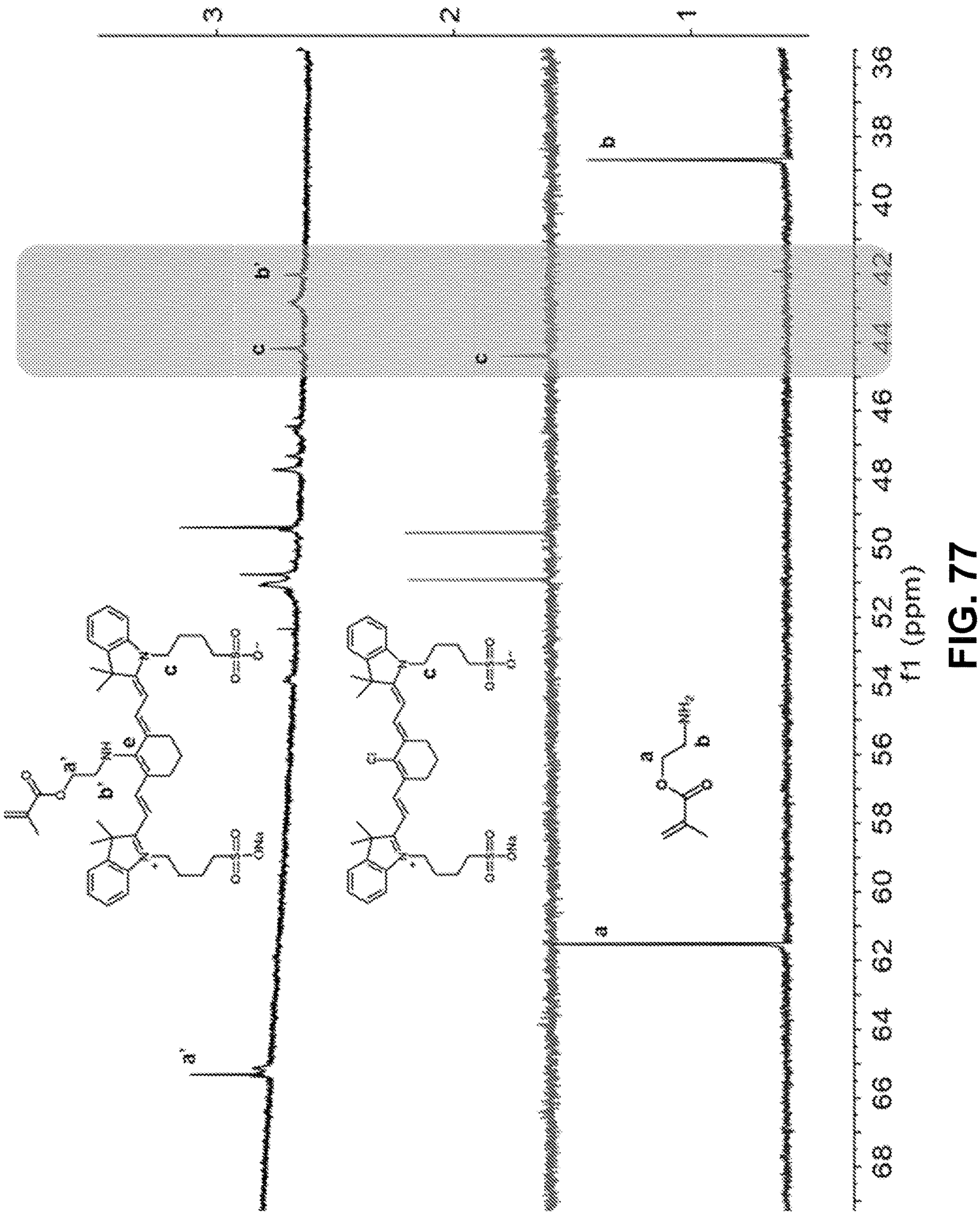
FIG. 77: $^{13}C$ NMR of Cy7-AEMA.

AEMA (8 mg, 0.060 mmol) and DIPEA (14 μL, 0.0798 mmol) were added into the reaction flask under argon. After 5 min, 15 mL anhydrous DMF and IR-783 (30 mg, 0.040 mmol) were added into the reaction. The reaction was kept in the dark for 8 h. Then DMF was removed by rotovap and dried under the vacuum. It was found that the product was water, oxygen, and heat sensitive, which prevented further purification. Both proton and carbon NMR showed the presence of AEMA and IR-783 as expected, with the carbon NMR showing a downfield shift of carbon a and b a consistent with the formation of a bond between the amine of AEMA and carbon e of IR-783 (FIG. 77). HR-MS (ESI-TOF): m/z (%) $[M-Na-H]^-$ calcd for $C_{44}H_{56}N_3NaO_7S_2$: 818.35, found: 818.39. Although AEMA was employed in this example to append a vinyl group to the fluorophore, any other suitable compound may be employed to link the fluorophore to a vinyl group.

Determination of the Extinction Coefficient for Dye Functionalized Monomers

Methacryloyloxy O-fluorescein, and methacryloxyethyl thiocarbamoyl rhodamine B are commonly employed in ex-vivo biological studies and are both commercially available. However, their extinction coefficients have not been reported.

Understanding the extinction coefficient of the monomer provides additional guidance for nano-tracer synthesis. Thus, the extinction coefficient of methacryloyloxy O-fluorescein, methacryloxyethyl thiocarbamoyl rhodamine B, Cy5.5-AEMA, and Cy7-AEMA was determined based on the Beer-Lambert law. Beer's law states that absorbance of a sample (Abs) is proportional to the molar extinction coefficient (c), light path length in centimeters (I), and the molar concentration (c).

Figure 78:
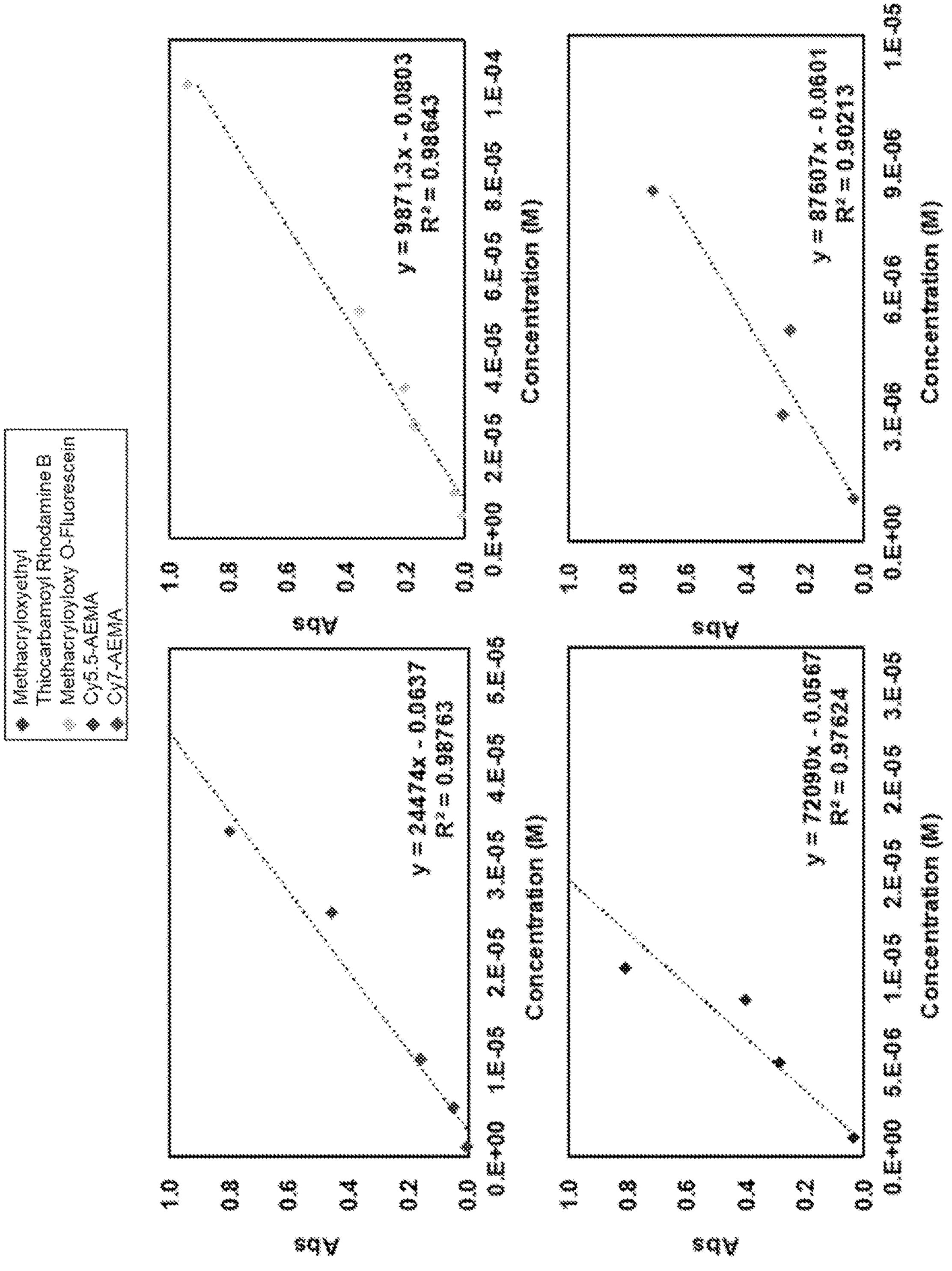
FIG. 78: Plots Used to Determine the Extinction Coefficients of Methacryloxyethyl Thiocarbamoyl Rhodamine B, Methacryloyloxy O-Fluorescein, Cy5.5-AEMA, and Cy7-AEMA.

The extinction coefficient of methacryloxyethyl thiocarbamoyl rhodamine B was measured in a mixture of 1% Methanol (MeOH) in Phosphate-buffered saline (PBS) buffer, and the extinction coefficient of methacryloyloxy O-fluorescein, Cy5.5-AEMA, Cy7-AEMA monomers were measured in a mixture of 1% THE in PBS buffer (FIG. 78). Table 4 lists the extinction coefficient for the dye monomers.

TABLE 4

Summary of the Extinction Coefficient for the 4 Dye Monomers

| Monomers | Extinction Coefficient ($L\ mol^{-1}cm^{-1}$) |
|---|---|
| Methacryloxyethyl Thiocarbamoyl Rhodamine B | 24474 |
| Methacryloyloxy O-Fluorescein | 9871 |
| Cy5.5-AEMA | 72090 |
| Cy7-AEMA | 87607 |

Summary of Excitation and Emission Maxima of Dye Monomers

The excitation and emission maxima for each of the monomers was measured by UV-Vis and fluorescence spectroscopy and shown in Table 5.

TABLE 5

Excitation and Emission Maxima of Dye Monomers

| Dye monomer | Excitation (nm) | Emission (nm) |
|---|---|---|
| Coumarin Acrylamide | 342 | 430 |
| Methacryloyloxy O-Fluorescein | 490 | 520 |
| Methacryloxyethyl Thiocarbamoyl Rhodamine B | 548 | 570 |
| Cy5.5-Methacrylamide | 672 | 700 |
| Cy5.5-AEMA | 680 | 700 |
| Cy7-AEMA | 750 | 773 |

Example 5: Polymerization Materials, Conditions, Methods, and Characterization This example demonstrates various aspects pertaining to the polymerization materials, conditions, methods, and characterization of a variety of nanoparticles and fluorophores.

Emulsion Polymerization and Monomer and Additives Selection

Emulsion polymerization is a common and scalable method for synthesizing latex particles. Emulsion polymerization is characterized by fast polymerization kinetics and the ability to achieve high molecular weights. Hence, it is widely used for industrial-scale production of a variety of materials including paints, coating, adhesives, and resins. In view of this widespread use, emulsion polymerization methods were utilized to synthesize all nano-tracers.

Figure 79:
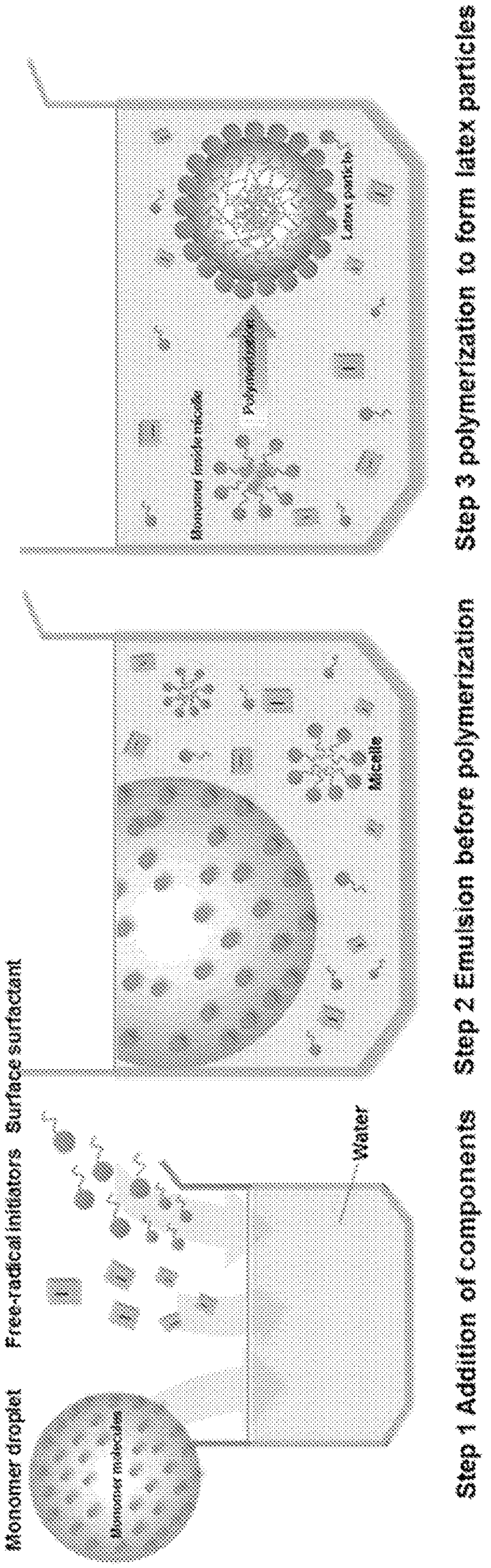
FIG. 79: Schematic Diagram of Emulsion Polymerization.

The mechanism of emulsion polymerization is shown in FIG. 79. Monomer molecules, surfactants, and free-radical initiators are added to water. The surfactant which is composed of a hydrophilic head group and a hydrophobic tail, coats on the surface of monomer droplets to form a stabilizing emulsion prior to polymerization. Polymerization takes place when initiators molecules diffuse into the micelles, inducing chain growth that forms the latex particle.

The composition of the monomer mixture is crucial for obtaining the desired characteristics of nano-tracers. In order to form the extremely fine, monodispersed spherical nanoparticles, the monomers should be considerably water-soluble under the polymerization condition. Thus, the formation of oil droplets that would be formed in conventional emulsion polymerization is prevented.

Monomers that have vinyl bonds are suitable for emulsion polymerization protocols. The total monomer content typically comprises about 25-30 wt. % of the solution. Suitable monomer functionalities include carboxyl, hydroxyl or amnio substituted vinyl monomers. The amount of cross-linker present in the monomer mixture typically is about 5-20 wt. %, with a preferred range of about 6-12%. Suitable compounds include ethylene glycol dimethacrylate or divinyl benzene. In some aspects, however, crosslinker is not present. Overall, about 40-70% of the monomers in the monomer mixture, in some aspects, are sparingly water-soluble with hydrophobic characteristics, since this results in freely suspended individual particles. Lacking these types of monomers, typically a gel of aggregated soft particles can be the final product. In some aspects, preferred monomers with hydrophobic characteristics include styrene, methyl methacrylate, or ethyl methacrylate.

Four monomers that were chosen for this example based on the above characteristics were 2-hydroxyethyl methacrylate (HEMA), methyl methacrylate (MMA), methacrylic acid (MAA), and ethylene glycol dimethacrylate (EGD). Poly(2-hydroxyethyl methacrylate) (PHEMA) is a biocompatible material with known hydrogel properties including the feature that hydroxyl groups protrude from the surface of the particles which make post-functionalization and modification possible if desired. Poly(methyl methacrylate) (PMMA) has been used in orthopedic surgery due to its high mechanical strength and essential hydrophobicity, making it a good candidate for the core of the nano-tracers. Moreover, MAA provides negative charge for the nano-tracers to prevent non-specific binding of biological materials in vivo and also facilitates retrograde transportation. EGD is used as a crosslinker inside the particles, providing extra rigidity.

There are two types of free radical initiators for emulsion polymerization: heat-based or photo-based. The most common heat-based initiators are ammonium persulfate (APS), catalytic inorganic persulfate, t-butyl peroctoate, and azo compounds such as azodiisobutyronitrile. Fora photo-based initiator, Sodium Phenyl-2,4,6-trimethylbenzoylphosphinate (SPTP) is a frequently used option.

Another typical additive to emulsion polymerization is a surface surfactant such as sodium dodecyl sulfate (SDS), sodium lauryl sulfate, TRITON X-100, and Polysorbate 20/80. Typically, the surfactant is removed from the final particle suspension prior to further biological or analytical use. Thus, in some aspects, typically about 0.03-0.5 wt. % of surfactant is used in polymerization.

Criteria for Design and Selection the Dye Monomer

There are at least three methods for incorporating color in a nano-tracer. A first method is a post polymerization approach where the functional groups of a plain nano-tracer are used to conjugate dye molecules to the surface of the nano-tracer. However, the amount of dye is limited by the nano-tracer's surface area and the yield of the conjugation reaction. A second method involves noncovalent encapsulation of dye molecules within a nanoparticle. However, in this method dye molecules may leak out of the nanoparticle, which can interfere with precise imaging. A third method, which is the method developed herein, involves direct incorporation of the dye into the polymer (e.g., within the interior bulk of the nanoparticle). This method relies on functionalizing the dye molecule with one or more polymerizable units, such as a vinyl group. Therefore, the dye monomer can be covalently bonded within and in some aspects on the surface of the nano-tracer. Since emulsion polymerization can be conducted on a relatively large scale, the amount of dye needed for each reaction would also be large in such situations.

Figure 80:
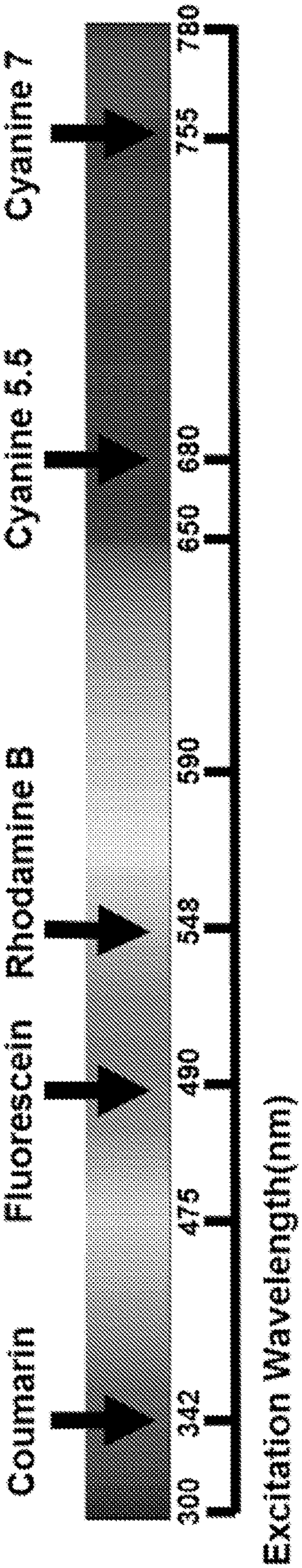
FIG. 80: Spectrum Overview of the Fluorescent Nano-tracers.

Five fluorescent dye monomers were chosen to sufficiently cover the electromagnetic spectrum, from ultraviolet to infrared (FIG. 80) (see also Table 5 above). The criteria for selecting and designing the monomers for this example include: 1) all monomers have either an acrylate or a methacrylate group as the polymerizable moiety to ensure that the monomers can be incorporated into the nano-tracers; and 2) all five colors cover a wide range of the spectrum but also be distinguishable from each other without crosstalk between color channels. This criterion ensures that when combining different types of nano-tracers that each color can be resolved at both the injection and target site in in vivo experiments. With respect to the colors themselves, coumarin acrylamide falls in the lower end of the spectrum, which is within the ultra-violet range. Fluorescein O-methacrylate and methacryloxyethyl thiocarbamoyl rhodamine B are in the middle part of the visible light spectrum and are also the two most-often used dyes in biological systems. These three dye monomers were purchased from either Sigma-Aldrich or Polysciences, Inc.

Cyanine 5.5 (Cy5.5) and Cyanine 7 (Cy7) are commonly used near-infrared dyes in living systems, as the emission maxima of these dyes are >600 nm, which is beyond the range of autofluorescence in most tissues. This, in turn, means there is a much lower background signal from the sample, so even though the extinction coefficients of these near-infrared dyes are lower than fluorescein and rhodamine, they appear visually brighter. However, near-infrared dyes are expensive, and a significant amount of dye is needed for the Nano-tracer synthesis.

Optimization of Polymerization Condition of Plain Nano-Tracers

HEMA and EGD were distilled at 90° C. in the presence of hydroquinone under vacuum. MMA and MAA were distilled at 90° C. in the presence of hydroquinone in vacuo. All the pre distilled monomers were stored under argon at −40° C. 50 mL nanopure $H_2O$ and a stir bar were placed in a Schlenk flask. Monomers were added to water, under the argon in the following order while stirring at 300 rpm: HEMA (0.981 mL, 8.10 mmol), MMA (1.973 mL, 18.58 mmol), MAA (0.345 mL, 4.06 mmol) and EGD (0.233 mL, 1.24 mmol). Sodium dodecyl sulfate (55 mg, 0.19 mmol) and ammonium persulfate (6 mg, 0.026 mmol) were then added to the flask. The monomers and dye mixture were stirred for 5 min at which point the flask was placed in an oil bath at 90° C. for 1 h. Over 1 h, the solution turned opaque/opalescent. At that time the solution was removed from the oil bath and allowed to rest at room temperature. The resulting NNTs were purified via dialysis into MILLI-Q water and further incubated with AG® 501-X8(D) mixed bed resin (analytical grade, with indicator dye, Bio-Rad) overnight to remove excess surfactant prior to in vitro and in vivo use.

Optimization of Polymerization Conditions for Cy5.5 Nano-Tracers

Cy5.5-Methacrylamide Linker Nano-Tracers

The polymerization conditions for Cy5.5-Methacrylamide containing nano-tracers were identical to those used for the plain nano-tracers until the SDS and AP solutions were added. Here, 40.5 mg Cy5.5-Methacrylamide monomer was first dissolved into 1 mL methanol (MeOH) followed by the addition of 1 mL of MILLI-Q water. This mixture was then added into the reaction flask where it was stirred for 5 min at which point the flask was placed in an oil bath at 90° C. for 1 h. After 1 h, the solution was removed from the oil bath and allowed to rest at room temperature.

Cy5.5-AEMA Nano-Tracers

The polymerization conditions for Cy5.5-AEMA nano-tracers were identical to those used for the plain nano-tracers until the SDS and AP solutions were added. Here, 36 mg Cy5.5-AEMA was dissolved into 1 mL mixture of the starting solution and 1 mL of MILLI-Q water. The color of the solution changed from blue to green. This mixture was added into the reaction flask, which was degassed three times prior to heating at 90° C. for 90 min. The final nano-tracer solution was blue in color after the polymerization had reached completion.

Optimization of Polymerization Condition for Cy7 Nano-Tracers

The polymerization conditions for Cy7 nano-tracers were identical to the plain nano-tracers until the SDS and AP solutions were added. The reaction was first degassed three times, then 15 mg Cy7-AEMA was dissolved into 8 mL of degassed MILLI-Q which was transferred into the flask by a cannula. The polymerization was left at 90° C. for 2 h. The final nano-tracer solution was dark green.

Optimization of Polymerization Condition for Coumarin Nano-Tracers

The polymerization conditions for Coumarin nano-tracers was identical to the plain nano-tracers until the SDS and AP solutions were added. Here, 15 mg coumarin acrylamide was dissolved into 0.6 mL tetrahydrofuran (THF) and added to the reaction flask. The reaction mixture was degassed three times before it was heated to 90° C. for 1 hr. After 1 h, the solution was removed from the oil bath and allowed to rest at room temperature.

Optimization of Polymerization Condition for Rhodamine Nano-Tracers

The polymerization conditions for the Rhodamine nano-tracers were identical to the plain nano-tracers until the SDS and AP solutions were added. Three different sets of conditions were tested to optimize the incorporation of the Rhodamine into the particles.

1. Rhodamine nano-tracer 1 (0.5 mmol in 5% MeOH): 20.47 mg methacryloxyethyl thiocarbamoyl rhodamine B was first dissolved into 50 μL MeOH, followed by 950 μL of MILLI-Q water.
2. Rhodamine nano-tracer 2 (0.5 mmol in 100% MeOH): 20.47 mg methacryloxyethyl thiocarbamoyl rhodamine B was dissolved into 500 μL MeOH.

3. Rhodamine nano-tracer 3 (1.0 mmol in 100% MeOH): 40.96 mg methacryloxyethyl thiocarbamoyl rhodamine B was dissolved into 1 mL MeOH.

The dye mixture was added to the reaction flask and stirred for 5 min at which point the flask was placed in the oil bath at 90° C. for 1 h. After 1 h, the solution was removed from the oil bath and allowed to rest at room temperature.

Optimization of Polymerization Condition for Fluorescein Nano-Tracers

The polymerization conditions for Fluorescein nano-tracers were identical to the plain nano-tracers until the SDS and AP solution were added. Three different sets of conditions were tested to optimize the incorporation of the Fluorescein into the particles.

1. Fluorescein nano-tracer 1 (1.1 mM methacryloyloxy O-fluorescein in 100% water Nano-tracers): 40 mg methacryloyloxy O-fluorescein was dissolved into 1 mL of MILLI-Q water.
2. Fluorescein nano-tracer 2 (1.1 mM in methacryloyloxy O-fluorescein 100% THF Nano-tracers): 40 mg methacryloyloxy O-fluorescein was dissolved into 500 μL THF.
3. Fluorescein nano-tracer 3 (4.5 mM in methacryloyloxy O-fluorescein 100% THF Nano-tracers): 100 mg methacryloyloxy O-fluorescein was dissolved into 1 mL THF.

The dye mixture was added to the reaction flask and stirred for 5 min at which point the flask was placed in the oil bath at 90° C. for 1 h. After 1 h, the solution was removed from the oil bath and allowed to rest at room temperature.

Exploration of Monomer Types for Retrograde Transport

The in vivo studies in this section, along with the surgery, dissection, and fixation of the brain, were performed as detailed elsewhere herein (e.g., Example 1). The neuronal projection system of V1 to LGN in the thalamus was chosen for the retrograde test. All the nano-tracers tested in this section are labeled with rhodamine dye.

Figure 69B:
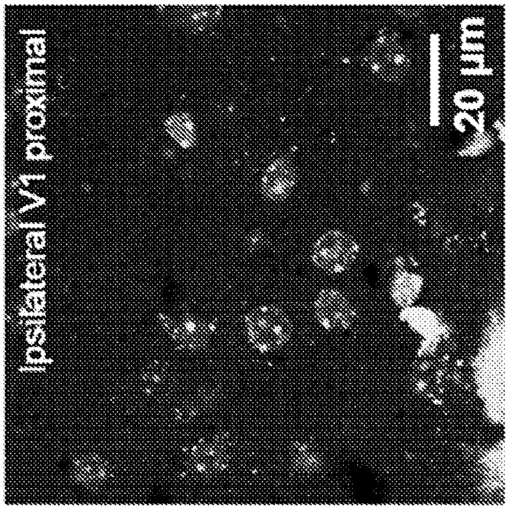
FIGS. 69A-69C: Retrograde Transportation Test of Nano-tracers without HEMA.
Figure 69C:
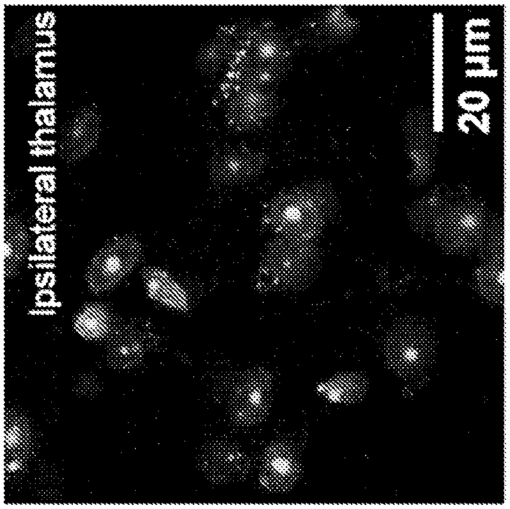
Figure 69A:
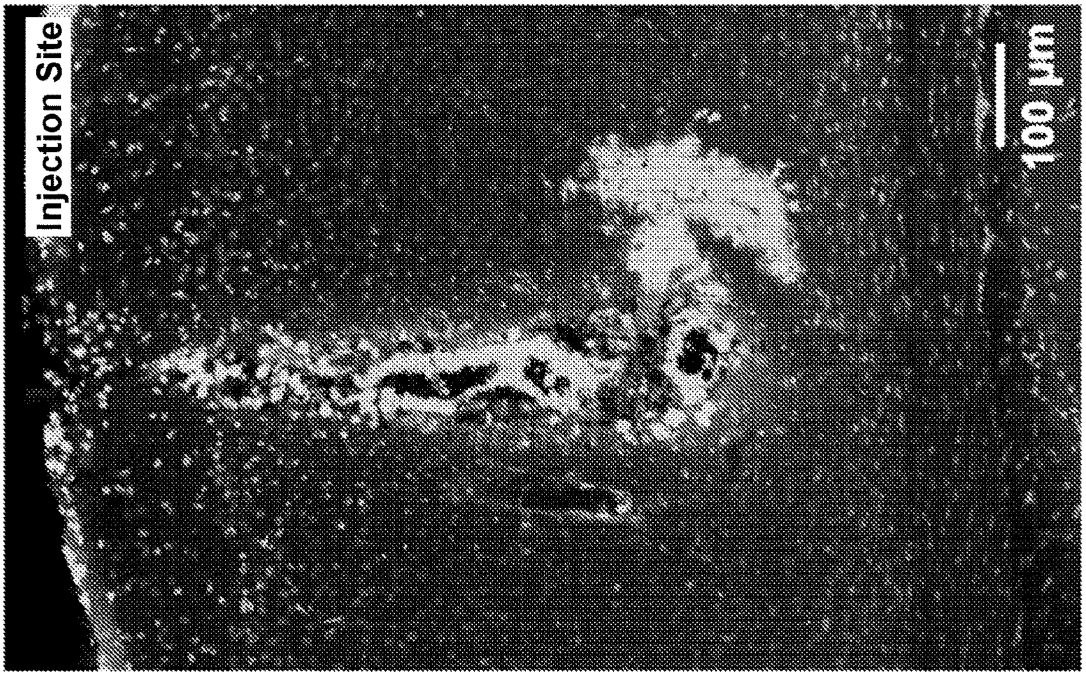

FIGS. 69A-69C shows the retrograde test of the nano-tracer without HEMA as prepared elsewhere in Example 5. Nano-tracers without HEMA were injected into the V1 area. FIG. 69A shows a rhodamine label trace at the needle site in the V1 region, therefore confirming a successful injection of rhodamine nano-tracers. Neurons are also labeled in the adjacent area to the injection site FIG. 69B. Further, the ipsilateral area of LGN in the thalamus was imaged to look for retrograde transport of nano-tracers (FIG. 69C). A strong fluorescence was observed, indicating that the retrograde transportation ability is retained when HEMA is not present in the nanoparticle.

Figure 70A:
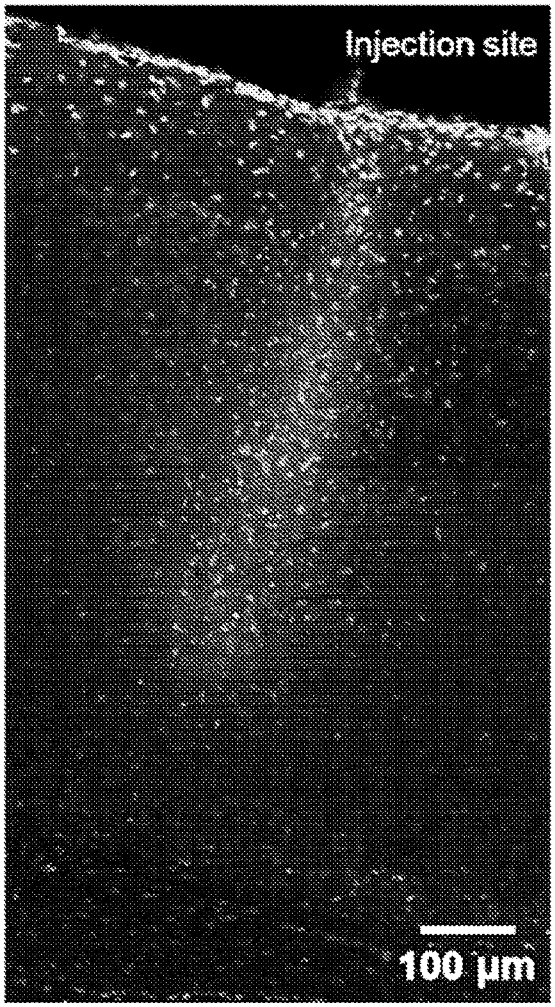
FIGS. 70A-70B: Retrograde Transportation Test of Nano-tracers without MMA in vivo.
Figure 70B:
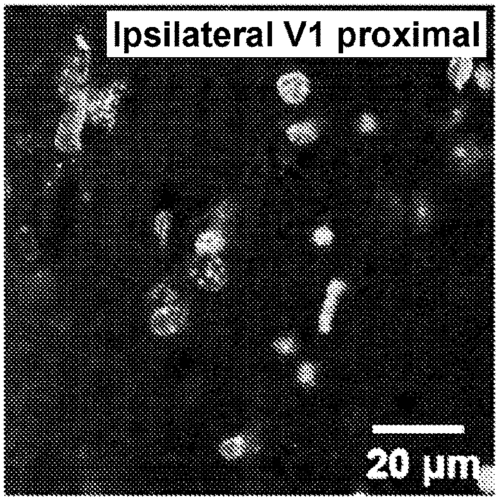

FIGS. 70A-70B demonstrate the retrograde test of the nano-tracer without MMA as prepared elsewhere in Example 5. A weak rhodamine trace at the injection area and rhodamine clusters in neurons proximal to the injection site were seen by confocal microscopy (FIGS. 70A-7B). However, no trace of nano-tracers was found in the thalamus. Considering that primary composition of nano-tracer is taken, these nano-tracers are much less dense than the other batches. Thus, under these specific circumstances, MMA may have a role in retrograde transportation.

Figure 71A:
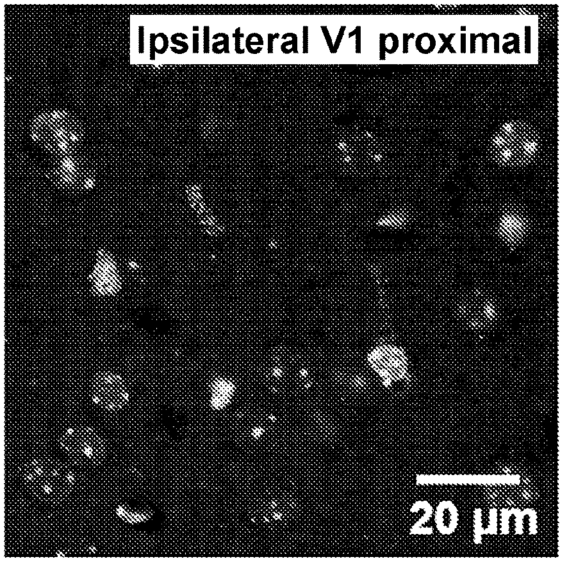
FIGS. 71A-71B: Retrograde Transportation Test of Nano-tracers without EGD in vivo.
Figure 71B:
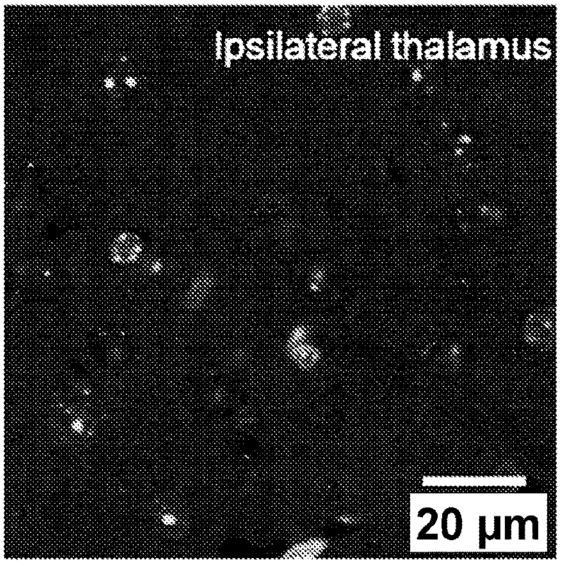
Figure 72B:
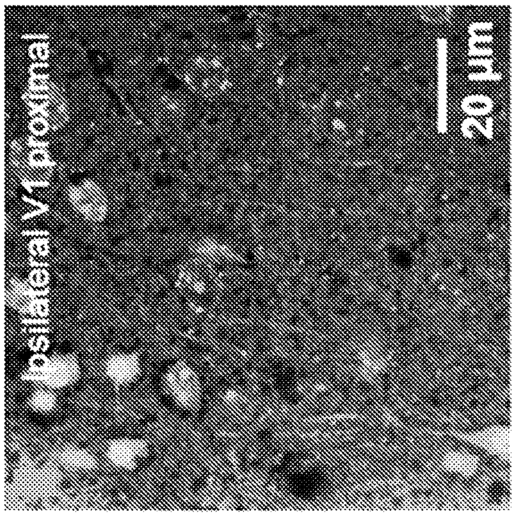
FIGS. 72A-72C: Retrograde Transportation Test of Nano-tracers without EGD in vivo.
Figure 72C:
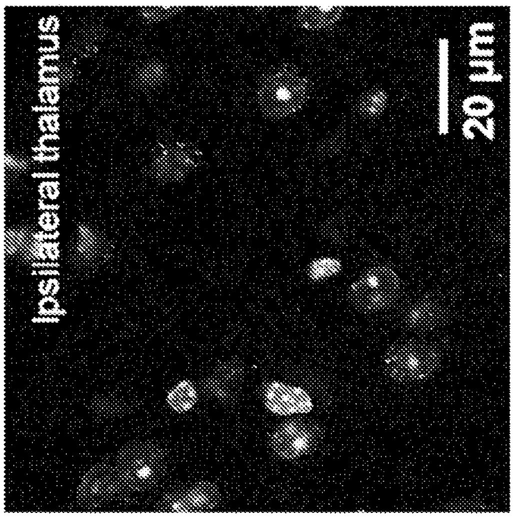
Figure 72A:
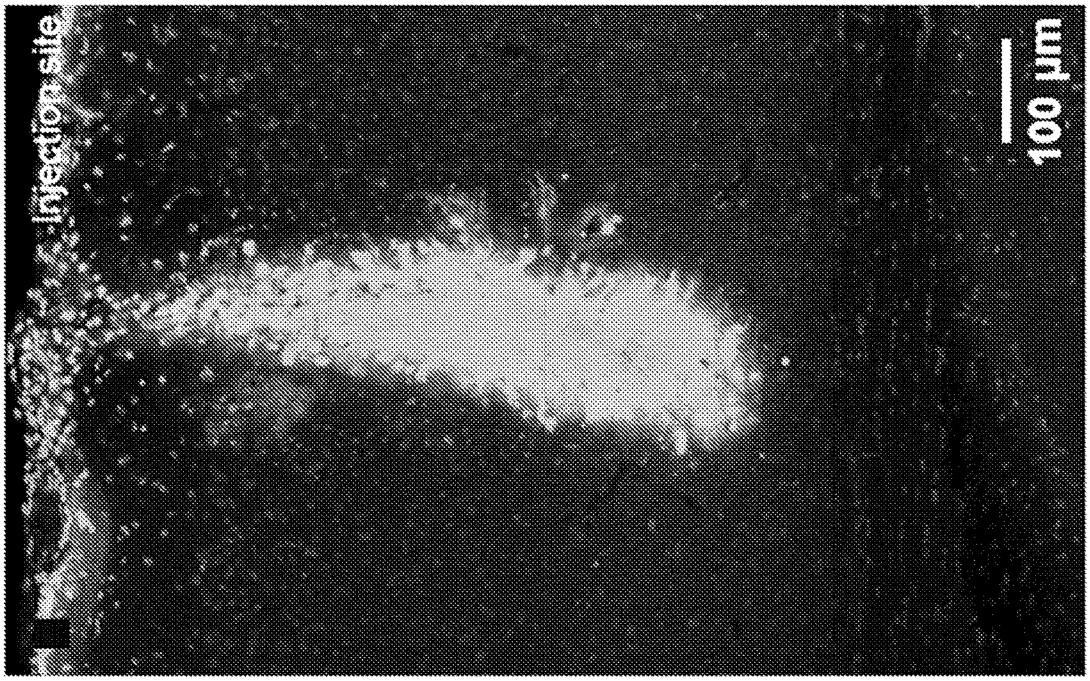

The same retrograde test in vivo experiment was conducted with nano-tracers without MAA (FIGS. 71A-71B) and nano-tracers without EGD from (FIGS. 72A-72C), both of which were prepared elsewhere in Example 5. The injection site with nano-tracers with MAA was not strongly labeled, but rhodamine clusters were observed in the neurons next to the injection site FIG. 71A). It was difficult to obtain a clear image of the nano-tracers in the thalamus. The rhodamine might have faded or dispersed (FIG. 71B). Therefore, the retrograde test result is unclear.

For the nano-tracers with EGD, confocal images (FIG. 72A) show a clear needle and rhodamine trace. During the injection, the rigidity of nano-tracers was much lower than other nano-tracers. Both the ipsilateral V1 proximal area (FIG. 72B) and the ipsilateral thalamus area (FIG. 72C) were labeled by the nano-tracers, indicating that under these circumstances EGD may not have a role in retrograde transportation.

Figure 73C:
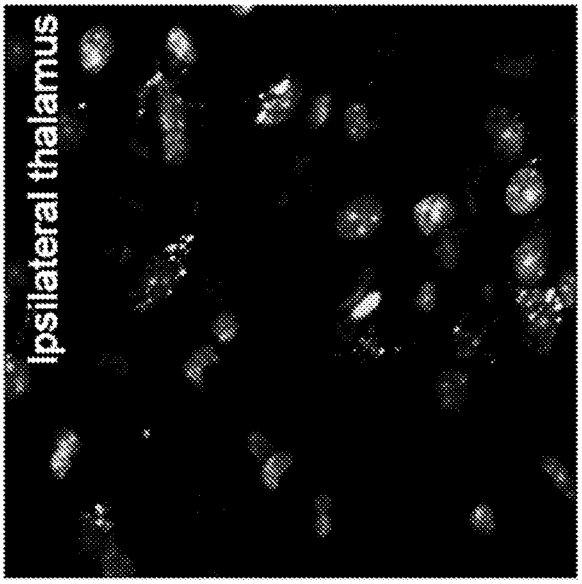
FIGS. 73A-73C: Retrograde Transportation Test of Nano-tracers with Methacrylamide in vivo.
Figure 73B:
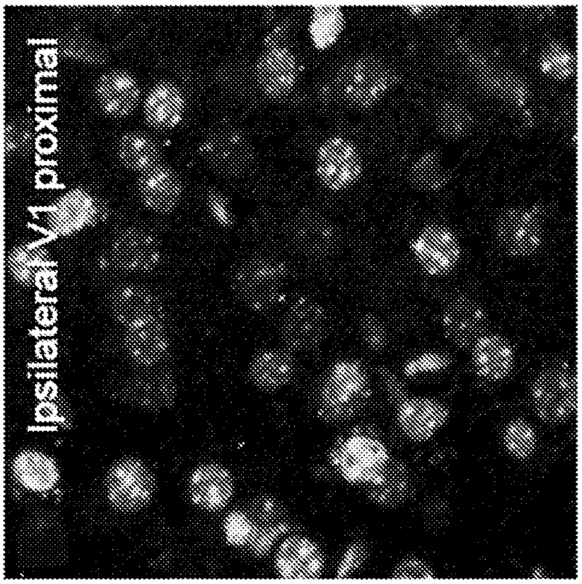
Figure 73A:
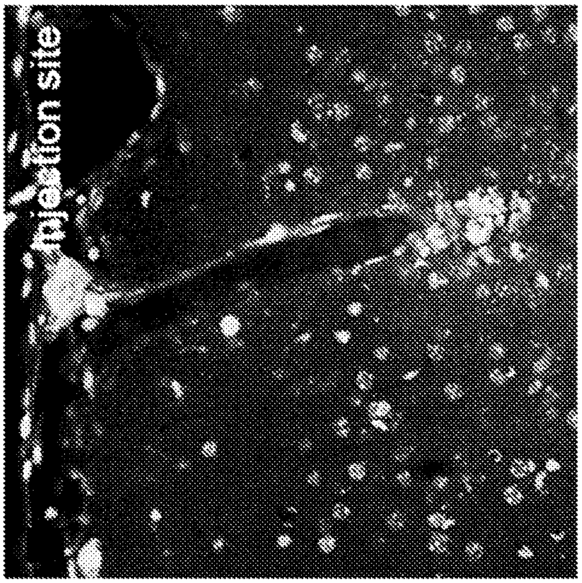

FIGS. 73A-73C present the retrograde test of the nano-tracer with methacrylamide as prepared elsewhere in Example 5. Nano-tracer with methacrylamide was injected to V1 area, and the coronal section of the mouse V1 region confirms with a rhodamine label trace and a needle trace FIG. 73A. Neurons are also labeled in the adjacent area to the injection site FIG. 73B. Further, ipsilateral area of LGN in the thalamus was imaged to look for retrograde transport of nano-tracers (FIG. 73C), we observed strong fluorescence, indicating that the retrograde transportation ability is retained when substituting MMA with methacrylamide.

These results indicate, for example, that a variety of monomers and resulting polymers may be employed in polymeric nanoparticles for retrograde transport in a neuron, thereby facilitating brain mapping and axonal tracing.

Exploration of Crosslinker Selections

The hydrophobicity of the crosslinker used in emulsion polymerization could affect the morphology and size of the resulting latex. It was suggested that high crosslinker concentration in the polymerization reaction leads to microgel or precipitation formation. Therefore, in addition to EGD, two other crosslinkers: Poly (ethylene glycol) (PEG) diacrylate 250 and PEG diacrylate 700 were examined.

The polymerization condition of nano-tracers using PEG diacrylate 250 or PEG diacrylate 700 was identical to the plain nano-tracer's polymerization condition except the EGD was substituted for one of the PEG crosslinkers listed above.

1. PEG diacrylate 250: 308.8 mg or 0.278 mL of PEG diacrylate 250 equivalent to the molar mass of EGD was added into the reaction mixture.
2. PEG diacrylate 700: 864 mg or 0.772 mL of PEG diacrylate 700 equivalent to the molar mass of EGD was added into the reaction mixture.

Exploration of Surfactant Selections

The primary function of surfactants in emulsion polymerization is to reduce interfacial tension. This function helps the reactive vinyl monomers emulsify and form stable colloidal dispersed nanoparticles. The concentration of surfactant used in emulsion polymerization usually is well above its critical micelle concentration (CMC). At concentrations above CMC, surfactants form micelles that are capable of encapsulating non-polar monomers. Traditional surfactant helps monomers stay inside the micelles and stabilizes the polymer particles during the nucleation and growth step.

Figure 81:
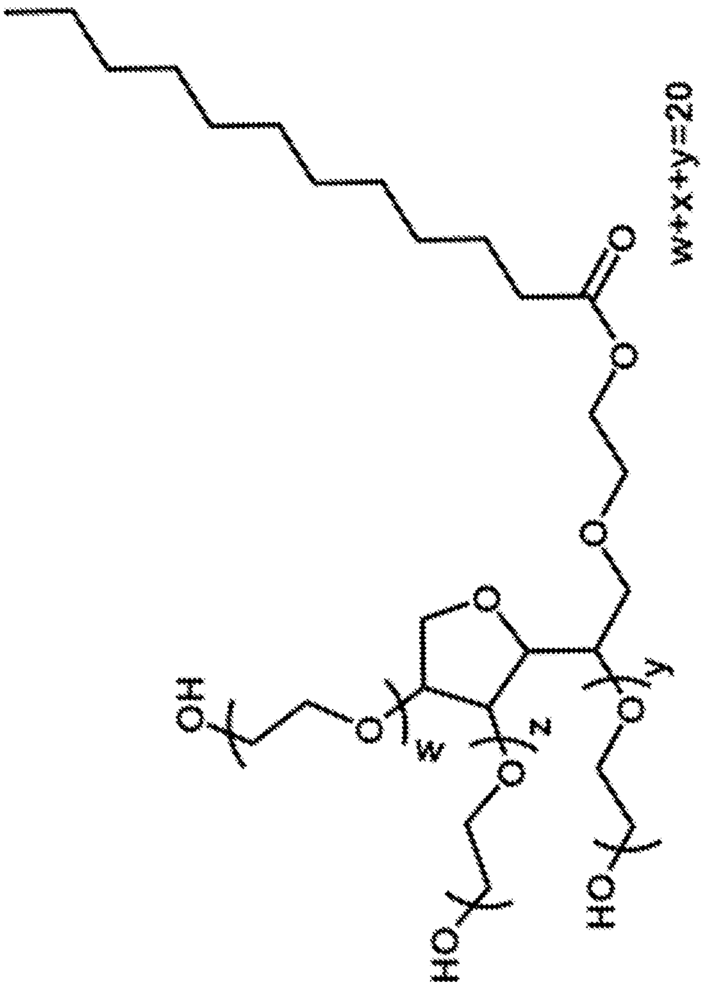
FIG. 81: Chemical Structure of TRITON X-100 and TWEEN 20.
Figure 81:
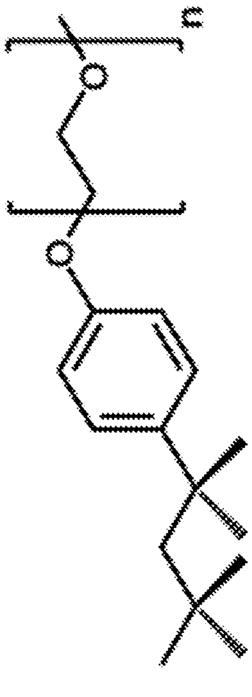

In this section, TRITON X-100 and TWEEN 20 were tested to gauge their effectiveness in nano-tracer synthesis (FIG. 81). TRITON X-100 is a non-ionic surfactant. It has a hydrophilic polyethylene oxide chain and an aromatic hydrocarbon lipophilic group on the other side. TWEEN 20 is also called polysorbate 20, and is also a non-ionic surfactant. The ethoxylation process leaves the molecule with 20 repeat units of polyethylene glycol.

The polymerization conditions for nano-tracers using TRITON X-100 or TWEEN was identical to the plain nano-tracers except SDS was substituted by one of the surfactants listed above.

1. TRITON X-100: 119.2 mg or 0.111 mL of TRITON X-100 equivalent to the molar mass of SDS was added into the reaction mixture.
2. TWEEN 20: 234 mg or 0.213 mL of TWEEN 20 equivalent to the molar mass of SDS was added into the reaction mixture.

Exploration of Radical Initiator Selections

Two common types of free radical initiators that have been used in emulsion polymerization are thermal and redox initiators. For thermal initiators, persulfate salts (such as AP) are regularly used. Here, sulfate radicals are generated by breaking the persulfate ion at temperatures above 50° C. Azobisisobutyronitrile (AIBN) is another commonly used thermal initiator. In addition, the combination of benzoyl peroxide (BPO)(oxidant) and dimethylaniline (DMA) (reductant) are reliable redox initiators(30) that do not induce heat to the reaction system.

Photo-initiators are a relatively new category used in emulsion polymerizations. This type of initiator is beneficial for temperature-sensitive polymerizations. Eosin Y-Triethylamine (TEA) is an example of a photo-redox initiator. Eosin Y is excited by green light and TEA reduces eosin Y. A resulting proton transfer produces two neutral radicals which initiate polymerization. SPTP is an example of a photolysis initiator. It is suggested that SPTP is the most effective free-radical initiator in terms of initiation and chain propagation in response to visible light irradiation in aqueous solution at room temperature.

Figure 82:
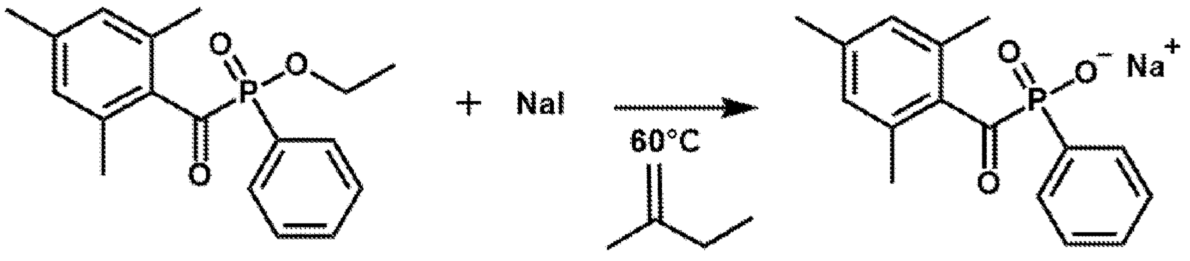
FIG. 82: Synthetic Scheme of SPTP.

The water-soluble photo-initiator SPTP was synthesized (FIG. 82) via solvolysis of ethyl phenyl-2,4,6-trim ethylbenzoyl-phosphinate (EPTP) in ethyl methyl ketone in the presence of sodium iodidev(33). EPTP (3.16 g, 10 mmol) and sodium iodide (1.60 g, 11 mmol) were dissolved in ethyl methyl ketone (30 mL) in a 50 mL Schlenk flask. The reaction was stirred in the dark under argon at 60° C. overnight. The resulting precipitate was washed with ethyl methyl ketone and dried under vacuum overnight. Yield: 2.02 g, 65%. $^1$H NMR ($D_2O$) δ: 7.5-7.8 ppm (5H, C6H5), 7.0 ppm (2H, C6H2(CH3)3), 2.31 ppm (3H, p-CH3), 2.08 ppm (6H, o-CH3).

Nano-Tracers were Synthesized Using the Photo-Initiator SPTP Under the Following Conditions:

365 nm UV light with 10 ml reaction scale: 10 mL nanopure $H_2O$ and a stir bar were placed in a 22 mL sealable glass vial. HEMA 0.981 mL, MMA 1.973 mL, MAA 0.345 mL, and EGD 0.233 mL were added to a separate vial under argon. 0.7 mL of this monomer mixer was added to the reaction vial while stirring at 300 rpm. Then 0.1 mL of a 220 mg/mL SDS solution and 0.167 mL of 30 mg/mL SPTP in MILLI-Q water were added to the flask. After 5 min of stirring, the reaction was placed under 365 nm UV light for 8 h. 405 nm Blue LED light with 50 ml reaction scale: 50 mL nanopure $H_2O$ and a stir bar were placed in a schlenk flask and stirred at 300 rpm under and argon atmosphere. To this was added HEMA 0.981 mL, MMA 1.973 mL, MAA 0.345 mL, and EGD 0.233 mL, respectively. Then 0.54 mL of a 220 mg/mL SDS solution and 0.5 mL of 30 mg/mL SPTP in MILLI-Q water were added into the flask. After 5 min of stirring, the reaction was placed under 405 nm Blue LED light for 8 h.

Characterization of Nano-Tracers

Plain Nano-Tracers

Figure 83A:
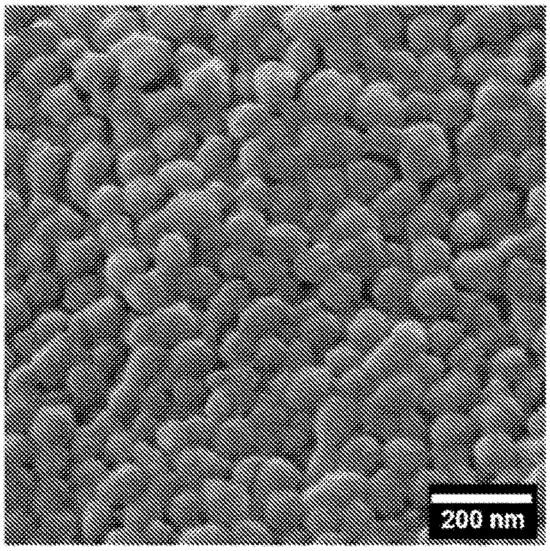
FIGS. 83A-83B: Electron Microscopy Graphs of Plain Nano-tracer.
Figure 83B:
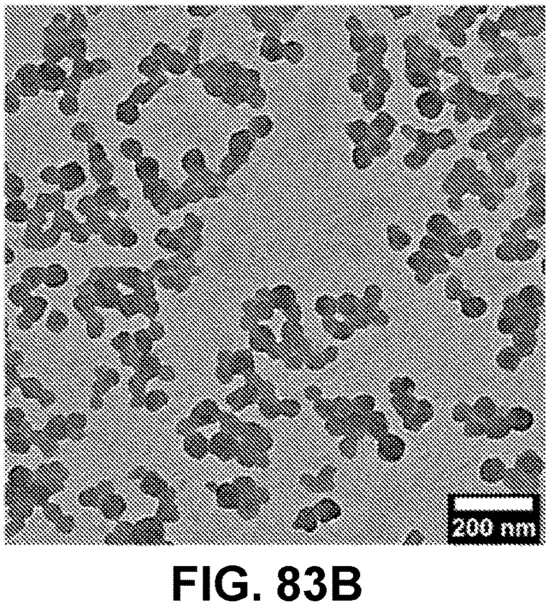
Figure 84:
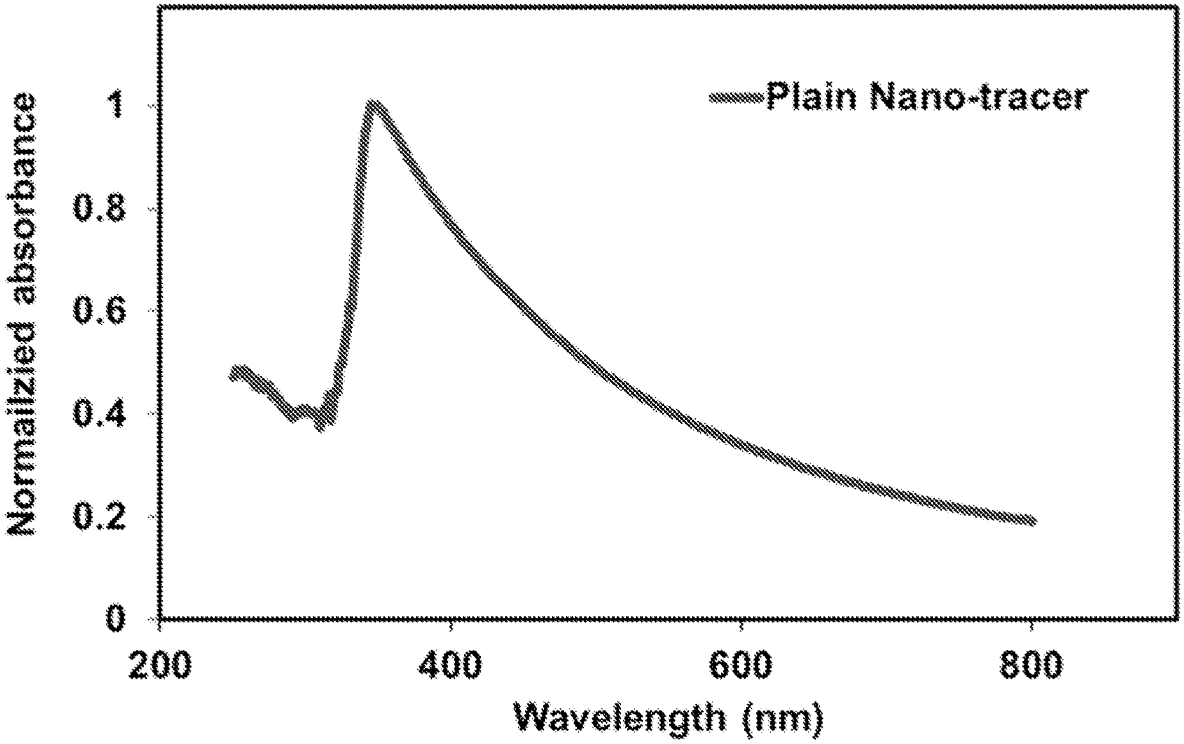
FIG. 84: UV-Vis Spectra of the Plain Nano-tracers.

FIGS. 83A-83B show scanning electron microscope (SEM) and uranyl acetate stained dry-state TEM images of plain nano-tracers. The diameter measured from the SEM images was 78±12 nm and 67±8 nm from the dry-state TEM images. The UV-Vis absorption of plain nano-tracer, shows a peak at 350 nm which is attributed to the inherent structure of nano-tracers (FIG. 84). To discern the concentrations of plain nano-tracers, we employed nanoparticle tracking analysis (NTA) and determined that the particle concentration of the plain nano-tracer was $9.66\times10^{11}$ particles per milliliter.

Cy5.5 Nano-Tracers

Cy5.5-Methacrylamide Linker Nano-Tracers

Figure 85:
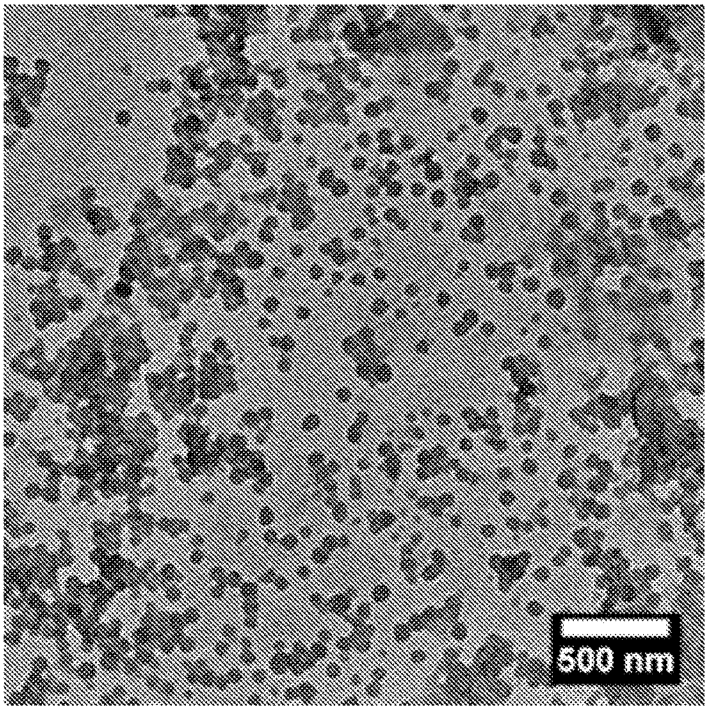
FIG. 85: TEM Image of Cy5.5-Methacrylamide Linker Nano-tracers.
Figure 86A:
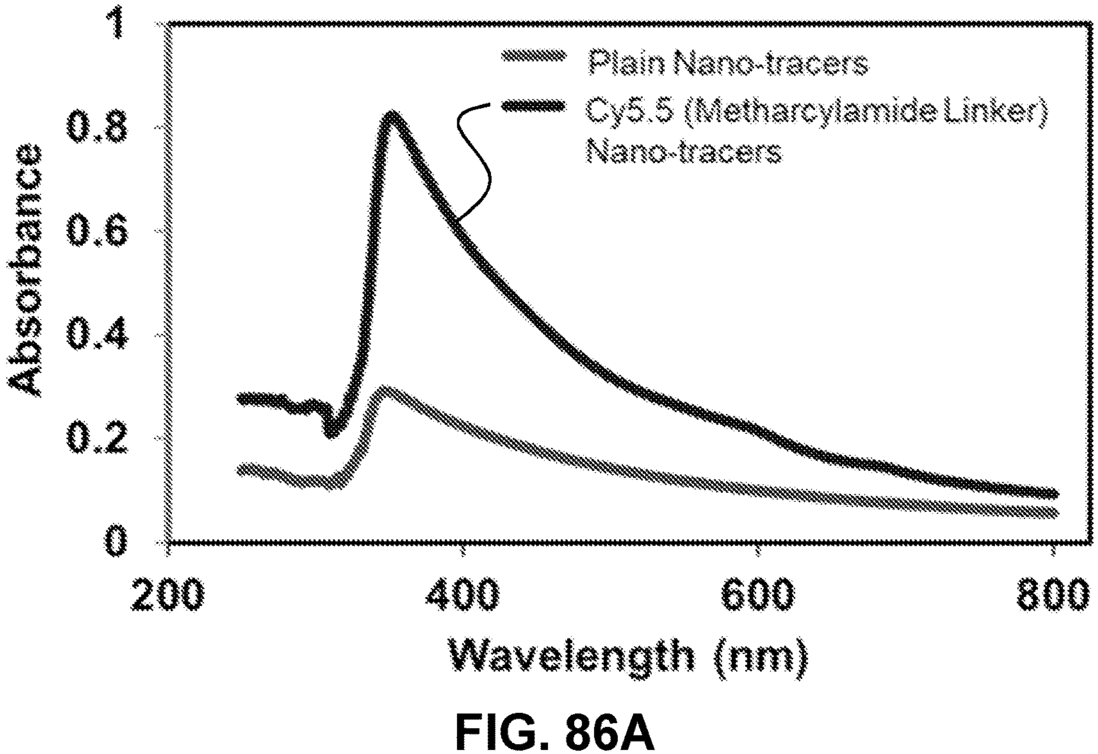
FIG. 86A: UV-Vis and (FIG. 86B) Fluorescence Spectra of Cy5.5-Methacrylamide Linker Nano-tracers.
Figure 86B:
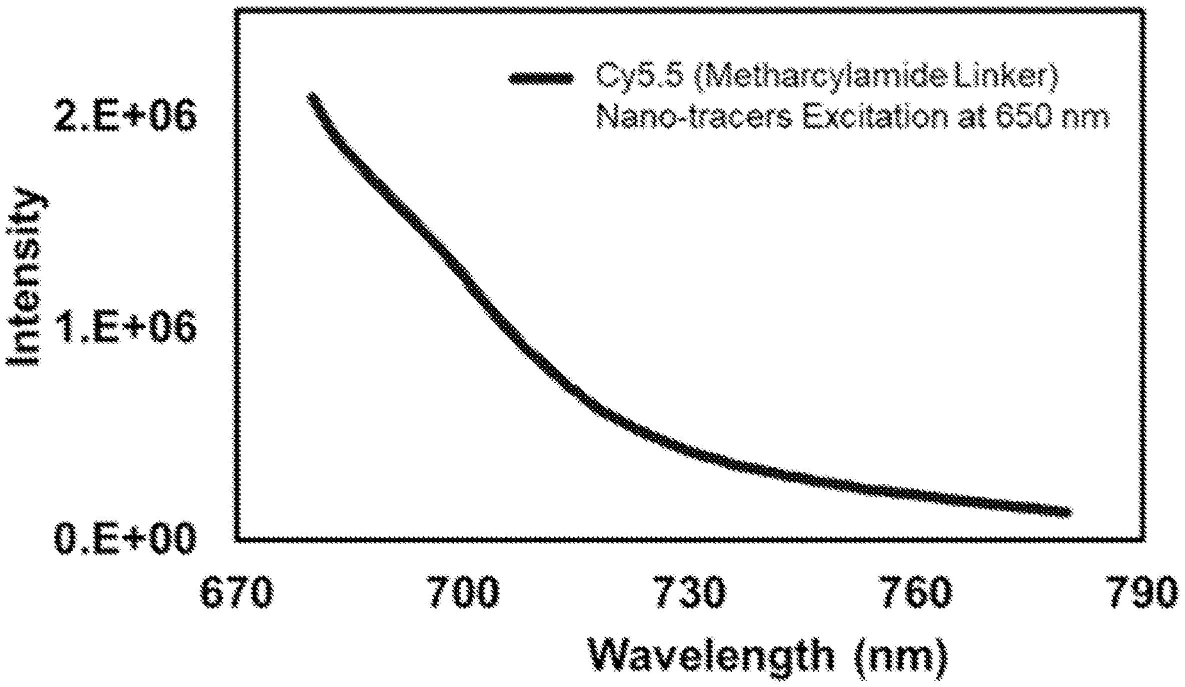

The morphology of Cy5.5-Methacrylamide nano-tracers was characterized by uranyl acetate stained dry-state TEM (FIG. 85). The diameter measured from the dry-state TEM was 80±10 nm. Excitation spectra of Cy5.5-Methacrylamide nano-tracers were acquired by UV-Vis and were overlaid with plain nano-tracers (FIG. 86A). Emission spectra were obtained by fluorescence spectroscopy with excitation at 650 nm (FIG. 86B). However, no excitation or emission peaks were observed, indicating little or no dye was incorporated to the nano-tracers.

Cy5.5-AEMA Nano-Tracers

Figure 87A:
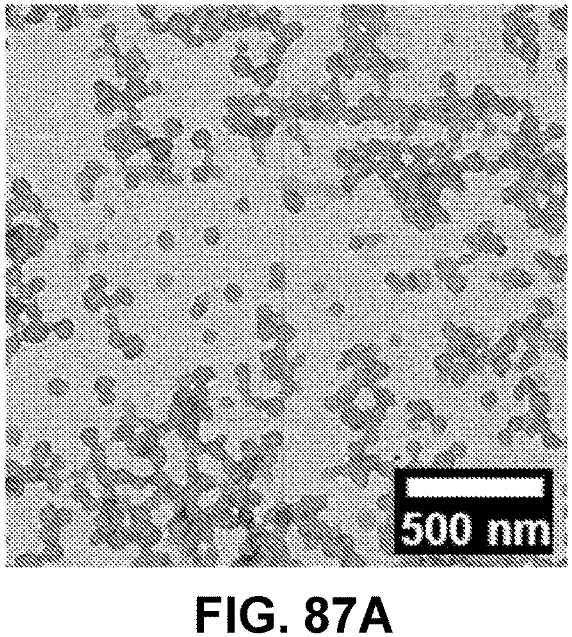
FIGS. 87A-87B: Electron Microscopy Graphs of Cy5.5-AEMA Nano-tracers.
Figure 87B:
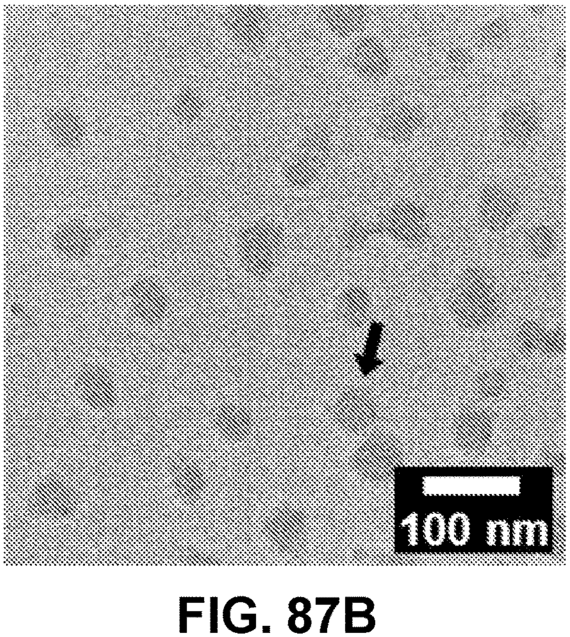

The morphology of Cy5.5-AEMA nano-tracers was characterized by uranyl acetate stained dry-state TEM and Cryogenic electron microscopy (cryo-EM) (FIGS. 87A-87B). The diameter measured from dry-state TEM was 45±8 nm, from cryo-EM was 47±10 nm.

Figure 88A:
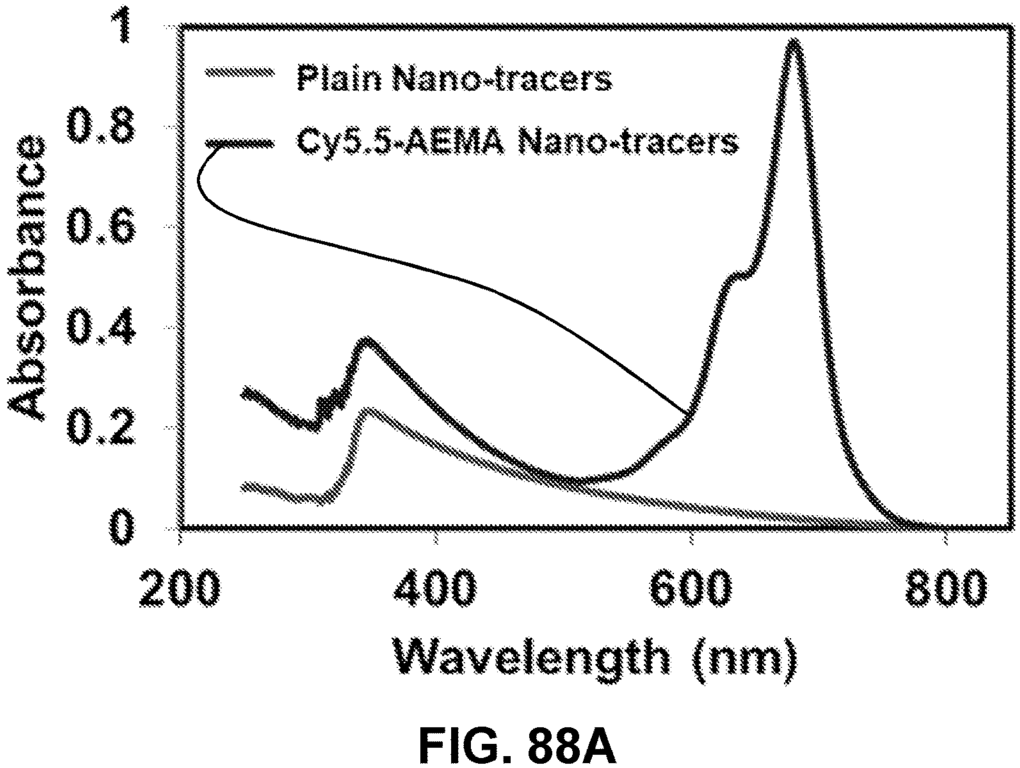
FIG. 88A: UV-Vis and (FIG. 88B) Fluorescence Spectra of Cy5.5-AEMA Nano-tracers.
Figure 88B:
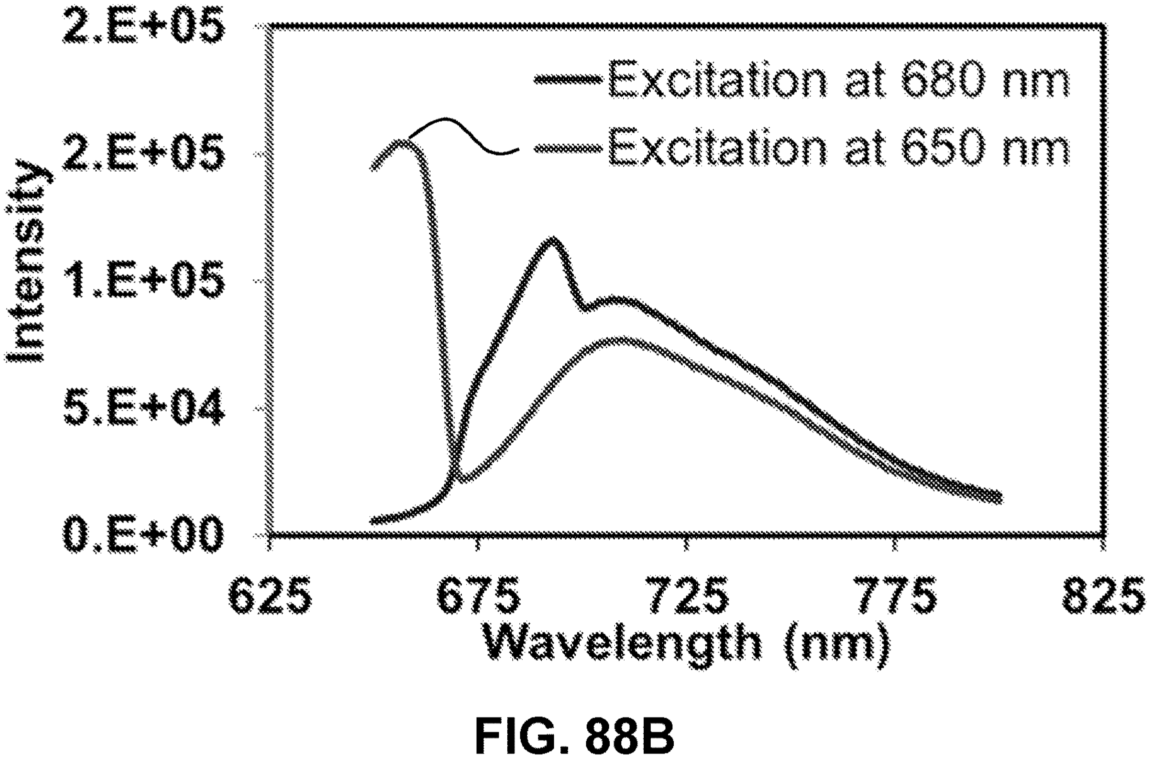

The excitation spectra of Cy5.5-AEMA nano-tracers was acquired by UV-Vis and overlaid with the plain nano-tracers (FIG. 88A). Emission spectra were obtained by fluorescence spectroscopy with excitation at 650 nm and 680 nm (FIG. 88B). The excitation maxima of Cy5.5-AEMA nano-tracers was found to be ($\lambda_{ex}$) 672 nm, while the emission maxima was found to be ($\lambda_{em}$) 700 nm.

Figure 89:
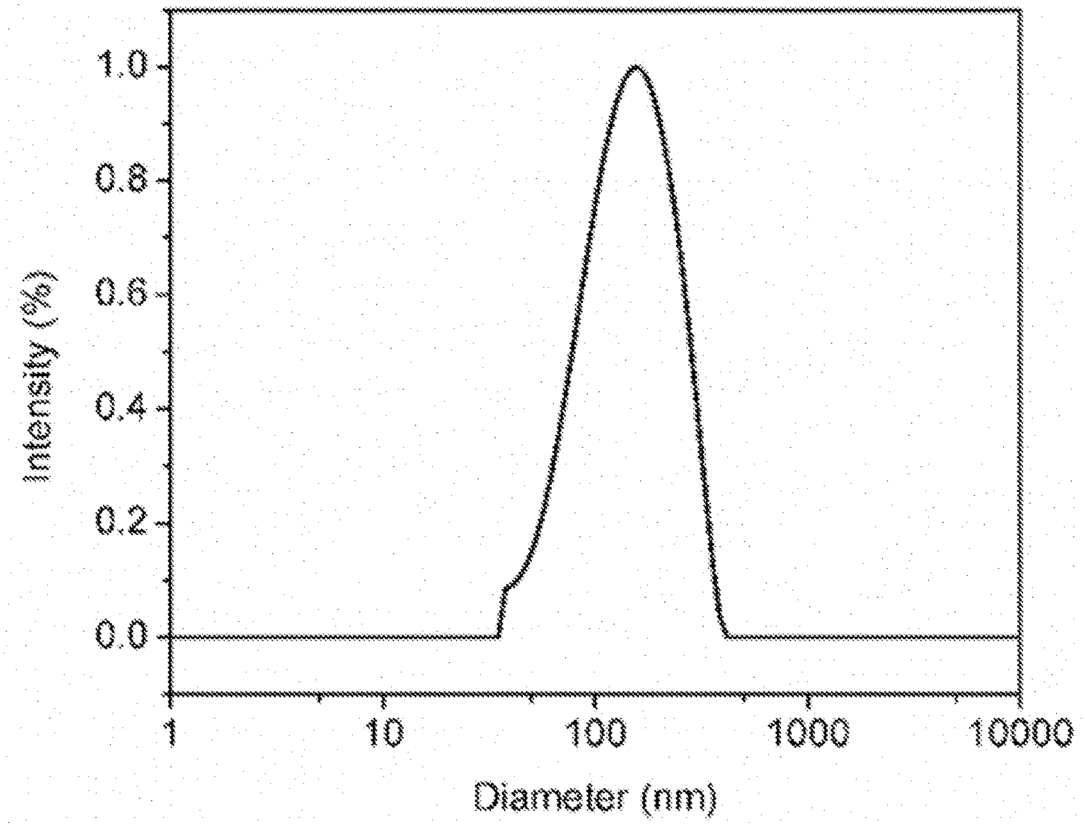
FIG. 89: Distributions of Hydrodynamic Diameter of Cy5.5-AEMA Nano-tracers.

NTA determined that the particle concentration of the Cy5.5-AEMA nano-tracer was $2.5\times10^{11}$ particles per milliliter. By dynamic light scattering (DLS), Cy5.5-AEMA nano-tracers exhibit a hydrodynamic diameter (Dh) of 102 nm, which is consistent with the results from both dry-state TEM and cryo-EM (FIG. 89). The Zeta potential of Cy5.5-AEMA nano-tracers was determined to be −46.1 mV, suggesting that the surface of nano-tracer is significantly negatively charged, which is attributed to MAA.

Cy7 Nano-Tracers

Figure 90:
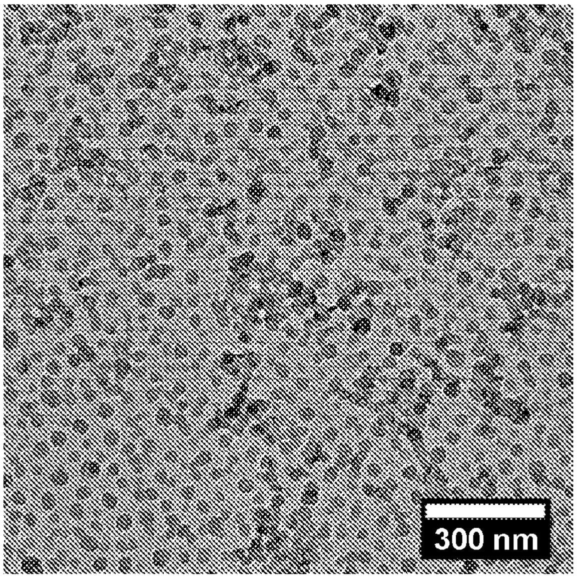
FIG. 90: TEM image of Cy7-AEMA Nano-tracers.
Figure 91A:
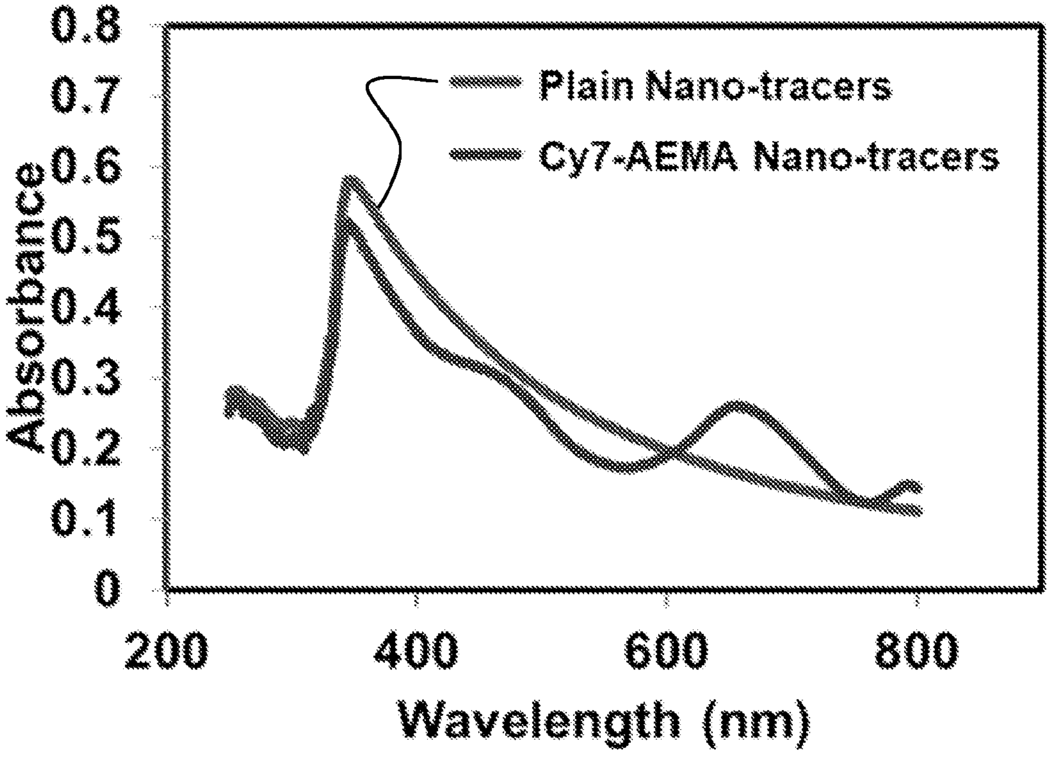
FIG. 91A: UV-Vis and (FIG. 91B) Fluorescence Spectra of Cy7-AEMA Nano-tracers.
Figure 91B:
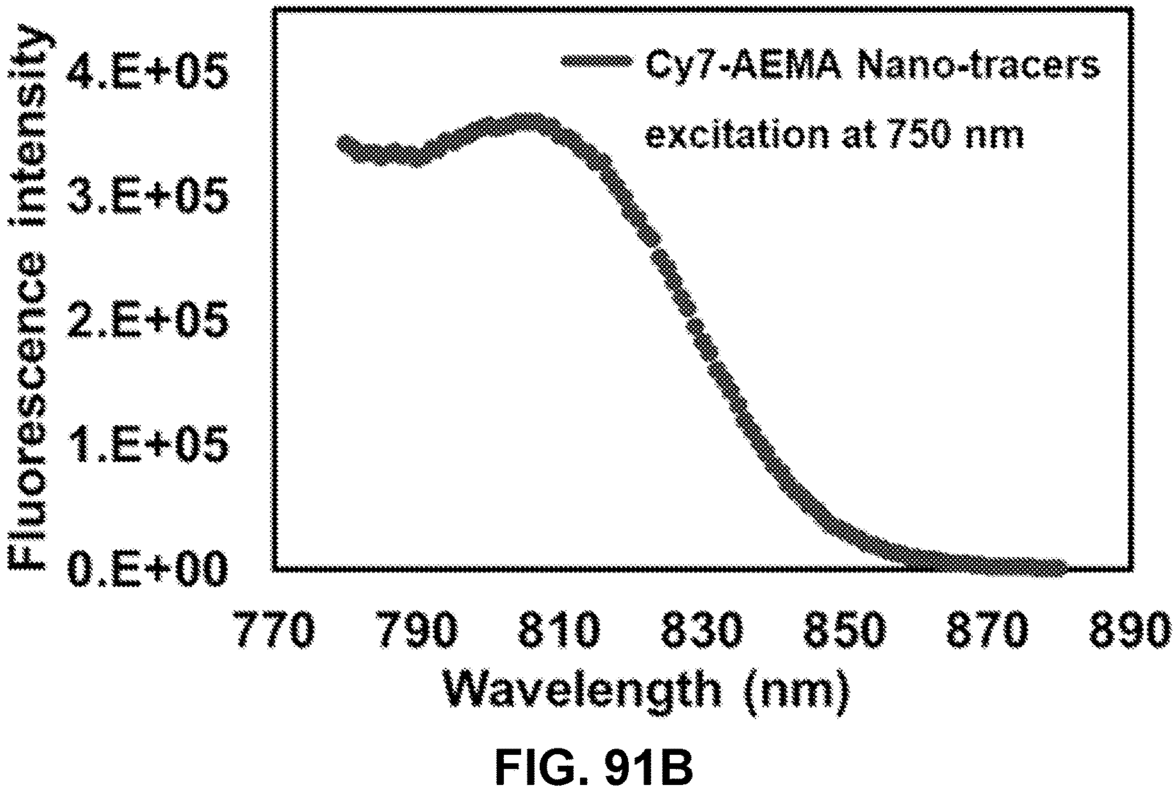

The morphology of Cy7-AEMA nano-tracers was characterized by uranyl acetate stained dry-state TEM (FIG. 90). The diameter measured from dry-state TEM was 61±14 nm. Excitation spectra of Cy7-AEMA nano-tracers were acquired by UV-Vis and were overlaid with plain nano-tracers (FIG. 91A). Emission spectra were obtained by fluorescence spectroscopy with excitation at 750 nm (FIG. 91B). The excitation maxima of Cy7-AEMA nano-tracers ($\lambda_{ex}$) was determined to be 657 nm, with an emission maxima determined to be ($\lambda_{em}$) 806 nm.

Figure 92:
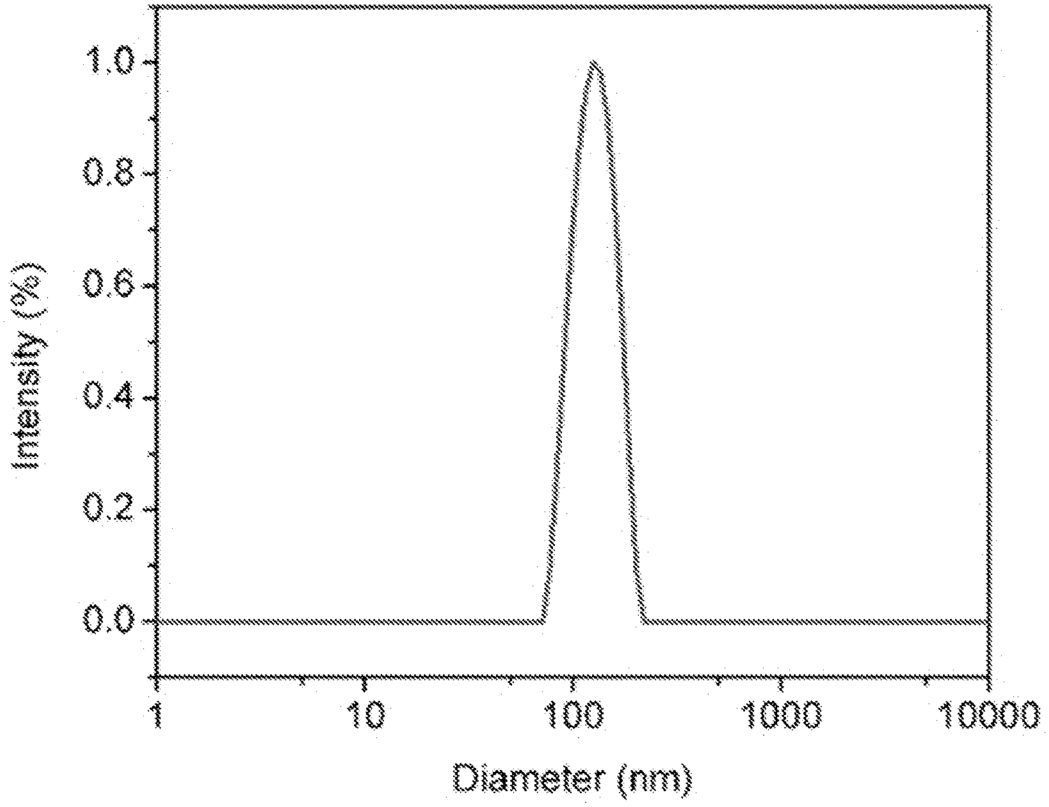
FIG. 92: Distribution of Hydrodynamic Diameter of Cy7-AEMA Nano-tracers.

The concentration of the Cy7-AEMA nano-tracer was determined to be $9.4\times10^{9}$ particles per milliliter by NTA. DLS of the Cy7-AEMA nano-tracers showed a Dh of 129.4 nm, which is larger than that determined by dry-state TEM which is attributed to the full hydration of the particles (FIG. 92). The Zeta potential of Cy7-AEMA nano-tracers was determined to be 33.4 mV.

Coumarin Nano-Tracers

Figure 93A:
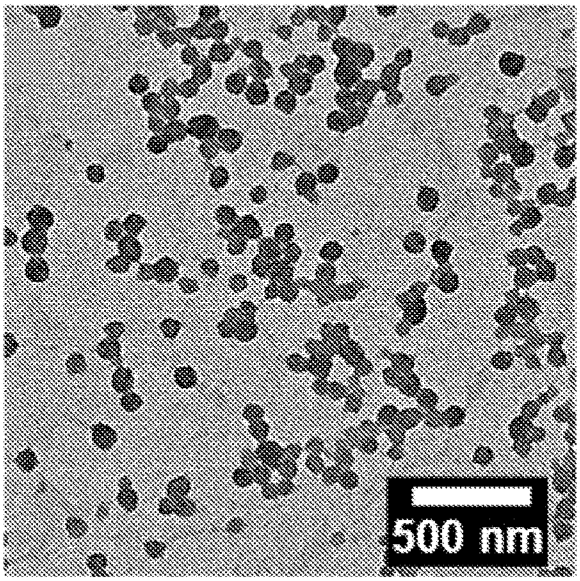
FIGS. 93A-93B: Electron Microscopy Graphs of Coumarin Nano-tracers.
Figure 93B:
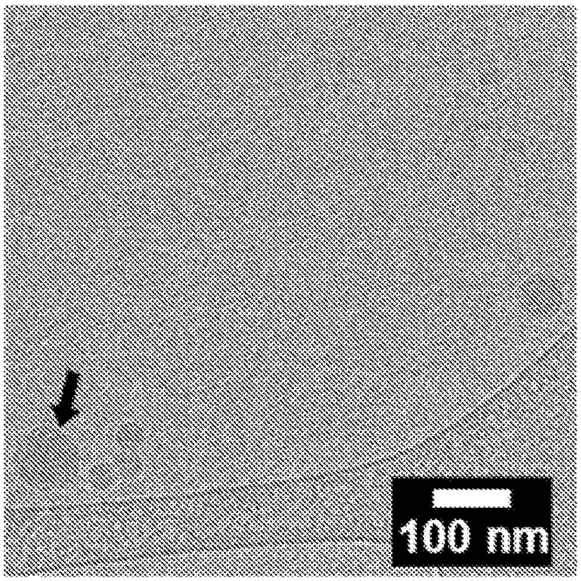

The morphology of Coumarin nano-tracers was characterized by uranyl acetate stained dry-state TEM and cryo-EM (FIGS. 93A-93B). The diameter measured from dry-state TEM was 57±12 nm, and 46±19 nm from cryo-EM.

Figure 94A:
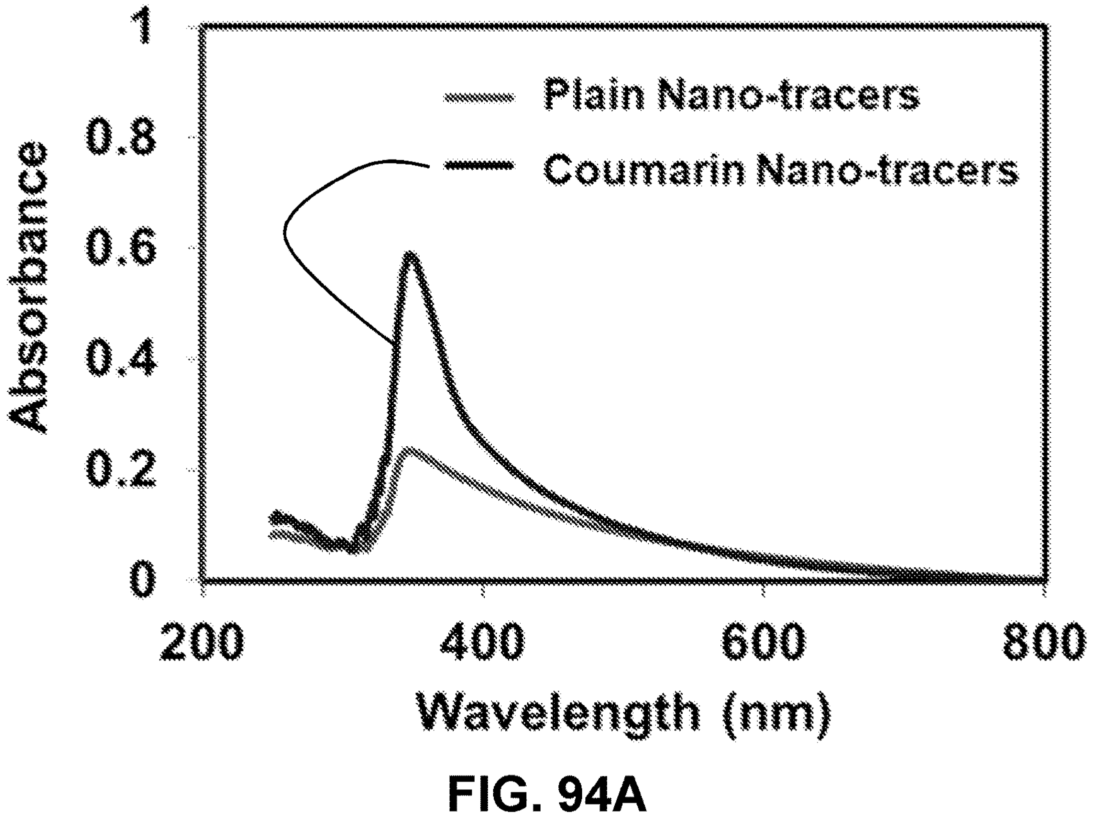
FIG. 94A: UV-Vis and (FIG. 94B) Fluorescence Spectra of Coumarin Nano-tracers.
Figure 94B:
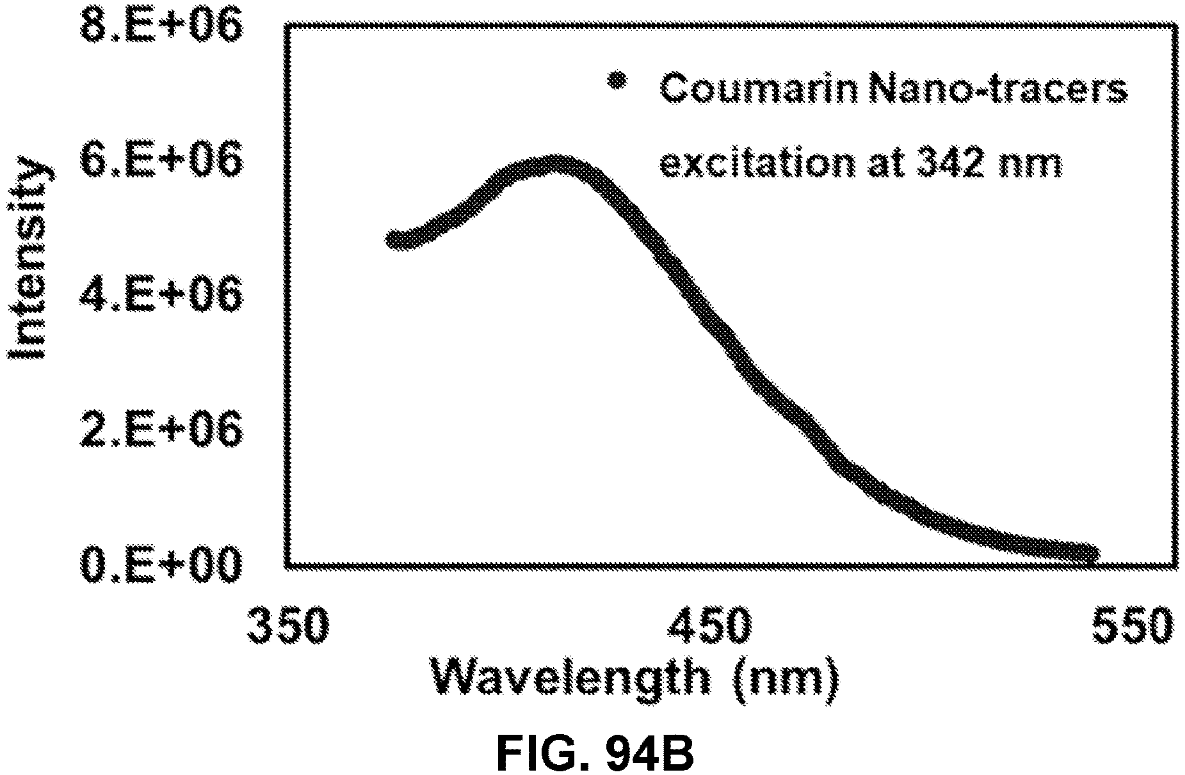

The excitation spectra of Coumarin nano-tracers was acquired by UV-Vis and overlaid with plain nano-tracers (FIG. 94A). Emission spectra were obtained by fluorescence spectroscopy with excitation at 342 nm (FIG. 94B). The excitation maxima of Coumarin nano-tracers ($\lambda_{ex}$) is 351 nm, with an emission maxima ($\lambda_{em}$) of 412 nm.

Figure 95:
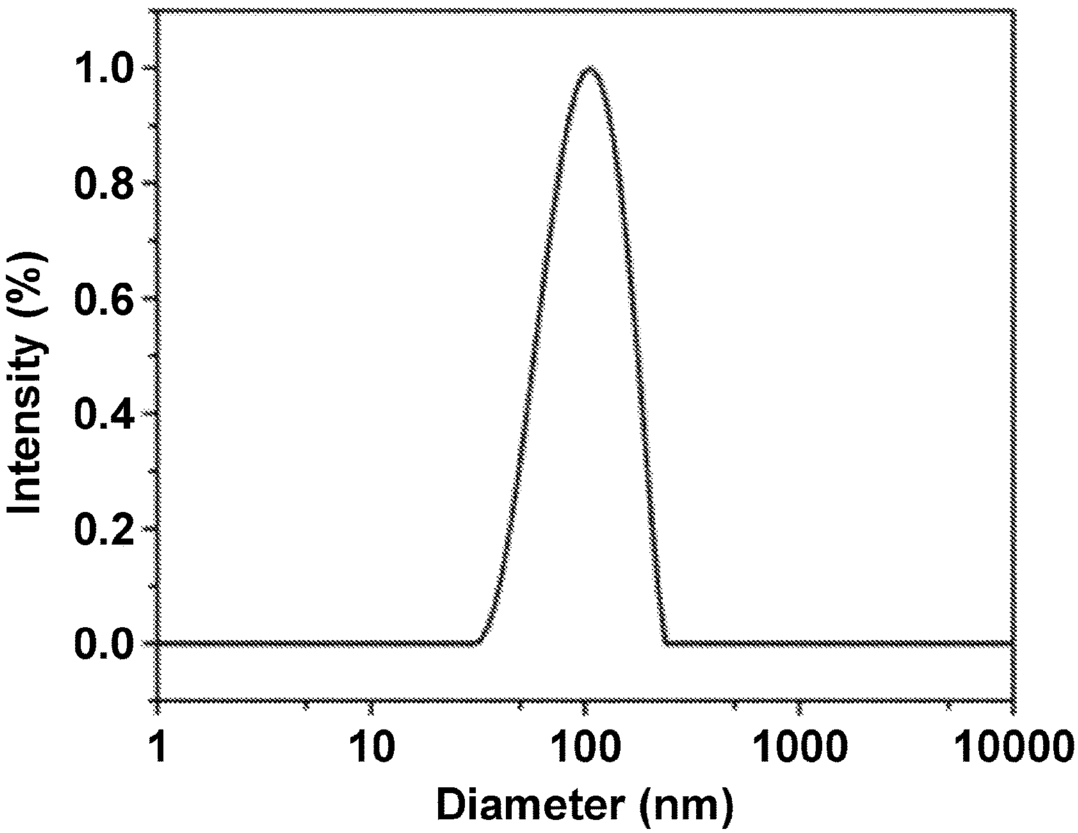
FIG. 95: Distribution of Hydrodynamic Diameter of Coumarin Nano-tracers.
Figure 96A:
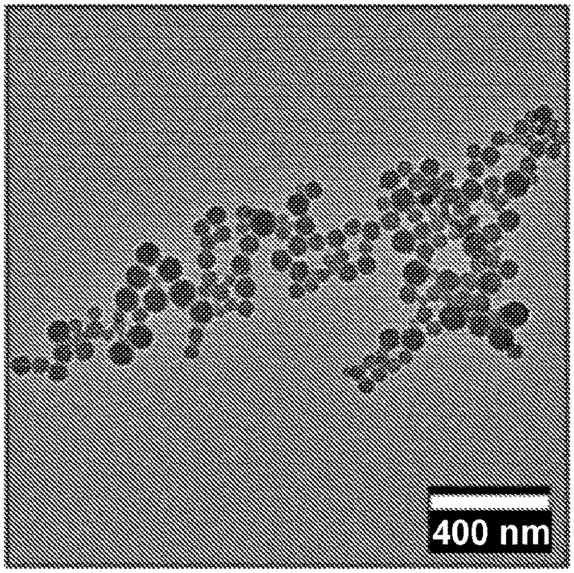
FIGS. 96A-96D: TEM Image of LUMAFLUOR Red and Rhodamine Nano-tracers.
Figure 96B:
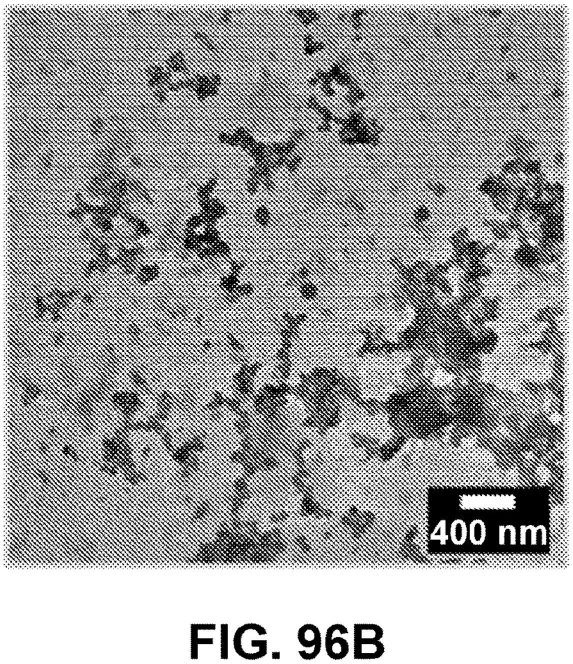
Figure 96C:
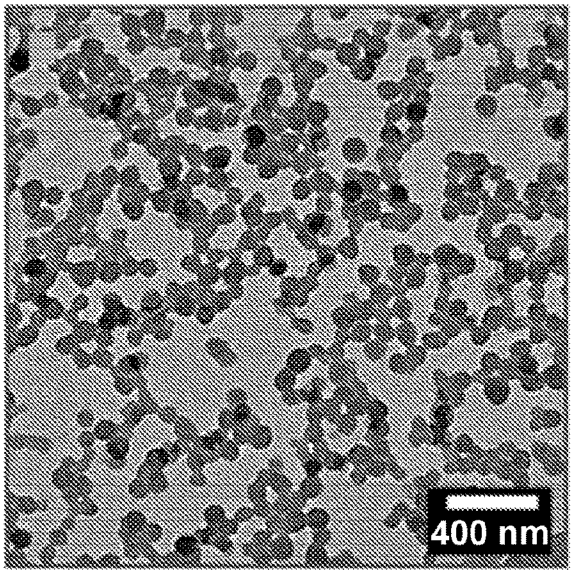
Figure 96D:
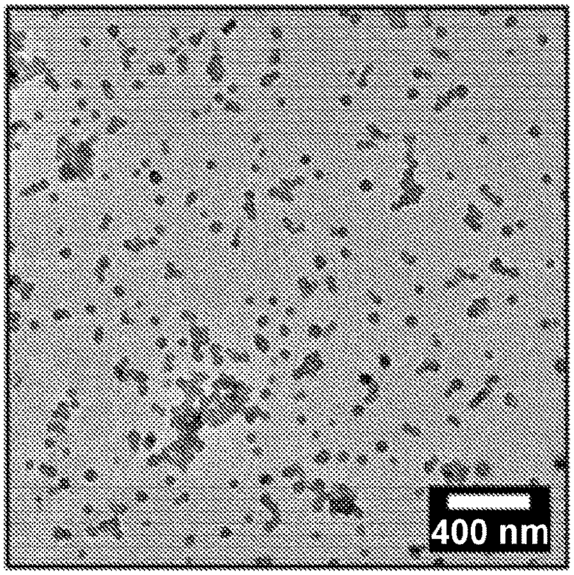

The concentration of coumarin nano-tracer particles was determined by NTA to be $3.2\times10^{11}$ particles per milliliter. By DLS, Coumarin nano-tracers exhibit a Dh of 106 nm, which is larger than that determined by dry-state TEM and cryo-EM which is attributed to the increased hydration of the particles (FIG. 95). The zeta potential of Coumarin nano-tracers was determined to be −34.3 mV.

Rhodamine Nano-Tracers

In order to achieve the maximum fluorescence intensity per particle, the polymerization condition of Rhodamine nano-tracers was screened. More specifically, the method of introducing water-insoluble methacryloxyethyl thiocarbamoyl rhodamine B to the reaction mixture was explored giving three sets of rhodamine labelled nano-tracers. Since the commercial Retro-beads LUMAFLUOR has a LUMAFLUOR Red color (Excitation maxima $\lambda_{ex}$=530 nm, Emission maxima $\lambda_{em}$=590 nm), the Rhodamine nano-tracers can be directly compared with LUMAFLUOR Red.

Figure 97:
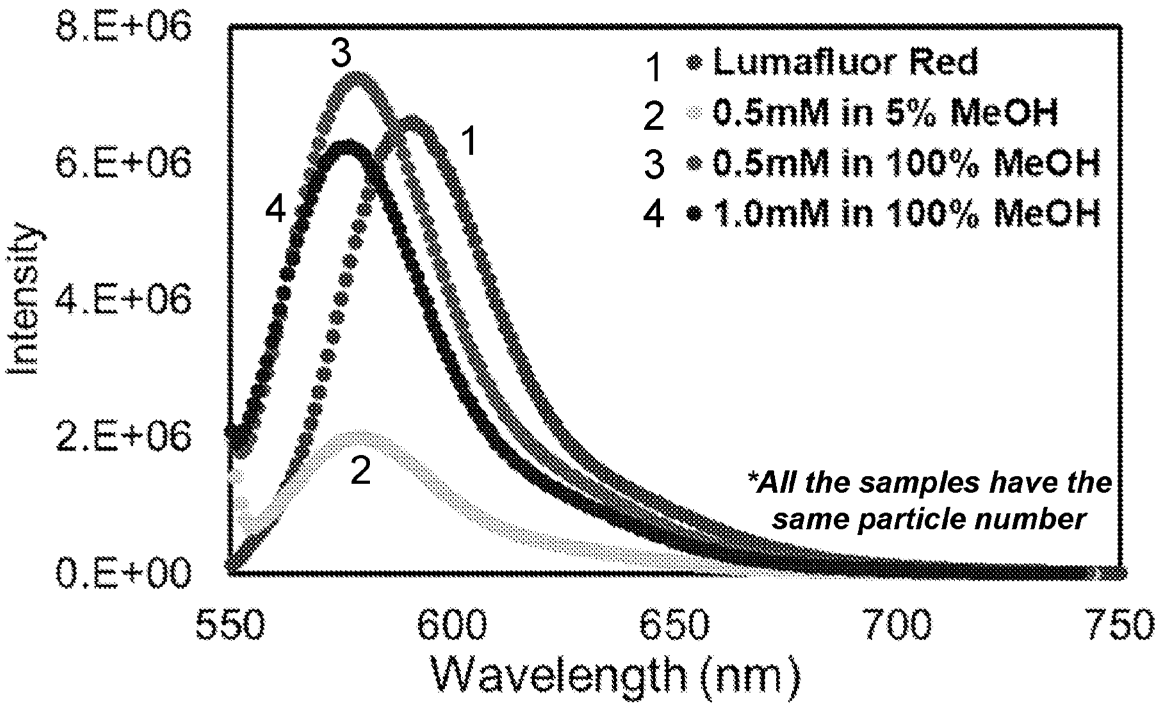
FIG. 97: Comparison of Fluorescence Spectra between Different Rhodamine Nano-tracers and LUMAFLUOR Red.

First, the morphologies of Rhodamine nano-tracers and LUMAFLUOR Red was characterized by uranyl acetate stained dry-state TEM (FIGS. 96A-96D). Particle concentrations were determined by NTA to be $1.15\times10^{12}$ particles per milliliter (LUMAFLUOR Red), $4.57\times10^{11}$ particles per milliliter (0.5 mmol in 5% MeOH Rhodamine nano-tracers), $2.3\times10^{12}$ particles per milliliter (0.5 mmol in 100% MeOH Rhodamine nano-tracers) and $1.53\times10^{12}$ particles per milliliter (1.0 mmol in 100% MeOH Rhodamine nano-tracers). Emission spectra were obtained by diluting all the samples to the same particle concentration (FIG. 97) so that the sample with the highest fluorescence intensity would be the best candidate of the Rhodamine nano-tracers for further use.

Moreover, the mass concentration of the nano-tracers can be determined by the mass differences of before and after lyophilizing 1 mL of the sample solution. The dye concentration per particle was calculated to be: $8.78\times10^{-12}$ mmol (0.5 mmol in 5% MeOH Rhodamine nano-tracers), $8.84\times10^{-12}$ mmol (0.5 mmol in 100% MeOH Rhodamine nano-tracers) and $3.3\times10^{-12}$ mmol (1.0 mmol in 100% MeOH Rhodamine nano-tracers).

Figure 98:
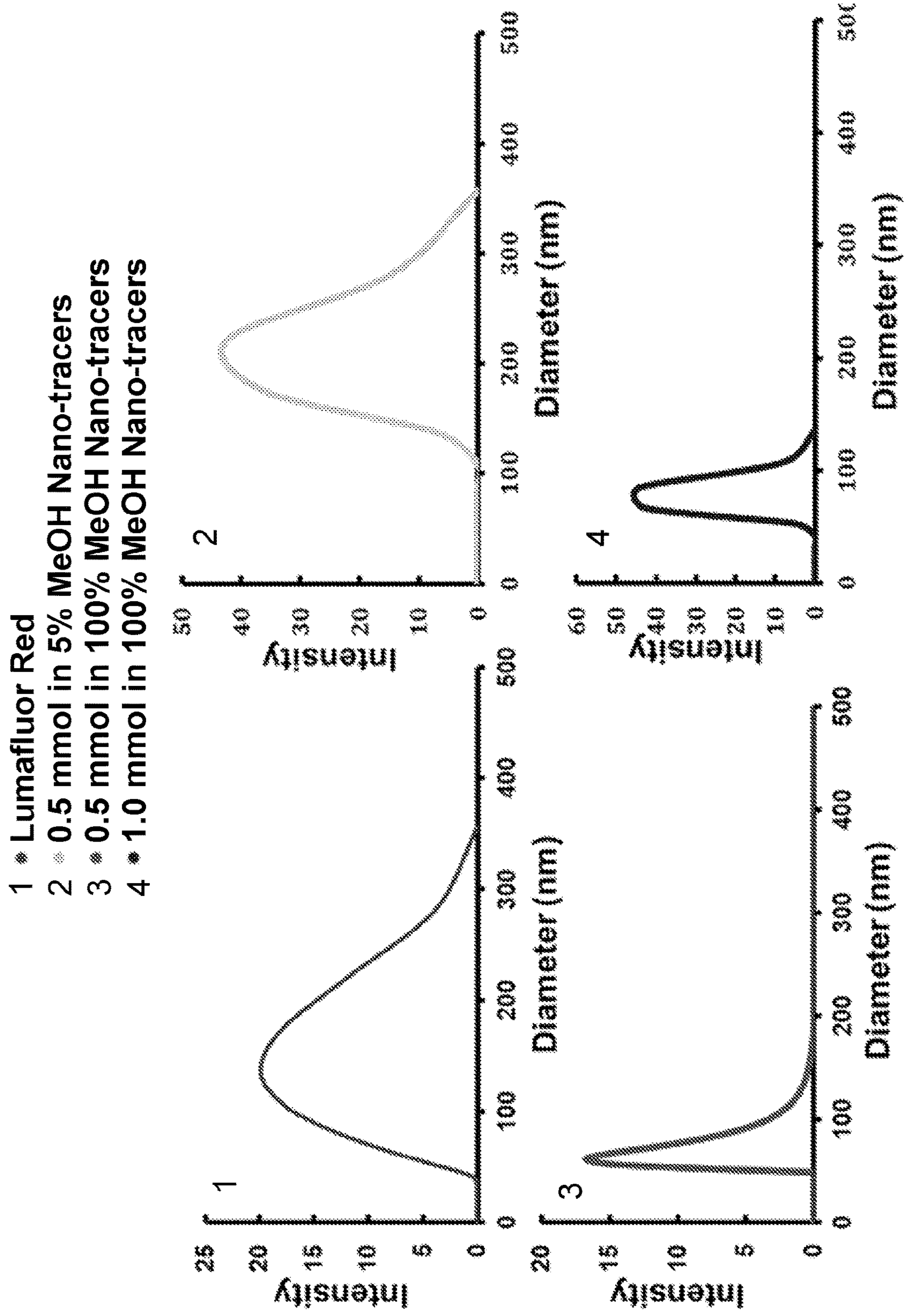
FIG. 98: Distributions of Hydrodynamic Diameter of Different Rhodamine Nano-tracers and LUMAFLUOR Red.

By DLS, the hydrodynamic diameter of LUMAFLUOR Red was 120 nm, 0.5 mmol in 5% MeOH Rhodamine nano-tracers was 225 nm, 0.5 mmol in 100% MeOH Rhodamine nano-tracers was 100 nm and 1.0 mmol in 100% MeOH Rhodamine nano-tracers was 76 nm (FIG. 98).

Based on the characterization results, the 0.5 mmol in 100% MeOH Rhodamine nano-tracer was the best Rhodamine nano-tracer candidate. All subsequent experiments that use a Rhodamine nano-tracer refers to the 0.5 mmol in 100% MeOH Rhodamine Nano-tracer.

Figure 99:
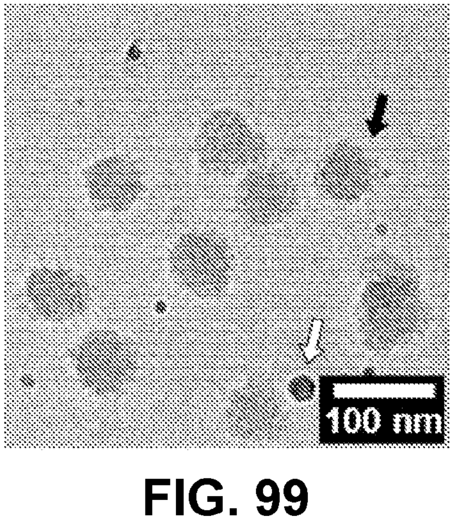
FIG. 99: Cryo-EM image of Rhodamine Nano-tracers.

Cryo-EM was used to verify that Rhodamine nano-tracers were monodispersed, with a diameter of 62±3 nm (FIG. 99).

Figure 100A:
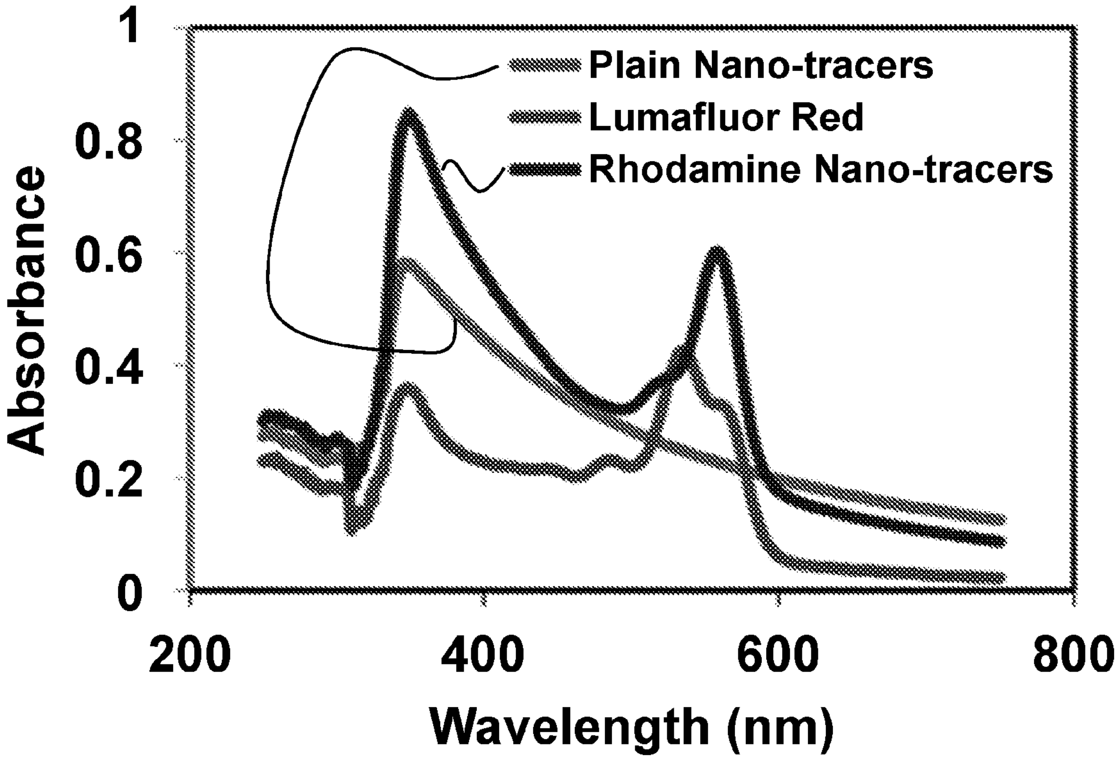
FIG. 100A: UV-Vis and (FIG. 100B) Fluorescence Spectra of Rhodamine Nano-tracers.
Figure 100B:
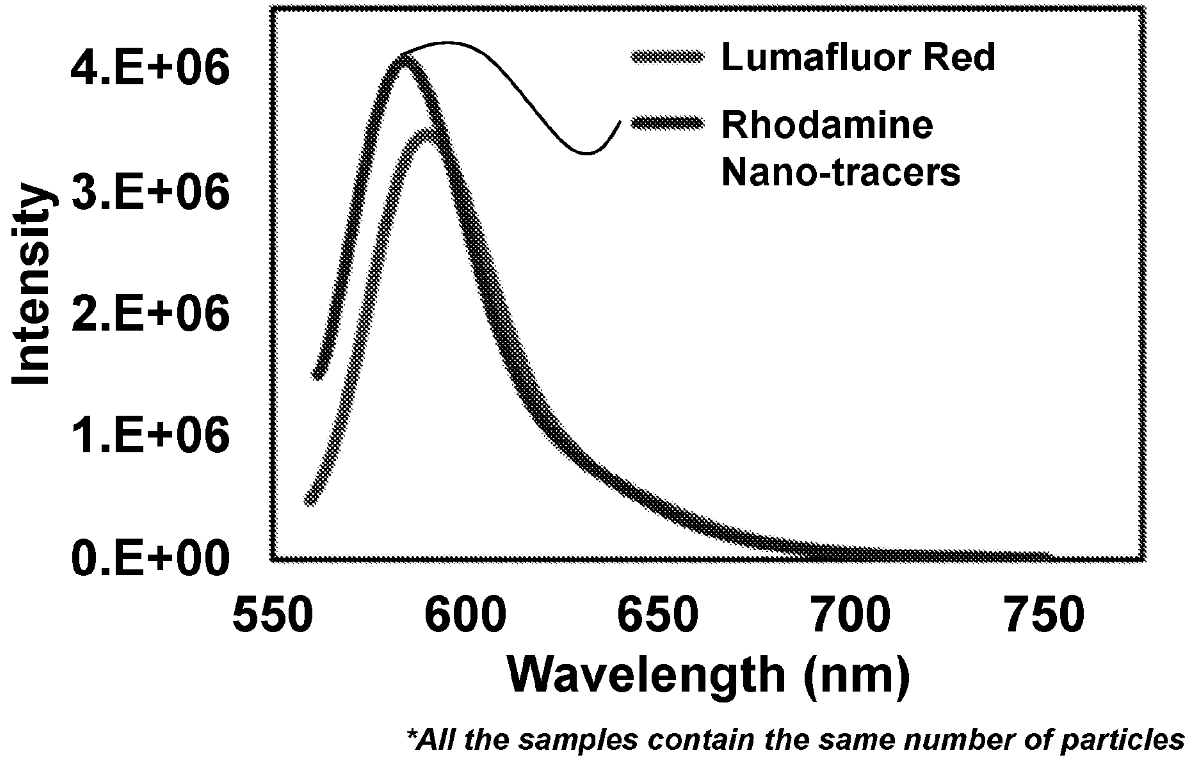
Figure 101A:
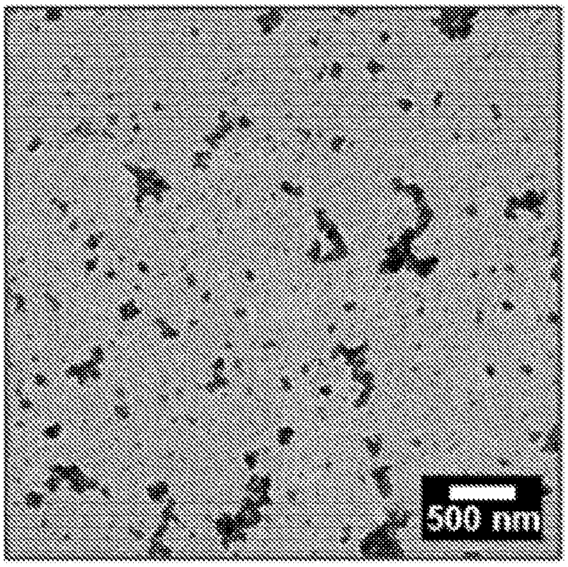
FIG. 101A-101D: TEM Image of LUMAFLUOR Green and Fluorescein Nano-tracers.
Figure 101B:
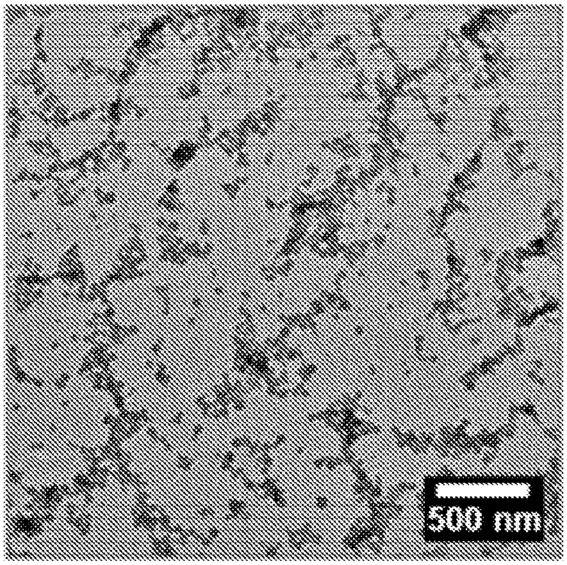
Figure 101C:
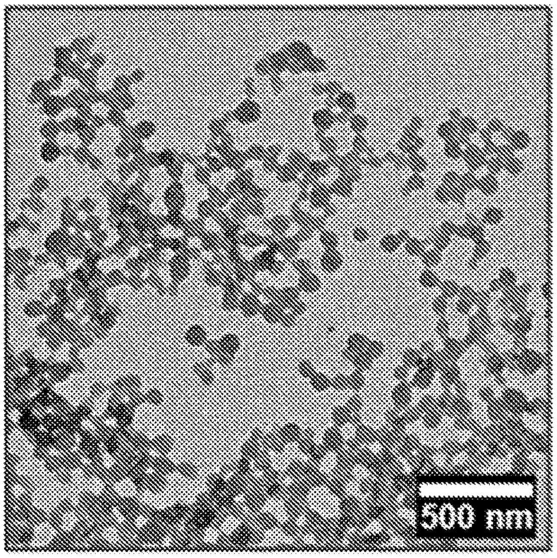
Figure 101D:
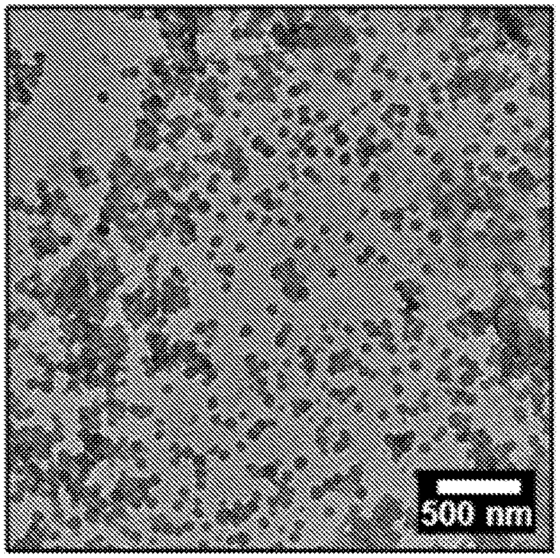

The excitation spectrum of Rhodamine nano-tracers was acquired by UV-Vis and was overlaid with plain nano-tracers and LUMAFLUOR Red (FIG. 100A). The emission spectrum was obtained by fluorescence spectroscopy and was overlaid with that of LUMAFLUOR Red (FIG. 100B). The excitation maxima of Rhodamine nano-tracers ($\lambda_{ex}$) was 558 nm, the emission maxima ($\lambda_{em}$) was 586 nm. A summary of Excitation and emission maxima of LUMAFLUOR Red and Rhodamine monomers are shown in Table 6. The zeta potential of Rhodamine nano-tracers was determined to be −35.2 mV, suggesting that the surface of nano-tracer was significantly negatively charged, which is attributed to the MAA.

TABLE 6

| Summary of Excitation and Emission Maxima of Rhodamine Related Monomer and Nano-tracers | | |
|---|---|---|
| Nano-tracers | Excitation (nm) | Emission (nm) |
| Methacryloxyethyl thiocarbamoyl rhodamine B | 548 | 570 |
| Rhodamine Nano-tracers | 558 | 586 |
| LUMAFLUOR Red | 530 | 590 |

Fluorescein Nano-Tracers

Similar to the Rhodamine nano-tracers, the optimization of the Fluorescein nano-tracers' polymerization conditions were evaluated to achieve the maximum fluorescence intensity per particle. The method of introducing the water-insoluble methacryloyloxy O-fluorescein to the reaction mixture was explored. Since the commercially available LUMAFLUOR Retro beads have a version with Green color (Excitation maxima $\lambda_{ex}$=460 nm, Emission maxima $\lambda_{em}$=505 nm), the Fluorescein nano-tracers can be directly compared with LUMAFLUOR Green.

Figure 102:
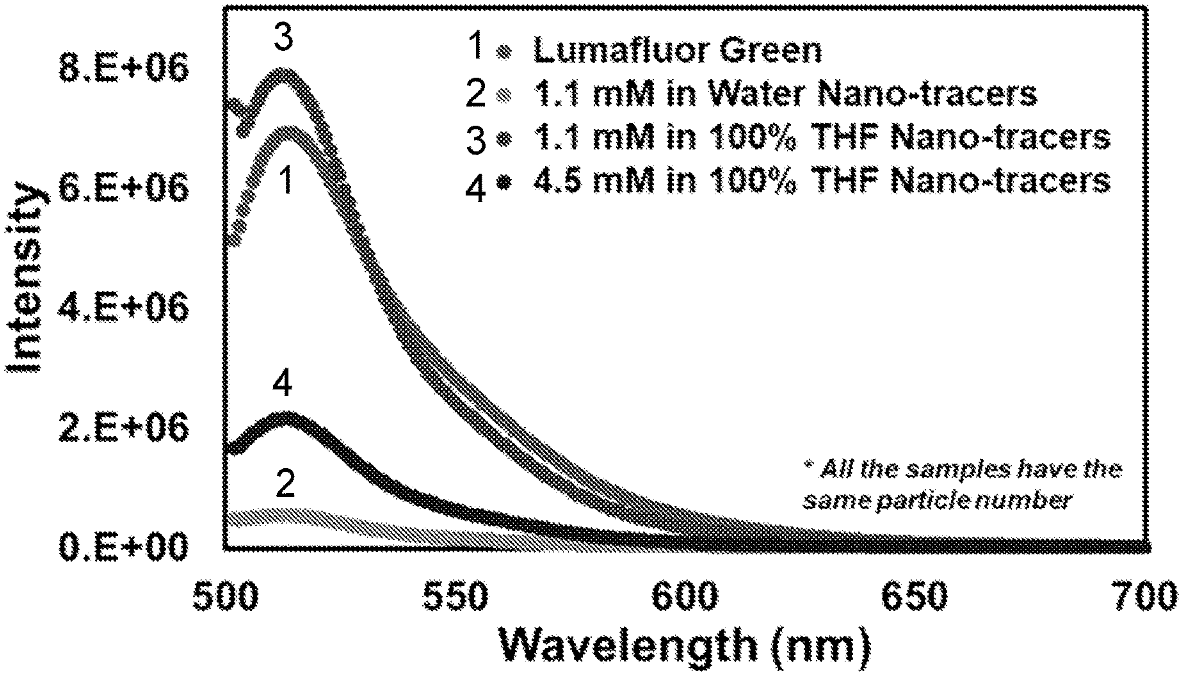
FIG. 102: Comparison of Fluorescence Spectra between Different Fluorescein Nano-tracers and LUMAFLUOR Green.

The morphologies of Fluorescein nano-tracers and LUMAFLUOR Green beads were characterized by uranyl acetate stained dry-state TEM (FIGS. 101A-101D). Particle concentrations of Rhodamine nano-tracers and LUMAFLUOR Green beads were determined by NTA to be $3.00\times10^{12}$ particles per milliliter (LUMAFLUOR Green beads), $9.76\times10^{11}$ particles per milliliter (1.1 mM methacryloyloxy O-fluorescein in 100% water nano-tracers), $2.1\times10^{11}$ particles per milliliter (1.1 mM methacryloyloxy O-fluorescein in 100% THF nano-tracers) and $3.84\times10^{12}$ particles per milliliter (4.5 mM methacryloyloxy O-fluorescein in 100% THF nano-tracers). Emission spectra were obtained by diluting all the samples to the same particle concentration (FIG. 102) so that the sample that had the highest fluorescence intensity would be the best candidate of the Fluorescein nano-tracers for further use.

Moreover, the mass concentration of the Fluorescein nano-tracers can be determined by using the same method used for the Rhodamine nano-tracers. The dye concentration per particle was calculated to be: $1.39\times10^{-17}$ mmol (1.1 mM methacryloyloxy O-fluorescein in 100% water nano-tracers), $2.04\times10^{-16}$ mmol (1.1 mM methacryloyloxy O-fluorescein in 100% THF nano-tracers) and $4.05\times10^{-17}$ mmol (4.5 mM methacryloyloxy O-fluorescein in 100% THF nano-tracers).

Figure 103:
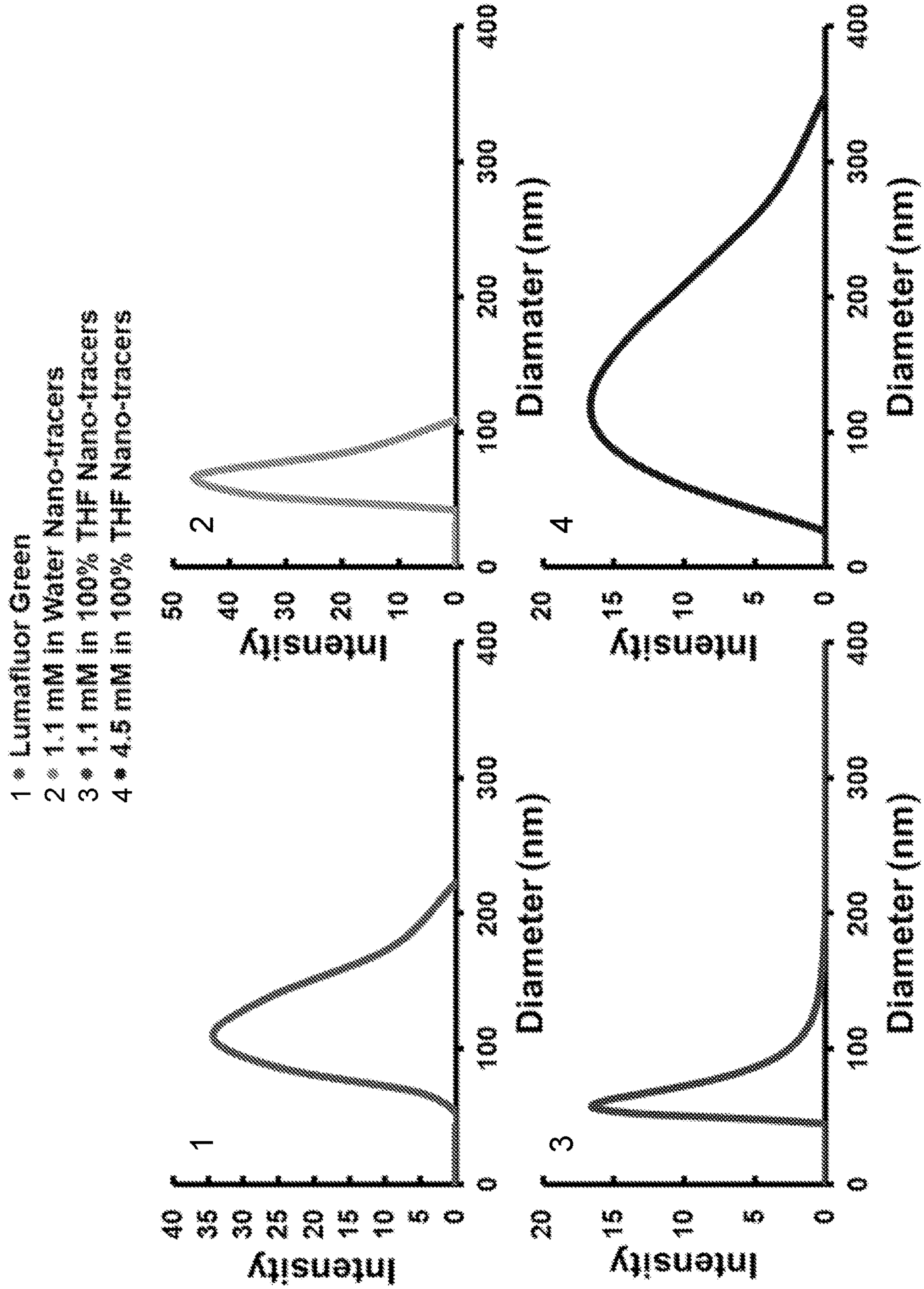
FIG. 103: Distributions of Hydrodynamic Diameter of Different Fluorescein Nano-tracers and LUMAFLUOR Green.

By DLS, the hydrodynamic diameter of LUMAFLUOR Green was 90 nm, 1.1 mM methacryloyloxy O-fluorescein in 100% water nano-tracers was 66 nm, 1.1 mM methacryloyloxy O-fluorescein in 100% THF nano-tracers was 104 nm, and 4.5 mM methacryloyloxy O-fluorescein in 100% THF nano-tracers was 100 nm (FIG. 103).

Based on the results above, the 1.1 mM methacryloyloxy O-fluorescein in 100% THF nano-tracer was the best Fluorescein nano-tracer candidate. All subsequent experiments that involve fluorescein nano-tracers refer to the 1.1 mM in 100% THF nano-tracer.

Figure 104:
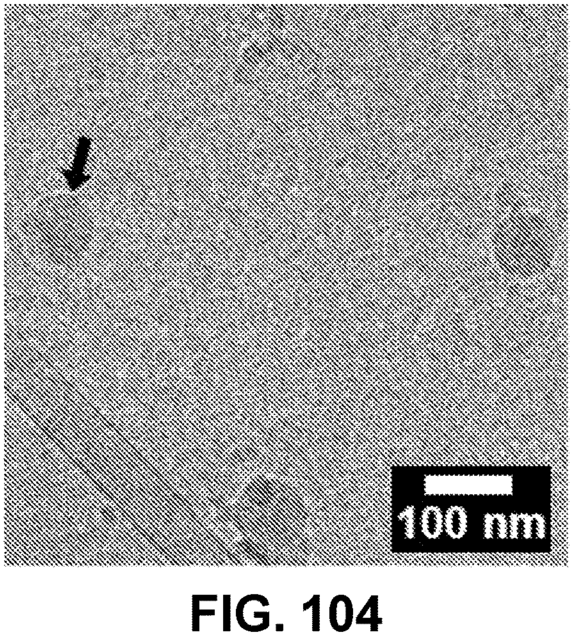
FIG. 104: Cryo-EM Image of Fluorescein Nano-tracers.

Cryo-EM verified Fluorescein nano-tracers was monodispersed, and the diameter was 78±17 n Cryo-EM verified that Fluorescein nano-tracers were monodispersed, with a diameter of 78±17 nm (FIG. 104).

Figure 105A:
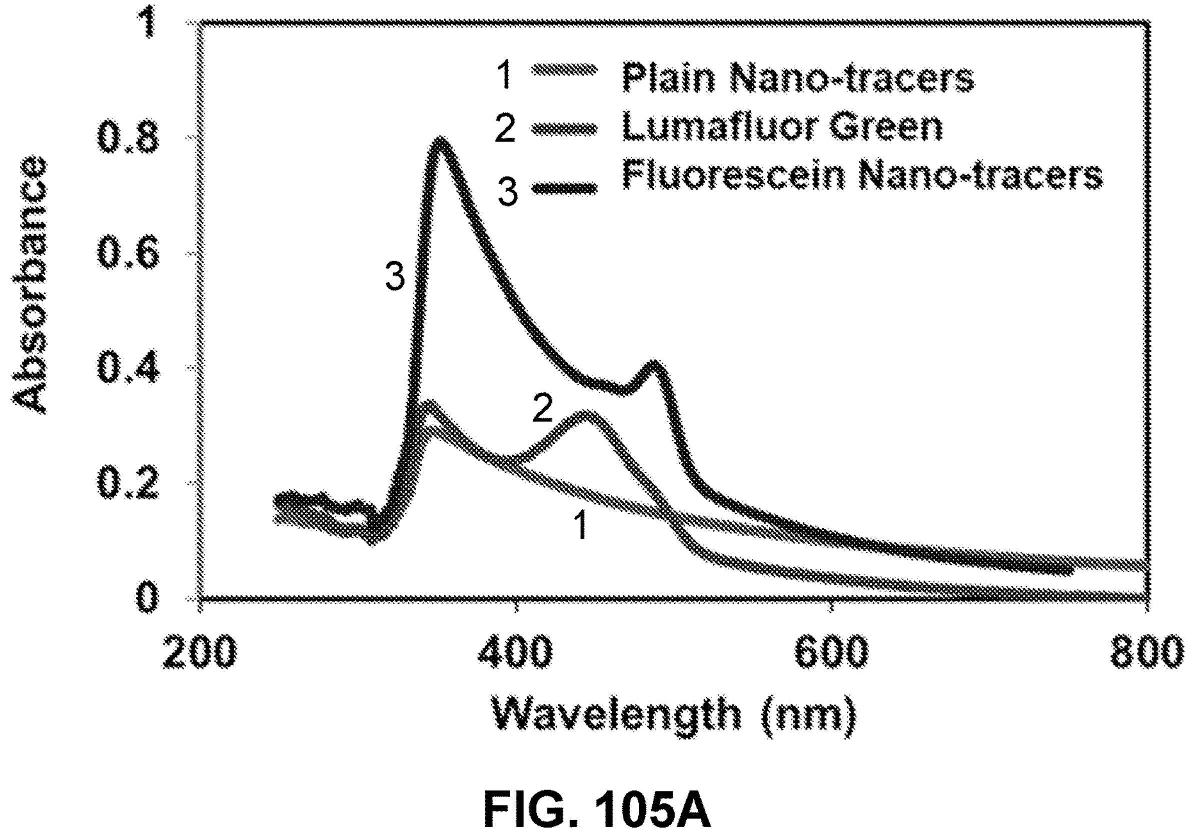
FIG. 105A: UV-Vis and (FIG. 1058) Fluorescence Spectra of Fluorescein Nano-tracers.
Figure 105B:
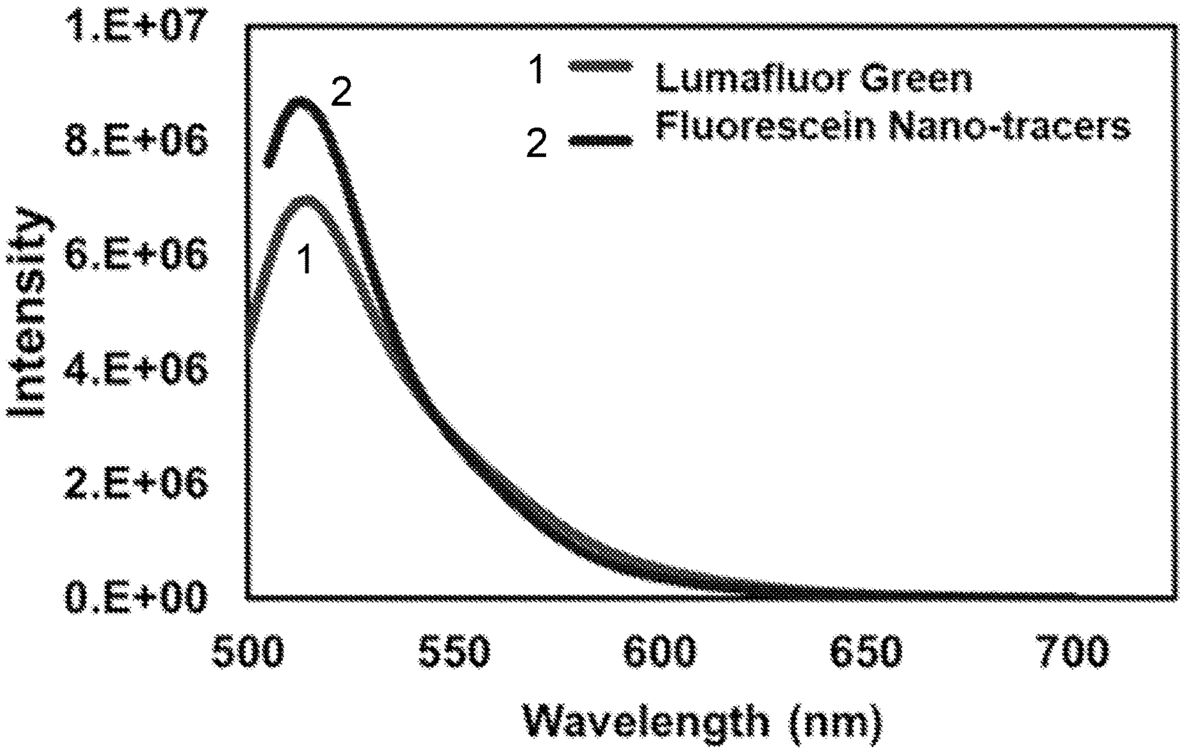
Figure 106A:
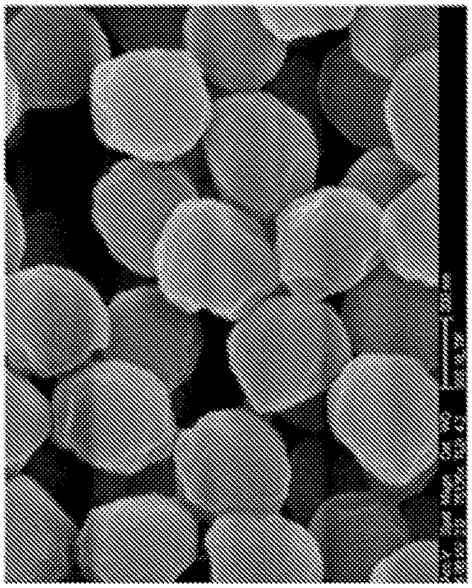
FIGS. 106A-106F: SEM Images of Tracers by Different Crosslinkers.
Figure 106B:
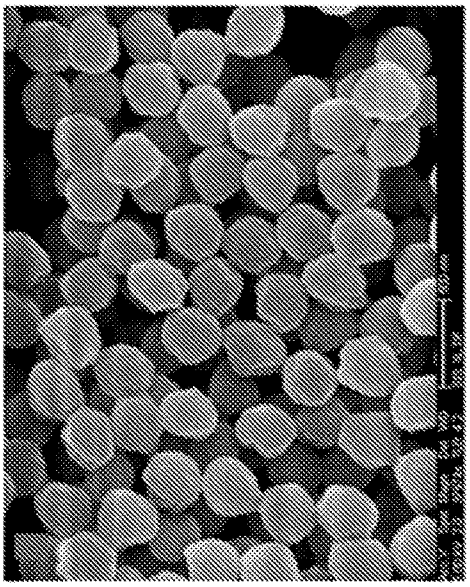
Figure 106C:
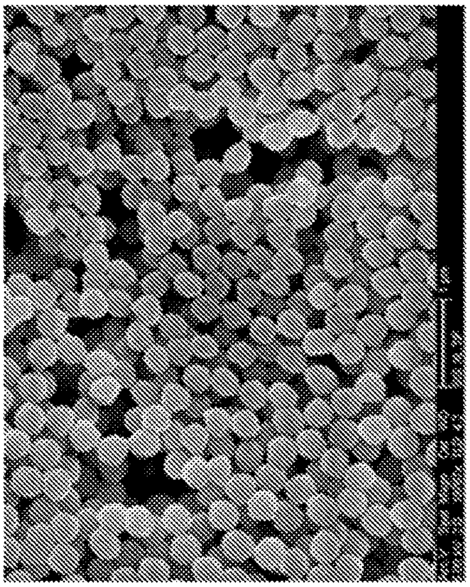
Figure 106D:
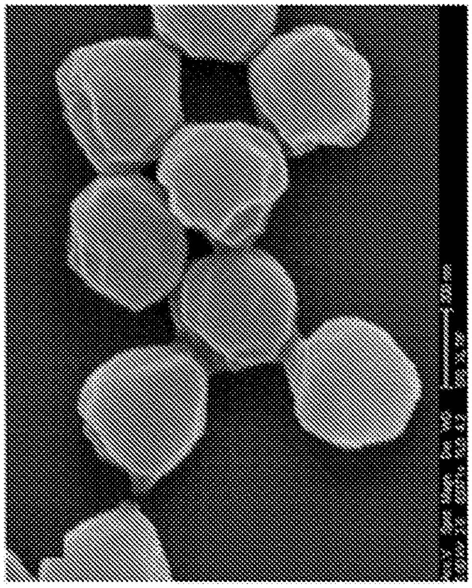
Figure 106E:
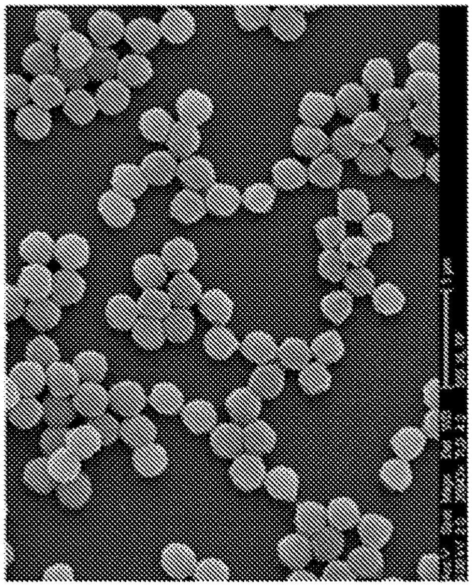
Figure 106F:
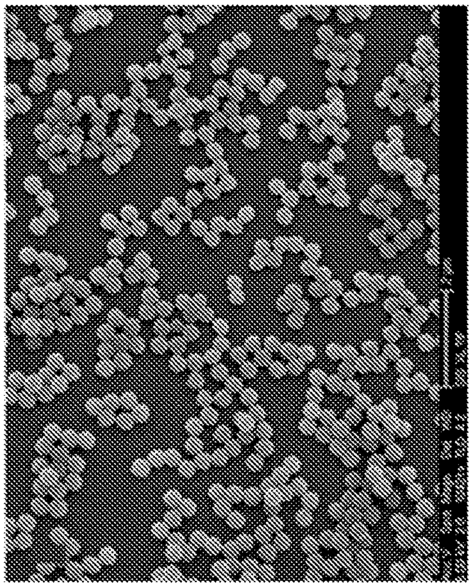
Figure 107A:
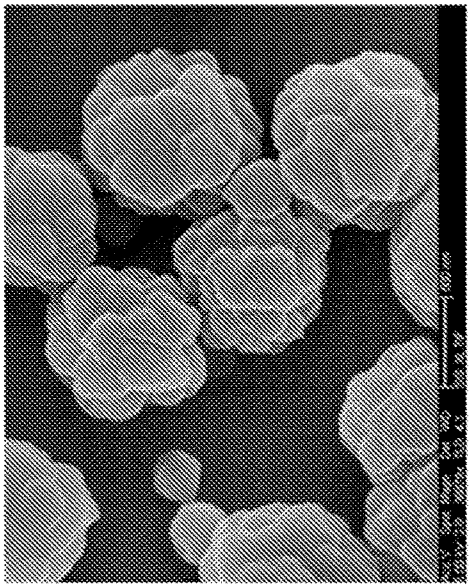
FIGS. 107A-107F: SEM Images of Tracers by Different Surfactants.
Figure 107B:
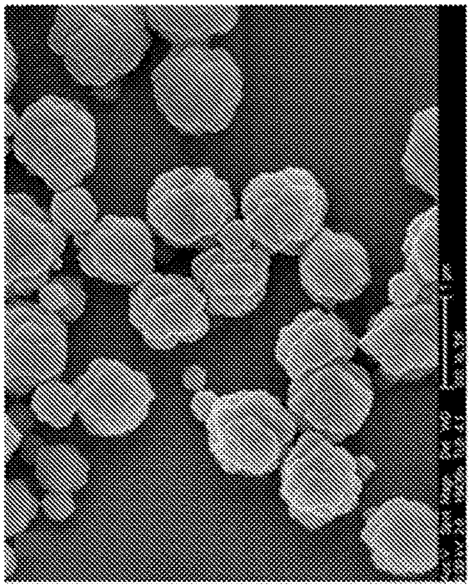
Figure 107C:
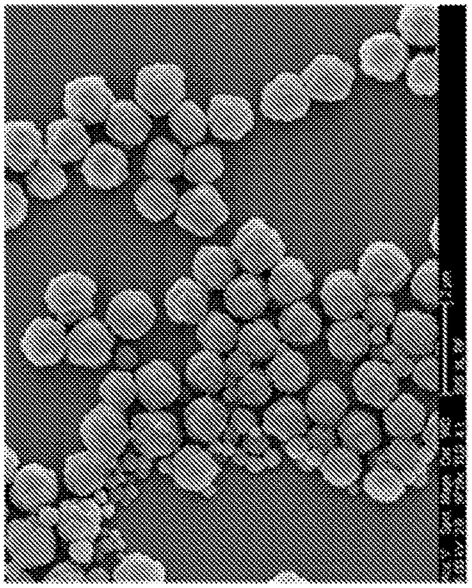
Figure 107D:
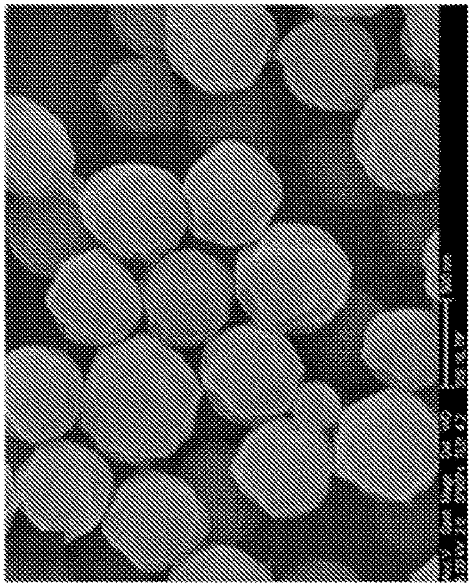
Figure 107E:
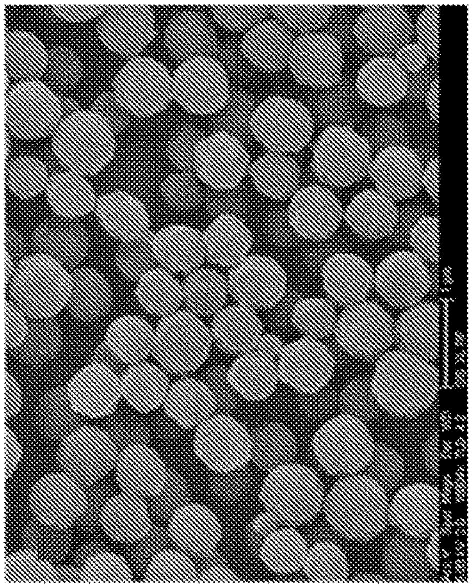
Figure 107F:
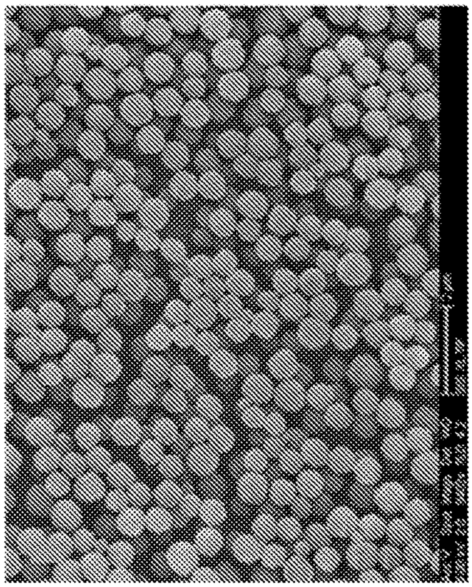

The excitation spectrum of Fluorescein nano-tracers was acquired by UV-Vis and was overlaid with plain nano-tracers and LUMAFLUOR Green particles (FIG. 105A). The emission spectrum was obtained by fluorescence spectroscopy and was overlaid with LUMAFLUOR Green excitation (FIG. 105B). The excitation maxima of Fluorescein nano-tracers ($\lambda_{ex}$) was found to be 490 nm, with an emission maxima ($\lambda_{em}$) of 513 nm. A summary of excitation and emission maxima for the particles can be found in Table 7. The zeta potential of Fluorescein nano-tracers was determined to be −33.2 mV, suggesting that the surface of the nano-tracers have significant negative charge which is attributed to the MAA.

TABLE 7

| Summary of Excitation and Emission Maxima of Nano-tracers | | |
|---|---|---|
| Nano-tracers | Excitation (nm) | Emission (nm) |
| Methacryloyloxy O-fluorescein | 490 | 520 |
| Fluorescein Nano-tracers | 490 | 513 |
| LUMAFLUOR Green | 450 | 505 |

Nano-Tracers Synthesized with Different Crosslinkers

The polymerization used PEG diacrylate 250 as the crosslinker, and it started to form precipitates after 40 min. Thus, the reaction was stopped at 40 min. After the reaction was cooled to room temperature, the reaction mixture was passed through filter paper to remove the precipitates. When the polymerization was performed with PEG diacrylate 700 as the crosslinker, no precipitation was observed so the reaction was stopped at 1 h. SEM images (FIGS. 106A-106F) showed that the resulting particles from both reactions were around 300 nm with rough surfaces.

Nano-Tracers Synthesized by Different Surfactants

The effect of the surfactant on the particle morphology was studied. The two polymerizations that contained TRITON x-100 or TWEEN 20 precipitated during the course of the reaction. After cooling to room temperature, the reaction mixtures were passed through filter paper to remove the precipitates. Around 40% of the liquid (20 mL) remained after the filtration process. SEM images (FIGS. 107A-107F) showed that the TRITON X-100 particles were micron-size spherical shape with asperous surfaces. The TWEEN 20 particles were around 500 nm, possessing slightly irregular spherical shapes with smoother surfaces.

Nano-Tracers Synthesized by Photo-Initiator SPTP

Figure 108A:
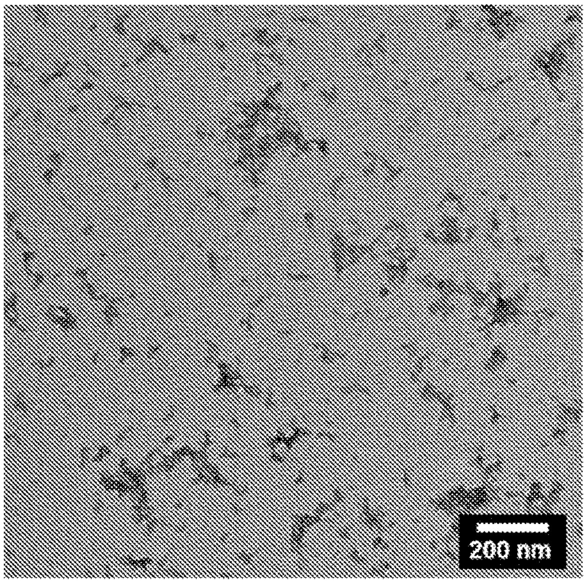
FIGS. 108A-108B: TEM Images of Tracers by Photo-initiator SPTP.
Figure 108B:
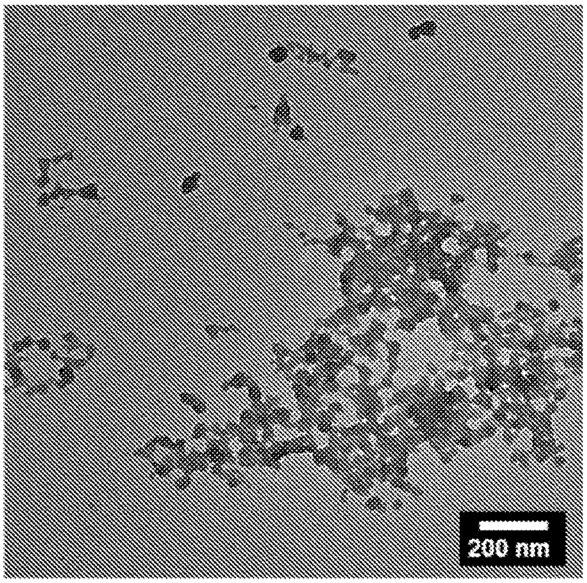
Figure 109:
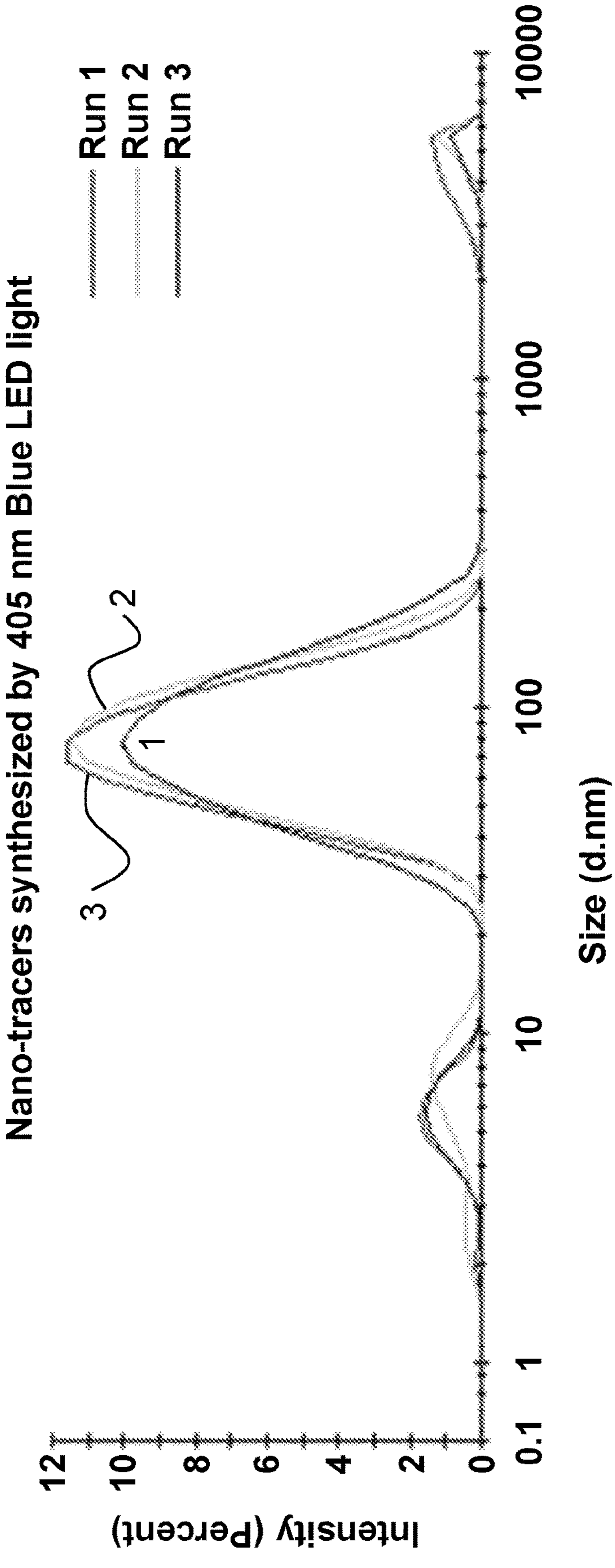
FIG. 109: Distributions of Hydrodynamic Diameter of Nano-tracers by Photo-initiator SPTP under 405 nm Blue LED light.

The morphologies of nano-tracers synthesized by photo-initiator SPTP were characterized by TEM (FIGS. 108A-108B). The diameter of nano-tracers synthesized using 365 nm UV light was 20±18 nm, and 55±14 nm for those synthesized using 405 nm from a Blue Light-emitting diode (LED). Based on the TEM images, using 405 nm Blue LED light and running larger scale reactions resulted in better control of particle formation and morphology. These nano-tracers were further examined by DLS to obtain their hydrodynamic diameter, which was 86 nm (FIG. 109). The size determined via DLS was slightly bigger than that from dry-state TEM due to the increased volume of the nano-tracers in their hydrated state.

Synthesis and Characterization of Nano-Tracers with Different Compositions for Screening Retrograde Transportation Ability Synthesis and Characterization of Nano-Tracers without HEMA The polymerization condition of the nano-tracers without HEMA was identical to the plain nano-tracer's polymerization condition (see section "Optimization of Polymerization Condition of Plain Nano-tracers") except there was no HEMA added into the reaction. 20.47 mg methacryloxyethyl thiocarbamoyl rhodamine B was first dissolved in 0.5 mL MeOH, and 0.5 mL of MILLI-Q water was added. This mixture was added to the reaction flask and the mixture stirred for 5 min at which point the flask was placed in the oil bath at 90° C. for 1 h. After 1 h, the solution was removed from the oil bath and allowed to rest at room temperature.

Figure 110A:
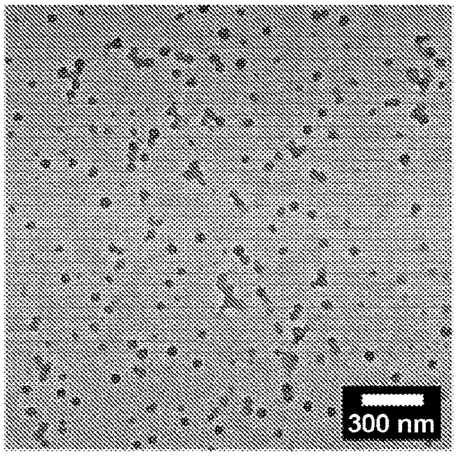
FIGS. 110A-110B: Characterization of Nano-tracers without HEMA.
Figure 110B:
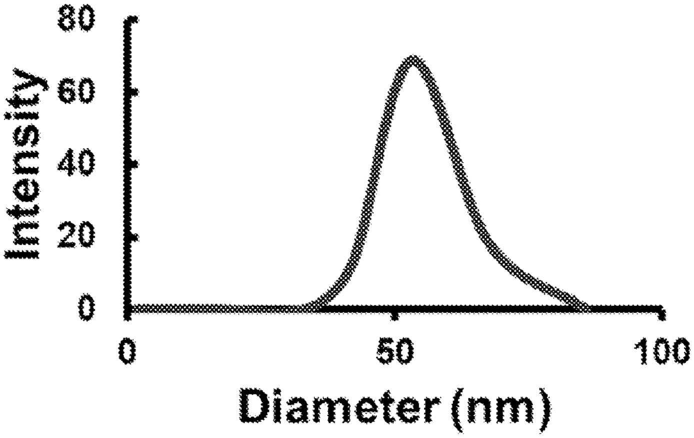
Figure 111A:
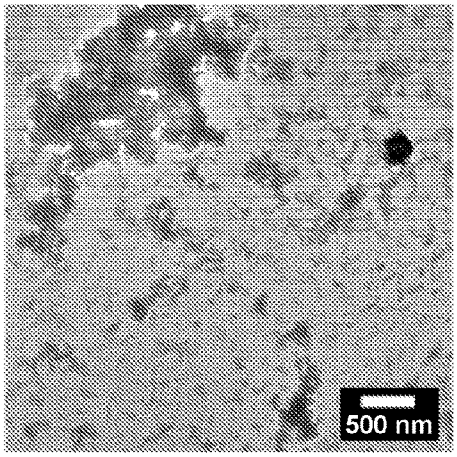
FIGS. 111A-111B: Characterization of Nano-tracers without MMA.
Figure 111B:
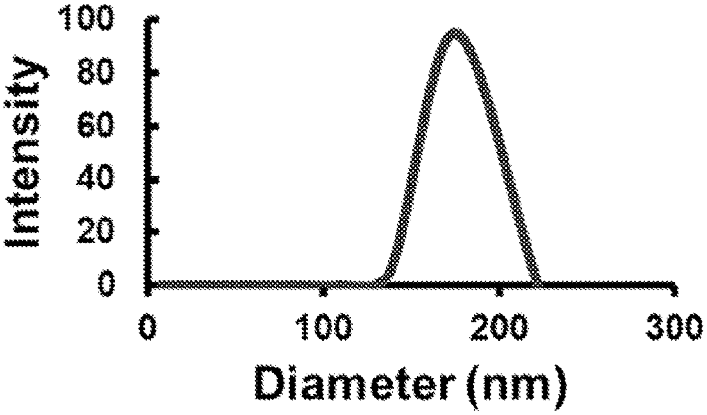

The morphologies were characterized by TEM (FIG. 110A). The diameter of nano-tracers without HEMA was 36±13 nm. These nano-tracers was further examined by DLS to obtain the hydrodynamic diameter, which was 53 nm (FIG. 1108, FIGS. 111A-111B). The mass concentration was 43.94 mg/mL.

Synthesis and Characterization of Nano-Tracers without MMA

The polymerization conditions for nano-tracers without MMA were identical to those used in the "Optimization of Polymerization Condition of Plain Nano-tracers" section, except there was no MMA added to the reaction.

The morphologies were characterized by TEM (FIG. 111A). There were some large aggregates and small particles. The hydrodynamic diameter of the nano-tracers without MMA was determined by DLS to be 175 nm (FIG. 111B).

Synthesis and Characterization of Nano-Tracers without MAA

The polymerization conditions for nano-tracers without MAA were identical to those used in the "Optimization of Polymerization Condition of Plain Nano-tracers" section except there was no MAA added to the reaction.

Figure 112A:
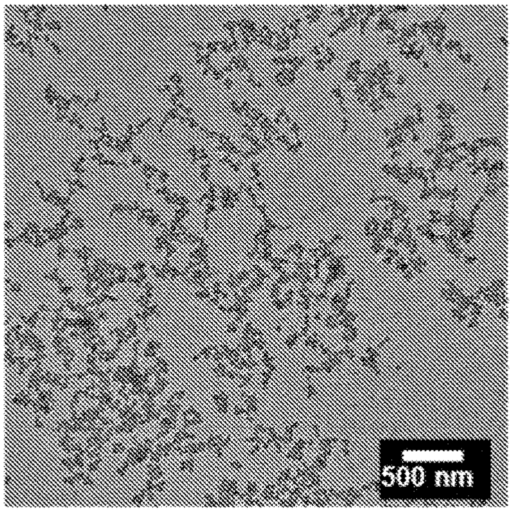
FIGS. 112A-112D: Characterization of Nano-tracers without MAA.
Figure 112B:
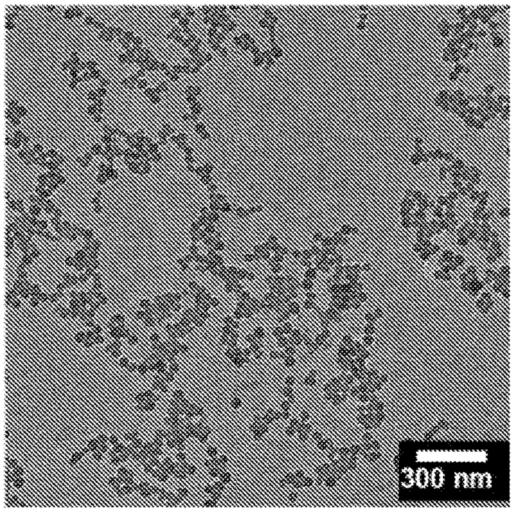
Figure 112C:
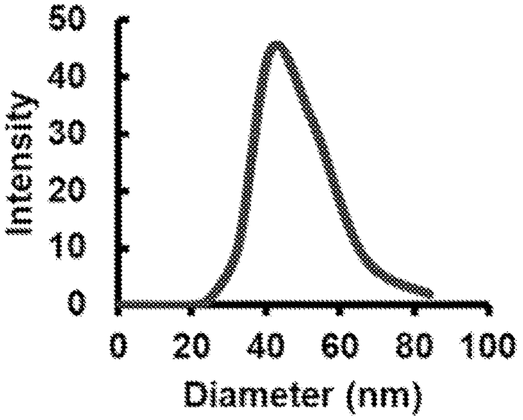
Figure 112D:
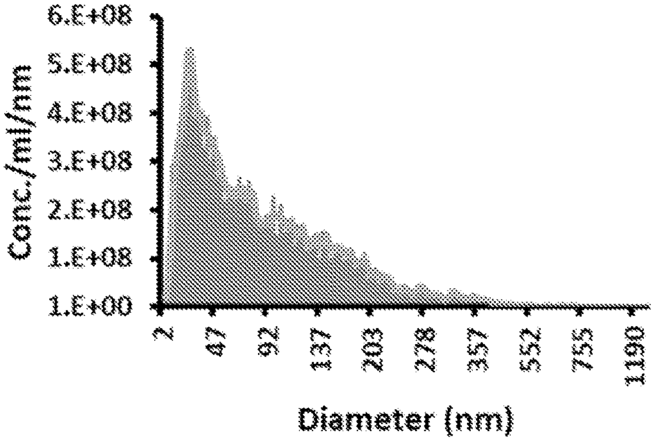

The morphologies were characterized by TEM (FIGS. 112A-112B). The diameter of nano-tracers without MAA calculated from the TEM images was 40±10 nm. These nano-tracers were further examined by DLS to obtain the hydrodynamic diameter which was found to be 45 nm (FIG. 112C). NTA showed a peak at 50 nm, indicating the diameter of the nano-tracers was around 50 nm (FIG. 112D). The diameters obtained from the three different techniques were in good agreement with each other. The zeta potential for the particles was determined to be −17.27 mV, while the mass concentration was determined to be 44.32 mg/mL.

Synthesis and Characterization of Nano-Tracers without EGD

The polymerization conditions for nano-tracers without EGD were identical to those used in the "Optimization of Polymerization Condition of Plain Nano-tracers" section except there was no EGD added to the reaction.

Figure 113A:
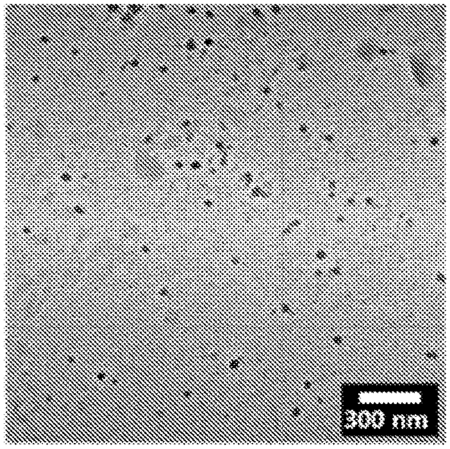
FIGS. 113A-113B: Characterization of Nano-tracers without EGD.
Figure 113B:
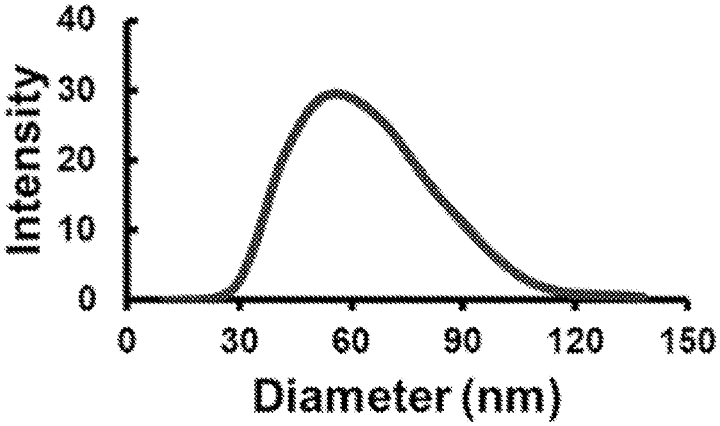

The morphologies were characterized by TEM (FIG. 113A) which showed some large aggregates and small particles. The Dh of the nano-tracers without EGD was determined by DLS to be 60 nm (FIG. 113B), and the mass concentration was determined to be 57.34 mg/mL.

Synthesis and Characterization of MMA Nano-Tracers

The polymerization conditions for MMA nano-tracers were identical to those used in the "Optimization of Polymerization Condition of Plain Nano-tracers" section except only MMA added to the reaction.

Figure 114A:
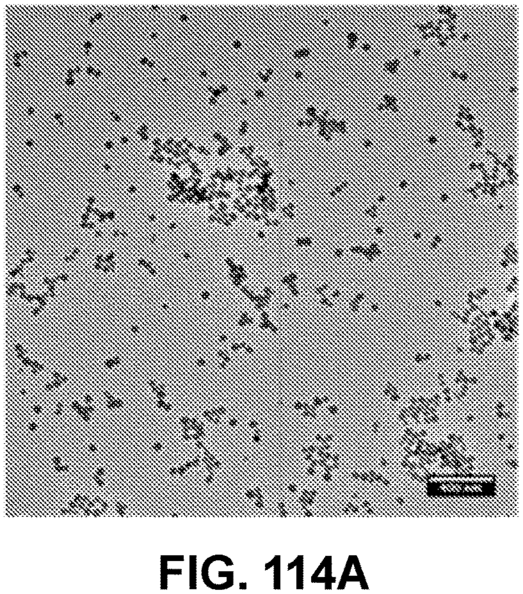
FIG. 114A-114B: Characterization of MMA Nano-tracers.
Figure 114B:
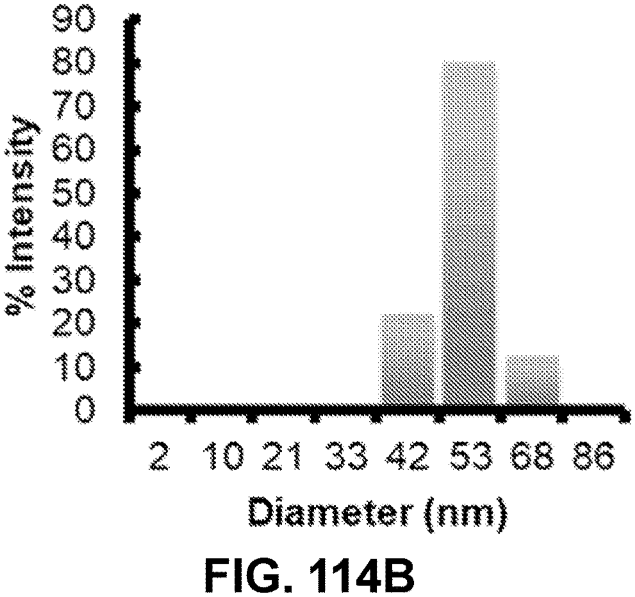

The morphologies were characterized by TEM (FIG. 114A) and mono-dispersed spherical particles were observed. These particles suffer damaged from the e-beam even in low magnification indicating the particles structure is not stable enough due to the absence of the crosslinker and/or other monomers. The Dh of the MMA nano-tracers was determined by DLS to be 50 nm (FIG. 1146).

Synthesis and Characterization of HEMA and MMA Nano-Tracers

The polymerization conditions for HEMA and MMA nano-tracers was identical to the conditions used in the "Optimization of Polymerization Condition of Plain Nano-tracers" section except there was no MAA and EGD added to reaction.

Figure 115A:
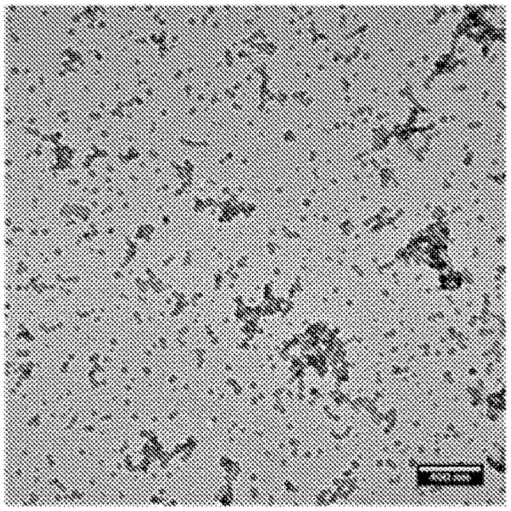
FIG. 115A-115B: Characterization of HEMA and MMA Nano-tracers.
Figure 115B:
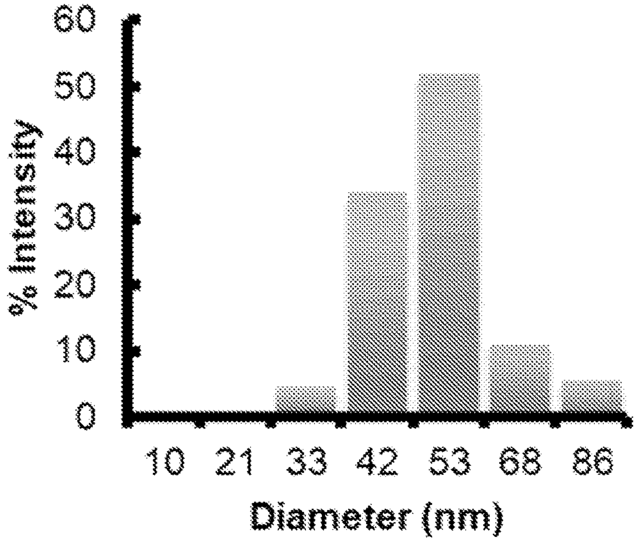

The morphologies were characterized by TEM (FIG. 115A) where mono-dispersed spherical particles were observed. The particles were damaged by the e-beam in TEM but were more stable than the MAA nano-tracers indicating that HEMA provides some structure support. The Dh of the HEMA and MMA nano-tracers was determined by DLS to be 50 nm (FIG. 115B).

Synthesis and Characterization of MMA and MAA Nano-Tracers

The polymerization conditions for MMA and MAA nano-tracers was identical to the conditions used in the "Optimization of Polymerization Condition of Plain Nano-tracers" section except there was no HEMA and EGD added to the reaction.

Figure 116A:
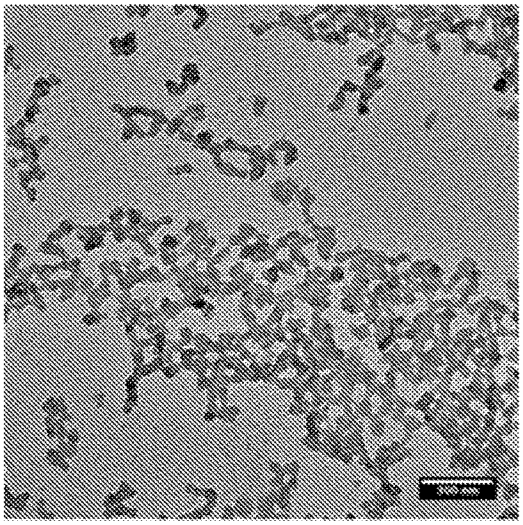
FIGS. 116A-116B: Characterization of MMA and MAA Nano-tracers.
Figure 116B:
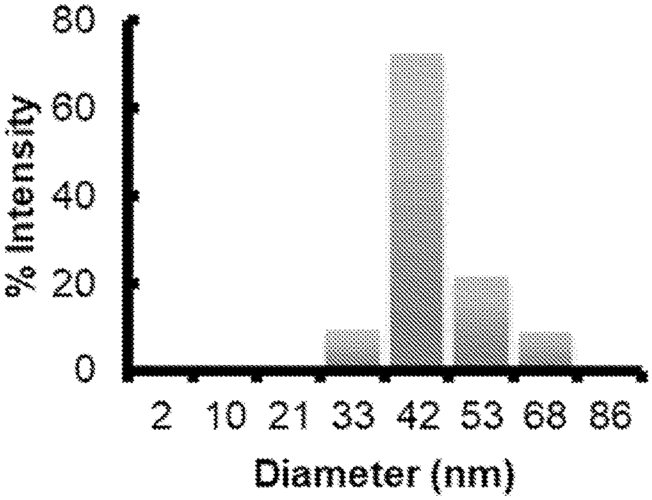

The morphologies were characterized by TEM (FIG. 116A) with mono-dispersed spherical particles observed. The particles were damaged by the e-beam in TEM and were less stable than the MAA nano-tracers indicating that MAA doesn't contribute to the structure support. The $D_h$ of the MMA and MAA nano-tracers was determined by DLS to be 42 nm (FIG. 1166).

Synthesis and Characterization of MMA and EGD Nano-Tracers

The polymerization conditions for the MMA and EGD nano-tracers were identical to those used in the "Optimization of Polymerization Condition of Plain Nano-tracers" section except there was no HEMA and MAA added to the reaction.

Figure 117A:
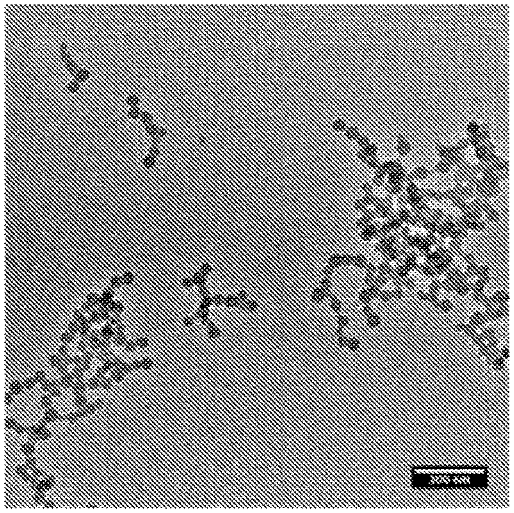
Figure 117B:
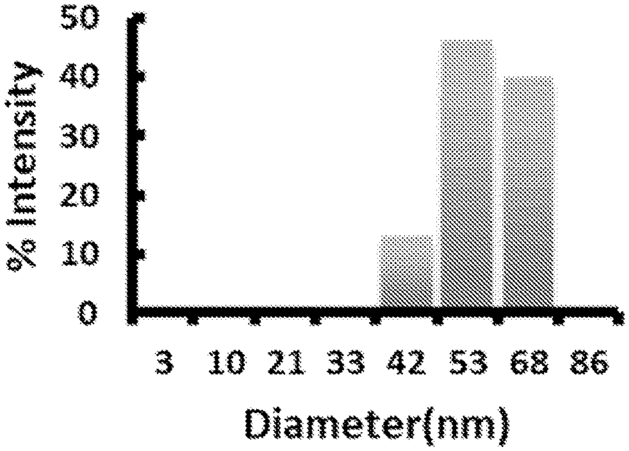
FIG. 117B: Distribution of Hydrodynamic Diameter.

The morphologies were characterized by TEM (FIG. 117A) with mono-dispersed spherical particles observed. The particles were stable under higher electron dose in TEM suggesting that EGD as a crosslinker helps to rigidify the particle's structure support. The $D_h$ of the MMA and EGD nano-tracers was determined by DLS to be 42 nm (FIG. 117B).

Synthesis and Characterization of Nano-Tracers with Methacrylamide

The polymerization conditions for nano-tracers with methacrylamide were identical to those used in the "Optimization of Polymerization Condition of Plain Nano-tracers" section except there no MMA was added to reaction. 50 mg of methacrylamide was dissolved in 1 mL of MILLI-Q water and added to the flask prior to the addition of the dye mixture. Other amounts of methacrylamide were tested, however, precipitates formed in all other quantities greater than 50 mg of monomer.

The morphologies of nano-tracers synthesized with methacrylamide were characterized by TEM (FIG. 118). Spherical particles with a diameter of 42±13 nm were observed. These nano-tracers were further examined by DLS to obtain the Dh, which was found to be 50 nm (FIG. 119). NTA showed a peak at 50 nm, consistent with the diameter of the nano-tracer obtained from both TEM and DLS. The zeta potential was determined to be −2.04 mV. Compared to the zeta potential of nano-tracers without MAA (−17.27 mV), this result suggests that methacrylamide significantly contributes to increasing the surface charge of the nano-tracers.

Synthesis and Characterization 2,3-Epoxypropylmethacrylate (EPMA) Nano-Tracers

The 2,3-epoxypropylmethacrylate (EPMA) nano-tracer's synthesis was based on the paper published by Paulke(34), with additional modifications. 50 mL nanopure $H_2O$ and a stir bar were placed in a Schlenk flask. EPMA 0.960 mL followed by MAA 0.049 mL were added to the flask under argon while stirring at 300 rpm. Then 0.75 mL of a 220 mg/mL SDS solution and 1 mL of a 48 mg/mL AP solution were added into the flask. 20.47 mg methacryloxyethyl thiocarbamoyl rhodamine B was dissolved into 500 μL MeOH and added to the reaction flask. The mixture was stirred for 5 min at room temperature then transferred to an oil bath at 90° C. for 1 h. Over the course of the reaction the solution turned significantly more opaque/opalescent. After 1 h, the solution was removed from the oil bath and allowed to rest at room temperature.

The morphologies of EPMA nano-tracers were characterized by TEM (FIG. 120) and shown to have a diameter of 33±9 nm. These nano-tracers were further examined by DLS to obtain the hydrodynamic diameter, which was measured to be 43 nm (FIG. 121). The mass concentration was determined to be 22.26 mg/mL.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

As used herein and in the appended claims, the singular forms “a”, “an”, and “the” include plural reference unless the context clearly dictates otherwise. Thus, for example, reference to “a cell” includes a plurality of such cells and equivalents thereof known to those skilled in the art. As well, the terms “a” (or “an”), “one or more” and “at least one” can be used interchangeably herein. It is also to be noted that the terms “comprising”, “including”, and “having” can be used interchangeably. The expression “of any of claims XX-YY” (wherein XX and YY refer to claim numbers) is intended to provide a multiple dependent claim in the alternative form, and in some embodiments is interchangeable with the expression “as in any one of claims XX-YY.”

When a group of substituents is disclosed herein, it is understood that all individual members of that group and all subgroups are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Certain molecules disclosed herein may contain one or more ionizable groups, groups from which a proton can be removed (e.g., —COOH) or added (e.g., amines) or which can be quaternized (e.g., amines). All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every device, system, formulation, combination of components, or method described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant’s invention, including compounds for which an enabling disclosure is provided in the references cited herein, are not intended to be included in the composition of matter claims herein.

As used herein, “comprising” is synonymous with “including,” “containing,” or “characterized by,” and is inclusive or open-ended and does not exclude additional, unrecited elements or method steps. As used herein, “consisting of” excludes any element, step, or ingredient not specified in the claim element. As used herein, “consisting essentially of” does not exclude materials or steps that do not materially affect the basic and novel characteristics of the claim. In each instance herein any of the terms “comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A composition comprising:

a first fluorophore moiety, and nanoparticles, wherein the nanoparticles comprise:

a first plurality of a first nanoparticle, the first nanoparticle comprising:

a first outer surface, a first interior bulk, and a first polymer, wherein the first polymer is covalently bonded to the first fluorophore moiety within the first interior bulk of the first nanoparticle, wherein, as measured by UV-Vis spectroscopy:

the composition comprises the first fluorophore moiety at least about 40 μM, and wherein the first fluorophore moiety comprises coumarin, and the composition comprises the coumarin at a concentration of at least about 40 μM, the first fluorophore moiety comprises fluorescein, and the composition comprises the fluorescein at a concentration of at least about 500 μM, the first fluorophore moiety comprises rhodamine B, and the composition comprises the rhodamine B at a concentration of at least about 380 μM, or the first fluorophore moiety comprises cyanine 5.5, and the composition comprises the cyanine 5.5 at a concentration of at least about 70 μM.

2. The composition of claim 1, wherein the first polymer comprises a polyacrylate, a polyacrylic acid, a polymethacrylate, a polymethacrylic acid, a polymethylmethacrylate (PMMA), a polyethylacrylate, a polyethylmethacrylate, a polypropylacrylate, a polypropylmethacrylate, a polybutylacrylate, a polybutylmethacrylate, a polyhydroxyalkyl methacrylate, a poly(2-hydroxyethyl)methacrylate, a poly (3-hydroxypropyl)methacrylate, a poly(hydroxyalkyl)acrylate, a poly(2-hydroxyethyl)acrylate, a poly(3-hydroxypropyl)acrylate, a polylaurylacrylate, a polystearylacrylate, a polyglycidylacrylate, a polyglycidylmethacrylate, a polyacrylonitrile, a polyacrylamide, a polyvinyl alcohol, a polyvinyl acetate, a polyvinyl butyral, a polyvinylpyrrolidone, a polystyrene, or any combination thereof.

3. The composition of claim 1, wherein the first polymer comprises at least one structure of formula (1) to (6) and (27):

(1)

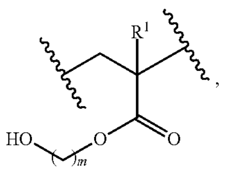

(2)

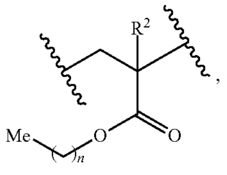

(3)

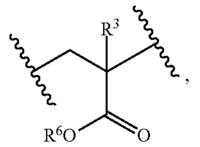

(4)

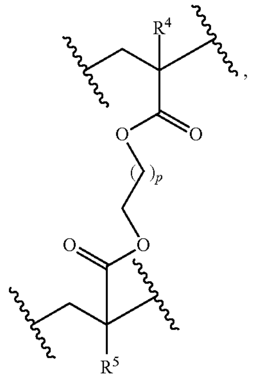

(5)

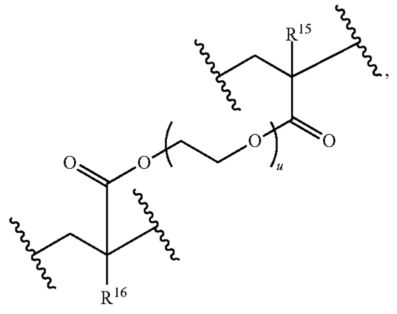

(6)

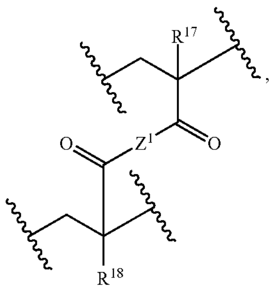

-continued (27)

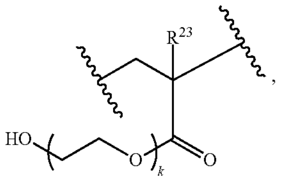

wherein:

m is 2 to 5, n is 0 to 5, k, p, and u independently are 1 to 5, $R^1$, $R^2$, $R^3$, $R^4$, $R^5$, $R^{15}$, $R^{16}$, $R^{17}$, $R^{18}$, and $R^{23}$ independently are H or methyl, $R^6$ is H or a metal ion, and $Z^1$ is a linking group comprising alkyl, aryl, ethylene glycol, oligo(ethylene glycol), poly(ethylene glycol), an amine, an ether, an ester, an amide, an ester when taken together with adjacent atoms, an amide when taken together with adjacent atoms, any substituted version thereof, or any combination thereof.

4. The composition of claim 3, wherein the first polymer is a copolymer comprising the structures of formulas (1) to (4); and wherein at least one of conditions (a) to (e) is satisfied:

(a) m is 2, (b) n is 0, (c) p is 1, (d) $R^1$, $R^2$, $R^3$, $R^4$, and $R^5$ are methyl, or (e) all of conditions (a) to (d) are satisfied.

5. The composition of claim 1, comprising a second fluorophore moiety, wherein the first polymer is covalently bonded to the second fluorophore moiety within the first interior bulk of the first nanoparticle, wherein the second fluorophore moiety comprises coumarin, fluorescein, rhodamine, rhodamine B, cyanine, cyanine 5.5, or cyanine 7.

6. The composition of claim 5, wherein the second fluorophor moiety comprises at least one structure of formula (15), (16), (18) and (23):

(15)

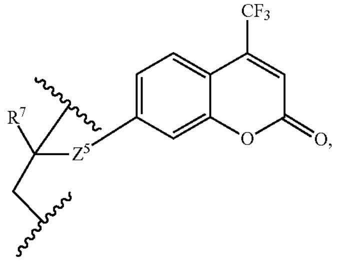

-continued

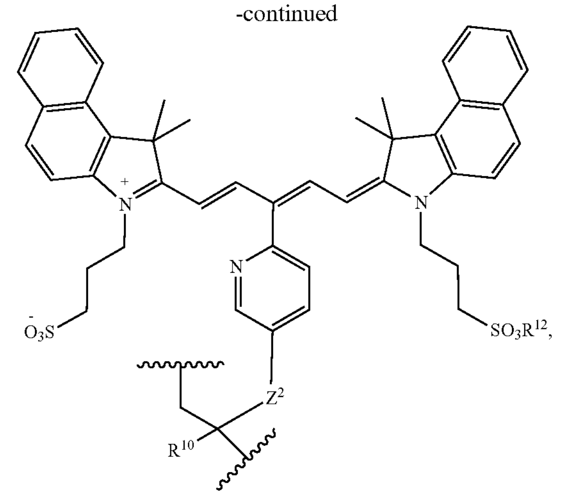

(18)

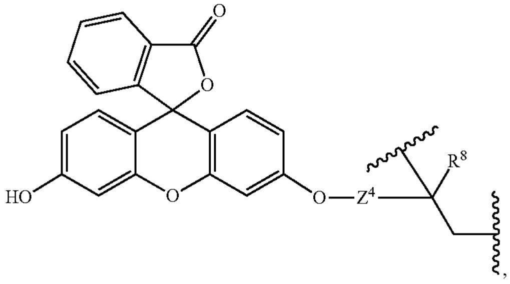

(23)

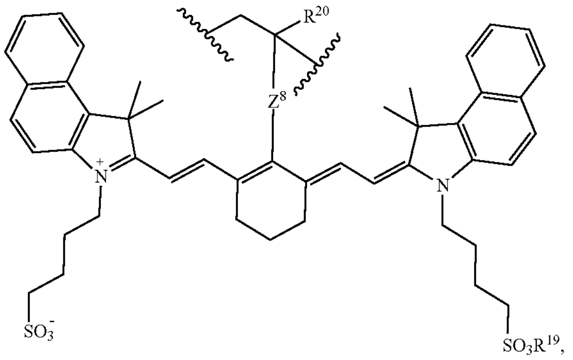

wherein:

$R^7$, $R^8$, $R^{10}$ and $R^{20}$ independently are H or methyl, $R^{11}$, $R^{12}$, and $R^{19}$ independently are H or a metal ion, and $Z^2$, $Z^3$, $Z^4$, $Z^5$, and $Z^8$ independently are a linking group comprising an alkyl, an aryl, ethylene glycol, oligo (ethylene glycol), an amine, an ether, an ester, an amide, a thiocarbamoyl, any substituted version thereof, or any combination thereof.

7. The composition of claim 1, wherein the nanoparticles comprise:

a diameter of about 30 to about 120 nm, as measured by uranyl acetate stained dry-state transmission electron microscopy, or a diameter of about 30 nm to about 120 nm, as measured by cryogenic electron microscopy, or a hydrodynamic diameter of about 50 nm to 200 nm, as measured by dynamic light scattering.

8. The composition of claim 1, wherein, as measured by UV-Vis spectroscopy:

the composition comprises the first fluorophore moiety at a concentration of about 40 μM to about 700 μM, as measured by UV-Vis spectroscopy, the first fluorophore moiety comprises coumarin, and the composition comprises the coumarin at a concentration of about 40 μM to about 120 μM, the first fluorophore moiety comprises fluorescein, and the composition comprises the fluorescein at a concentration of about 500 μM to about 700 μM, the first fluorophore moiety comprises rhodamine B, and the composition comprises the rhodamine B at a concentration of about 380 μM to about 550 μM, or the first fluorophore moiety comprises cyanine 5.5, and the composition comprises the cyanine 5.5 at a concentration of about 70 μM to about 200 μM.

9. The composition of claim 1, wherein, when the composition is injected into viable neural tissue of a mouse:

the nanoparticles are transported in axons in a retrograde fashion along an entorhinal cortex (EC) to first hippocampal region (CA1) pathway, or the nanoparticles are transported in axons in a retrograde fashion along a lateral geniculate nucleus (LGN) to primary visual cortex (V1) pathway.

10. The composition of claim 1, wherein the nanoparticles are prepared by a process comprising emulsion polymerization of a mixture comprising:

a vinyl-containing first fluorophore, and at least one vinyl-containing monomer, wherein the first fluorophore moiety is derived from the vinyl-containing first fluorophore.

11. The composition of claim 10, wherein the vinyl-containing first fluorophore comprises coumarin, fluorescein, rhodamine B, or cyanine 5.5.

12. The composition of claim 10, wherein the vinyl-containing first fluorophor comprises a structure of formula (7) (8), (10)-(12), 14, and (24) to (26):

(7)

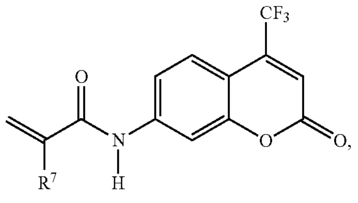

(8)

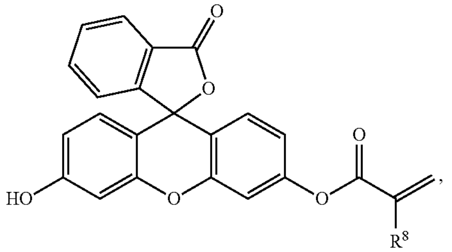

-continued (10)

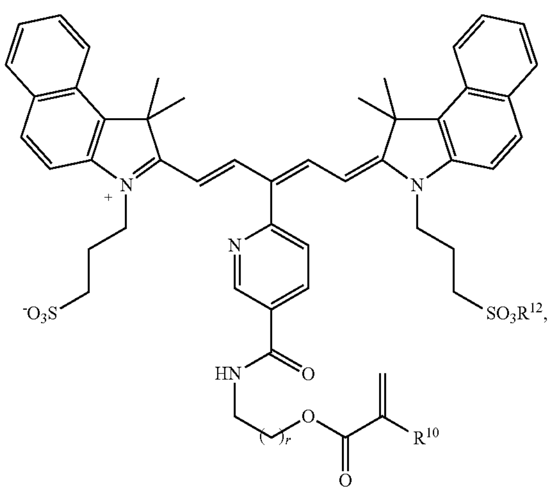

(11)

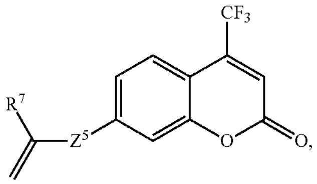

(12)

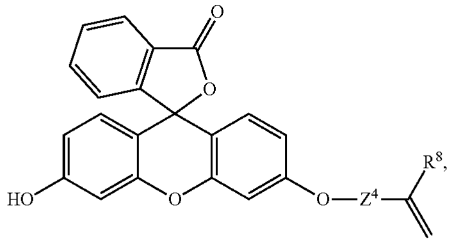

(14)

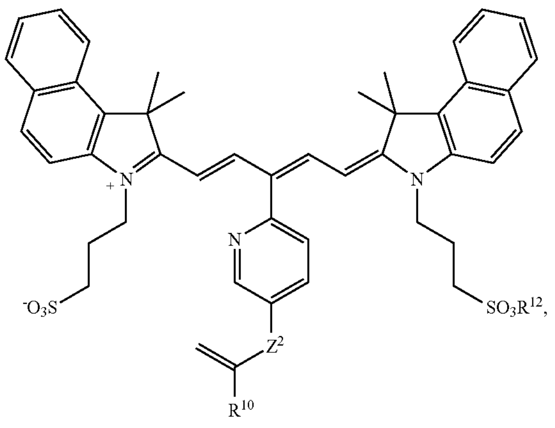

-continued (24)

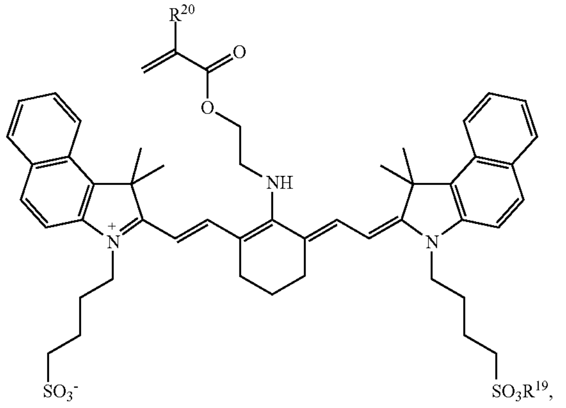

(25)

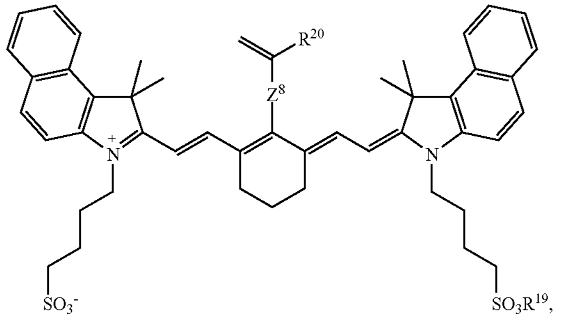

(26)

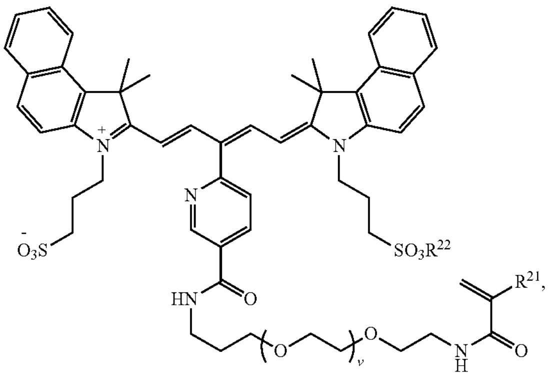

wherein:

$R^7$, $R^8$, $R^{10}$, $R^{20}$ and $R^{21}$ independently are H or methyl, q and r independently are 1 to 5, v is 0 to 5, $R^{12}$, $R^{19}$, and $R^{22}$ independently are H or a metal ion, and $Z^2$, $Z^3$, $Z^4$, $Z^5$, and $Z^8$ independently are a linking group comprising an alkyl, an aryl, ethylene glycol, oligo (ethylene glycol), an amine, an ether, an ester, an amide, a thiocarbamoyl, any substituted version thereof, or any combination thereof.

13. The composition of claim 10, wherein the at least one vinyl-containing monomer comprises an acrylate, a methacrylate, methyl methacrylate, methacrylic acid, acrylic acid, 2-hydroxyethyl methacrylate, 2-hydroxyethyl acrylate, 3-hydroxypropyl acrylate, 3-hydroxyethyl methacrylate, ethylacrylate, ethylmethacrylate, propylacrylate, propylmethacrylate, butylacrylate, butylmethacrylate, laurylacrylate, laurylmethacrylate, stearylacrylate, stearylmethacrylate, glycidylacrylate, glycidylmethacrylate, acrylonitrile, acrylamide, vinylalcohol, vinylacetate, vinylbutyral, vinylpyrrolidone, styrene, or any combination thereof.

14. The composition of claim 10, further comprising at least one crosslinker.

15. The composition of claim 1, wherein the first nanoparticle further comprises a chelate moiety covalently bonded to the first polymer within the first interior bulk of the first nanoparticle.

16. The composition of claim 15, wherein the chelate moiety comprises a magnetic resonance imaging (MRI) contrast agent, a positron emission tomography (PET) contrast agent, a single-photon emission computerized tomography (SPECT) contrast agent, or any combination thereof.

17. The composition of claim 15, wherein the chelate moiety comprises gadolinium, copper, indium, yttrium, yttrium(54), or any combination thereof.

18. The composition of claim 1, further comprising a second fluorophore moiety having a different emission maximum than the first fluorophore moiety, wherein the nanoparticles further comprise:

a second plurality of a second nanoparticle, the second nanoparticle comprising:

a second outer surface, a second interior bulk, and a second polymer, wherein the second polymer is covalently bonded to the second fluorophore moiety within the second interior bulk of the second nanoparticle.

19. The composition of claim 18, wherein the first nanoparticle is substantially free of a fluorophore moiety other than the first fluorophore moiety, or wherein the second nanoparticle is substantially free of a fluorophore moiety other than the second fluorophore moiety.

20. The composition of claim 18, wherein the first nanoparticle further comprises the second fluorophore moiety, or wherein the second nanoparticle further comprises the first fluorophore moiety.

21. The composition of claim 1, wherein the first fluorophore moiety comprises cyanine 5.5, and the composition comprises the cyanine 5.5 at a concentration of about 70 μM to about 200 μM, as measured by UV-Vis spectroscopy.

22. A composition comprising:

a first fluorophore moiety, and nanoparticles, wherein the nanoparticles comprise:

a first plurality of a first nanoparticle, the first nanoparticle comprising:

a first outer surface, a first interior bulk, and a first polymer, wherein the first polymer is covalently bonded to the first fluorophore moiety within the first interior bulk of the first nanoparticle, wherein, as calculated from nanoparticle concentration per mL of the composition and concentration of the first fluorophore moiety in the composition:

the composition comprises the first fluorophore moiety at a concentration of about $1.00\times10^{-13}$ μmol/nanoparticle to about $32.0\times10^{-13}$ μmol/nanoparticle, the first fluorophore moiety comprises coumarin, and the nanoparticles comprise the coumarin at a concentration of about $1.00\times10^{-13}$ μmol/nanoparticle to about $5.00\times10^{-13}$ μmol/nanoparticle, the fluorophore moiety comprises fluorescein, and the nanoparticles comprise the fluorescein at a concentration of about $25.0\times10^{-13}$ μmol/nanoparticle to about $32.0\times10^{-13}$ μmol/nanoparticle, the fluorophore moiety comprises rhodamine B, and the nanoparticles comprise the rhodamine B at a concentration of about $1.00\times10^{-13}$ μmol/nanoparticle to about $5.00\times10^{-13}$ μmol/nanoparticle, the fluorophore moiety comprises cyanine 5.5, and the nanoparticles comprise the cyanine 5.5 at a concentration of about $2.00\times10^{-13}$ μmol/nanoparticle to about $10.0\times10^{-13}$ μmol/nanoparticle, or the first fluorophore moiety comprises cyanine 7, and the nanoparticles comprise the cyanine 7 at a concentration of about $1.00\times10^{-13}$ μmol/nanoparticle to about $5.00\times10^{-13}$ μmol/nanoparticle.

23. A composition comprising:

a first fluorophore moiety, and nanoparticles, wherein the nanoparticles comprise:

a first plurality of a first nanoparticle, the first nanoparticle comprising:

a first outer surface, a first interior bulk, and a first polymer, wherein the first polymer is covalently bonded to the first fluorophore moiety within the first interior bulk of the first nanoparticle, wherein, when measured at a concentration of about $2.1\times10^{11}$ to about $3.2\times10^{11}$ particles per mL, the composition comprises an absorption peak in a UV-Vis spectrum, and wherein the first fluorophore moiety comprises coumarin, and when measured at a concentration of about $3.2\times10^{11}$ nanoparticles per mL, the nanoparticles comprise an excitation maximum of about 340 nm to about 360 nm and an emission maximum of about 402 nm to about 422 nm, the first fluorophore moiety comprises fluorescein, and when measured at a concentration of about $2.1\times10^{11}$ nanoparticles per mL, the nanoparticles comprise an excitation maximum of about 480 nm to about 500 nm and an emission maximum of about 503 nm to about 523 nm, the first fluorophore moiety comprises rhodamine B, and when measured at a concentration of about $23\times10^{11}$ nanoparticles per mL, the nanoparticles comprise an excitation maximum of about 548 nm to about 568 nm and an emission maximum of about 576 nm to about 596 nm, the first fluorophore moiety comprises cyanine 5.5, and when measured at a concentration of about $2.5\times10^{11}$ nanoparticles per mL, the nanoparticles comprise an excitation maximum of about 662 nm to about 682 nm and an emission maximum of about 690 nm to about 710 nm, or the first fluorophore moiety comprises cyanine 7, and when measured at a concentration of about $9.4\times10^{9}$ nanoparticles per mL, the nanoparticles comprise an excitation maximum of about 647 nm to about 667 nm and an emission maximum of about 796 nm to about 816 nm.

24. A method of brain mapping or tracing an axonal projection, the method comprising:

subjecting a first neuron in a first location to the composition of claim 1 to form a first infused neuron, and imaging the first infused neuron using at least one of fluorescence spectroscopy, magnetic resonance imaging (MRI), positron emission tomography (PET), single-photon emission computerized tomography (SPECT), or any combination thereof, optionally wherein the first nanoparticle further comprises a chelate moiety covalently bonded to the first polymer within the first interior bulk of the first nanoparticle and the chelate moiety comprises a magnetic resonance imaging (MRI) contrast agent, a positron emission tomography (PET) contrast agent, single-photon emission computerized tomography (SPECT) contrast agent, or any combination thereof.

25. The method of claim 24, further comprising:

subjecting a second neuron in a second location to the composition to form a second infused neuron, and imaging the second infused neuron using at least one of fluorescence spectroscopy, magnetic resonance imaging (MRI), positron emission tomography (PET), single-photon emission computerized tomography (SPECT), or any combination thereof, wherein the first and second locations are different.

26. The method of claim 25, wherein the first and second locations are in a hippocampus.

* * * * *